US009890148B2

(12) United States Patent
Ungashe et al.

(10) Patent No.: US 9,890,148 B2
(45) Date of Patent: Feb. 13, 2018

(54) ARYL SULFONAMIDES

(71) Applicant: ChemoCentryx, Inc., Mountain View, CA (US)

(72) Inventors: Solomon Ungashe, Fremont, CA (US); John J. Wright, Redwood City, CA (US); Andrew Pennell, San Francisco, CA (US); Zheng Wei, Union City, CA (US); Anita Melikian, Mountain View, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 0 days.

(21) Appl. No.: 14/551,438

(22) Filed: Nov. 24, 2014

(65) Prior Publication Data

US 2015/0080351 A1  Mar. 19, 2015

Related U.S. Application Data

(63) Continuation of application No. 13/852,167, filed on Mar. 28, 2013, now abandoned, which is a continuation of application No. 13/245,568, filed on Sep. 26, 2011, now abandoned, which is a continuation of application No. 12/137,006, filed on Jun. 11, 2008, now abandoned, which is a continuation of application No. 10/846,241, filed on May 13, 2004, now Pat. No. 7,240,055, which is a continuation-in-part of application No. 10/716,170, filed on Nov. 17, 2003, now Pat. No. 6,939,885.

(60) Provisional application No. 60/427,670, filed on Nov. 18, 2002.

(51) Int. Cl.
| | | |
|---|---|---|
| C07D 417/12 | (2006.01) |
| C07D 213/26 | (2006.01) |
| C07D 213/50 | (2006.01) |
| C07D 213/52 | (2006.01) |
| C07D 213/70 | (2006.01) |
| C07D 213/74 | (2006.01) |
| C07D 213/84 | (2006.01) |
| C07D 213/89 | (2006.01) |
| C07D 241/12 | (2006.01) |
| C07D 405/12 | (2006.01) |
| C07D 413/12 | (2006.01) |
| A61K 31/4409 | (2006.01) |
| A61K 31/443 | (2006.01) |
| A61K 31/4439 | (2006.01) |
| A61K 31/4545 | (2006.01) |
| A61K 31/496 | (2006.01) |
| A61K 31/5377 | (2006.01) |
| A61K 31/541 | (2006.01) |
| A61K 45/06 | (2006.01) |
| C07D 239/26 | (2006.01) |
| C07D 401/12 | (2006.01) |
| C07D 409/12 | (2006.01) |

(52) U.S. Cl.
CPC .......... *C07D 417/12* (2013.01); *A61K 31/443* (2013.01); *A61K 31/4409* (2013.01); *A61K 31/4439* (2013.01); *A61K 31/4545* (2013.01); *A61K 31/496* (2013.01); *A61K 31/5377* (2013.01); *A61K 31/541* (2013.01); *A61K 45/06* (2013.01); *C07D 213/26* (2013.01); *C07D 213/50* (2013.01); *C07D 213/52* (2013.01); *C07D 213/70* (2013.01); *C07D 213/74* (2013.01); *C07D 213/84* (2013.01); *C07D 213/89* (2013.01); *C07D 239/26* (2013.01); *C07D 241/12* (2013.01); *C07D 401/12* (2013.01); *C07D 405/12* (2013.01); *C07D 409/12* (2013.01); *C07D 413/12* (2013.01)

(58) Field of Classification Search
CPC .. C07D 213/26; C07D 213/50; C07D 213/52; C07D 213/70; C07D 213/74; C07D 213/84; C07D 213/89; C07D 241/12; C07D 405/12; C07D 413/12; C07D 239/26
USPC ....... 514/156, 256, 314, 318, 336, 340, 354; 544/58.6, 131, 365; 546/194, 268.4, 546/283.7, 328
See application file for complete search history.

(56) References Cited

U.S. PATENT DOCUMENTS

| | | | |
|---|---|---|---|
| 2,997,368 A | 8/1961 | Barent et al. |
| 3,121,103 A | 2/1964 | Keller et al. |
| 3,344,183 A | 9/1967 | Reeder et al. |
| 3,442,946 A | 5/1969 | Keller et al. |
| 3,534,062 A | 10/1970 | Wright et al. |

(Continued)

FOREIGN PATENT DOCUMENTS

| | | |
|---|---|---|
| CH | 561703 | 5/1975 |
| DE | 3544409 A1 | 10/1986 |

(Continued)

OTHER PUBLICATIONS

Anthony et al. "Preparation of arylsulfo . . . " CA142:155671 (2005).*

(Continued)

*Primary Examiner* — Heidi Reese
(74) *Attorney, Agent, or Firm* — Brinks Gilson & Lione; Ryan L. Marshall

(57) ABSTRACT

Compounds are provided that act as potent antagonists of the CCR9 receptor, and which have been further confirmed in animal testing for inflammation, one of the hallmark disease states for CCR9. The compounds are generally aryl sulfonamide derivatives and are useful in pharmaceutical compositions, methods for the treatment of CCR9-mediated diseases, and as controls in assays for the identification of CCR9 antagonists.

11 Claims, 1 Drawing Sheet

(56) References Cited

U.S. PATENT DOCUMENTS

| | | | |
|---|---|---|---|
| 4,166,452 A | 9/1979 | Generales, Jr. | |
| 4,256,108 A | 3/1981 | Theeuwes | |
| 4,265,874 A | 5/1981 | Bonsen et al. | |
| 4,372,975 A | 2/1983 | Mouzin et al. | |
| 4,954,518 A | 9/1990 | Takano et al. | |
| 4,992,091 A | 2/1991 | Vinogradoff et al. | |
| 4,997,940 A | 3/1991 | Vinogradoff et al. | |
| 5,021,591 A | 6/1991 | Vinogradoff et al. | |
| 5,071,468 A | 12/1991 | Astles et al. | |
| 5,093,364 A | 3/1992 | Richards et al. | |
| 5,155,121 A | 10/1992 | Niewohner et al. | |
| 5,163,995 A | 11/1992 | Van Heertum et al. | |
| 5,185,348 A | 2/1993 | Niewohner et al. | |
| 5,217,521 A | 6/1993 | Durr | |
| 5,338,755 A | 8/1994 | Wagnon et al. | |
| 5,481,005 A | 1/1996 | Wagnon et al. | |
| 5,541,186 A | 7/1996 | Breu et al. | |
| 5,571,775 A | 11/1996 | Van Heertum et al. | |
| 5,589,478 A | 12/1996 | Yamada et al. | |
| 5,780,488 A | 7/1998 | Bergman et al. | |
| 5,973,148 A | 10/1999 | Ringer et al. | |
| 6,136,971 A | 10/2000 | Harrington et al. | |
| 6,200,995 B1 | 3/2001 | De la Brouse-Elwood et al. | |
| 6,297,195 B1 | 10/2001 | Gesing et al. | |
| 6,297,239 B1 | 10/2001 | deSolms et al. | |
| 6,316,450 B1 | 11/2001 | Bromidge et al. | |
| 6,403,607 B1 | 6/2002 | Hidaka et al. | |
| 6,432,624 B1 | 8/2002 | Kikuchi et al. | |
| 6,653,332 B2 | 11/2003 | Jaen et al. | |
| 6,939,885 B2 * | 9/2005 | Ungashe | C07C 311/21 514/358 |
| 7,227,035 B2 | 6/2007 | Ungashe et al. | |
| 7,282,502 B2 | 10/2007 | Fleming et al. | |
| 7,321,001 B2 * | 1/2008 | Fu | C07C 205/37 514/562 |
| 7,335,653 B2 | 2/2008 | Ungashe et al. | |
| 7,420,055 B2 | 9/2008 | Ungashe et al. | |
| 7,582,661 B2 | 9/2009 | Ugashe et al. | |
| 7,659,272 B2 | 2/2010 | Fleming et al. | |
| 7,999,109 B2 | 8/2011 | Fleming et al. | |
| 8,030,517 B2 | 10/2011 | Fleming et al. | |
| 8,110,576 B2 * | 2/2012 | Ibrahim | C07D 487/04 514/249 |
| 8,211,896 B2 | 7/2012 | Ungashe et al. | |
| 2002/0009116 A1 | 1/2002 | Kobayashi et al. | |
| 2002/0012680 A1 | 1/2002 | Patel et al. | |
| 2002/0013314 A1 | 1/2002 | Zhu et al. | |
| 2002/0013315 A1 | 1/2002 | Teall | |
| 2002/0037905 A1 | 3/2002 | Dahl et al. | |
| 2002/0037928 A1 | 3/2002 | Jaen et al. | |
| 2002/0065303 A1 | 5/2002 | Zhu et al. | |
| 2002/0072530 A1 | 6/2002 | Zhu et al. | |
| 2002/0103202 A1 | 8/2002 | Pinto et al. | |
| 2003/0060460 A1 | 3/2003 | Ohuchida et al. | |
| 2003/0139390 A1 | 7/2003 | McGee et al. | |
| 2006/0111351 A1 * | 5/2006 | Ungashe | C07D 213/26 514/235.2 |
| 2006/0134566 A1 * | 6/2006 | Hoshimiya | G03C 1/10 430/502 |
| 2010/0234364 A1 * | 9/2010 | Basak | A61K 31/44 514/227.5 |
| 2013/0267492 A1 * | 10/2013 | Ungashe | C07D 213/26 514/210.2 |

FOREIGN PATENT DOCUMENTS

| | | |
|---|---|---|
| DE | 3825041 A1 | 2/1990 |
| EP | 0 015 214 B1 | 9/1980 |
| EP | 0 526 348 A1 | 2/1993 |
| EP | 0 556 673 B1 | 2/1993 |
| EP | 0 613 894 A1 | 9/1994 |
| GB | 884 847 | 12/1961 |
| GB | 1 332 697 | 10/1973 |
| WO | WO 93/03013 | 2/1993 |
| WO | WO 94/20142 | 9/1994 |
| WO | WO 95/33462 | 12/1995 |
| WO | WO 96/08483 | 3/1996 |
| WO | WO 97/28129 | 8/1997 |
| WO | WO 98/11218 | 3/1998 |
| WO | WO 98/28270 | 7/1998 |
| WO | WO 98/50029 | 11/1998 |
| WO | WO 99/17777 | 4/1999 |
| WO | WO 99/32433 | 7/1999 |
| WO | WO 99/38845 | 8/1999 |
| WO | WO 99/42465 | 8/1999 |
| WO | WO 99/55324 | 11/1999 |
| WO | WO 99/55663 | 11/1999 |
| WO | WO 00/05214 | 2/2000 |
| WO | WO 00/62778 | 10/2000 |
| WO | WO 01/00579 A1 | 1/2001 |
| WO | WO 01/09097 A1 | 2/2001 |
| WO | WO 01/17971 A1 | 3/2001 |
| WO | WO 01/19788 A2 | 3/2001 |
| WO | WO 01/19798 A2 | 3/2001 |
| WO | WO 01/32646 A2 | 5/2001 |
| WO | WO 01/56607 A1 | 8/2001 |
| WO | WO 01/56989 A2 | 8/2001 |
| WO | WO 01/57003 A1 | 8/2001 |
| WO | WO 01/57020 A1 | 8/2001 |
| WO | WO 01/60319 A2 | 8/2001 |
| WO | WO 02/00633 A1 | 1/2002 |
| WO | WO 02/18326 A1 | 3/2002 |
| WO | WO 02/30358 A2 | 4/2002 |
| WO | WO 02/054867 A1 | 7/2002 |
| WO | WO 02/055501 A2 | 7/2002 |
| WO | WO 02/059080 A2 | 8/2002 |
| WO | WO 03/099773 A1 | 12/2003 |
| WO | WO 2005/004810 A2 | 1/2005 |
| WO | WO 2007/014008 A2 | 2/2007 |
| WO | WO 2007/014054 A2 | 2/2007 |

OTHER PUBLICATIONS

Descamps et al. "Substituted sulfon . . . " CA88:6709 (1978).*
Fu et al. "Preparation of arylsulf . . . " CA141:123471 (2004).*
Gahman et al. "Nitrogen-containing . . . " CA146:13164 (2006).*
Hoshimiya et al. "Silver halide . . . " CA145:92872 (2006).*
Ibrahim et al. "Prepartion of pyrrolo[2,3 . . . " CA152:37608 (2009).*
Sato "Pyrazolotriazole . . . " CA113:241390 (1990).*
Improper Markush, Fed. Reg. vol. 76(27) p. 7162-7175, slide 1, 64067 (2011).*
Nandi, B Tett Lett 2000 vol. 41 pp. 7259-7262.*
Berman et al., Immunol. Invest., 17, pp. 625-677, 1988.
Burns "Composition and methods . . . " Ca 139:17596 (2003).
Campbell, et al., J. Exp. Med., 195(1), pp. 135-141, 2002.
Cohen et al. "cytokine function . . . " CA 125:31527 (1996).
Dahinden, et al., J. Exp. Med., 179, pp. 751-756, 1994.
Dannhardt, et al., 37 Eur.J.Med.Chem., pp. 147-161, 2002.
Davidson et al., J Exp Med., 184, pp. 241-251, 1996.
ESPICOM "GSK/chemocyntryx . . . " Espicom pharm$Med Device News (2006).
IMS R&D Fucus "Chemokine receptor antagonist . . . " Sep. 2006.
Kavanaugh et al., J. Immunol., 146, pp. 4149-4156, 1991.
Kontoyiannis et al., Immunity, 10, pp. 387-398, 1999.
Kosiewicz et al., J Clin Invest., 107(6), pp. 695-702, 2001.
Kunkel, et al., J. Exp. Med. 192(5), pp. 761-767, 2000.
Lothrop et al., J.Amer.Chem.Coc., CODEN:JACSAT, 63, pp. 2564-2567, 1941.
Murphy, Rev. Immun., 12, pp. 593-633, 1994.
Neote, et al., Cell, 72, pp. 415-425, 1993.
Oba et al. "MIP-1alpha . . . " CA 142:461958 (2005).
Panwala, et al., J Immunol., 161, pp. 5733-5744, 1998.
Papadakis, et al., J. Immunol., 165, pp. 5069-5076, 2000.
Powrie et al., Int Immunol., 5(11), pp. 1461-1471, 1993.
Qiuping Z et al., Cancer Res., 63, pp. 6469-6477, 2003.
Schaarschmidt; Herzenberg, ChemBer., CODEN:CHBEAM, 53, pp. 1388-1399, 1920.
Schall, Cytokine, 3, pp. 165-183, 1991.

(56) References Cited

OTHER PUBLICATIONS

Schall, et al., Curr. Opin. Immunol., 6, pp. 865-873, 1994.
Science IP Search Report (Mar. 1, 2005).
SciFinder Search Results (Feb. 19, 2004).
SciFinder Search Results (Feb. 20, 2004).
Search Report (Sep. 3, 2002).
Silverman, Richard B., "The Organic Chemistry of Drug Design and Drug Action," Academic Press, pp. 65-73 (1993).
Silvestri et al., Medicinal Chemistry Research, 11(4), pp. 195-218, 2002.
Street et al., Journal of Chemical Research, Synopses, (5), pp. 154-155, 1987.
Tan et al. "All roads lead to . . . " SciSearch 15762026 (2006).
Targan et al., N Engl J Med., 337(15), pp. 1029-1035, 1997.
Uehara, et al., J. Immunol, 168(6), pp. 2811-2819, 2002.
Ullmann; Bleier, Chem.Ber., CODEN:CHBEAM, 35, pp. 4273-4280, 1902.
Van Riper, et al., J. Exp. Med., 177, pp. 851-856, 1993.
Volkonen et al., "N-(2-Benzoyl-chlorophenyl)-4-chloro-benzenesulfonamide," Acta Cryst.E64, o737 (2008).
Wurbel, et al., Blood, 98(9), pp. 2626-2632, 2001.
Youn BS, et al., Apoptosis, 7, pp. 271-276, 2002.
Youn et al. "Blocking . . . " CA 135:613109 (2001).
Zaballos, et al., J. Immunol., 162, pp. 5671-5675, 1999.

\* cited by examiner

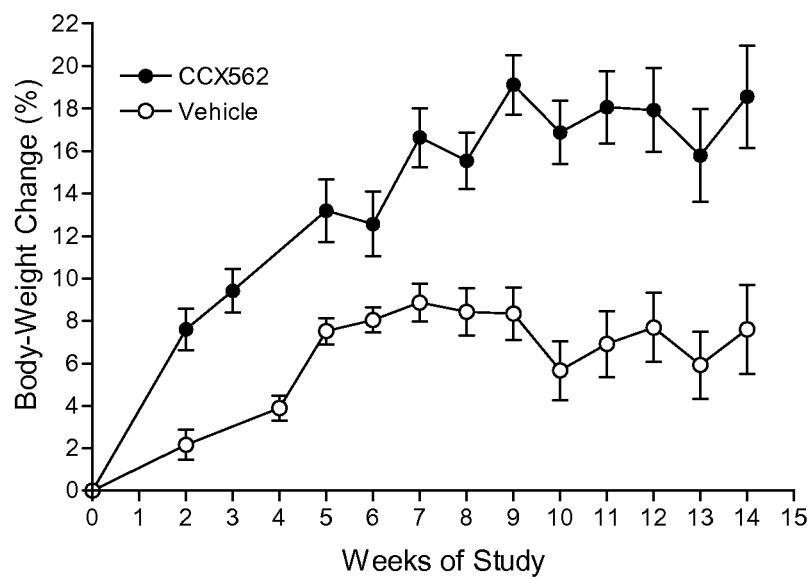

ARYL SULFONAMIDES

RELATED APPLICATIONS

This application is a continuation of U.S. application Ser. No. 13/852,167, filed Mar. 28, 2013, which application is a continuation of U.S. application Ser. No. 13/245,568, filed Sep. 26, 2011, which application is a continuation of U.S. application Ser. No. 12/137,006, filed Jun. 11, 2008, which application is a continuation of U.S. application Ser. No. 10/846,241, filed May 13, 2004, now U.S. Pat. No. 7,420,055, which application is a continuation-in-part of U.S. application Ser. No. 10/716,170, filed Nov. 17, 2003, now U.S. Pat. No. 6,939,885, which application claims priority to U.S. Provisional Application No. 60/427,670, filed Nov. 18, 2002. The disclosures of these priority applications are incorporated by reference herein in their entirety.

BACKGROUND OF THE INVENTION

The present invention provides compounds, pharmaceutical compositions containing one or more of those compounds or their pharmaceutically acceptable salts, which are effective in inhibiting the binding or function of various chemokines, such TECK, to the CCR9 receptor. As antagonists or modulators for the CCR9 receptor, the compounds and compositions have utility in treating inflammatory and immune disorder conditions and diseases.

Chemokines are chemotactic cytokines that are released by a wide variety of cells and attract various types of immune system cells, such as macrophages, T cells, eosinophils, basophils and neutrophils, to sites of inflammation (reviewed in Schall, *Cytokine*, 3:165-183 (1991), Schall, et al., *Curr. Opin. Immunol.*, 6:865 873 (1994) and Murphy, *Rev. Immun.*, 12:593-633 (1994)). In addition to stimulating chemotaxis, other changes can be selectively induced by chemokines in responsive cells, including changes in cell shape, transient rises in the concentration of intracellular free calcium ions ([$Ca^{2+}$]), granule exocytosis, integrin up-regulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

T lymphocyte (T cell) infiltration into the small intestine and colon has been linked to the pathogenesis of Coeliac diseases, food allergies, rheumatoid arthritis, human inflammatory bowel diseases (IBD) which include Crohn's disease and ulcerative colitis. Blocking trafficking of relevant T cell populations to the intestine can lead to an effective approach to treat human IBD. More recently, chemokine receptor 9 (CCR9) has been noted to be expressed on gut-homing T cells in peripheral blood, elevated in patients with small bowel inflammation such as Crohn's disease and celiac disease. The only CCR9 ligand identified to date, TECK (thymus-expressed chemokine) is expressed in the small intestine and the ligand receptor pair is now thought to play a pivotal role in the development of IBD. In particular, this pair mediates the migration of disease causing T cells to the intestine. See for example, Zaballos, et al., *J. Immunol.*, 162(10):5671-5675 (1999); Kunkel, et al., *J. Exp. Med.* 192(5):761-768 (2000); Papadakis, et al., *J. Immunol.*, 165(9):5069-5076 (2000); Papadakis, et al., *Gastroenterology*, 121(2):246-254 (2001); Campbell, et al., *J. Exp. Med.*, 195(1):135-141 (2002); Wurbel, et al., *Blood*, 98(9):2626-2632 (2001); and Uehara, et al., *J. Immunol*, 168(6):2811-2819 (2002).

The identification of compounds that modulate the function of CCR9 represents an attractive new family of therapeutic agents for the treatment of inflammatory and other conditions and diseases associated with CCR9 activation, such as inflammatory bowel disease.

BRIEF SUMMARY OF THE INVENTION

The present invention is directed to compounds and pharmaceutically acceptable salts thereof, compositions, and methods useful in modulating CCR9 chemokine activity. The compounds and salts thereof, compositions, and methods described herein are useful in treating or preventing CCR9-mediated conditions or diseases, including certain inflammatory and immunoregulatory disorders and diseases.

In one embodiment, the inventive compounds are of the formula (I):

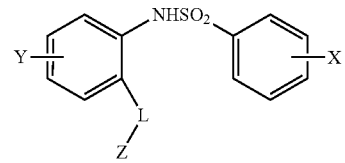

where X, Y and Z are as defined below. Salts of these compounds are also within the scope of the invention.

In another aspect, the present invention provides compositions useful in modulating CCR9 chemokine activity. In one embodiment, a composition according to the present invention comprises a compound according to the invention and a pharmaceutically acceptable carrier or excipient.

In yet another aspect, the present invention provides a method of modulating CCR9 function in a cell, comprising contacting the cell with a therapeutically effective amount of a compound or composition according to the invention.

In still another aspect, the present invention provides a method for modulating CCR9 function, comprising contacting a CCR9 protein with a therapeutically effective amount of a compound or composition according to the invention.

In still another aspect, the present invention provides a method for treating a CCR9-mediated condition or disease, comprising administering to a subject a safe and effective amount of a compound or composition according to the invention.

In addition to the compounds provided herein, the present invention further provides pharmaceutical compositions containing one or more of these compounds, as well as methods for the use of these compounds in therapeutic methods, primarily to treat diseases associated with CCR9 signaling activity.

BRIEF DESCRIPTION OF THE FIGURE

FIG. 1 is a graph showing in vivo efficacy for the CCR9 antagonist tested in the examples. Closed triangle: vehicle; Open circle: CCR9 antagonist of the formula:

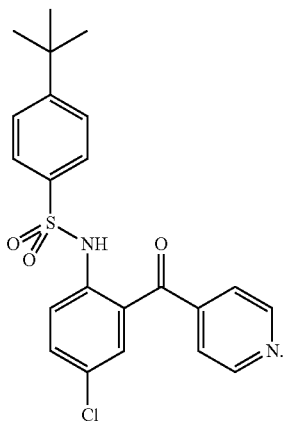 [SMILES: CC(C)(C)c1ccc(S(=O)(=O)Nc2ccc(Cl)cc2C(=O)c2ccncc2)cc1]

DETAILED DESCRIPTION OF THE INVENTION

General

The present invention is directed to compounds and salts thereof, compositions and methods useful in the modulation of chemokine receptor function, particularly CCR9 function. Modulation of chemokine receptor activity, as used herein in its various forms, is intended to encompass antagonism, agonism, partial antagonism, inverse agonism and/or partial agonism of the activity associated with a particular chemokine receptor, preferably the CCR9 receptor. Accordingly, the compounds of the present invention are compounds which modulate at least one function or characteristic of mammalian CCR9, for example, a human CCR9 protein. The ability of a compound to modulate the function of CCR9, can be demonstrated in a binding assay (e.g., ligand binding or agonist binding), a migration assay, a signaling assay (e.g., activation of a mammalian G protein, induction of rapid and transient increase in the concentration of cytosolic free calcium), and/or cellular response assay (e.g., stimulation of chemotaxis, exocytosis or inflammatory mediator release by leukocytes).

Abbreviations and Definitions

When describing the compounds, compositions, methods and processes of this invention, the following terms have the following meanings, unless otherwise indicated.

"Alkyl" by itself or as part of another substituent refers to a hydrocarbon group which may be linear, cyclic, or branched or a combination thereof having the number of carbon atoms designated (i.e., $C_{1-8}$ means one to eight carbon atoms). Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl, bicyclo[2.2.1]heptane, bicyclo[2.2.2]octane, etc. Alkyl groups can be substituted or unsubstituted, unless otherwise indicated. Examples of substituted alkyl include haloalkyl, thioalkyl, aminoalkyl, and the like.

"Alkenyl" refers to an unsaturated hydrocarbon group which may be linear, cyclic or branched or a combination thereof. Alkenyl groups with 2-8 carbon atoms are preferred. The alkenyl group may contain 1, 2 or 3 carbon-carbon double bonds. Examples of alkenyl groups include ethenyl, n-propenyl, isopropenyl, n-but-2-enyl, n-hex-3-enyl, cyclohexenyl, cyclopentenyl and the like. Alkenyl groups can be substituted or unsubstituted, unless otherwise indicated.

"Alkynyl" refers to an unsaturated hydrocarbon group which may be linear, cyclic or branched or a combination thereof. Alkynyl groups with 2-8 carbon atoms are preferred. The alkynyl group may contain 1, 2 or 3 carbon-carbon triple bonds. Examples of alkynyl groups include ethynyl, n-propynyl, n-but-2-ynyl, n-hex-3-ynyl and the like. Alkynyl groups can be substituted or unsubstituted, unless otherwise indicated.

"Aryl" refers to a polyunsaturated, aromatic hydrocarbon group having a single ring (bicyclic) or multiple rings (preferably bicyclic) which can be fused together or linked covalently. Aryl groups with 6-10 carbon atoms are preferred. Examples of aryl groups include phenyl and naphthalene-1-yl, naphthalene-2-yl, biphenyl and the like. Aryl groups can be substituted or unsubstituted, unless otherwise indicated.

"Halo" or "halogen", by itself or as part of a substituent refers to a chlorine, bromine, iodine, or fluorine atom. Additionally, "haloalkyl", as a substituted alkyl group, refers to a monohaloalkyl or polyhaloalkyl group, most typically substituted with from 1-3 halogen atoms. Examples include 1-chloroethyl, 3-bromopropyl, trifluoromethyl and the like.

"Heterocyclyl" refers to a saturated or unsaturated non-aromatic group containing at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Examples of heterocycle groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like. Preferred heterocyclic groups are monocyclic, though they may be fused or linked covalently to an aryl or heteroaryl ring system.

Exemplary heterocyclic groups may be represented by formula (A) below:

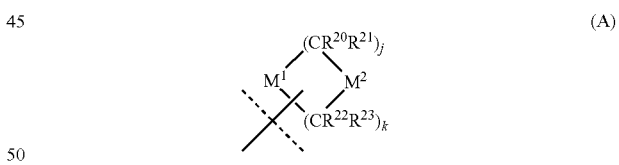

(A)

where formula (A) is attached via a free valence on either $CR^{20}R^{21}$; $CR^{22}R^{23}$, $M^1$ or $M^2$;

$M^1$ represents O, $NR^{24}$, $S(O)_l$;

$M^2$ represents $CR^{25}R^{26}$, O, $S(O)_l$, $NR^{24}$;

l is 0, 1 or 2;

j is 1, 2 or 3;

k is 1, 2 or 3, with the proviso that j+k is 3, 4, or 5; and $R^{20}$, $R^{21}$, $R^{22}$, $R^{23}$, $R^{24}$, $R^{25}$, and $R^{26}$ are independently selected from the group consisting of hydrogen, halogen, unsubstituted or substituted $C_{1-8}$ alkyl, unsubstituted or substituted $C_{2-8}$ alkenyl, unsubstituted or substituted $C_{2-8}$ alkynyl, —$COR^{27}$, —$CO_2R^{27}$, —$C(O)NR^{27}R^{28}$, —$NR^{27}COR^{28}$, —$S(O)_2R^{28}$, —$S(O)_2NR^{28}R^{29}$, —$NS(O)_2R^{28}R^{29}$—$NR^{28}R^{29}$, —$OR^{28}$, —$V^1COR^{28}$, —$V^1CO_2R^{28}$, —$V^1C(O)NR^{28}R^{29}$, —$V^1NR^{28}COR^{29}$, —$V^1S(O)_2R^{28}$, —$V^1S(O)_2NR^{28}R^{29}$, —$V^1NS(O)_2R^{28}R^{29}$, —$V^1NR^{28}R^{29}$, —$V^1OR^{28}$, where $V^1$ is a member selected from the group consisting of $C_{1-4}$ alkylene, $C_{2-4}$ alkenylene and $C_{2-4}$ alkynylene, and $R^{27}$, $R^{28}$ and $R^{29}$ are independently selected from the group consisting of hydrogen or $C_{1-8}$ alkyl, and where the aliphatic portions of each of the $R^{20}$, $R^{21}$, $R^{22}$, $R^{23}$, $R^{24}$, $R^{25}$, $R^{26}$, $R^{27}$, $R^{28}$ and $R^{29}$ substituents are optionally substituted with from one to three members selected from the group consisting of halogen, —OH, —$OR^{30}$, —$OC(O)NHR^{30}$, —$OC(O)NR^{30}R^{31}$, —SH, —$SR^{30}$, —$S(O)R^{30}$, —$S(O)_2R^{30}$, —$S(O)_2NH_2$, —$S(O)_2NHR^{30}$, —$S(O)_2NR^{30}R^{31}$, —$NHS(O)_2R^{30}$, —$C(O)NH_2$, —$C(O)NHR^{30}$, —$C(O)NR^{30}R^{31}$, —$C(O)R^{30}$, —$NHC(O)R^{30}$, —$NR^{30}C(O)R^{31}$, —$NHC(O)NH_2$, —$NR^{30}C(O)NH_2$, —$NR^{30}C(O)NHR^{31}$, —$NHC(O)NHR^{30}$, —$NR^{30}C(O)NR^{30}R^{31}$, —$NHC(O)NR^{30}R^{31}$, —$CO_2H$, —$CO_2R^{30}$, —$NHCO_2R^{30}$, —$NR^{30}CO_2R^{31}$, —CN, —$NO_2$, —$NH_2$, —$NHR^{30}$, —$NR^{30}R^{31}$, —$NR^{30}S(O)NH_2$ and —$NR^{30}S(O)_2NHR^{31}$, where $R^{30}$ and $R^{31}$ are independently an unsubstituted $C_{1-6}$ alkyl. Additionally, any two of $R^{20}$, $R^{21}$, $R^{22}$, $R^{23}$, $R^{24}$, $R^{25}$, $R^{26}$ may be combined to form a bridged or spirocyclic ring system.

Preferably, the number of $R^{20}+R^{21}+R^{22}+R^{23}$ groups that are other than hydrogen is 0, 1 or 2. More preferably, $R^{20}$, $R^{21}$, $R^{22}$, $R^{23}$, $R^{24}$, $R^{25}$, and $R^{26}$ are independently selected from the group consisting of hydrogen, halogen, unsubstituted or substituted $C_{1-8}$ alkyl, —$C(O)R^{28}$, —$CO_2R^{28}$, —$C(O)NR^{28}R^{29}$, —$NR^{28}C(O)R^{29}$, —$S(O)_2R^{28}$, —$S(O)_2NR^{28}R^{29}$, —$NS(O)_2R^{28}R^{29}$, —$NR^{28}R^{29}$, —$OR^{28}$, where $R^{28}$ and $R^{29}$ are independently selected from the group consisting of hydrogen, unsubstituted $C_{1-8}$ alkyl and where the aliphatic portions of each of the $R^{20}$, $R^{21}$, $R^{22}$, $R^{23}$, $R^{24}$, $R^{25}$ and $R^{26}$ substituents are optionally substituted with from one to three members selected from the group consisting of halogen, —OH, —$OR^{30}$, —$OC(O)NHR^{30}$, —$OC(O)NR^{30}R^{31}$, —SH, —$SR^{30}$, —$S(O)R^{30}$, —$S(O)_2R^{30}$, —$S(O)_2NH_2$, —$S(O)_2NHR^{30}$, —$S(O)_2NR^{30}R^{31}$, —$NHS(O)_2R^{30}$, —$NR^{30}S(O)_2R^{31}$, —$C(O)NH_2$, —$C(O)NHR^{30}$, —$C(O)NR^{30}R^{31}$, —$C(O)R^{30}$, —$NHC(O)R^{30}$, —$NR^{30}C(O)R^{31}$, —$NHC(O)NH_2$, —$NR^{30}C(O)NH_2$, —$NR^{30}C(O)NHR^{31}$, —$NHC(O)NHR^{30}$, —$NR^{30}C(O)NR^{30}R^{31}$, —$NHC(O)NR^{30}R^{31}$, —$CO_2H$, —$CO_2R^{30}$, —$NHCO_2R^{30}$, —$NR^{30}CO_2R^{31}$, —CN, —$NO_2$, —$NH_2$, —$NHR^{30}$, —$NR^{30}R^{31}$, —$NR^{30}S(O)NH_2$ and —$NR^{30}S(O)_2NHR^{31}$, where $R^{30}$ and $R^{31}$ are independently an unsubstituted $C_{1-6}$ alkyl.

More preferably, $R^{20}$, $R^{21}$, $R^{22}$, $R^{23}$, $R^{24}$, $R^{25}$, and $R^{26}$ are independently hydrogen or $C_{1-4}$alkyl. In another preferred embodiment, at least three of $R^{20}$, $R^{21}$, $R^{22}$, $R^{23}$, $R^{24}$, $R^{25}$, and $R^{26}$ are hydrogen.

"Heteroaryl" refers to an aromatic group containing at least one heteroatom. Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl. Preferred heteroaryl groups are those having at least one aryl ring nitrogen atom, such as quinolinyl, quinoxalinyl, purinyl, benzimidazolyl, benzopyrazolyl, benzotriazolyl, benzothiazolyl, indolyl, quinolyl, isoquinolyl and the like. Preferred 6-ring heteroaryl systems include pyridyl, pyridazinyl, pyrazinyl, pyrimidinyl, triazinyl and the like. Preferred 5-ring heteroaryl systems include isothiazolyl, pyrazolyl, imidazolyl, thienyl, furyl, triazolyl, tetrazolyl, oxazolyl, isoxazolyl, oxadiazolyl, thiadiazolyl, pyrrolyl, thiazolyl and the like.

Heterocyclyl and heteroaryl can be attached at any available ring carbon or heteroatom. Each heterocyclyl and heteroaryl may have one or more rings. When multiple rings are present, they can be fused together or linked covalently. Each heterocyclyl and heteroaryl must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Heterocyclyl and heteroaryl groups can be substituted or unsubstituted, unless otherwise indicated. For substituted groups, the substitution may be on a carbon or heteroatom. For example, when the substitution is =O, the resulting group may have either a carbonyl (—C(O)—) or a N-oxide (—$N^+$—$O^-$) or —S(O)— or —$S(O)_2$—.

Suitable substituents for substituted alkyl, substituted alkenyl, and substituted alkynyl include halogen, —CN, —$CO_2R'$, —C(O)R', —C(O)NR'R", oxo (=O or —$O^-$), —OR', —OC(O)R', —OC(O)NR'R"—$NO_2$, —NR'C(O)R", —NR'''C(O)NR'R", —NR'R", —$NR'CO_2R"$, —$NR'S(O)_2R'''$, —SR', —S(O)R', —$S(O)_2R'$, —$S(O)_2NR'R"$, —SiR'R"R''', —$N_3$, substituted or unsubstituted $C_{6-10}$ aryl, substituted or unsubstituted 5- to 10-membered heteroaryl, and substituted or unsubstituted 3- to 10-membered heterocyclyl, in a number ranging from zero to (2 m'+1), where m' is the total number of carbon atoms in such radical.

Suitable substituents for substituted aryl, substituted heteroaryl and substituted heterocyclyl include halogen, —CN, —$CO_2R'$, —C(O)R', —C(O)NR'R", oxo (=O or —$O^-$), —OR', —OC(O)R', —OC(O)NR'R", —$NO_2$, —NR'C(O)R", —NR'C(O)NR"R''', —NR'R", —$NR'CO_2R"$, —$NR'S(O)_2R"$, —SR', —S(O)R', —$S(O)_2R"$, —$S(O)_2NR'R"$, —NR'—C(NHR")=NR''', —SiR'R"R''', —$N_3$, substituted or unsubstituted $C_{1-8}$ alkyl group, substituted or unsubstituted $C_{6-10}$ aryl group, substituted or unsubstituted 5- to 10-membered heteroaryl, and substituted or unsubstituted 3- to 10-membered heterocyclyl, in a number ranging from zero to the total number of open valences on the aromatic ring system.

As used above, R', R" and R''' each independently refer to a variety of groups including hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, substituted or unsubstituted arylalkyl, substituted or unsubstituted aryloxyalkyl. When R' and R" are attached to the same nitrogen atom, they can be combined with the nitrogen atom to form a 3-, 4-, 5-, 6-, or 7-membered ring (for example, —NR'R" includes 1-pyrrolidinyl and 4-morpholinyl).

Two of the substituents on adjacent atoms of an aryl or heteroaryl ring may optionally be replaced with a substituent of the formula -T-C(O)—$(CH_2)_q$—U—, where T and U are independently —NR"", —O—, —$CH_2$— or a single bond, and q is an integer of from 0 to 2. Alternatively, two of the substituents on adjacent atoms of the aryl or heteroaryl ring may optionally be replaced with a substituent of the formula -A-$(CH_2)_r$—B—, where A and B are independently —$CH_2$—, —O—, —NR""—, —S—, —S(O)—, —$S(O)_2$—, —$S(O)_2NR""$— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR''''—, —S—, —S(O)—, —S(O)$_2$—, or —S(O)$_2$NR'—. The substituent R'''' in —NR''''— and —S(O)$_2$NR''''— is selected from hydrogen or unsubstituted C$_{1-6}$ alkyl.

"Heteroatom" is meant to include oxygen (O), nitrogen (N), sulfur (S) and silicon (Si).

"Pharmaceutically acceptable" carrier, diluent, or excipient is a carrier, diluent, or excipient compatible with the other ingredients of the formulation and not deleterious to the recipient thereof.

"Pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like.

Also included are salts of amino acids such as arginate and the like, and salts of organic acids like glucuronic or galactunoric acids and the like (see, for example, Berge, S. M., et al, "Pharmaceutical Salts", *J. Pharmaceutical Science*, 1977, 66:1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Salt thereof" refers to a compound formed when the hydrogen of an acid is replaced by a cation, such as a metal cation or an organic cation and the like. Preferably, the salt is a pharmaceutically-acceptable salt, although this is not required for salts of intermediate compounds which are not intended for administration to a patient.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

"Therapeutically effective amount" refers to an amount sufficient to effect treatment when administered to a patient in need of treatment.

"Treating" or "treatment" as used herein refers to the treating or treatment of a disease or medical condition (such as a bacterial infection) in a patient, such as a mammal (particularly a human or a companion animal) which includes: ameliorating the disease or medical condition, i.e., eliminating or causing regression of the disease or medical condition in a patient; suppressing the disease or medical condition, i.e., slowing or arresting the development of the disease or medical condition in a patient; or alleviating the symptoms of the disease or medical condition in a patient.

Certain compounds of the present invention can exist in unsolvated forms as well as solvated forms, including hydrated forms. In general, both solvated forms and unsolvated forms are intended to be encompassed within the scope of the present invention. Certain compounds of the present invention may exist in multiple crystalline or amorphous forms (i.e., as polymorphs). In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Compounds that Modulate CCR9 Activity

The present invention provides compounds that modulate CCR9 activity. Specifically, the invention provides compounds having anti-inflammatory or immunoregulatory activity. The compounds of the invention are thought to interfere with inappropriate T-cell trafficking by specifically modulating or inhibiting a chemokine receptor function. Chemokine receptors are integral membrane proteins which interact with an extracellular ligand, such as a chemokine, and mediate a cellular response to the ligand, e.g., chemotaxis, increased intracellular calcium ion concentration, etc. Therefore, modulation of a chemokine receptor function, e.g., interference with a chemokine receptor ligand interaction, will modulate a chemokine receptor mediated response, and treat or prevent a chemokine receptor mediated condition or disease. Modulation of a chemokine receptor function includes both inducement and inhibition of the function. The type of modulation accomplished will depend on the characteristics of the compound, i.e., antagonist or full, partial or inverse agonist.

Without intending to be bound by any particular theory, it is believed that the compounds provided herein interfere with the interaction between a chemokine receptor and one or more cognate ligands. In particular, it is believed that the compounds interfere with the interaction between CCR9 and a CCR9 ligand, such as TECK. Compounds contemplated by the invention include, but are not limited to, the exemplary compounds provided herein and salts thereof.

For example, compounds of this invention act as potent CCR9 antagonists, and this antagonistic activity has been further confirmed in animal testing for inflammation, one of the hallmark disease states for CCR9. Accordingly, the compounds provided herein are useful in pharmaceutical compositions, methods for the treatment of CCR9-mediated diseases, and as controls in assays for the identification of competitive CCR9 antagonists.

CCR9 Antagonists as Treatments of Cancer

In additional to inflammatory diseases, cancers that are caused by uncontrolled proliferation of T cells may be treated with a CCR9 antagonist. Certain types of cancer are caused by T cells expressing chemokine receptor CCR9. For example, thymoma and thymic carcinoma are diseases in which cancer cells are found in the tissues of the thymus, an organ where lymphocyte development occurs. T cells in the thymus, called thymocytes, are known to express functional CCR9; its ligand is highly expressed in the thymus. Another example is the acute lymphocytic leukemia (ALL), also called acute lymphoblastic leukemia and acute, is a common leukemia, which can occur in children as well as adults. Recent studies have shown that T cells in patients with ALL selectively express high level of CCR9 (Qiuping Z et al., Cancer Res. 2003, 1; 63(19):6469-77).

Chemokine receptors have been implicated in cancer. Although the exact mechanisms of chemokine receptors' involvements have yet to be full understood, such receptors are known to promote the growth of cancer cells (proliferation), facilitate the spread of cancer cells (metastasis) or help them resist program cell death (apoptosis). For example, CCR9 in a cancer T cell line MOLT-4 provides the cells with a survival signal, allowing them to resist apoptosis (Youn B S, et al., Apoptosis. 2002 June; 7(3):271-6). In the cases of thymoma, thymic carcinoma and acute lymphocytic leukemia, it is likely that CCR9 plays a key in the survival and proliferation these cells. Thus, blocking the signaling of CCR9 should help prevent their expansion and metastasis.

Compounds of the Invention

The compounds provided herein have the general formula (I):

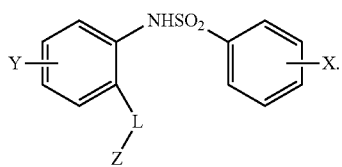

X Substituents

X represents from 1 to 5 substituents independently selected from the group consisting of halogen, substituted or unsubstituted $C_{1-8}$ alkyl, substituted or unsubstituted $C_{2-8}$ alkenyl, substituted or unsubstituted $C_{2-8}$ alkynyl, —CN, —$NO_2$, —$C(O)R^1$, —$CO_2R^1$, —$C(O)NR^1R^2$, —$OR^1$, —$OC(O)R^1$, —$OC(O)NR^1R^2$, —$NO_2$, —$NR^3C(O)R^1$, —$NR^3C(O)NR^1R^2$, —$NR^1R^2$, —$NR^3CO_2R^1$, —$NR^3S(O)_2R^1$, —$SR^1$, —$S(O)R^1$, —$S(O)_2R^1$, —$S(O)_2NR^1R^2$, substituted or unsubstituted $C_{6-10}$ aryl, substituted or unsubstituted 5- to 10-membered heteroaryl, and substituted or unsubstituted 3- to 10-membered heterocyclyl;

suitable substituted $C_{1-8}$ alkyl, substituted $C_{2-8}$ alkenyl, or substituted $C_{2-8}$ alkynyl may have from 1-5 substituents independently selected from the group consisting of halogen, —OH, —CN, —$NO_2$, =O, —$OC(O)R^1$, —$OR^1$, —$C(O)R^1$, —$C(O)NR^1R^2$, —$OC(O)NR^1R^2$, —$NR^2C(O)R^1$, —$NR^1C(O)NR^2R^3$, —$CO_2R^1$, —$NR^1R^2$, —$NR^2CO_2R^1$, —$SR^1$, —$S(O)R^1$, —$S(O)_2R^1$, —$S(O)_2NR^1R^2$, —$NR^1S(O)_2R^2$, unsubstituted or substituted aryl, unsubstituted or substituted heteroaryl, and unsubstituted or substituted heterocyclyl;

suitable substituted $C_{6-10}$ aryl, substituted 5- to 10-membered heteroaryl, or substituted 3- to 10-membered heterocyclyl, may have from 1-4 substituents independently selected from the group consisting of halogen, unsubstituted $C_{1-8}$ alkyl, unsubstituted $C_{1-8}$ haloalkyl, unsubstituted 4- to 7-membered heterocycle, —CN, —$NO_2$, —$OR^1$, =O, —$OC(O)R^1$, —$CO_2R^1$, —$C(O)R^1$, —$C(O)NR^1R^2$, —$OC(O)NR^1R^2$, —$NR^2C(O)R^1$, —$NR^1C(O)NR^2R^3$, —$NR^1R^2$, —$NR^2CO_2R^1$, —$SR^1$, —$S(O)R^1$, —$S(O)_2R^1$, —$S(O)_2NR^1R^2$, and —$NR^1S(O)_2R$, with the proviso that if X represents a heterocycle, suitable substituents preferably do not include another heterocycle;

$R^1$, $R^2$ and $R^3$ are each independently selected from the group consisting of hydrogen, $C_{1-8}$ alkyl, $C_{2-8}$ alkenyl, $C_{2-8}$ alkynyl, aryl-$C_{1-4}$ alkyl, aryloxy-$C_{1-4}$ alkyl, $C_{6-10}$ aryl, 5- to 10-membered heteroaryl, and 3- to 10-membered heterocycle, or where $R^1$ and $R^2$, or $R^3$ and $R^2$, or $R^1$ and $R^3$, may together with the atom(s) to which they are attached, form an substituted or unsubstituted 5-, 6-, or 7-membered ring;

and where the aliphatic and aromatic portions of $R^1$, $R^2$ and $R^3$ are optionally further substituted with from 1 to 3 substituents selected from the group consisting of halogen, —OH, —$OR'''$, —$OC(O)NHR'''$, —$OC(O)NR'''R''$, —SH, —$SR'''$, —$S(O)R'''$, —$S(O)_2R'''$, —$S(O)_2NH_2$, —$S(O)_2NHR'''$, —$S(O)_2NR'''R''$, —$NHS(O)_2R'''$, —$NR'''S(O)_2R''$, —$C(O)NH_2$, —$C(O)NHR'''$, —$C(O)N(R''')_2$, —$C(O)R'''$, —$NHC(O)R'''$, —$NR'''C(O)R''$, —$NHC(O)NH_2$, —$NR'''C(O)NH_2$, —$NR'''C(O)NHR''$, —$NHC(O)NHR'''$, —$NR^oC(O)NR'''R''$, —$NHC(O)N(R''')_2$, —$CO_2H$, —$CO_2R'''$, —$NHCO_2R'''$, —$NR'''CO_2R''$, —CN, —$NO_2$, —$NH_2$, —$NHR''$, —$NR'''R''$, —$NR'''S(O)NH_2$ and —$NR'''S(O)_2NHR''$, where $R'''$, $R''$, and $R^o$ are each independently unsubstituted $C_{1-6}$ alkyl.

Y Substituents

Y represents from 1 to 4 substituents, each independently selected from the group consisting of halogen, —CN, —$NO_2$, —$C(O)R^4$, —$CO_2R^4$, —$SR^4$, —$S(O)R^4$, —$S(O)_2R^4$, and unsubstituted or substituted $C_{1-4}$ alkyl;

suitable substituted $C_{1-4}$ alkyl may have from 1 to 3 substituents independently selected from the group consisting of halogen, —$OR^7$, —CN, —$NO_2$, =O, —$OC(O)R^4$, —$CO_2R^4$, —$C(O)R^4$, —$CONR^4R^5$, —OC(O)NR$^4$R$^5$, —NR$^4$C(O)R$^5$, —NR$^4$C(O)NR$^5$R$^6$, —NR$^4$R$^5$, —NR$^4$CO$_2$R$^5$, —SR$^4$, —SO$_2$R$^4$, —SO$_2$R$^4$, —SO$_2$NR$^4$R$^5$, and —NR$^4$SO$_2$R$^5$;

R$^4$, R$^5$ and R$^6$ are each independently selected from the group consisting of hydrogen, C$_{1-8}$ alkyl, C$_{2-8}$ alkenyl, C$_{2-8}$ alkynyl, C$_{6-10}$ aryl, and 5- to 10-membered heteroaryl; or where R$^4$ and R$^5$, or R$^6$ and R$^4$ or R$^5$ and R$^6$, together with the atom to which they are attached, form a substituted or unsubstituted 5-, 6- or 7-membered ring;

and where the aliphatic and aromatic portions of R$^4$, R$^5$, and R$^6$ are optionally further substituted with from 1 to 3 substituents selected from the group consisting of halogen, —OH, —OR$^m$, —OC(O)NHR$^m$, —OC(O)NR$^m$R$^n$, —SH, —SR$^m$, —S(O)R$^m$, —S(O)$_2$R$^m$, —S(O)$_2$NH$_2$, —S(O)$_2$NHR$^m$, —S(O)$_2$NR$^m$R$^n$, —NHS(O)$_2$R$^m$, —NR$^m$S(O)$_2$R$^n$, —C(O)NH$_2$, —C(O)NHR$^m$, —C(O)N(R$^m$)$_2$, —C(O)R$^m$, —NHC(O)R$^m$, —NR$^m$C(O)R$^n$, —NHC(O)NH$_2$, —NR$^m$C(O)NH$_2$, —NR$^m$C(O)NHR$^n$, —NHC(O)NHR$^m$, —NR$^o$C(O)NR$^m$R$^n$, —NHC(O)N(R$^m$)$_2$, —CO$_2$H, —CO$_2$R$^m$, —NHCO$_2$R$^m$, —NR$^m$CO$_2$R$^n$, —CN, —NO$_2$, —NH$_2$, —NHR$^n$, —NR$^m$R$^n$, —NR$^m$S(O)NH$_2$ and —NR$^m$S(O)$_2$NHR$^n$, where R$^m$, R$^n$, and R$^o$ are each independently unsubstituted C$_{1-6}$ alkyl.

Linkers

L is —C(O)—, —S—, —SO— or —S(O)$_2$—.

Z Substituents

Z represents either unsubstituted or substituted monocyclic or bicyclic 5- to 10-membered heteroaryl; unsubstituted or substituted monocyclic or bicyclic 3- to 10-membered heterocyclyl; or NR$^7$R$^8$.

When Z is NR$^7$R$^8$, R$^7$ and R$^8$ are each independently selected from the group consisting of hydrogen, C$_{1-8}$ alkyl, C$_{2-8}$ alkenyl, C$_{2-8}$ alkynyl, C$_{6-10}$ aryl, C$_{1-8}$ alkylaryl, C$_{1-8}$ alkylheteroaryl, 5- to 10-membered heteroaryl and 3- to 10-membered heterocycle, or R$^7$ and R$^8$, may together with the atom(s) to which they are attached, form an substituted or unsubstituted 5-, 6-, or 7-membered ring; and where the aliphatic and aromatic portions of R$^7$ and R$^8$ can be substituted with 1 to 3 substituents selected from the group consisting of halogen, —OH, —OR$^m$, —OC(O)NHR$^m$, —OC(O)NR$^m$R$^n$, —SH, —SR$^m$, —S(O)R$^m$, —S(O)$_2$R$^m$, —S(O)$_2$NH$_2$, —S(O)$_2$NHR$^m$, —S(O)$_2$NR$^m$R$^n$, —NHS(O)$_2$R$^m$, —NR$^m$S(O)$_2$R$^n$, —C(O)NH$_2$, —C(O)NHR$^m$, —C(O)N(R$^m$)$_2$, —C(O)R$^m$, —NHC(O)R$^m$, —NR$^m$C(O)R$^n$, —NHC(O)NH$_2$, —NR$^m$C(O)NH$_2$, —NR$^m$C(O)NHR$^n$, —NHC(O)NHR$^m$, —NR$^o$C(O)NR$^m$R$^n$, —NHC(O)N(R$^m$)$_2$, —CO$_2$H, —CO$_2$R$^m$, —NHCO$_2$R$^m$, —NR$^m$CO$_2$R$^n$, —CN, —NO$_2$, —NH$_2$, —NHR$^n$, —NR$^m$R$^n$, —NR$^m$S(O)NH$_2$ and —NR$^m$S(O)$_2$NHR$^n$, where R$^m$, R$^n$, and R$^o$ are each independently unsubstituted C$_{1-6}$ alkyl.

When Z is a substituted heteroaryl or substituted heterocyclyl, it may have from 1 to 5 substituents independently selected from the group consisting of halogen, unsubstituted or substituted C$_{1-8}$ alkyl, unsubstituted or substituted C$_{2-8}$ alkenyl, unsubstituted or substituted C$_{2-8}$ alkynyl, =O, —CN, —NO$_2$, —OR$^7$, —OC(O)R$^7$, —CO$_2$R$^7$, —C(O)R$^7$, —CONR$^7$R$^8$, —OC(O)NR$^7$R$^8$, —NR$^7$C(O)R$^8$, —NR$^7$C(O)NR$^8$R$^9$, —NR$^7$R$^8$, —NR$^7$CO$_2$R$^8$, —SR$^7$, —S(O)R$^7$, —S(O)$_2$R$^7$, —SO$_2$NR$^7$R$^8$, —NR$^7$SO$_2$R$^8$, unsubstituted or substituted C$_{6-10}$ aryl, unsubstituted or substituted 5- to 10-membered heteroaryl and unsubstituted or substituted 3- to 10-membered heterocyclyl;

suitable substituted C$_{1-8}$ alkyl, C$_{2-8}$ alkenyl and C$_{2-8}$ alkynyl substituents on Z may have from 1 to 5 substituents independently selected from the group consisting of halogen, —OR$^7$, —CN, —NO$_2$, =O, —CN, —NO$_2$, —OC(O)R$^7$, —CO$_2$R$^7$, —C(O)R$^7$, —CONR$^7$R$^8$, —OC(O)NR$^7$R$^8$, —NR$^7$C(O)R$^8$, —NR$^7$C(O)NR$^8$R$^9$, —NR$^7$R$^8$, —NR$^7$CO$_2$R$^8$, —SR$^7$, —S(O)R$^7$, —S(O)$_2$R$^7$, —SO$_2$NR$^7$R$^8$, —NR$^7$SO$_2$R$^8$, unsubstituted or substituted phenyl, unsubstituted or substituted 5- or 6-membered heteroaryl, or unsubstituted or substituted 4- to 7-membered heterocyclyl;

suitable substituted aryl, heteroaryl and heterocyclyl substituents on Z may have from 1 to 5 substituents independently selected from the group consisting of halogen, —OR$^7$, —CN, —NO$_2$, =O, —OC(O)R$^7$, —OC(O)R$^7$, —CO$_2$R$^7$, —C(O)R$^7$, —CONR$^7$R$^8$, —OC(O)NR$^7$R$^8$, —NR$^7$C(O)R$^8$, —NR$^7$C(O)NR$^8$R$^9$, —NR$^7$R$^8$, —NR$^7$CO$_2$R$^8$, —SR$^7$, —SOR$^7$, —SO$_2$R$^7$, —SO$_2$NR$^7$R$^8$, —NR$^7$SO$_2$R$^8$, unsubstituted 4- to 7-membered heterocyclyl, unsubstituted C$_{1-8}$ alkyl and unsubstituted C$_{1-8}$ haloalkyl;

R$^7$, R$^8$ and R$^9$ are each independently selected from the group consisting of hydrogen, C$_{1-8}$ alkyl, C$_{2-8}$ alkenyl, C$_{2-8}$ alkynyl, C$_{6-10}$ aryl, 5 to 10 membered heteroaryl and 3- to 10-membered heterocycle, or R$^7$ and R$^8$, or R$^8$ and R$^9$, or R$^7$ and R$^9$, may together with the atom(s) to which they are attached, form a substituted or unsubstituted 5-, 6-, or 7-membered ring, and;

where the aliphatic and aromatic portions of R$^7$, R$^8$ and R$^9$ are optionally further substituted with 1 to 3 substituents selected from the group consisting of halogen, —OH, —OR$^m$, —OC(O)NHR$^m$, —OC(O)NR$^m$R$^n$, —SH, —SR$^m$, —S(O)R$^m$, —S(O)$_2$R$^m$, —S(O)$_2$NH$_2$, —S(O)$_2$NHR$^m$, —S(O)$_2$NR$^m$R$^n$, —NHS(O)$_2$R$^m$, —NR$^m$S(O)$_2$R$^n$, —C(O)NH$_2$, —C(O)NHR$^m$, —C(O)N(R$^m$)$_2$, —C(O)R$^m$, —NHC(O)R$^m$, —NR$^m$C(O)R$^n$, —NHC(O)NH$_2$, —NR$^m$C(O)NH$_2$, —NR$^m$C(O)NHR$^n$, —NHC(O)NHR$^m$, —NR$^o$C(O)NR$^m$R$^n$, —NHC(O)N(R$^m$)$_2$, —CO$_2$H, —CO$_2$R$^m$, —NHCO$_2$R$^m$, —NR$^m$CO$_2$R$^n$, —CN, —NO$_2$, —NH$_2$, —NHR$^n$, —NR$^m$R$^n$, —NR$^m$S(O)NH$_2$ and —NR$^m$S(O)$_2$NHR$^n$, where R$^m$, R$^n$, and R$^o$ are each independently unsubstituted C$_{1-6}$ alkyl;

with the proviso that excluded from the scope of formulae (I,II) are the following compounds:

N-[4-Chloro-2-(pyridine-2-carbonyl)-phenyl]-4-methyl-benzenesulfonamide

N-[4-Chloro-2-(2-trifluoromethyl-pyridine-4-carbonyl)-phenyl]-4-isopropoxy-benzenesulfonamide 4-Chloro-N-[4-chloro-2-(pyridine-2-carbonyl)-phenyl]-benzenesulfonamide N-[4-Chloro-2-(pyridine-4-carbonyl)-phenyl]-4-iso-propoxy-benzenesulfonamide N-[4-Chloro-2-(pyridine-3-carbonyl)-phenyl]-4-methoxy-benzenesulfonamide 4-Isopropoxy-N-[2-(pyridine-4-carbonyl)-4-trifluoromethyl-phenyl]-benzenesulfonamide 4-Chloro-N-[4-chloro-2-(pyridine-3-carbonyl)-phenyl]-benzenesulfonamide 4-Ethoxy-N-[2-(pyridine-4-carbonyl)-4-trifluoromethyl-phenyl]-benzenesulfonamide N-[4-Chloro-2-(1-oxy-pyridine-4-carbonyl)-phenyl]-4-iso-propoxy-benzenesulfonamide N-[4-Chloro-2-(2-trifluoromethyl-pyrimidine-5-carbonyl)-phenyl]-4-isopropoxy-benzenesulfonamide N-[4-Chloro-2-(pyridazine-4-carbonyl)-phenyl]-4-iso-propoxy-benzenesulfonamide N-[4-Chloro-2-(pyridine-2-carbonyl)-phenyl]-4-methoxy-benzenesulfonamide N-[4-Chloro-2-(6-trifluoromethyl-pyridazine-4-carbonyl)-phenyl]-4-isopropoxy-benzenesulfonamide N-[4-Chloro-2-(pyridine-3-carbonyl)-phenyl]-4-methyl-benzenesulfonamide N-[4-Chloro-2-(pyrimidine-5-carbonyl)-phenyl]-4-isopropoxy-benzenesulfonamide N-[4-Chloro-2-(pyridine-4-carbonyl)-phenyl]-4-ethoxy-benzenesulfonamide N-[4-Chloro-2-(pyridine-4-carbonyl)-phenyl]-4-ethyl-benzenesulfonamide N-[4-Chloro-2-(pyridine-4-carbonyl)-phenyl]-4-isopropyl-benzenesulfonamide N-[4-Chloro-2-(pyridine-4-carbonyl)-phenyl]-4-isobutyl-benzenesulfonamide Known Compounds Compounds of the formula (I) where X is methyl when Z is 2-thiophene, 2-(3-hydroxy-1H-indole) or 3-(1-methyl-pyridinium) are known, but not as CCR9 antagonists.

In another embodiment, the present invention provides compounds of the formula (II) and pharmaceutically acceptable salts and N-oxides thereof:

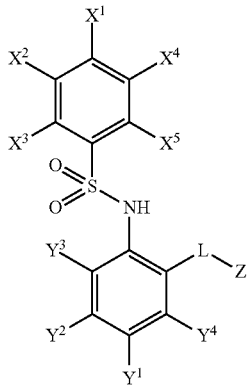

(II)

where L and Z are defined as in formula (I);

$X^1$, $X^2$, $X^3$, $X^4$, $X^5$ are each independently selected from the group consisting of hydrogen, halogen, —CN, —NO$_2$, —OR$^1$, —C(O)R$^1$, —CO$_2$R$^1$, —OC(O)NR$^1$R$^2$, —SR$^1$, —SOR$^1$, —SO$_2$R$^1$, —NR$^1$R$^2$, —NR$^1$C(O)R$^2$, —NR$^1$C(O)$_2$R$^2$, —NR$^1$(CO)NR$^1$R$^2$, unsubstituted or substituted C$_{1-8}$ alkyl, unsubstituted or substituted C$_{2-8}$ alkenyl, unsubstituted or substituted C$_{2-8}$ alkynyl, unsubstituted or substituted C$_{6-10}$ aryl, unsubstituted or substituted 5- or 6-membered heteroaryl, and unsubstituted or substituted 4- to 7-membered heterocyclyl, with the proviso that one of $X^1$, $X^2$, $X^3$, $X^4$, $X^5$ is other than hydrogen.

When $X^1$, $X^2$, $X^3$, $X^4$, or $X^5$ is substituted C$_{1-8}$ alkyl, substituted C$_{2-8}$ alkenyl and substituted C$_{2-8}$ alkynyl, it may have from 1 to 3 substituents independently selected from the group consisting of halogen, —CN, =O, —OC(O)R$^1$, —OR$^1$, —C(O)R$^1$, —CONR$^1$R$^2$, —NR$^2$C(O)R$^1$, —CO$_2$R$^1$, —NR$^1$R$^2$, —SR$^1$, —S(O)R$^1$, —S(O)$_2$R$^1$, —NR$^1$SO$_2$R$^2$, unsubstituted or substituted aryl, unsubstituted or substituted heterocyclyl, and unsubstituted or substituted heteroaryl. Preferred substituted C$_{1-8}$ alkyl have from 1 to 3 substituents independently selected from the group consisting of halogen, —CN, =O, —OR$^1$, —C(O)R$^1$, —CONR$^1$R$^2$, —NR$^2$C(O)R$^1$, —CO$_2$R$^1$, —NR$^1$R$^2$, —SO$_2$R$^1$, unsubstituted or substituted 5- or 6-membered heteroaryl and 5- or 6-membered unsubstituted or substituted heterocyclyl.

When $X^1$, $X^2$, $X^3$, $X^4$, or $X^5$ is substituted C$_{6-10}$ aryl, substituted 5- or 6-membered heteroaryl and substituted 4- to 7-membered heterocycle, it may have from 1 to 3 substituents independently selected from the group consisting of halogen, —CN, —OR$^1$, =O, —OC(O)R$^1$, —CO$_2$R$^1$, —C(O)R$^1$, —CONR$^1$R$^2$, —NR$^2$C(O)R$^1$, —NR$^1$R$^2$, —SR$^1$, —S(O)R$^1$, —S(O)$_2$R$^1$, —NR$^1$SO$_2$R$^2$, unsubstituted C$_{1-8}$ alkyl, and unsubstituted C$_{1-8}$ haloalkyl.

When $X^1$, $X^2$, $X^3$, $X^4$, or $X^5$ is substituted 5- or 6-membered heteroaryl or substituted 5- or 6-membered heteroaryl, it preferably has from 1 to 3 substituents independently selected from the group consisting of halogen, —OR$^1$, —C(O)R$^1$, —CONR$^1$R$^2$, —NR$^2$C(O)R$^1$, —NR$^1$R$^2$, —SO$_2$R$^1$, unsubstituted or substituted C$_{1-8}$ alkyl, and unsubstituted or substituted C$_{1-8}$ haloalkyl.

$Y^1$, $Y^2$, $Y^3$ and $Y^4$ are each independently selected from the group consisting of hydrogen, halogen, —CN, —NO$_2$, —OR$^7$, —C(O)R$^4$, —SR$^4$, —CF$_3$, —SOR$^4$, and —SO$_2$R$^4$.

A compound of the present invention can have one the following formulae:

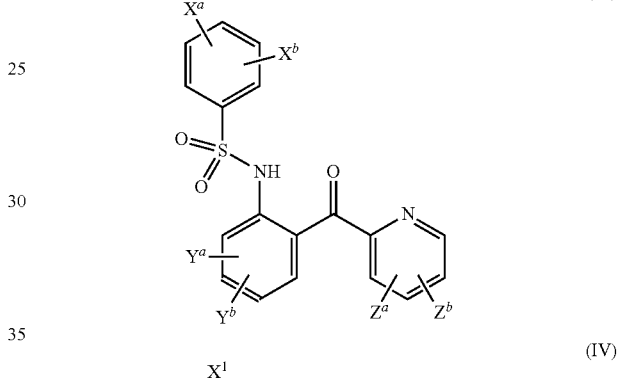

(III)

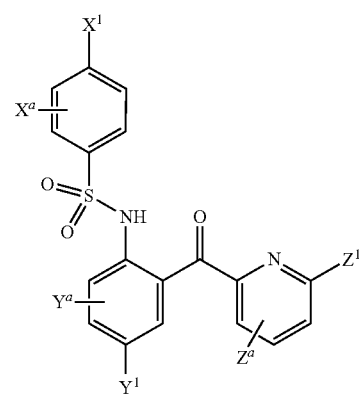

(IV)

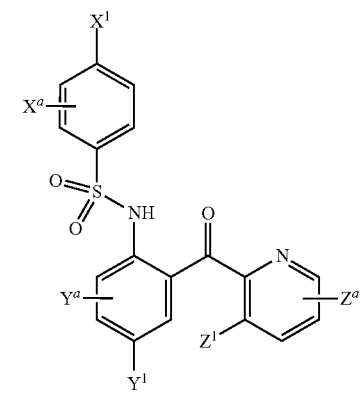

(V)

(VI) 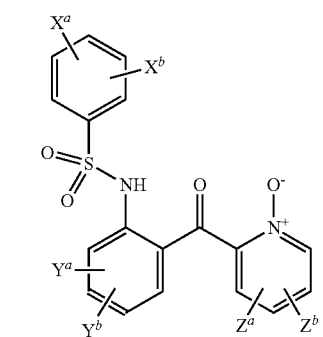
(VII) 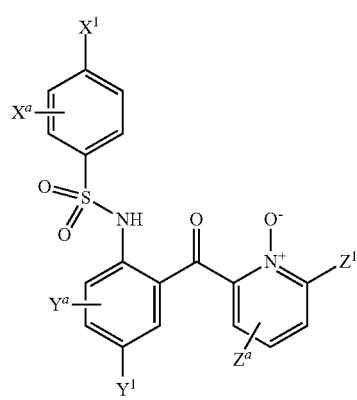
(VIII) 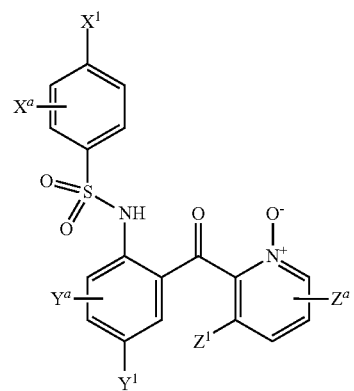
(IX) 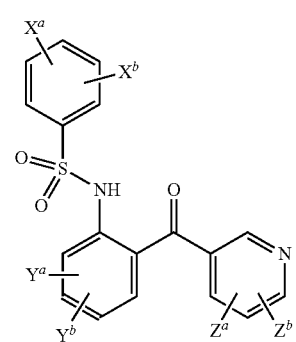
(X) 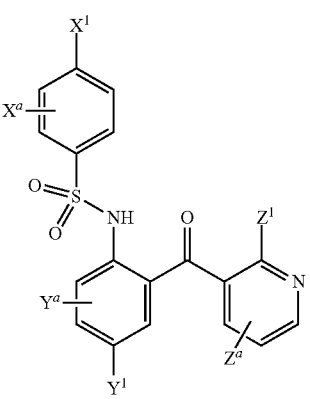
(XI) 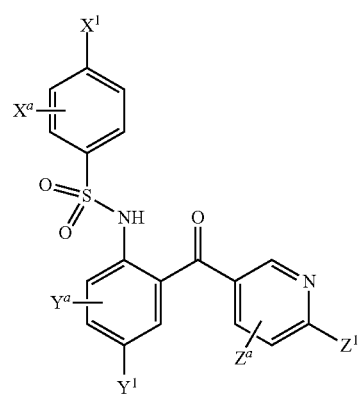
(XII) 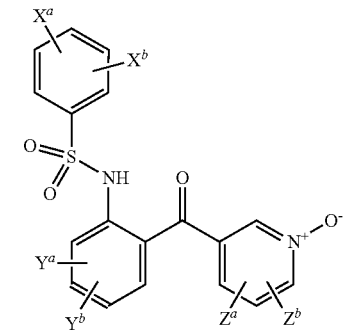
(XIII) 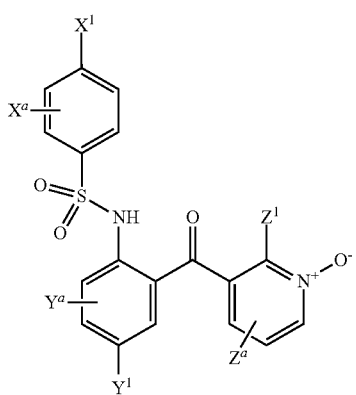

-continued
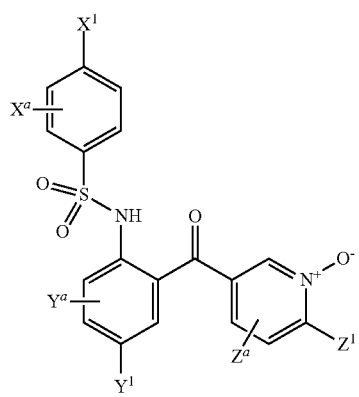
(XIV)
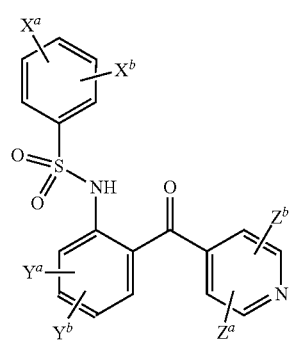
(XV)
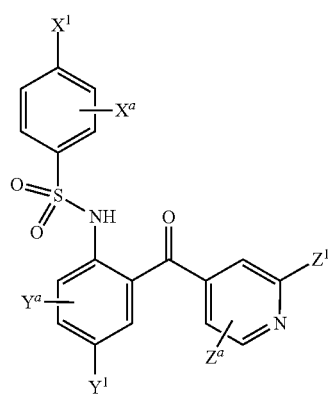
(XVI)
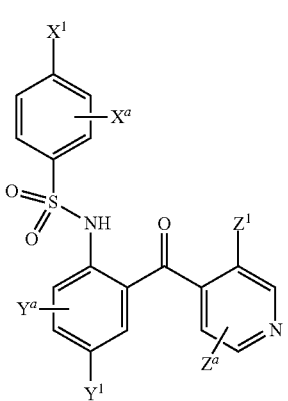
(XVII)
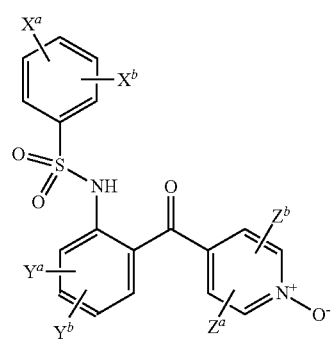
(XVIII)
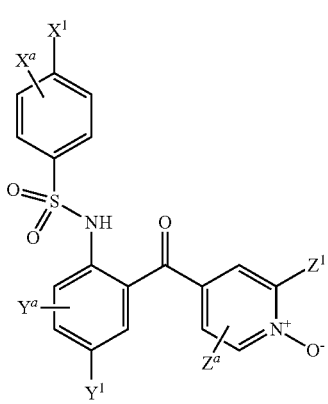
(XIX)
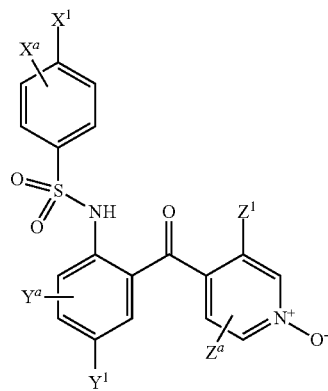
(XX)
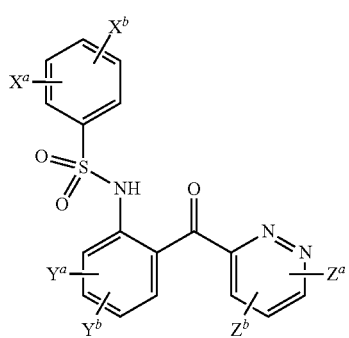
(XXI)

(XXII)
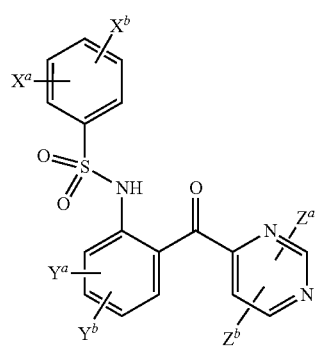
(XXIII)
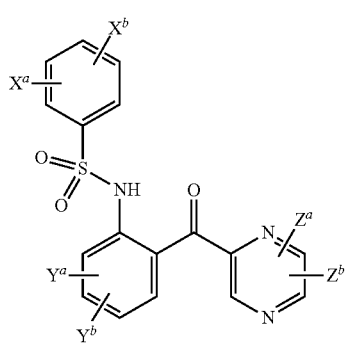
(XXIV)
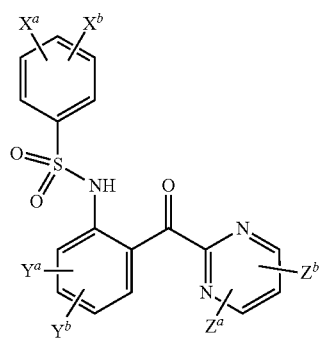
(XXV)
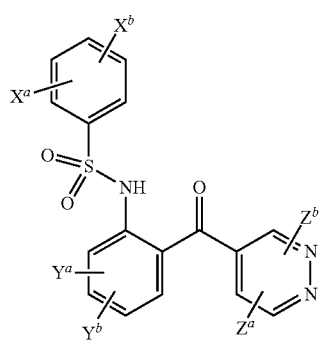
(XXVI)
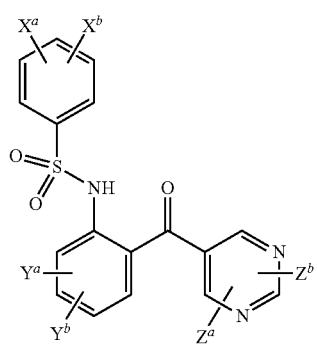
(XXVII)
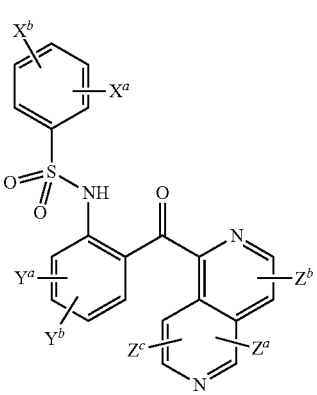
(XXVIII)
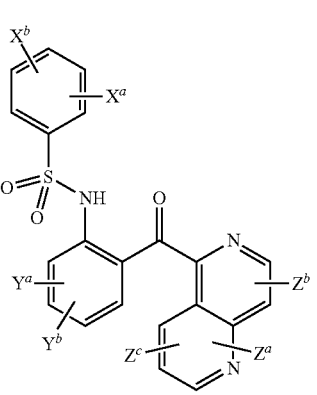
(XXIV)
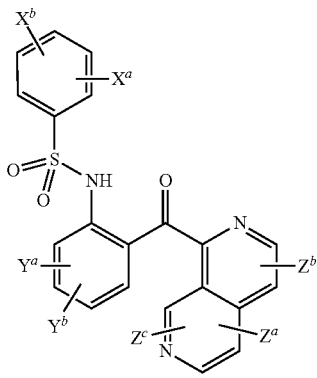

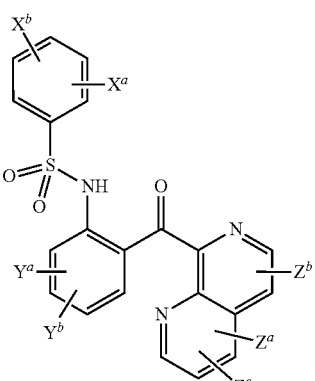
(XXX)
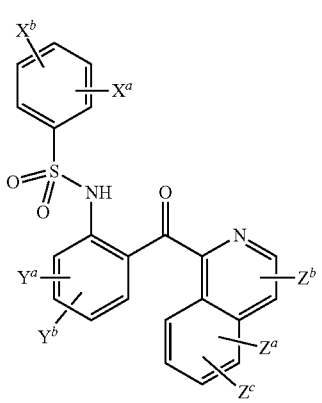
(XXXI)
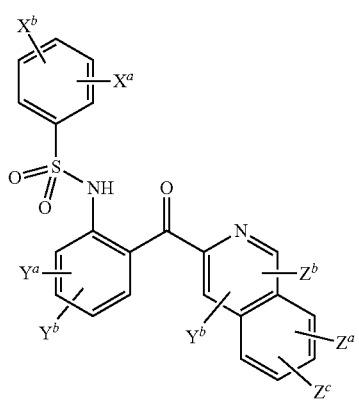
(XXXII)
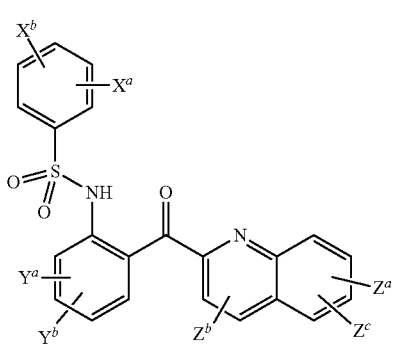
(XXXIII)
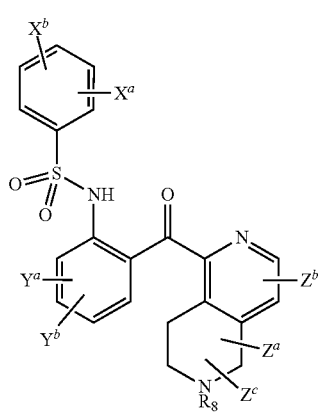
(XXXIV)
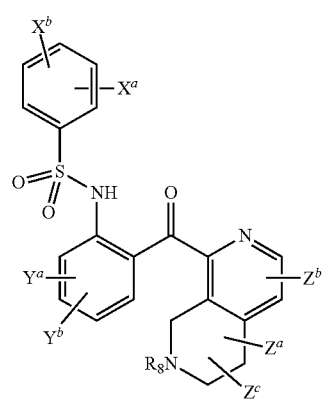
(XXXV)
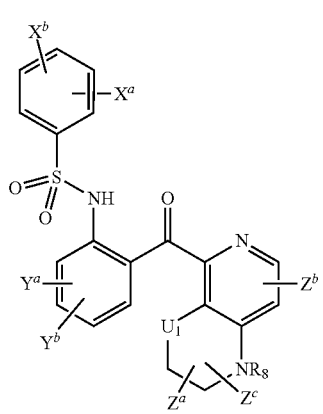
(XXXVI)
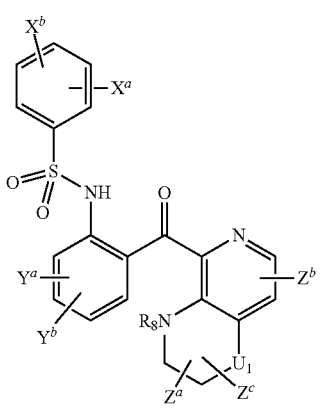
(XXXVII)

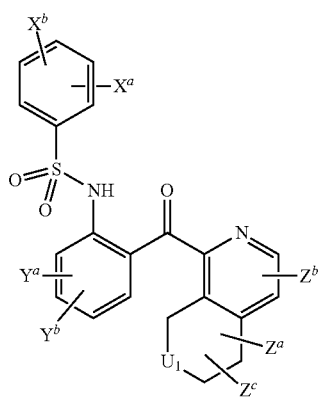
(XXXVIII)
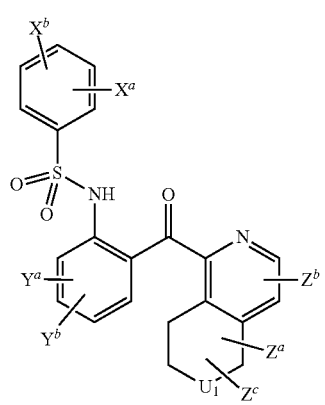
(XXXIX)
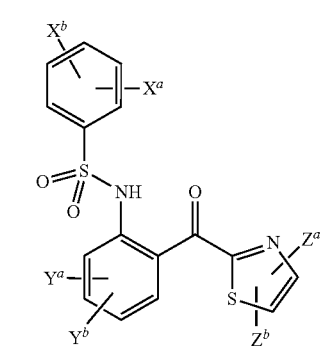
(XL)
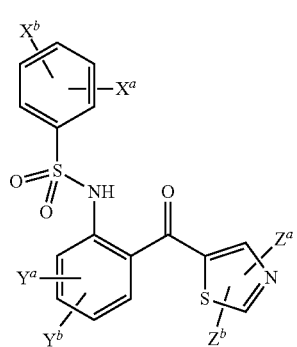
(XLI)
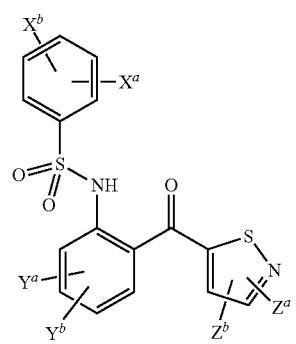
(XLII)
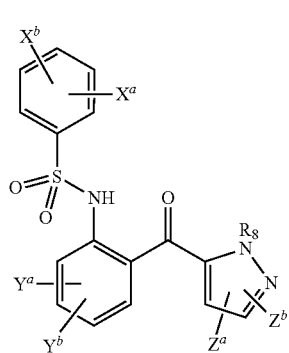
(XLIII)
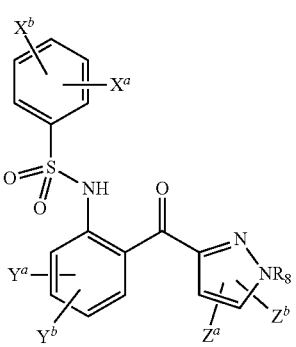
(XLIV)
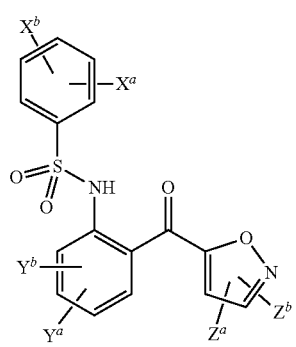
(XLV)

(XLVI)
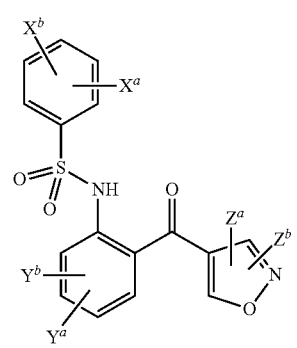
(XLVII)
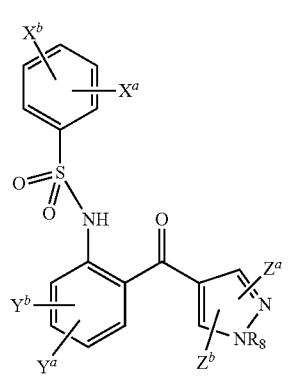
(XLVIII)
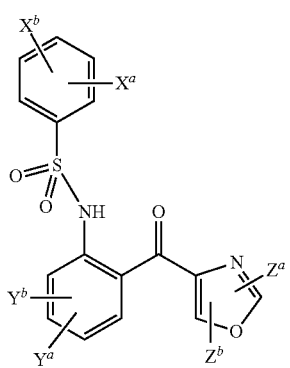
(XLIX)
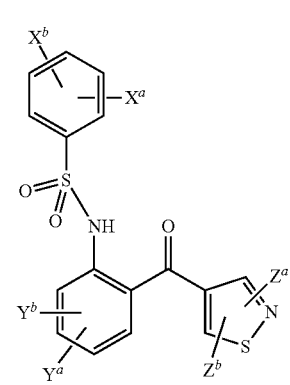
(L)
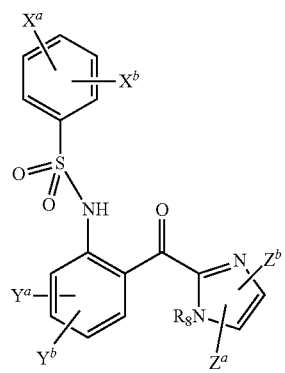
(LI)
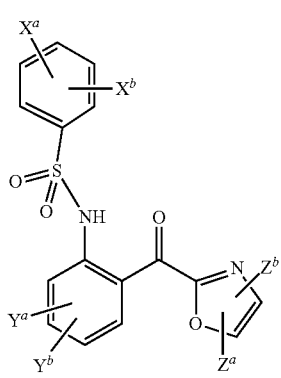
(LII)
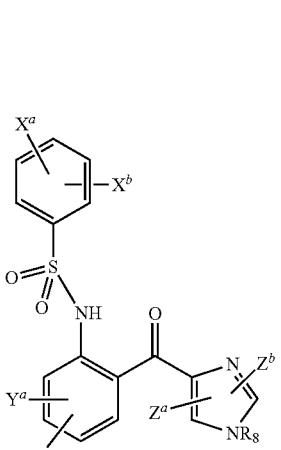
(LIII)
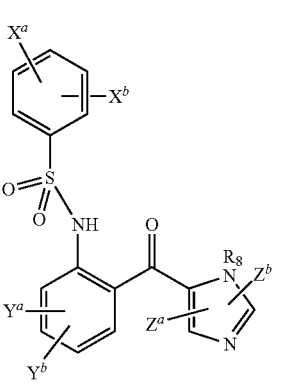

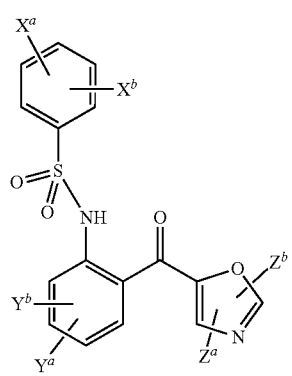
(LIV)
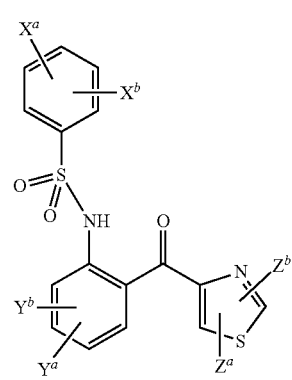
(LV)
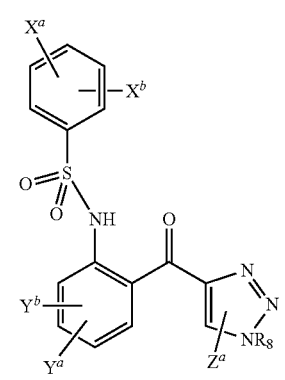
(LVI)
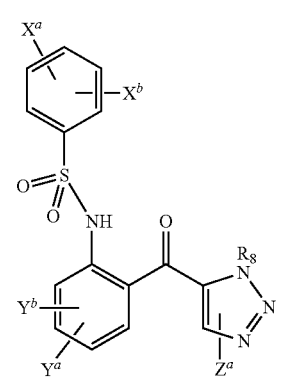
(LVII)
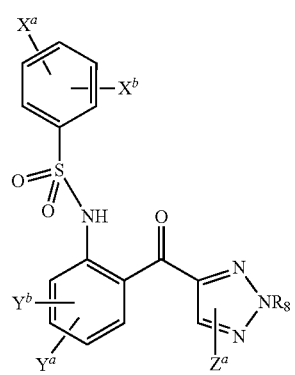
(LVIII)
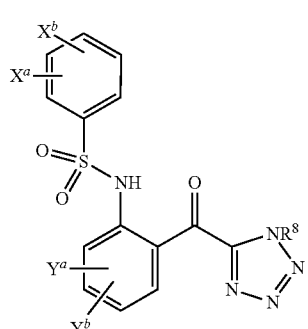
(LIX)
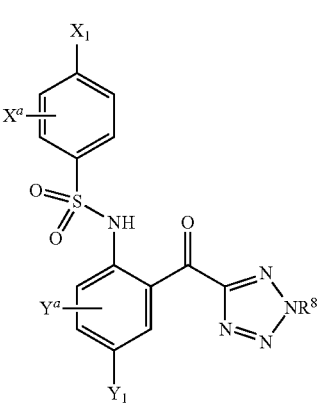
(LX)
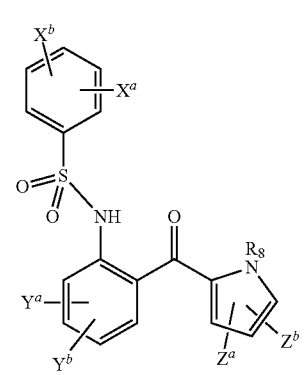
(LXI)

(LXII)
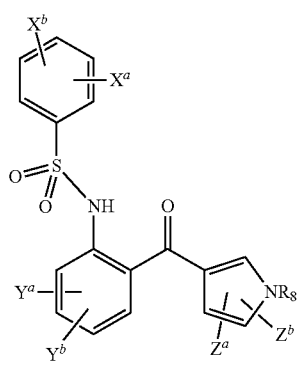
(LXIII)
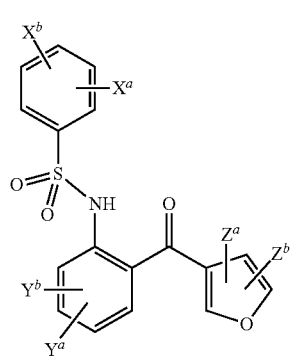
(LXIV)
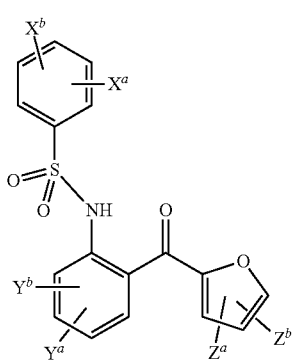
(LXV)
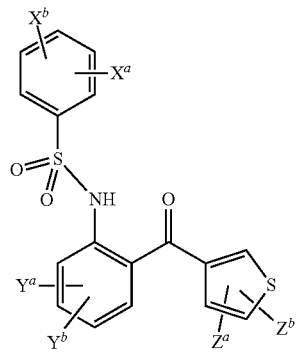
(LXVI)
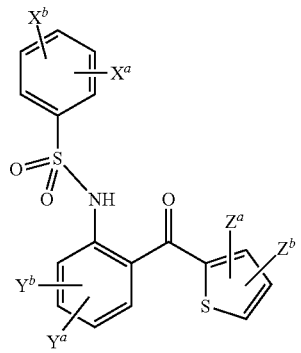
(LXVII)
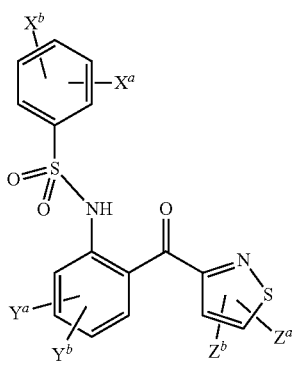
(LXVIII)
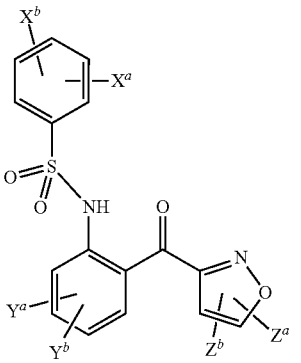
(LXIX)
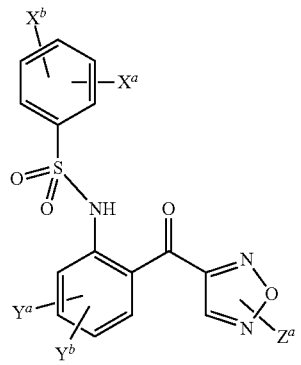

(LXX)
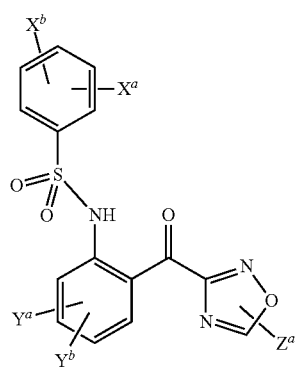
(LXXI)
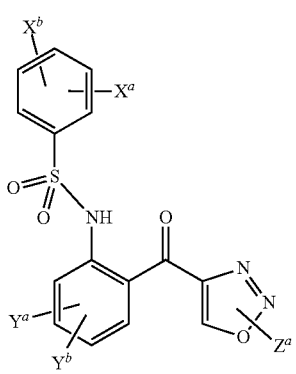
(LXXII)
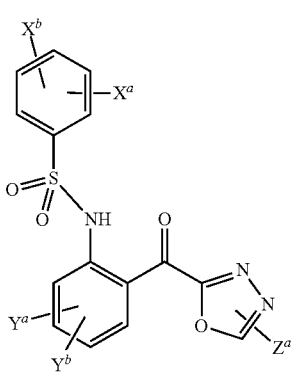
(LXXIII)
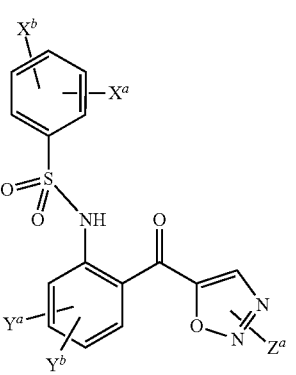
(LXXIV)
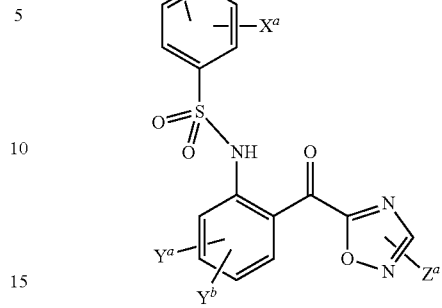
Compounds of the present invention are also represented by the following formula:
(LXXV)
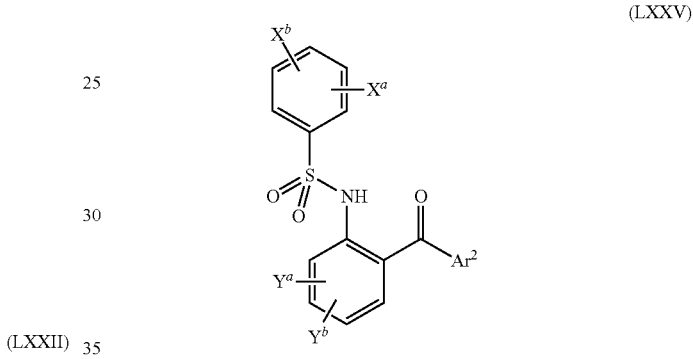
where $Ar^2$ is selected from the following residues
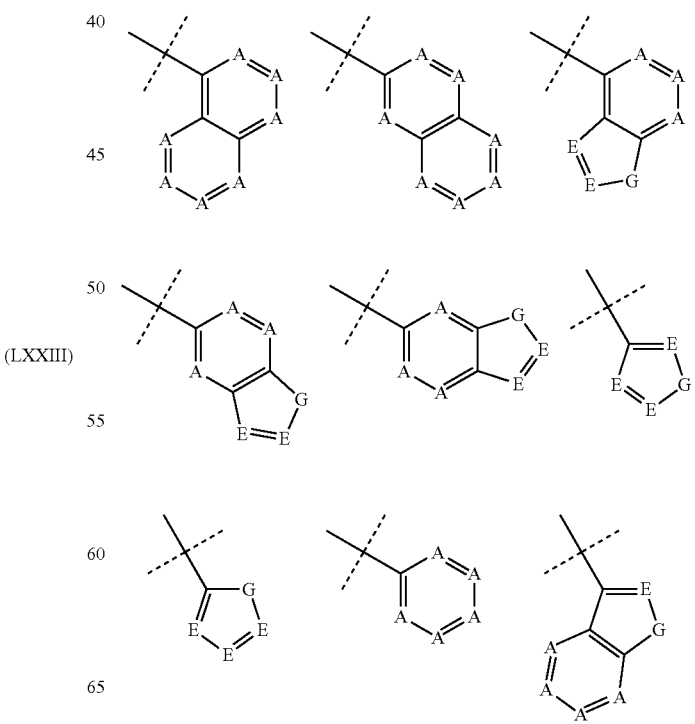

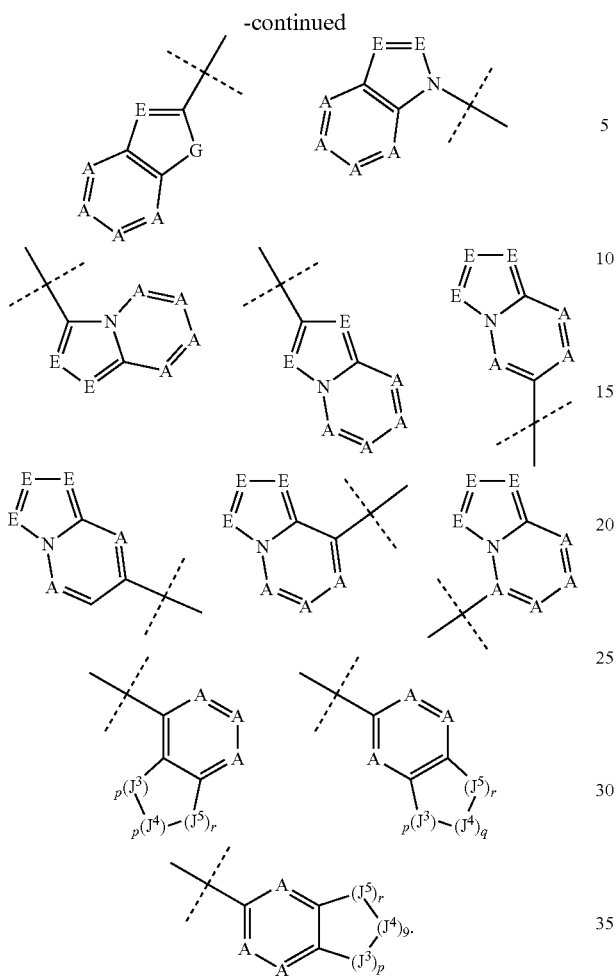

In each of the formula (III-LXXV);

$X^1$, $X^a$ and $X^b$ are each independently as defined for $X^1$ in formula (II);

$Y^1$ and $Y^a$ and $Y^b$ are each independently as defined for $Y^1$ in formula (II); and $Z^1$, $Z^1$, $Z^a$, $Z^b$ and $Z^c$ are independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, —CN, =O, —$NO_2$, —$OR^{10}$, —$OC(O)R^{10}$, —$CO_2R^{10}$, —$C(O)R^{10}$, —$C(O)NR^{11}R^{12}$, —$OC(O)NR^{11}R^{12}$, —$NR^{10}C(O)R^{11}$, —$NR^{10}C(O)NR^{11}R^{12}$, —$NR^{11}R^{12}$, —$NR^{10}CO_2R^{11}$, —$SR^{10}$, —$S(O)R^{10}$, —$S(O)_2R^{10}$, —$S(O)_2NR^{11}R^{12}$, —$NR^{10}S(O)_2R^{11}$, substituted or unsubstituted $C_{6-10}$ aryl, substituted or unsubstituted 5- to 10-membered heteroaryl and substituted or unsubstituted 3- to 10-membered heterocyclyl;

suitable substituted $C_{1-8}$ alkyl, $C_{2-8}$ alkenyl, $C_{2-8}$ alkynyl may have from 1 to 3 substituents independently selected from the group consisting of halogen, —$OR^{10}$, —CN, —$NO_2$, =O, —$OC(O)R^{10}$, —$CO_2R^{10}$, —$C(O)R^{10}$, —$C(O)NR^{10}R^{11}$, —$OC(O)NR^{10}R^{11}$, —$NR^{10}C(O)R^{11}$, —$NR^{10}C(O)NR^{11}R^{12}$, —$NR^{10}R^{11}$, —$NR^{10}CO_2R^{11}$, —$SR^{10}$, —$S(O)R^{10}$, —$S(O)_2R^{10}$, —$S(O)_2NR^{10}R^{11}$, —$NR^{10}S(O)_2R^{11}$, unsubstituted or substituted phenyl, unsubstituted or substituted 5- or 6-membered heteroaryl, or unsubstituted or substituted 3- to 6-membered heterocyclyl;

suitable substituted aryl, heteroaryl and heterocyclyl substituents may have from 1 to 3 substituents independently selected from the group consisting of halogen, —$OR^{10}$, —CN, —$NO_2$, =O, —$OC(O)R^{10}$, —$OC(O)R^{10}$, —$CO_2R^{10}$, —$C(O)R^{10}$, —$C(O)NR^{10}R^{11}$, —$OC(O)NR^{10}R^{11}$, —$NR^{10}C(O)R^{11}$, —$NR^{10}C(O)NR^{11}R^{12}$, —$NR^{10}R^{11}$, —$NR^{10}CO_2R^{11}$, —$SR^{10}$, —$S(O)R^{10}$, —$S(O)_2R^{10}$, —$S(O)_2NR^{10}R^{11}$, —$NR^{10}S(O)_2R^{11}$, unsubstituted 4- to 7-membered ring heterocyclyl, unsubstituted $C_{1-8}$ alkyl and unsubstituted $C_{1-8}$ haloalkyl;

$R^{10}$, $R^{11}$ and $R^{12}$ are each selected from hydrogen, $C_{1-8}$ alkyl, $C_{2-8}$ alkenyl, $C_{2-8}$ alkynyl, aryl, heteroaryl, or where $R^{10}$ and $R^{11}$, or $R^{11}$ and $R^{12}$, or $R^{10}$ and $R^{12}$, together with the atom(s) to which they are attached, form an substituted or unsubstituted 5-, 6-, or 7-membered ring; and where the aliphatic and aromatic portions of $R^{10}$, $R^{11}$ and $R^{12}$ are optionally further substituted with from 1 to 3 substituents selected from the group consisting of halogen, —OH, —$OR'''$, —$OC(O)NHR'''$, —$OC(O)NR'''R''$, —SH, —$SR'''$, —$S(O)R'''$, —$S(O)_2R'''$, —$S(O)_2NH_2$, —$S(O)_2NHR'''$, —$S(O)_2NR'''R''$, —$NHS(O)_2R'''$, —$NR'''S(O)_2R''$, —$C(O)NH_2$, —$C(O)NHR'''$, —$C(O)N(R''')_2$, —$C(O)R'''$, —NHC(O)R'''$, —$NR'''C(O)R''$, —$NHC(O)NH_2$, —$NR'''C(O)NH_2$, —$NR'''C(O)NHR''$, —NHC(O)NHR'''$, —$NR°C(O)NR'''R''$, —$NHC(O)N(R''')_2$, —$CO_2H$, —$CO_2R'''$, —$NHCO_2R'''$, —$NR'''CO_2R''$, —CN, —$NO_2$, —$NH_2$, —$NHR''$, —$NR'''R''$, —$NR'''S(O)NH_2$, and —$NR'''S(O)_2NHR''$, where $R'''$, $R''$, and $R°$ are each independently unsubstituted $C_{1-6}$ alkyl; with the proviso that excluded from the scope of formulae (III-LXXV) are the compounds disclosed in [0056].

Compounds covered by this invention also include;

N-[4-Chloro-2-(pyridine-2-carbonyl)-phenyl]-4-methyl-benzenesulfonamide

N-[4-Chloro-2-(2-trifluoromethyl-pyridine-4-carbonyl)-phenyl]-4-isopropoxy-benzenesulfonamide 4-Chloro-N-[4-chloro-2-(pyridine-2-carbonyl)-phenyl]-benzenesulfonamide N-[4-Chloro-2-(pyridine-4-carbonyl)-phenyl]-4-isopropoxy-benzenesulfonamide N-[4-Chloro-2-(pyridine-3-carbonyl)-phenyl]-4-methoxy-benzenesulfonamide 4-Isopropoxy-N-[2-(pyridine-4-carbonyl)-4-trifluoromethyl-phenyl]-benzenesulfonamide 4-Chloro-N-[4-chloro-2-(pyridine-3-carbonyl)-phenyl]-benzenesulfonamide 4-Ethoxy-N-[2-(pyridine-4-carbonyl)-4-trifluoromethyl-phenyl]-benzenesulfonamide N-[4-Chloro-2-(1-oxy-pyridine-4-carbonyl)-phenyl]-4-isopropoxy-benzenesulfonamide N-[4-Chloro-2-(2-trifluoromethyl-pyrimidine-5-carbonyl)-phenyl]-4-isopropoxy-benzenesulfonamide N-[4-Chloro-2-(pyridazine-4-carbonyl)-phenyl]-4-isopropoxy-benzenesulfonamide N-[4-Chloro-2-(pyridine-2-carbonyl)-phenyl]-4-methoxy-benzenesulfonamide N-[4-Chloro-2-(6-trifluoromethyl-pyridazine-4-carbonyl)-phenyl]-4-isopropoxy-benzenesulfonamide N-[4-Chloro-2-(pyridine-3-carbonyl)-phenyl]-4-methyl-benzenesulfonamide N-[4-Chloro-2-(pyrimidine-5-carbonyl)-phenyl]-4-isopropoxy-benzenesulfonamide N-[4-Chloro-2-(pyridine-4-carbonyl)-phenyl]-4-ethoxy-benzenesulfonamide N-[4-Chloro-2-(pyridine-4-carbonyl)-phenyl]-4-ethyl-benzenesulfonamide N-[4-Chloro-2-(pyridine-4-carbonyl)-phenyl]-4-isopropyl-benzenesulfonamide N-[4-Chloro-2-(pyridine-4-carbonyl)-phenyl]-4-isobutyl-benzenesulfonamide.

The following descriptions and embodiments only refer to those formulae (I-LXXV) that are applicable (i.e., those formulae with the applicable substituents).

In formulae (III-LXXV), $U_1$ is selected from the group consisting of $CH_2$, O, and $NR^8$, where $R^8$ is as defined in formula (I).

In formulae (III-LXXV), $R^8$ is as defined in formula (I). In one preferred embodiment, $R^8$ is hydrogen or unsubstituted $C_{1-6}$ alkyl.

In formula (LXXV), $J_3$, $J_4$ and $J_5$ are selected from the group consisting of $CR^{30}R^{31}$, O, $S(O)_s$, $NR^{32}$, where s is 0, 1 or 2 with the proviso that p+q+r is 3, 4 or 5; and with the proviso that the resulting ring system does not contain a hydrazine functionality, a peroxide functionality nor a hydroxylamine derived functionality, and where $R^{30}$, $R^{31}$ and $R^{32}$ are as defined for $R^{20}$ in formula (A). In one preferred embodiment, $R^{30}$, $R^{31}$ and $R^{32}$ are each independently hydrogen or unsubstituted $C_{1-6}$ alkyl.

In formula (LXXV), A is CZ', N or $N^+$—$O^-$, where Z' is an $Ar^2$ substituent, as defined for formula (I), independently selected from the group consisting of halogen, substituted or unsubstituted $C_{1-8}$ alkyl, substituted or unsubstituted $C_{2-8}$ alkenyl, substituted or unsubstituted $C_{2-8}$ alkynyl, —CN, =O, —$NO_2$, —$OR^7$, —$OC(O)R^7$, —$CO_2R^7$, —$C(O)R^7$, —$C(O)NR^8R^9$, —$OC(O)NR^8R^9$, —$NR^7C(O)R^8$, —$NR^7C(O)NR^8R^9$, —$NR^8R^9$, —$NR^7CO_2R^8$, —$SR^7$, —$S(O)R^7$, —$S(O)_2R^7$, —$S(O)_2NR^8R^9$, —$NR^7S(O)_2R^8$, substituted or unsubstituted $C_{6-10}$ aryl, substituted or unsubstituted 5- to 10-membered heteroaryl and substituted or unsubstituted 3- to 10-membered heterocyclyl;

suitable substituted $C_{1-8}$ alkyl, substituted $C_{2-8}$ alkenyl, substituted $C_{2-8}$ alkynyl, substituted $C_{6-10}$ aryl, substituted 5- to 10-membered heteroaryl, and substituted 3- to 10 membered heterocyclyl and $R^7$, $R^8$, and $R^9$ are as defined for formula (I).

In formula (LXXV), E is CZ' or N.

In formula (LXXV), G is O, S, $NR^7$, where $R^7$ is as defined above.

Embodiments of the Invention

In the following embodiments, when one substituent is specified, the remaining substituents remain as defined during their first appearance, unless otherwise specified. For example, if $X^1$ is defined, then $X^2$, $X^3$, $X^4$, and $X^5$ remain as defined in formula (II).

In the following embodiments, the substituents refer to formula in which they are present. Not all substituents are found in all formula Linkers In one embodiment of formulae (I) and (II), L is preferably —C(O)—.

In another embodiment of formulae (I) and (II), L is preferably —S—, —S(O)—, or —S(O)$_2$—.

In another embodiment of formulae (I) and (II), when Z is substituted or unsubstituted 5-membered heteroaryl, L is preferably —S—, —S(O)—, or —S(O)$_2$—.

X Substituents

In one embodiment of formula (II), $X^1$, $X^2$, $X^3$, $X^4$, $X^5$ are preferably independently selected from the group consisting of hydrogen, halogen, —CN, —$NO_2$, —$OR^1$, —$C(O)R^1$, —$SO_2R^1$, —$NR^1R^2$, unsubstituted or substituted $C_{1-8}$ alkyl, unsubstituted or substituted phenyl, unsubstituted or substituted 5- or 6-membered heteroaryl, or unsubstituted or substituted 5- or 6-membered heterocyclyl. More preferably, at least one X substituent is situated para to the sulfonamido bond as defined in formula (I). Preferably, either 3 or 4 substituents represented by $X^1$, $X^2$, $X^3$, $X^4$, $X^5$ are hydrogen, and the remaining 1 or 2 substituents are selected from the above group with the proviso that at least one substituent is other than hydrogen.

In one embodiment of each of the formulae (I-LXXV), at least one of $X^a$, $X^b$, $X^1$, $X^2$, $X^3$, $X^4$, $X^5$ or at least one X is a 6-membered hetaryl selected from the group consisting of pyridyl, pyridazinyl, pyrazinyl, pyrimidinyl and triazinyl.

In one embodiment of each of the formulae (I-LXXV), at least one of $X^a$, $X^b$, $X^1$, $X^2$, $X^3$, $X^4$, $X^5$ or at least one X is a substituted or unsubstituted 6-ring heteroaryl selected from pyrimidinyl and pyridinyl.

In one embodiment of each of the formulae (I-LXXV), at least one of $X^a$, $X^b$, $X^1$, $X^2$, $X^3$, $X^4$, $X^5$ or at least one X is a 5-membered heteroaryl systems selected from the group consisting of isothiazolyl, pyrazolyl, imidazolyl, triazolyl, tetrazolyl, oxazolyl, isoxazolyl, oxadiazolyl, thiadiazolyl, pyrrolyl and thiazolyl.

In one embodiment of each of the formulae (I-LXXV), at least one of $X^a$, $X^b$, $X^1$, $X^2$, $X^3$, $X^4$, $X^5$ or at least one X is a substituted 5-membered heteroaryl selected from pyrazolyl, tetrazolyl, oxazolyl, isoxazolyl, oxadiazolyl, pyrrolyl, furyl and thienyl. Preferably, at least one of the substituent on X, $X^a$, $X^b$, $X^1$, $X^2$, $X^3$, $X^4$ or $X^5$ is an unsubstituted 5-ring heteroaryl system selected from pyrazolyl, tetrazolyl, oxazolyl, isoxazolyl, oxadiazolyl, pyrrolyl, furyl and thienyl. More preferably, at least one of the substituent on X, $X^a$, $X^b$, $X^1$, $X^2$, $X^3$, $X^4$ or $X^5$ is oxazolyl.

In one embodiment of each of the formulae (I-LXXV), at least one of $X^a$, $X^b$, $X^1$, $X^2$, $X^3$, $X^4$, $X^5$ or at least one X is a heterocyclic group represented by formula (A) as defined in [0022], [0023] and [0024].

In one embodiment of each of the formulae (I-LXXV), at least one of $X^a$, $X^b$, $X^1$, $X^2$, $X^3$, $X^4$, $X^5$ or at least one X is a substituted or unsubstituted heterocyclyl selected from the group including pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, and tetrahydrothiophene.

In one embodiment of each of the formulae (I-LXXV), at least one of $X^a$, $X^b$, $X^1$, $X^2$, $X^3$, $X^4$, $X^5$ or at least one X is substituted or unsubstituted heterocyclic group selected from the group consisting of pyrrolidinyl, piperidinyl, piperazinyl, morpholinyl, 1,3-dioxalanyl, thiomorpholinyl, thiomorpholinyl-S,S-dioxide, piperazinyl and pyranyl.

In one embodiment of each of the formulae (I-LXXV), at least one of $X^a$, $X^b$, $X^1$, $X^2$, $X^3$, $X^4$, $X^5$ or at least one X is a substituted $C_{1-8}$ alkyl, where suitable substituents are as defined for formula (II). Preferably, the substituent is a substituted or unsubstituted heterocyclic group of the formula (A). More preferably, the substituent is selected from the group including pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, and tetrahydrothiophene.

In one embodiment of each of the formulae (I-LXXV), when a heterocyclic group represented by formula (A) is present, $R^{20}$, $R^{21}$, $R^{22}$, $R^{23}$, $R^{24}$, $R^{25}$, and $R^{26}$ are independently hydrogen or $C_{1-4}$alkyl. In another preferred embodiment, at least three of $R^{20}$, $R^{21}$, $R^{22}$, $R^{23}$, $R^{24}$, $R^{25}$, and $R^{26}$ are hydrogen, j is 1 or 2, k is 1 or 2 with the proviso that j+k is 3 or 4. In another preferred embodiments, at least five of $R^{20}$, $R^{21}$, $R^{22}$, $R^{23}$, $R^{24}$, $R^{25}$, and $R^{26}$ are hydrogen, j is 1 or 2, k is 1 or 2 with the proviso that j+k is 3 or 4.

In one embodiment of each of the formulae (I-LXXV), at least one of $X^a$, $X^b$, $X^1$, $X^2$, $X^3$, $X^4$, $X^5$ or at least one X is a substituted $C_{1-8}$ alkyl, where suitable substituents are as defined for formula (II). In one preferred embodiment, the substituted $C_{1-8}$ alkyl is substituted with a 5- or 6-membered heteroaryl selected from the group consisting of pyridyl, pyridazinyl, pyrazinyl, pyrimidinyl, triazinyl, isothiazolyl, pyrazolyl, imidazolyl, thienyl, furyl, triazolyl, tetrazolyl, oxazolyl, isoxazolyl, oxadiazolyl, thiadiazolyl, pyrrolyl, and thiazolyl. More preferably, the substituted $C_{1-8}$ alkyl is substituted with oxazolyl.

In one embodiment of each of the formulae (I-LXXV), a suitable substituent for substituted $C_{1-8}$ alkyl (as X, $X^1$, $X^2$, $X^3$, $X^4$, $X^5$, $X^a$, $X^b$, or X) can be selected from the group consisting of —ON, —$OR^1$, —$C(O)R^1$, —$CO_2R^1$, —$O(CO)R^1$, —$SO_2R^1$ and halogen.

In one embodiment of each of the formulae (I-LXXV), at least one of $X^a$, $X^b$, $X^1$, $X^2$, $X^3$, $X^4$, $X^5$ or at least one X is an unsubstituted $C_{1-8}$ alkyl.

In one embodiment of each of the formulae (I-LXXV), at least one of $X^a$, $X^b$, $X^1$, $X^2$, $X^3$, $X^4$, $X^5$ or at least one X is t-butyl.

In one embodiment of each of the formulae (I-LXXV), at least one of $X^a$, $X^b$, $X^1$, $X^2$, $X^3$, $X^4$, $X^5$ or at least one X is oxazolyl.

In one embodiment of each of the formulae (I-LXXV), at least one of $X^a$, $X^b$, $X^1$, $X^2$, $X^3$, $X^4$, $X^5$ or at least one X is morpholinyl.

In one embodiment of each of the formulae (I-LXXV), at least one of $X^a$, $X^b$, $X^1$, $X^2$, $X^3$, $X^4$, $X^5$ or at least one X is isopropoxy.

In one embodiment of each of the formulae (I-LXXV), at least one of $X^a$, $X^b$, $X^1$, $X^2$, $X^3$, $X^4$, $X^5$ or at least one X is trifluoromethoxy.

In one embodiment of each of the formulae (I-LXXV), at least one of $X^a$, $X^b$, $X^1$, $X^2$, $X^3$, $X^4$, $X^5$ or at least one X is —$SO_2R^3$.

In one embodiment of each of the formulae (I-LXXV), at least one of $X^a$, $X^b$, $X^1$, $X^2$, $X^3$, $X^4$, $X^5$ or at least one X is ethyl.

In one embodiment of each of the formulae (I-LXXV), at least one of $X^a$, $X^b$, $X^1$, $X^2$, $X^3$, $X^4$, $X^5$ or at least one X is isopropyl.

In one embodiment of each of the formulae (I-LXXV), at least one of $X^a$, $X^b$, $X^1$, $X^2$, $X^3$, $X^4$, $X^5$ or at least one X is a cyano, halogen or trifluoromethyl group.

In one embodiment of each of the formulae (I-LXXV), at least one of $X^a$, $X^b$, $X^1$, $X^2$, $X^3$, $X^4$, $X^5$ or at least one X is —$C(Me)_2CH_2OH$.

In one embodiment of each of the formulae (I-LXXV), at least one of $X^a$, $X^b$, $X^1$, $X^2$, $X^3$, $X^4$, $X^5$ or at least one X is —(O)Me.

In one embodiment of each of the formulae (I-LXXV), at least one of $X^a$, $X^b$, $X^1$, $X^2$, $X^3$, $X^4$, $X^5$ or at least one X is —$(CH_2)_2CO_2Me$.

In one embodiment of each of the formulae (I-LXXV), at least one of $X^a$, $X^b$, $X^1$, $X^2$, $X^3$, $X^4$, $X^5$ or at least one X is isoamyl.

In one embodiment of each of the formulae (I-LXXV), at least one of $X^a$, $X^b$, $X^1$, $X^2$, $X^3$, $X^4$, $X^5$ or at least one X is 1-3, dioxalanyl.

In one embodiment of each of the formulae (I-LXXV), at least one of $X^a$, $X^b$, $X^1$, $X^2$, $X^3$, $X^4$, $X^5$ or at least one X is furyl.

In one embodiment of each of the formulae (I-LXXV), at least one of $X^a$, $X^b$, $X^1$, $X^2$, $X^3$, $X^4$, $X^5$ or at least one X is pyrazolyl.

In one embodiment of each of the formulae (I-LXXV), at least one of $X^a$, $X^b$, $X^1$, $X^2$, $X^3$, $X^4$, $X^5$ or at least one X is thienyl.

In one embodiment, the remaining substituents are hydrogen. In another embodiment, the remaining substituents are selected from the group consisting of hydrogen, halogen, cyano, or trifluoromethyl.

In one embodiment of formula (II), at least one of $X^1$, $X^2$, $X^3$, $X^4$, and $X^5$ is other than hydrogen.

In one embodiment of formula (II), $X^1$ is other than hydrogen and at least 2 of $X^2$, $X^3$, $X^4$, and $X^5$ are hydrogen. Preferably, at least 3 of $X^2$, $X^3$, $X^4$, and $X^5$ are hydrogen; more preferably, $X^2$, $X^3$, $X^4$, and $X^5$ are hydrogen.

In one embodiment of each of the formulae (III-LXXV), at least one of $X^1$, $X^a$, and $X^b$ is a substituted or unsubstituted 5- or 6-membered heteroaryl ring selected from the group consisting of pyridyl, pyridazinyl, pyrazinyl, pyrimidinyl, triazinyl, isothiazolyl, pyrazolyl, imidazolyl, thienyl, furyl, triazolyl, tetrazolyl, oxazolyl, isoxazolyl, oxadiazolyl, thiadiazolyl, pyrrolyl, and thiazolyl.

In one embodiment of each of the formulae (III-LXXV), at least one of $X^1$, $X^a$, and $X^b$ is a substituted or unsubstituted 5- or 6-membered heterocyclic ring, and the heterocycle is selected from the group consisting of pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, and tetrahydrothiophene.

In one embodiment of each of the formulae (I-LXXV), at least one of X, $X^1$, $X^2$, $X^3$, $X^4$, $X^5$, $X^a$, and $X^b$ are independently selected from the group consisting of:

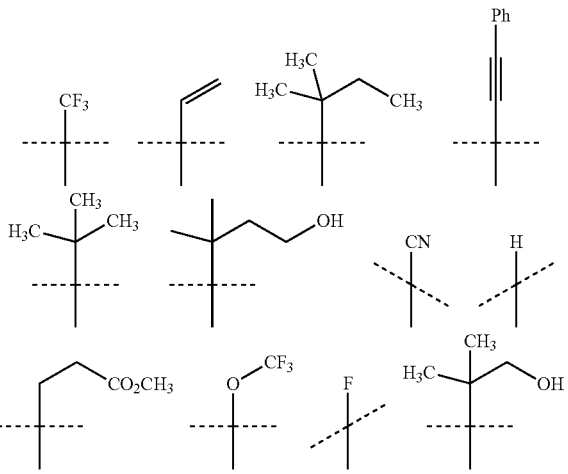

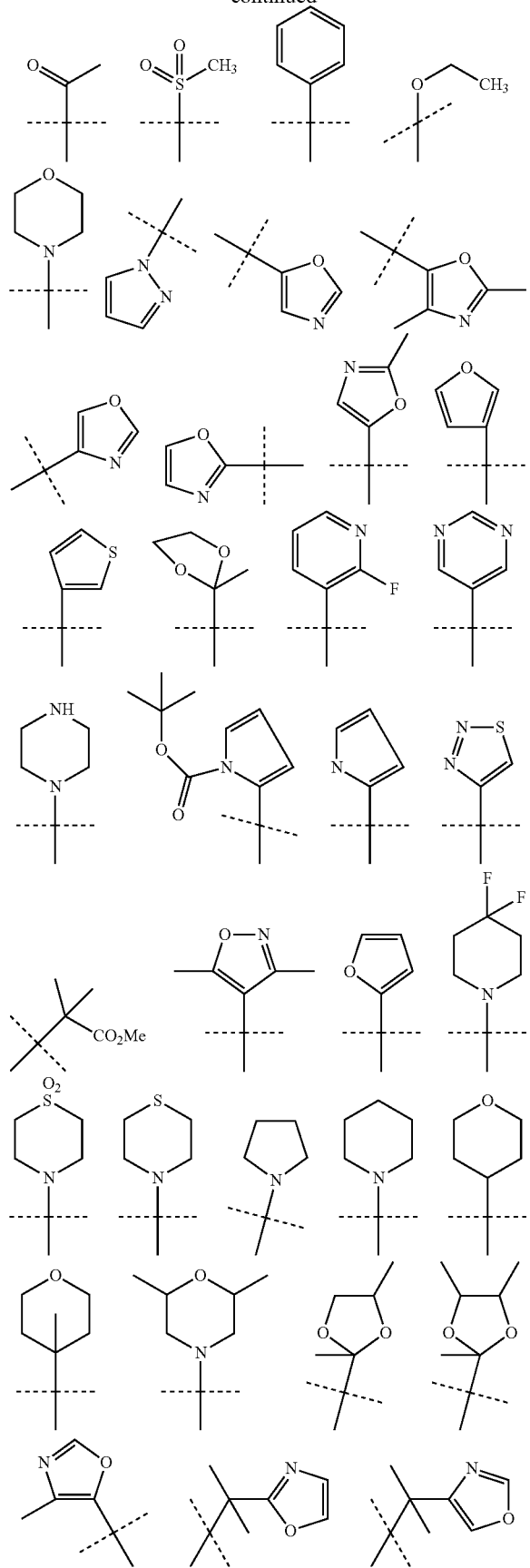
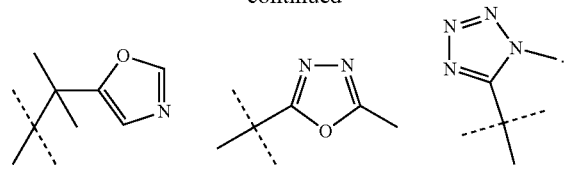
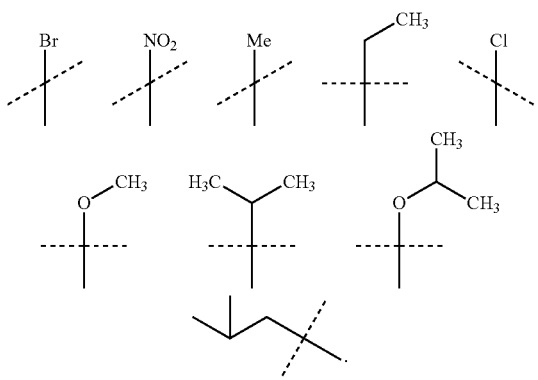

In one embodiment of each of the formulae (I-LXXV), at least one of X, $X^1$, $X^2$, $X^3$, $X^4$, $X^5$, $X^a$, and $X^b$ are independently selected from the group consisting of:

In one embodiment for each of the formulae (III-LXXV), one of $X^1$ or $X^b$ is selected from the group unsubtituted C1-8 alkyl, oxazolyl, morpholinyl, isopropoxy, trifluoromethoxy, -SO2R3, ethyl, isopropyl, cyano, halogen, trifluoromethyl group, -C(Me)2CH2OH, -C(O)Me, -(CH2)2CO2Me, iso-amyl, 1- 3,dioxalanyl, furyl, pyrazolyl, thienyl, or hydrogen, and $X^a$ is selected from the group consisting of —F, —Cl, —CN or —CF$_3$. Preferably, one of $X^1$ or $X^b$ is selected from the group defined as described above, and $X^a$ is hydrogen.

In one embodiment of each of the formulae (I-LXXV), X, $X^1$, $X^a$, and $X^b$ are independently selected from the group consisting of hydrogen, halogen, —CN, —NO$_2$, —OH, —OR$^3$ (but not —OMe, —O$^i$Pr, —OEt), —C(O)R$^3$, —CO$_2$R$^3$, —O(CO)R$^3$, —OC(O)NR$^3$R$^4$, —SR$^3$, —S(O)R$^3$, —NR$^3$R$^3$, —NR$^5$C(O)R$^3$, —NR$^5$C(O)$_2$R$^3$, unsubstituted C$_{1-8}$ alkyl (but not ethyl, methyl, iso-propyl, isoamyl), C$_{1-8}$ haloalkyl (but not —CF$_3$), unsubstituted C$_{2-8}$ alkenyl, unsubstituted C$_{2-8}$ alkynyl, or substituted or unsubstituted phenyl, with the proviso that at least one substituent is other than hydrogen.

In one embodiment of each of the formulae (I-LXXV), X, $X^1$, $X^a$, and $X^b$ are independently selected from the group consisting hydrogen, —OMe, —O$^i$Pr, —OEt, ethyl, methyl, iso-propyl, isoamyl, or —CF$_3$ with the proviso that at least one substituent is other than hydrogen.

In one embodiment of each of the formulae (III-LXXV), $X^1$, $X^a$, and $X^b$ are independently selected from the group consisting of hydrogen, —S(O)$_2$R$^3$, —NR$^5$C(O)NR$^3$R$^4$, —NR$^5$S(O)$_2$R$^3$, —S(O)$_2$NR$^3$R$^4$, substituted C$_{1-8}$ alkyl (but not C$_{1-8}$ haloalkyl), substituted C$_{2-8}$ alkenyl, substituted C$_{2-8}$ alkynyl, substituted or unsubstituted 5- or 6-membered heteroaryl, or substituted or unsubstituted 4- to 7-membered heterocyclyl, with the proviso that at least one substituent is other than hydrogen.

In one embodiment of each of the formulae (III-LXXV), $X^1$, $X^a$, and $X^b$ are independently selected such that at least one substituent is unsubstituted C$_{1-8}$ alkyl.

In one embodiment of each of the formulae (III-LXXV), $X^1$, $X^a$, and $X^b$ are independently selected from the group consisting of hydrogen, —$NO_2$, —$OR^3$, —$C(O)R^3$, —$S(O)_2R^3$, —$NR^3R^4$, substituted or unsubstituted $C_{1-8}$ alkyl, substituted or unsubstituted phenyl, substituted or unsubstituted 5- or 6-membered heteroaryl, or substituted or unsubstituted 5- or 6-membered heterocyclyl. Preferably, $X^a$ is hydrogen. In another preferred embodiment, $X^a$ is fluorine, chlorine, —CN, —$CF_3$.

In one embodiment of each of the formulae (III-LXXV), $X^a$ is hydrogen, and $X^b$ is other than hydrogen.

In one embodiment of each of the formulae (III-LXXV), $X^a$ is hydrogen, and $X^1$ is other than hydrogen.

In one embodiment of each of the formulae (III-LXXV), $X^a$ is hydrogen and $X^1$ is $C_{1-8}$ alkyl, having 1 to 3 substituents independently selected from the group consisting of halogen, —CN, =O, —$OC(O)R^3$, —$OR^3$, —$C(O)R^3$, —$C(O)NR^3R^4$, —$NR^4C(O)R^3$, —$CO_2R^3$, —$NR^3R^4$, —$SR^3$, —$S(O)R^3$, —$S(O)_2R^3$, —$NR^3S(O)_2R^4$, substituted or unsubstituted phenyl, and substituted or unsubstituted 5- or 6-membered heteroaryl, and substituted or unsubstituted 4- to 7-membered heterocycle. In another embodiment, $X^a$ is halogen, —$CF_3$, or —CN.

In one embodiment of each of the formulae (III-LXXV), $X^a$ is hydrogen and $X^1$ is unsubstituted $C_{1-8}$ alkyl. In another embodiment, $X^a$ is halogen, —$CF_3$, or —CN.

In one embodiment of each of the formulae (III-LXXV), $X^a$ is hydrogen and $X^b$ is $C_{1-8}$ alkyl, having 1 to 3 substituents independently selected from the group consisting of halogen, —CN, =O, —$OC(O)R^3$, —$OR^3$, —$C(O)R^3$, —$C(O)NR^3R^4$, —$NR^5C(O)R^3$, —$CO_2R^3$, —$NR^3R^4$, —$S(O)_2R^3$, substituted or unsubstituted phenyl, and substituted or unsubstituted 5- or 6-membered heteroaryl and substituted or unsubstituted 4- to 7-membered heterocycle. In another embodiment, $X^a$ is halogen, —$CF_3$, or —CN.

In one embodiment of each of the formulae (III-LXXV), $X^a$ is hydrogen and $X^b$ is unsubstituted $C_{1-8}$ alkyl. In another embodiment, $X^a$ is halogen, —$CF_3$, or —CN.

In one embodiment of each of the formulae (III-LXXV), $X^a$ is hydrogen and $X^1$ is $C_{6-10}$ aryl or a heteroaryl, having from 0 to 3 substituents independently selected from the group consisting of halogen, —CN, —$OR^3$, =O, —$OC(O)R^3$, —$CO_2R^3$, —$C(O)R^3$, —$C(O)NR^3R^4$, —$NR^5C(O)R^3$, —$NR^3R^4$, —$SR^3$, —$S(O)R^3$, —$S(O)_2R^3$, —$NR^5S(O)_2R^3$, and unsubstituted $C_{1-8}$ alkyl or unsubstituted $C_{1-8}$ haloalkyl. In other embodiments, $X^a$ is halogen, —CN, or —$CF_3$.

In one embodiment of each of the formulae (III-LXXV), $X^a$ is hydrogen and $X^b$ is $C_{6-10}$ aryl or a heteroaryl, having from 0 to 3 substituents independently selected from the group consisting of halogen, —CN, —$OR^3$, =O, —$NO_2$, —$OC(O)R^3$, —$CO_2R^3$, —$C(O)R^3$, —$C(O)NR^3R^4$, —$NR^5C(O)R^3$, —$NR^3R^4$, —$SR^3$, —$S(O)R^3$, —$S(O)_2R^3$, —$NR^5S(O)_2R^3$, and unsubstituted $C_{1-8}$ alkyl or unsubstituted $C_{1-8}$ haloalkyl. In other embodiments, $X^a$ is halogen, —CN, or —$CF_3$.

In one embodiment of each of the formulae (III-LXXV), $X^a$ is hydrogen and $X^1$ is substituted phenyl, having from 1 to 3 substituents independently selected from the group consisting of halogen, —$OR^3$, —$NO_2$, =O—$C(O)R^3$, —$C(O)NR^3R^4$, —$NR^5C(O)R^3$, —$NR^3R^4$, —$SR^3$, —$NR^5S(O)_2R^3$, —$S(O)_2R^3$, and unsubstituted $C_{1-8}$ alkyl or unsubstituted $C_{1-8}$ haloalkyl. In other embodiments, $X^a$ is halogen, —CN, or —$CF_3$.

In one embodiment of each of the formulae (III-LXXV), $X^a$ is hydrogen and $X^b$ is phenyl, having from 1 to 3 substituents independently selected from the group consisting of halogen, —$OR^3$, =O, —$NO_2$, —$C(O)R^3$, —$C(O)NR^3R^4$, —$NR^5C(O)R^3$, —$NR^3R^4$, —$SR^3$, —$NR^5S(O)_2R^3$, —$S(O)_2R^3$, and unsubstituted $C_{1-8}$ alkyl or unsubstituted $C_{1-8}$ haloalkyl. In other embodiments, $X^a$ is halogen, —CN, or —$CF_3$.

In one embodiment of each of the formulae (III-LXXV), $X^a$ is hydrogen and $X^1$ is substituted or unsubstituted 5- or 6-membered heteroaryl, having from 0 to 3 substituents independently selected from the group consisting of halogen, —$OR^3$, —$NO_2$, =O—$C(O)R^3$, —$C(O)NR^3R^4$, —$NR^5C(O)R^3$, —$NR^3R^4$, —$SR^3$, —$NR^5S(O)_2R^3$, —$S(O)_2R^3$, and unsubstituted $C_{1-8}$ alkyl or unsubstituted $C_{1-8}$ haloalkyl. In other embodiments, $X^a$ is selected from halogen, —CN, or —$CF_3$.

In one embodiment of each of the formulae (III-LXXV), $X^a$ is hydrogen and $X^b$ is a 5- or 6-membered substituted or unsubstituted heteroaryl, having from 0 to 3 substituents independently selected from the group consisting of halogen, —$OR^3$, =O, —$NO_2$, —$C(O)R^3$, —$C(O)NR^3R^4$, —$NR^5C(O)R^3$, —$NR^3R^4$, —$SR^3$, —$NR^5S(O)_2R^3$, —$S(O)_2R^3$, and unsubstituted $C_{1-8}$ alkyl or unsubstituted $C_{1-8}$ haloalkyl. In other embodiments, $X^a$ is halogen, —CN, or —$CF_3$.

In one embodiment of each of the formulae (III-LXXV), $X^a$ is hydrogen and $X^1$ is a 4- to 7-membered heterocyclyl, having 0 to 3 substituents independently selected from the group consisting of unsubstituted $C_{1-8}$ alkyl, unsubstituted $C_{1-8}$ haloalkyl, —$OR^3$, —$OC(O)R^3$, —$CO_2R^3$, —$C(O)R^3$, —$C(O)NR^3R^4$, —$NR^3R^4$, —$NR^5C(O)R^3$, —$S(O)_2R^3$, —$SR^3$ and —$NR^5S(O)_2R^3$. In other embodiments, $X^a$ is selected from halogen, —CN, and —$CF_3$.

In one embodiment of each of the formulae (III-LXXV), $X^a$ is hydrogen and $X^b$ is a 4- to 7-membered heterocyclyl, having from 0 to 3 substituents independently selected from the group consisting of unsubstituted $C_{1-8}$ alkyl, unsubstituted $C_{1-8}$ haloalkyl, —$OR^3$, —OH, —$NR^5C(O)R^3$, —$OC(O)R^3$, —$CO_2R^3$, —$C(O)R^3$, —$C(O)NR^3R^4$, —$NR^3R^4$, —$S(O)_2R^3$, —$SR^3$ and —$NR^5S(O)_2R^3$. In other embodiments, $X^a$ is selected from halogen, —CN, and —$CF_3$.

In one embodiment of each of the formulae (III-LXXV), $X^a$ is hydrogen and $X^1$ is a 5- or 6-membered heterocyclyl, having 0 to 2 substituents independently selected from the group consisting of unsubstituted $C_{1-8}$ alkyl or unsubstituted $C_{1-8}$ haloalkyl. In other embodiments, $X^a$ is selected from halogen, —CN, and —$CF_3$.

In one embodiment of each of the formulae (III-LXXV), $X^a$ is hydrogen and $X^b$ is a 5- or 6-membered heterocyclyl, having 0 to 2 substituents independently selected from the group consisting of unsubstituted $C_{1-8}$ alkyl or unsubstituted $C_{1-8}$ haloalkyl. In other embodiments, $X^a$ is selected from halogen, —CN, and —$CF_3$ In one embodiment, in each of formulae (III-LXXV), $X^a$ is hydrogen and $X^b$ is selected from the group consisting of —CN, —$CF_3$, halogen, —$OR^3$, —$S(O)_2R^3$, —$C(O)R^3$, and a substituted or unsubstituted $C_{1-8}$ alkyl, a substituted or unsubstituted 5- or 6-membered heteroaryl, and a substituted or unsubstituted 4- to 7-membered heterocycle. In other embodiments, $X^a$ is selected from halogen, —CN, or —$CF_3$.

In one embodiment, in each of formulae (III-LXXV), $X^a$ is hydrogen and $X^1$ is selected from the group consisting of —CN, —$CF_3$, halogen, —$OR^3$, —$S(O)_2R^3$, —$C(O)R^3$, and a substituted or unsubstituted $C_{1-8}$ alkyl, a substituted or unsubstituted 5- or 6-membered heteroaryl, and a substituted or unsubstituted 4- to 7-membered heterocycle. In other embodiments, $X^a$ is selected from halogen, —CN, or —$CF_3$.

In embodiments for each of the formulae (III-LXXV) where $X^1$ or $X^b$ is either a substituted $C_{1-8}$ alkyl, a substituted 5- or 6-membered heteroaryl, or a substituted 4- to 7-membered heterocycle, the aromatic or aliphatic portions of $X^1$ or $X^b$ may have from 1 to 3 substituents independently selected from the group consisting of halogen, —CN, =O, —OC(O)R$^3$, —OR$^3$, —C(O)R$^3$, —C(O)NR$^3$R$^4$, —NR$^5$C(O)R$^3$, —CO$_2$R$^3$, —NR$^3$R$^4$, —S(O)$_2$R$^3$, substituted or unsubstituted phenyl, substituted or unsubstituted 5- or 6-membered heteroaryl, substituted or unsubstituted 4- to 7-membered heterocycle.

In one embodiment of formula (II), $X^2$, $X^3$ and $X^5$ are hydrogen; $X^1$ and $X^4$ are selected from the group consisting of halogen, —CN, —NO$_2$, —OH, —OR$^3$, —C(O)R$^3$, —CO$_2$R$^3$, —O(CO)R$^3$, —OC(O)NR$^3$R$^4$, —SR$^3$, —S(O)R$^3$, —S(O)$_2$R$^3$, —NR$^3$R$^3$, —NR$^5$C(O)R$^3$, —NR$^5$C(O)$_2$R$^3$, —NR$^5$C(O)NR$^3$R$^4$, —NR$^5$S(O)$_2$R$^3$, —S(O)$_2$NR$^3$R$^4$, substituted or unsubstituted $C_{1-8}$ alkyl, substituted or unsubstituted $C_{2-8}$ alkenyl, substituted or unsubstituted $C_{2-8}$ alkynyl, substituted or unsubstituted phenyl, substituted or unsubstituted 5- or 6-membered heteroaryl, or substituted or unsubstituted 4- to 7-membered heterocyclyl.

In one embodiment of formula (II), $X^4$, $X^2$, $X^3$ and $X^5$ are hydrogen; and $X^1$ is selected from the group consisting of halogen, —CN, —NO$_2$, —OH, —OR$^3$, —C(O)R$^3$, —CO$_2$R$^3$, —O(CO)R$^3$, —OC(O)NR$^3$R$^4$, —SR$^3$, —S(O)R$^3$, —S(O)$_2$R$^3$, —NR$^3$R$^3$, —NR$^5$C(O)R$^3$, —NR$^5$C(O)$_2$R$^3$, —NR$^5$C(O)NR$^3$R$^4$, —NR$^5$S(O)$_2$R$^3$, —S(O)$_2$NR$^3$R$^4$, substituted or unsubstituted $C_{1-8}$ alkyl, substituted or unsubstituted $C_{2-8}$ alkenyl, substituted or unsubstituted $C_{2-8}$ alkynyl, substituted or unsubstituted phenyl, substituted or unsubstituted 5- or 6-membered heteroaryl, or substituted or unsubstituted 4- to 7-membered heterocyclyl.

In one embodiment of formulae (II), $X^2$, $X^3$ and $X^5$ are hydrogen, $X^4$ is selected from the group consisting of hydrogen, fluorine, chlorine, —CN and trifluoromethoxy, and $X^1$ is selected from the group consisting of —CN, —CF$_3$, halogen, —OR$^3$, —S(O)$_2$R$^3$, —C(O)R$^3$, and a substituted or unsubstituted $C_{1-8}$ alkyl, a substituted or unsubstituted 5- or 6-membered heteroaryl, and a substituted or unsubstituted 4- to 7-membered heterocycle.

In embodiments of each of formulae (III-LXXV), $X^a$ and $X^b$ are hydrogen; and $X^1$ is selected from the group consisting of halogen, —CN, —NO$_2$, —OH, —OR$^3$, —C(O)R$^3$, —CO$_2$R$^3$, —O(CO)R$^3$, —OC(O)NR$^3$R$^4$, —SR$^3$, —S(O)R$^3$, —S(O)$_2$R$^3$, —NR$^3$R$^3$, —NR$^5$C(O)R$^3$, —NR$^5$C(O)$_2$R$^3$, —NR$^5$C(O)NR$^3$R$^4$, —NR$^5$S(O)$_2$R$^3$, —S(O)$_2$NR$^3$R$^4$, substituted or unsubstituted $C_{1-8}$ alkyl, substituted or unsubstituted $C_{2-8}$ alkenyl, substituted or unsubstituted $C_{2-8}$ alkynyl, substituted or unsubstituted phenyl, substituted or unsubstituted 5- or 6-membered heteroaryl, and substituted or unsubstituted 4- to 7-membered heterocyclyl.

In embodiments of each of formulae (III-LXXV), $X^1$ and $X^b$ are hydrogen; and $X^a$ is selected from the group consisting of halogen, —CN, —NO$_2$, —OH, —OR$^3$, —C(O)R$^3$, —CO$_2$R$^3$, —O(CO)R$^3$, —OC(O)NR$^3$R$^4$, —SR$^3$, —S(O)R$^3$, —S(O)$_2$R$^3$, —NR$^3$R$^3$, —NR$^5$C(O)R$^3$, —NR$^5$C(O)$_2$R$^3$, —NR$^5$C(O)NR$^3$R$^4$, —NR$^5$S(O)$_2$R$^3$, —S(O)$_2$NR$^3$R$^4$, substituted or unsubstituted $C_{1-8}$ alkyl, substituted or unsubstituted $C_{2-8}$ alkenyl, substituted or unsubstituted $C_{2-8}$ alkynyl, substituted or unsubstituted phenyl, substituted or unsubstituted 5- or 6-membered heteroaryl, and substituted or unsubstituted 4- to 7-membered heterocyclyl.

In one embodiment in each of formulae (III-LXXV), $X^a$ and $X^b$ are selected from the group consisting of hydrogen, fluorine, chlorine, —CN and trifluoromethoxy, and $X^1$ is selected from the group consisting of —CN, —CF$_3$, halogen, —OR$^3$, —S(O)$_2$R$^3$, —C(O)R$^3$, and substituted or unsubstituted $C_{1-8}$ alkyl, substituted or unsubstituted 5- or 6-membered heteroaryl, and substituted or unsubstituted 4- to 7-membered heterocycle.

In one preferred embodiment of formula (II), $X^2$, $X^3$ and $X^5$ are hydrogen, $X^4$ is selected from the group consisting of hydrogen, fluorine, chlorine, —CN and trifluoromethoxy and $X^1$ is selected from one of the residues shown below:

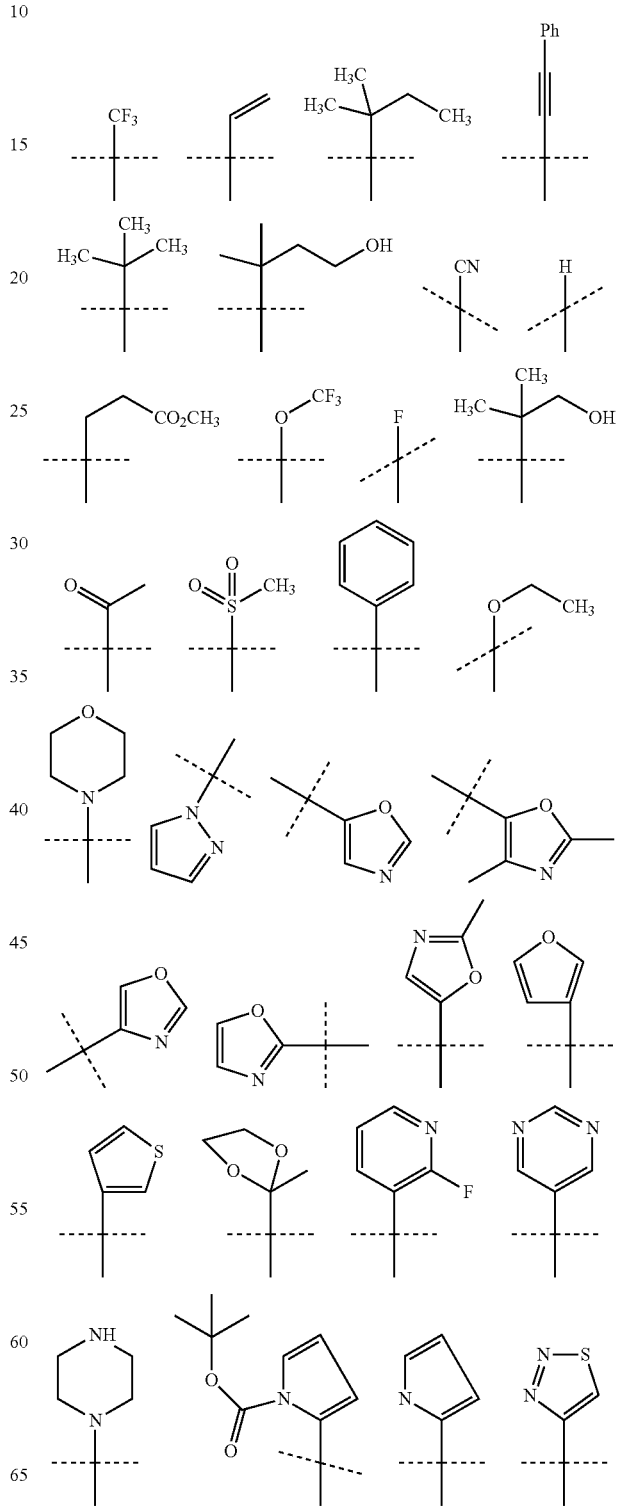

-continued
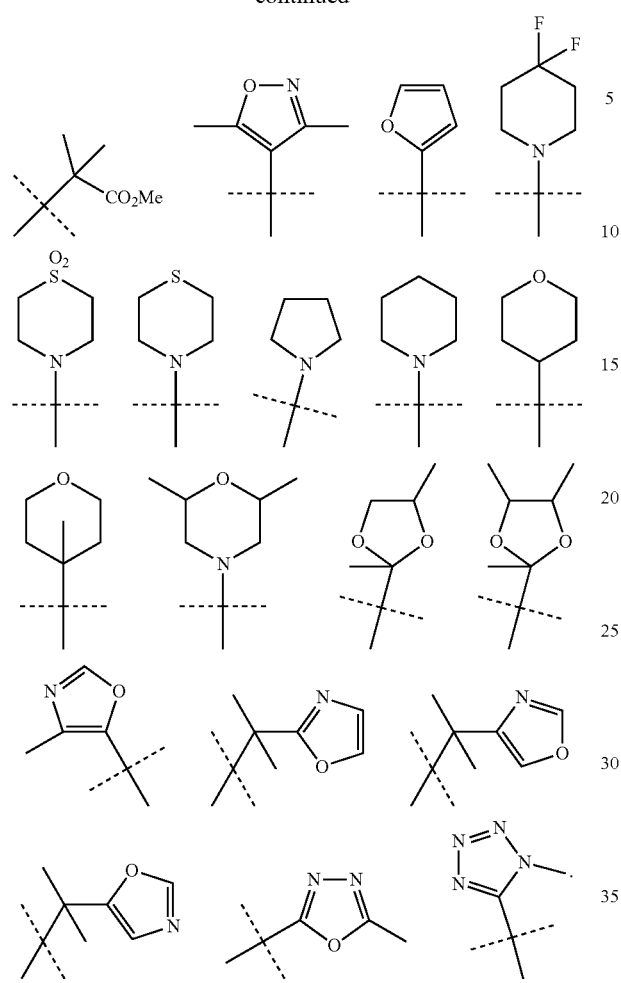
with the proviso that at least one of the substituents is other than hydrogen;
$Y^3$ is hydrogen; when $Y^1$ is chlorine or bromine, then $Y^2$ and $Y^4$ are hydrogen; alternatively when $Y^1$ is fluorine, then $Y^2$ and $Y^4$ are hydrogen or fluorine;
$Ar_2$ is selected from the following group consisting of:
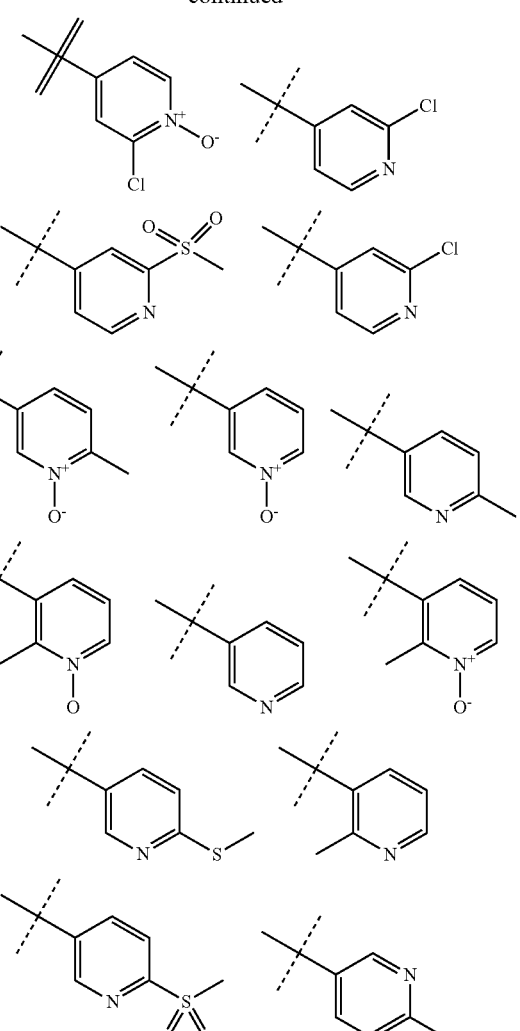
-continued
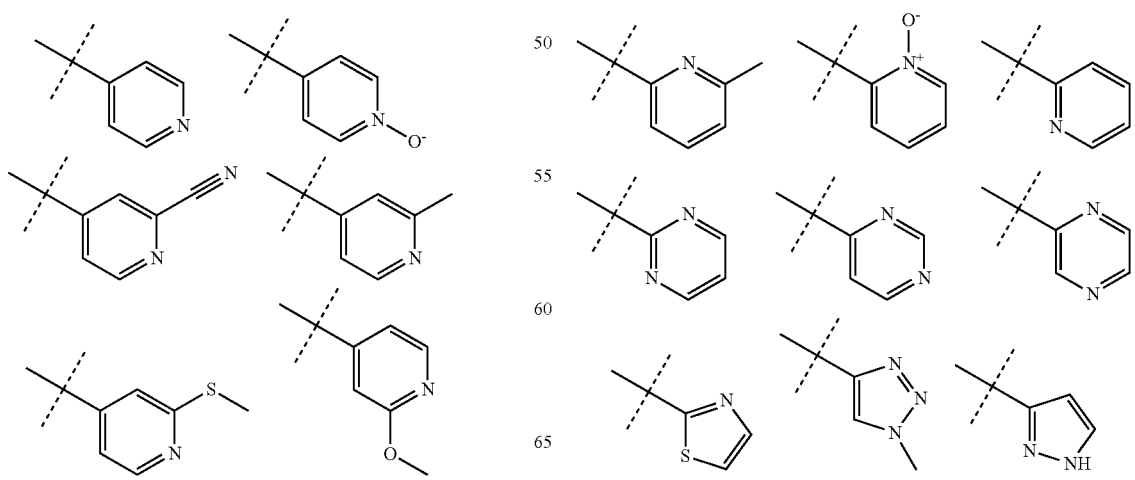

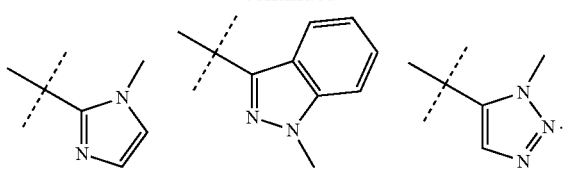

In one preferred embodiment of formula (II), $X^2$, $X^3$ and $X^5$ are hydrogen, $X^4$ is selected from the group consisting of hydrogen, fluorine, chlorine, —CN and trifluoromethoxy and $X^1$ is selected from one of the residues shown below:

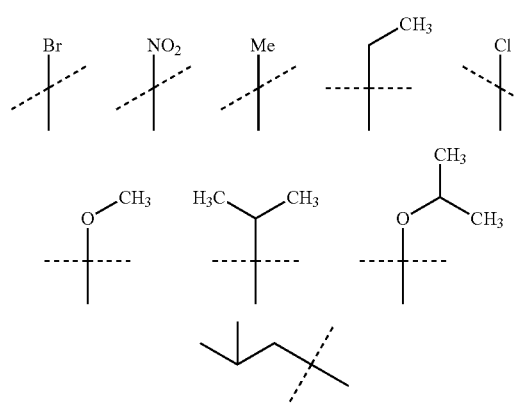

with the proviso that at least one of the substituents is other than hydrogen;

$Y^3$ is hydrogen; when $Y^1$ is chlorine or bromine, then $Y^2$ and $Y^4$ are hydrogen; alternatively when $Y^1$ is fluorine, then $Y^2$ and $Y^4$ are hydrogen or fluorine; and $Ar_2$ is selected from the following group consisting of:

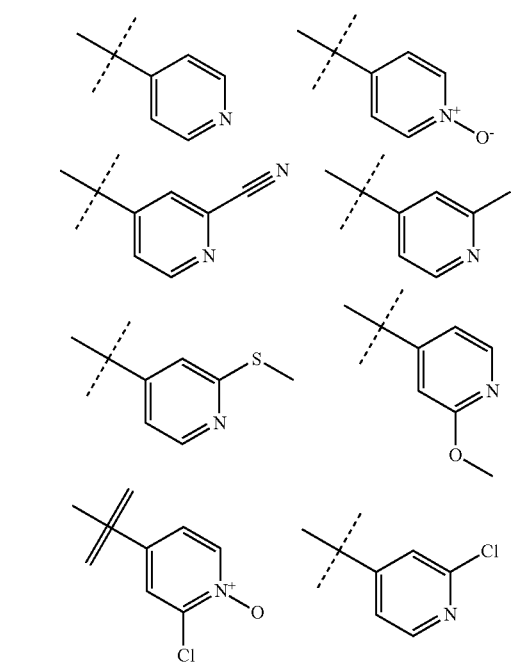

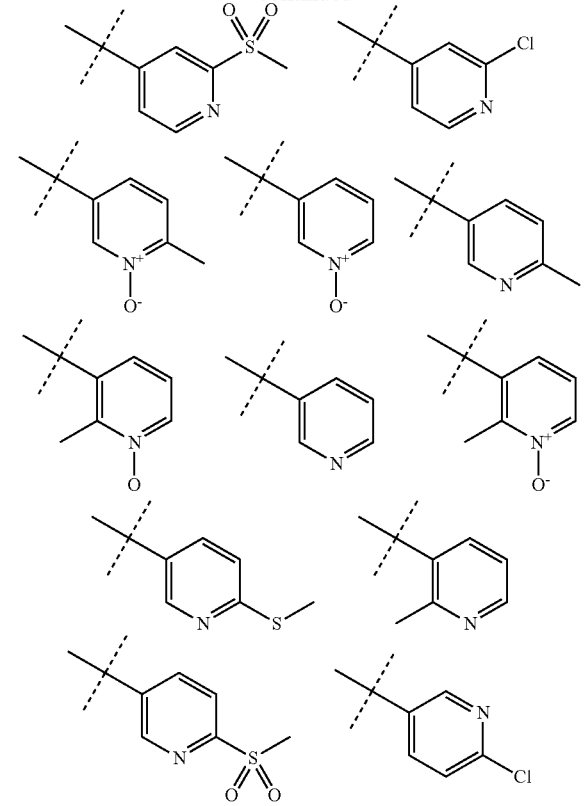

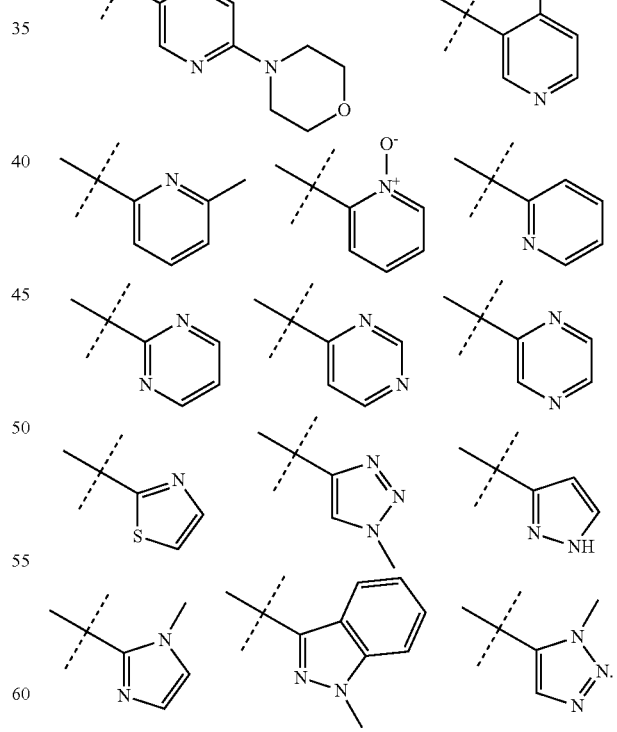

In one embodiment of each of formulae (III-LXXIV), $X^a$ is selected from the group consisting of hydrogen, fluorine, chlorine, —CN and trifluoromethoxy, and $X^1$ or $X^b$ is selected from one of the residues shown below.

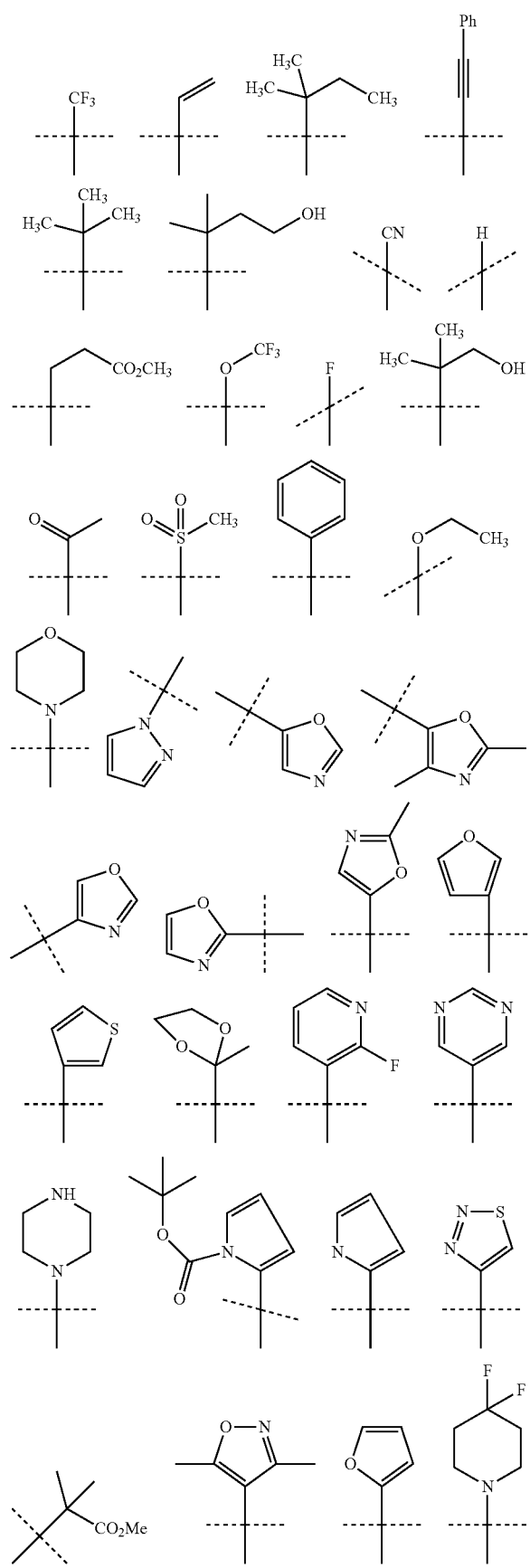

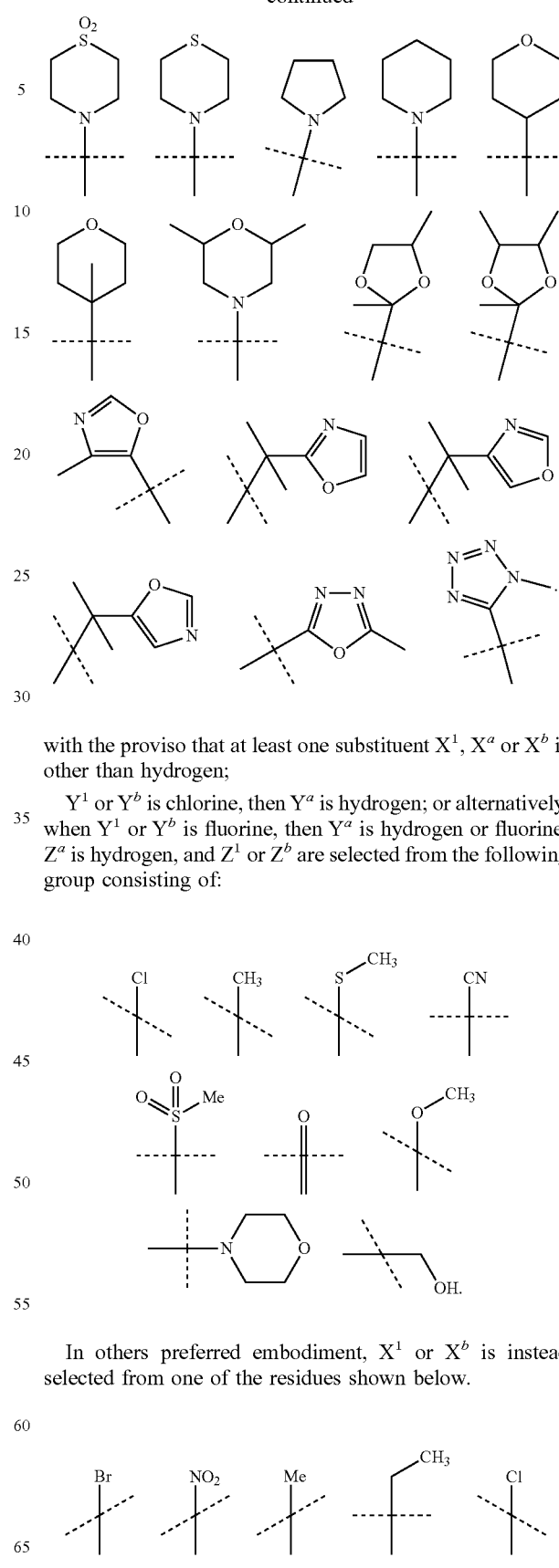

with the proviso that at least one substituent $X^1$, $X^a$ or $X^b$ is other than hydrogen;

$Y^1$ or $Y^b$ is chlorine, then $Y^a$ is hydrogen; or alternatively, when $Y^1$ or $Y^b$ is fluorine, then $Y^a$ is hydrogen or fluorine; $Z^a$ is hydrogen, and $Z^1$ or $Z^b$ are selected from the following group consisting of:

In others preferred embodiment, $X^1$ or $X^b$ is instead selected from one of the residues shown below.

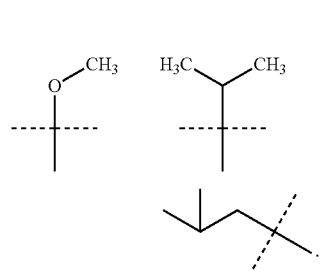
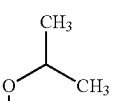

In one embodiment in each of formulae (III-LXXIV), $X^a$ is selected from the group consisting of hydrogen, fluorine, chlorine, —CN and trifluoromethoxy, and $X^1$ or $X^b$ is selected from one of the residues shown below.

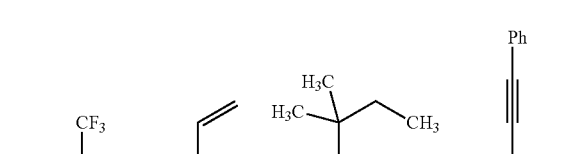
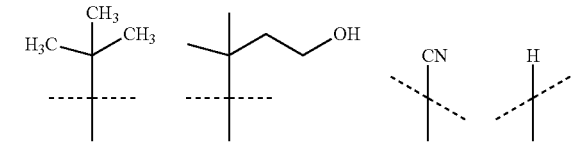
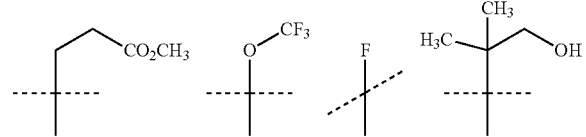
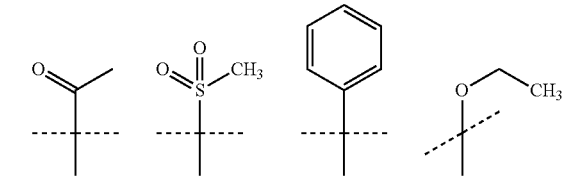
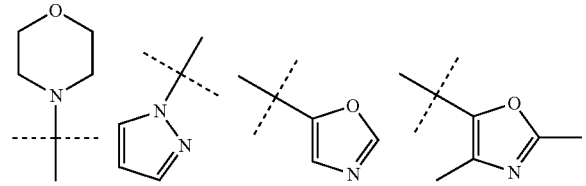
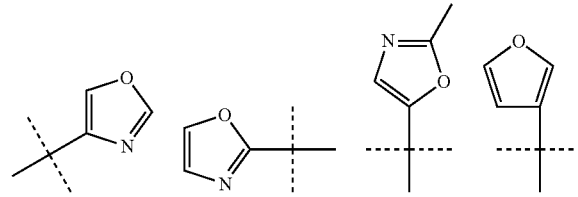
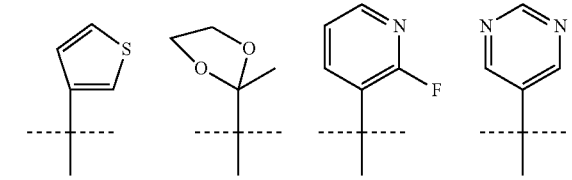

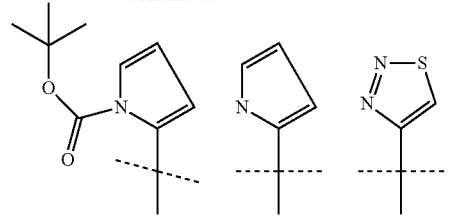
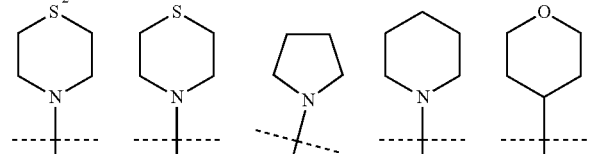
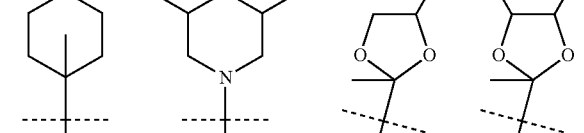
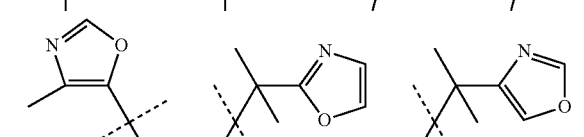
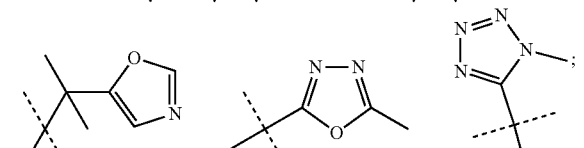

with the proviso that at least one substituent $X^1$, $X^a$ or $X^b$ is other than hydrogen; $Y^1$ or $Y^b$ is chlorine, then $Y^a$ is hydrogen; or alternatively, when $Y^1$ or $Y^b$ is fluorine, then $Y^a$ is hydrogen or fluorine; and $Z^1$, $Z^a$ and $Z^b$ are all simultaneously hydrogen.

In others preferred embodiment, $X^1$ or $X^b$ is instead selected from one of the residues shown below.

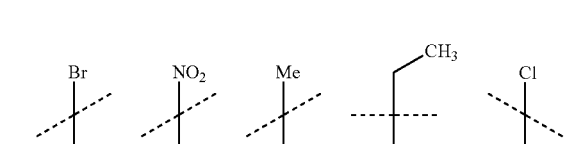
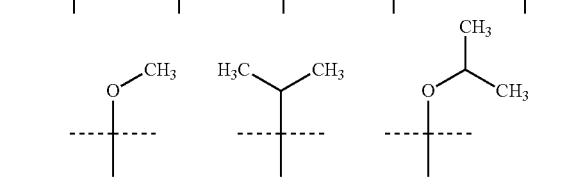

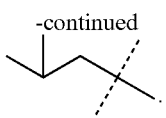

In one embodiment of each of the formulae (I-LXXV), X, $X^1$, $X^2$, $X^3$, $X^4$, $X^5$, $X^a$, or $X^b$ are each independently selected from the group consisting of hydrogen, —CH=CH$_2$, phenylacetylene, t-butyl, -hydroxybutyl, —C(CH$_3$)$_2$CH$_2$CH$_2$OH, —CH$_2$CH$_2$CO$_2$Me, —OCF$_3$, —C(O)Me, —SO$_2$Me, pyrazole, oxazole, and morpholinyl, with the proviso that at least one non-hydrogen substituent is present.

In one embodiment of each of the formulae (I-LXXV), X, $X^1$, $X^2$, $X^3$, $X^4$, $X^5$, $X^a$, or $X^b$ are each independently selected from the group consisting of hydrogen, —CF$_3$, isoamyl, ethyl (Et), i-propyl ($^i$Pr), —C(CH$_3$)$_2$CH$_2$CH$_3$, —OMe, —O—$^i$Pr, phenyl (Ph), and —OEt, with the proviso that at least one non-hydrogen substituent is present.

Y Substituents

In one embodiment of (II), at least two substituents from the group $Y^1$, $Y^2$, $Y^3$ and $Y^4$ are hydrogen, with the proviso that at least one is other than hydrogen. Preferably, $Y^1$, $Y^2$, $Y^3$ and $Y^4$ are selected from the group consisting of halogen, —CN, —NO$_2$, —CF$_3$, and —SO$_2R^4$, with the proviso that only one or two substituents are other than hydrogen, and with the proviso that at least one substituent is halogen. Most preferably, at least one substituent is a halogen atom located para to the sulfonamide bond as defined in formula (I).

In one embodiment of any of formula (I) or (II), when Y, $Y^1$, $Y^2$, $Y^3$ or $Y^4$ is substituted alkyl, it preferably has from 1 to 3 substituents independently selected from the group consisting of halogen, —OR$^4$, —CN, —NO$_2$, =O, —OC(O)R$^4$, —CO$_2R^4$, —C(O)R$^4$, —CONR$^4R^5$, —NR$^4$C(O)R$^5$, —NR$^4R^5$, —NR$^4$, —SR$^4$, —SOR$^4$, —SO$_2R^4$, and —NR$^4$SO$_2R^5$.

In one embodiment of any of formulae (I) and (II), at least one of Y, $Y^1$, $Y^2$, $Y^3$, $Y^4$ and $Y^5$ is other than hydrogen.

In one embodiment of any of formulae (I) and (II), at least one of Y, $Y^1$, $Y^2$, $Y^3$, $Y^4$ and $Y^5$ is halogen, —CN, —NO$_2$, —OR$^6$, —C(O)R$^6$, —SR$^6$, —CF$_3$, —S(O)R$^6$, and —S(O)$_2R^{13}$ and substituted or unsubstituted C$_{1-4}$ alkyl.

In one embodiment of any of formulae (III-LXXV), one of $Y^1$, $Y^a$ and $Y^b$ is hydrogen and the other is not hydrogen.

In one embodiment of any of formulae (III-LXXV), $Y^1$, $Y^a$ and $Y^b$ represent from 1 to 3 substituents independently selected from the group consisting of hydrogen, halogen, —CN, —NO$_2$, —OR$^6$, —C(O)R$^6$, —SR$^6$, —CF$_3$, —S(O)R$^6$, and —S(O)$_2R^6$ and substituted or unsubstituted C$_{1-6}$ alkyl.

In one embodiment of any of formulae (III-LXXV), $Y^1$, $Y^a$ and $Y^b$ represent from 1 to 3 substituents independently selected from the group consisting of hydrogen, halogen, —CN, —NO$_2$, —CF$_3$, and —S(O)$_2$Me.

In one embodiment of any of formulae (III-LXXV), one of $Y^1$, $Y^a$ and $Y^b$ is halogen and the other is selected from the group consisting of hydrogen, halogen, —CN, —NO$_2$, —OH, —OR$^6$, —C(O)R$^6$, —CO$_2R^6$, —SR$^6$, —S(O)R$^6$, —S(O)$_2R^6$ and substituted or unsubstituted C$_{1-4}$ alkyl.

In one embodiment in any of formulae (III-LXXV), one of $Y^1$, $Y^a$ and $Y^b$ is substituted alkyl, having from 1 to 3 substituents independently selected from the group consisting of halogen, —OH, —OR'", —CN, —NO$_2$, =O, —OC(O)R'", —CO$_2$R'", —C(O)R'", —C(O)NHR", —C(O)NH$_2$, —C(O)NR'"R", —NR'"C(O)R", —NHC(O)R", —NR'"R", —NHR'", —NH$_2$, —SR'", —S(O)R'", —S(O)$_2$R'", —NR'"S(O)$_2$R", and —NHS(O)$_2$R'" where R'" and R" are each independently unsubstituted C$_{1-6}$ alkyl.

In one embodiment of any of formulae (III-LXXV), $Y^1$ and $Y^a$ are each independently selected from the group consisting of hydrogen, halogen, —CN, —NO$_2$, —OH, —OR$^6$, —C(O)R$^6$, —CO$_2R^6$, —SR$^6$, —S(O)R$^6$, —S(O)$_2R^6$, and substituted or unsubstituted C$_{1-4}$ alkyl, with the proviso that $Y^1$ and $Y^a$ cannot both be hydrogen simultaneously.

In one embodiment of any of formulae (III-LXXV), $Y^1$ and $Y^a$ are each independently hydrogen or halogen, with the proviso that one of $Y^1$ and $Y^a$ is halogen. Preferably, one halogen atom is located para to the sulfonamide bond.

In one embodiment of any of formulae (III-LXXV), $Y^1$ or $Y^b$ is hydrogen and $Y^a$ is chloro, fluoro or bromo; $Y^a$ is hydrogen and $Y^1$ or $Y^b$ is chloro, fluoro or bromo; $Y^a$ and $Y^1$ or $Y^b$ are both chloro, fluoro, or bromo (particularly fluoro).

Z Substituents

In one embodiment of formulae (I) and (II), Z represents an unsubstituted or substituted 5- or 6-membered heteroaryl. Suitably substituted 5- or 6-membered heteroaryls may have from 1 to 3 substituents independently selected from the group consisting of halogen, unsubstituted or substituted C$_{1-8}$ alkyl, unsubstituted or substituted C$_{2-8}$ alkenyl, unsubstituted or substituted C$_{2-8}$ alkynyl, =O, —CN, —NO$_2$, —OR$^7$, —OC(O)R$^7$, —CO$_2R^7$, —C(O)R$^7$, —CONR$^7R^8$, —NR$^7$C(O)R$^8$, —NR$^7R^8$, —SR$^7$, —SOR$^7$, —SO$_2R^7$, —SO$_2$NR$^7R^8$, —NR$^7$SO$_2R^8$, unsubstituted or substituted phenyl, unsubstituted or substituted 5- or 6-membered heteroaryl, and unsubstituted or substituted 4- to 7-membered heterocyclyl. If present, one substituent is preferably located ortho to one of the heteroatoms in the ring or is an oxygen atom directly connected to a ring heteroatom (i.e. N-oxide).

In one embodiment of formulae (I) and (II), Z represents unsubstituted or substituted 6-membered heteroaryl with up to 3 nitrogen atoms and with from 0 to 3 substituents independently selected from the group consisting of halogen, unsubstituted or substituted C$_{1-8}$ alkyl, unsubstituted or substituted C$_{2-8}$ alkenyl, unsubstituted or substituted C$_{2-8}$ alkynyl, =O, —CN, —NO$_2$, —OR$^7$, —OC(O)R$^7$, —CO$_2R^7$, —C(O)R$^7$, —CONR$^7R^8$, —NR$^7$C(O)R$^8$, —NR$^7R^8$, —SR$^7$, —S(O)R$^7$, —S(O)$_2R^7$, —SO$_2$NR$^7R^8$, —NR$^7$SO$_2R^8$, unsubstituted or substituted phenyl, unsubstituted or substituted 5- and 6-membered heteroaryl, and unsubstituted or substituted 4- to 7-membered heterocyclyl.

In one embodiment of formulae (I) and (II), Z can be any unsubstituted or substituted chemically allowed regioisomer of pyridyl, pyrimidinyl, pyridazinyl, pyrazinyl and the like and their respective N-oxides. In preferred embodiments, Z is pyridinyl with from 0 to 3 substituents; pyrimidinyl with from 0 to 3 substituents; pyrazinyl with from 0 to 3 substituents; or pyridazinyl with from 0 to 3 substituents (especially, where one ring nitrogen has a =O substituent).

In one embodiment of formulae (I) and (II), Z represents unsubstituted or substituted 6-membered heteroaryl with 1 to 2 nitrogen atoms and with 0 or 2 substituents independently selected from the group consisting of halogen, unsubstituted or substituted C$_{1-6}$ alkyl, =O, —CN, —NO$_2$, —OR$^7$, —C(O)R$^7$, —CONR$^7R^8$, —NR$^7$C(O)R$^8$, —NR$^7R^8$, —SR$^7$, —SOR$^7$, —SO$_2R^7$, —SO$_2$NR$^7R^8$, —NR$^7$SO$_2R^8$, unsubstituted or substituted 5- or 6-membered heteroaryl and a unsubstituted or substituted 4- to 7-membered heterocyclyl. In this embodiment, Z can be any chemically allowed regioisomer of pyridyl, pyrimidinyl, pyridazinyl, pyrazinyl and the like, and their respective N-oxides.

When a substituent on Z is substituted C$_{1-8}$ alkyl, substituted C$_{2-8}$ alkenyl or substituted C$_{2-8}$ alkynyl, it may have from 1 to 3 substituents independently selected from the group consisting of halogen, —OR$^7$, =O, —CO$_2$R$^7$, —C(O)R$^7$, —CONR$^7$R$^8$, —NR$^7$C(O)R$^8$, —NR$^7$R$^8$, —SR$^7$, —SOR$^7$, —SO$_2$R$^7$, —NR$^7$SO$_2$R$^8$, unsubstituted or substituted phenyl, unsubstituted or substituted 5- or 6-membered heteroaryl, and unsubstituted or substituted 4- to 7-membered heterocyclyl. More preferably, it has from 1 to 3 substituents independently selected from the group consisting of halogen, —OR$^7$, =O, —C(O)R$^7$, —CO$_2$R$^7$, —CONR$^7$R$^8$, —NR$^7$C(O)R$^8$, —NR$^7$R$^8$, —SR$^7$, —S(O)R$^7$, —S(O)$_2$R$^7$, —SO$_2$NR$^7$R$^8$, —NR$^7$SO$_2$R$^8$, and 4- to 7-membered heterocyclyl.

When a substituent on Z is substituted phenyl, substituted 5- or 6-membered heteroaryl or substituted 4- to 7-membered heterocyclyl, it have from 1 to 3 substituents independently selected from the group consisting of halogen, —OR$^7$, —CN, —NO$_2$, =O, —OC(O)R$^7$, —CO$_2$R$^7$, —C(O)R$^7$, —CONR$^7$R$^8$, —NR$^7$C(O)R$^8$, —NR$^7$R$^8$, —SR$^7$, —S(O)R$^7$, —S(O)$_2$R$^7$, —NR$^7$SO$_2$R$^8$, unsubstituted 4- to 7-membered heterocyclyl, unsubstituted C$_{1-8}$ alkyl and unsubstituted C$_{1-8}$ haloalkyl, with the proviso that if the suitable substituent on residue Z is heterocyclic, substituents on this heterocycle preferably do not include another heterocycle.

In one embodiment of any of formulae (I) and (II), Z is a substituted or unsubstituted 5- to 10-membered heteroaryl, having 0 to 4 substituents as defined in formula (I).

In one embodiment of any of formulae (I) and (II), Z is a substituted or unsubstituted 3- to 10-membered heterocycle, having 0 to 3 substituents as defined in formula (I).

In one embodiment of any of formulae (I) and (II), Z is a substituted or unsubstituted 3- to 10-membered heterocycle selected from the group consisting of pyrrolidine, piperidine, imidazolidine, pyrazolidine, butyrolactam, valerolactam, imidazolidinone, hydantoin, phthalimide, piperidine, 1,4-dioxane, morpholine, thiomorpholine, thiomorpholine-S,S-dioxide, piperazine, pyran, pyridone, 3-pyrroline, thiopyran, pyrone, tetrahydrofuran, and tetrahydrothiophene.

In one embodiment of any of formulae (I) and (II), Z is any substituted or unsubstituted chemically allowed regioisomers of pyridyl, pyrimidinyl, pyridazinyl, pyrazinyl and the like and their respective N-oxides.

In one embodiment of any of formulae (I) and (II), Z is a substituted or unsubstituted 2-pyridyl.

In one embodiment of any of formulae (I) and (II), Z is a substituted or unsubstituted 2-pyridyl-N-oxide.

In one embodiment of any of formulae (I) and (II), Z is a substituted or unsubstituted 3-pyridyl.

In one embodiment of any of formulae (I) and (II), Z is a substituted or unsubstituted 3-pyridyl-N-oxide.

In one embodiment of any of formulae (I) and (II), Z is a substituted or unsubstituted 4-pyridyl.

In one embodiment of any of formulae (I) and (II), Z is a substituted or unsubstituted 4-pyridyl-N-oxide.

In one embodiment of any of formulae (I) and (II), Z is a substituted or unsubstituted pyrazolyl.

In one embodiment of any of formulae (I) and (II), Z is a substituted or unsubstituted imidazolyl.

In one embodiment of any of formulae (I) and (II), Z is a substituted or unsubstituted thiazolyl.

In one embodiment of any of formulae (I) and (II), Z is a substituted or unsubstituted triazolyl.

In one embodiment of any of formulae (I) and (II), Z is pyridinyl with from 0 to 3 substituents; pyrimidinyl with from 0 to 3 substituents; pyrazinyl with from 0 to 3 substituents; or pyridazinyl with from 0 to 3 substituents (especially, where one ring nitrogen has a =O substituent).

In one embodiment of any of formulae (I) and (II), Z is pyrazolyl with from 0 to 3 substituents; or imidazolyl with from 0 to 3 substituents, or thiazolyl with from 0 to 3 substituents, or triazolyl with from 0 to 3 substituents.

In one embodiment in any of the formulae (I) and (II), Z is substituted or unsubstituted 6-membered heteroaryl with 1 to 2 nitrogen atoms and with 0 to 2 substituents independently selected from the group consisting of unsubstituted C1-6 alkyl, =O, C1-6 haloalkyl, —COOH, —NO2, or —OR10. In this embodiment, Z can be any chemically allowed regioisomer of pyridyl, pyrimidinyl, pyridazinyl, pyrazinyl and the like, and their respective N-oxides.

In one embodiment in any of the formulae (I) and (II), Z is substituted or unsubstituted 6-membered heteroaryl with 1 to 2 nitrogen atoms and with 0 to 2 substituents independently selected from the group consisting of —CH3, =O, —CF3, —OCH3. In this embodiment, Z can be any chemically allowed regioisomer of pyridyl, pyrimidinyl, pyridazinyl, pyrazinyl and the like, and their respective N-oxides.

In one embodiment in any of the formulae (I) and (II), Z is substituted or unsubstituted 6-membered heteroaryl with 1 to 2 nitrogen atoms and with 0 to 2 substituents independently selected from the group consisting of halogen, substituted C$_{1-6}$ alkyl (but not C$_{1-6}$ haloalkyl), unsubstituted or substituted C$_{1-6}$ alkenyl, unsubstituted or substituted C$_{1-6}$ alkynyl, =O, —CN, —C(O)R$^{10}$, —C(O)NR$^{10}$R$^{11}$, —NR$^{10}$S(O)R$^{11}$, —NR$^{11}$R$^{12}$, —SR$^{10}$, —S(O)R$^{10}$, —S(O)$_2$R$^{10}$, —S(O)$_2$NR$^{11}$R$^{12}$, —NR$^{10}$S(O)$_2$R$^{11}$, —OC(O)R$^{10}$, —CO$_2$R$^{10}$ (but not —CO$_2$H), —OC(O)NR$^{11}$R$^{12}$, —NR$^{10}$C(O)NR$^{11}$R$^{12}$, —NR$^{10}$CO$_2$R$^{11}$, unsubstituted or substituted 5- or 6-membered heteroaryl and a unsubstituted or substituted 3- to 7-membered heterocyclyl. Preferred substituents include chlorine, =O, —CN, —SCH$_3$, —SO$_2$CH$_3$. In this embodiment, Z can be any chemically allowed regioisomer of pyridyl, pyrimidinyl, pyridazinyl, pyrazinyl and the like, and their respective N-oxides.

In one embodiment in any of the formulae (I) and (II), at least one substituent on the group Z is cyano.

In one embodiment in any of the formulae (I) and (II), at least one substituent on the group Z is —S(O)$_2$R$^7$. In one particular embodiment, R$^7$ is methyl.

In one embodiment in any of the formulae (I) and (II), at least one substituent on the group Z is halogen, particularly chlorine.

In one embodiment in any of the formulae (I) and (II), at least one substituent on the group Z is —OR$^7$. In one particular embodiment, R$^7$ is methyl.

In one embodiment in any of the formulae (I) and (II), at least one substituent on the group Z is —SR$^7$. In one particular embodiment, R$^7$ is methyl.

In one embodiment in any of the formulae (I) and (II), at least one substituent on the group Z is unsubstituted C$_{1-6}$ alkyl (in particular methyl) or C$_{1-6}$ haloalkyl (in particular —CF$_3$).

In one embodiment in any of the formulae (I) and (II), at least one substituent on the group Z is substituted C$_{1-6}$ alkyl (preferably not C$_{1-6}$ haloalkyl).

In one embodiment in any of the formulae (I) and (II), no substituents, except hydrogen, exist on the group Z.

In one embodiment in any of the formulae (I) and (II), Z is a substituted or unsubstituted 6-membered heteroaryl with 1 to 2 nitrogen atoms and with 0 to 2 substituents independently selected from the group consisting of halogen, substituted C$_{1-6}$ alkyl (but not C$_{1-6}$ haloalkyl), unsubstituted or substituted C$_{1-6}$ alkenyl, unsubstituted or substituted C$_{1-6}$ alkynyl, =O, —CN, —C(O)R$^{10}$, —C(O)NR$^{10}$R$^{11}$, —NR$^{10}$C(O)R$^{11}$, —NR$^{11}$R$^{12}$, —SR$^{10}$, —S(O)R$^{10}$, —S(O)₂R¹⁰, —S(O)₂NR¹¹R¹², —NR¹⁰S(O)₂R¹¹, —OC(O)R¹⁰, —CO₂R¹⁰ (but not —CO₂H), —OC(O)NR¹¹R¹², —NR¹⁰C(O)NR¹¹R¹², —NR¹⁰CO₂R¹¹, unsubstituted or substituted 5- or 6-membered heteroaryl and a unsubstituted or substituted 3- to 7-membered heterocyclyl. Preferred substituents include chlorine, =O, —CN, —SCH₃, —SO₂CH₃. In this embodiment, Z can be any chemically allowed regioisomer of pyridyl, pyrimidinyl, pyridazinyl, pyrazinyl and the like, and their respective N-oxides.

In one embodiment of any of formulae (I) and (II), Z is a substituted or unsubstituted C₆₋₁₀ aryl or substituted or unsubstituted 5- to 10-membered heteroaryl selected from pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl.

In one embodiment of any of formulae (I) and (II), Z is a substituted or unsubstituted heterocyclic ring system selected from pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran or tetrahydrothiophene. Preferably, Z is selected from substituted and unsubstituted piperidine, substituted and unsubstituted piperazine, and substituted and unsubstituted morpholine.

In one embodiment of any of formulae (I) and (II) when Z is —NR⁷R⁸, R⁷ is hydrogen and R⁸ is preferably selected from the group consisting of substituted or unsubstituted C₆₋₁₀ aryl, substituted or unsubstituted C₁₋₈ alkyl(C₁₋₆)aryl, substituted or unsubstituted C₁₋₈ alkyl(5 to 10 membered) heteroaryl, and substituted or unsubstituted 5 to 10 membered heteroaryl.

In one embodiment of any of formulae (I) and (II), Z is a substituted or unsubstituted 6-membered heteroaryl selected from the group consisting of pyridyl, pyridazinyl, pyrazinyl, pyrimidinyl, and triazinyl.

In one embodiment of any of formulae (I) and (II), Z is a substituted or unsubstituted 5-membered heteroaryl selected from the group consisting of isothiazolyl, pyrazolyl, imidazolyl, thienyl, furyl, triazolyl, tetrazolyl, oxazolyl, isoxazolyl, oxadiazolyl, thiadiazolyl, pyrrolyl, and thiazolyl.

In one embodiment of any of formulae (I) and (II), Z is a heterocycle selected from the group consisting of pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, and tetrahydrothiophene.

In one embodiment in any of the formulae (I) and (II), Z is a heterocyclic group represented by formula (A).

In one embodiment of each of the formulae (I) and (II), at least one substituent on Z is a heterocyclyl selected from the group including pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, or tetrahydrothiophene.

In other embodiments of each of the formulae (I) and (II), when formula (A) is present, R²⁰, R²¹, R²², R²³, R²⁴, R²⁵, and R²⁶ are independently hydrogen or C₁₋₄alkyl. In another preferred embodiment, at least three of R²⁰, R²¹, R²², R²³, R²⁴, R²⁵, and R²⁶ are hydrogen, j is 1 or 2, k is 1 or 2 with the proviso that j+k is 3 or 4. In another preferred embodiments, at least five of R²⁰, R²¹, R²², R²³, R²⁴, R²⁵, and R²⁶ are hydrogen, j is 1 or 2, k is 1 or 2 with the proviso that j+k is 3 or 4.

In one embodiment of any of formulae (I) and (II), Z is monocyclic.

In one embodiment of any of the formulae (I) and (II), heterocycle groups as substituents on Z are represented by formula (A) as defined in [0022], [0023], and [0024].

In one embodiment of any of the formulae (I) and (II), at least one substituent on the group Z is a heterocyclyl selected from the group including pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, and tetrahydrothiophene.

In one embodiment of any of formulae (I) and (II), Z is the following residue:

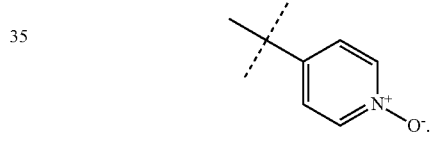

In another embodiment of any of formulae (I) and (II), Z is selected from one of the following residues:

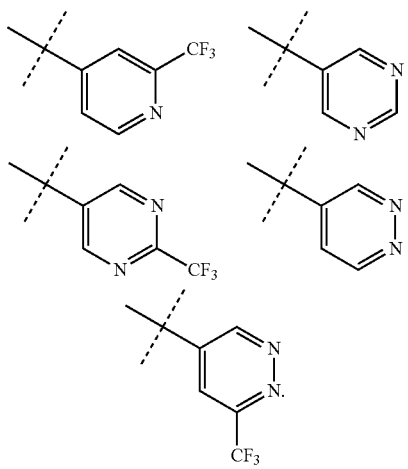

In another embodiment of any of formulae (I) and (II), Z is selected from one of the following residues:

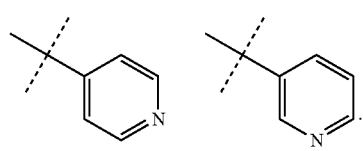

In another embodiment of any of formulae (I) and (II), Z is selected from one of the following residues:

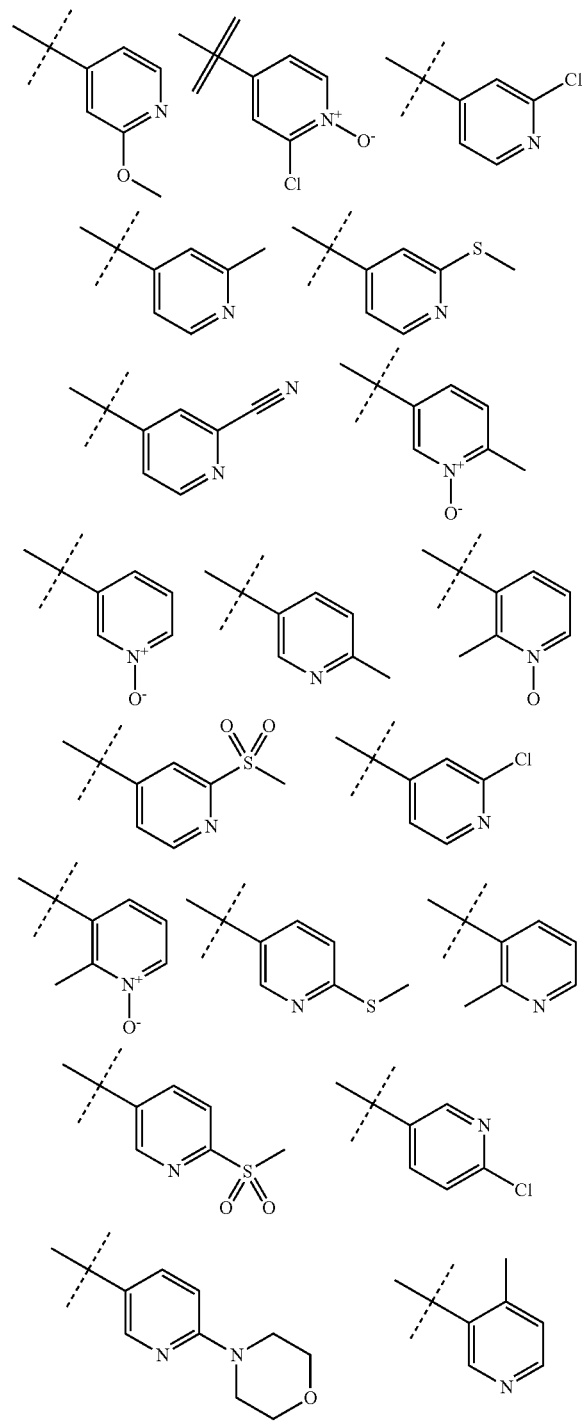

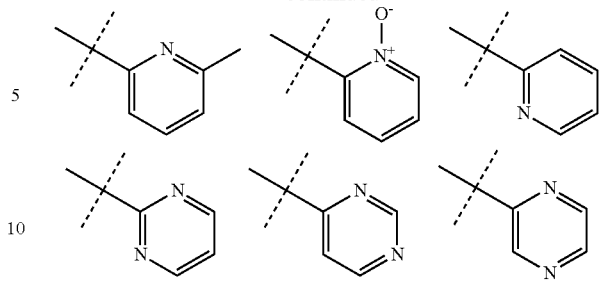

-continued

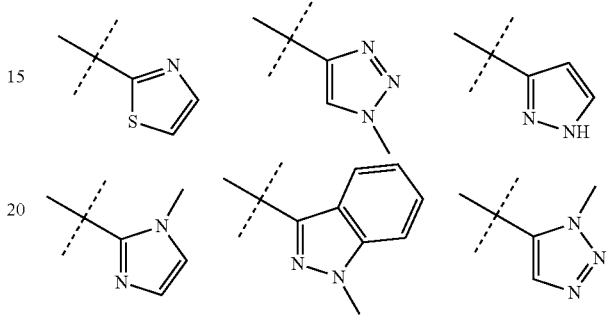

In one embodiment of any of formulae (I) and (II), Z has one or more substituents selected from the group consisting of:

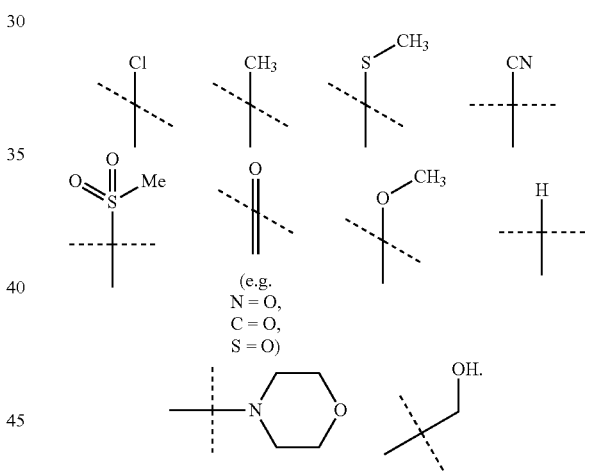

with the proviso that at least one substituent is other than hydrogen. In another embodiment, all substituents on Z are hydrogen.

In one embodiment of any of formulae (III-LXXV), Z', $Z^1$, $Z^a$, $Z^b$ and $Z^c$ are independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, =O, —CN, —NO$_2$, —OR$^{10}$, —OC(O)R$^{10}$, —CO$_2$R$^{10}$, —C(O)R$^{10}$, —C(O)NR$^{11}$R$^{12}$, —NR$^{10}$C(O)R$^{11}$, —NR$^{11}$R$^{12}$, —SR$^{10}$, —S(O)R$^{10}$, —S(O)$_2$R$^{10}$, —S(O)$_2$NR$^{11}$R$^{12}$, —NR$^{10}$S(O)$_2$R$^{11}$, —OC(O)NR$^{11}$R$^{12}$, —NR$^{10}$C(O)NR$^{11}$R$^{12}$, substituted or unsubstituted phenyl, substituted or unsubstituted 5- or 6-membered heteroaryl, and substituted or unsubstituted 4- to 7-membered heterocyclyl. If present, one substituent is preferably located ortho to one of the heteroatoms in the heteroaryl Z ring. Alternatively, one substituent, =O, may be directly connected to a ring heteroatom in the heteroaryl Z ring.

In one embodiment, any of formulae (III-LXXV), Z', $Z^1$, $Z^a$, $Z^b$ and $Z^c$ are independently selected from the group consisting of unsubstituted $C_{1-6}$ alkyl (not -Me), =O, $C_{1-6}$ haloalkyl (not —$CF_3$), —COOH, —$NO_2$, or —$OR^{10}$ (not —OMe). In this embodiment, Z can be any chemically allowed regioisomer of pyridyl, pyrimidinyl, pyridazinyl, pyrazinyl and the like, and their respective N-oxides.

In one embodiment, any of formulae (III-LXXV), Z', $Z^1$, $Z^a$, $Z^b$ and $Z^c$ are independently selected from the group consisting of —$CH_3$, =O, —$CF_3$, —$OCH_3$. In this embodiment, Z can be any chemically allowed regioisomer of pyridyl, pyrimidinyl, pyridazinyl, pyrazinyl and the like, and their respective N-oxides.

In one embodiment, any of formulae (III-LXXV), Z', $Z^1$, $Z^a$, $Z^b$ and $Z^c$ are independently selected from the group consisting of halogen, substituted $C_{1-6}$ alkyl (but not $C_{1-6}$ haloalkyl), unsubstituted or substituted $C_{1-6}$ alkenyl, unsubstituted or substituted $C_{1-6}$ alkynyl, =O, —CN, —$C(O)R^{10}$, —$C(O)NR^{10}R^{11}$, —$NR^{10}C(O)R^{11}$, —$NR^{11}R^{12}$, —$SR^{10}$, —$S(O)R^{10}$, —$S(O)_2R^{10}$, —$S(O)_2NR^{11}R^{12}$, —$NR^{10}S(O)_2R^{11}$, —$OC(O)R^{10}$, —$CO_2R^{10}$ (but not —$CO_2H$), —$OC(O)NR^{11}R^{12}$, —$NR^{10}C(O)NR^{11}R^{12}$, —$NR^{10}CO_2R^{11}$, unsubstituted or substituted 5- or 6-membered heteroaryl and a unsubstituted or substituted 4- to 7-membered heterocyclyl. Preferred substituents include chlorine, =O, —CN, —$SCH_3$, —$SO_2CH_3$. In this embodiment, Z can be any chemically allowed regioisomer of pyridyl, pyrimidinyl, pyridazinyl, pyrazinyl and the like, and their respective N-oxides.

In one embodiment in any of the formulae (III-LXXV), at least one substituent Z', $Z^1$, $Z^a$, $Z^b$ and $Z^c$ is cyano.

In one embodiment in any of the formulae (III-LXXV), at least one substituent Z', $Z^1$, $Z^a$, $Z^b$ and $Z^c$ is —$S(O)_2R^7$. In one particular embodiment, $R^7$ is methyl.

In one embodiment in any of the formulae (III-LXXV), at least one substituent Z', $Z^1$, $Z^a$, $Z^b$ and $Z^c$ is halogen (in particular chlorine).

In one embodiment in any of the formulae (III-LXXV), at least one substituent Z', $Z^1$, $Z^a$, $Z^b$ and $Z^c$ is —$OR^7$. In one particular embodiment, $R^7$ is methyl.

In one embodiment in any of the formulae (III-LXXV), at least one substituent Z', $Z^1$, $Z^a$, $Z^b$ and $Z^c$ is —$SR^7$. In one particular embodiment, $R^7$ is methyl.

In one embodiment in any of the formulae (III-LXXV), at least one substituent Z', $Z^1$, $Z^a$, $Z^b$ and $Z^c$ is unsubstituted $C_{1-6}$ alkyl (in particular methyl) or $C_{1-6}$ haloalkyl (in particular —$CF_3$).

In one embodiment in any of the formulae (III-LXXV), at least one substituent Z', $Z^1$, $Z^a$, $Z^b$ and $Z^c$ is substituted $C_{1-6}$ alkyl (preferably not $C_{1-6}$ haloalkyl).

In one embodiment in any of the formulae (III-LXXV), all substituents Z', $Z^1$, $Z^a$, $Z^b$ and $Z^c$ are hydrogen.

In one embodiment of any of formulae (III-LXXV), where at least one of Z', $Z^1$, $Z^a$, $Z^b$ and $Z^c$ are a substituted or unsubstituted 4- to 7-membered heterocycle, such suitable heterocyclic groups are represented by formula (A) as defined in [0022], [0023], and [0024]. Preferably, $R^{20}$, $R^{21}$, $R^{22}$, $R^{23}$, $R^{24}$, $R^{25}$, and $R^{26}$ are independently hydrogen or $C_{1-4}$alkyl. In another preferred embodiment, at least three of $R^{20}$, $R^{21}$, $R^{22}$, $R^{23}$, $R^{24}$, $R^{25}$, and $R^{26}$ are hydrogen, j is 1 or 2, k is 1 or 2 with the proviso that j+k is 3 or 4. In another preferred embodiments, at least five of $R^{20}$, $R^{21}$, $R^{22}$, $R^{23}$, $R^{24}$, $R^{25}$, and $R^{26}$ are hydrogen, j is 1 or 2, k is 1 or 2 with the proviso that j+k is 3 or 4.

In one embodiment of any of formulae (III-LXXV), at least one of Z', $Z^1$, $Z^a$, $Z^b$ and $Z^c$ is a unsubstituted or substituted heterocyclyl selected from the group including pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, and tetrahydrothiophene.

In one embodiment of any of formulae (III-LXXV), at least one of Z', $Z^1$, $Z^a$, $Z^b$ and $Z^c$ is a substituted or unsubstituted 5- or 6-membered heteroaryl selected from the group consisting of pyridyl, pyridazinyl, pyrazinyl, pyrimidinyl, triazinyl, isothiazolyl, pyrazolyl, imidazolyl, thienyl, furyl, triazolyl, tetrazolyl, oxazolyl, isoxazolyl, oxadiazolyl, thiadiazolyl, pyrrolyl, and thiazolyl.

In one embodiment of any of formulae (III-LXXV), when Z', $Z^1$, $Z^a$, $Z^b$ and $Z^c$ are substituted $C_{1-8}$ alkyl, substituted $C_{2-8}$ alkenyl or substituted $C_{2-8}$ alkynyl, it preferably has from 1 to 3 substituents independently selected from the group consisting of halogen, —OH, —$OR^{10}$, =O, —$CO_2R^{10}$, —$C(O)R^{10}$, —$C(O)NR^{11}R^{12}$, —$NR^{10}C(O)R^{11}$, —$NR^{11}R^{12}$, —$SR^{10}$, —$S(O)R^{10}$, —$S(O)_2R^{10}$, —$NR^{10}S(O)_2R^{11}$, substituted or unsubstituted phenyl, substituted or unsubstituted 5- or 6-membered heteroaryl, and substituted or unsubstituted 4- to 7-membered heterocyclyl. More preferably, it has from 1 to 3 substituents independently selected from the group consisting of halogen, —OH, —$OR^{10}$, =O, —$C(O)R^{10}$, —$CO_2R^{10}$, —$C(O)NR^{11}R^{12}$, —$NR^{10}C(O)R^{11}$, —$NR^{11}R^{12}$, —$SR^{10}$, —$S(O)R^{10}$, —$S(O)_2R^{10}$, —$S(O)_2NR^{11}R^{12}$, —$NR^{10}S(O)_2R^{11}$, and 4- to 7-membered heterocyclyl.

In one embodiment of each of the formulae (III-LXXV) when at least one of Z', $Z^1$, $Z^a$, $Z^b$ and $Z^c$ is a substituted $C_{1-8}$ alkyl, at least one substituent is a substituted or unsubstituted 4- to 7-membered heterocyclyl represented by formula (A) as defined in [0022], [0023], and [0024]. Preferably, $R^{20}$, $R^{21}$, $R^{22}$, $R^{23}$, $R^{24}$, $R^{25}$, and $R^{26}$ are independently hydrogen or $C_{1-4}$alkyl. In another preferred embodiment, at least three of $R^{20}$, $R^{21}$, $R^{22}$, $R^{23}$, $R^{24}$, $R^{25}$, and $R^{26}$ are hydrogen, j is 1 or 2, k is 1 or 2 with the proviso that j+k is 3 or 4. In another preferred embodiments, at least five of $R^{20}$, $R^{21}$, $R^{22}$, $R^{23}$, $R^{24}$, $R^{25}$, and $R^{26}$ are hydrogen, j is 1 or 2, k is 1 or 2 with the proviso that j+k is 3 or 4.

In one embodiment of each of the formulae (III-LXXV) when at least one of Z', $Z^1$, $Z^a$, $Z^b$ and $Z^c$ is a substituted $C_{1-8}$ alkyl, at least one substituent is selected from the group including pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, and tetrahydrothiophene.

In one embodiment of each of the formulae (III-LXXV) when at least one of Z', $Z^1$, $Z^a$, $Z^b$ and $Z^c$ is a substituted $C_{1-8}$ alkyl, at least one substituent is a substituted or unsubstituted 5- or 6-membered heteroaryl selected from the group consisting of pyridyl, pyridazinyl, pyrazinyl, pyrimidinyl, triazinyl, isothiazolyl, pyrazolyl, imidazolyl, thienyl, furyl, triazolyl, tetrazolyl, oxazolyl, isoxazolyl, oxadiazolyl, thiadiazolyl, pyrrolyl, and thiazolyl.

In one embodiment of the formulae (III-LXXV), Z', $Z^1$, $Z^a$, $Z^b$ or $Z^c$ are selected from one of the following residues

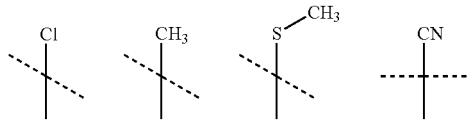

63

-continued

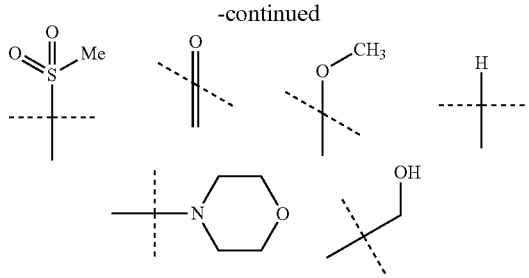

with the proviso that at least one of Z', $Z^1$, $Z^a$, $Z^b$ or $Z^c$ are other than hydrogen.

In one embodiment of the formulae (III-LXXV), Z', $Z^1$, $Z^a$, $Z^b$ or $Z^c$ are each hydrogen.

In embodiments of the formulae (XVIII, XIX, XX), $Z^1$, $Z^a$, $Z^b$ or $Z^c$ are selected such that the residue Z (as defined for formula II) is:

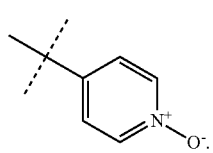

In embodiments of the formulae (XV-XVII, XXVI, XXV), $Z^1$, $Z^a$, $Z^b$ or $Z^c$ are selected such that the residue Z (as defined for formula II) is selected from the group consisting of:

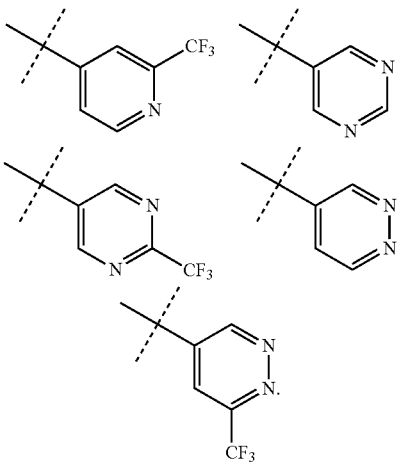

In embodiments of the formulae (IX, X, XI, XV, XVI, XVII), $Z^1$, $Z^a$, $Z^b$ or $Z^c$ are selected such that the residue Z (as defined for formula II) is selected from the group consisting of:

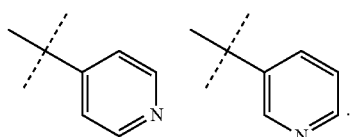

In embodiments of the formulae (III, IV, V, VI, VII, IX, X, XI, XII, XIII, XIV, XV, XVI, XVIII, XIX, XXII, XXIII, XXV, XL, XLIII, L, LVI), $Z^1$, $Z^a$, $Z^b$ or $Z^c$ are selected such that the residue Z (as defined for formula II) is selected from the group consisting of:

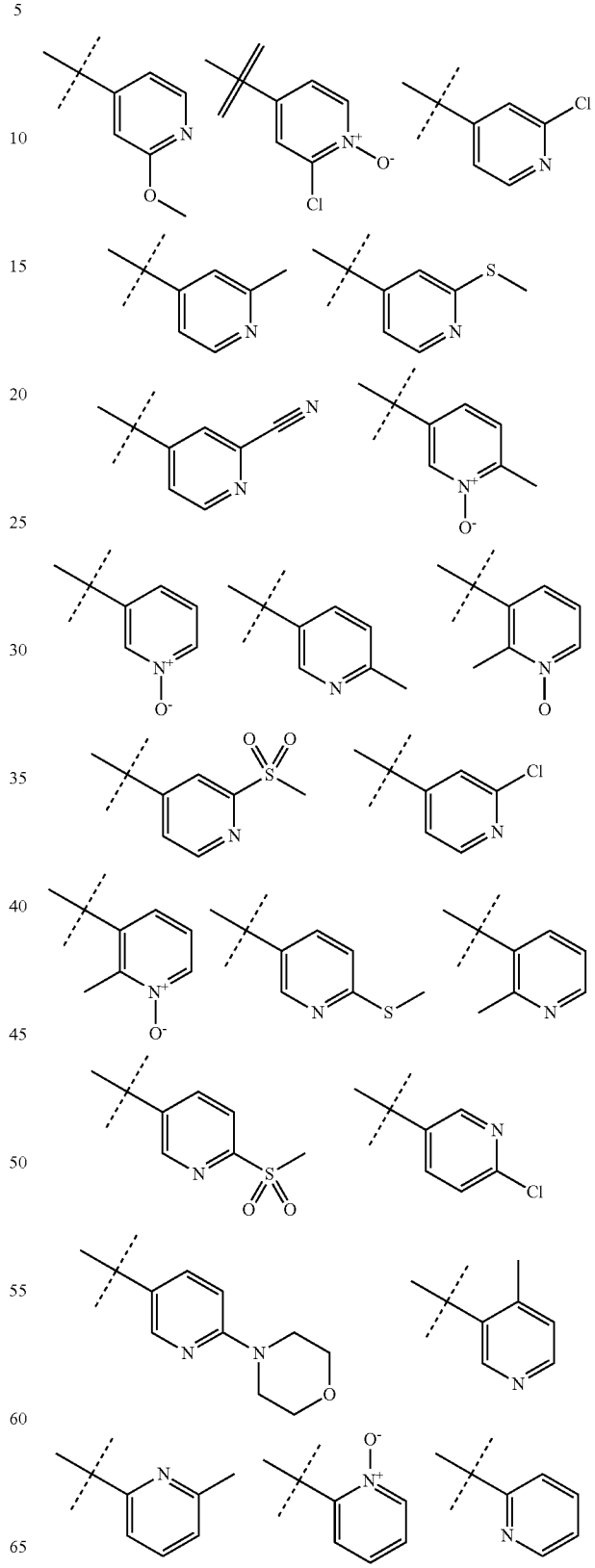

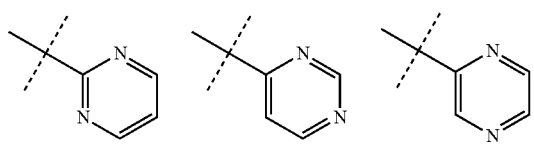

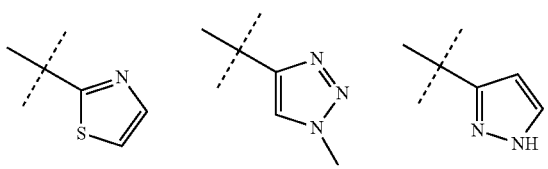

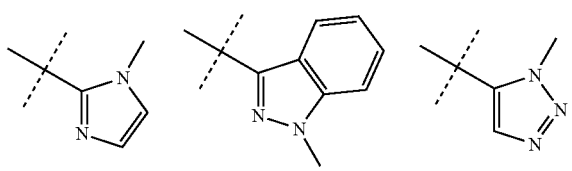

In one embodiment of any of formulae (III-LXXV), when Z', Z¹, $Z^a$, $Z^b$ and $Z^c$ is substituted heterocyclyl or heteroaryl, it preferably has from 0 to 2 substituents independently selected from the group consisting of substituted or unsubstituted $C_{1-8}$ alkyl, —$OR^{10}$, —OH, —$C(O)R^{10}$, —$C(O)NR^{11}R^{12}$, —$NR^{11}R^{12}$, and —$S(O)_2R^{10}$.

In one embodiment of any of formulae (I-LXXV), Z', Z¹, $Z^a$, $Z^b$, and $Z^c$ are each independently hydrogen, halogen, —CN, —$OR^7$, —$NR^7R^8$, —$SR^7$ (e.g., thiomethyl), —$SOR^7$, and —$SO_2R^7$ (e.g., methylsulfonyl), unsubstituted or substituted $C_{1-6}$ alkoxyl (e.g., methoxy), unsubstituted or substituted $C_{1-6}$ alkyl (e.g., methyl), unsubstituted or substituted phenyl, or unsubstituted or substituted 5- or 6-membered heterocyclyl.

In one embodiment, compounds are represented by the formula (LXXVI):

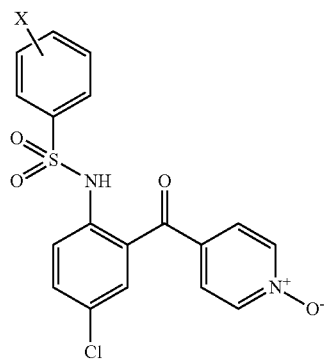

LXXVI where X represents $OCF_3$, tert-butyl, ethyl, oxazole, $C(O)CH_3$, CN, fluorine, $CF_3$, isopropyoxy, isoamyl, or hydroxybutyl.

In one embodiment, compounds are represented by the formula (LXXVI):

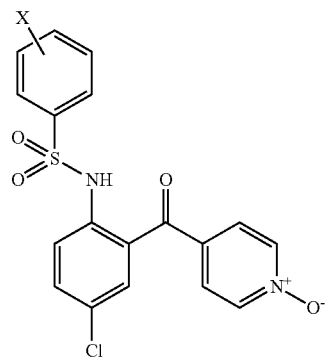

LXXVI where X represents isopropyl.

In one embodiment, compounds are represented by the formula (LXXVII):

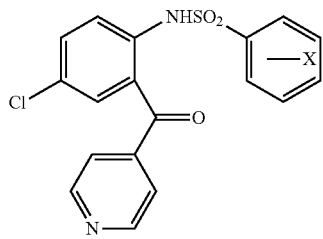

LXXVII where X is $OCF_3$, tert-butyl, ethyl, isopropyl, oxazole, $C(O)CH_3$, CN, fluorine, $CF_3$, isopropoxy, isoamyl, or hydroxybutyl.

Compositions that Modulate CCR9 Activity

In another aspect, the present invention provides compositions that modulate CCR9 activity. Generally, the compositions for modulating chemokine receptor activity in humans and animals will comprise a pharmaceutically acceptable excipient or diluent and a compound having the formula provided above as formula (I).

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 20020012680, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated enterically or otherwise by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules where the active ingredient is mixed with an inert solid diluent, for example, calcium carbonate, calcium phosphate or kaolin, or as soft gelatin capsules where the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil in water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative. and flavoring and coloring agents. Oral solutions can be prepared in combination with, for example, cyclodextrin, PEG and surfactants.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non toxic parenterally acceptable diluent or solvent, for example as a solution in 1,3-butane diol. Among the acceptable vehicles and solvents that may be employed are water, Ringer's solution and isotonic sodium chloride solution. In addition, sterile, axed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. Additionally, the compounds can be administered viaocular delivery by means of solutions or ointments. Still further, transdermal delivery of the subject compounds can be accomplished by means of iontophoretic patches and the like.

For topical use, creams, ointments, jellies, solutions or suspensions containing the compounds of the present invention are employed. As used herein, topical application is also meant to include the use of mouth washes and gargles.

The pharmaceutical compositions and methods of the present invention may further comprise other therapeutically active compounds as noted herein, such as those applied in the treatment of the above mentioned pathological conditions.

Methods of Treating CCR9-Mediated Conditions or Diseases

In yet another aspect, the present invention provides methods of treating or preventing a CCR9-mediated condition or disease by administering to a subject having such a condition or disease a therapeutically effective amount of any compound of formula (I) above. Compounds for use in the present methods include those compounds according to formula (I), those provided above as embodiments, those specifically exemplified in the Examples below, and those provided with specific structures herein. The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the phrase "CCR9-mediated condition or disease" and related phrases and terms refer to a condition or disease characterized by inappropriate, i.e., less than or greater than normal, CCR9 functional activity. Inappropriate CCR9 functional activity might arise as the result of CCR9 expression in cells which normally do not express CCR9, increased CCR9 expression (leading to, e.g., inflammatory and immunoregulatory disorders and diseases) or decreased CCR9 expression. Inappropriate CCR9 functional activity might also arise as the result of TECK secretion by cells which normally do not secrete TECK, increased TECK expression (leading to, e.g., inflammatory and immunoregulatory disorders and diseases) or decreased TECK expression. A CCR9-mediated condition or disease may be completely or partially mediated by inappropriate CCR9 functional activity. However, a CCR9-mediated condition or disease is one in which modulation of CCR9 results in some effect on the underlying condition or disease (e.g., a CCR9 antagonist results in some improvement in patient well being in at least some patients).

The term "therapeutically effective amount" means the amount of the subject compound that will elicit the biological or medical response of a cell, tissue, system, or animal, such as a human, that is being sought by the researcher, veterinarian, medical doctor or other treatment provider.

Diseases and conditions associated with inflammation, immune disorders, infection and cancer can be treated or prevented with the present compounds, compositions, and methods. In one group of embodiments, diseases or conditions, including chronic diseases, of humans or other species can be treated with inhibitors of CCR9 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as fibromyalagia, scleroderma, ankylosing spondylitis, juvenile RA, Still's disease, polyarticular juvenile RA, pauciarticular juvenile RA, polymyalgia rheumatica, rheumatoid arthritis, psoriatic arthritis, osteoarthritis, polyarticular arthritis, multiple sclerosis, systemic lupus erythematosus, type I diabetes, type II diabetes, glomerulonephritis, and the like, (10) graft rejection (including allograft rejection), (11) graft-v-host disease (including both acute and chronic), (12) other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout, (13) immune mediated food allergies such as Coeliac (Celiac) disease (14) pulmonary fibrosis and other fibrotic diseases, and (15) irritable bowel syndrome.

In another group of embodiments, diseases or conditions can be treated with modulators and agonists of CCR9 function. Examples of diseases to be treated by modulating CCR9 function include cancers, cardiovascular diseases, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions. The term "organ transplant conditions" is means to include bone marrow transplant conditions and solid organ (e.g., kidney, liver, lung, heart, pancreas or combination thereof) transplant conditions.

Preferably, the present methods are directed to the treatment of diseases or conditions selected from inflammatory bowel disease including Crohn's disease and Ulcerative Colitis, allergic diseases, psoriasis, atopic dermatitis and asthma, autoimmune disease such as rheumatoid arthritis and immune-mediated food allergies such as Coelaic disease.

Depending on the disease to be treated and the subject's condition, the compounds and compositions of the present invention may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional non toxic pharmaceutically acceptable carriers, adjuvants and vehicles appropriate for each rouse of administration. The present invention also contemplates administration of the compounds and compositions of the present invention in a depot formulation.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

In still other embodiments, the present methods are directed to the treatment of allergic diseases, where a compound or composition of the invention is administered either alone or in combination with a second therapeutic agent, where said second therapeutic agent is an antihistamine. When used in combination, the practitioner can administer a combination of the compound or composition of the present invention and a second therapeutic agent. Also, the compound or composition and the second therapeutic agent can be administered sequentially, in any order.

In yet other embodiments, the present methods are directed to the treatment of psoriasis where a compound or composition of the invention is used alone or in combination with a second therapeutic agent such as a corticosteroid, a lubricant, a keratolytic agent, a vitamin $D_3$ derivative, PUVA and anthralin.

In other embodiments, the present methods are directed to the treatment of atopic dermatitis using a compound or composition of the invention either alone or in combination with a second therapeutic agent such as a lubricant and a corticosteroid.

In further embodiments, the present methods are directed to the treatment of asthma using a compound or composition of the invention either alone or in combination with a second therapeutic agent such as a β2-agonist and a corticosteroid.

The compounds and compositions of the present invention can be combined with other compounds and compositions having related utilities to prevent and treat the condition or disease of interest, such as inflammatory conditions and diseases, including inflammatory bowel disease, allergic diseases, psoriasis, atopic dermatitis and asthma, and those pathologies noted above. Selection of the appropriate agents for use in combination therapies can be made one of ordinary skill in the art. The combination of therapeutic agents may act synergistically to effect the treatment or prevention of the various disorders. Using this approach, one may be able to achieve therapeutic efficacy with lower dosages of each agent, thus reducing the potential for adverse side effects.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

EXAMPLES

Reagents and solvents used below can be obtained from commercial sources such as Aldrich Chemical Co. (Milwaukee, Wis., USA). $^1$H-NMR were recorded on a Varian Mercury 400 MHz NMR spectrometer. Significant peaks are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM $NH_4OAc$ in acetonitrile/water as delivery system.

Compounds within the scope of this invention can be synthesized as described below, using a variety of reactions known to the skilled artisan. A sample of useful routes to both the benzophenone and heteroaryl derived subunits and to fully elaborated sulfonamide molecules of formula (I) within this claim are provided below. In the descriptions of the syntheses that follow, some precursors were obtained from commercial sources. These commercial sources include Aldrich Chemical Co., Acros Organics, Ryan Scientific Incorporated, Oakwood Products Incorporated, Lancaster Chemicals, Sigma Chemical Co., Lancaster Chemical Co., TCI-America, Alfa Aesar, Davos Chemicals, and GFS Chemicals.

Compounds of the invention can be prepared using conventional synthetic methodology. Examples of approaches that may be taken to synthesize these compounds are shown below. Nonetheless, one skilled in the art will recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are within the scope of the invention.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Preparation of CCR 9 Modulators

The following examples are offered to illustrate, but not to limit, the claimed invention.

Additionally, those skilled in the art will recognize that the molecules claimed in this patent may be synthesized using a variety of standard organic chemistry transformations.

Certain general reaction types employed widely to synthesize target compounds in this invention are summarized in the examples. Specifically, generic procedures for sulfonamide formation, pyridine N-oxide formation and 2-aminophenyl-arylmethanone synthesis via Friedel-Crafts type approaches are given, but numerous other standard chemistries are described within and were employed routinely.

While not intended to be exhaustive, representative synthetic organic transformations which can be used to prepare compounds of the invention are included below.

These representative transformations include; standard functional group manipulations; reduction such as nitro to amino; oxidations of functional groups including alcohols and pyridines; aryl substitutions via IPSO or other mechanisms for the introduction of a variety of groups including nitrile, methyl and halogen; protecting group introductions and removals; Grignard formation and reaction with an electrophile; metal-mediated cross couplings including but not limited to Buckvald, Suzuki and Sonigashira reactions; halogenations and other electrophilic aromatic substitution reactions; diazonium salt formations and reactions of these species; etherifications; cyclative condensations, dehydrations, oxidations and reductions leading to heteroaryl groups; aryl metallations and transmetallations and reaction of the ensuing aryl-metal species with an electrophile such as an acid chloride or Weinreb amide; amidations; esterifications; nuclephilic substitution reactions; alkylations; acylations; sulfonamide formation; chlorosulfonylations; ester and related hydrolyses, and the like.

Compounds of the invention, including those listed in the table of activities, can be made by the methods and approaches described in the following experimental section and by the use of standard organic chemistry transformations well known to those skilled in the art.

The following general procedures summarize methodologies frequently utilized to synthesize the intermediates and compounds of the invention. Specific examples of the use of these general methodologies is given in the detailed experimental sections for individual compounds.

Additionally, various organic chemistry transformations are described, as they relate to the synthesis of specific comounds of the invention. These specific synthetic approaches and methodologies can also be applied, in a general sense, to access general classes of compounds claimed in this invention.

Additionally, it is envisaged that many standard organic chemistry transformations, well known to those skilled in the art, including but not limited to those outlined previously in the introductory comments section to the preparation of CCR9 modulators, can be applied to enable the synthesis of broad classes of compounds and intermediates of the invention.

General Procedure for the Preparation of N-Aryl-benzenesulfonamides

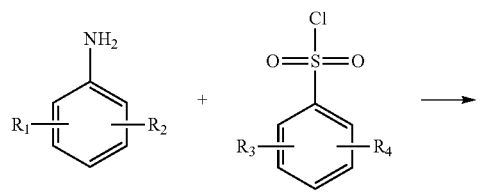

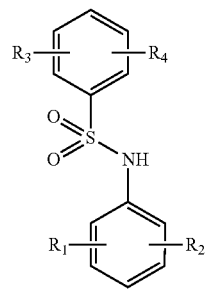

To the desired aniline (0.5 mmol) dissolved in pyridine and cooled in an ice-water bath was added a solution of an aryl sulfonyl chloride (0.5 mmol) dissolved in cold pyridine. The reaction mixture was then heated to 60° C. with gentle shaking for 16 h. Evaporation of the solvent with standard workup followed by either flash chromatography or reversed phase HPLC yielded the corresponding N-aryl-benzenesulfonamides.

General Procedure for the Synthesis of (2-Aminophenyl)-pyridinyl-methanones and (2-Amino-phenyl)-heteroaryl-methanones

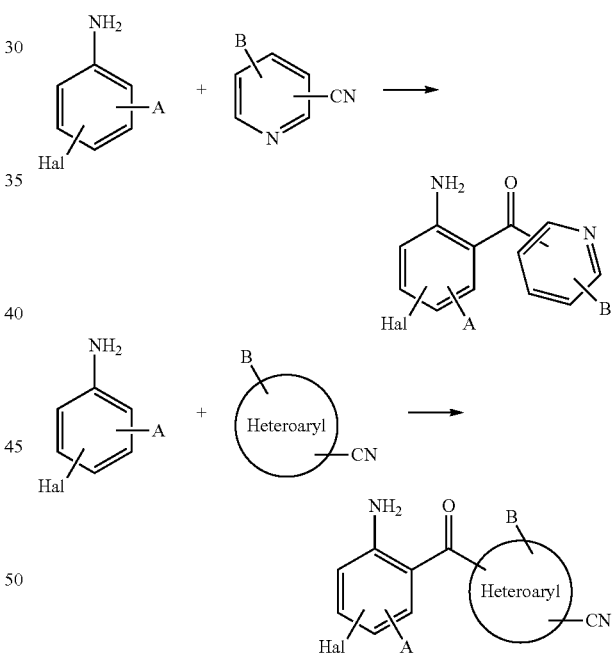

To 12.5 mL 1 M BCl$_3$ (12 mmol, 1.2 eq.) in methylene chloride stirred at 0° C. was added a solution of the desired haloaniline (10 mmol, 1.0 eq.) in 15 mL of TCE drop wise over 20 minutes. After 10 minutes the desired cyanopyridine (11 mmol, 1.1 eq.) was added followed by AlCl$_3$ (15 mmol, 1.5 eq.). The reaction was brought to RT, stirred for an hour then heated at 80-90° C. until all of the DCM was distilled off. The reaction mixture was then refluxed at 160° C. for 4 hours, cooled to RT and stirred overnight. 10 mL 3 M HCl were carefully added and the mixture was refluxed at 120° C. for 2-3 hours while reaction progress was monitored by LC/MS. The crude reaction was cooled to RT and 100 mL water were added. The crude mixture was extracted with DCM (2×50 mL), the aqueous layer was set aside and the organic layer was back extracted with 50 mL 1 $\underline{M}$ HCl (aq.). All aqueous layers were combined, brought to pH 12 with 3 $\underline{M}$ NaOH (aq.) and extracted with DCM (4×50 mL). The DCM layer was dried on $Na_2SO_4$, filtered and concentrated by rotary evaporation. The crude product was washed liberally with $Et_2O$ and dried under vacuum, and further purified by conventional techniques such as column chromatography when necessary.

Alternate General Procedure (2) for the Synthesis of (2-Amino-phenyl)-pyridinyl-methanones and (2-Amino-phenyl)-heteroaryl-methanones

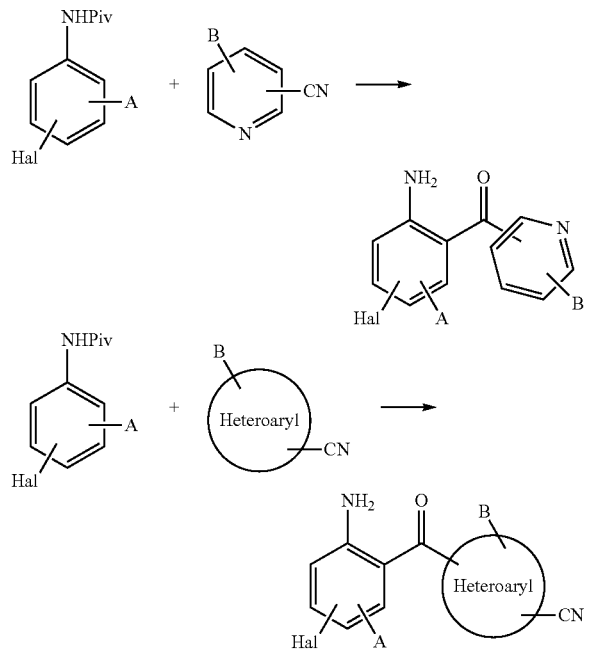

To a solution of desired aniline (40 mmol) in 25 mL pyridine was added 5.3 mL (43.1 mmol) of pivaloyl chloride and the reaction mixture stirred overnight at room temperature. The mixture was poured into vigorously stirring 6M HCl, and the solids were collected by vacuum filtration, washed well with $H_2O$, and dried in vacuo.

2,2-dimethyl propanamide protected aniline (0.0095 mol) in dry THF (40 ml) was cooled to −5° C. n-Butyl lithium (24 ml, 1.2 M, 0.0284 mol) was added dropwise and the reaction stirred at the same temperature for 2 h. The reaction mixture was cooled to −70° C. and to this was added the desired aryl or heteroaryl carboxylic acid (0.0142 mol), dissolved in dry THF (10 ml), dropwise. The mixture was stirred at room temperature for 18 h, quenched with water and extracted with ethyl acetate. The extract was washed with brine solution and concentrated. The product was purified by column using 5-10% of ethyl acetate in pet ether as eluent.

Removal of the pivaloyl protecting group form the amino ketone (0.4 g, 0.0013 mol) in 2 ml of methanol was effected via addition of potassium hydroxide (0.48 g, 0.00857 mol) in 1.2 ml of water. The reaction mixture was heated at 70° C. for 6 h, diluted with water and extracted with ethyl acetate. The extract was washed with water, brine and concentrated. The crude material was purified by column chromatography.

Alternatively, 6N HCl (10 ml) and intermediate pivaloyl protected aminoketone (1.2 g, 3.755 mmol) were heated at 90° C. overnight, cooled to room temperature, the reaction mixture basified by adding saturated sodium bicarbonate solution and extracted with ether. The organic layer was washed with brine, dried over sodium sulfate and concentrated. The product was purified by column chromatography.

Alternate General Procedure (3) for the Synthesis of (2-Amino-phenyl)-pyridinyl-methanones and (2-Amino-phenyl)-heteroaryl-methanones

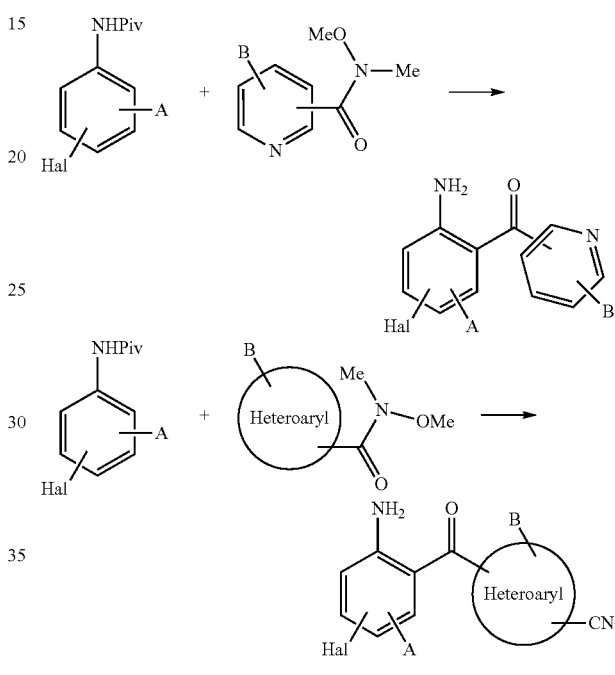

Trimethylacetyl chloride was added drop wise to a solution of desired aniline in dry pyridine and the reaction was stirred under nitrogen overnight. About half of the pyridine was removed by rotary evaporation, then the mixture was treated with 6M hydrochloric acid and extracted with ethyl acetate. The extracts were washed with saturated aqueous $NaHCO_3$ and with water, then were dried (MgSO4), filtered and concentrated by rotary evaporation.

EDC and desired heteroaryl carboxylic acid were stirred in acetonitrile-THF with N,O-dimethylhydroxylamine hydrochloride and triethylamine. After stirring overnight at ambient temperature, the resulting reaction mixture was added to ice water and extracted with ethyl acetate (3×100 mL). The extracts were dried, filtered, and concentrated.

To a stirred solution of the pivaloyl protected intermediate in dry THF was added 2.5M n-butyllithium in hexane at −40° C. and the mixture was stirred at 0° C. for 2 h. A solution of the Weinreb amide in dry THF was added dropwise and the reaction was stirred at ambient temp overnight. The mixture was diluted with water and extracted with ethyl acetate and the organic layer was dried ($MgSO_4$), filtered and concentrated, to yield, after purification by HPLC or column chromatography, the pivaloyl protected aminoketone intermediate.

Deprotection with 70% sulfuric acid was carried out at 75° C. and progress monitored by LC/MS. The reaction was allowed to cool to ambient temperature, and was washed with ether-hexane. The acidic aqueous layer was cooled in an ice bath and aqueous NaOH was added drop wise to basify the mixture. The product was extracted with ethyl acetate and the extracts were washed with saturated aqueous NaHCO3 (2×100 mL), with saturated aqueous sodium chloride, dried (MgSO$_4$), filtered and concentrated, yielding the desired (2-Amino-phenyl)-heteroaryl-methanone.

General Procedure for the Synthesis of Sulfonamide Pyridine-N-Oxides

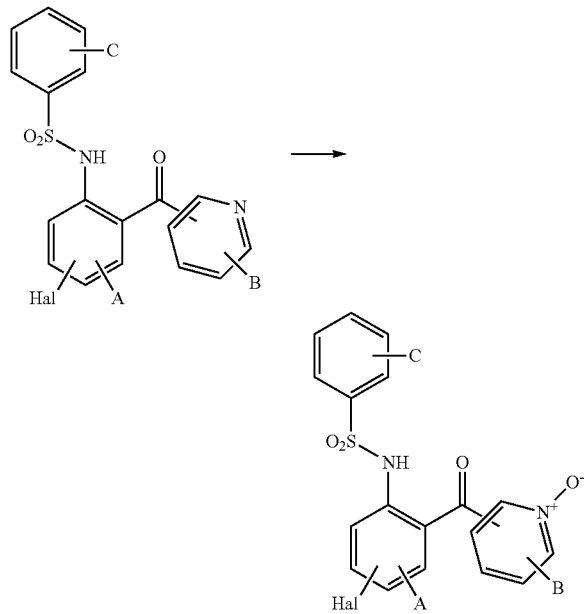

The desired N-Aryl-benzenesulfonamide (250 µmol) was dissolved in 2 mL DCM and m-CPBA (1.0-1.5 eq) was then added. The reaction was shaken at RT and monitored by LC-MS. Additional m-CPBA was added as needed in aliquots until the reaction was complete. In most cases the reaction required 15-24 h rxn time. Standard workup led to the isolation of crude products, which were purified by column chromatography.

General Procedure for the Synthesis of Substituted Phenyl Sulfonyl Chlorides via Chlorosulfonation

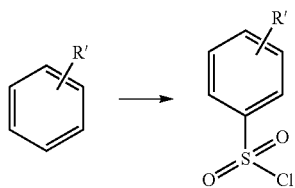

The desired benzene derivative (1.4 mmol) was dissolved in CHCl$_3$ (15 mL) at 0° C., and to this was added chlorosulfonic acid (4.2 mmol). After 30 minutes, the reaction mixture was warmed to room temperature, and additional chlorosulfonic acid (4.2 mmol) was added. After a further hour, the reaction mixture was cooled to 0° C., and crushed ice added to the reaction. The reaction mixture was partitioned between 1M pH7 phosphate buffer and ether, and the ether layer washed with saturated aqueous NaCl, dried over Na$_2$SO$_4$, filtered, and concentrated in vacuo to yield crude product.

General Procedure for the Synthesis of Substituted Phenyl Sulfonyl Chlorides via Diazonium Salt Intermediates

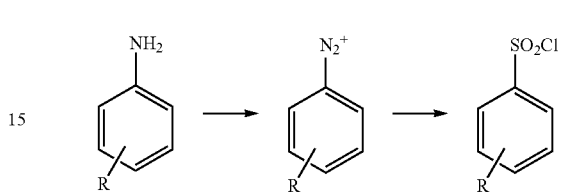

The desired aniline (0.0848 mol) was added slowly to concentrated HCl (109.2 ml), the reaction stirred at room temperature for 15 min, then cooled to 0° C., sodium nitrite (6.2 g, 0.1103 mol in 26 ml of water) added dropwise and the reaction stirred for 15 min.

Separately, distilled water (0.198 ml) was cooled to 0° C. and thionyl chloride (42.9 g, 0.3605 mol) was added dropwise, the mixture warmed to and stirred at room temperature for 17 h, then re-cooled to 0° C., and copper (I) chloride (0.120 g) added in small portions with further stirring for 30 mins to yield a yellowish green solution (Solution A).

This Cu(I) solution (A) was added dropwise to the aniline/HCl solution at −5° C., and stirring continued at 0° C. for 75 min. The reaction mixture was diluted with chloroform. The organic layer was separated, washed with brine, dried over sodium sulphate and concentrated in vacuo.

General Procedure for the Synthesis of Heterocyclyl Substituted Phenylsulfonyl Derivatives

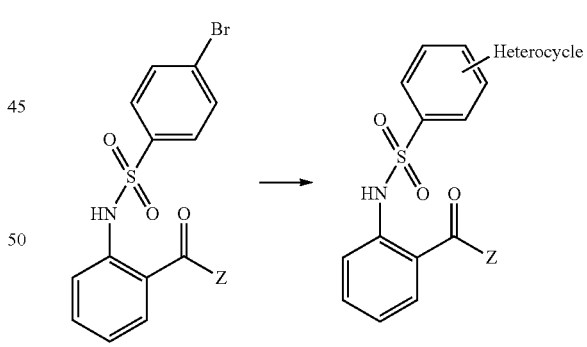

The desired bromobenzenesulfonamide derivative (0.22 mmol) was dissolved in 6 ml anhydrous dioxane, and to this solution was added potassium phosphate tribasic monohydrate (1.32 mmol), rac-2,2'-bis(diphenylphosphino)-1,1'-binaphthyl (0.032 mmol), followed by the desired heterocycle (1.1 mmol). The mixture was purged under nitrogen, and Pd (dba)$_3$ (0.01 mmol) was added. The reaction mixture was heated overnight at 90° C., cooled, water (5 mL) added, and extracted with ethyl acetate 3 times. The combined organic layer was washed with brine, dried over magnesium sulfate, filtered and concentrated. The crude reaction mixture was purified using HPLC.

General Procedure for the Synthesis of Heteroaryl Substituted Phenylsulfonyl Derivatives

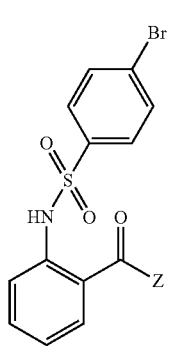 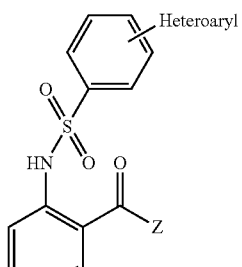

The desired bromobenzenesulfonamide derivative (0.25 g, 0.55 mmol) was dissolved in 2.5 ml of anhydrous dimethylformamide. To this solution was added 0.14 g (1.3 mmol) sodium carbonate, suitable heteroaryl-3-boronic acid (0.68 mmol), and Pd(PPh$_3$)$_4$ 19 mg (0.014 mmol). The reaction mixture was heated overnight at 80° C. under a nitrogen atmosphere. The mixture was quenched with water and extracted 3 times with dichloromethane. The organic layer was dried over magnesium sulfate, filtered, and concentrated, and the crude product purified by flash column chromatography.

Examples of Alternate Approaches Towards the Syntheses of Functionalized Alkyl Phenyl Sulfonyl Chlorides and Alkylsulfonyl Phenyl Sulfonyl Chlorides i)

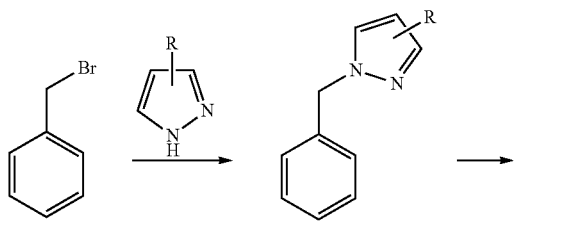

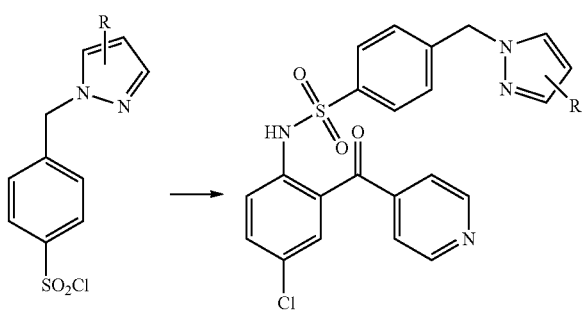

ii)

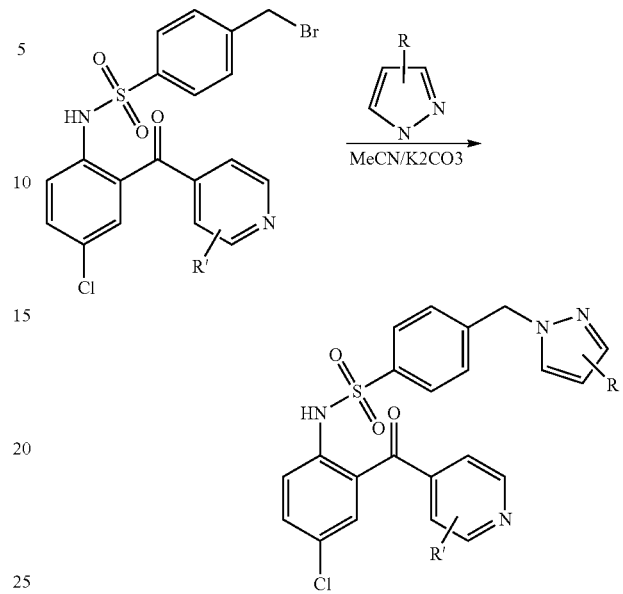

iii)

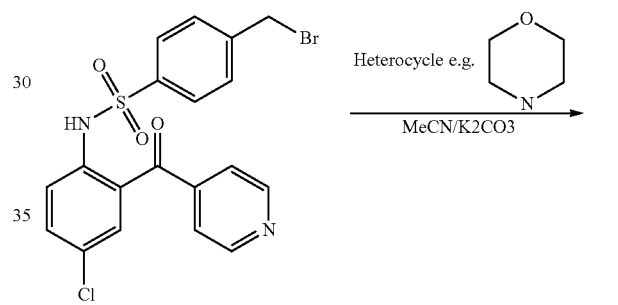

iv)

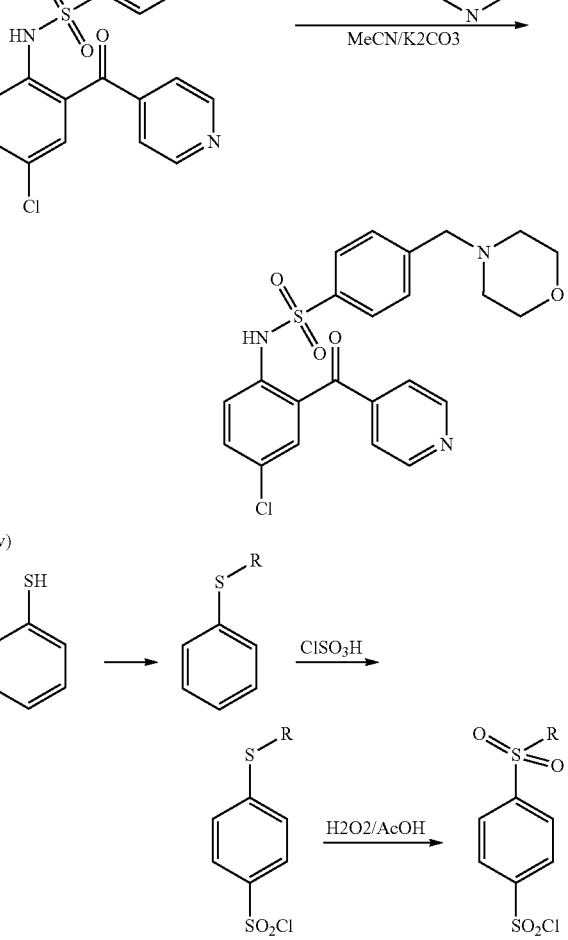

Examples of Alternate Approaches Towards the Synthesis of
(2-Amino-phenyl)-heteroaryl-methanones
i)
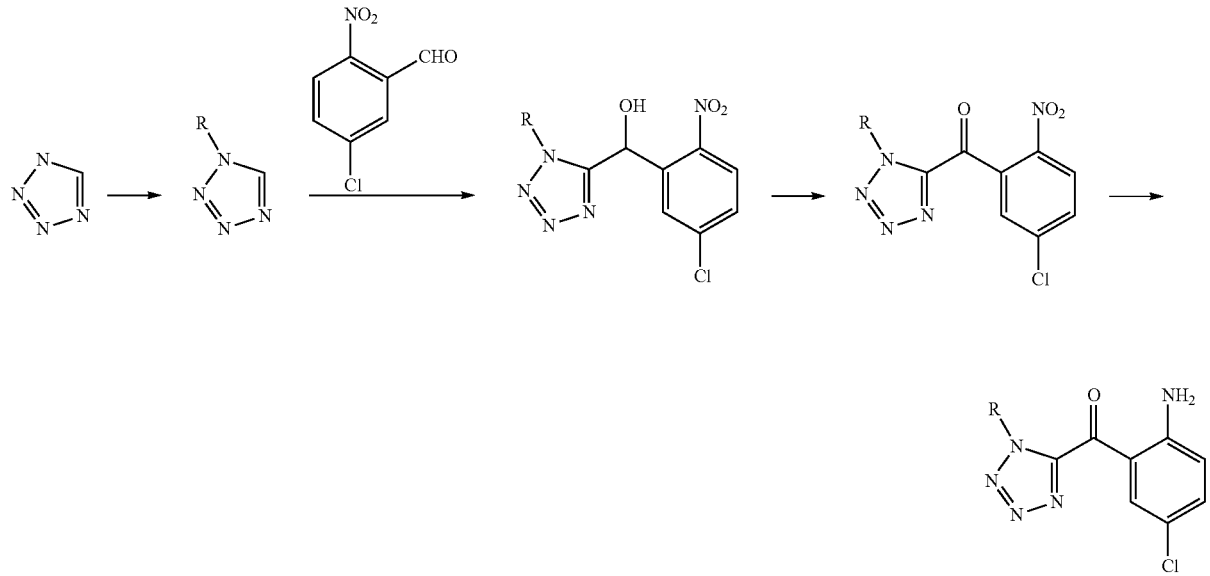
ii)
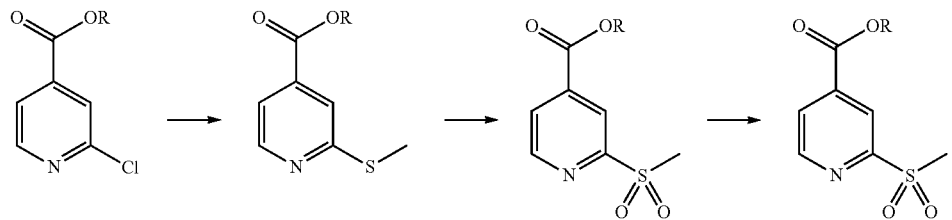
iii)
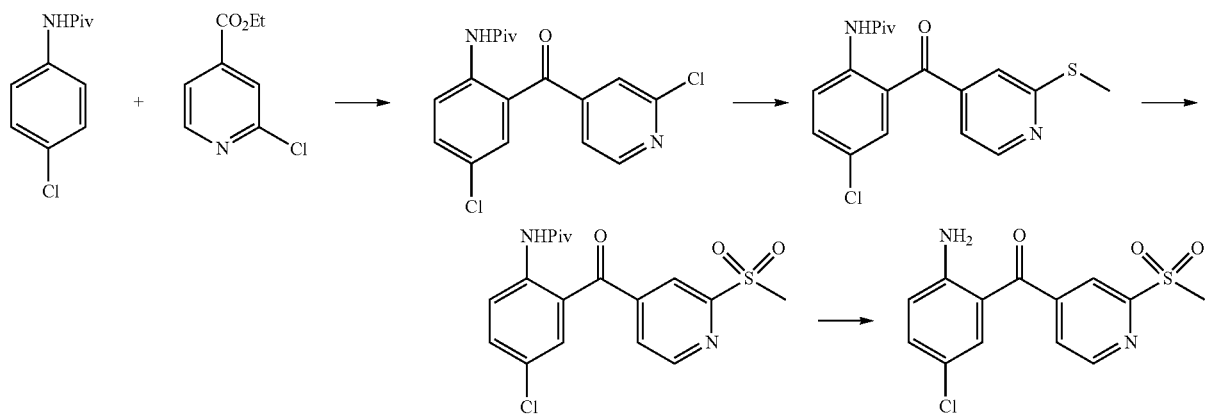

-continued
iv)
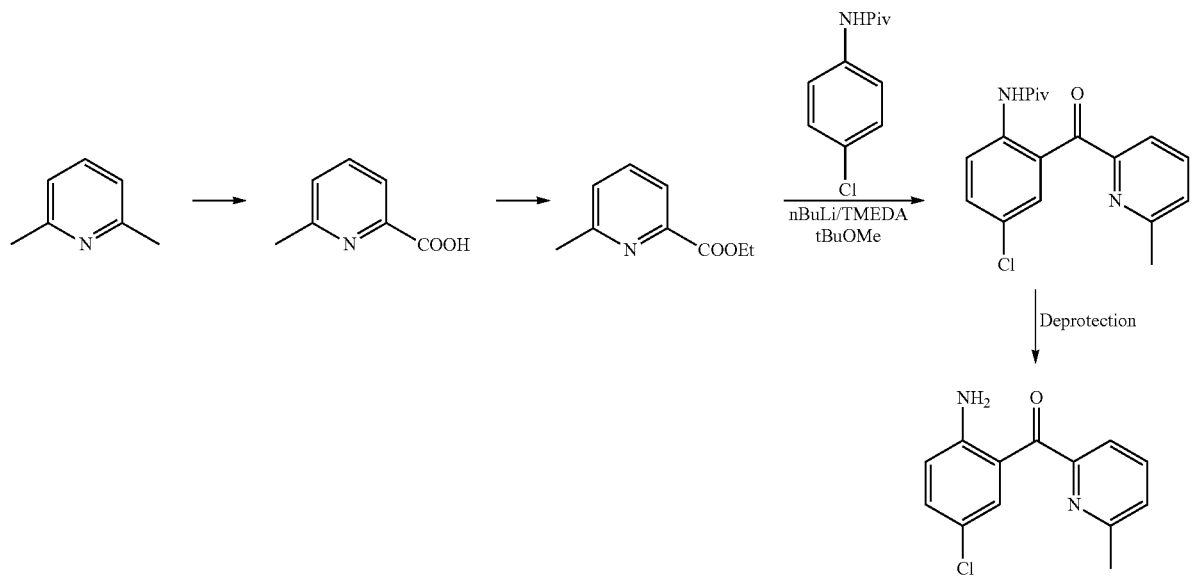
v)
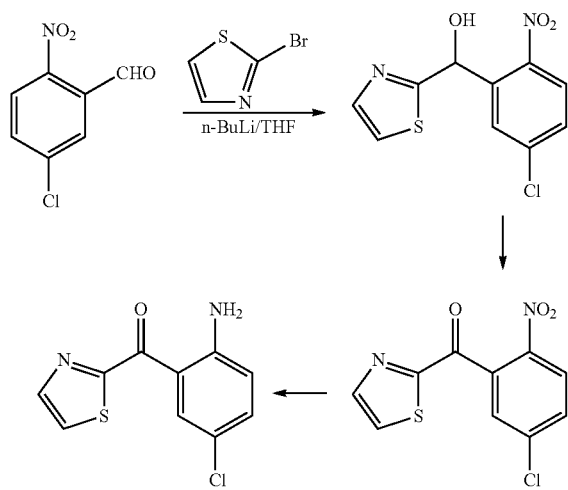
vi)
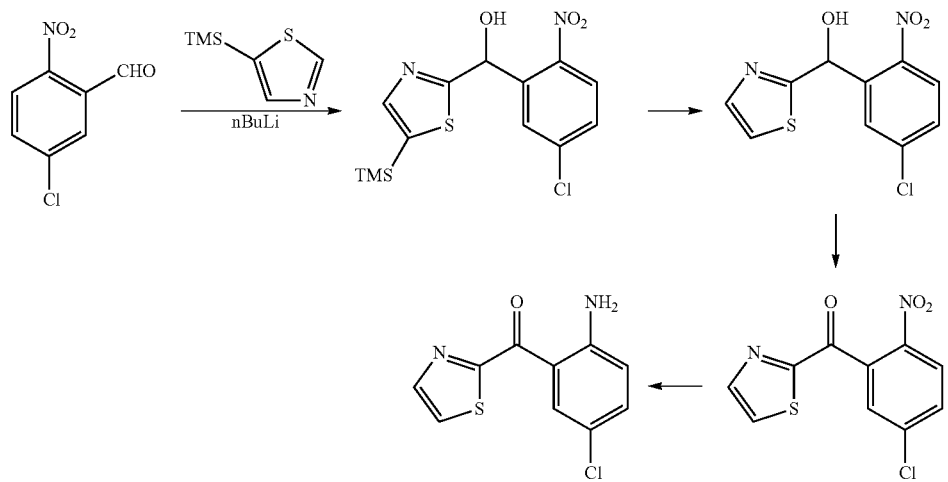

vii)

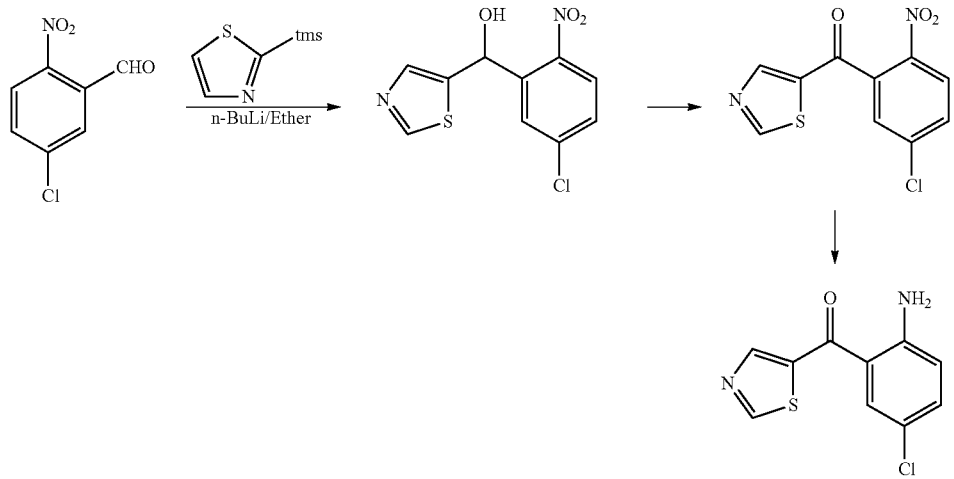

viii)

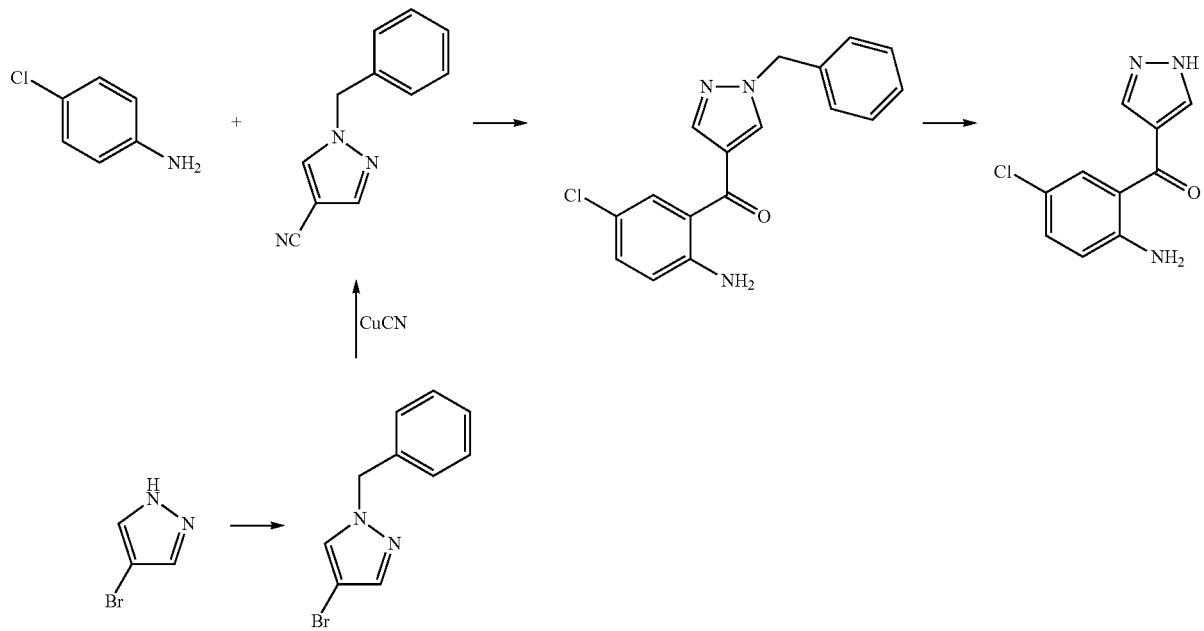

Syntheses of (2-Amino-phenyl)-pyridinyl-methanones and (2-Amino-phenyl)-heteroaryl-methanones Synthesis of(2-Amino-5-chloro-phenyl)-pyridin-4-yl-methanone

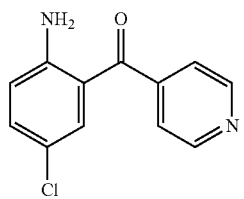 [SMILES: Nc1ccc(Cl)cc1C(=O)c1ccncc1]

A solution of 4-chloroaniline (2.0 g, 16 mmol) in 30 mL of TCE was added drop wise to a solution of BCl₃ (1M in DCM) (24 ml, 24 mmol) with ice bath cooling, over a period of 15 min and the reaction mixture stirred at that temperature for an additional 10 min. 4-Cyanopyridine (2.0 g, 19 mmol) and AlCl₃ (3.0 g, 22 mmol) were added with ice-water cooling. The solution was allowed to warm to room temperature and stirred for 30 min. The resulting solution was refluxed at 160° C. for 4 h and stirred at room temperature overnight. The reaction mixture was then treated with 30 mL of 3N HCl and the mixture was refluxed at 110° C. for 1.5 h. The reaction mixture was allowed to cool down to room temperature and the solution was adjusted to pH12 with 6N NaOH and then diluted water and DCM. The resulting two layers were separated and the aqueous layer was extracted with DCM three times and the organic layers combined and dried over sodium sulfate. After removal of the solvent, the resulting solid was washed with ether to yield (2-amino-5-chloro-phenyl)-pyridin-4-yl-methanone (2.8 g, 75%).

Synthesis of(2-Amino-5-chloro-phenyl)-(6-methyl-pyridin-2-yl) methanone

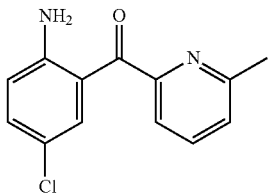 [SMILES: Cc1cccc(C(=O)c2cc(Cl)ccc2N)n1]

To 20 mL 1M BCl3 (20 mmol, 2.3 eq.) in DCM stirred at 0° C. was added a solution of 1.1 g 4-chloroaniline (8.6 mmol, 1.0 eq.) in 15 mL of TCE drop wise over five minutes. After 10 minutes 1.1 g of 2-cyano-6-methyl pyridine (1.1 eq.) were added to the reaction mixture and after 2 minutes 1.6 g AlCl₃ (12 mmol, 1.4 eq.) was added. After 5 minutes the reaction was brought to RT, stirred for an hour then heated at 160° C. for 17 hours. 100 mL 3M HCl were added and the reaction is monitored by LC/MS. After 6 hours the reaction was removed from heat, cooled to RT and 300 mL water were added. The crude mixture was extracted with DCM (1×500 mL), the aqueous layer was set aside and the organic layer was back extracted with 300 mL 3M HCl (aq.). All aqueous layers were combined, brought to pH 11 with 3M NaOH (aq.) and extracted with DCM. The DCM layer was dried on Na₂SO₄, filtered and concentrated by rotary evaporation. Preparatory chromatography afforded the product as a cream colored solid which was converted to its HCl salt before being characterized. ¹H NMR: δ (ppm): 2.83 (s, 3H), 7.32 (d, J=2.0 Hz, 1H), 7.34 (d, J=1.6 Hz, 1H), 7.49 (d, J=7.6 Hz, 1H), 7.82-7.85 (m, 2H), 7.99 (t, J=7.6 Hz, H), 8.27 (d, J=7.6 Hz, 1H), 10.83 (s, 1H). MS: (M+H)/z=247.0

Synthesis of(5-chloro-2-nitro-phenyl)-(6-chloro-pyridin-3-yl)-methanol

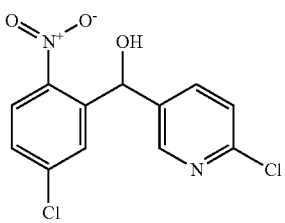 [SMILES: O=[N+]([O-])c1ccc(Cl)cc1C(O)c1ccc(Cl)nc1]

A solution of 1.0 g 2-chloro-5-iodopyridine (4.1 mmol, 1.0 eq.) in 10 mL anhyd. THF was stirred at −40° C. to −50° C. After five minutes, 2.2 mL of 2.1 M ⁱPrMgBr/THF (4.6 mmol, 1.1 eq.) were added drop wise over 1 minute and the reaction mixture is maintained at −40 to −50° C. for 30 minutes. 1.3 g 2-nitro-5-chlorobenzaldehyde (7.0 mmol, 1.7 eq.) was then added and the reaction was maintained at −50° C. After 1 hour, the reaction was allowed to warm to −10° C., and quenched with 50 mL saturated brine after a further fifteen minutes. The crude product was extracted with EtOAc, dried on Na₂SO₄ and concentrated by rotary evaporation to yield desired product. MS: (M+H)/z=298.9

Synthesis of(5-Chloro-2-nitro-phenyl)-(6-chloro-pyridin-3-yl)-methanone

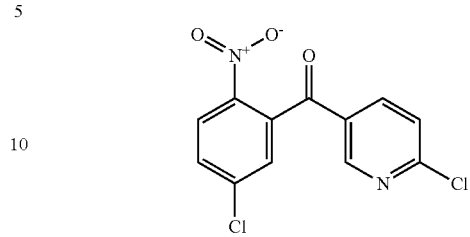

To (5-Chloro-2-nitro-phenyl)-(6-chloro-pyridin-3-yl)-methanol was added an excess (ca. 2 eq.) of PDC in DCM. The suspension was shaken at room temperature overnight. The reaction was monitored by LC-MS, another 1-2 eq. of PDC was added and the reaction was shaken for another 6 hours. The crude product was filtered through Celite and purified by flash chromatography (silica gel, DCM). ¹H NMR (CDCl₃): δ (ppm): 7.50 (d, J=2.4 Hz, 1H), 7.79 (d, J=8.0 Hz, 1H), 7.68 & 7.70 (dd, J=8.8 Hz, 2.0 Hz, 1H), 8.09-8.11 (m, 1H), 8.24 (d, J=8.8 Hz, 1H), 8.57 (d, J=2.0 Hz, 1H. MS: (M+H)/z=296.9

Synthesis of(2-Amino-5-chloro-phenyl)-(6-chloro-pyridin-3-yl)-methanone

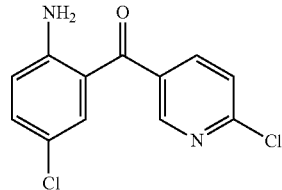 [SMILES: Nc1ccc(Cl)cc1C(=O)c1ccc(Cl)nc1]

3-(5-chloro-2-nitrophenyl)-pyridinylmethanone was added to a mixture of concentrated HCl, DMF, SnCl₂ and heated at 130° C. The reaction was monitored by LC/MS and removed from heat after 2 h. The crude reaction was treated with aq. K₂CO₃, extracted into DCM and concentrated by rotary evaporation. The crude product was purified by preparatory chromatography. MS: (M+H)/z=267.0

Synthesis ofN-(4-Chloro-phenyl)-2,2-dimethyl-propionamide

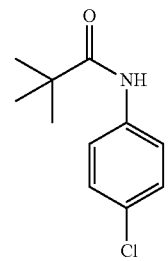

To a solution of 4-chloroaniline (5.0 g, 39.2 mmol) in 25 mL pyridine was added 5.3 mL (43.1 mmol) of pivaloyl chloride and the reaction mixture stirred overnight at room temperature. The mixture was poured into vigorously stirring 6M HCl, and the solids were collected by vacuum filtration, washed well with H₂O, and dried in vacuo to yield the title compound. 1H NMR (CDCl3) δ 7.47 (d, J=9.2 Hz, 2H) 7.30 (s, 1H) 7.27 (d, J=8.8 Hz, 2H) 1.32 (s, 9H) MS (ES) m/z=212.1

Synthesis of N-[4-chloro-2-(hydroxy-pyridin-3-yl-methyl)-phenyl]-2,2-dimethyl-propionamide

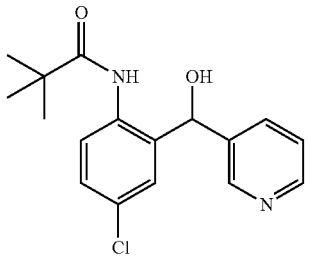 [SMILES: CC(C)(C)C(=O)Nc1ccc(Cl)cc1C(O)c1cccnc1]

N-(4-Chloro-phenyl)-2,2-dimethyl-propionamide (3.0, 14.2 mmol) was dissolved in 15 mL THF in a dry 100 mL flask fitted with a rubber septa and nitrogen inlet and cooled to 0° C. in ice water bath for 25 minutes. A solution of 2.5M BuLi in hexane (17.0 mL, 42.6 mmol) was added and the mixture stirred for 45 minutes. To the thick yellow precipitate that formed was added a solution of pyridine-3-carboxaldehyde (3.03 g, 28.4 mmol) in 15 mL THF. The ice bath was removed and the mixture was allowed to stir at room temperature for 45 minutes and the reaction was quenched with 25 mL H₂O. The mixture was transferred to a separating funnel, and the aqueous phase was discarded. The organics were dried in vacuo to yield product as an orange oil. 1H NMR (CDCl3) δ 8.85 (m, 1H) 8.54 (m, 1H) 8.42 (m, 1H) 8.10 (dd, J=8.8 Hz, 2.8 Hz, 1H) 7.50 (d, J=8.0 Hz, 1H) 7.31 (m, 1H) 7.23 (m, 1H) 7.10 (m, 1H) 5.85 (m, 1H) 1.70 (d, 1H) 1.08 (s, 9H); MS (ES) m/z=319.1 (MH)⁺

Synthesis of N-[4-chloro-2-(pyridine-3-carbonyl)-phenyl]-2,2-dimethyl-propionamide

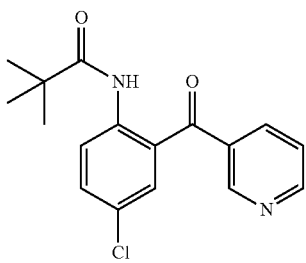 [SMILES: CC(C)(C)C(=O)Nc1ccc(Cl)cc1C(=O)c1cccnc1]

N-[4-chloro-2-(hydroxy-pyridin-3-yl-methyl)-phenyl]-2,2-dimethyl-propionamide (1.0 g, 3.14 mmol) was dissolved in 5 mL pyridine and treated with CrO₃ (0.75 g, 7.5 mmol, 2.39 eq). The mixture was stirred under N₂ at room temperature for five hours, diluted with 20 mL 1:2 EtOAc/H₂O, and filtered through Celite. The aqueous phase was separated and discarded, then the organics dried under vacuum yielding product (680 mg, 70%). 1H NMR (CDCl3) δ 11.06 (s, 1H) 8.92 (d, J=2.4 Hz, 1H) 8.84 (d, J=8.0 Hz, 1H) 8.73 (d, J=9.2 Hz, 1H) 8.00 (d, J=8.0 Hz, 1H) 7.56 (dd, J=11.2 Hz, 2.0 Hz, 1H) 7.48 (m, 2H) 1.36 (s, 9H) MS (ES) m/z=317.1 (MH)⁺

Synthesis of (2-amino-5-chloro-phenyl)-pyridin-3-yl-methanone

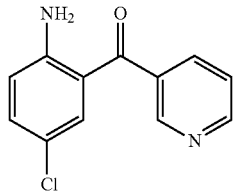 [SMILES: Nc1ccc(Cl)cc1C(=O)c1cccnc1]

N-[4-chloro-2-(pyridine-3-carbonyl)-phenyl]-2,2-dimethyl-propionamide (0.65 g) was suspended in 5 mL of 70% H₂SO₄ and heated at 95° C. in oil bath overnight. After cooling to room temperature the solution was added drop wise with stirring to 20 mL of 40% NaOH solution placed in an ice-water bath. The fine yellow precipitate formed was collected by vacuum filtration, washed well with water and dried under vacuum to give 370 mg of product. 1H NMR (CDCl3) δ 8.84 (dd, J=2.4 Hz, 0.8 Hz, 1H) 8.77 (dd, J=4.8 Hz, 2.0 Hz, 1H) 7.93 (dt, J=8.4 Hz, 2.0 Hz, 1H) 7.43 (m, 1H) 7.35 (d, J=2.0 Hz, 1H) 7.25 (d, J=0.8 Hz, 1H) 6.71 (d, J=8.8 Hz, 1H) 6.21 (s, 2H) MS (ES) m/z=233.0 (MH)⁺

Synthesis of 2-methyl-isonicotinonitrile

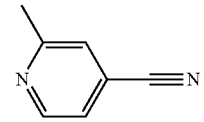

Dimethyl sulfate (18.3 mL, 192.4 mmol) was added to stirring 2-picoline-N-oxide (20 g) over a 10 minute period. The reaction was exothermic and the material quickly became homogeneous. The mixture was heated in a 60° C. oil bath for 2 hours, then the volatiles were removed under vacuum and the pale yellow oil was diluted with 25 mL H₂O and added drop wise over 10 minutes to 160 mL of 25% (w/v) KCN/H₂O. After stirring for 3.5 hours the yellow precipitate formed was collected by vacuum filtration and purified by column chromatography (EtOAc/Hexane) to yield 13.0 g of product (60%). 1H NMR (CDCl3) δ 8.66 (d, J=4.8 Hz, 1H) 7.37 (s, 1H) 7.31 (d, J=4.4 Hz, 1H) 2.62 (s, 3H) 2.62 (s, 3H); MS (ES) m/z=119.0

Synthesis of (2-amino-5-chloro-phenyl)-(2-methyl-pyridin-4-yl)-methanone

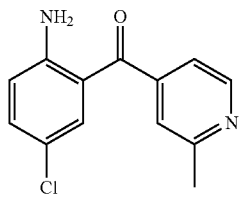 [SMILES: Cc1cc(C(=O)c2cc(Cl)ccc2N)ccn1]

The title compound was prepared according to the general procedure for the Synthesis of (2-Amino-phenyl)-aryl-methanones, using 4-chloro-phenylamine (1.8 g, 14.2 mmol) and 2-methyl-isonicotinonitrile (2.0 g, 16.9 mmol). 1H NMR (CDCl3) δ 8.64 (d, J=4.8 Hz, 1H) 7.28 (m, 3H) 7.20 (d, J=6.0 Hz, 1H) 6.70 (d, J=12.4 Hz, 1H) 6.28 (s, 2H) 2.66 (s, 3H) MS (ES) m/z=247.0

Synthesis of(2-amino-5-chloro-phenyl)-pyridin-2-yl-methanone

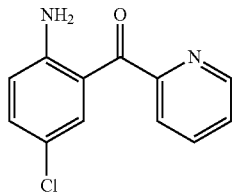 [SMILES: Nc1ccc(Cl)cc1C(=O)c1ccccn1]

To a solution of 2-bromopyridine (5 ml, 52 mmol) in Et₂O (60 ml) was added 40 ml of a n-butyllithium (1.6M in hexane, 64 mmol) drop wise at −40° C. over 30 min under a nitrogen atmosphere. The resulting yellow solution was stirred for a further 1 hr at −50° C. to −30° C. In a separate flask, a solution of 2-amino-5-chlorobenzoic acid (2.05 g, 12 mmol) in dry THF (90 ml), under nitrogen atmosphere and with ice-cooling, was added in one portion to the solution prepared as described above. The reaction mixture was stirred for 2 hrs at 0° C. and then chlorotrimethylsilane (30 ml) was added at 0° C. with stirring. The reaction mixture was allowed to warm to room temperature and 1 N HCl aq (100 ml) was added. The resulting two-phase system was separated. The aqueous phase was adjusted to pH12 with 6N NaOH solution and extracted with ethyl acetate (2×150 ml). The combined organic extractions were dried over Na₂SO₄. After removal of solvent, the residue was purified by the flash chromatography using ethyl acetate/hexane (1:4) as eluent. Crystallization of the product from Et₂O/hexane mixture gave 1.26 g (45%) of desired product as yellow solid. ¹H-NMR (DMSO-d₆, 500 MHz): δ 6.90 (1H, d, J=9 Hz), 7.31 (1H, dd, J=9 and 2.5 Hz), 7.40 (2H, br), 7.53 (1H, d, J=2.5 Hz), 7.61 (1H, m), 7.79 (1H, d, J=8 Hz), 8.03 (1H, m), 8.69 (1H, m). MS: (ESI⁺): 233.2 (M+1).

Synthesis of(2-Amino-5-chloro-phenyl)-(3-methyl-pyridin-4-yl)-methanone

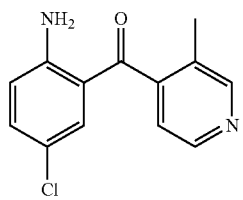 [SMILES: Cc1cnccc1C(=O)c1cc(Cl)ccc1N]

To a solution of 3-picoline (50 g, 0.48 mol) in glacial acetic acid (150 ml) was added hydrogen peroxide (25 ml) at RT. The mixture was heated to 90° C. for 3 hr. The mixture was cooled to RT and more hydrogen peroxide (18.5 ml) was added slowly. The mixture was again heated to 90° C. for 19 hr. The excess peroxide was carefully decomposed using Pd—C (2.5 g) at 0° C. Pd—C was removed by filtration, and the filtrate was concentrated and crude 3-methyl pyridine-1-oxide was purified by fractional distillation in vacuo.

A solution of 3-methyl pyridine-1-oxide (10 g, 0.092 mol) in methyl iodide (15 ml) was left at rt for 18 hr and the solid was filtered. The filtrate was diluted with diethyl ether and extracted with water (40 ml). The solid was re-dissolved in the aqueous extract, 1,4-dioxane (50 ml) was added, followed by potassium cyanide (15 g, 0.23 mol) and the mixture was stirred at RT for 3 hr. The product was extracted with chloroform. The chloroform layer was washed with water, brine and dried over sodium sulfate. The solvent was removed in vacuo and the crude product was purified by fractional distillation (61-62° C./0.2 mm) to yield a white low melting solid.

BCl₃ (24 ml, 1M in DCM, 0.024 mol) was added slowly to a solution of 4-chloroaniline (2 g, 0.016 mol) in 30 ml of trichloroethylene over a period of 15 min. at 0° C. and stirred at this temperature for an additional 10 min. 4-Cyano-3-methylpyridine (2.2 g, 0.019 mol) and AlCl₃ (3 g, 0.022 mol) were added at 0° C. The solution was allowed to warm to RT and stirred for 30 min. The solution was then heated at 80-90° C. for 1 hr. and the DCM was distilled off. The resulting solution was refluxed at 115° C. for 4 hr and stirred at RT overnight. 3N HCl (20 ml) was added and the mixture refluxed at 100° C. for 2 hr. The reaction mixture was cooled to 0° C. and adjusted to pH-12 with 6N NaOH. The reaction mixture was extracted with DCM, and the DCM layer washed with water, brine and dried over Na₂SO₄. The solvent was removed, and the crude was purified by column chromatography over silica gel to yield a yellow solid.

Synthesis of(2-Amino-4,5-difluoro-phenyl)-pyridin-4-yl-methanone

Iron powder (28.1 g, 0.502 mol) was added as small portions to 1,2-difluoro nitrobenzene (20.0 g, 0.126 mol) in methanol (200 ml) and heated

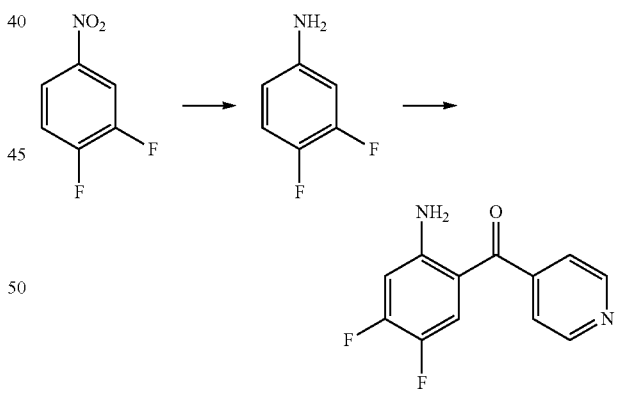

to 60° C. Ammonium chloride (48.4 g, 0.91 mol) in water (100 ml) was added drop wise and the reaction mixture refluxed for 5 hr. The reaction mixture was filtered over Celite and washed with methanol. Methanol was removed, and the aqueous layer was extracted with ethylacetate, washed with brine, dried over sodium sulphate and concentrated to yield 1,2-difluoro-4-aminobenzene.

BCl₃ (6.2 ml, 1M in DCM) was added drop wise to 1,2-difluoro-4aminobenzene (0.5 g, 0.004 mol) in trichloroethylene (6.5 ml) at 0° C. and this mixture stirred for 15 min. 4-Cyanopyridine (0.48 g, 0.005 mol) was added and the solution was warmed to RT and stirred for 30 min. The solution was then heated at 80-90° C. for 1 h. The resulting solution was refluxed at 160° C. for 4 hr and stirred at RT over night. 3N HCl was added to the reaction mixture and refluxed at 110° C. for 1.5 h. The reaction mixture was cooled to RT and made basic (pH=12) with 6N NaOH. The reaction mixture was diluted with water and DCM. The resulting two layers were separated and the aqueous layer was extracted with DCM, dried over sodium sulphate and concentrated. The compound was purified by column chromatography using silica gel to yield title compound.

Synthesis of(6-Amino-2,3-difluoro-phenyl)-pyridin-4-yl-methanone

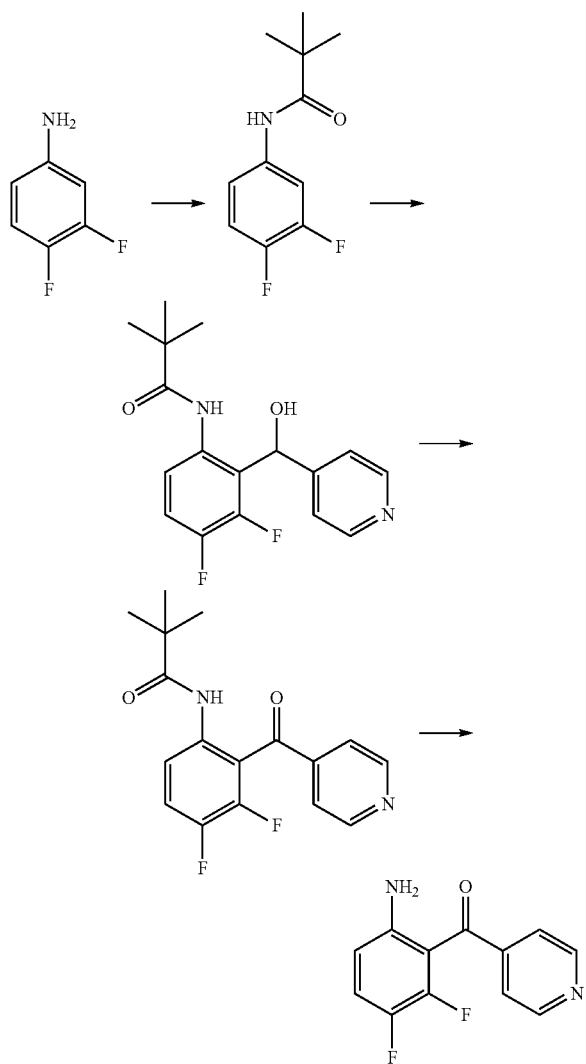

To 3,4-Difluoroaniline (2.0 g, 0.0153 mol) and triethylamine (3.1 g, 0.0307 mol) in dry benzene (100 ml) was added trimethylacetylchloride (2.3 g, 0.0184 mol) slowly at 0° C. and the reaction mixture stirred at RT overnight. The reaction mixture was then quenched with water and extracted with ethyl acetate. The organic layer was washed with water, brine, dried over sodium sulfate and concentrated. Compound was recrystallized from petroleum ether.

This protected 3,4-difluoroaniline (2.7 g, 0.0126 mol) was taken in dry THF (25 ml) and under nitrogen t-butyllithium (2.02 g, 0.032 mol) was added drop wise at −78° C. Stirring was continued at −78° C. for 2 h. 4-Pyridine carboxaldehyde (3.55 g, 0.033 mol) dissolved in dry THF (10 ml) was added slowly. The reaction mixture was warmed to room temperature and stirred over night. The reaction mixture was then quenched with water and extracted with ether. The organic layer was washed with brine, dried over sodium sulfate and concentrated. Compound was purified by column chromatography to yield carbinol.

To carbinol (2.6 g, 0.0031 mol) in 17.3 ml of pyridine was added a suspension of chromium trioxide (0.705 g, 0.007 mol) in pyridine (6.0 ml) under a nitrogen atmosphere. The resulting mixture was allowed to stir at RT over night. The reaction mixture was poured into water and extracted with ether. The ether extract was washed with brine, dried over sodium sulfate and concentrated. The compound was purified by column chromatography to yield the protected precursor to the title compound.

To this pivaloyl protected amino ketone (1.7 g, 0.0053 mol) was added 70% sulfuric acid (14.6 ml) and the reaction mixture heated to 95-100° C. overnight. The reaction mixture was basified by using 10% sodium hydroxide and extracted with dichloromethane. The organic layer was washed with water, brine, dried over sodium sulfate and concentrated. The product obtained was purified by column chromatography to yield title compound.

Synthesis of(2-Amino-5-chloro-4-methoxy-phenyl)-pyridin-4-yl-methanone

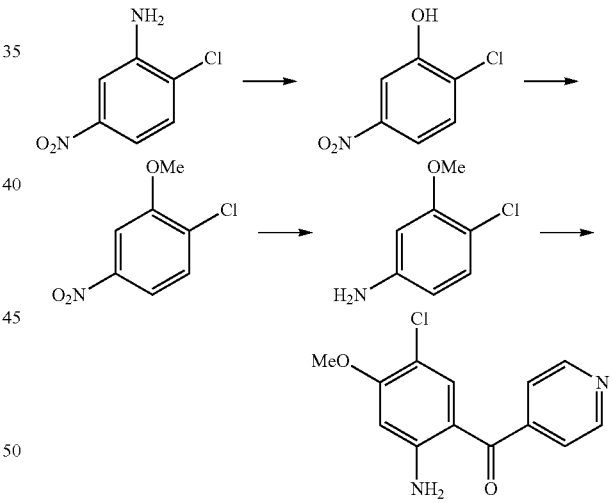

5-Nitro-2-chloro aniline (50.0 g, 0.289 mol) in 30% sulfuric acid (300 ml) was stirred at RT for 2 h. Sodium nitrite (21.0 g, 0.304 mol) in water (50 ml) was added slowly at 0° C. After 15 mins, this solution was added slowly to dilute sulfuric acid (50%, 250 ml) at 110° C. Stirring was continued for 15 min. The reaction mixture was cooled to RT, ice water was added, extracted with ethylacetate, washed with water, brine and dried over $Na_2SO_4$. The phenol product obtained upon concentration was purified by column chromatography.

$K_2CO_3$ (23.84 g, 0.172 mol) was added to 2-chloro-5-nitrophenol (10.0 g, 0.058 mol) in acetonitrile (100 ml) at RT. After cooling to 0° C., methyl iodide (19.6 g, 0.138 mol) was added slowly and the reaction mixture stirred at RT overnight. Water (100 ml) was added and the aqueous layer extracted with ethyl acetate. The organic layer was washed with water, brine and dried over Na₂SO₄. The product obtained upon concentration was purified by column chromatography to yield the anisole.

2-Chloro-5-nitro anisole (6.0 g, 0.032 mol) in MeOH (45 ml) was added slowly to stannous chloride (15.1 g, 0.08 mol) in conc. HCl (110 ml) at 40° C. and the temperature was slowly raised to 50° C. Stirring was continued for 2 h. After cooling to RT, the reaction mixture was basified with 50% NaOH solution, extracted by ethyl acetate, washed with water, then brine and dried over Na₂SO₄. 3-Methoxy-4-chloroaniline was obtained upon concentration and was purified further by column chromatography.

To 3-Methoxy-4-chloroaniline (2.0 g, 0.0126 mol) in trichloroethylene (30 ml) was added BCl₃ (2.18 g, 1 M solution in DCM, 0.0188 mol) at 0° C. After stirring for 10 min, 4-cyanopyridine (1.6 g, 0.0153 mol) and AlCl₃ (2.35 g, 0.018 mol) were added and the temperature was raised to RT, with further stirring for 30 min. The temperature was raised further to 85° C. and maintained at the same temperature for 1 h. DCM was distilled off and the solution was stirred at 115° C. for 4 h and then at RT over night. 3N HCl was added at RT and the reaction mixture refluxed for 1.5 h. The reaction mixture was allowed to cool and made basic using NaOH (6 N), diluted with water and extracted with DCM, washed with water, brine and dried over Na₂SO₄. The crude title compound was obtained upon concentration and was purified by column chromatography.

Synthesis of(2-Amino-5-chloro-phenyl)-pyrimidin-4-yl-methanone

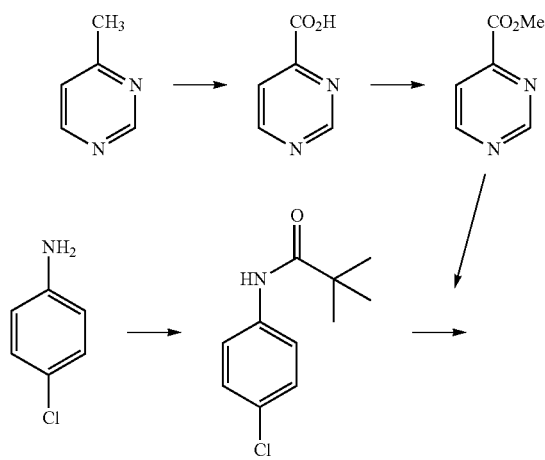

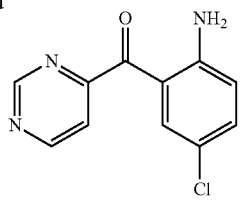

To 4-Methyl pyrimidine (5.0 g, 0.053 mol) in pyridine (55 ml) was added selenium dioxide (8.82 g, 0.079 mol) at RT with stirring. The reaction mixture was stirred at 55° C. for 2 h and at 80° C. for 3.5 hr. After cooling to RT and stirring over night, the reaction mixture was filtered and the residue was washed with pyridine. The combined pyridine solution was concentrated and the carboxylic acid obtained was washed with water to remove traces of selenium dioxide. Yield: 5.3 g, 80.5%.

To Pyrimidine-4-carboxylic acid (5.0 g, 0.04 mol) in methanol (170 ml) was added conc. HCl (2 ml) at RT. After refluxing overnight, the reaction mixture was cooled to RT and neutralized with 10% sodium bicarbonate solution and concentrated. The ester was extracted with diethyl ether, dried over Na₂SO₄ and concentrated to get the methyl ester as a yellow solid, yield: 3.3 g, 57.55%.

Trimethyl acetylchloride (11.30 g, 0.093 mol) was added to a benzene (500 ml) solution of triethylamine (15.75 g, 0.155 mol) and 4-chloroaniline (10.0 g, 0.078 mol) at 0° C. The reaction mixture was warmed to RT and stirred for 3 h. The reaction mixture was then quenched with water, extracted with ethyl acetate, washed with water, brine solution and dried over Na₂SO₄. The solid product obtained was crystallized from pet ether. Yield: 14.0 g, 84.43%.

To N-(4-chlorophenyl)-2,2-dimethyl propanamide (3.5 g, 0.0165 mol) in THF (50 ml) at 0° C. was added n-butyl lithium in hexane (2.64 g, 1.2 M, 0.041 mol). Stirring was continued at 0° C. for 2 h, the reaction then cooled to −70° C., pyrimidine-4-methyl carboxylate (3.18 g, 0.023 mol) in THF (25 ml) was then added slowly and the solution was warmed to RT and stirred overnight. Diethyl ether (50 ml) and water (50 ml) were added and the organic layer was separated. The aqueous layer was further extracted with ether. The combined ether layers were washed with water, brine and dried over Na₂SO₄. The product obtained upon concentration was purified by column chromatography. Yield: 1.7 g, 32.69%.

The protected amino ketone (1.7 g, 0.0054 mol) in sulfuric acid (10 ml, 70%) was heated at 95° C. over night. The reaction mixture was cooled to RT and basified with 10% NaOH, extracted with DCM, washed with water, brine and dried over Na₂SO₄. The product obtained upon concentration was purified by column chromatography using basic alumina to yield title compound (0.20 g, 16%).

Synthesis of(6-Amino-3-chloro-2-methoxy-phenyl)-pyridin-4-yl-methanone

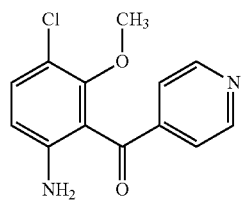 [SMILES: COc1c(Cl)ccc(N)c1C(=O)c1ccncc1]

5-Nitro-2-chloro aniline (50.0 g, 0.289 mol) in 30% sulfuric acid (300 ml) was stirred at RT for 2 h. Sodium nitrite (21.0 g, 0.304 mol) in water (50 ml) was added slowly at 0° C. and maintained at this temperature for 15 min. This diazotized solution was added slowly to dilute sulfuric acid (50%, 250 ml) at 110° C. Stirring was continued for 15 min. After cooling to RT, ice water was added, the mixture extracted with ethylacetate, washed with water, brine and dried over Na$_2$SO$_4$. The product obtained upon concentration was purified by column chromatography. Yield 12.0 g, 24.0%.

To K$_2$CO$_3$ (23.84 g, 0.172 mol) and 2-chloro-5-nitrophenol (10.0 g, 0.0576 mol) in acetonitrile (100 ml) was added methyl iodide (19.60 g, 0.138 mol) at 0° C. The reaction mixture was warmed to RT and stirred overnight. Water was added and extracted with ethyl acetate. The organic layer was washed with water, brine and dried over Na$_2$SO$_4$. The product obtained upon concentration was purified by column chromatography. Yield: 6.0 g, 55.55%.

2-Chloro-5-nitro anisole (6.0 g, 0.032 mol) in MeOH (45 ml) was added slowly to stannous chloride (15.1 g, 0.08 mol) in conc. HCl (110 ml) at 40° C. and the temperature was slowly raised to 50° C. Stirring was continued for 2 h, the reaction cooled to RT, basified with 50% NaOH solution and extracted by ethyl acetate. The organic layer was washed with water, brine and dried over Na$_2$SO$_4$. The product obtained upon concentration was purified by column chromatography. Yield: 4.0 g, 79.36%.

To triethylamine (3.83 g, 0.037 mol) and 3-methoxy-4-chloro aniline (3.0 g, 0.0190 mol) in benzene (50 ml) was added trimethylacetylchloride (2.75 g, 0.022 mol) slowly at 0° C. The temperature was raised to RT and stirred overnight. The reaction mixture was added to ice and extracted with ethyl acetate. The organic layer was washed with water, brine, dried over Na$_2$SO$_4$ and concentrated. Yield: 3.7 g, 80.43%.

To N-pivaloyl-3-methoxy-4-chloroaniline (1.50 g, 0.0062 mol) in THF (30 ml) was added n-butyl lithium (1.0 g, 0.0156 mol) at 0° C. and the reaction stirred for 2 hr. After cooling to −70° C., methyl isonicotinate (1.3 g, 0.0094 mol) in THF (12 ml) was added slowly. The reaction was warmed to rt and stirred overnight and then quenched with water and extracted with ether. The water layer was further extracted and the combined ether layers were washed with water, brine and dried over Na$_2$SO$_4$. The product obtained upon concentration was purified by column chromatography. Yield 0.50 g, 23.25%.

The protected ketone from step 5 (0.500 g, 0.0014 mol) was suspended in concentrated HCl (5 ml) at RT, then the temperature was raised to 95° C. and the mixture stirred overnight. The mixture was cooled to RT, basified with 20% NaOH solution and extracted with DCM. The combined organic layer was washed with water, brine and dried over Na$_2$SO$_4$. The product obtained upon concentration was purified by column chromatography using basic alumina to yield title compound (0.140 g, 37.33%).

Synthesis of(2-Amino-5-chloro-phenyl)-(2-methyl-pyridin-4-yl)-methanone

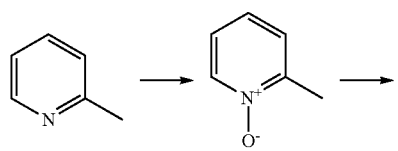

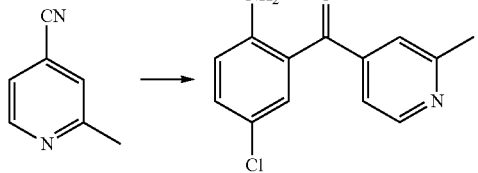

To a solution of 2-picoline (50 g, 0.48 mol) in glacial acetic acid (150 ml) was added hydrogen peroxide (25 ml) at RT. The mixture was heated to 90° C. for 3 hr. The mixture was cooled to RT and more hydrogen peroxide (18.5 ml) was added slowly. The mixture was again heated to 90° C. for 19 hr. The excess peroxide was cautiously decomposed using Pd—C (2.5 g) at 0° C. Pd—C was filtered, the filtrate was concentrated and the crude 2-methyl pyridine-1-oxide was purified by fractional distillation under vacuum. Yield: 40 g, 69%.

A solution of 2-methyl pyridine-1-oxide (10 g, 0.092 mol) in methyl iodide (15 ml) was stirred at RT for 18 hr. The solid was filtered. The filtrate was diluted with diethyl ether, extracted with water (40 ml). The solid was re-dissolved in the aqueous layer, 1,4-dioxane (50 ml) was added, followed by potassium cyanide (15 g, 0.23 mol). The mixture was stirred at RT for 3 hr. The product was extracted with chloroform. The chloroform layer was washed with water, brine and dried over sodium sulfate. The solvent was removed under vacuo and the crude material was purified by fractional distillation (61-62° C./0.2 mm) to yield a white low melting solid (6 g, 35%).

BCl$_3$ (24 ml, 1M in DCM, 0.024 mol) was added slowly to a solution of 4-chloroaniline (2 g, 0.016 mol) in 30 ml of trichloroethylene over a period of 15 min. at 0° C. and stirred at this temperature for an additional 10 min. 4-Cyano-2-methylpyridine (2.2 g, 0.019 mol) and AlCl$_3$ (3 g, 0.022 mol) were added at 0° C. The solution was warmed to RT and stirred for 30 min. The solution was then heated at 80-90° C. for 1 h and the DCM was distilled off. The resulting solution was refluxed at 115° C. for 4 hr and stirred at RT over night. 3N HCl (20 ml) was added to the mixture and refluxed at 100° C. for 2 hr. The reaction mixture was cooled to 0° C. and was made basic (pH-12) with 6N NaOH and the reaction mixture was extracted with DCM. The DCM layer was washed with water, brine and dried over Na$_2$SO$_4$. The solvent was removed, the crude was purified by column chromatography (silica gel) to yield title compound as yellow solid (1.55 g, 40%).

Synthesis of(2-Amino-4-chloro-phenyl)-pyridin-4-yl-methanone

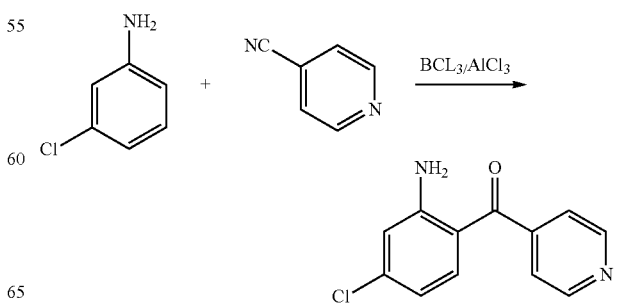

To BCl₃ (1M in DCM) (24 mL, 24 mmol), cooled to 0° C., a solution of 3-chloroaniline (2.0 g, 16 mmol) in 30 mL of TCE was added drop wise over a period of 15 min and the mixture stirred at that temperature for an additional 10 min. 4-cyanopyridine (2.0 g, 19 mmol) and AlCl₃ (3.0 g, 22 mmol) was added under ice-water cooling. The solution was allowed to warm to rt and stirred for 30 min. The solution was then heated at 80-90° C. for 1 h and the DCM distilled off. The resulting solution was refluxed at 160° C. for 4 h and stirred at rt overnight. 3N HCl (20 ml approx.) was added to the reaction mixture and then refluxed at 110° C. for 1.5 hr. The reaction mixture was cooled to rt and the solution was made basic (pH 12) with 6N NaOH. The reaction mixture was diluted with water and DCM. The resulting two layers were separated and the aqueous layer was extracted with DCM (3×150 mL), and dried (Na₂SO₄). After removal of solvent, the solid was washed with Et₂O to give 650 mg (24%) of desired product.

Synthesis of(2-Amino-3-chloro-phenyl)-pyridin-4-yl-methanone

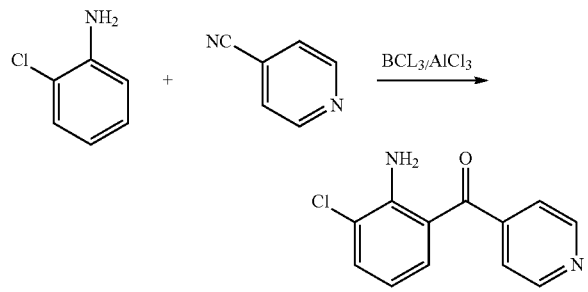

To a solution of BCl₃ (1M in DCM) (24 mL, 24 mmol), cooled to 0° C., was added a solution of 2-chloroaniline (2.0 g, 16 mmol) in 30 mL of TCE drop wise over a period of 15 min and the reaction stirred for an additional 10 min. 4-cyanopyridine (2.0 g, 19 mmol) and AlCl₃ (3.0 g, 22 mmol) were added under ice-water cooling. The solution was allowed to warm to rt and stirred for 30 min. The solution was then heated at 80-90° C. for 1 h and the DCM distilled off. The resulting solution was refluxed at 160° C. for 4 h and stirred at rt overnight. 3N HCl (20 ml approx.) was added to the reaction mixture and refluxed at 110° C. for 1.5 hr. The reaction mixture was cooled to rt and the solution was made basic (pH 12) with 6N NaOH. The reaction mixture was diluted with water and DCM. The resulting layers were separated and the aqueous layer was extracted with DCM (3×150 mL), and the combined organic layers dried (Na₂SO₄). After removal of solvent, the solid was washed with Et₂O to give 600 mg (21%) of desired product.

Synthesis of(2-Amino-5-bromo-phenyl)-pyridin-4-yl-methanone

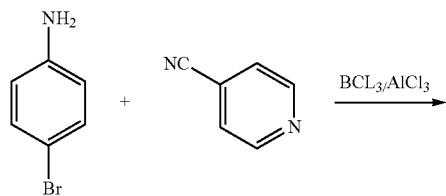

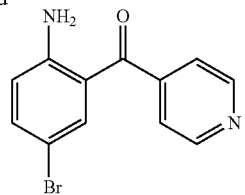

To a solution of BCl₃ (1M in DCM) (18 mL, 18 mmol), cooled to 0° C., was added drop wise over a period of 15 min a solution of 4-bromoaniline (2 g, 11.6 mmol) in 30 mL of TCE and the mixture stirred for an additional 10 min. 4-cyanopyridine (2.0 g, 19 mmol) and AlCl₃ (3.0 g, 22 mmol) were added under ice-water cooling. The solution was warmed to rt and stirred for 30 min. The solution was then heated at 80-90° C. for 1 h and the DCM distilled off. The resulting solution was refluxed at 160° C. for 4 h and stirred at rt overnight. 3N HCl (20 ml approx.) was added to the reaction mixture and refluxed at 110° C. for 1.5 hr. The reaction mixture was allowed to cool down and the solution was made basic (pH 12) with 6N NaOH. The reaction mixture was diluted with water and DCM. The resulting two layers were separated and the aqueous layer was extracted with DCM (3×150 mL), and the combined organic layers dried (Na₂SO₄). After removal of solvent, the solid was washed with Et₂O to give 1.050 g of desired product.

Synthesis of(2-amino-5-fluoro-phenyl)-pyridin-4-yl-methanone

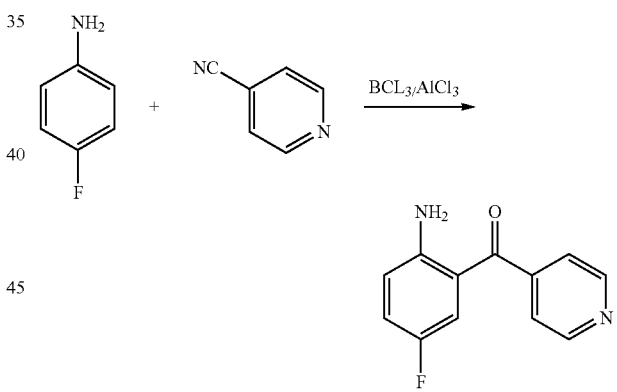

To a solution of BCl₃ (1M in DCM) (27 mL, 27 mmol), cooled to 0° C., was added drop wise over a period of 15 min a solution of 4-fluoroaniline (2.0 g, 18 mmol) in 30 mL of TCE and the mixture stirred at that temperature for an additional 10 min. 4-cyanopyridine (2.6 g, 25 mmol) and AlCl₃ (3.0 g, 22 mmol) were added under ice-water cooling. The solution was allowed to warm to rt and then stirred for 30 min. The solution was then heated at 80-90° C. for 1 h and the DCM distilled off. The resulting solution was refluxed at 160° C. for 4 h and stirred at rt overnight. 3N HCl (20 ml approx.) was added to the reaction mixture and refluxed at 110° C. for 1.5 hr. The reaction mixture was allowed to cool down and the solution was made basic (pH 12) with 6N NaOH. The reaction mixture was diluted with water and DCM. The resulting two layers were separated and the aqueous layer was extracted with DCM (3×150 mL), and the combined organic layers dried (Na₂SO₄). After removal of solvent, the solid was washed with Et₂O to give 1.05 g (27%) of desired product.

Synthesis of (2-Amino-5-chloro-phenyl)-(1-methyl-1H-imidazol-2-yl)-methanone

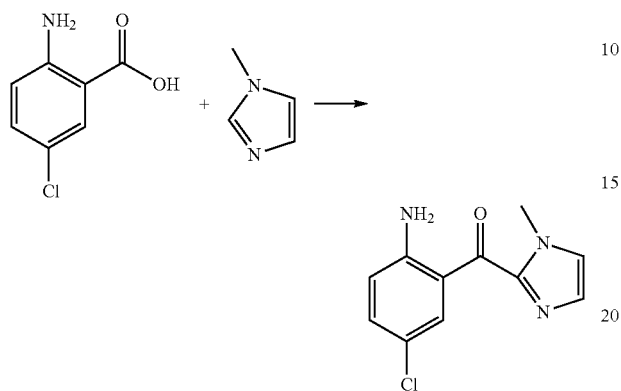

To a solution of ⁿBuLi (0.0730 mol) in hexane was added N-methyl imidazole (0.0608 mol) drop wise at −40° C. over 30 min under a nitrogen atmosphere. The resulting yellow solution was stirred for a further 3 hr at rt, and then refluxed for 1 h. 2-amino-5-chlorobenzoic acid (1.74 g, 0.01014 mole) in dry ether (60 ml) was then added to the reaction mixture. The reaction mixture was stirred overnight at rt. To the reaction mixture was added saturated NH₄Cl solution and the resulting mixture extracted with ethyl acetate (2×150 ml). The combined organic layers were dried over Na₂SO₄. After removal of solvent, the residue was purified by the flash chromatography using ethyl acetate/hexane (1:4) as eluent. Crystallization of the product from Et₂O/hexane mixture gave 300 mg (13.7%) of product as yellow solid.

Synthesis of (2-Amino-5-chloro-phenyl)-(2-methyl-pyridin-3-yl methanone

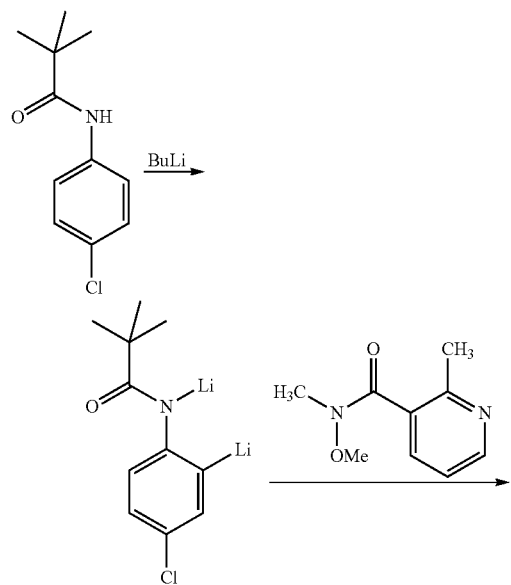

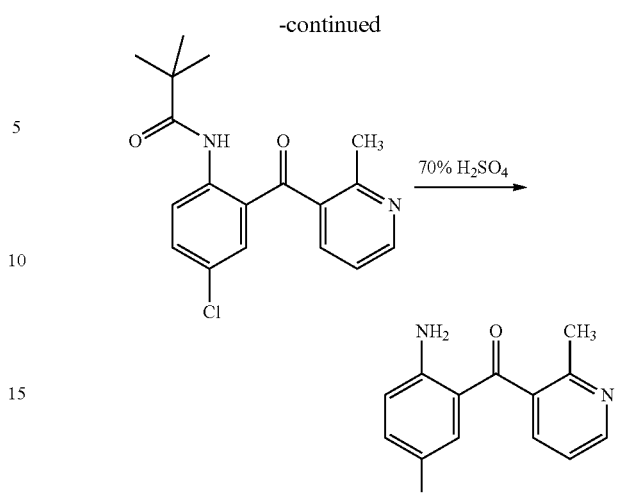

Trimethylacetyl chloride (35 g) was added drop wise to a solution of 4-chloroaniline (31.9 g) in dry pyridine and the reaction was stirred under nitrogen overnight. About half of the pyridine was removed by rotary evaporation, then the mixture was treated with 6M hydrochloric acid and extracted with ethyl acetate. The extracts were washed with saturated aqueous NaHCO3 and with water, then were dried (MgSO4), filtered and concentrated by rotary evaporation. The resulting crystalline product was vacuum filtered and dried at high vacuum to constant weight, resulting in a good yield of N-(4-chloro-phenyl)-2,2-dimethyl-propionamide as fine needles. EDC (10 g) and 2-methyl-nicotinic acid (7.15 g) were magnetically stirred in acetonitrile-THF with N,O-dimethylhydroxylamine hydrochloride (9.75 g) and triethylamine (25 mL). After stirring overnight at ambient temperature, the resulting white suspension was added to ice water and extracted with ethyl acetate (3×100 mL). The extracts were dried, filtered, and concentrated to give a light amber oil.

To a magnetically stirred solution of N-(4-chloro-phenyl)-2,2-dimethyl-propionamide (3.16 g, 14.9 mmol) in dry THF was added 2.5M n-butyllithium in hexane at −40° C. and the mixture was stirred at 0° C. for 2 h and a suspension of white solid resulted. A solution of the Weinreb amide (1.80 g, 10.0 mmol) in dry THF was added drop wise and the reaction was stirred at ambient temp overnight. The mixture was diluted with water and extracted with ethyl acetate and the organic layer was dried (MgSO4), filtered and concentrated. Chromatography on silica gel (20-30% EtOAc/Hexane) provided the desired N-[4-Chloro-2-(2-methyl-pyridine-3-carbonyl)-phenyl]-2,2-dimethyl-propionamide as a waxy bright yellow solid (2.28 g, 6.89 mmol): ¹H NMR (CDCl3) δ 11.71 (s, 1H, NH), 8.82 (d, 1H, J=9.2 Hz), 8.67 (dd, 1H, J=4.8 Hz, J=1.8 Hz), 7.55 (m, 2H), 7.28 (d, 1H, J=2.5 Hz), 7.25 (m, 1H), 2.54 (s, 3H), 1.39 (s, 9H).

The N-[4-chloro-2-(2-methyl-pyridine-3-carbonyl)-phenyl]-2,2-dimethyl-propionamide intermediate (2.28 g, 6.89 mmol) was magnetically stirred with 70% sulfuric acid and heated at 75° C. and progress of the solvolysis was monitored by LC/MS. The reaction was allowed to cool to ambient temperature, and was washed with ether-hexane to remove oily by-products. The acidic aqueous layer was cooled in an ice bath and aqueous NaOH was added drop wise to basify the mixture. The product was extracted with ethyl acetate and the extracts were washed with saturated aqueous NaHCO3 (2×100 mL), with saturated aqueous sodium chloride, dried (MgSO4), filtered and concentrated. The bright yellow product crystallized on standing: ¹H NMR (CDCl3) δ 8.54 (dd, 1H, J=5.2 Hz, J=1.6 Hz), 7.45 (dd, 1H, J=7.6 Hz, J=1.5 Hz), 7.15 (m, 2H), 7.00 (d, 1H, J=2.6 Hz), 6.61 (d, 1H, J=9.1 Hz), 6.39 (br s, 2H), 2.42 (s, 3H).

Synthesis of(2-Amino-5-chloro-phenyl)-(6-methyl-pyridin-3-yl)-methanone

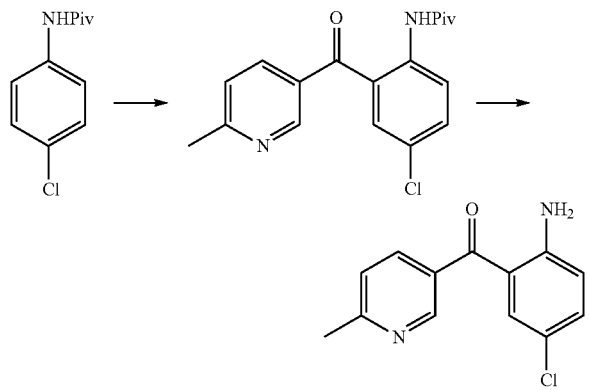

To N-(4-Chlorophenyl)-2,2-dimethyl propanamide (50 g. 0.236 mol) in THF (800 ml) was added n-butyl lithium (37.76 g, 0.59 mol) at −5° C. After 3 hours, the reaction mixture was cooled to −70° C. and methyl-6-methyl nicotinate (50 g, 0.330 mol) in THF (400 ml) was added slowly. After one more hour at −70° C., the reaction was warmed to room temperature, stirred over night, then quenched with water and the product extracted with ether. The organic layer was washed with water, brine, dried over sodium sulfate and concentrated in vacuo. The crude intermediate was purified by column chromatography.

To this crude product (15 g, 0.0453 mol) was added 40% KOH (75 ml) solution in methanol (150 ml) and the reaction mixture heated at 65° C. for 24 h. After Concentration and extraction with ethyl ether, the organic layer was washed with water, brine, dried over sodium sulphate and concentrated. The crude product was purified by column chromatography using basic alumina to yield title compound.

¹H NMR (CDCl₃): 2.66 (s, 3H), 6.13 (bs, 2H, NH₂), 6.7 (d, 1H, ³J=9 Hz), 7.28 (m, 2H), 7.39 (s, 1H), 7.85 (d, 1H, ³J=9 Hz), 8.75 (s, 1H). ¹³C NMR (CDCl₃): 24.5, 118.5, 120.2, 122.8, 132.1, 132.6, 134.5, 136.7, 149.3, 149.4, 161.7, 195.6. LC-MS m/z=247.2 (M+H)⁺. HPLC [c18 BDS 25 min column, flow=0.8 ml/min (70:30; ACN:0.1% TFA), rt=4.8 min].

Synthesis of(2-Amino-5-chloro-phenyl)-([1H]-pyrazol-3-yl)-methanone

To N-(4-Chlorophenyl)-2,2-dimethyl propanamide (2.6 g, 12.293 mmol) in THF (40 ml) was added n-butyl lithium (1.966 g, 30.732 mmol) at −5° C. and the reaction mixture maintained at 0° C. for 3 h. After cooling to −70° C., ethyl-(1-Boc) pyrazole-5-carboxylate (4.13 g, 17.20 mmol) in THF (20 ml) was added, the reaction mixture stirred for 1 hour, then allowed to warm to RT and stirred over night, then quenched with water and the reaction mixture extracted with ether, washed with water, brine and dried over sodium sulphate and concentrated in vacuo. The crude intermediate was purified by column chromatography.

6N HCl (10 ml) and the crude intermediate (1.0 g, 2.466 mmol) were then heated at 90° C. overnight, cooled to room temperature, basified by adding saturated sodium bicarbonate solution, extracted with ether and the organic layer was again washed with brine, dried over sodium sulphate and concentrated in vacuo. The product was purified by column chromatography using basic alumina. ¹H NMR (CDCl₃): 6.11 (bs, 2H, NH₂), 6.7 (d, 1H, ³J=6.6 Hz), 6.89 (s, 1H), 7.28 (m, 1H), 7.7 (s, 1H), 8.2 (s, 1H), 10.75 (bs, 1H). ¹³C NMR (CDCl₃): 109.25, 118.4, 118.5, 120.5, 132.4, 134.5, 149.4, 186.6. LC-MS m/z=222 (M+H)⁺. HPLC [c18 BDS 25 min coloum, flow=0.8 ml/min (70:30; ACN:0.1% TFA), rt=4.11 min].

Synthesis of(6-Amino-2,3-difluoro-phenyl)-pyridin-3-yl-methanone

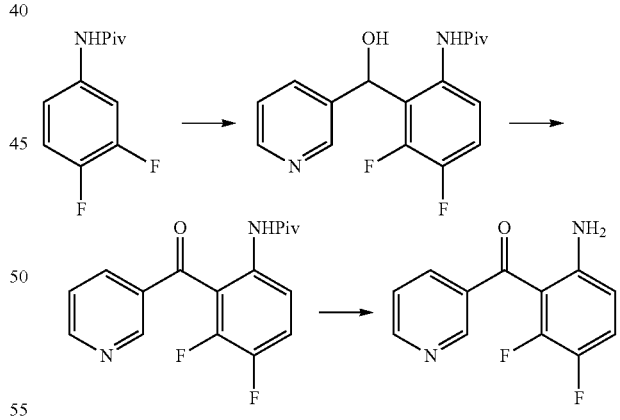

To 3,4-Difluoro phenyl-2,2-dimethyl propanamide (0.5 g, 0.0023 mol) in dry THF (5 mL) was added n-butyl lithium (0.375 g, 0058 mol) dropwise at −78° C., and the reaction mixture stirred for 3 hours. 3-Pyridine carboxyaldehyde (0.658 g, 0.0060 mol) in 5 ml dry THF was added drop wise. The reaction mixture was warmed to room temperature and stirred overnight, quenched with water, and extracted ethyl acetate. The organic layer was washed with water, brine and dried over sodium sulfate and concentrated. Crude intermediate was purified by column chromatography using 30% ethylacetate in hexane solution. ¹H NMR (CDCl₃): 5.28 (bs, 2H, NH$_2$), 6.49 (m, 1H), 7.17 (dd, 1H), 7.43 (m, 1H), 8.0 (m, 1H), 8.79 (m, 1H), 8.94 (s, 1H). $^{13}$C NMR (CDCl3): 109.7, 109.8, 111.8, 122.3, 122.5, 123.2, 135.2, 135.8, 140.4, 140.5, 142.8, 142.9, 145.9, 147.9, 148.1, 149.6, 150.4, 150.6, 152.7, 192.4. LC-MS m/z=235 (M+H)$^+$. HPLC [c18 BDS 25 min column, flow=0.8 ml/min (70:30; ACN:0.1% TFA), rt=4.07 min].

To Chromium trioxide (0.493 g, 0.0049 mol) in 6 ml dry pyridine under a nitrogen atmosphere was added crude intermediate (0.7 g, 0.0021 mol) in 8 ml pyridine dropwise, the reactionmixture stirred at RT for overnight, diluted with diethyl ether, filtered through Celite, the filtrate was washed with water, then brine again, then dried over sodium sulfate and concentrated in vacuo. Crude compound was purified by column chromatography using 35% ethyl acetate in hexane solution, reduced in vacuo, and to this material was added 5 ml of 70% sulphuric acid, and the resulting reaction mixture heated to 98° C. overnight, then basified with 10% sodium bicarbonate solution, and extracted with dichloromethane. The organic layer was dried over sodium sulfate and concentrated. Title compound was purified by column chromatography using 15% ethyl acetate in hexane.

Synthesis of(6-Amino-3,4-difluoro-phenyl)-pyridin-3-yl-methanone

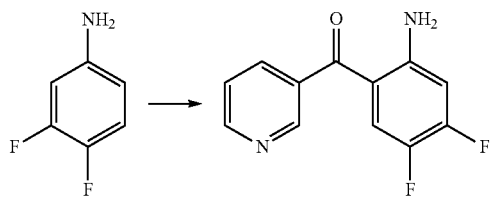 [SMILES: Nc1ccc(F)c(F)c1 ; Nc1cc(F)c(F)cc1C(=O)c1cccnc1]

BCl$_3$ (6.2 ml, 1M in DCM) was added dropwise to 1,2-difluoro-4-aminobenzene (0.5 g, 0.004 mol) in trichloroethylene (6.5 ml) at 0° C., the reaction mixture stirred for 15 min, then 3-Cyanopyridine (0.48 g, 0.005 mol) added and the solution warmed to room temperature and stirred for 30 min. The solution was then heated at 80-90° C. for 1 h. The resulting solution was refluxed at 160° C. for 4 hr, then stirred at room temperature over night, then 3N HCl was added to the reaction mixture and again refluxed at 110° C. for 1.5 h. The reaction mixture was cooled to RT and made basic (pH=12) with 6N NaOH. The reaction mixture was diluted with water and dichloromethane. The resulting two layers were separated and the aqueous layer was extracted with dichloromethane, dried over sodium sulfate and concentrated. The compound was purified by column chromatography on silica gel. $^1$H NMR (CDCl$_3$): 6.29 (bs, 2H, NH$_2$), 6.56 (m, 1H), 7.25 (m, 1H), 7.46 (m, 1H), 7.93 (m, 1H), 8.80 (m, 1H), 8.85 (s, 1H). $^{13}$C NMR (CDCl$_3$): 104.5, 104.7, 112.7, 121.3, 123.3, 135.1, 136.1, 142.5, 149.3, 149.5, 152.0, 153.8, 153.9, 156.3, 194.7. LC-MS m/e=235 (M+H)+. HPLC [c18 BDS 25 min column, flow=0.8 ml/min (70:30; ACN:0.1% TFA), rt=4.34 min].

Synthesis of(2-Amino-5-chloro-phenyl)-pyrazin-2-yl-methanone

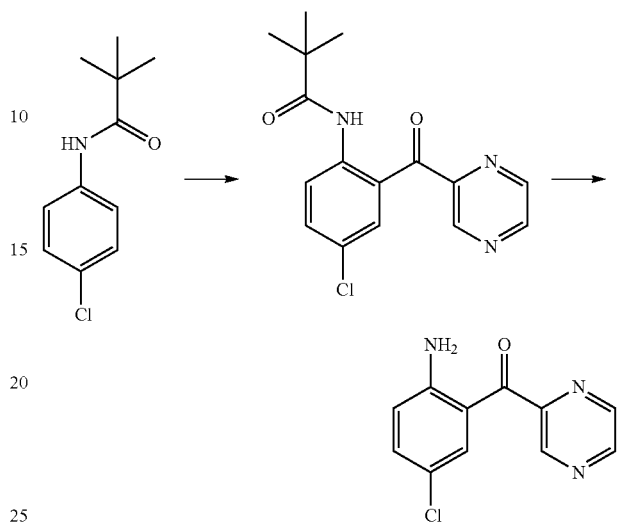

To N-(4-Chlorophenyl)-2,2-dimethylpropanamide (10.0 g, 0.047 mol) in dry THF (160 ml) at 0° C. was added n-butyl lithium (0.0117 mol) and the reaction mixture stirred at 0° C. for 2 h. The solution was cooled to −75° C., methyl pyrazinate (9.0 g, 0.0657 mol) in THF (90 ml) was added slowly and the reaction stirred at room temperature overnight, then diluted with ether and the aqueous layer was extracted with ether. The combined organic layer was washed with water, brine and concentrated. The intermediate was purified by column with 5% of ethyl acetate in pet ether.

To the Pivaloylamido intermediate (1.2 g, 0.0037 mol) in methanol (25 ml) was added 2.2 ml of 40% aq. KOH solution. The reaction was heated at 65° C. for 24 h, then diluted with water and extracted with ether. The ether layer was washed with wash, brine and concentrated. The product was purified by column chromatography (6% ethyl acetate in pet ether).

Synthesis of(2-Amino-5-chloro-phenyl)-pyridazin-4-yl-methanone

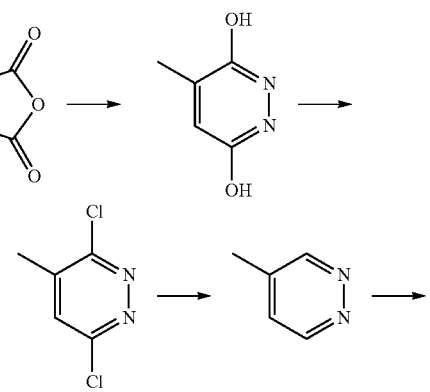

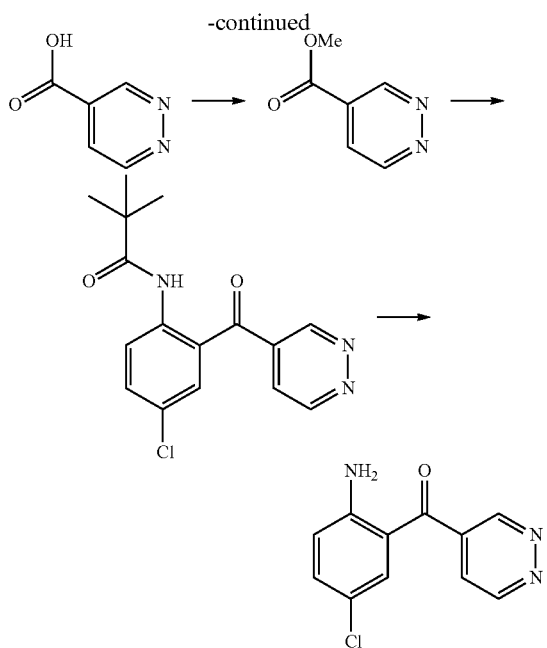

Citraconic anhydride (53.4 g, 0.476 mol) was added to a boiling water (130 ml) solution of hydrazine dihydrochloride (50 g, 0.476 mol). The solution was stirred at 90° C. for 5 h. The reaction mixture was then cooled to 0° C. and the white solid filtered, washed with cold water and dried in vacuo.

4-Methyl-3,6-pyridazinediol (57.0 g, 0.45 mol) in phosphorus oxychloride (480 ml) was refluxed at 80° C. for 5 h. The excess of the phosphorus oxychloride was removed under high vacuum and the red colored residue was poured on to ice. The solid separated out was filtered, washed with cold water and dried. Yield: 64.7 g, 87%.

To 4-Methyl-3,6-dichloropyridazine (64.7 g, 0.397 mol) in 150 ml absolute ethanol was added aqueous ammonia (80 ml). The solution was purged with nitrogen gas for 10 min, 10% palladium on carbon (3.24 g) was added and the mixture hydrogenated at room temperature for 8 h at 3 kg/cm2 pressure. The reaction mixture was filtered and ethanol was removed in vacuo. The residue was basified with 20% sodium hydroxide solution and extracted with dichloromethane (3×150 ml). The organic layer was dried with sodium sulfate and concentrated.

4-Methyl pyridazine (31.5 g, 0.335 mol) was dissolved in pyridine (315 ml) and stirred for 15 mins at RT. Selenium dioxide (55.75 g, 0.5025 mol) was added and the solution was stirred for 15 min. The dark orange reaction mixture was then heated at 55° C. for 2 h and at 80° C. for 3.5 h. The resulting dark brown reaction mixture was cooled to room temperature and stirred overnight. The reaction mixture was filtered through Celite and concentrated. The solid obtained was suspended in 250 ml of water and stirred vigorously for 1 h. The solid was filtered and washed with water (100 ml) and dried in vacuo.

A suspension of pyridazine-4-carboxylic acid (10.0 g, 0.04 mol) in 100 ml of DCM and 50 ml of diethyl ether was cooled to −10° C. Potassium hydroxide (34.0 g) was dissolved in water (65 ml), cooled to −15° C. and ether (50 ml) was added. To this biphase solution nitrosomethyl urea (20.0 g) was added portion wise at −15° C. with occasional manual stirring. After complete addition (about 30 min) the ether layer became yellow. This solution was decanted into another conical flask containing potassium hydroxide pellets in 10 ml diethyl ether and the solution was stirred manually at −15° C. for 15 min. This solution was then transferred to the suspension of the pyridazine-4-carboxylic acid and the reaction mixture was stirred at −15° C. for 1 h. The reaction mixture was then warmed to room temperature and concentrated.

N-4-Chlorophenyl-2,2-dimethylpropanamide (8.0 g, 0.0378 mol) in dry THF (128 ml) was cooled to 0° C. n-Butyllithium (6.048 g, 0.0528 mol) was added dropwise at 0° C. and stirred at 0° C. for 2.5 h. The reaction mixture was then cooled to −78° C. and a THF (65 ml) solution of methylpyridazine-4-carboxylate (7.3 g, 0.0528 mol) was added dropwise. After the addition, the reaction mixture was stirred at the same temperature for 1 h and warmed to room temperature and stirred for 16 h. The reaction mixture was diluted with 150 ml diethyl ether and washed with water. The aqueous washing was extracted with 4×100 ml of diethylether. The combined organic layer was washed with brine, dried over sodium sulfate and concentrated. The compound was purified column chromatography using pet ether-ethylacetate as the eluent.

The protected amino ketone (1.0 g, 0.0031 mol) in 10 ml of HBr was heated at 80° C. for 4 h. The reaction mixture was cooled to 0° C., neutralised using aqueous sodium bicarbonate, extracted with diethylether (3×50 ml), and the combined organic layer was washed with brine, dried over sodium sulfate and concentrated. The crude compound was purified by column chromatography (basic alumina) using chloroform as eluent.

Synthesis of(2-Amino-5-chloro-phenyl)-pyridazin-4-yl-methanone

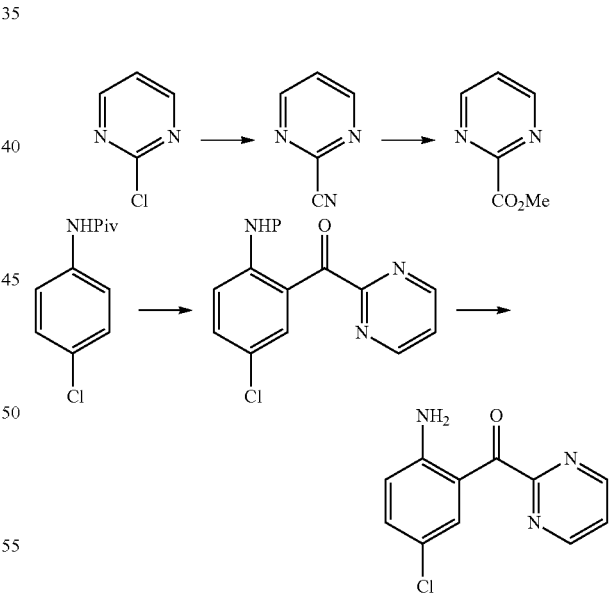

2-Chloropyrimidine (8.0 g, 0.699 mol) and sodium cyanide (5.6 g, 0.1139 mol) in dry DMF (80 ml) was stirred at 65° C. for 24 h. The mixture was quenched with water (400 ml) and stirred for 0.5 h. The product was extracted with ethyl acetate, the ethyl acetate layer was dried over $Na_2SO_4$ and concentrated under reduced pressure. The crude was purified by column chromatography over silica gel (pet ether/ethyl acetate) to afford 2-cyano pyrimidine as a white solid.

Dry hydrogen chloride gas was passed through a solution of 2-cyanopyrimidine (3.5 g, 0.0333 mol) in dry methanol (100 ml) for 1 h, and the well stoppered mixture was allowed to stand for 72 h. The mixture was concentrated under reduced pressure. The residue was basified with NaHCO$_3$ solution (10%) and the product was extracted with dichloromethane. The dichloromethane layer was dried over Na$_2$SO$_4$, and concentrated under reduced pressure. The crude ester was purified by crystallization from pet ether/diethyl ether, to yield a white solid.

N-(4-Chlorophenyl)-2,2-dimethyl propanamide (2.0 g, 0.0095 mol) in dry THF (40 ml) was cooled to −5° C. n-Butyl lithium (24 ml, 1.2 M, 0.0284 mol) was added dropwise and stirred at the same temperature for 2 h. The reaction mixture was cooled to −70° C. and methyl pyridin-2-carboxylate (1.96 g, 0.0142 mol) dissolved in dry THF (10 ml) and added dropwise. The mixture was stirred at RT for 18 h. The reaction mixture was quenched with water and extracted with ethyl acetate. The extract was washed with brine solution and concentrated. The product was purified by column using 5-10% of ethyl acetate in pet ether as eluent.

To the protected amino ketone (0.4 g, 0.0013 mol) in 2 ml of methanol was added potassium hydroxide (0.48 g, 0.00857 mol) in 1.2 ml of water. The reaction mixture was heated at 70° C. for 6 h. The reaction mixture was diluted with water and extracted with ethyl acetate. The extract was washed with water, brine and concentrated. The crude material was purified by column (5% of ethyl acetate in pet ether).

Synthesis of(2-Amino-5-chloro-phenyl)-(3-methoxy-pyridin-4-yl)methanone

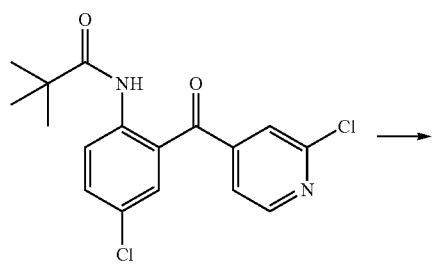

N-Pivaloyl protected 2-chlorophenyl derivative (0.500 g, 0.0014 mol) was dissolved in 11 ml of methanol and 40% KOH solution was added. The reaction mixture was refluxed under nitrogen atmosphere for 28 h. The reaction mixture was cooled to room temperature and concentrated. The residue was extracted with (3×50 ml) diethyl ether. The combined organic layer was washed with water, dried over sodium sulfate and reduced in vacuo. The crude product was purified by column chromatography using basic alumina.

Synthesis of(2-Amino-5-chloro-phenyl)-([1H]-1-methyl-pyrazol-5-yl)-methanone

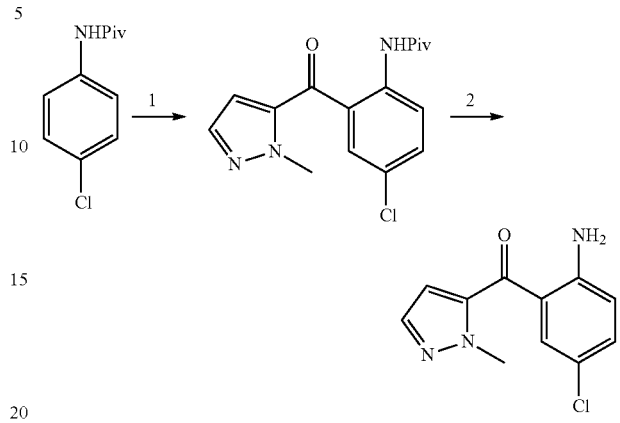

To N-(4-Chlorophenyl)-2,2-dimethyl propanamide (2.0 g, 9.456 mmol) in THF (32 ml) at −5° C. was added n-butyl lithium (1.51 g, 23.64 mmol) slowly. The temperature was maintained at 0° C. for 3 h, then cooled to −70° C., then ethyl-1-methyl-1H-pyrazole-5-carboxylate (2.03 g, 13.23 mmol) in THF (16 ml) was added and the temperature was maintained at −70° C. for 1 h. The reaction mixture was warmed to RT and stirred overnight, water was added and the mixture extracted with ether, washed with water, brine, dried over sodium sulphate and concentrated. The crude intermediate was purified by column chromatography.

6N HCl (10 ml) and intermediate (1.2 g, 3.755 mmol) were heated at 90° C. overnight, cooled to room temperature, the reaction mixture basified by adding saturated sodium bicarbonate solution and extracted with ether. The organic layer was washed with brine, dried over sodium sulfate and concentrated. The product was purified by column chromatography using basic alumina. $^1$H NMR (CDCl$_3$): 6.11 (bs, 2H, NH$_2$), 6.7 (d, 1H, $^3$J=6.6 Hz), 6.89 (s, 1H), 7.28 (m, 1H), 7.7 (s, 1H), 8.2 (s, 1H), 10.75 (bs, 1H). $^{13}$C NMR (CDCl$_3$): 109.25, 118.4, 118.5, 120.5, 132.4, 134.5, 149.4, 186.6. LC-MS m/e 222 (M+H)$^+$. HPLC [c18 BDS 25 min column, flow=0.8 ml/min (70:30; ACN:0.1% TFA), rt=4.11 min].

Synthesis of(2-Amino-5-chloro-phenyl)-([1H]-1-methyl-pyrazol-3-yl)-methanone

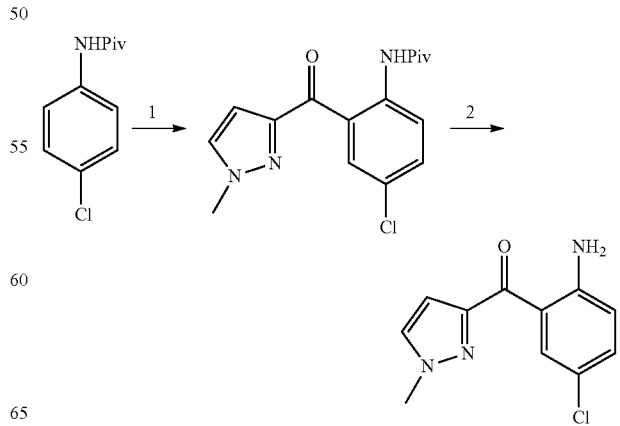

To N-(4-Chlorophenyl)-2,2-dimethyl propanamide (2.0 g, 9.456 mmol) in THF (32 ml) at −5° C. was added n-butyl lithium (1.51 g, 23.64 mmol) slowly. The temperature was maintained at 0° C. for 3 h, then cooled to −70° C., then ethyl-1-methyl-1H-pyrazole-5-carboxylate (2.03 g, 13.23 mmol) in THF (16 ml) was added and the temperature was maintained at −70° C. for 1 h. The reaction mixture was warmed to RT and stirred overnight, water was added and the mixture extracted with ether, washed with water, brine, dried over sodium sulphate and concentrated. The crude intermediate was purified by column chromatography.

6N HCl (10 ml) and intermediate (1.2 g, 3.755 mmol) were heated at 90° C. overnight, cooled to room temperature, the reaction mixture basified by adding saturated sodium bicarbonate solution and extracted with ether. The organic layer was washed with brine, dried over sodium sulfate and concentrated. The product was purified by column chromatography using basic alumina.

Synthesis of(2-Amino-5-chloro-phenyl)-(3-methoxy-pyridin-4-yl)methanone

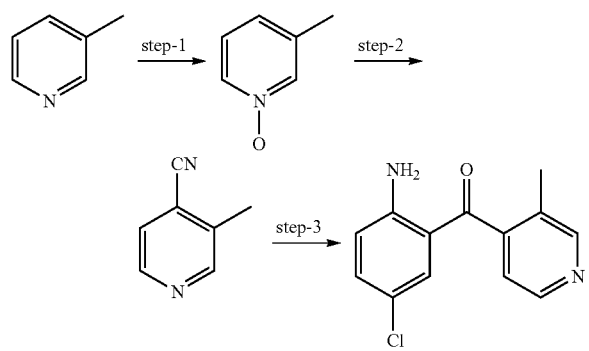

To a solution of 3-picoline (50 g, 0.48 mol) in glacial acetic acid (150 ml) was added hydrogen peroxide (25 ml) at room temperature. The mixture was heated to 90° C. for 3 hr. The mixture was then cooled to RT and more hydrogen peroxide (18.5 ml) was added slowly. The mixture was again heated to 90° C. for 19 hr. The excess peroxide was cautiously decomposed by Pd—C (2.5 g) at 0° C., the Pd—C was filtered, the filtrate was concentrated yielding crude 3-methyl pyridine-1-oxide which was purified by fractional distillation in vacuo.

A solution of 3-methyl pyridine-1-oxide (10 g, 0.092 mol) in methyl iodide (15 ml) was left standing for 18 hr. The solid was filtered. The filtrate was diluted with diethyl ether, extracted with water (40 ml). The solid was dissolved in the aqueous layer in a 250 ml 3-necked RB flask. 1,4-dioxane (50 ml) was added, followed by potassium cyanide (15 g, 0.23 mol). The mixture was stirred at RT for 3 hr. The product was extracted with chloroform, the chloroform layer was washed with water, brine and dried over sodium sulfate. The solvent was removed in vacuo and the crude was purified by fractional distillation (61-62° C./0.2 mm) as white low melting solid.

BCl₃ (24 ml, 1M in DCM, 0.024 mol) was added slowly to a solution of 4-chloroaniline (2 g, 0.016 mol) in 30 ml of trichloroethylene over a period of 15 min. at 0° C. and stirred at this temperature for an additional 10 min. 4-Cyano-3-methylpyridine (2.2 g, 0.019 mol) and AlCl₃ (3 g, 0.022 mol) were added 0° C. The solution was allowed to warm to RT and stirred for 30 min. The solution was then heated at 80-90° C. for 1 hr. and the DCM was distilled off. The resulting solution was refluxed at 115° C. for 4 hr and stirred at RT over night. 3N HCl (20 ml) was added to the mixture and refluxed at 100° C. for 2 hr. The reaction mixture was cooled to 0° C. and was made basic (pH-12) with 6N NaOH and the reaction mixture was extracted with DCM. The dichloromethane layer was washed with water, brine and dried over Na₂SO₄. The solvent was removed, and the crude material was purified by column chromatography on silica gel.

Synthesis of(2-Amino-5-chloro-phenyl)-(6-methyl-pyridin-3-yl)-methanone

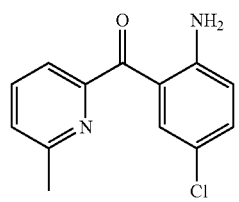 [SMILES: Cc1cccc(C(=O)c2cc(Cl)ccc2N)n1]

2,6-lutidine (107 g, 1 mol) was dissolved in water (2.5 L) and heated to 70° C. To and KMnO₄ (335 g, 2.1 mol) added in 10 portions (each portion was added at 1½ hours interval). After complete addition of KMnO₄, the reaction mixture was heated at 70° C. for another 5 h. The hot reaction mixture was then filtered through a celite bed and the residue was washed with hot water repeatedly. The filtrate was extracted with ethyl acetate and the ethyl acetate layer was discarded. The aqueous layer was concentrated to 500 ml and acidified with HCl to pH exactly to 3.3. Benzene was added to the aqueous layer and water was evaporated. Benzene was added to the concentrated reaction mixture and refluxed for 10 minutes, filtered hot and concentrated.

The intermediate 6-methyl picolinic acid (55 g, 0.0401 mol) was dissolved in absolute ethanol (800 ml), conc. H₂SO₄ (55 ml) was added and the reaction refluxed overnight. Ethyl alcohol was distilled out, water (200 ml) added and the pH was brought to 9 adding solid NaHCO₃. The reaction was extracted with ethyl acetate, the organic layer washed with brine, dried over Na₂SO₄ and concentrated to yield the intermediate ester.

4-chloropivanilide (20 g, 0.0945 mol) was dissolved in t-butyl methyl ether (200 ml) and distilled tetra methyl ethylene diamine (TMEDA) (14.2 mL, 0.0945 mol), the reaction cooled to −20° C. and n-butyl lithium (0.22 mol, 2.7 molar solution in hexane) was added. The temperature was maintained between 0 and 5° C. for 2 h, then cooled to −15° C. and the intermediate ester (15.6 g, 0.0945 mol) was added. After a further 30 minutes, the reaction mixture was quenched with 3N HCl and extracted with ethyl acetate. The ethyl acetate layer was separated and the HCl layer was basified. The aqueous layer was again extracted with ethyl acetate. Both the organic phases were combined, washed with brine and dried over Na₂SO₄. The crude material obtained on concentration of the dried organic phase was subjected to column chromatography (using 60-120 mesh size silica gel. Ethyl acetate: pet ether (10:100)) to afford pivaloyl protected intermediate as a yellow solid (15 g, 47.9%).

The pivaloyl protected intermediate (15 g, 0.0453 mols) was dissolved in methanol 150 ml), 40% KOH solution (60 ml) was added to it and then heated overnight at 65° C. under N₂ atmosphere. The reaction mixture was concentrated and the aqueous layer was extracted with ethyl acetate. The ethyl acetate layer was washed with brine, dried over Na₂SO₄ and concentrated to afford the crude compound. The compound was purified by column chromatography (using 60-120 mesh size silica gel. Ethyl acetate: pet ether (7:100)) to obtain pure title compound (8.5 g, 80.50%).

Synthesis of(2-Amino-5-chloro-phenyl)-(1H-[1,2,3] triazol-4-yl)-methanone

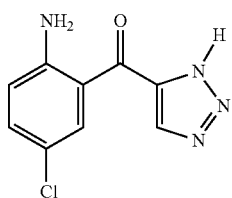 [SMILES: Nc1ccc(Cl)cc1C(=O)c1cnn[nH]1]

The title compound was prepared according to the procedure previously described in the literature (EPO 0 574 781 A2).

Synthesis of(5-Chloro-2-nitro-phenyl)-(3-methyl-[1, 2,3]triazol-4-yl)-methanone and (5-Chloro-2-nitro-phenyl)-(1-methyl-[1,2,3]triazol-4-yl) methanone

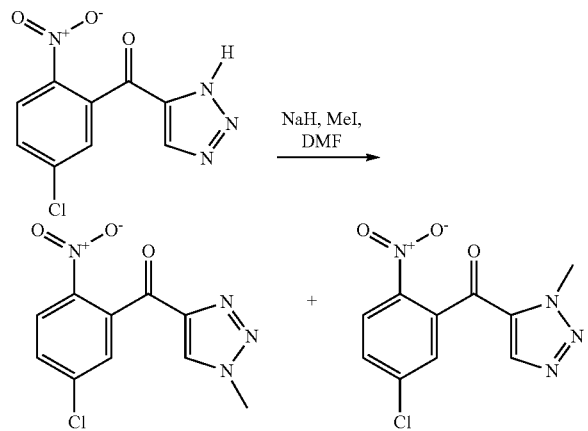

To 250 mg (1 mmol) of (5-Chloro-2-nitro-phenyl)-(3H-[1,2,3]triazol-4-yl)-methanone (M. C. Hsu, D. M. Huryn, and S. Y. K. Tam; EP 0 574 781 A2, filed 5 Jun. 1993) and 214 mg (1.5 mmol) of iodomethane in 6 ml of anhydrous N,N-Dimethylformamide at 0° C. was added 80 mg (2 mmol) of 60% sodium hydride in oil. After 10 minutes, the flask was taken out of the ice bath, and the mixture was stirred for an additional hour. The reaction was quenched with water, partitioned between water and ethyl acetate, and the phases were separated. The ethyl acetate phase was washed twice with water, once with brine, dried over Na₂SO₄, filtered, and concentrated in vacuo to a solid. The solid was chromatographed, using a 20% ethyl acetate in hexane to a 40% ethyl acetate in hexane gradient, to give the two title products as pure isomers.

Synthesis of(2-Amino-5-chloro-phenyl)-(1-methyl-[1,2,3]triazol-4-yl) methanone

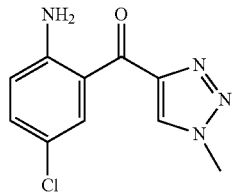 [SMILES: Cn1cc(C(=O)c2cc(Cl)ccc2N)nn1]

To 51 mg (0.19 mmol) of (5-Chloro-2-nitro-phenyl)-(1-methyl-[1,2,3]triazol-4-yl)-methanone in 2 ml of methanol were added 0.05 ml of 12M HCl and 200 mg (0.89 mmol) of stannous (II) chloride monohydrate, and the mixture was heated at 100° C. for four hours. The mixture was then cooled to ambient temperature, partitioned between 1M NaOH and ethyl acetate, and the phases were separated. The ethyl acetate phase was washed once each with water and brine, dried over Na₂SO₄, filtered, and concentrated in vacuo to a solid. The solid was chromatographed to give the title product as a yellow solid.

Synthesis of(2-Amino-5-chloro-phenyl)-(3-methyl-[1,2,3]triazol-4-yl)-methanone

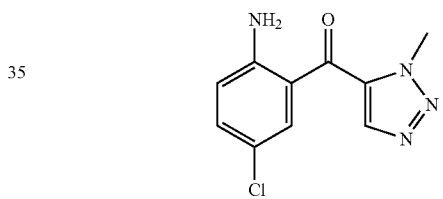

To 31 mg (0.12 mmol) of (5-Chloro-2-nitro-phenyl)-(3-methyl-[1,2,3]triazol-4-yl)-methanone in 1.5 ml of methanol were added 0.05 ml of 12M HCl and 200 mg (0.89 mmol) of stannous (II) chloride monohydrate, and the mixture was heated at 100° C. for four hours. The mixture was then cooled to ambient temperature, partitioned between 1M NaOH and ethyl acetate, and the phases were separated. The ethyl acetate phase was washed once each with water and brine, dried over Na₂SO₄, filtered, and concentrated in vacuo to a solid. The solid was chromatographed to give the title product as a yellow solid.

Synthesis of(2-Amino-5-chloro-phenyl)-(ozaxol-4-yl)-methanone

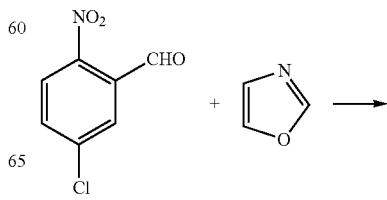

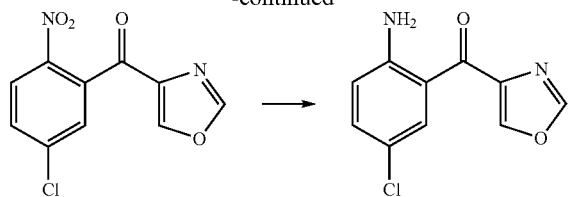

n-Butyllithium (0.01739 mol, 2.5 molar in hexane) was added to a solution of oxazole (1 g, 0.015 mol) in dry THF (55 ml) at −78° C. The reaction mixture was maintained at −78° C. for 0.5 h and 2-nitro-5-chloro benzaldehyde (2.68 g, 0.01449 mol) in dry THF (10 mL) was added. Then the temperature was brought to −25° C. and quenched with saturated NH$_4$Cl solution. The reaction mixture was diluted with ethyl acetate. The organic layer was collected, washed with brine solution, dried over Na$_2$SO$_4$ and concentrated. The product crude material obtained was purified by column chromatography (using 60-120 mesh size silica gel. Pet ether: Ethyl Acetate (100:18)) to obtain the intermediate secondary alcohol.

Pyridiniumchlorochromate (PCC) (3.55 g, 0.0165 mol) was added to a solution of the alcohol (1.4 g, 0.0055 mol) in dry dichloromethane (200 ml), silica gel (10 g) was added and the reaction mixture stirred at room temperature for 48 h. The solid was filtered off and the filtrate concentrated. The solid residue obtained was purified by column chromatography (using 60-120 mesh size silica gel. Pet ether: Ethyl Acetate (100:13) as eluent) to obtain intermediate nitroketone.

The nitroketone (800 mg, 0.00344 mol) was dissolved in ethanol (25 ml), Pd—C (500 mg) was added to it and the reaction mixture heated to 60° C. and to the hot solution was added hydrazine hydrate (0.344 g, 0.00688 mol). The reaction mixture was then heated at 90° C. for 15 min. The Pd—C was filtered off from the reaction mixture and the filtrate was concentrated. This residue was dissolved in DCM and the DCM layer washed with water, brine, dried over Na$_2$SO$_4$ and concentrated to obtain pure title compound.

Synthesis of(2-Amino-5-chloro-phenyl)-(thiazol-5-yl)-methanone

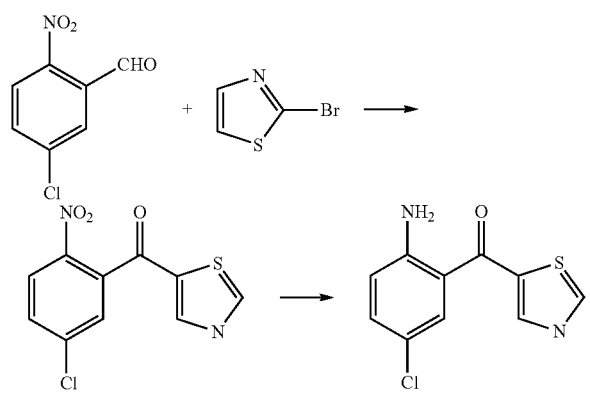

n-BuLi (0.0609 mol, 2.5 molar solution in hexane) was taken in dry ether and cooled to −78° C. and 2-bromo thiazole (10 gm, 0.0609 mol) solution in ether (20 ml) was added during 40 min. This reaction mixture was stirred at −78° C. for 0.5 h and a solution of trimethylchlorosilane (6.58 g, 0.0609 mol) in dry ether was added and stirring continued for another 1 h. After quenching with saturated NaHCO3 solution, the organic layer was collected and concentrated. The residue so obtained was purified by distillation under reduced pressure.

2-trimethylsilylthiazole (1 g, 0.00636 mol) was dissolved in dry THF (25 ml) and cooled to −78° C. n-BuLi (0.0876 mol, 2.5 molar solution in hexane) was added at −78° C. and the temperature maintained at −78° C. for 0.5 h. 2-nitro-5-chloro benzaldehyde (1.18 g, 0.00636 mol) in THF (10 ml) was added at −78° C. After addition was completed, the temperature was raised to −25° C. The reaction mixture was quenched with saturated NH$_4$Cl solution at −25° C. and diluted with ethyl acetate. The organic layer was washed with brine, dried over Na$_2$SO$_4$ and concentrated. The product was purified by column chromatography (using 60-120 mesh size silica gel. Pet ether: Ethyl Acetate (100:15) as eluent).

Pyridiniumchlorochromate (PCC) (1.27 g, 0.0059 mol) was added to a solution of the intermediate alcohol (800 mg, 0.00295 mol) in dry DCM (1500 ml) followed by silica gel (10 g) and the reaction mixture stirred for 48 h. The solid was filtered off and the filtrate concentrated. The solid residue obtained was purified by column chromatography (using 60-120 mesh size silica gel. Pet ether: Ethyl Acetate (100:13) as eluent) to obtain nitroketone.

The nitroketone (790 mg, 0.00295 mol) was dissolved in ethanol (25 ml), Pd—C (500 mg) was added to it and heated to 60° C. and to this hot solution was added hydrazine hydrate (0.294 g, 0.00588 mol). The reaction was then heated at 90° C. for 15 min. The Pd—C was filtered off and the filtrate was concentrated. This residue was dissolved in DCM and the DCM layer washed with water, brine, dried over Na$_2$SO$_4$ and concentrated to obtain pure title compound Synthesis of(2-amino-5-chloro-phenyl)-pyridin-2-yl-methanone

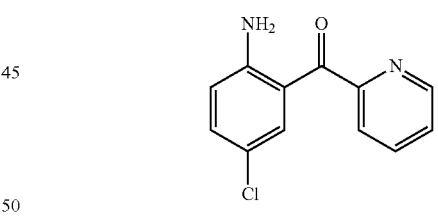

To a stirred solution of N-(4-chlorophenyl)-2,2-dimethylpropanamide (0.5 g, 0.0024 mol) and TMEDA (0.278 g, 0.024 mol) in tert-butyl methyl ether (10 mL) was added n-BuLi (0.384 g, 0.006 mol) at a temperature of −20° C. The mixture was allowed to stir at 0 to 5° C. for 2 h, then cooled to −20° C. and methyl 2-pyridine carboxylate (0.46 g, 0.0034 mol) added. The reaction mixture was maintained at −15° C. for half an hour, the mixture was stirred at room temperature overnight, then quenched with HCl (5 mL, 1.5 N), diluted with water, extracted with ethyl acetate (20 mL×2), washed again with water, brine and dried over anhydrous sodium sulfate. The crude product obtained upon evaporation was purified by column chromatography using ethyl acetate:pet ether (7:93).

To a stirred solution of the intermediate pivaloyl protected ketone (0.33 g, 0.001 mol) in methanol (10 mL) added potassium hydroxide solution (2 mL, 40%) and the reaction refluxed at 70° C. for 15 h. The methanol was distilled off under vacuum and the residue obtained was extracted with ethylacetate (20 mL×3), washed with water, brine and dried over anhydrous sodium sulphate. The product obtained upon concentration was recrystallized from ether and pet ether to yield title compound.

Syntheses of Substituted Phenyl Sulfonyl Chlorides, Including Heteroaryl, Heterocycyl and [Heteroaryl]Alkyl Substituted Systems Synthesis of N-Methoxy-N-methyl-2-phenyl-isobutyramide

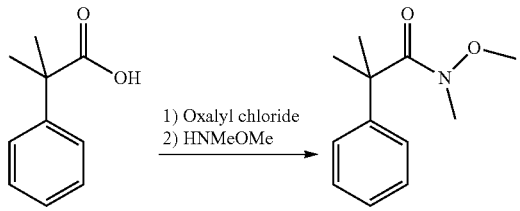

To 6.55 g (39.7 mmol) of 2-phenyl-isobutyric acid in 100 ml of dry methylene chloride at ambient temperature was added 12.5 g (99 mmol) of oxalyl chloride. The bubbling stopped after 2 hours, and the solution was concentrated in vacuo to give a clear oil.

The clear oil from above was dissolved in 30 ml of dichloromethane, and was added to a rapidly stirring biphasic mixture of 150 ml of saturated sodium bicarbonate containing 7.9 g (79 mmol) of methoxymethylamine hydrochloride and 120 ml of dichloromethane at 0° C. The mixture was allowed to warm to ambient temperature after 10 minutes, and the reaction was done after an additional 40 minutes as judged by TLC. The mixture was extracted once with 400 ml of ether, and the ether phase was washed once each with 1M HCl and brine, dried over Na$_2$SO$_4$, filtered, and concentrated in vacuo to the title product as a clear oil.

Synthesis of 3-Methyl-3-phenyl-butan-2-one

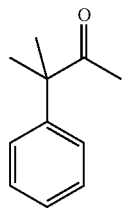

To 2.1 g (10.1 mmol) of N-Methoxy-N-methyl-2-phenyl-isobutyramide in 80 ml of dry tetrahydrofuran at ambient temperature was added 6.7 ml (20.2 mmol) of 3M methymagnesium bromide in heptane, and the solution was warmed to 60° C. After 6 hours, the mixture was allowed to cool to ambient temperature and was quenched with 1M HCl. The resulting mixture was partitioned between water and ether, and the phases were separated. The ether phase was washed once each with 1M HCl and brine, dried over Na$_2$SO$_4$, filtered, and concentrated in vacuo to an oil. The oil was chromatographed to give the title compound as a clear oil: $^1$H NMR CDCl$_3$ δ (ppm): 1.49 (s, 6H), 1.93 (s, 3H), 7.24-7.34 (m, 5H).

Synthesis of 4-(1-Methyl-1-phenyl-ethyl)-oxazole

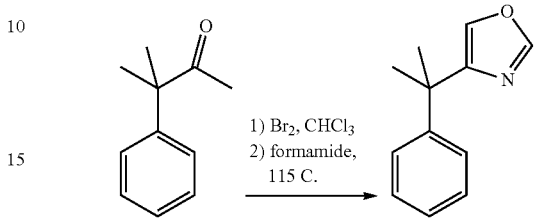

To 1.34 g (8.2 mmol) of 3-Methyl-3-phenyl-butan-2-one in 25 ml of dry chloroform at ambient temperature was added 1.44 g (9.0 mmol) of bromine, and the solution was warmed to 45° C. After 1 hour, the solution was allowed to cool to ambient temperature and was concentrated in vacuo to an orange oil.

1.72 g (7.1 mmol) of the oil was mixed with 20 ml of anhydrous formamide, and the mixture was heated at 115° C. for 2.5 hours. The mixture was allowed to cool to ambient temperature, partitioned between water and ether, and the phases were separated. The ether phase was washed once each with water and brine, dried over Na$_2$SO$_4$, filtered, and concentrated in vacuo to an oil. The oil was chromatographed to give the title compound as a colorless solid: $^1$H NMR CDCl$_3$ δ (ppm): 1.68 (s, 6H), 7.16-7.35 (m, 6H), 7.81 (s, 1H).

Synthesis of 4-(1-Methyl-1-oxazol-4-yl-ethyl)-benzenesulfonyl chloride

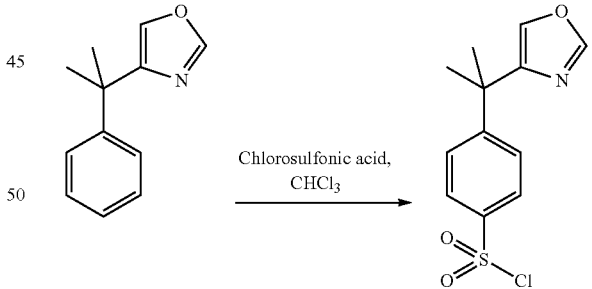

To 261 mg (1.4 mmol) of 4-(1-Methyl-1-phenyl-ethyl)-oxazole in 15 ml of chloroform at 0° C. was added 0.49 gm (4.2 mmol) of chlorosulfonic acid. After 30 minutes, the solution was allowed to warm to ambient temperature and an additional 0.49 gm (4.2 mmol) of chlorosulfonic acid was added. After one hour, the mixture was cooled in an ice/water bath, and crushed ice was added to the reaction. The mixture was partitioned between 1M pH=7 phosphate buffer and ether, and the phases were separated. The ether phase was washed with brine, dried over Na$_2$SO$_4$, filtered, and concentrated in vacuo to give the crude title product as an oil.

Synthesis of 2-Methyl-2-phenylpropionyl chloride

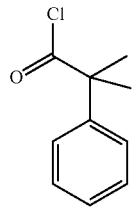

A solution of 2-Methyl-2-phenylpropionic acid (10 mmol, 1.0 eq.) and oxalyl chloride (40 mmol, 4.0 eq.) in dichloromethane (30 mL) was stirred at room temperature for 18 h. The mixture was concentrated in vacuo to afford the title compound as a yellow oil.

Synthesis of 5-(1-Methyl-1-phenylethyl)oxazole

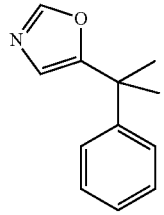

To a solution of methyl isocyanide (1.3 mmol, 1.3 eq.) in THF (5 mL) at −78° C. was added dropwise a solution of n-BuLi in Hexane (2.5 M, 1.3 mmol, 1.3 eq.). The resulting yellowish solution was stirred at −78° C. for an additional 45 min and 2-Methyl-2-phenylpropionyl chloride (1.0 mmol, 1.0 eq.) was slowly added. The mixture was stirred at −78° C. for an additional 1 h and allowed to warm to room temperature followed by the addition of saturated aqueous NaCl solution (5 mL). The mixture was extracted by EtOAc (3×5 mL) and the combined organic extracts were washed by saturated aqueous NaCl solution, dried by Na$_2$SO$_4$, filtered and evaporated in vacuo. The residue was further purified by flash chromatography (silica gel, 10% EtOAc/Hexanes) to afford 5-(1-Methyl-1-phenylethyl)oxazole as a colorless oil (101 mg, 54%). $^1$H NMR: δ (400 MHz, CDCl$_3$) 7.74 (s, 1H), 7.30 (m, 2H), 7.23 (m, 3H), 6.85 (s, 1H), 1.69 (s, 6H). MS (M+H$^+$): 188.1

Synthesis of 4-(1-Methyl-1-oxazol-5-yl-ethyl)benzenesulfonyl chloride

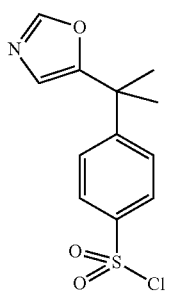 [SMILES: CC(C)(c1ccc(S(=O)(=O)Cl)cc1)c1cnco1]

A solution of 5-(1-Methyl-1-phenylethyl)oxazole (3.87 mmol, 1.0 eq.) in CDCl$_3$ (0.3 mL) was stirred at 0° C. and chlorosulfonic acid (11.7 mmol, 3.0 eq.) was slowly added in. The mixture was heated to 60° C. for 3 h and cooled to room temperature. The solution was further mixed with crushed ice (15 g) and extracted with EtOAc (3×15 mL). The extracts were combined, washed by saturated aqueous NaCl solution, dried by MgSO$_4$, filtered and concentrated in vacuo to afford the title compound as a pale yellow oil (697 mg, 63%) which was used as it was. $^1$H NMR: δ (400 MHz, CDCl$_3$) 7.97 (d, 2H), 7.83 (s, 1H), 7.47 (d, 2H), 6.96 (s, 1H), 1.74 (s, 6H). MS (M+H$^+$): 286.0

Synthesis of 4-(2-methyl-oxazol-5-yl)-benzenesulfonyl chloride

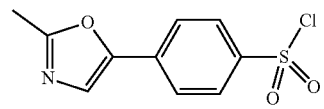

2-Methyl-5-phenyl-oxazole (1.6 g, 10 mmol), prepared according to the literature procedure (Varma, R. S.; Kumar, D. J. Heterocyclic Chem., 1998, 35, 1533), was dissolved in chlorosulfonic acid (10 mL) and stirred at room temperature for 16 h. The reaction mixture was added to crushed ice (50 g) and the product was extracted with ether (3×50 mL). The combined organic extract was dried over anhydrous Na2SO4 and ether was evaporated. The product was purified by flash chromatography (silica-gel, 5-20% ethylacetate/hexane mobile phase) to yield 0.82 g of the desired title compound as tan solid. MS: m/z 258.0 (M$^+$+1).

Synthesis of 2-Phenethyloxazole

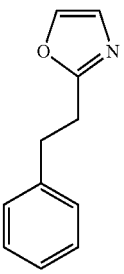 [SMILES: c1ccc(CCc2ncco2)cc1]

A mixture of hydrocinamoyl chloride (5 mmol, 1.0 eq.), 1,2,3-triazole (7 mmol, 1.4 eq.) and K$_2$CO$_3$ (10 mmol, 2.0 eq.) in tetramethylenesulfone (10 mL) was heated to 140° C. for 15 minutes and was allowed to cool to room temperature. The mixture was diluted with aqueous saturated NaCl solution (30 mL) and extracted with EtOAc (3×10 mL). The extracts were combined, dried by Na$_2$SO$_4$, filtered and concentrated in vacuo. The residue was further purified by flash column chromatography (silica gel, 10% EtOAc/hexanes) to afford 1 as a colorless oil (784 mg, 91%). $^1$H NMR: δ (400 MHz, CDCl$_3$) 7.55 (d, 1H), 7.29 (m, 2H), 7.20 (m, 3H), 7.02 (s, 1H), 3.10 (s, 4H). MS (M+H$^+$): 174.0

Synthesis of 4-(2-Oxazol-2-yl-ethyl)benzenesulfonyl chloride

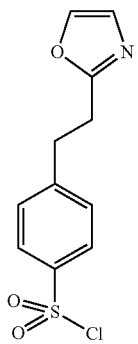 [SMILES: O=S(=O)(Cl)c1ccc(CCc2ncco2)cc1]

A solution of 2-Phenethyloxazole (1.74 mmol, 1.0 eq.) in CDCl$_3$ (0.2 mL) was stirred at 0° C. and chlorosulfonic acid (6.96 mmol, 4.0 eq.) was slowly added in. The mixture was heated to 60° C. for 1 h and cooled to room temperature. The solution was further mixed with crushed ice (5 g) and extracted with EtOAc (3×5 mL). The extracts were combined, washed by saturated aqueous NaCl solution, dried by MgSO$_4$, filtered and concentrated in vacuo. The residue was further purified by flash column chromatography (silica gel, 10% EtOAc/hexanes) to afford 2 as a white solid (275 mg, 58%). $^1$H NMR: δ (400 MHz, CDCl$_3$) 7.95 (d, 2H), 7.58 (s, 1H), 7.44 (d, 2H), 7.04 (s, 1H), 3.25 (t, 2H), 3.16 (t, 2H). MS (M+H$^+$): 372.0

Synthesis of 4-(4-methyl-oxazol-5-yl)-benzenesulfonyl chloride

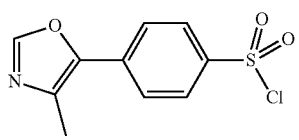 [SMILES: Cc1ncoc1-c1ccc(S(=O)(=O)Cl)cc1]

4-methyl-5-phenyl-oxazole (1.6 g, 10 mmol), prepared according to the literature (Heterocycles, 1977, 7, 77-80), was dissolved in chlorosulfonic acid (10 mL) and stirred at room temperature for 4 h. The reaction mixture was added to crushed ice (50 g) and the product was extracted with ether (3×50 mL). The combined organic extract was dried over anhydrous Na$_2$SO4 and ether was evaporated. The product was purified by flash chromatography (silica-gel, 5-20% ethylacetate/hexane mobile phase) to yield 0.91 g of the desired title compound light yellow solid. MS: m/z 258.0 (M$^+$+1).

Synthesis of 4-ethoxycarbonyl-benzenesulfonyl chloride

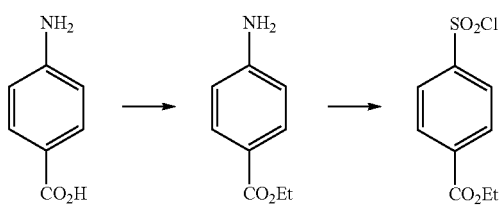 [SMILES: Nc1ccc(C(=O)O)cc1 ; CCOC(=O)c1ccc(N)cc1 ; CCOC(=O)c1ccc(S(=O)(=O)Cl)cc1]

To 4-Aminobenzoic acid (10.0 g, 0.0729 mol) in 100 ml of absolute ethanol was added 10.4 ml of concentrated sulphuric acid dropwise and the mixture refluxed overnight. The reaction mixture was then neutralized with saturated sodium bicarbonate solution and concentrated to remove ethanol. The aqueous layer was extracted with ethyl acetate, the organic layer was washed with brine, dried over sodium sulfate and concentrated.

To water (0198.8 ml) at 0° C. was added thionyl chloride (42.9 g, 0.3605 mol) dropwise. The reaction was stirred at 18° C. for 17 h, then cooled to −2° C. to 0° C., then copper (I) chloride (0.120 g) was added in small portions to get a yellowish green solution.

Ethyl 4-aminobenzoate (14.0 g, 0.0848 mol) was added slowly to concentrated HCl (109.2 ml) and stirred at RT for 15 min, then the reaction was cooled to −5° C. to 0° C. Sodium nitrite (6.2 g, 0.1103 mol) in 26 ml of water was added dropwise and stirring at the same temperature continued for 15 min.

The thionyl chloride derived solution was added dropwise to solution B at −5° C. to 0° C., followed by stirring at 0° C. for 75 min. The reaction mixture was diluted with chloroform. The organic layer was separated, dried over sodium sulphate and concentrated.

Synthesis of 4-(1-Methyl-1-oxazol-2-yl-ethyl)-benzenesulfonyl chloride

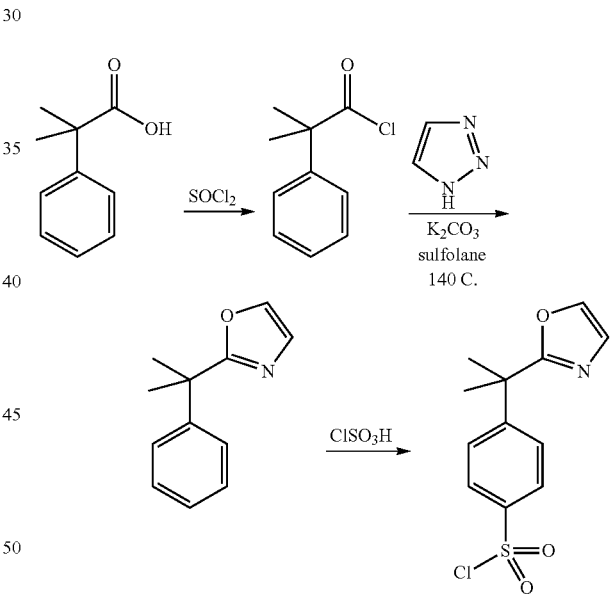

2-Methyl-2-phenyl-propionic acid (8.2 g, 50 mmol) dissolved in 50 mL thionyl chloride was stirred at room temperature for 2 h and heated at 80 C. for an additional 1 h. The excess thionyl chloride was evaporated under vacuum to yield light brown oil. To this oil was added 1,2,3-triazole (4.8 g 70 mmol), K2CO3 (13.8 g, 100 mmol) and tetramethylene sulfone (50 mL) and the mixture was heated at 140 C. for about 30 min and was allowed to cool to room temperature. The reaction mixture was added to water (100 mL) and extracted with ethylacetate (3×50 mL). The combined organic extract was washed with saturated brine dried over anhydrous sodium sulfate and the solvent was evaporated. The residue was further purified by flash column chromatography (silica gel, 0-20% EtOAc/hexanes) to afford 2-(1-methyl-1-phenyl-ethyl)-oxazole as a viscous oil (6.7 g). MS: m/z 188 (M$^+$+1). The viscous oil was cooled on ice bath and treated with chlorosulfonic acid (15 mL). After stirring for 1 h on ice bath the mixture was allowed to warm to room temperature and stir overnight.

Crushed ice (50 g) was added and the mixture stirred till all the ice melted. The product was extracted with ether (3×50 mL), dried over anhydrous sodium sulfate, concentrated by rotary evaporation and further purified by flash chromatography to yield tan solid (7.1 g). MS: m/z 286 (M$^+$+1).

Synthesis of(oxazol-5-yl)-benzenesulfonyl chloride

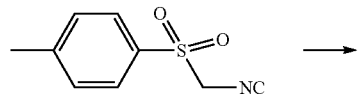

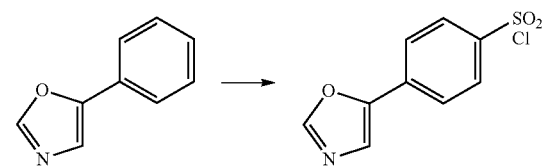

To Benzaldehyde (5.0 g) in methanol (50 ml) was added dry potassium carbonate (7.2 g) followed by TosMIC (10.0 g). The reaction mixture was stirred at 65° C. for 2 h. The solvent was evaporated and the residue was dissolved in ethyl acetate. The ethyl acetate solution was washed with water, brine and concentrated, to yield a yellow solid.

5-Phenyloxazole (2.0 g, mmol) in chloroform (50 ml) was cooled to 0° C. using an ice bath. Chlorosulfonic acid 4.8 g (2.7 ml, 3 eq) of was added slowly with stirring. The reaction mixture was heated to 70° C. for 16 h. The reaction mixture was then cooled to RT, quenched with ice and extracted with chloroform. The organic layer was washed with cold water, brine and concentrated. The brown solid obtained was purified by column chromatography using 5% ethyl acetate in pet ether as eluent, to yield a yellow solid.

Synthesis of4-(4-Methyl-tetrahydro-pyran-4-yl)-benzenesulfonyl chloride

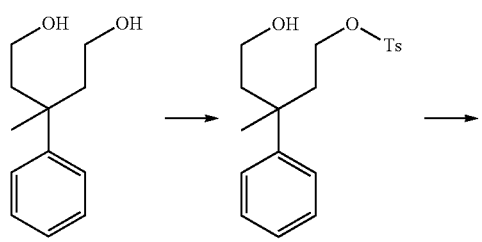

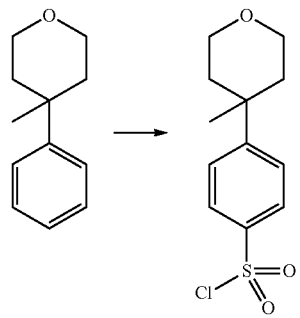

Synthesis of3-Methyl-3-phenyl-pentane-1,5-diol

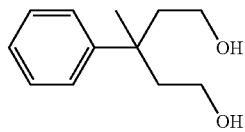

The title compound was prepared was the procedure described in the literature (S. M. McElvain and David H. Clemens; J. Am. Chem. Soc. 1958, 3915-3923). MS: m/z 195.1 (M$^+$+1).

Synthesis of4-Methyl-4-phenyl-tetrahydro-pyran

3-Methyl-3-phenyl-pentane-1,5-diol (3.88 g, 20 mmol), Ag$_2$O (6.95 g (30 mmol), potassium iodide (0.66 g, 4 mmol) were suspended in 50 mL DCM and treated with a solution of p-toluenesulfonyl chloride (4.19 g, 22 mmol) in 30 mL DCM. The mixture was allowed to stir under nitrogen atmosphere for 16 h. The crude reaction mixture was applied on a short plug of silica gel column and the product was collected by washing with DCM. The solvent was evaporated and the residue was dissolved in dry THF (30 mL) and added drop wise to a suspension of NaH (0.8 g of 60% suspension in mineral oil, 20 mmol) in THF (30 ml). The reaction mixture was allowed to stir at room temperature for 24 h and was then diluted with 60 mL ether and washed with water (60 mL). The aqueous phase was washed once with ether (30 mL) and the organic extracts were combined, washed with brine, dried over Na$_2$SO4 and the solvent was evaporated by rotary evaporation. The product was purified by flash chromatography on silica gel column using 0-5% hexane/ethylacetate solvent mixture as the mobile phase. MS: m/z 177.1 (M$^+$+1).

Synthesis of 4-(4-Methyl-tetrahydro-pyran-4-yl)-benzenesulfonyl chloride

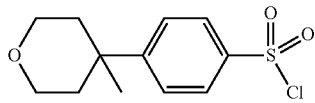 [SMILES: CC1(c2ccc(S(=O)(=O)Cl)cc2)CCOCC1]

To a magnetically stirred mixture of 4-methyl-4-phenyl-tetrahydro-pyran (1.10 g, 6.24 mmol) in dry methylene chloride (50 mL) cooled in an ice bath was added 2.07 mL of chlorosulfonic acid (3.64 g, 31.2 mmol) dropwise under dry nitrogen. The reaction was stirred overnight at room temperature; the reaction was added to ice and the product was extracted with methylene chloride (3×100 mL). The organic layer was washed with saturated brine, dried (MgSO$_4$), filtered and concentrated. e product was chromatographed on silica gel using ethyl acetate-hexane mixtures (2-20% hexane). Removal of solvent provided pure product as a colorless syrup which crystallized on standing: $^1$H NMR (CDCl$_3$) δ 7.99 (d, 2H, J=8.8 Hz), 7.56 (d, 2H, J=8.8 Hz), 3.79 (ddd, 1H, J=11.7 Hz, J=8.4 Hz, J=3.3 Hz), 3.70 (ddd, 1H, J=11.7 Hz, J=6.0 Hz, J=3.8 Hz), 2.11 (ddd, 1H, J=13.8 Hz, J=8.4 Hz, J=3.8 Hz), 1.81 (dm, 1H, J=13.8 Hz), 1.35 (s, 3H). MS: m/z 275 (M$^+$+1).

Synthesis of 3-([1H]-112-methyl-tetrazol-3-yl)-benzenesulfonyl chloride

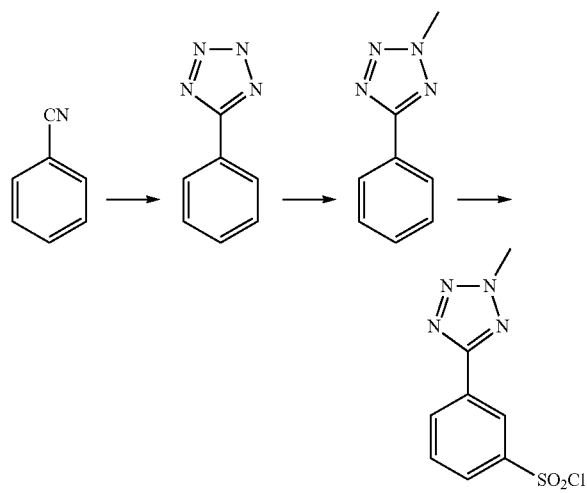

Benzonitrile (10 g, 97 mmol), sodium azide (6.93 g, 106.6 mmol) and NH$_4$Cl (5.7 g, 106.6 mmol) in dry DMF (100 ml) were refluxed at 160° C. overnight and the reaction mixture was then poured into ice cold water, the pH was adjusted to 2 by adding 2N HCl and the solid filtrate collected to yield the phenyltetrazole.

5-phenyl-2-H-tetrazole (4 g, 27.36 mmol) was taken into NaOH (2.18 g, 54 mmol, dissolved in 10 ml of water), cooled to 0° C., methyl iodide (8.5 g, 60 mmol, dissolved in 40 ml acetone) was added and the reaction mixture was refluxed at 55° C. for 2 hours. The solvent was evaporated and the residue was dissolved in benzene. The benzene layer was washed with water, brine, dried over anhydrous Na$_2$SO$_4$ and concentrated. The residue was purified by column chromatography using 60-120 mesh size silica gel (10% ethyl acetate in pet-ether as eluent) to obtain 2-methyl-5-phenyl-2H-tetrazole as white solid (2 g, 46%).

2-methyl-5-phenyl-2H-tetrazole (0.5 g, 3.12 mmol) was taken into chlorosulfonic acid (5 ml) and heated to 80° C. overnight. The reaction mixture was then cooled to 0° C., quenched with ice cold water and extracted with ethyl acetate. The organic phase was washed with water, brine solution, dried over anhydrous Na$_2$SO$_4$ and concentrated. The residue was crystallized from dichloromethane to yield title compound.

Synthesis of N-[4-chloro-2-(pyridine-4-carbonyl)-phenyl]-4-(2-methyl[1,3]dioxolan-2-yl)-benzenesulfonamide

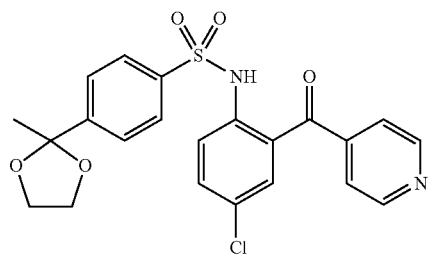 [SMILES: CC1(c2ccc(S(=O)(=O)Nc3ccc(Cl)cc3C(=O)c3ccncc3)cc2)OCCO1]

A solution consisting of 0.21 g of 4-acetyl-N-[4-chloro-2-(hydroxy-pyridin-4-yl-methyl)-phenyl]-benzenesulfonamide, 2 mL anhydrous THF, 50 µL AcOH and 400 µL ethylene glycol was prepared in a vial. The vial was heated by swaying gently in front of a heat gun, cooled for one minute and 400 µL 46.5% BF$_3$:Et$_2$O were immediately added. The vial was quickly shaken, left standing and an LC-MS sample was taken after 1 minute of reaction. After another minute the reaction mixture was partitioned between 10 mL DCM and 10 mL H$_2$O. To the reaction mixture was then added an additional 20 mL DCM and 20 mL aqueous 1 M NaOH. The pH of the aqueous layer was brought to 3 using HCl and then quickly brought to pH 8-9 using saturated NaHCO$_3$. The DCM layer was collected, the aqueous layer was extracted with DCM (2×20 mL) and all organic layers were combined and concentrated by rotary evaporation. The product was isolated by preparative HPLC, and the fractions containing the product were concentrated to a volume of 15 mL. To this solution was added 3 mL 3 M NaOH and 0.52 g KMnO4. The reaction was stirred at RT, monitored by LC-MS and additional KMnO4 (0.55 g×2) was added at intervals of ca. 2 hours. After a total rxn time of ca. 5 h, the crude mixture was brought to pH 4 using 10% AcOH, extracted with DCM (125 mL) and washed with saturated aqueous NaHCO$_3$. The DCM was removed by rotary evaporation and the product was obtained by preparative HPLC. MS: m/z 459 (M$^+$+1).

The procedure described above was used to synthesize analogous compounds as described for the following two compounds shown below:

N-[4-Chloro-2-(pyridine-4-carbonyl)-phenyl]-4-(2,4-dimethyl-[1,3]dioxolan-2-yl)-benzenesulfonamide

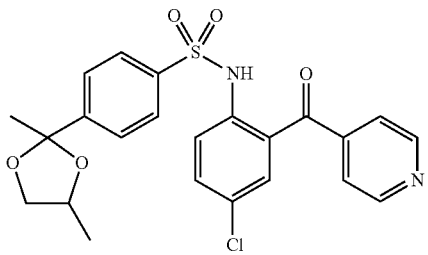 [SMILES: CC1COC(C)(c2ccc(S(=O)(=O)Nc3ccc(Cl)cc3C(=O)c3ccncc3)cc2)O1]

The title compound was prepared using 4-Acetyl-N-[4-chloro-2-(hydroxy-pyridin-4-yl-methyl)-phenyl]-benzenesulfonamide and propane-1,2-diol following the procedure described in the preceding example. MS: m/z 473 M$^+$+1).

N-[4-Chloro-2-(pyridine-4-carbonyl)-phenyl]-4-((4R,5S)-2,4,5-trimethyl-[1,3]dioxolan-2-yl)-benzenesulfonamide

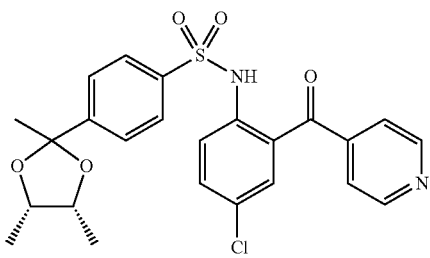 [SMILES: C[C@@H]1OC(C)(c2ccc(S(=O)(=O)Nc3ccc(Cl)cc3C(=O)c3ccncc3)cc2)O[C@@H]1C]

The title compound was prepared using 4-Acetyl-N-[4-chloro-2-(hydroxy-pyridin-4-yl-methyl)-phenyl]-benzenesulfonamide and (2R,3S)-Butane-2,3-diol following the procedure described in the preceding two examples. MS: m/z 487 M$^+$+1).

Synthesis of 4-Chloro-2-(pyridine-4-carbonyl)-phenyl]-3-([1H]-1l2-methyl-tetrazol-3-yl)-benzenesulfonamide

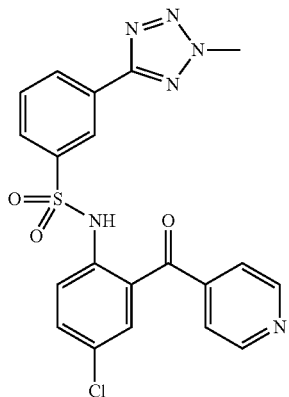 [SMILES: Cn1nnc(-c2cccc(S(=O)(=O)Nc3ccc(Cl)cc3C(=O)c3ccncc3)c2)n1]

3-([1H]-1-methyl-tetrazol-3-yl)-benzenesulfonyl chloride (0.3 g, 1.28 mmol) and the parent benzophenone (0.5 g, 1.93 mmol) were dissolved in dry pyridine (10 ml) and heated overnight at 100° C. The reaction mixture was then diluted with dichloromethane and this layer was washed with water and brine solution, dried over anhydrous Na$_2$SO$_4$ and concentrated. The residue was purified by column chromatography using 60-120 mesh size silica gel (Pet ether/ethyl acetate as eluent) to afford the title compound as yellow solid.

Synthesis of 4-Bromo-N-[4-chloro-2-(pyridine-4-carbonyl)-phenyl]-benzenesulfonamide

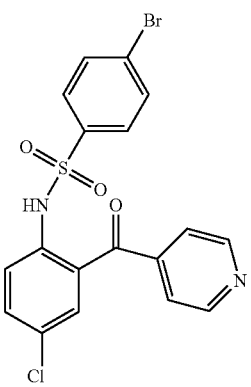 [SMILES: O=C(c1ccncc1)c1cc(Cl)ccc1NS(=O)(=O)c1ccc(Br)cc1]

4-Bromo-benzenesulfonyl chloride 27.5 g (107 mmol) was dissolved in 180 ml of anhydrous pyridine. To this solution was added (2-amino-5-chloro-phenyl)-pyridin-4-yl-methanone 25 g (107 mmol). The reaction mixture was stirred under nitrogen 5 hour at 80° C. and pyridine was then evaporated under vacuum. The resulting crude material was dissolved in dichloromethane, and extracted with saturated bicarbonate solution. The combined organic layer was washed with brine dried over magnesium sulfate, filtered and concentrated, then ethyl acetate (50 mL) added to the solid, the solid was filtered, washed again with ethyl acetate, to yield a pale yellow solid: LC-MSD, m/z for C$_{18}$H$_{12}$BrClN$_2$O$_3$S [M+H]+: 452.9

Retention time on reverse phase HPLC gradient 20%-95%: 7 minutes: 4.307

Synthesis of N-[4-Chloro-2(pyridine-4-carbonyl)-phenyl]-4-morpholin-4-yl-benzenesulfonamide

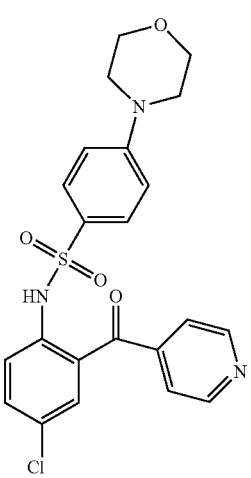 [SMILES: O=C(c1ccncc1)c1cc(Cl)ccc1NS(=O)(=O)c1ccc(N2CCOCC2)cc1]

4-Bromo-N-[4-chloro-2-(pyridine-4-carbonyl)-phenyl]-benzenesulfonamide 0.1 g (0.22 mmol), was dissolved in 6 ml anhydrous dioxane, and to this solution was added potassium phosphate tribasic monohydrate 0.3 g (1.32 mmol), rac-2,2'-bis(diphenylphosphino)-1,1'-binaphthyl 0.02 g (0.032 mmol), followed by morpholine 0.95 g (1.1 mmol). The mixture was purged under nitrogen, and Pd(dba)$_3$ 10 mg (0.01 mmol) was added. The reaction mixture was heated overnight at 90° C., cooled, water (5 mL) added, and extracted with ethyl acetate 3 times. The combined organic layer was washed with brine, dried over magnesium sulfate, filtered and concentrated. The crude reaction mixture was purified using HPLC with a gradient of 20 to 95% acetonitrile over 40 minutes, to yield a yellow solid: LC-MSD, m/z for $C_{22}H_{20}ClN_3O_4S$ [M+H]+: 458

R. time Reverse phase HPLC gradient 20%-95% in 7 minutes: 3.952

Synthesis of N-[4-Chloro-2-(pyridine-4-carbonyl)-phenyl]-4-piperidin-1-yl-benzenesulfonamide

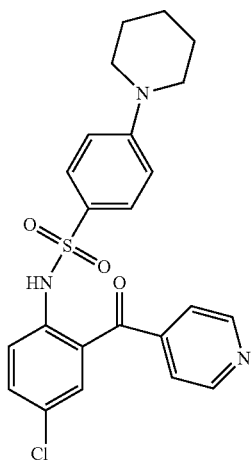 [SMILES: O=C(c1ccncc1)c1cc(Cl)ccc1NS(=O)(=O)c1ccc(N2CCCCC2)cc1]

The title compound was prepared according to the general procedure for the synthesis of heterocyclyl and heteroaryl substituted phenylsulfonyl derivatives previously described, using 4-Bromo-N-[4-chloro-2-(pyridine-4-carbonyl)-phenyl]-benzenesulfonamide 0.3 g (0.66 mmol), potassium phosphate tribasic monohydrate 0.91 g (3.96 mmol), rac-2,2'-bis(diphenylphosphino)-1,1'-binaphthyl 0.12 g (0.198 mmol), piperidine 0.28 g (3.3 mmol) and Pd (dba)$_3$ 60 mg (0.066 mmol) in 6 ml dioxane. The crude reaction mixture was purified using HPLC to yield the title compound as a yellow solid.

LC-MSD, m/z for $C_{23}H_{22}ClN_3O_3S$ [M+H]+: 456

R. time Reverse phase HPLC gradient 20%-95% in 7 minutes: 5.037

Synthesis of N-[4-chloro-2-(pyridine-4-carbonyl)-phenyl]-4-pyrrolidin-1-yl-benzenesulfonamide

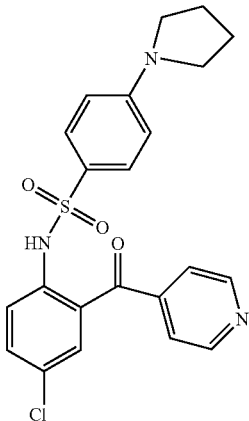 [SMILES: O=C(c1ccncc1)c1cc(Cl)ccc1NS(=O)(=O)c1ccc(N2CCCC2)cc1]

The title compound was prepared according to the general procedure for the synthesis of heterocyclyl and heteroaryl substituted phenylsulfonyl derivatives previously described, using 4-Bromo-N-[4-chloro-2-(pyridine-4-carbonyl)-phenyl]-benzenesulfonamide 0.3 g (0.66 mmol), potassium phosphate tribasic monohydrate 0.91 g (3.96 mmol), rac-2,2'-bis(diphenylphosphino)-1,1'-binaphthyl 0.12 g (0.198 mmol), pyrrolidine 0.23 g (3.3 mmol) and Pd (dba)$_3$ 60 mg (0.066 mmol) in 6 ml dioxane, yielding title compound after HPLC purification: LC-MSD, m/z for $C_{22}H_{20}ClN_3O_3S$ [M+H]+: 442.1

R. time Reverse phase HPLC gradient 20%-95% in 7 minutes: 4.853

Synthesis of N-[4-Chloro-2(pyridine-4-carbonyl)-phenyl]-4-(1,1-dioxo-thiomorpholin-4-yl)-benzenesulfonamide

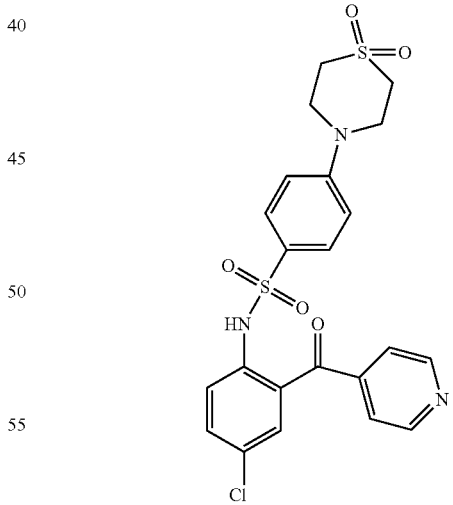

The title compound was prepared according to the general procedure for the synthesis of heterocyclyl and heteroaryl substituted phenylsulfonyl derivatives previously described, using 4-Bromo-N-[4-chloro-2-(pyridine-4-carbonyl)-phenyl]-benzenesulfonamide 0.3 g (0.66 mmol), potassium phosphate tribasic monohydrate 0.91 g (3.96 mmol), rac-2,2'-bis(diphenylphosphino)-1,1'-binaphthyl 0.12 g (0.198 mmol), thiomorpholine 1,1-dioxide 0.44 g (3.3 mmol) and Pd (dba)₃ 60 mg (0.066 mmol) in 6 ml dioxane, followed by work up and HPLC purification: LC-MSD, m/z for $C_{22}H_{20}ClN_3O_3S_2$ [M+H]+: 502

R. time Reverse phase HPLC gradient 20%-95% in 7 minutes: 3.743

Synthesis of N-[4-Chloro-2-(pyridine-4-carbonyl)-phenyl]-4-(cis-2,6-dimethyl-morpholin-4-yl)-benzenesulfonamide

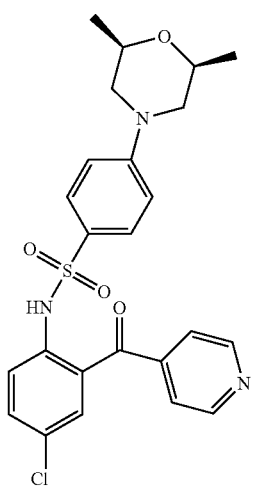 [SMILES: C[C@@H]1CN(c2ccc(S(=O)(=O)Nc3ccc(Cl)cc3C(=O)c3ccncc3)cc2)C[C@H](C)O1]

The title compound was prepared according to the general procedure for the synthesis of heterocyclyl and heteroaryl substituted phenylsulfonyl derivatives previously described, using 4-Bromo-N-[4-chloro-2-(pyridine-4-carbonyl)-phenyl]-benzenesulfonamide 0.3 g (0.66 mmol), potassium phosphate tribasic monohydrate 0.91 g (3.96 mmol), rac-2,2'-bis(diphenylphosphino)-1,1'-binaphthyl 0.12 g (0.198 mmol), cis-2,6-dimethylmorpholine 0.37 g (3.3 mmol) and Pd (dba)₃ 60 mg (0.066 mmol) in 6 ml dioxane, followed by work up and HPLC purification: LC-MSD, m/z for $C_{24}H_{24}ClN_3O_4S$ [M+H]+: 486.0

R. time Reverse phase HPLC gradient 20%-95% in 7 minutes: 4.539

Synthesis of N-[4-Chloro-2-(pyridine-4-carbonyl)-phenyl]-4-thiomorpholin-4-yl-benzenesulfonamide

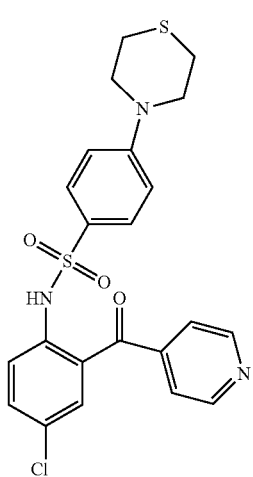 [SMILES: O=C(c1ccncc1)c1cc(Cl)ccc1NS(=O)(=O)c1ccc(N2CCSCC2)cc1]

The title compound was prepared according to the general procedure for the synthesis of heterocyclyl and heteroaryl substituted phenylsulfonyl derivatives previously described, using 4-Bromo-N-[4-chloro-2-(pyridine-4-carbonyl)-phenyl]-benzenesulfonamide 0.3 g (0.66 mmol), potassium phosphate tribasic monohydrate 0.91 g (3.96 mmol), rac-2,2'-bis(diphenylphosphino)-1,1'-binaphthyl 0.12 g (0.198 mmol), thiomorpholine 0.34 g (3.3 mmol) and Pd (dba)₃ 60 mg (0.066 mmol) in 3 ml DMF followed by work up and HPLC purification: LC-MSD, m/z for $C_{22}H_{20}ClN_3O_3S_2$ [M+H]+: 474.0

R. time Reverse phase HPLC gradient 20%-95% in 7 minutes: 4.714

Synthesis of N-[4-Chloro-2(pyridine-4-carbonyl)-phenyl]-4-piperazin-1-yl-benzenesulfonamide

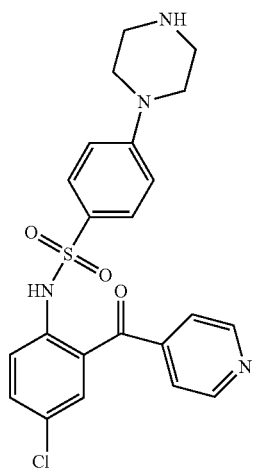 [SMILES: O=C(c1ccncc1)c1cc(Cl)ccc1NS(=O)(=O)c1ccc(N2CCNCC2)cc1]

The title compound was prepared according to the general procedure for the synthesis of heterocyclyl and heteroaryl substituted phenylsulfonyl derivatives previously described, using 4-Bromo-N-[4-chloro-2-(pyridine-4-carbonyl)-phenyl]-benzenesulfonamide 0.1 g (0.22 mmol), potassium phosphate tribasic monohydrate 0.30 g (1.2 mmol), rac-2,2'-bis(diphenylphosphino)-1,1'-binaphthyl 0.02 g (0.032 mmol), piperazine-1-carboxylic acid tert-butyl ester 0.18 g (1 mmol) and Pd (II) trifluoroacetate 10 mg (0.01 mmol) in 6 ml dioxane. The compound was then deprotected to yield free amine using dichloromethane (2 mL) with trifluoroacetic acid (3 mL) for 1 hour at room temperature. The crude material was concentrated under vacuo, purified by HPLC, to give yellow solid.

LC-MSD, m/z for $C_{22}H_{21}ClN_4O_3S$ [M+2H]+: 458.0

R. time Reverse phase HPLC gradient 20%-95% in 7 minutes: 3.952

Synthesis of 4-Azetidin-1-yl-N-[4-chloro-2-(pyridine-4-carbonyl)-phenyl]-benzenesulfonamide

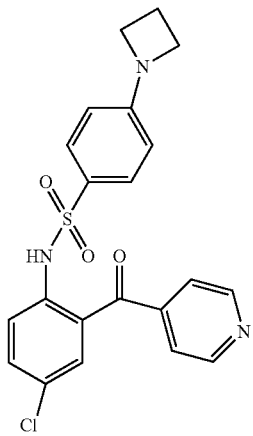 [SMILES: O=C(c1ccncc1)c1cc(Cl)ccc1NS(=O)(=O)c1ccc(N2CCC2)cc1]

The title compound was prepared according to the general procedure for the synthesis of heterocyclyl and heteroaryl substituted phenylsulfonyl derivatives previously described, using 4-Bromo-N-[4-chloro-2-(pyridine-4-carbonyl)-phenyl]-benzenesulfonamide 0.3 g (0.66 mmol), potassium phosphate tribasic monohydrate 0.91 g (3.96 mmol), rac-2,2'-bis(diphenylphosphino)-1,1'-binaphthyl 0.12 g (0.198 mmol), azetidine 0.18 g (3.3 mmol) and Pd (dba)$_3$ 60 mg (0.066 mmol) in 3 ml DMF, followed by workup and HPLC purification.

LC-MSD, m/z for $C_{21}H_{18}ClN_3O_3S$ [M+H]+: 428
R. time Reverse phase HPLC gradient 20%-95% in 7 minutes: 4.77

Synthesis of 4-Bromo-N-[4-chloro-2-(pyridine-3-carbonyl)-phenyl]-benzenesulfonamide

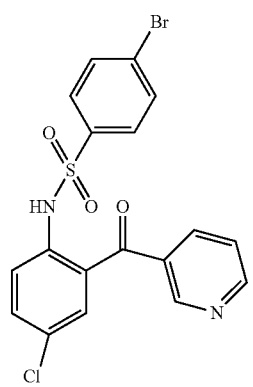 [SMILES: O=C(c1cccnc1)c1cc(Cl)ccc1NS(=O)(=O)c1ccc(Br)cc1]

The title compound was prepared according to the general procedures for the synthesis of N-Aryl-benzenesulfonamides previously described using (2-amino-5-chloro-phenyl)-pyridin-3-yl-methanone 5 g (21.5 mmol) and 4-bromobenzenesulfonyl chloride 5.78 g (21.5 mmol), in 150 ml anhydrous pyridine, overnight at 80° C., followed by flash column chromatography on silica gel to yield a salmon color solid.

LC-MSD, m/z for $C_{18}H_{12}BrClN_2O_3S$ [M+H]+: 452.9
R. time Reverse phase HPLC gradient 20%-95% in 7 minutes: 4.584

Synthesis of N-[4-Chloro-2-(pyridine-3-carbonyl)-phenyl]-4-(cis-2,6-dimethyl-morpholin-4-yl)-benzensulfonamide

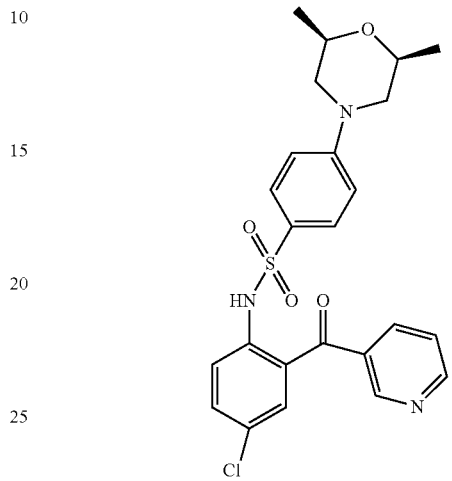

The title compound was prepared according to the general procedure for the synthesis of heterocyclyl and heteroaryl substituted phenylsulfonyl derivatives previously described, using 4-Bromo-N-[4-chloro-2-(pyridine-3-carbonyl)-phenyl]-benzenesulfonamide 0.3 g (0.66 mmol), potassium phosphate tribasic monohydrate 0.91 g (3.96 mmol), rac-2,2'-bis(diphenylphosphino)-1,1'-binaphthyl 0.12 g (0.198 mmol), cis-2,6-dimethylmorpholine 0.37 g (3.3 mmol) and Pd (dba)$_3$ 60 mg (0.066 mmol) in 3 ml DMF, followed by work up and HPLC purification to yield yellow title compound.

LC-MSD, m/z for $C_{24}H_{24}ClN_3O_4S$ [M+H]+: 516.1
R. time Reverse phase HPLC gradient 20%-95% in 7 minutes: 4.242

Synthesis of 4-Bromo-N-[4-chloro-2-(6-methyl-pyridine-3-carbonyl)-phenyl]-benzenesulfonamide

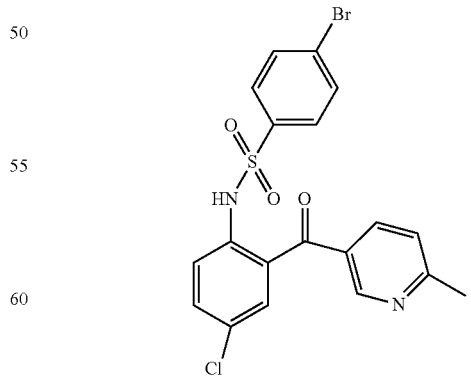

The title compound was prepared according to the general procedures for the synthesis of N-Aryl-benzenesulfonamides previously described using (2-amino-5-chloro-phenyl)-(6-methyl-pyridin-3-yl)-ethanone 1.5 g (6.1 mmol), and 4-bromo-benzenesulfonyl chloride 1.55 g (6.1 mmol), stirred in 12 ml anhydrous pyridine, for 2 days room temperature, yielded title compound as a yellow solid.

LC-MSD, m/z for $C_{19}H_{14}BrClN_2O_3S$ [M+H]+: 466.9

R. time Reverse phase HPLC gradient 20%-95% in 7 minutes: 4.77

Synthesis ofN-[4-Chloro-2-(6-methyl-pyridine-3-carbonyl)-phenyl]-4-(cis-2,6-dimethyl-morpholin-4-yl)-benzensulfonamide

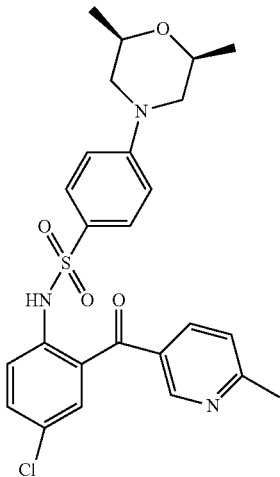 [SMILES: Cc1ccc(C(=O)c2cc(Cl)ccc2NS(=O)(=O)c2ccc(N3C[C@@H](C)O[C@@H](C)C3)cc2)cn1]

The title compound was prepared according to the general procedure for the synthesis of heterocyclyl and heteroaryl substituted phenylsulfonyl derivatives previously described, using 4-Bromo-N-[4-chloro-2-(6-methyl-pyridine-3-carbonyl)-phenyl]-benzenesulfonamide. 0.3 g (0.66 mmol), potassium phosphate tribasic monohydrate 0.91 g (3.96 mmol), rac-2,2'-bis(diphenylphosphino)-1,1'-binaphthyl 0.12 g (0.198 mmol), cis-2,6-dimethylmorpholine 0.37 g (3.3 mmol) and Pd (dba)$_3$ 60 mg (0.066 mmol) in 3 ml DMF, followed by workup and HPLC purification to yield yellow title compound.

LC-MSD, m/z for $C_{25}H_{26}ClN_3O_4S$ [M+H]+: 500.1

R. time Reverse phase HPLC gradient 20%-95% in 7 minutes: 4.796

Synthesis of4-Bromo-N-[4-chloro-2-(2-pyridine-4-carbonyl)-phenyl]-3-fluoro-benzenesulfonamide

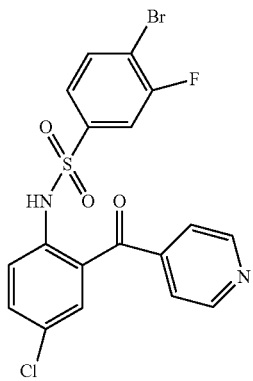 [SMILES: O=C(c1ccncc1)c1cc(Cl)ccc1NS(=O)(=O)c1ccc(Br)c(F)c1]

The title compound was prepared according to the general procedures for the synthesis of N-Aryl-benzenesulfonamides previously described using (2-amino-5-chloro-phenyl)-pyridine-4-yl-methanone 2 g (7.8 mmol), and 4-bromo-3-fluoro-benzenesulfonyl chloride 2.56 g (9.4 mmol), with stirring in 14.4 ml anhydrous pyridine, at 80° C. overnight, to yield yellow title compound.

LC-MSD, m/z for $C_{18}H_{21}BrFClN_2O_3S$ [M+H]+: 470.9

R. time Reverse phase HPLC gradient 20%-95% in 7 minutes: 4.78

Synthesis ofN-[4-Chloro-2-(pyridine-4-carbonyl)-phenyl]-3-fluoro-4-morpholin-4-yl-benzenesulfonamide

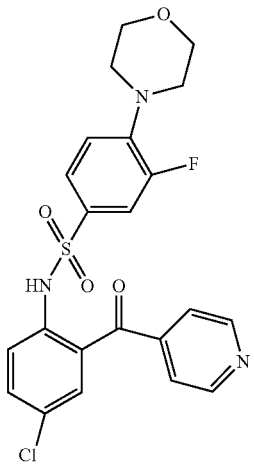 [SMILES: O=C(c1ccncc1)c1cc(Cl)ccc1NS(=O)(=O)c1ccc(N2CCOCC2)c(F)c1]

The title compound was prepared according to the general procedure for the synthesis of heterocyclyl and heteroaryl substituted phenylsulfonyl derivatives previously described, using 4-Bromo-N-[4-chloro-2-(2-pyridine-4-carbonyl)-phenyl]-3-fluoro-benzenesulfonamide. 0.15 g (0.3 mmol), potassium phosphate tribasic monohydrate 0.41 g (18 mmol), rac-2,2'-bis(diphenylphosphino)-1,1'-binaphthyl 0.03 g (0.045 mmol), morpholine 0.13 g (1.5 mmol) and Pd (dba)$_3$ 10 mg (0.011 mmol) in 2 ml DMF, followed by workup and HPLC purification.

LC-MSD, m/z for $C_{22}H_{19}ClN_3O_4SF$ [M+H]+: 476.0

R. time Reverse phase HPLC gradient 20%-95% in 7 minutes: 4.472

Synthesis of N-[4-Chloro-2-(pyridine-4-carbonyl)-phenyl]-4-(cis-2,6-dimethyl-morpholin-4-)yl-3-fluoro-benzenesulfonamide

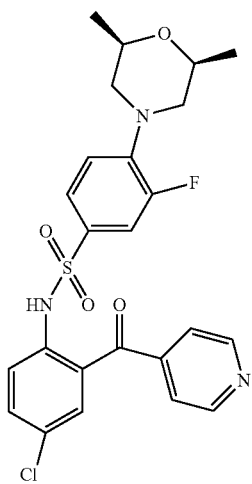 [SMILES: C[C@@H]1CN(c2ccc(S(=O)(=O)Nc3ccc(Cl)cc3C(=O)c3ccncc3)cc2F)C[C@H](C)O1]

The title compound was prepared according to the general procedure for the synthesis of heterocyclyl and heteroaryl substituted phenylsulfonyl derivatives previously described, using 4-Bromo-N-[4-chloro-2-(2-pyridine-4-carbonyl)-phenyl]-3-fluoro-benzenesulfonamide. 0.15 g (0.3 mmol), potassium phosphate tribasic monohydrate 0.41 g (1.8 mmol), rac-2,2'-bis(diphenylphosphino)-1,1'-binaphthyl 0.05 g (0.09 mmol), cis-2,6-dimethyl-morpholin 0.13 g (1.5 mmol) and Pd (dba)$_3$ 0.4 mg (0.04 mmol) in 2 ml DMF, followed by workup and purification using silica gel chromatography (gradient of dichloromethane to 1-1 dichloromethane-ethyl acetate), to yield a light yellow solid.

LC-MSD, m/z for $C_{24}H_{23}ClN_3O_4SF$ [M+H]+: 504.1
R. time Reverse phase HPLC gradient 20%-95% in 7 minutes: 5.024

Synthesis of 4-Bromo-N-[4,5-difluoro-2-(pyridine-3-carbonyl)-phenyl]-benzenesulfonamide

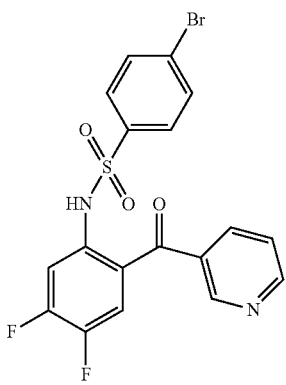 [SMILES: O=C(c1cccnc1)c1cc(F)c(F)cc1NS(=O)(=O)c1ccc(Br)cc1]

The title compound was prepared according to the general procedures for the synthesis of N-Aryl-benzenesulfonamides previously described using (2-amino-4,5-difluoro-phenyl)-pyridin-3-yl-methanone 1 g (4.27 mmol) and 4-bromo-benzenesulfonyl chloride 1.15 g (4.27 mmol) with stirring in 20 ml pyridine. Purification on silica gel with flash column chromatography yielded light orange solid LC-MSD, m/z for $C_{18}H_{11}N_2O_2SF_2$ [M+H]+:454.9
R. time Reverse phase HPLC gradient 20%-95% in 7 minutes: 4.574

Synthesis of N-[4,5-Difluoro-2-(pyridine-3-carbonyl)-phenyl]-4-morpholin-4-yl-benzenesulfonamide

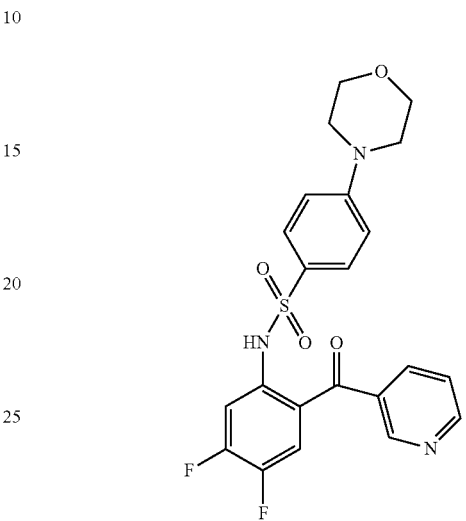

The title compound was prepared according to the general procedure for the synthesis of heterocyclyl and heteroaryl substituted phenylsulfonyl derivatives previously described, using 4-Bromo-N-[4,5-difluoro-2-(pyridine-3-carbonyl)-phenyl]-benzenesulfonamide 0.2 g (0.44 mmol), potassium phosphate tribasic monohydrate 0.607 g (2.64 mmol), rac-2,2'-bis(diphenylphosphino)-1,1'-binaphthyl 0.082 g (0.06 mmol), morpholine 0.30 g (2.2 mmol) and Pd (dba)$_3$ 0.06 g (0.06 mmol) in 2 ml DMF. HPLC purification gave yellow title compound.

LC-MSD, m/z for $C_{22}H_{19}N_3O_4SF_2$ [M+H]+: 502
R. time Reverse phase HPLC gradient 20%-95% in 7 minutes: 3.918

Synthesis of 4-Bromo-N-[4-chloro-2-(6-methyl-pyridine-3-carbonyl)-phenyl]-3-fluoro-benzenesulfonamide

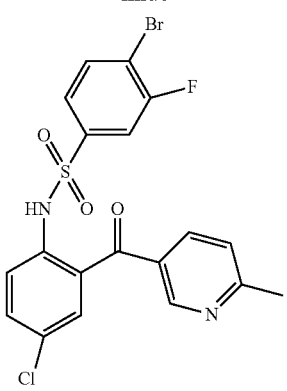

The title compound was prepared according to the general procedures for the synthesis of N-Aryl-benzenesulfonamides previously described using (2-amino-5-chloro-phenyl)-(6-methyl-pyridin-3-yl)-methanone 2.4 g (8.77 mmol) and 4-bromo-3-fluoro-benzenesulfonyl chloride 2.16 g (8.77 mmol) stirred in 14 ml pyridine. Purification on silica gel with flash column chromatography gave a light orange solid.

LC-MSD, m/z for $C_{19}H_{13}N_2O_3S$ FBrCl [M+H]+: 484.9

R. time Reverse phase HPLC gradient 20%-95% in 7 minutes: 4.875

Synthesis of N-[4-Chloro-2-(6-methyl-pyridine-3-carbonyl)-phenyl]-3-fluoro-4-morpholin-4-yl-benzenesulfonamide

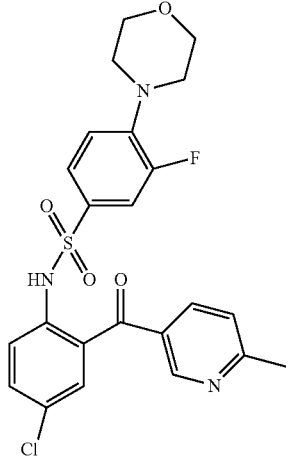 [SMILES: Cc1ccc(C(=O)c2cc(Cl)ccc2NS(=O)(=O)c2ccc(N3CCOCC3)c(F)c2)cn1]

The title compound was prepared according to the general procedure for the synthesis of heterocyclyl and heteroaryl substituted phenylsulfonyl derivatives previously described, using 4-Bromo-N-[4-chloro-2-(6-methyl-pyridine-3-carbonyl)-phenyl]-3-fluoro-benzenesulfonamide 0.2 g (0.4 mmol), potassium phosphate tribasic monohydrate 0.570 g (2.4 mmol), rac-2,2'-bis(diphenylphosphino)-1,1'-binaphthyl 0.077 g (0.12 mmol), morpholine 0.17 g (2 mmol) and Pd (dba)$_3$ 0.057 g (0.06 mmol) in 2 ml DMF. HPLC purification gave a yellow compound.

LC-MSD, m/z for $C_{23}H_{21}ClN_3O_4S$ F [M+H]+: 490.1

R. time Reverse phase HPLC gradient 20%-95% in 7 minutes: 4.603

Synthesis of N-[4-Chloro-2-(6-methyl-pyridine-3-carbonyl)-phenyl]-4-(cis-2,6-dimethyl-morpholin-4-yl)-3-fluoro-benzenesulfonamide

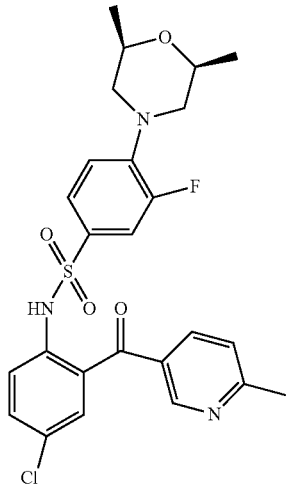 [SMILES: Cc1ccc(C(=O)c2cc(Cl)ccc2NS(=O)(=O)c2ccc(N3C[C@@H](C)O[C@@H](C)C3)c(F)c2)cn1]

The title compound was prepared according to the general procedure for the synthesis of heterocyclyl and heteroaryl substituted phenylsulfonyl derivatives previously described, using 4-Bromo-N-[4-chloro-2-(6-methyl-pyridine-3-carbonyl)-phenyl]-3-fluoro-benzenesulfonamide 0.2 g (0.4 mmol), potassium phosphate tribasic monohydrate 0.570 g (2.4 mmol), rac-2,2'-bis(diphenylphosphino)-1,1'-binaphthyl 0.077 g (0.12 mmol), cis-2,6-dimethyl-morpholine 0.23 g (2 mmol) and Pd (dba)$_3$ 0.057 g (0.06 mmol) in 2 ml DMF. HPLC purification gave yellow compound.

LC-MSD, m/z for $C_{25}H_{25}ClN_3O_4S$ F [M+H]+: 518.1

R. time Reverse phase HPLC gradient 20%-95% in 7 minutes: 5.084

Synthesis of 4-Bromo-N-[4-chloro-2-(pyridine-3-carbonyl)-phenyl]-3-fluoro-benzenesulfonamide

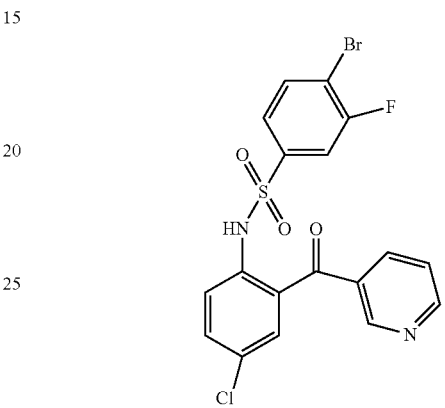

The title compound was prepared according to the general procedures for the synthesis of N-Aryl-benzenesulfonamides previously described using (2-amino-5-chloro-phenyl)-(pyridin-3-yl)-methanone 2 g (8.7 mmol) and 4-bromo-3-fluoro-benzenesulfonyl chloride 2.35 g (8.77 mmol) in 15 ml pyridine. Purification with silica chromatography eluted with dichlorometane:10-ethyl acetate gave a yellow powder.

LC-MSD, m/z for $C_{18}H_{11}ClN_2O_4SBrF$ [M+H]+: 470

R. time Reverse phase HPLC gradient 20%-95% in 7 minutes: 4.801

Synthesis of N-[4-Chloro-2-(pyridine-3-carbonyl)-phenyl]-4-(cis-2,6-dimethyl-morpholine-4-yl]-3-fluoro-benzenesulfonamide

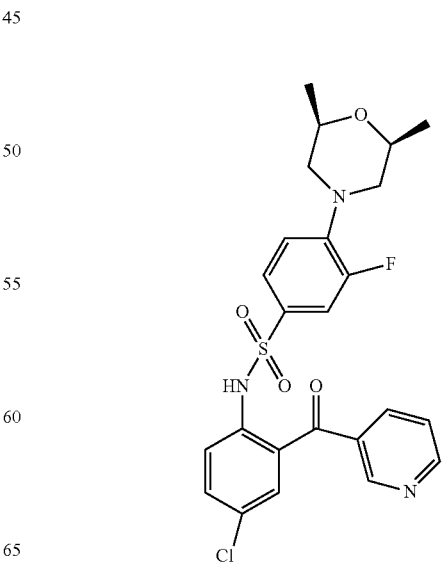

The title compound was prepared according to the general procedure for the synthesis of heterocyclyl and heteroaryl substituted phenylsulfonyl derivatives previously described, using 4-Bromo-N-[4-chloro-2-(pyridine-3-carbonyl)-phenyl]-3-fluoro-benzenesulfonamide 0.2 g (0.42 mmol), potassium phosphate tribasic monohydrate 0.58 g (2.56 mmol), rac-2,2'-bis(diphenylphosphino)-1,1'-binaphthyl 0.079 g (0.12 mmol), cis-2,6-dimethyl-morpholine 0.24 g (2.13 mmol) and Pd (dba)$_3$ 0.057 g (0.06 mmol) in 2 ml DMF. HPLC purification gave a pale yellow compound.

LC-MSD, m/z for $C_{24}H_{23}ClN_3O_4S$ F [M+H]+: 504.1

R. time Reverse phase HPLC gradient 20%-95% in 7 minutes: 5.026

Synthesis of N-[4-Chloro-2-(1-oxy-pyridine-4-carbonyl)-phenyl]-4-morpholin-4-yl-benzenesulfonamide

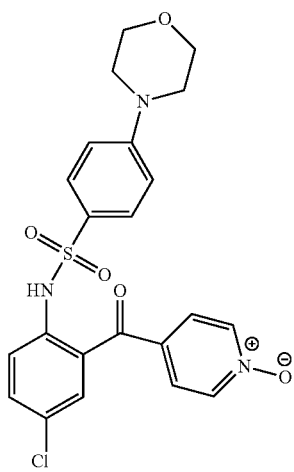 [SMILES: O=C(c1cc[n+]([O-])cc1)c1cc(Cl)ccc1NS(=O)(=O)c1ccc(N2CCOCC2)cc1]

The title compound was prepared according to the general procedure for the synthesis of heterocyclyl substituted phenylsulfonyl derivatives previously described, using 4-Bromo-N-[4-chloro-2-(1-oxy-pyridine-4-carbonyl)-phenyl]-benzenesulfonamide 0.3 g (0.66 mmol), potassium phosphate tribasic monohydrate 0.911 g (3.96 mmol), rac-2,2'-bis(diphenylphosphino)-1,1'-binaphthyl 0.12 g (0.18 mmol), morpholine 0.26 g (3 mmol) and Pd (dba)$_3$ 0.16 g (0.18 mmol) in 2 ml DMF. HPLC purification gave yellow compound LC-MSD, m/z for $C_{22}H_{20}ClN_3O_5S$ [M+H]+: 474.0

R. time Reverse phase HPLC gradient 20%-95% in 7 minutes: 3.660

Synthesis of N-[4-Chloro-2-(1-oxy-pyridine-4-carbonyl)-phenyl]-4-(cis-2,6-dimethyl-morpholin-4-yl)-benzenesulfonamide

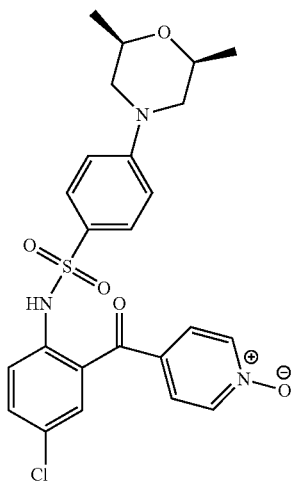 [SMILES: C[C@@H]1CN(c2ccc(S(=O)(=O)Nc3ccc(Cl)cc3C(=O)c3cc[n+]([O-])cc3)cc2)C[C@H](C)O1]

The title compound was prepared according to the general procedure for the synthesis of heterocyclyl substituted phenylsulfonyl derivatives previously described, using 4-Bromo-N-[4-chloro-2-(1-oxy-pyridine-4-carbonyl)-phenyl]-benzenesulfonamide 0.3 g (0.66 mmol), potassium phosphate tribasic monohydrate 0.911 g (3.96 mmol), rac-2,2'-bis(diphenylphosphino)-1,1'-binaphthyl 0.12 g (0.18 mmol), cis-2,6-dimethyl-morpholine 0.37 g (3 mmol) and Pd (dba)$_3$ 0.12 g (0.12 mmol) in 2 ml DMF. Purification by HPLC gave yellow compound.

LC-MSD, m/z for $C_{24}H_{24}ClN_3O_5S$ [M+H]+: 502.1

R. time Reverse phase HPLC gradient 20%-95% in 7 minutes: 3.852

Synthesis of N-[4-Chloro-2-(1-oxy-pyridine-4-carbonyl)-phenyl]-4-(cis-2,6-dimethyl-morpholin-4-yl)-3-fluoro-benzenesulfonamide

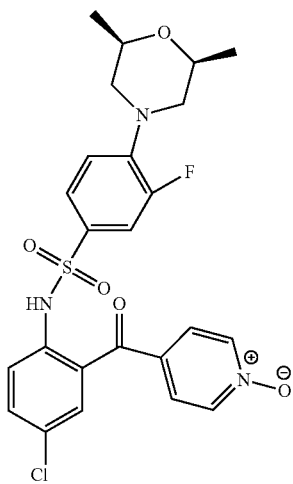 [SMILES: C[C@@H]1CN(c2ccc(S(=O)(=O)Nc3ccc(Cl)cc3C(=O)c3cc[n+]([O-])cc3)cc2F)C[C@H](C)O1]

The title compound was prepared according to the general procedure for the synthesis of heterocyclyl and heteroaryl substituted phenylsulfonyl derivatives previously described, using 4-Bromo-N-[4-chloro-2-(1-oxy-pyridine-4-carbonyl)-phenyl]-3-fluoro-benzenesulfonamide 0.25 g (0.5 mmol), potassium phosphate tribasic monohydrate 0.68 g (3 mmol), rac-2,2'-bis(diphenylphosphino)-1,1'-binaphthyl 0.09 g (0.14 mmol), cis-2,6-dimethyl-morpholine 0.3 g (2.5 mmol) and Pd (dba)$_3$ 0.135 g (0.14 mmol) in 2 ml DMF. HPLC purification gave a yellow compound.

LC-MSD, m/z for $C_{24}H_{23}ClN_3O_5S$ F [M+H]+: 520.1

R. time Reverse phase HPLC gradient 20%-95% in 7 minutes: 4.446

Synthesis of N-[4-Chloro-2-(1-oxy-pyridine-3-carbonyl)-phenyl]-4-(cis-2,6-dimethyl-morpholin-4-yl)-3-fluoro-benzenesulfonamide

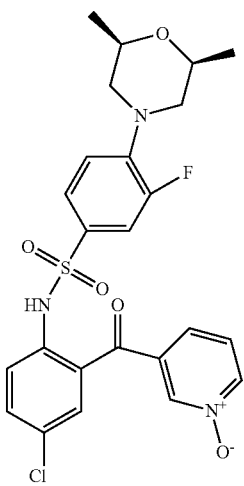 [SMILES: C[C@@H]1CN(c2ccc(S(=O)(=O)Nc3ccc(Cl)cc3C(=O)c3ccc[n+]([O-])c3)cc2F)C[C@H](C)O1]

The title compound was prepared according to the general procedure for the synthesis of heterocyclyl and heteroaryl substituted phenylsulfonyl derivatives previously described LC-MSD, m/z for $C_{24}H_{23}ClN_3O_5S$ F [M+H]+: 502.1, 503.1

R. time Reverse phase HPLC gradient 20%-95% in 7 minutes: 4.230

Synthesis of N-[4-Chloro-2-(1-oxy-pyridine-3-carbonyl-6-methyl)-phenyl]-4-(morpholin-4-yl)-3-fluoro-benzenesulfonamide

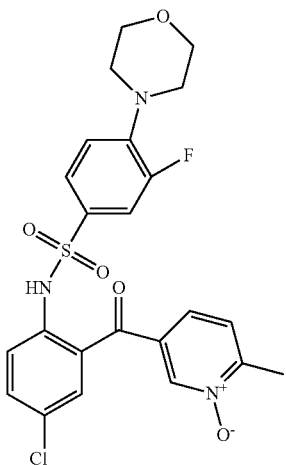 [SMILES: Cc1ccc(C(=O)c2cc(Cl)ccc2NS(=O)(=O)c2ccc(N3CCOCC3)c(F)c2)c[n+]1[O-]]

The title compound was prepared according to the general procedure for the synthesis of heterocyclyl and heteroaryl substituted phenylsulfonyl derivatives previously described LC-MSD, m/z for $C_{24}H_{23}ClN_3O_5S$ F [M+H]+: 488.0, 489.0

R. time Reverse phase HPLC gradient 20%-95% in 7 minutes: 3.801

Synthesis of N-[4-Chloro-2-(1-oxy-pyridine-3-carbonyl-6-methyl)-phenyl]-4-(cis-2,6-dimethyl-morpholin-4-yl)-3-fluoro-benzenesulfonamide

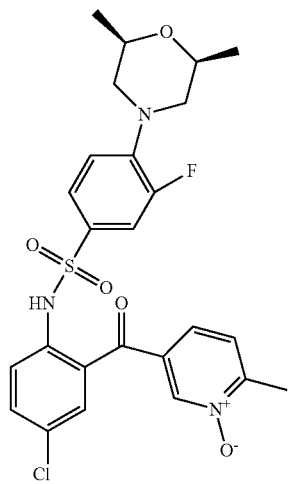 [SMILES: Cc1ccc(C(=O)c2cc(Cl)ccc2NS(=O)(=O)c2ccc(N3C[C@@H](C)O[C@@H](C)C3)c(F)c2)c[n+]1[O-]]

The title compound was prepared according to the general procedure for the synthesis of heterocyclyl and heteroaryl substituted phenylsulfonyl derivatives previously described LC-MSD, m/z for $C_{24}H_{23}ClN_3O_5S$ F [M+H]+: 516.0, 517.0

R. time Reverse phase HPLC gradient 20%-95% in 7 minutes: 4.242

Synthesis of N-[4-Chloro-2-(1-oxy-pyridine-4-carbonyl)-phenyl]-4-morpholin-4-yl-3-fluoro-benzenesulfonamide

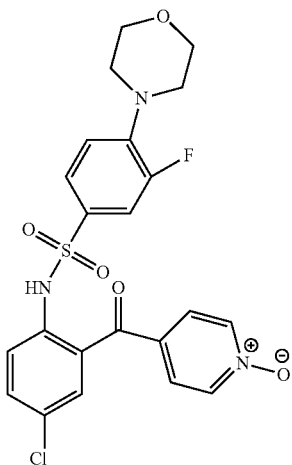 [SMILES: O=C(c1cc[n+]([O-])cc1)c1cc(Cl)ccc1NS(=O)(=O)c1ccc(N2CCOCC2)c(F)c1]

The title compound was prepared according to the general procedure for the synthesis of heterocyclyl and heteroaryl substituted phenylsulfonyl derivatives previously described, using 4-Bromo-N-[4-chloro-2-(1-oxy-pyridine-4-carbonyl)-phenyl]-3-fluoro-benzenesulfonamide 0.25 g (0.5 mmol), potassium phosphate tribasic monohydrate 0.68 g (3 mmol), rac-2,2'-bis(diphenylphosphino)-1,1'-binaphthyl 0.09 g (0.14 mmol), morpholine 0.21 g (1.5 mmol) and Pd (dba)$_3$ 0.135 g (0.14 mmol) in 2 ml DMF. HPLC purification gave yellow compound.

LC-MSD, m/z for $C_{22}H_{19}ClN_3O_5S$ F [M+H]+: 492.0

R. time Reverse phase HPLC gradient 20%-95% in 7 minutes: 3.966

Synthesis of N-[4-Chloro-2-(pyridine-4-carbonyl)-phenyl]-4-furan-3-yl-benzenesulfonamide

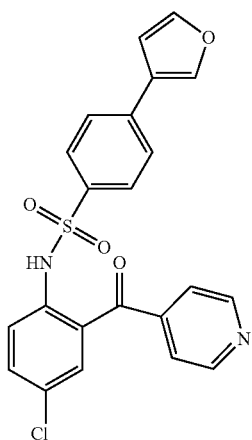 [SMILES: O=C(c1ccncc1)c1cc(Cl)ccc1NS(=O)(=O)c1ccc(-c2ccoc2)cc1]

4-bromo-N-[4-chloro-2-(pyridine-4-carbonyl)-phenyl]-benzenesulfonamide 0.25 g (0.55 mmol) was dissolved in 2.5 ml of anhydrous dimethylformamide. To this solution was added 0.14 g (1.3 mmol) sodium carbonate, furan-3-boronic acid 0.77 g (0.68 mmol), and Pd(PPh$_3$)$_4$ 19 mg (0.014 mmol). The reaction mixture was heated overnight at 80° C. under a nitrogen atmosphere. The mixture was quenched with water and extracted 3 times with dichloromethane. The organic layer was dried over magnesium sulfate, filtered, and concentrated. Purification by flash column chromatography with a gradient 100% hexane to ethylacetate: hexane 1-1, gave the desired compound as a white powder.

LC-MSD, m/z for $C_{22}H_{15}ClN_2O_4S$ [M+H]+: 439

R. time Reverse phase HPLC gradient 20%-95% in 7 minutes: 4.512

Synthesis of N-[4-Chloro-2-(pyridine-4-carbonyl)-phenyl]-4-thiophen-2-yl-benzenesulfonamide

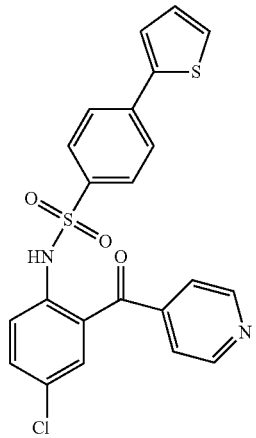 [SMILES: O=C(c1ccncc1)c1cc(Cl)ccc1NS(=O)(=O)c1ccc(-c2cccs2)cc1]

To 4-bromo-N-[4-chloro-2-(pyridine-4-carbonyl)-phenyl]-benzenesulfonamide 0.12 g (0.26 mmol), sodium carbonate 70 mg (0.65 mmol), thiopehene-2-boronic acid 42 mg (0.32 mmol), and Pd (PPh$_3$)$_4$ 18 mg (0.004 mmol) was added DMF (1 mL). The reaction mixture was heated overnight at 80° C. under a nitrogen atmosphere. The mixture was quenched with water and extracted 3 times with dichloromethane. The organic layer was dried over magnesium sulfate, filtered, and concentrated. HPLC Purification gave off white solid.

LC-MSD, m/z for $C_{22}H_{15}ClN_2O_3S_2$ [M+H]+:455

R. time Reverse phase HPLC gradient 20%-95% in 7 minutes: 4.827

Synthesis of N-[4-Chloro-2-(pyridine-4-carbonyl)-phenyl]-4-(2-fluoro-pyridin-3-yl)-benzenesulfonamide

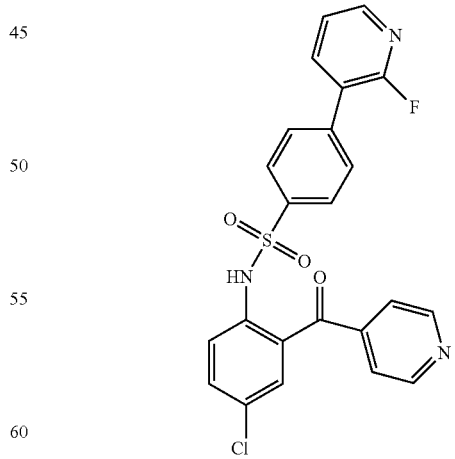

To 4-bromo-N-[4-chloro-2-(pyridine-4-carbonyl)-phenyl]-benzenesulfonamide 0.10 g (0.21 mmol), sodium carbonate 70 mg (0.65 mmol), 2-fluoropyridine-3-boronic acid hydrate 76 mg (0.53 mmol), Pd (PPh$_3$)$_4$ 15.2 mg (0.013 mmol) was added DMF (1 mL). The reaction mixture was heated overnight at 80° C. under a nitrogen atmosphere. The mixture was quenched with water and extracted 3 times with dichloromethane. The organic layer was dried over magnesium sulfate, filtered, and concentrated. HPLC purification gave off white solid LC-MSD, m/z for $C_{23}H_{15}ClFN_2O_3S_2$ [M+H]+: 452.9

R. time Reverse phase HPLC gradient 20%-95% in 7 minutes: 4.427

Synthesis of N-[4-Chloro-2-(pyridine-4-carbonyl)-phenyl]-4-pyrimidin-5-yl-benzenesulfonamide

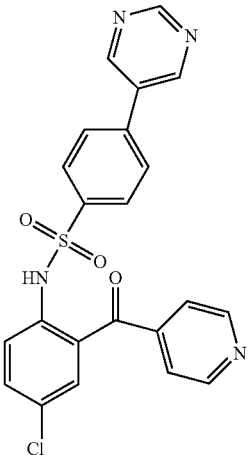 [SMILES: O=C(c1ccncc1)c1cc(Cl)ccc1NS(=O)(=O)c1ccc(-c2cncnc2)cc1]

To 4-bromo-N-[4-chloro-2-(pyridine-4-carbonyl)-phenyl]-benzenesulfonamide 0.10 g (0.21 mmol), sodium carbonate 127 mg (1.17 mmol), pyrimidine-5-boronic acid 95 mg (0.76 mmol), Pd (PPh$_3$)$_4$ 22.8 mg (0.019 mmol) was added DMF (1 mL). The reaction mixture was heated overnight at 80° C. under a nitrogen atmosphere. The mixture was quenched with water and extracted 3 times with dichloromethane. The organic layer was dried over magnesium sulfate, filtered, and concentrated. HPLC purification gave an off white solid.

LC-MSD, m/z for $C_{22}H_{15}ClFN_4O_3S$ [M+H]+: 451

R. time Reverse phase HPLC gradient 20%-95% in 7 minutes: 3.510

Synthesis of N-[4-Chloro-2-(pyridine-4-carbonyl)-phenyl]-4-quinolin-3-yl-benzenesulfonamide

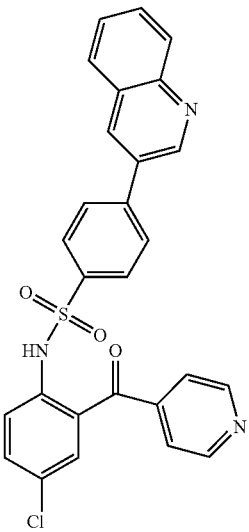 [SMILES: O=C(c1ccncc1)c1cc(Cl)ccc1NS(=O)(=O)c1ccc(-c2cnc3ccccc3c2)cc1]

To 4-bromo-N-[4-chloro-2-(pyridine-4-carbonyl)-phenyl]-benzenesulfonamide 0.10 g (0.21 mmol), sodium carbonate 150 mg (1.4 mmol), isoquinoline-4-boronic acid 152 mg (0.87 mmol), Pd (PPh$_3$)$_4$ 30 mg (0.025 mmol) was added DMF (1 mL). The reaction mixture was heated overnight at 80° C. under a nitrogen atmosphere. The mixture was quenched with water and extracted 3 times with dichloromethane. The organic layer was dried over magnesium sulfate, filtered, and concentrated. HPLC purification gave off white solid.

LC-MSD, m/z for $C_{27}H_{18}ClN_3O_3S$ [M+H]+: 500.0

R. time Reverse phase HPLC gradient 20%-95% in 7 minutes: 4.398

Synthesis of 2-{4-[4-Chloro-2-(pyridine-4-carbonyl)-phenylsulfamoyl]-phenyl}-pyrrole-1-carboxylic acid tert-butyl ester

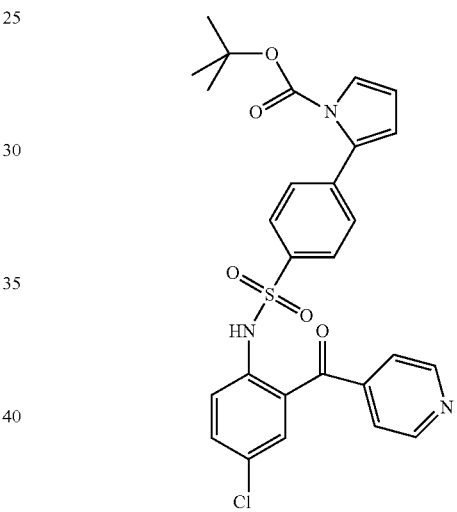

To 4-bromo-N-[4-chloro-2-(pyridine-4-carbonyl)-phenyl]-benzenesulfonamide 0.25 g (0.55 mmol), sodium carbonate 146 mg (1.4 mmol), 1-N—BOC-pyrrole-2-boronic acid 145 mg (0.68 mmol), Pd (PPh$_3$)$_4$ 19 mg (0.016 mmol), was added DMF (2.5 mL). The reaction mixture was heated overnight at 80° C. under a nitrogen atmosphere. The mixture was quenched with water and extracted 3 times with dichloromethane. The organic layer was dried over magnesium sulfate, filtered, and concentrated. HPLC purification gave a light yellow solid.

LC-MSD, m/z for $C_{27}H_{24}ClN_3O_5S$ [M+H]+: 538.1

R. time Reverse phase HPLC gradient 20%-95% in 7 minutes: 5.431

Synthesis of 2-{4-[4-Chloro-2-(pyridine-4-carbonyl)-phenylsulfamoyl]-phenyl}-indole-1-carboxylic acid tert-butyl ester

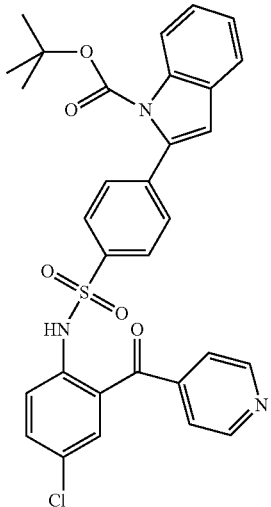 [SMILES: CC(C)(C)OC(=O)n1c(-c2ccc(S(=O)(=O)Nc3ccc(Cl)cc3C(=O)c3ccncc3)cc2)cc2ccccc21]

To 4-bromo-N-[4-chloro-2-(pyridine-4-carbonyl)-phenyl]-benzenesulfonamide 0.25 g (0.55 mmol), sodium carbonate 146 mg (1.4 mmol), 1-N—BOC-indole-2-boronic acid 180 mg (0.68 mmol), Pd (PPh$_3$)$_4$ 19 mg (0.016 mmol), was added DMF (2.5 mL). The reaction mixture was heated overnight at 80° C. under a nitrogen atmosphere. The mixture was quenched with water and extracted 3 times with dichloromethane. The organic layer was dried over magnesium sulfate, filtered, and concentrated. HPLC purification gave an off white solid.

LC-MSD, m/z for C$_{31}$H$_{26}$ClN$_3$O$_5$S [M+H]+: 588.1
R. time Reverse phase HPLC gradient 20%-95% in 7 minutes: 5.925

Synthesis of N-[4-Chloro-2-(pyridine-4-carbonyl)-phenyl]-4-(1H-pyrrol-2-yl)-benzenesulfonamide

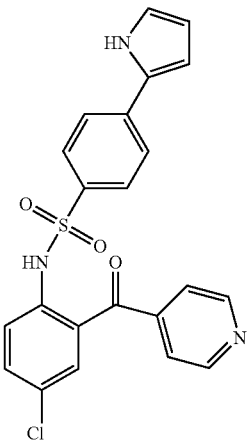 [SMILES: O=C(c1ccncc1)c1cc(Cl)ccc1NS(=O)(=O)c1ccc(-c2ccc[nH]2)cc1]

To a mixture of dichloromethane (1 ml) and trifluoroacetic acid (0.3 ml) stirred at room temperature was added 2-{4-[4-Chloro-2-(pyridine-4-carbonyl)-phenylsulfamoyl]-phenyl}-pyrrole-1-carboxylic acid tert-butyl ester 70 mg (0.13 mmol). The reaction mixture was followed using thin layer chromatography (eluted with ethyl acetate:1-hexane:1), and after completion saturated aqueous sodium bicarbonate solution was added, the reaction mixture concentrated and purified using preparative HPLC (20%-70% acetonitrile gradient), to yield a white powder.

LC-MSD, m/z for C$_{22}$H$_{15}$ClN$_3$O$_3$S [M+H]+: 438.0
R. time Reverse phase HPLC gradient 20%-95% in 7 minutes: 5.226

Synthesis of N-[4-Chloro-2-(pyridine-4-carbonyl)-phenyl]-4-(1H-indol-2-yl)-benzenesulfonamide

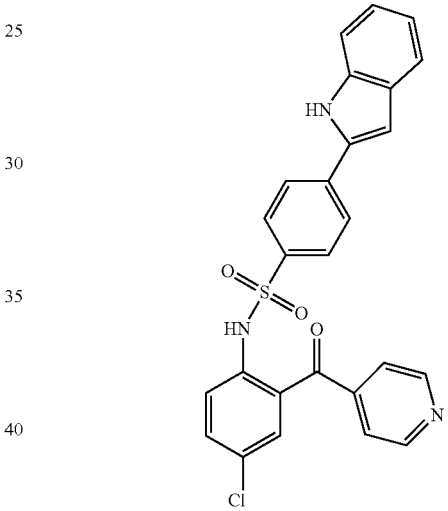

To a mixture of dichloromethane (1 ml) and trifluoroacetic acid (0.3 ml) stirred at room temperature was added 2-{4-[4-Chloro-2-(pyridine-4-carbonyl)-phenylsulfamoyl]-phenyl}-indole-1-carboxylic acid tert-butyl ester 0.1 g (0.17 mmol). The reaction mixture was followed using thin layer chromatography, and after completion saturated aqueous sodium bicarbonate solution was added, the reaction mixture concentrated and purified using preparative HPLC to yield to off white solid.

LC-MSD, m/z for C$_{26}$H$_{18}$ClN$_3$O$_3$S [M+H]+: 488.0
R. time Reverse phase HPLC gradient 20%-95% in 7 minutes: 5.013

Synthesis of N-[4-Chloro-2-(pyridine-4-carbonyl)-phenyl]-4-(3,5-dimethyl-isoxazol-4-yl)-benzenesulfonamide

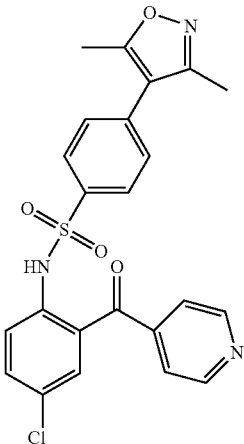 [SMILES: Cc1noc(C)c1-c1ccc(S(=O)(=O)Nc2ccc(Cl)cc2C(=O)c2ccncc2)cc1]

To 4-bromo-N-[4-chloro-2-(pyridine-4-carbonyl)-phenyl]-benzenesulfonamide 0.260 mg (0.57 mmol), sodium carbonate 178 mg (1.69 mmol), 3,5-dimethylisoxazole-4-boronic acid 150 mg (1.4 mmol), Pd (PPh$_3$)$_4$ 23 mg (0.019 mmol), was added DMF (1.5 mL). The reaction mixture was heated overnight at 80° C. under a nitrogen atmosphere. The mixture was quenched with water and extracted 3 times with dichloromethane. The organic layer was dried over magnesium sulfate, filtered, and concentrated. HPLC purification (gradient 20 to 70% in 50 minutes), gave a white powder.

LC-MSD, m/z for C$_{23}$H$_{18}$ClN$_3$O$_4$S [M+H]+: 468.0

R. time Reverse phase HPLC gradient 20%-95% in 7 minutes: 4.475

Synthesis of N-[4-Chloro-2-(pyridine-4-carbonyl)-phenyl]-4-furan-2-yl-benzenesulfonamide

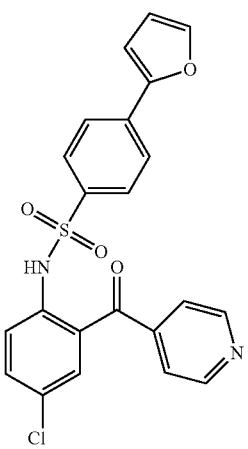 [SMILES: O=C(c1ccncc1)c1cc(Cl)ccc1NS(=O)(=O)c1ccc(-c2ccco2)cc1]

To 4-bromo-N-[4-chloro-2-(pyridine-4-carbonyl)-phenyl]-benzenesulfonamide 0.25 mg (0.55 mmol), sodium carbonate 0.21 g (2 mmol), furan 2-boronic acid 0.11 g (1 mmol), Pd (PPh$_3$)$_4$ 38 mg (0.032 mmol), was added DMF (2.5 mL). The reaction mixture was heated overnight at 80° C. under a nitrogen atmosphere. The mixture was quenched with water and extracted 3 times with dichloromethane. The organic layer was dried over magnesium sulfate, filtered, and concentrated. Purification using column chromatography (hexane: ethyl acetate 2:1, gave a pale yellow powder.

LC-MSD, m/z for C$_{22}$H$_{15}$ClN$_2$O$_4$S [M+H]+: 439.0

R. time Reverse phase HPLC gradient 20%-95% in 7 minutes: 4.769

Synthesis of 4-(4-Acetyl-piperazin-1-yl)-N-[4-chloro-2-(pyridine-4-carbonyl)-phenyl]-benzenesulfonamide

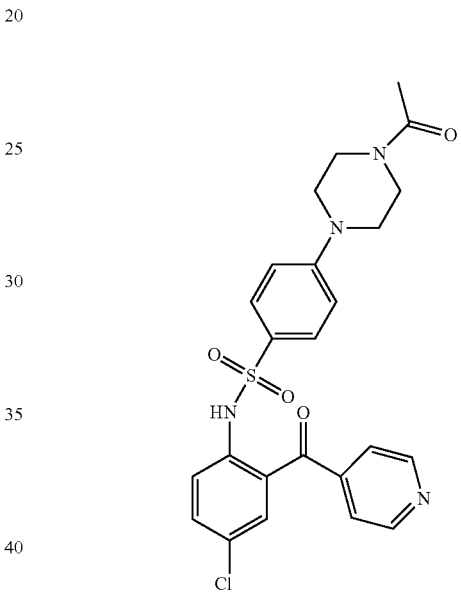

N-[4-Chloro-2(pyridine-4-carbonyl)-phenyl]-4-piperazin-1-yl-benzenesulfonamide 0.11 g (0.24 mmol) was dissolved in 1 ml dichloromethane, under nitrogen at 0° C., and to this solution was added triethylamine 0.05 ml (0.36 mmol) and acetic anhydride 0.027 ml (0.29 mmol). The reaction mixture was stirred at 0° C. for 30 minutes. Saturated aqueous sodium bicarbonate (3 mL) was added, followed by extraction, 3 times, with dichloromethane. The combined organic layers was dried over magnesium sulfate, filtered and concentrated in vacuo. The title compound was purified using flash column chromatography on silica, eluted with ethyl-acetate 100% followed by dichloromethane-methanol, to yield a pale yellow compound.

LC-MSD, m/z for C$_{24}$H$_{23}$ClN$_4$O$_4$S [M+H]+: 499.0

R. time Reverse phase HPLC gradient 20%-95% in 7 minutes: 3.785

Synthesis of N-[4-Chloro-2-(pyridine-4-carbonyl)-phenyl]-4-[4-(2,2,2-trifluoro-ethyl)-piperazin-1-yl]-benzenesulfonamide

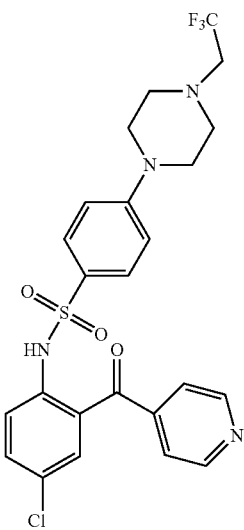 [SMILES: O=C(c1ccncc1)c1cc(Cl)ccc1NS(=O)(=O)c1ccc(N2CCN(CC(F)(F)F)CC2)cc1]

N-[4-Chloro-2(pyridine-4-carbonyl)-phenyl]-4-piperazin-1-yl-benzenesulfonamide 0.1 g (0.24 mmol) was dissolved in acetone (1.1 ml), and to this solution was added trifluoro-methanesulfonic acid 2,2,2-trifluoro-ethyl ester 70.8 mg (0.28 mmol). The mixture was refluxed for 5 hours. The reaction was cooled to room temperature, quenched with saturated aqueous sodium bicarbonate, and extracted with dichloromethane (3 times). The combined organic layer was dried over magnesium sulfate, filtered and concentrated in vacuo, to yield to 24 mg a pale yellow compound.

LC-MSD, m/z for $C_{24}H_{22}ClN_4O_3SF_3$ [M+H]+: 539.1

R. time Reverse phase HPLC gradient 20%-95% in 7 minutes: 4.976

Synthesis of N-[4-Chloro-2-(pyridine-4-carbonyl)-phenyl]-4-[1,2,3]thiadiazol-4-yl-benzenesulfonamide

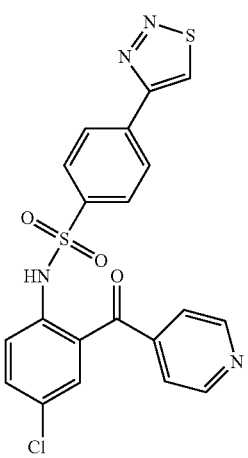 [SMILES: O=C(c1ccncc1)c1cc(Cl)ccc1NS(=O)(=O)c1ccc(-c2csnn2)cc1]

(2-amino-5-chloro-phenyl)-pyridin-4-yl-methanone 0.2 g (0.86 mmol) was dissolved in anhydrous pyridine (1 mL)m, and to this solution was added 4-[1,2,3]-thiadiazole-4-yl-benzenesulfonyl chloride 0.24 g (0.94 mmol). The mixture was stirred overnight at 80° C. under nitrogen, and the pyridine then removed in vacuo. Water was added and the reaction mixture extracted with dichloromethane (3 times). The organic layers were combined, dried over magnesium sulfate, filtered and concentrated in vacuo. HPLC purification yielded a white powder.

LC-MSD, m/z for $C_{20}H_{13}ClN_4O_3S_2$ [M+H]+: 466.9

R. time Reverse phase HPLC gradient 20%-95% in 7 minutes: 3.82

Syntheses of N-Aryl-benzenesulfonamides

Synthesis of N-[4-Chloro-2-(pyridine-4-carbonyl)-phenyl]-4-oxazol-5-yl-benzenesulfonamide

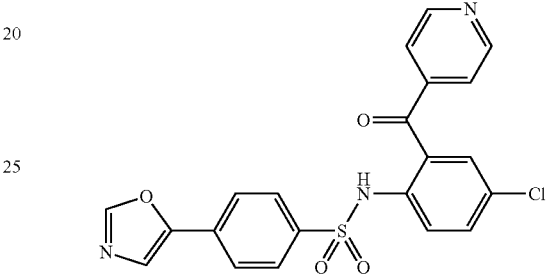

The title compound was prepared according to the general procedure for the synthesis of N-Aryl-benzenesulfonamides previously described using 116 mg of (2-Amino-5-chloro-phenyl)-pyridin-4-yl-methanone and 122 mg 4-oxazol-5-yl-benzenesulfonyl chloride. Purification by purification by reversed phase HPLC gave pure product. $^1$H-NMR (400 MHz, CDCl$_3$): δ 7.21 (dd, H, J=1.5, 4.4 Hz), 7.30 (d, 1H, J=2.5 Hz), 7.42 (s, 1H), 7.54 (dd, 1H, J=2.5, 8.8 Hz), 7.61 (d, 2H, J=8.4 Hz), 7.77 (s, 1H), 7.78 (d, 2H, J=8.4 Hz), 7.95 (s, 1H), 8.69 (d, 2H, J=5.8 Hz), 10.06 (br, 1H). MS: m/z 440.9 (M$^+$+1).

Synthesis of 4-tert-Butyl-N-[4-chloro-2-(pyridine-4-carbonyl)-phenyl]-benzenesulfonamide

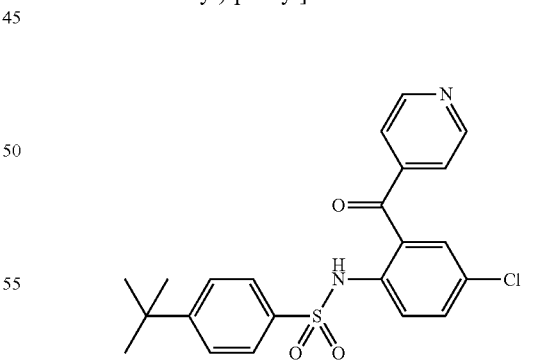

The title compound was prepared according to the general procedure for the synthesis of N-Aryl-benzenesulfonamides previously described using 116 mg of (2-Amino-5-chloro-phenyl)-pyridin-4-yl-methanone and 116 mg of 4-tert-Butyl-benzenesulfonyl chloride. $^1$H-NMR (400 MHz, CDCl$_3$): δ 1.25 (s, 9H), 7.02 (d, 1H, J=8.4 Hz). 7.44 (m, 3H), 7.66 (d, 2H, J=8.4), 7.79 (d, 1H, J=2.4 Hz), 8.11 (d, 2H, J=6.4), 8.88 d, 2H, J=6.0 Hz), 10.51 (s, 1H). MS: m/z 429.9 (M$^+$+1).

Synthesis of N-[4-Chloro-2-(pyridine-4-carbonyl)-phenyl]-4-methoxy-benzenesulfonamide

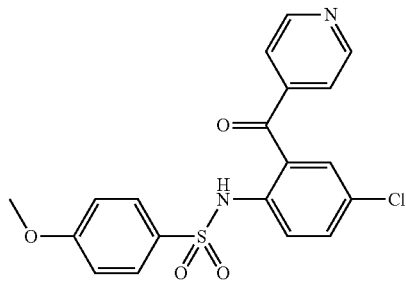 [SMILES: COc1ccc(S(=O)(=O)Nc2ccc(Cl)cc2C(=O)c2ccncc2)cc1]

The title compound was prepared according to the general procedure for the synthesis of N-Aryl-benzenesulfonamides previously described using 116 mg of (2-Amino-5-chloro-phenyl)-pyridin-4-yl-methanone and 101 mg of 4-methoxy-benzenesulfonyl chloride. $^1$H-NMR (400 MHz, CDCl$_3$): δ 3.74 (s, 3H), 6.77 (d, 2H, J=8.8 Hz), 7.21 (m, 2H), 7.27 (d, 1H, J=2 Hz), 7.52 (dd, 1H, J=8.8 Hz, 2.8 Hz), 7.63 (m, 2H), 7.76 (d, 1H, J=8.8 Hz), 8.76 (d, 2H, J=5.6 Hz), 9.88 (s, 1H). MS: m/z 403.9 (M$^+$+1).

Synthesis of N-[4-Bromo-2-(pyridine-4-carbonyl)-phenyl]-4-methoxy-benzenesulfonamide

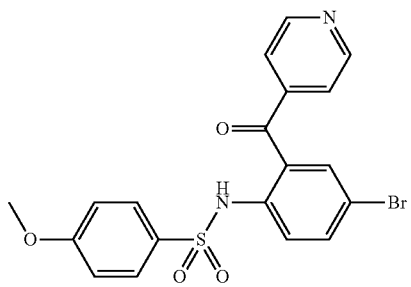 [SMILES: COc1ccc(S(=O)(=O)Nc2ccc(Br)cc2C(=O)c2ccncc2)cc1]

The title compound was prepared according to the general procedure for the synthesis of N-Aryl-benzenesulfonamides previously described using 138 mg of (2-amino-5-bromo-phenyl)-pyridin-4-yl-methanone and 101 mg of 4-methoxy-benzenesulfonyl chloride. $^1$H-NMR (400 MHz, CDCl$_3$): δ 3.69 (s, 3H), 6.68 (d, 2H, J=8.8 Hz), 7.36-7.47 (m, 4H), 7.46, 7.55-7.69 (m, 5H), 9.65 (s, 1H). MS: m/z 448.3 (M$^+$+1).

Synthesis of 4-tert-Butyl-N-[4-fluoro-2-(pyridine-4-carbonyl)-phenyl]-benzenesulfonamide

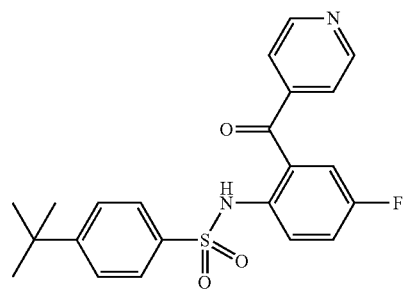 [SMILES: CC(C)(C)c1ccc(S(=O)(=O)Nc2ccc(F)cc2C(=O)c2ccncc2)cc1]

The title compound was prepared according to the general procedure for the synthesis of N-Aryl-benzenesulfonamides previously described using 108 mg of (2-Amino-5-fluoro-phenyl)-pyridin-4-yl-methanone and 116 mg of 4-tert-butyl-benzenesulfonyl chloride. $^1$H-NMR (400 MHz, CDCl$_3$): δ 1.25 (s, 9H), 6.98 (dd, 1H, J=8.8 Hz, 3.2 Hz), 7.30-7.38 (m, 3H), 7.43 (m, 2H), 7.62 (m, 2H), 7.80 (dd, 1H, 9.2 Hz, 4.8 Hz), 8.82 (d, 2H, 4.8 Hz), 9.82 (s, 1H). MS: m/z 413.5 (M$^+$+1).

Synthesis of N-[4-Bromo-2-(pyridine-4-carbonyl)-phenyl]-4-tert-butyl-benzenesulfonamide

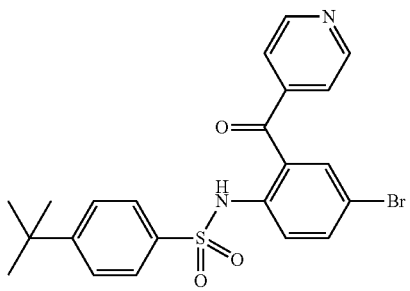 [SMILES: CC(C)(C)c1ccc(S(=O)(=O)Nc2ccc(Br)cc2C(=O)c2ccncc2)cc1]

The title compound was prepared according to the general procedure for the synthesis of N-Aryl-benzenesulfonamides previously described using 138 mg of (2-Amino-5-bromo-phenyl)-pyridin-4-yl-methanone and 116 mg of 4-tert-butyl-benzenesulfonyl chloride. $^1$H-NMR (400 MHz, CDCl$_3$): δ 1.27 (3, 9H), 7.41 (m, 3H), 7.50 (dd, 2H, J=4.8 Hz, 1.6 Hz), 7.67-72 (m, 4H), 8.85 (d, 2H, J=6 Hz), 10.19 (s, 1H). MS: m/z 473.9 (M$^+$+1).

Synthesis of 4-tert-Butyl-N-[5-chloro-2-(pyridine-4-carbonyl)-phenyl]-benzenesulfonamide

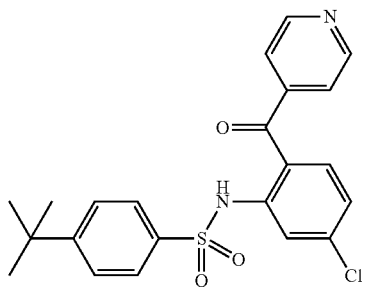 [SMILES: CC(C)(C)c1ccc(S(=O)(=O)Nc2cc(Cl)ccc2C(=O)c2ccncc2)cc1]

The title compound was prepared according to the general procedure for the synthesis of N-Aryl-benzenesulfonamides previously described using 116 mg of (2-amino-4-chloro-phenyl)-pyridin-4-yl-methanone and 116 mg of 4-tert-butyl-benzenesulfonyl chloride. $^1$H-NMR (400 MHz, CDCl$_3$): δ 1.30 (s, 9H), 7.04 (d, 1H, J=8.4 Hz), 7.25 (d, 1H, J=8.4 Hz), 7.45-7.52 (m, 4H), 7.74 (dd, 2H, J=8.8 Hz, 1.6 Hz), 7.52 (dd, 2H, J=4.4 Hz, 1.6 Hz), 7.78 (m, 2H), 7.84 (d, 1H, 1.6 Hz), 8.84 (d, 2H, J=5.6 Hz), 10.61 (s, 1H). MS: m/z 429.0 (M$^+$+1).

Synthesis of N-[4-Bromo-2-(pyridine-4-carbonyl)-phenyl]-4-trifluoromethoxy-benzenesulfonamide

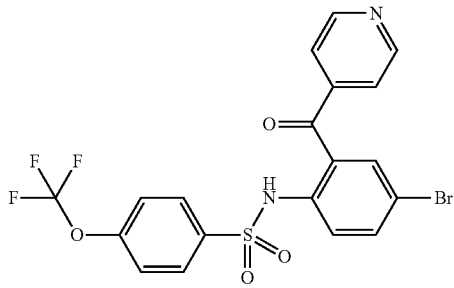 [SMILES: O=C(c1ccncc1)c1cc(Br)ccc1NS(=O)(=O)c1ccc(OC(F)(F)F)cc1]

The title compound was prepared according to the general procedure for the synthesis of N-Aryl-benzenesulfonamides previously described using 138 mg of (2-Amino-5-bromo-phenyl)-pyridin-4-yl-methanone and 130 mg of 4-trifluoromethoxy-benzenesulfonyl chloride. $^1$H-NMR (400 MHz, CDCl$_3$): δ 7.21 (d, 2H, J=8.8 Hz), 7.35 (m, 2H), 7.45 (s, 1H), 7.70 (m, 2H), 7.83 (m, 2H), 8.82 (dd, 2H, J=4.8 Hz, 1.6 Hz), 10.21 (s, 1H). MS: m/z 502.3 (M$^+$+1).

Synthesis of 4-Bromo-N-[4-chloro-2-(pyridine-4-carbonyl)-phenyl]-benzenesulfonamide

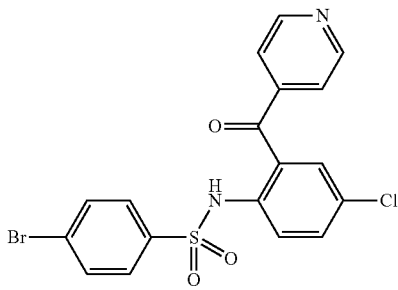 [SMILES: O=C(c1ccncc1)c1cc(Cl)ccc1NS(=O)(=O)c1ccc(Br)cc1]

The title compound was prepared according to the general procedure for the synthesis of N-Aryl-benzenesulfonamides previously described using 116 mg of (2-amino-5-chloro-phenyl)-pyridin-4-yl-methanone and 122 mg of 4-bromo-benzenesulfonyl chloride. $^1$H-NMR (400 MHz, CDCl$_3$): δ 7.21 (d, 1H, J=2.4 Hz), 7.49-7.61 (m, 5H), 7.73 (d, 1H, J=8.8 Hz), 8.86 (dd, 2H, J=4.4 Hz, 1.2 Hz), 10.00 (s, 1H). MS: m/z 451.9 (M$^+$+1)

Synthesis of N-[4-Chloro-2-(pyridine-4-carbonyl)-phenyl]-3-cyano-benzenesulfonamide

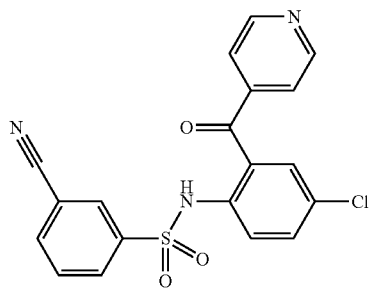 [SMILES: N#Cc1cccc(S(=O)(=O)Nc2ccc(Cl)cc2C(=O)c2ccncc2)c1]

The title compound was prepared according to the general procedure for the synthesis of N-Aryl-benzenesulfonamides previously described using 116 mg of (2-amino-5-chloro-phenyl)-pyridin-4-yl-methanone and 100 mg of 3-cyano-benzenesulfonyl chloride. $^1$H-NMR (400 MHz, CDCl$_3$): δ 7.36 (d, 1H, J=2.4 Hz), 7.57-7.62 (m, 4H), 7.68 (d, 1H, J=8.8 Hz), 7.80 (m, 1H), 8.04 (m, 2H), 8.90 (dd, 2H, J=4.8 Hz, 1.6 Hz), 10.3 (b, 1H). MS: m/z 398.8 (M$^+$+1).

Synthesis of N-[4-Chloro-2-(pyridine-4-carbonyl)-phenyl]-4-methanesulfonyl-benzenesulfonamide

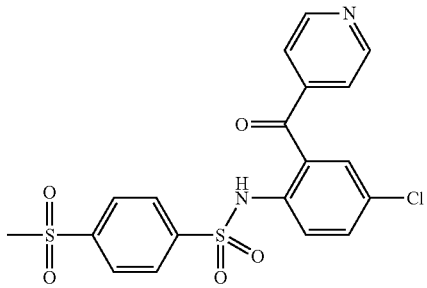 [SMILES: CS(=O)(=O)c1ccc(S(=O)(=O)Nc2ccc(Cl)cc2C(=O)c2ccncc2)cc1]

The title compound was prepared according to the general procedure for the synthesis of N-Aryl-benzenesulfonamides previously described using 116 mg of (2-amino-5-chloro-phenyl)-pyridin-4-yl-methanone and 127 mg of 4-methanesulfonyl-benzenesulfonyl chloride. $^1$H-NMR (400 MHz, CDCl$_3$): δ 3.06 (s, 3H), 7.31 (d, 1H, J=2.0 Hz), 7.45 (m, 2H), 7.58 (dd, 1H, J=8.8 Hz, 2.8 Hz), 7.99 (b, 4H), 8.88 (dd, 2H, J=4.8 Hz, 1.6 Hz), 10.29 (b, 1H). MS: m/z 451.9 (M$^+$+1).

Synthesis of 4-tert-Butyl-N-[4-chloro-2-(pyrimidine-4-carbonyl)-phenyl]-benzenesulfonamide

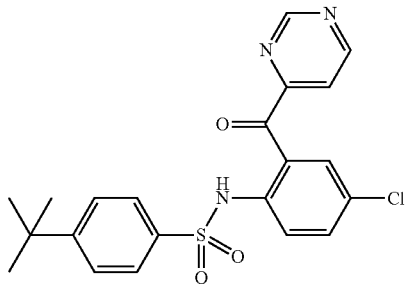 [SMILES: CC(C)(C)c1ccc(S(=O)(=O)Nc2ccc(Cl)cc2C(=O)c2ccncn2)cc1]

The title compound was prepared according to the general procedure for the synthesis of N-Aryl-benzenesulfonamides previously described using 116 mg of (2-Amino-5-chloro-phenyl)-pyrimidin-4-yl-methanone and 116 mg of 4-tert-butyl-benzenesulfonyl chloride. $^1$H-NMR (400 MHz, CDCl$_3$): δ 1.23 (s, 9H), 7.40 (d, 2H, J=8.4 Hz), 7.51 (dd, 1H, J=8.8 Hz, 2 Hz), 7.71-7.80 (m, 6H), 9.03 (d, 1H, J=4.8 Hz), 9.33 (d, 1.2 Hz), 10.91 (b, 1H). MS: m/z 434.0 (M$^+$+1).

Synthesis of Biphenyl-4-sulfonic acid [4-chloro-2-(pyridine-4-carbonyl)-phenyl]-amide

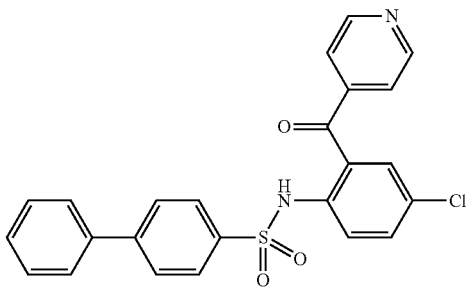 [SMILES: O=C(c1ccncc1)c1cc(Cl)ccc1NS(=O)(=O)c1ccc(-c2ccccc2)cc1]

The title compound was prepared according to the general procedure for the synthesis of N-Aryl-benzenesulfonamides previously described using 116 mg of (2-amino-5-chlorophenyl)-pyridin-4-yl-methanone and 126 mg of biphenyl-4-sulfonyl chloride. $^1$H-NMR (400 MHz, CDCl$_3$): δ 7.24 (m, 1H), 7.36 (m, 2H), 7.42 (m, 5H), 7.56 (m, 3H), 7.77-7.84 (m, 3H), 8.73 (d, 2H, J=4.4 Hz), 10.01 (s, 1H). MS: m/z 449.0 (M$^+$+1).

Synthesis of 4-tert-Butyl-N-[4-chloro-2-(3-methyl-pyridine-4-carbonyl)-phenyl]-benzenesulfonamide

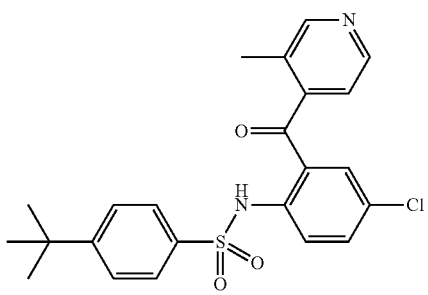 [SMILES: Cc1cnccc1C(=O)c1cc(Cl)ccc1NS(=O)(=O)c1ccc(C(C)(C)C)cc1]

The title compound was prepared according to the general procedure for the synthesis of N-Aryl-benzenesulfonamides previously described using 123 mg of (2-Amino-5-chlorophenyl)-(3-methyl-pyridin-4-yl)-methanone and 116 mg of 4-tert-butyl-benzenesulfonyl chloride. $^1$H-NMR (400 MHz, CDCl$_3$): δ 1.32 (s, 9H), 2.19 (s, 3H), 7.04 (d, 1H, J=1.4 Hz), 7.21 (d, 1H, J=5.2 Hz), 7.48 (d, 2H, J=8.8 Hz), 7.52 (dd, 1H, J=8.8 Hz, 2.4 Hz), 7.77-7.83 (m, 3H), 8.64 (d, 1H, J=5.2 Hz), 8.71 (s, 1H), 10.75 (s, 1H). MS: m/z 443.0 (M$^+$+1).

Synthesis of N-[4-Chloro-2-(pyridine-4-carbonyl)-phenyl]-4-trifluoromethyl-benzenesulfonamide

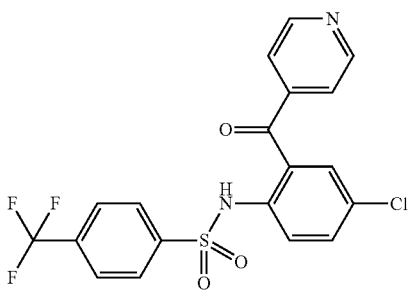 [SMILES: O=C(c1ccncc1)c1cc(Cl)ccc1NS(=O)(=O)c1ccc(C(F)(F)F)cc1]

The title compound was prepared according to the general procedure for the synthesis of N-Aryl-benzenesulfonamides previously described using 116 mg of (2-amino-5-chlorophenyl)-pyridin-4-yl-methanone and 122 mg of 4-Trifluoromethyl-benzenesulfonyl chloride. $^1$H-NMR (400 MHz, CDCl$_3$): δ 7.31 (d, 1H, J=2.8 Hz), 7.36 (m, 2H), 7.54-7.59 (m, 2H), 7.73 (d, 1H, J=8.0 Hz), 7.77 (d, 1H, J=9.2 Hz), 7.97 (d, 1H, J=8.0 Hz), 8.00 (s, 1H), 8.82 (dd, 2H, J=6.0 Hz, 1.2 Hz), 10.16 (s, 1H). MS: m/z 441.8 (M$^+$+1).

Synthesis of 4-tert-Butyl-N-[4,5-difluoro-2-(pyridine-4-carbonyl)-phenyl]-benzenesulfonamide

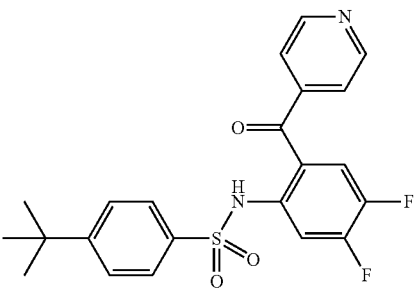 [SMILES: CC(C)(C)c1ccc(S(=O)(=O)Nc2cc(F)c(F)cc2C(=O)c2ccncc2)cc1]

The title compound was prepared according to the general procedure for the synthesis of N-Aryl-benzenesulfonamides previously described using 117 mg of (2-Amino-4,5-difluoro-phenyl)-pyridin-4-yl-methanone and 116 mg of 4-tert-butyl-benzenesulfonyl chloride. $^1$H-NMR (400 MHz, CDCl$_3$): δ 1.28 (s, 9H), 7.17 (t, 1H, J=8.4 Hz), 7.45 (d, 2H, J=8.4 Hz), 7.54 (d, 2H, J=4.4 Hz), 7.64 (dd, 1H, J=11.6 Hz, 6.8 Hz), 7.72 (d, 2H, J=8.4 Hz), 8.85 (d, 2H, J=5.2 Hz), 10.42 (s, 1H). MS: m/z 431.1 (M$^+$+1).

Synthesis of 4-tert-Butyl-N-[4-chloro-2-(6-morpholin-4-yl-pyridine-3-carbonyl)-phenyl]-benzenesulfonamide

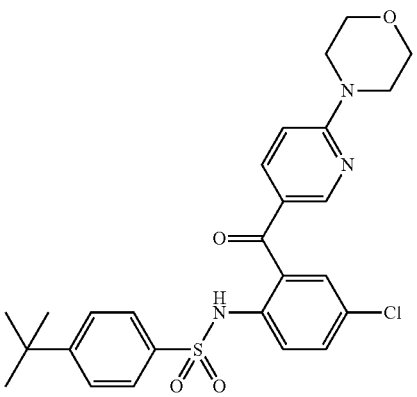 [SMILES: CC(C)(C)c1ccc(S(=O)(=O)Nc2ccc(Cl)cc2C(=O)c2ccc(N3CCOCC3)nc2)cc1]

The title compound was prepared according to the general procedure for the synthesis of N-Aryl-benzenesulfonamides previously described using 158 mg of (2-Amino-5-chlorophenyl)-(6-morpholin-4-yl-pyridin-3-yl)-methanone and 116 mg of 4-tert-butyl-benzenesulfonyl chloride. $^1$H-NMR (400 MHz, CDCl$_3$): δ 1.22 (s, 3H), 3.76 (t, 4H, J=4.6 Hz), 3.857 (t, 4H, J=4.6 H), 8.78 (d, 1H, J=9.2 Hz), 7.30 (m, 2H), 7.34 (m, 1H), 7.46 (m, 1H), 7.54-7.56 (m, 3H), 7.99 (d, 1H, J=9.2 Hz), 8.16 (v, 1H), 9.29 (s, 1H). MS: m/z 515.1 (M$^+$+1).

Synthesis of N-[4-Chloro-2-(6-methyl-pyridine-3-carbonyl)-phenyl]-4-oxazol-5-yl-benzenesulfonamide

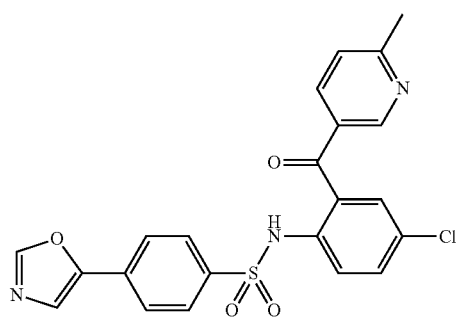 [SMILES: Cc1ccc(C(=O)c2cc(Cl)ccc2NS(=O)(=O)c2ccc(-c3cnco3)cc2)cn1]

The title compound was prepared according to the general procedure for the synthesis of N-Aryl-benzenesulfonamides previously described using 123 mg of (2-Amino-5-chloro-phenyl)-(6-methyl-pyridin-3-yl)-methanone and 122 mg of 4-oxazol-5-yl-benzenesulfonyl chloride. $^1$H-NMR (400 MHz, CDCl$_3$): δ 2.63 (s, 3H), 7.33 (m, 2H), 7.37 (s, 1H), 7.56 (m, 3H), 7.67-7.3 (m, 3H), 7.94 (m, 1H), 7.97 (s, 1H), 8.52 (b, 1H), 9.45 (s, 1H). MS: m/z 454.1 (M$^+$+1).

Synthesis of 4-tert-Butyl-N-[4-chloro-2-(2-methyl-sulfanyl-pyridine-4-carbonyl)-phenyl]-benzenesulfonamide

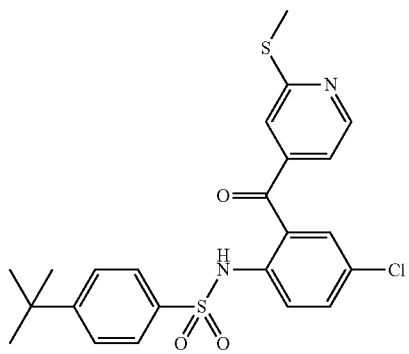 [SMILES: CSc1cc(C(=O)c2cc(Cl)ccc2NS(=O)(=O)c2ccc(C(C)(C)C)cc2)ccn1]

4-tert-Butyl-N-[4-chloro-2-(2-chloro-pyridine-4-carbonyl)-phenyl]-benzenesulfonamide (475 mg, 1.0 mmol) was dissolved in 10 mL dry THF and treated with solid sodium thiomethoxide (355 mg, 5 mmol) and the mixture heated at 70° C. for 16 h. The solvent was concentrated to about 2 mL and added to 5 mL cold 1M HCl. The light yellow solid precipitate was collected by filtration and product was purified by HPLC. $^1$H-NMR (400 MHz, CDCl$_3$): δ 1.26 (s, 9H), 2.61 (s, 3H), 6.86 (d, 1H, J=5.2 Hz), 7.18 (s, 1H), 7.28 (d, 1H, J=2.4 Hz), 7.39 (d, 2H, J=8.8 Hz), 7.51 (dd, 1H, J=8.8 Hz, 2.4 Hz), 7.67 (m, 2H), 7.76 (d, 1H, J=8.8 Hz), 8.56 (d, 1H, J=5.2 Hz), 10.13 (s, 1H). MS: m/z 476.1 (M$^+$+1).

Synthesis of N-[4-Chloro-2-(2-methyl-pyridine-4-carbonyl)-phenyl]-4-oxazol-5-yl-benzenesulfonamide

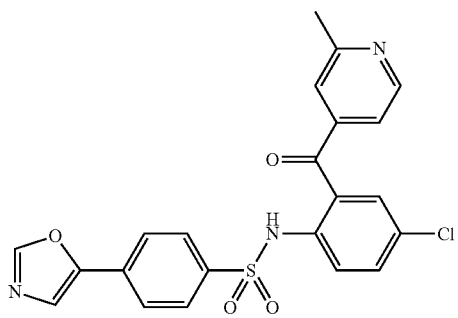 [SMILES: Cc1cc(C(=O)c2cc(Cl)ccc2NS(=O)(=O)c2ccc(-c3cnco3)cc2)ccn1]

The title compound was prepared according to the general procedure for the synthesis of N-Aryl-benzenesulfonamides previously described using 123 mg of (2-Amino-5-chloro-phenyl)-(2-methyl-pyridin-4-yl)-methanone and 122 mg of 4-oxazol-5-yl-benzenesulfonyl chloride. $^1$H-NMR (400 MHz, CDCl$_3$): δ 2.78 (s, 3H), 7.29 (d, 1H, J=2.8 Hz), 7.45 (m, 2H), 7.48 (s, 1H), 7.55 (dd, 1H, J=9.2 Hz, 2.8 Hz)), 7.67 (m, 3H), 7.83 (d, 2H, J=8.4 Hz), 8.03 (s, 1H), 8.81 (d, 1H, J=5.6 Hz), 10.10 (s, 1H). MS: m/z 454.9 (M$^+$+1).

Synthesis of N-[4-Chloro-2-(1-oxy-pyridine-4-carbonyl)-phenyl]-4-(2-hydroxy-1,1-dimethyl-ethyl)-benzenesulfonamide

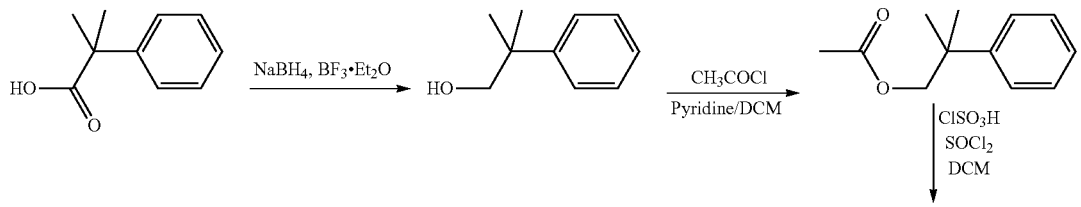

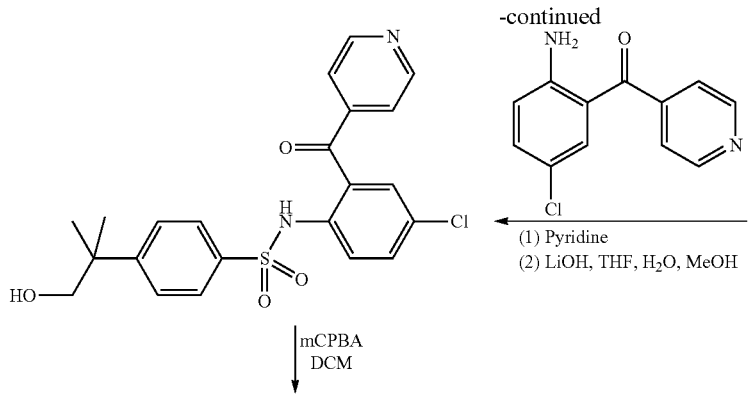

-continued

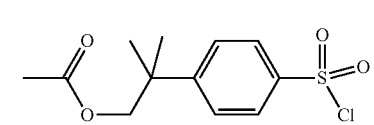

(1) Pyridine
(2) LiOH, THF, H₂O, MeOH mCPBA
DCM

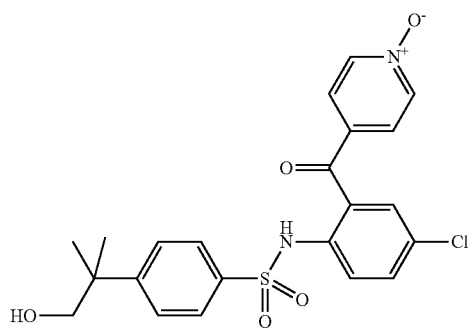

To a suspension of NaBH₄ (0.70 g, 18.3 mmol) in dry THF (20 mL) was added BF₃.Et₂O (0.25 mL, 20.1 mmol) drop wise at 0° C. over 5 min and the mixture was stirred for 30 min. A solution of 2-methyl-2-phenyl-propionic acid (1.0 g, 6.1 mmol) in dry THF (10 mL) was added drop wise at 0° C. over 30 min, and the mixture was stirred at room temperature for 4 h. Methanol was slowly added to the reaction mixture until hydrogen evolution stopped. The mixture was diluted with 10% HCl and extracted twice with EtOAc. The organic layer was dried over Na₂SO₄ and then under vacuum to yield colorless oil.

This material was dissolved in DCM (25 mL), pyridine (1.2 mL, 15.3 mmol) and acetyl chloride (2.2 mL, 30.5 mmol) added, and the reaction mixture left to stir at room temperature overnight. The reaction mixture was washed with 10% HCl and the organic layer was dried over MgSO₄.

The material was then dissolved in DCM (25 mL) and cooled to 0° C. Chlorosulfonic acid (1.2 mL, 18 mmol) was added drop wise over 15 minutes and the mixture was stirred at the same temperature for 3H. The volatiles were evaporated and SOCl₂ (10 mL) was added and the mixture stirred at room temperature for 3 h. The excess SOCl₂ was evaporated and the residue was treated with ice-water and extracted with ether. The organic layer was washed with water and brine, dried over MgSO₄ and concentrated in vacuo to afford the aryl sulfonyl chloride as a yellowish oil.

This oil was treated with a solution of (2-amino-5-chloro-phenyl)-pyridin-4-yl-methanone (1.2 g, 5 mmol) in 10 mL pyridine and heated at 60 C. for 4 h. The solvent was evaporated and the residue suspended in 3M HCl (10 mL) and stirred at room temperature for 16 h. The reaction mixture was put in an ice bath and neutralized with concentrated NaOH solution. The white precipitate formed was collected by filtration, washed with water and dried in vacuo and purified by flash chromatography to yield 320 mg of N-[4-Chloro-2-(pyridine-4-carbonyl)-phenyl]-4-(2-hydroxy-1,1-dimethyl-ethyl)-benzenesulfonamide.

Oxidation of this intermediate with mCPBA according to the general procedure gave N-[4-chloro-2-(1-oxy-pyridine-4-carbonyl)-phenyl]-4-(2-hydroxy-1,1-dimethyl-ethyl)-benzenesulfonamide. ¹H-NMR (400 MHz, CDCl₃): δ 1.24 (s, 6H), 3.58 (s, 2H), 7.29 (d, 1H, J=2.4 Hz), 7.37 (m, 4H), 7.53 (m, 2H), 7.62 (m, 2H), 7.78 (d, 1H, J=8.8 Hz), 8.23 (d, 2H, J=6.8 Hz), 9.51 (s, 1H). MS: m/z 461.1 (M⁺+1).

Synthesis of N-[4-chloro-2-(pyridine-4-carbonyl)-phenyl]-4-ethyl-benzenesulfonamide

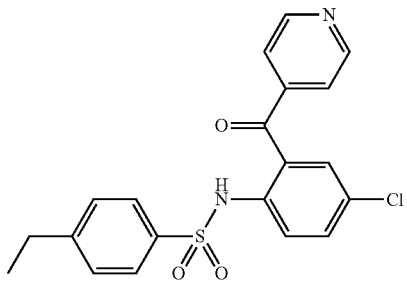 [SMILES: CCc1ccc(S(=O)(=O)Nc2ccc(Cl)cc2C(=O)c2ccncc2)cc1]

The title compound was prepared according to the general procedure for the synthesis of N-Aryl-benzenesulfonamides previously described using 116 mg of (2-amino-5-chloro-phenyl)-pyridin-4-yl-methanone and 102 mg of 4-ethyl-benzenesulfonyl chloride. ¹H-NMR (400 MHz, CDCl₃): δ 0.94 (t, 3H, J=7.6 Hz), 2.38 (q, 2H, J=15.2 Hz, 7.6 Hz), 6.94 (d, 2H, J=6.8 Hz), 7.16 (m, 2H), 7.23 (m, 1H), 7.30 (m, 4H), 8.60 (b, 2H), 9.73 (b, 1H). MS: m/z 401.1 (M⁺+1).

Synthesis of N-[4-Chloro-2-(pyrimidine-2-carbonyl)-phenyl]-4-oxazol-5-yl-benzenesulfonamide

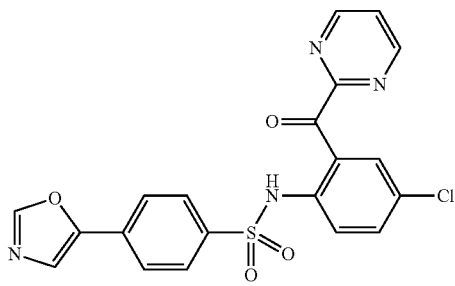 [SMILES: O=C(c1ncccn1)c1cc(Cl)ccc1NS(=O)(=O)c1ccc(-c2cnco2)cc1]

The title compound was prepared according to the general procedure for the synthesis of N-Aryl-benzenesulfonamides previously described using 116 mg of (2-Amino-5-chloro-phenyl)-pyrimidin-2-yl-methanone and 122 mg of 4-oxazol-5-yl-benzenesulfonyl chloride. $^1$H-NMR (400 MHz, CDCl$_3$): δ 7.43 (s, 1H), 7.45 (m, 1H), 7.50 (m, 1H), 7.55 (m, 1H), 7.64 (m, 2H), 7.66 (d, 1H, J=8.8 Hz), 7.86 (m, 2H), 7.97 (s, 1H), 8.86 (d, 2H), 10.63 (s, 1H). MS: m/z 441.9 (M$^+$+1).

Synthesis of N-[4-chloro-2-(pyrimidine-4-carbonyl)-phenyl]-4-oxazol-5-yl-benzenesulfonamide

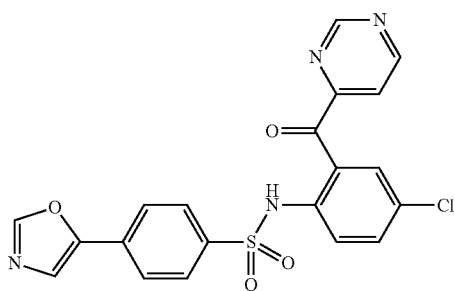 [SMILES: O=C(c1ccncn1)c1cc(Cl)ccc1NS(=O)(=O)c1ccc(-c2cnco2)cc1]

The title compound was prepared according to the general procedure for the synthesis of N-Aryl-benzenesulfonamides previously described using 116 mg of (2-Amino-5-chloro-phenyl)-pyrimidin-4-yl-methanone and 122 mg of 4-oxazol-5-yl-benzenesulfonyl chloride. $^1$H-NMR (400 MHz, CDCl$_3$): δ 7.43 (s, 1H), 7.53 (dd, 1H, J=8.8 Hz, 2.4 Hz), 7.62 (m, 2H), 7.75 (m, 2H), 7.80 (m, 3H), 7.98 (s, 1H), 8.99 (d, 1H, J=5.2 Hz), 9.25 (b, 1H), 10.29 (b, 1H). MS: m/z 441.9 (M$^+$+1).

Synthesis of N-[4-Chloro-2-(pyridine-3-carbonyl)-phenyl]-4-oxazol-5-yl-benzenesulfonamide

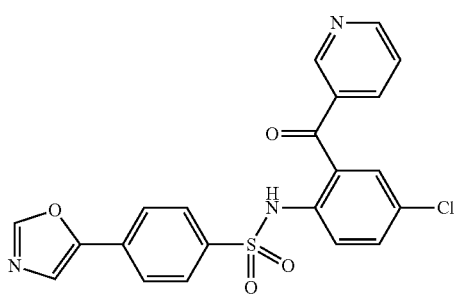 [SMILES: O=C(c1cccnc1)c1cc(Cl)ccc1NS(=O)(=O)c1ccc(-c2cnco2)cc1]

The title compound was prepared according to the general procedure for the synthesis of N-Aryl-benzenesulfonamides previously described using 116 mg of (2-Amino-5-chloro-phenyl)-pyridin-3-yl-methanone and 122 mg of 4-oxazol-5-yl-benzenesulfonyl chloride. $^1$H-NMR (400 MHz, CDCl$_3$): δ 7.23 (m, 2H), 7.42-7.47 (m, 3H), 7.58-7.62 (m, 3H), 7.71 (dt, 1H, J=7.6 Hz, 2.0 Hz), 7.88 (s, 1H), 8.45 (b, 1H), 8.58 (bd, 1H, J=3.6 Hz), 9.67 (s, 1H). MS: m/z 458.1 (M$^+$+1)

Synthesis of 4-tert-Butyl-N-[4-chloro-2-(pyridine-2-carbonyl)-phenyl]-benzenesulfonamide

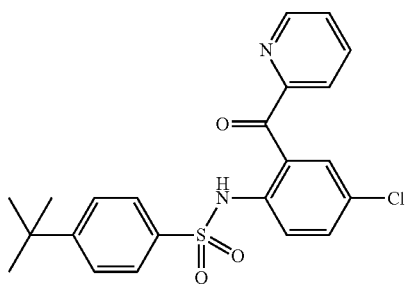 [SMILES: CC(C)(C)c1ccc(S(=O)(=O)Nc2ccc(Cl)cc2C(=O)c2ccccn2)cc1]

The title compound was prepared according to the general procedure for the synthesis of N-Aryl-benzenesulfonamides previously described using 116 mg of (2-Amino-5-chloro-phenyl)-pyridin-2-yl-methanone and 116 mg of 4-tert-Butyl-benzenesulfonyl chloride. $^1$H-NMR (400 MHz, CDCl$_3$): δ 1.24 (s, 9H), 7.34-7.38 (m, 2H), 7.47 (dd, 1H, J=8.8 Hz, 2.4 Hz), 7.60 (m, 1H), 7.65-7.68 (m, 4H), 7.85 (d, 1H, J=8 Hz), 8.00 (td, 1H, J=7.6 Hz, 2 Hz), 8.71 (bd, 1H, J=4.8 Hz). MS: m/z 429.9 (M$^+$+1).

Synthesis of N-[4-Chloro-2-(pyridine-4-carbonyl)-phenyl]-4-(1,1-dimethyl-propyl)-benzenesulfonamide

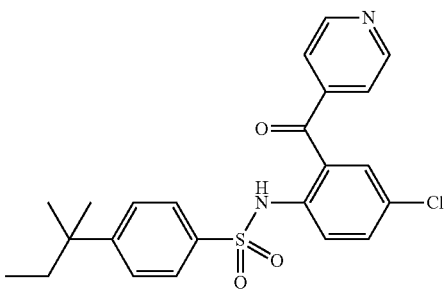 [SMILES: CCC(C)(C)c1ccc(S(=O)(=O)Nc2ccc(Cl)cc2C(=O)c2ccncc2)cc1]

The title compound was prepared according to the general procedure for the synthesis of N-Aryl-benzenesulfonamides previously described using 116 mg of (2-amino-5-chloro-phenyl)-pyridin-4-yl-methanone and 123 mg of 4-(1,1-dimethyl-propyl)-benzenesulfonyl chloride. $^1$H-NMR (400 MHz, CDCl$_3$): δ 0.59 (t, 3H, J=7.2 Hz), 1.23 (s, 6H), 1.61 (q, 2H, J=7.2 Hz), 7.28 (d, 1H, J=2.8 Hz), 7.36 (m, 2H), 7.53 (m, 3H), 7.67-7.74 (m, 3H), 8.84 (m, 2H), 10.14 (s, 1H). MS: m/z 443.9 (M$^+$+1).

Synthesis of 4-tert-butyl-N-[4-chloro-2-(2-chloro-pyridine-4-carbonyl)-phenyl]-benzenesulfonamide

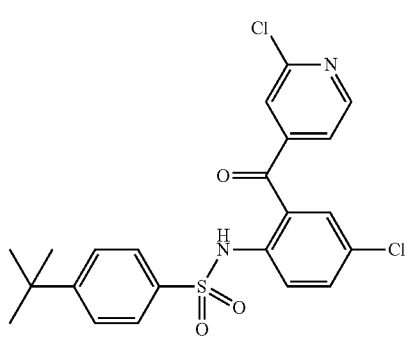 [SMILES: CC(C)(C)c1ccc(S(=O)(=O)Nc2ccc(Cl)cc2C(=O)c2ccnc(Cl)c2)cc1]

The title compound was prepared according to the general procedure for the synthesis of N-Aryl-benzenesulfonamides previously described using 133 mg of (2-Amino-5-chloro-phenyl)-(2-chloro-pyridin-4-yl)-methanone and 116 mg of 4-tert-Butyl-benzenesulfonyl chloride. $^1$H-NMR (400 MHz, CDCl$_3$): δ 1.26 (s, 9H), 7.18 (dd, 5.2 Hz, 1.6 Hz), 7.25 (m, 1H), 7.32 (m, 1H), 7.41 (d, 2H, J=6.4 Hz), 7.54 (dd, 1H, J=9.2 Hz, 2.4 Hz), 7.67 (m, 2H), 7.77 (d, 1H, J=8.8 Hz), 8.55 (d, 1H, J=5.2 Hz), 10.09 (s, 1H). MS: m/z 463.0 (M$^+$+1).

Synthesis of N-[4-Chloro-2-(6-methyl-pyridine-2-carbonyl)-phenyl]-4-oxazol-5-yl-benzenesulfonamide

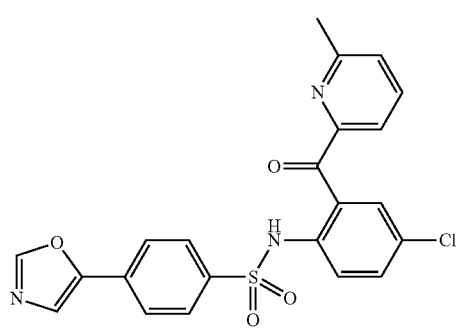 [SMILES: Cc1cccc(C(=O)c2cc(Cl)ccc2NS(=O)(=O)c2ccc(-c3cnco3)cc2)n1]

The title compound was prepared according to the general procedure for the synthesis of N-Aryl-benzenesulfonamides previously described using 123 mg of (2-Amino-5-chloro-phenyl)-(6-methyl-pyridin-2-yl)-methanone and 122 mg of 4-oxazol-5-yl-benzenesulfonyl chloride $^1$H-NMR (400 MHz, CDCl$_3$): δ 2.67 (s, 3H), 7.46-7.50 (m, 4H), 7.61-7.70 (m, 4H), 7.65 (m, 2H), 7.94-8.00 (m, 1H), 8.15 (s, 1H). MS: m/z 454.0 (M$^+$+1).

Synthesis of 4-tert-Butyl-N-[4-chloro-2-(2-methyl-pyridine-4-carbonyl)-phenyl]-benzenesulfonamide

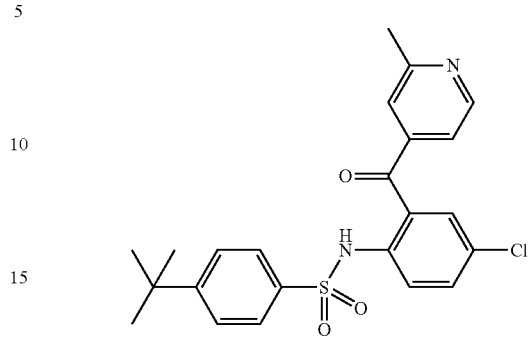

The title compound was prepared according to the general procedure for the synthesis of N-Aryl-benzenesulfonamides previously described using 123 mg of (2-Amino-5-chloro-phenyl)-(2-methyl-pyridin-4-yl)-methanone and 116 mg of 4-tert-Butyl-benzenesulfonyl chloride. $^1$H-NMR (400 MHz, CDCl$_3$): δ 1.26 (s, 9H), 2.63 (s, 3H) 7.29 (d, 1H, J=2.8 Hz), 7.45-7.55 (m, 3H), 7.67 (m, 2H), 7.83 (m, 2H), 8.03 (s, 1H), 8.81 (d, 1H, J=5.6 Hz), 10.10 (s, 1H). MS: m/z 443.9 (M$^+$+1).

Synthesis of 4-tert-Butyl-N-[4-chloro-2-(6-methyl-sulfanyl-pyridine-3-carbonyl)-phenyl]-benzenesulfonamide

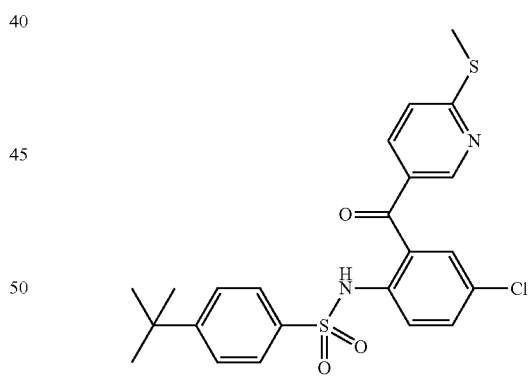

4-tert-Butyl-N-[4-chloro-2-(6-chloro-pyridine-3-carbonyl)-phenyl]-benzenesulfonamide (231 mg, 0.5 mmol) was dissolved in dry THF (5 mL) and treated with sodium thiomethoxide (175 mg, 2.5 mmol) and the mixture was heated at 70° C. for 4 h. The solvent was evaporated and the residue suspended in water (5 mL) and the product was precipitated by the drop wise addition of 3M HCl and purified by HPLC. $^1$H-NMR (400 MHz, CDCl$_3$): δ 1.19 (s, 9H), 2.60 (s, 3H), 7.21-7.28 (m, 3H), 7.31 (m, 1H), 7.50-7.54 (m, 3H), 7.65 (dd, 1H, J=8.4 Hz, 2.4 Hz), 7.78 (d, 1H, J=8.8 Hz), 8.19 (m, 1H), 9.62 (s, 1H). MS: m/z 476.0 (M$^+$+1).

Synthesis of 4-tert-Butyl-N-[4-chloro-2-(6-methanesulfonyl-pyridine-3-carbonyl)-phenyl]-benzenesulfonamide

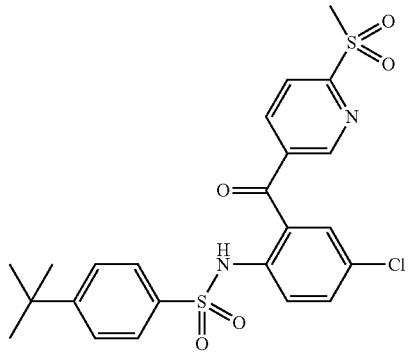 [SMILES: CC(C)(C)c1ccc(S(=O)(=O)Nc2ccc(Cl)cc2C(=O)c2ccc(S(C)(=O)=O)nc2)cc1]

4-tert-Butyl-N-[4-chloro-2-(6-methylsulfanyl-pyridine-3-carbonyl)-phenyl]-benzenesulfonamide (48 mg, 0.1 mmol) and mCPBA (35 mg, 0.2 mmol) were dissolved in DCM (4 mL) and the mixture stirred at room temperature overnight. The solvent was evaporated and product was purified by HPLC. $^1$H-NMR (400 MHz, CDCl$_3$): δ 1.25 (s, 9H), 3.30 (s, 3H), 7.27 (m, 1H), 7.38 (m, 2H), 7.56 (dd, 1H, J=8.8 Hz, 2.8 Hz), 7.66 (m, 2H), 7.80 (d, 1H, J=8.8 Hz), 8.04 (dd, 1H, J=8 Hz, 2 Hz), 8.18 (d, 1H, J=8.0 Hz), 8.61 (m, 1H), 10.00 (s, 1H). MS: m/z 508.0 (M$^+$+1).

Synthesis of 4-tert-Butyl-N-[3,4-difluoro-2-(pyridine-4-carbonyl)-phenyl]-benzenesulfonamide

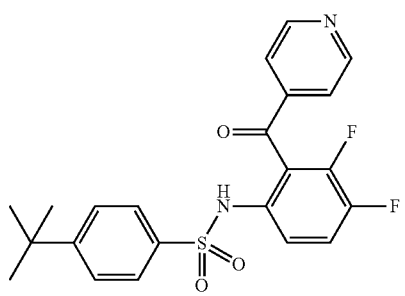 [SMILES: CC(C)(C)c1ccc(S(=O)(=O)Nc2ccc(F)c(F)c2C(=O)c2ccncc2)cc1]

The title compound was prepared according to the general procedure for the synthesis of N-Aryl-benzenesulfonamides previously described using 117 mg of (6-Amino-2,3-difluoro-phenyl)-pyridin-4-yl-methanone and 116 mg of 4-tert-Butyl-benzenesulfonyl chloride. $^1$H-NMR (400 MHz, CDCl$_3$): δ 1.22 (s, 9H), 7.31 (d, 2H, J=8.4 Hz), 7.40-7.47 (m, 3H), 7.55 (d, 2H, J=8.4 Hz), 7.59 (m, 1H), 8.69 (b, 1H), 8.82 (d, 2H, J=6.0 Hz). MS: m/z 431.0 (M$^+$+1).

Synthesis of 4-tert-Butyl-N-[4-chloro-2-(pyrazine-2-carbonyl)-phenyl]-benzenesulfonamide

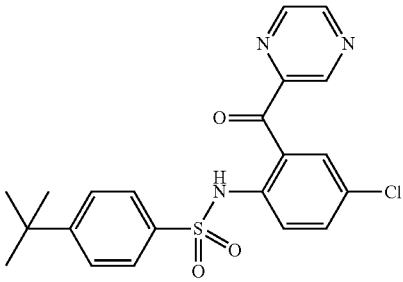 [SMILES: CC(C)(C)c1ccc(S(=O)(=O)Nc2ccc(Cl)cc2C(=O)c2cnccn2)cc1]

The title compound was prepared according to the general procedure for the synthesis of N-Aryl-benzenesulfonamides previously described using 117 mg of (2-Amino-5-chlorophenyl)-pyrazin-2-yl-methanone and 116 mg of 4-tert-butyl-benzenesulfonyl chloride. $^1$H-NMR (400 MHz, CDCl$_3$): δ 1.24 (s, 9H), 7.38 (dm, 2H, J=6.8 Hz), 7.50 (dd, 1H, J=9.2 Hz, 1.6 Hz), 7.70 (m, 2H), 7.76 (m, 1H), 7.80 (m, 1H), 8.62 (m, 1H), 8.77 (m, 1H), 9.06 (m, 1H), 10.37 (s, 1H). MS: m/z 430.0 (M$^+$+1).

Synthesis of N-[4-Chloro-2-(pyridine-4-carbonyl)-phenyl]-4-isopropoxy-benzenesulfonamide

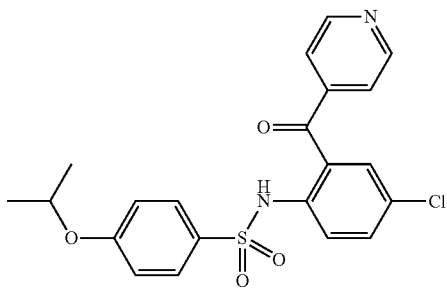 [SMILES: CC(C)Oc1ccc(S(=O)(=O)Nc2ccc(Cl)cc2C(=O)c2ccncc2)cc1]

The title compound was prepared according to the general procedure for the synthesis of N-Aryl-benzenesulfonamides previously described using 116 mg of (2-Amino-5-chlorophenyl)-pyridin-4-yl-methanone and 117 mg of 4-Isopropoxy-benzenesulfonyl chloride. $^1$H-NMR (400 MHz, CDCl$_3$): δ 1.01 (d, 6H, J=5.6 Hz), 4.27 (m, 1H), 6.51 (d, 2H, J=8.8 Hz), 6.87 (d, 1H, J=8.8 Hz), 7.15-7.25 (m, 4H), 7.60 (d, 2H, J=6.0 Hz), 8.64 (d, 2H, J=6 Hz), 9.60 (s, 1H). MS: m/z 431.9 (M$^+$+1).

Synthesis of N-[4-Bromo-2-(pyridine-4-carbonyl)-phenyl]-4-isopropoxy-benzenesulfonamide

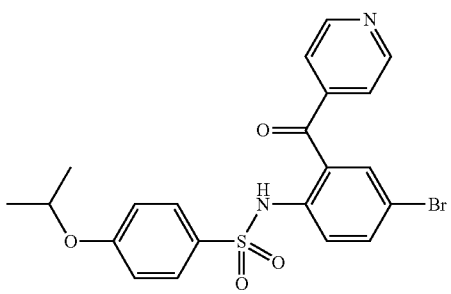 [SMILES: CC(C)Oc1ccc(S(=O)(=O)Nc2ccc(Br)cc2C(=O)c2ccncc2)cc1]

The title compound was prepared according to the general procedure for the synthesis of N-Aryl-benzenesulfonamides previously described using 138 mg of (2-Amino-5-bromophenyl)-pyridin-4-yl-methanone and 117 mg of 4-Isopropoxy-benzenesulfonyl chloride. $^1$H-NMR (400 MHz, CDCl$_3$): δ 1.31 (d, 6H, J=6 Hz), 4.49 (q, 1H, J=6.0 Hz), 6.73 (d, 2H, J=6.8 Hz), 7.39 (m, 3H), 7.63-7.70 (m, 4H), 8.82 (d, 2H, J=6.0 Hz), 9.99 (s, 1H). MS: m/z 476.0 (M$^+$+1)

Synthesis of N-[4-Bromo-2-(pyridine-4-carbonyl)-phenyl]-4-ethyl-benzenesulfonamide

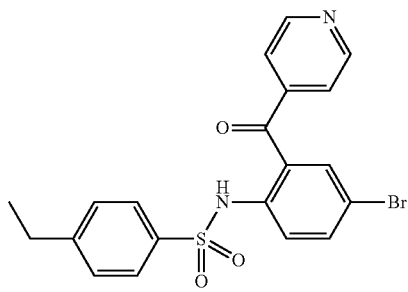 [SMILES: CCc1ccc(S(=O)(=O)Nc2ccc(Br)cc2C(=O)c2ccncc2)cc1]

The title compound was prepared according to the general procedure for the synthesis of N-Aryl-benzenesulfonamides previously described using 138 mg of (2-Amino-5-bromophenyl)-pyridin-4-yl-methanone and 102 mg of 4-ethyl-benzenesulfonyl chloride. $^1$H-NMR (400 MHz, CDCl$_3$): δ 1.19 (t, 3H, J=7.6 Hz), 2.62 (q, 2H, J=7.6 Hz), 7.20 (d, 2H, J=8.8 Hz, 7.38 (m, 3H), 7.65-7.72 (m, 4H), 8.81 (d, 2H, 6.4 Hz), 10.06 (s, 1H). MS: m/z 446.0 (M$^+$+1).

Synthesis of N-[4-Bromo-2-(pyridine-4-carbonyl)-phenyl]-4-trifluoromethoxy-benzenesulfonamide

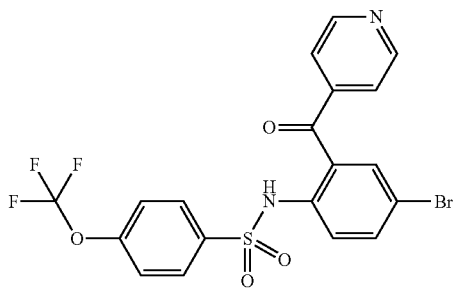 [SMILES: O=C(c1ccncc1)c1cc(Br)ccc1NS(=O)(=O)c1ccc(OC(F)(F)F)cc1]

The title compound was prepared according to the general procedure for the synthesis of N-Aryl-benzenesulfonamides previously described using 138 mg of (2-Amino-5-bromophenyl)-pyridin-4-yl-methanone and 130 mg of 4-Trifluoromethoxy-benzenesulfonyl chloride. $^1$H-NMR (400 MHz, CDCl$_3$): δ 7.23 (d, 2H, J=8.0 Hz), 7.45 (m, 3H), 7.71 (m, 2H), 7.85 (d, 2H, J=8.8 Hz), 8.85 (d, 2H, J=6.4 Hz), 10.23 (s, 1H). MS: m/z 502.9 (M$^+$+1).

Synthesis of 4-tert-Butyl-N-[4-chloro-2-(2-cyano-pyridine-4-carbonyl)-phenyl]-benzenesulfonamide

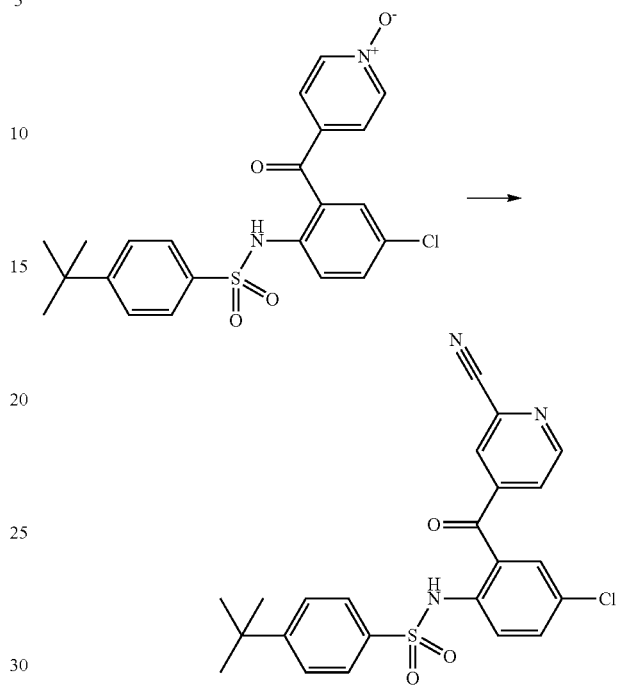

Dimethyl sulfate (126 mg, 1 mmol) and 4-tert-butyl-N-[4-chloro-2-(1-oxy-pyridine-4-carbonyl)-phenyl]-benzenesulfonamide (445 mg, 1 mmol) were dissolved in dry THF (5 mL). The reaction mixture was stirred at room temperature for 1 hour and at 60° C. for two hours. After cooling to room temperature, to the solution was added 25% (w/v) aqueous KCN solution (5 mL) and the mixture stirred for 16 h. The solvent was evaporated in vacuo and the product was purified by HPLC. $^1$H-NMR (400 MHz, CDCl$_3$): δ 1.27 (s, 9H), 7.22 (d, 1H, J=2.0 Hz), 7.41-7.47 (m, 3H), 7.56 (dd, 1H, J=2.4 Hz), 7.69 (m, 3H), 7.79 (d, 1H, J=9.2 Hz), 8.87 (d, 1H, J=5.2 Hz), 10.06 (s, 1H). MS: m/z 454.0 (M$^+$+1).

Synthesis of 4-tert-Butyl-N-[4-chloro-2-(2-methanesulfonyl-pyridine-4-carbonyl)-phenyl]-benzenesulfonamide

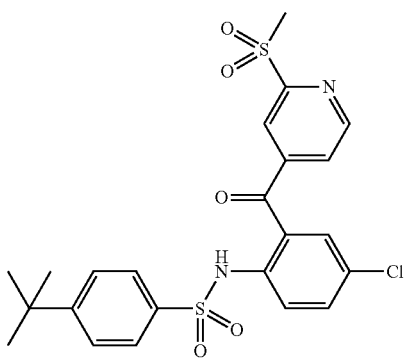 [SMILES: CC(C)(C)c1ccc(S(=O)(=O)Nc2ccc(Cl)cc2C(=O)c2ccnc(S(C)(=O)=O)c2)cc1]

4-tert-Butyl-N-[4-chloro-2-(2-chloro-pyridine-4-carbonyl)-phenyl]-benzenesulfonamide (232 mg, 0.5 mmol) was dissolved in dry THF (5 mL) and treated with sodium thiomethoxide (175 mg, 2.5 mmol) and the mixture was heated at 70° C. for 16 h. The solvent was evaporated and the residue suspended in water (5 mL) and the product was precipitated by the drop wise addition of 3M HCl. The precipitate was collected by filtration, dissolved in DCM (10 mL) and treated with mCPBA (172 mg, 1 mmol). After stirring at room temperature for 16 h, the DCM solution was washed with saturated NaHCO$_3$ solution (10 mL). The organic layer was washed with water, dried and the solvent was evaporated. The product was purified by HPLC to give white powder after lyophilization. $^1$H-NMR (400 MHz, CDCl$_3$): δ 1.28 (s, 9H), 3.30 (s, 3H), 7.24 (d, 1H, J=2.4 Hz), 7.45 (d, 2H, J=8.0 Hz), 7.48 (m, 1H), 7.54 (dd, 1H, J=8.8 Hz, 2.4 Hz), 7.74 (d, 2H, J=8.0 Hz), 7.78 (d, 1H, J=8.8 Hz), 8.87 (d, 1H, J=5.2 Hz), 10.23 (s, 1H). MS: m/z 507.0 (M$^+$+1).

Synthesis of N-[4-Bromo-2-(pyridine-4-carbonyl)-phenyl]-4-methanesulfonyl-benzenesulfonamide

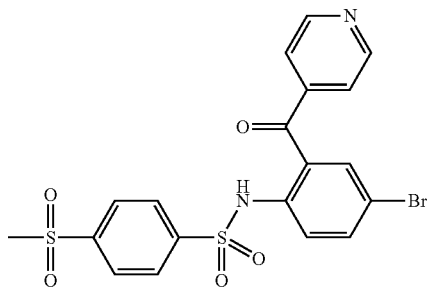 [SMILES: CS(=O)(=O)c1ccc(S(=O)(=O)Nc2ccc(Br)cc2C(=O)c2ccncc2)cc1]

The title compound was prepared according to the general procedure for the synthesis of N-Aryl-benzenesulfonamides previously described using 138 mg of (2-Amino-5-bromo-phenyl)-phenyl-methanone and 127 mg of 4-Methanesulfonyl-benzenesulfonyl chloride. $^1$H-NMR (400 MHz, CDCl$_3$): δ 3.07 (s, 3H), 7.45 (d, 1H, J=2.0 Hz), 7.49 (d, 2H, J=6.0 Hz), 7.15 (m, 3H), 8.00 (s, 4H), 8.89 (d, 2H, J=6.0 Hz), 10.32 (b, 1H). MS: m/z 496.9.0 (M$^+$+1).

Synthesis of 4-Acetyl-N-[4-bromo-2-(pyridine-4-carbonyl)-phenyl]-benzenesulfonamide

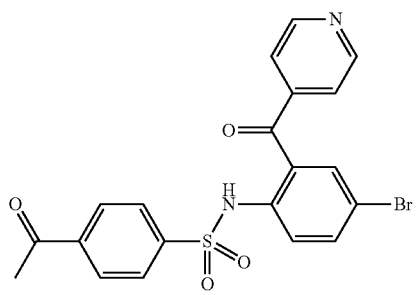 [SMILES: CC(=O)c1ccc(S(=O)(=O)Nc2ccc(Br)cc2C(=O)c2ccncc2)cc1]

The title compound was prepared according to the general procedure for the synthesis of N-Aryl-benzenesulfonamides previously described using 138 mg of (2-Amino-5-bromo-phenyl)-phenyl-methanone and 109 mg of 4-acetyl-benzenesulfonyl chloride. $^1$H-NMR (400 MHz, CDCl$_3$): δ 2.59 (s, 3H), 7.44 (d, 1H, J=2.0 Hz), 7.56 (d, 2H, J=6.4 Hz, 7.64-7.71 (m, 2H), 7.90 (d, 2H, J=8.8 Hz), 7.97 (d, 2H, J=8.8 Hz), 8.88 (d, 2H, J=6.4 Hz), 10.24 (b, 1H). MS: m/z 459.8 (M$^+$+1).

Synthesis of 4-tert-Butyl-N-[4-chloro-2-(6-methyl-pyridine-2-carbonyl)-phenyl]-benzenesulfonamide

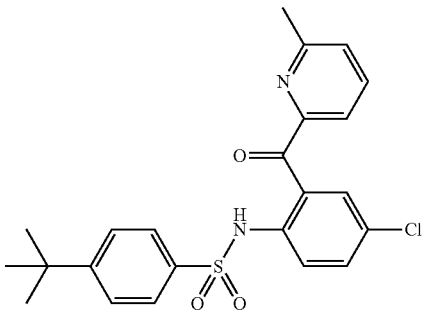 [SMILES: Cc1cccc(C(=O)c2cc(Cl)ccc2NS(=O)(=O)c2ccc(C(C)(C)C)cc2)n1]

The title compound was prepared according to the general procedure for the synthesis of N-Aryl-benzenesulfonamides previously described using (2-Amino-5-chloro-phenyl)-(6-methyl-pyridin-2-yl)-methanone and 4-tert-Butyl-benzenesulfonyl chloride and purified by HPLC. $^1$H NMR: δ 1.29 (s, 9H), 2.94 (s, 3H), 7.42-7.46 (m, 3H), 7.51 (d, J=8.8 Hz, 1H), 7.58 (d, J=2.0 Hz, 1H), 7.62 (d, J=7.2 Hz, 1H), 7.66 (d, J=6.8 Hz, 1H), 7.74 (d, J=8.0 Hz, 1H), 8.1 (bs, 1H). MS: M/z 443.1 (M$^+$+1).

Synthesis of 4-tert-Butyl-N-[4-chloro-2-(6-chloro-pyridine-3-carbonyl)-phenyl]-benzenesulfonamide

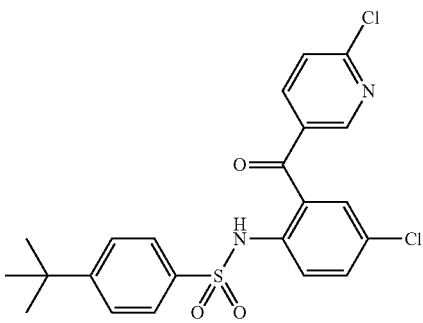 [SMILES: CC(C)(C)c1ccc(S(=O)(=O)Nc2ccc(Cl)cc2C(=O)c2ccc(Cl)nc2)cc1]

The title compound was prepared according to the general procedure for the synthesis of N-Aryl-benzenesulfonamides previously described using (2-Amino-5-chloro-phenyl)-(6-chloro-pyridin-3-yl)-methanone and 4-tert-butyl-benzenesulfonyl chloride and purified by HPLC. $^1$H NMR: δ 1.21 (s, 9H), 7.30 (d, J=2.4 Hz, 1H), 7.33 (d, J=6.6 Hz, 2H), 7.43 (d, J=8.0 Hz, 1H), 7.52 & 7.55 (dd, J=8.8 Hz, 2.8 Hz, 1H), 7.60 (d, J=7.0 Hz, 1H), 7.79 (m, 3H), 8.27 (d, J=2.0 Hz, 1H), 9.73 (s, 1H). MS: M/z 463.0 (M$^+$+1).

Synthesis of N-[4-Chloro-2-(pyridine-3-carbonyl)-phenyl]-4-trifluoromethoxy-benzenesulfonamide

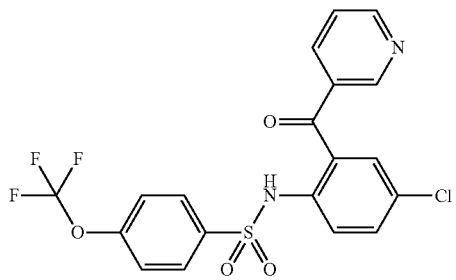 [SMILES: O=C(c1cccnc1)c1cc(Cl)ccc1NS(=O)(=O)c1ccc(OC(F)(F)F)cc1]

The title compound was prepared according to the general procedure for the synthesis of N-Aryl-benzenesulfonamides previously described using (2-amino-5-chloro-phenyl)-pyridin-3-yl-methanone and 4-Trifluoromethoxy-benzenesulfonyl chloride and purified by HPLC. $^1$H NMR: δ 6.93 (d, J=8.0 Hz, 1H), 7.51 (d, J=8.8 Hz, 2H), 7.58-7.61 (m, 3H), 7.67 (d, J=8.8 Hz, 2H), 8.03-8.05 (m, 1H), 8.74 (d, J=1.6 Hz, 1H), 8.79 & 8.80 (dd, J=6.0 Hz, 1.6 Hz, 1H), 9.73 (s, 1H). MS: M/z 456.9 (M$^+$+1).

Synthesis of N-[4-Chloro-2-(pyridine-3-carbonyl)-phenyl]-4-methanesulfonyl-benzenesulfonamide

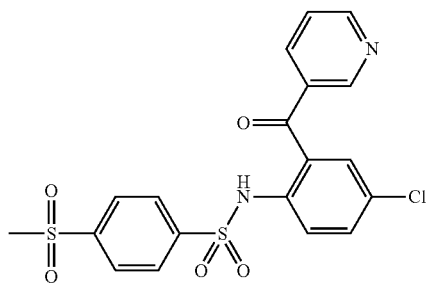 [SMILES: CS(=O)(=O)c1ccc(S(=O)(=O)Nc2ccc(Cl)cc2C(=O)c2cccnc2)cc1]

The title compound was prepared according to the general procedure for the synthesis of N-Aryl-benzenesulfonamides previously described using (2-amino-5-chloro-phenyl)-pyridin-3-yl-methanone and 4-Methanesulfonyl-benzenesulfonyl chloride and purified by HPLC. $^1$H NMR (CDCl$_3$): δ 3.01 (s, 3H), 7.36-7.37 (d, J=2.4 Hz, 1H), 7.43 (m, 1H), 7.54 & 7.57 (dd, J=8.8 Hz, 2.4 Hz, 1H), 7.70-7.73 (m, 1H), 7.77 (d, J=8.8 Hz, 1H), 7.90 (m, 4H), 8.59 (d, J=2.0 Hz, 1H), 8.80 & 8.82 (dd, J=4.8 Hz, 1.6 Hz, 1H), 9.98 (s, 1H). MS: M/z 450.9 (M$^+$+1).

Synthesis of N-[4-Chloro-2-(pyridine-4-carbonyl)-phenyl]-4-trifluoromethoxy-benzenesulfonamide

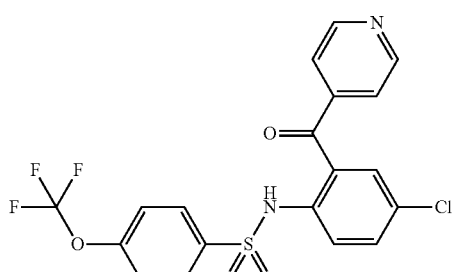

The title compound was prepared according to the general procedure for the synthesis of N-Aryl-benzenesulfonamides previously described using (2-amino-5-chloro-phenyl)-pyridin-4-yl-methanone and 4-Trifluoromethoxy-benzenesulfonyl chloride and purified by HPLC. $^1$H NMR (DMSO-d6): δ 6.90 (d, J=8.4 Hz, 1H), 7.50 (d, J=8.8 Hz, 2H), 7.49-7.61 (m, 4H), 7.66 (d, J=8.8 Hz, 2H), 8.81 (d, J=4.8 Hz, 2H), 10.26 (s, 1H). MS: M/z 456.9 (M$^+$+1).

Synthesis of N-[4-Chloro-2-(pyridine-3-carbonyl)-phenyl]-4-isopropoxy-benzenesulfonamide

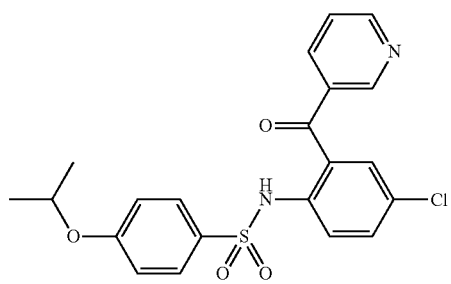 [SMILES: CC(C)Oc1ccc(S(=O)(=O)Nc2ccc(Cl)cc2C(=O)c2cccnc2)cc1]

The title compound was prepared according to the general procedure for the synthesis of N-Aryl-benzenesulfonamides previously described using (2-amino-5-chloro-phenyl)-pyridin-3-yl-methanone and 4-isopropoxy-benzenesulfonyl chloride and purified by HPLC. $^1$H NMR (CDCl$_3$): δ 1.19 (s, 3H), 1.20 (s, 3H), 4.35-4.38 (m, 1H), 6.63 (d, J=9.2 Hz, 2H), 7.24 (m, 2H), 7.35-7.38 (m, 1H), 7.43 (d, J=2.4 Hz, 1H), 7.45-7.49 (m, 2H), 7.62 (d, J=8.8 Hz, 1H), 7.70-7.73 (m, 1H), 8.51 (bs, 1H), 8.68 (bs, 1H), MS: M/z=431.0 (M$^+$+1).

Synthesis of 4-Chloro-N-[4-chloro-2-(pyridine-4-carbonyl)-phenyl]-benzenesulfonamide

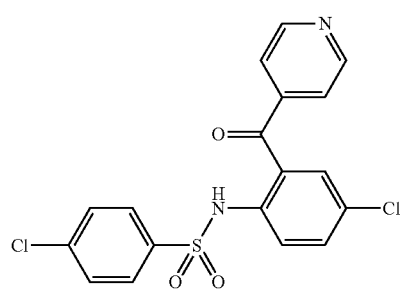 [SMILES: O=C(c1ccncc1)c1cc(Cl)ccc1NS(=O)(=O)c1ccc(Cl)cc1]

The title compound was prepared according to the general procedure for the synthesis of N-Aryl-benzenesulfonamides previously described using (2-amino-5-chloro-phenyl)-pyridin-4-yl-methanone and 4-chloro-benzenesulfonyl chloride and purified by HPLC. $^1$H NMR (CDCl$_3$): δ 7.20 (dd, 2H, J=4.4 Hz, 2.0), 7.31 (m, 2H), 7.53 (dd, 1H, J=8.8 Hz, 2.8 Hz), 7.65 (m, 2H), 7.76 (d, 1H, J=8.8 Hz), 8.79 (dd, 2H, J=4.4 Hz, 1.6 Hz), 10.00 (s, 1H). MS: m/z 407.1 (M$^+$+1).

Synthesis of 4-tert-Butyl-N-[4-chloro-2-(pyridine-3-carbonyl)-phenyl]-benzenesulfonamide

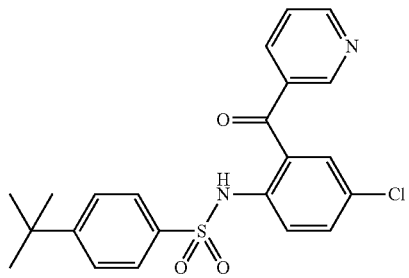 [SMILES: CC(C)(C)c1ccc(S(=O)(=O)Nc2ccc(Cl)cc2C(=O)c2cccnc2)cc1]

To (2-amino-5-chloro-phenyl)-pyridin-3-yl-methanone (150 mg, 0.64 mmol) dissolved in 750 uL pyridine was added 4-tert-butylbenzenesulfonyl chloride (225 mg, 0.97 mmol) and the mixture stirred at 60° C. overnight. The reaction mixture was diluted with 1.0 mL $H_2O$ and the precipitate formed was collected by vacuum filtration. The crude product was recrystallized from EtOAc/hexane yielding 190 mg of pure title compound. 1H NMR (CDCl3) δ 9.87 (s, 1H), 8.79 (d, J=4.8 Hz, 1H), 8.52 (s, 1H), 7.79 (d, J=8.8 Hz, 2H), 7.61 (d, J=8.8 Hz, 2H), 7.52 (dd, J=8.8 Hz, 2.4 Hz, 1H), 7.40 (dd, J=7.6 Hz, 4.8 Hz, 1H), 7.33-7.31 (m, 3H), 1.22 (s, 9H). MS: m/z=429.0 ($M^+$+1).

Synthesis of N-[4-Chloro-2-(2-methyl-pyridine-4-carbonyl)-phenyl]-4-trifluoromethoxy-benzenesulfonamide

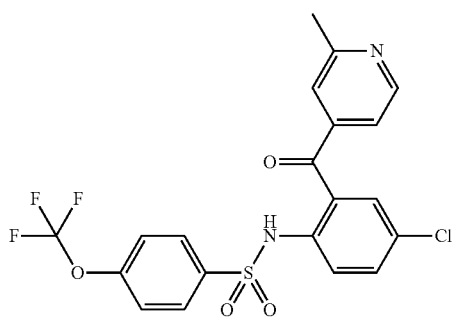 [SMILES: Cc1cc(C(=O)c2cc(Cl)ccc2NS(=O)(=O)c2ccc(OC(F)(F)F)cc2)ccn1]

The title compound was prepared according to the general procedure for the synthesis of N-Aryl-benzenesulfonamides previously described using (2-Amino-5-chloro-phenyl)-(2-methyl-pyridin-4-yl)-methanone and 4-trifluoromethoxy-benzenesulfonyl chloride and purified by HPLC. 1H NMR (CDCl3) δ 10.17 (s, 1H) 8.63 (d, J=4 Hz, 1H) 7.78 (m, 3H) 7.51 (s, 1H) 7.30 (s, 1H) 7.17 (s, 1H) 7.09 (s, 1H) 6.97 (d, J=4 Hz, 2H) 2.64 (s, 3H). MS (ES) m/z=471.0 ($M^+$+1).

Synthesis of N-[4-Chloro-2-(2-methyl-pyridine-4-carbonyl)-phenyl]-4-isopropoxy-benzenesulfonamide The title compound was prepared according to the general procedure for the synthesis of N-Aryl-benzenesulfonamides previously described using (2-Amino-5-chloro-phenyl)-(2-methyl-pyridin-4-yl)-methanone and 4-isopropoxy-benzenesulfonyl chloride and purified by HPLC. 1H NMR (CDCl3) δ 9.94 (s, 1H) 8.61 (d, J=5 Hz, 1H) 7.78 (d, J=8.8, 1H) 7.61 (d, J=8 Hz, 1H) 7.50 (dd, J=11 Hz, 2 Hz, 2H) 7.27 (d, J=2.4 Hz, 1H) 7.07 (s, 1H) 6.96 (d, J=4 Hz, 1H) 6.75 (d, J=8.8 Hz, 2H) 4.47 (m, 1H) 2.63 (s, 3H) 1.27 (s, 6H). MS (ES) m/z=445.0 ($M^+$+1).

Synthesis of 4-Acetyl-N-[4-chloro-2-(2-methyl-pyridine-4-carbonyl)-phenyl]-benzenesulfonamide

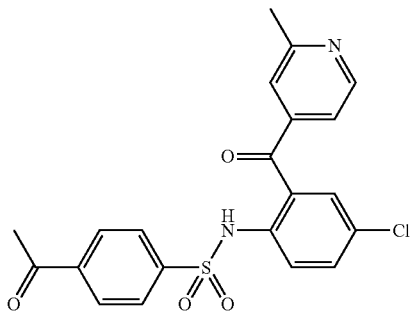 [SMILES: CC(=O)c1ccc(S(=O)(=O)Nc2ccc(Cl)cc2C(=O)c2ccnc(C)c2)cc1]

The title compound was prepared according to the general procedure for the synthesis of N-Aryl-benzenesulfonamides previously described using (2-Amino-5-chloro-phenyl)-(2-methyl-pyridin-4-yl)-methanone and 4-acetyl-benzenesulfonyl chloride and purified by HPLC. 1H NMR (CDCl3) δ 8.50 (d, J=4.8 Hz, 1H) 7.67-7.25 (m, 5H) 7.20-6.85 (m, 4H) 2.52 (s, 3H) 2.45 (s, 3H). MS: (ES) m/z=429.0 ($M^+$+1).

Synthesis of N-[4-Chloro-2-(2-methyl-pyridine-4-carbonyl)-phenyl]-4-methanesulfonyl-benzenesulfonamide

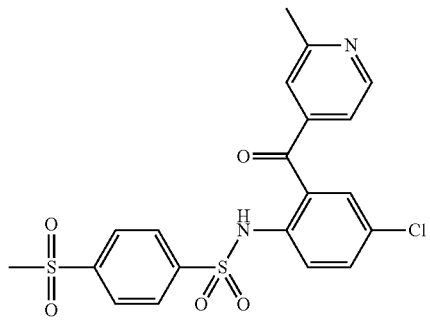 [SMILES: Cc1cc(C(=O)c2cc(Cl)ccc2NS(=O)(=O)c2ccc(S(C)(=O)=O)cc2)ccn1]

The title compound was prepared according to the general procedure for the synthesis of N-Aryl-benzenesulfonamides previously described using (2-Amino-5-chloro-phenyl)-(2-methyl-pyridin-4-yl)-methanone and 4-methanesulfonyl-benzenesulfonyl chloride and purified by HPLC. 1H NMR (CDCl3) δ 10.38 (s, 1H) 8.64 (s 1H) 7.95 (s, 4H) 7.72 (s, 1H) 7.51 (s, 1H) 7.31 (s, 1H) 7.11 (s, 1H) 6.99 (s, 1H) 3.04 (s, 3H) 2.64 (s, 3H). MS: (ES) m/z=464.9 (M⁺+1).

Synthesis of 3-{4-[4-Chloro-2-(2-methyl-pyridine-4-carbonyl)-phenylsulfamoyl]-phenyl}-propionic acid methyl ester

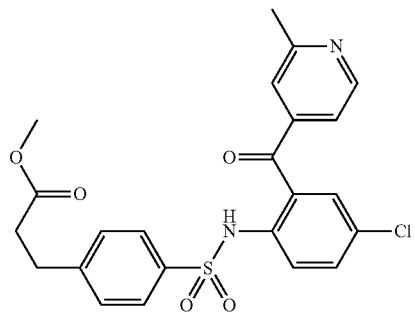 [SMILES: COC(=O)CCc1ccc(S(=O)(=O)Nc2ccc(Cl)cc2C(=O)c2ccnc(C)c2)cc1]

The title compound was prepared according to the general procedure for the synthesis of N-Aryl-benzenesulfonamides previously described using (2-Amino-5-chloro-phenyl)-(2-methyl-pyridin-4-yl)-methanone and 3-(4-chlorosulfonyl-phenyl)-propionic acid methyl ester and purified by HPLC. 1H NMR (CDCl3) δ 10.13 (s, 1H) 8.62 (d, J=4.8 Hz, 1H) 7.73 (d, J=8.8 Hz, 1H) 7.65 (d, J=8.8 Hz, 2H) 7.49 (dd, J=8.8 Hz, 2.4 Hz, 1H) 7.28 (d, J=2.4 Hz, 1H) 7.19 (d, J=12 Hz, 2H) 7.13 (s, 1H) 6.95 (d, J=4.8 Hz, 1H) 3.62 (s, 3H) 2.90 (t, J=8 Hz, 2H) 2.63 (s, 3H) 2.56 (t, J=8 Hz, 2H). MS: m/z=473.0 (M⁺+1).

Synthesis of N-[4-Chloro-2-(pyridine-4-carbonyl)-phenyl]-4-iodo-benzenesulfonamide

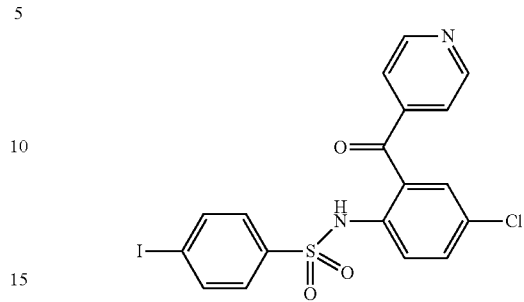

To a magnetically stirred mixture of precursor amino-ketone (2.32 g, 10.0 mmol) in dry pyridine (20 mL) was added a solution of pipsyl chloride (4.78 g, 15.8 mmol) in toluene (20 mL) under dry nitrogen. The addition was performed over a 2 h period. The reaction was stirred overnight at 50° C., then additional pipsyl chloride (850 mg), as a solution in toluene, was added. After 6 h, the reaction was concentrated and the residue was taken up in ethyl acetate. The organic layer was washed with water, then the mixture was filtered. The layers were separated and the organic layer was dried (MgSO₄), filtered and concentrated to provide crystalline material. ¹H-NMR (CDCl3) δ 9.95 (br s, 1H, NH), 8.82 (dm, 2H, J=5.2 Hz), 7.76 (d, 1H, J=8.8 Hz), 7.54 (dm, 1H, J=8.8 Hz, J=2.6 Hz), 7.41 (dm, 2H, J=8.8 Hz), 7.30 (d, 1H, J=2.6 Hz), 7.30 (d, 1H, J=2.6 Hz), 7.19 (dm, 2H, J=5.2 Hz). MS: m/z 499 (M+1).

Synthesis of N-[4-Chloro-2-(pyridine-4-carbonyl)-phenyl]-4-(2,4-dimethyl-oxazol-5-yl)-benzenesulfonamide

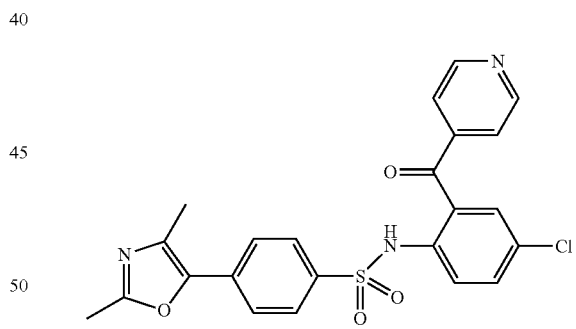

Trifluoromethanesulfonic acid (4.5 mmol) was added to a stirred solution of iodobenzene diacetate (0.39 g, 1.2 mmol) in acetonitrile (10 mL) and stirred at ambient temperature for 20 minutes. To this reaction propiophenone (1.0 mmol) was added and the reaction was refluxed for 2.5 h. After completion of the reaction, as judged by TLC, excess acetonitrile was evaporated and the crude product was extracted into dichloromethane (3×40 mL). The combined organic extracts were then washed with saturated aqueous sodium bicarbonate (2×50 mL), dried (MgSO4), filtered and concentrated to give a dark amber waxy solid. The product was purified by column chromatography on silica gel using ethyl acetate-hexane (5:95, 10:90) to furnish a crystalline solid.

2,4-dimethyl-5-phenyloxazole (53 mg, 0.31 mmol) was treated with chlorosulfonic acid (3.0 equivalents) in dry dichloromethane (8 mL) at 0° C. The solution was allowed to slowly warm to room temperature and monitored by LC/MS for complete reaction, then the reaction was washed with cold water. The organic layer was dried over magnesium sulfate, filtered and concentrated.

The residue was treated with thionyl chloride (2 equivalents) in dry dichloromethane (5 mL). The desired product was isolated by concentration of the reaction mixture to give 4-(2,4-dimethyl-oxazol-5-yl)benzenesulfonyl chloride, which was used immediately in the next step: mass spectrum m/z 272 (M+1);

To a magnetically stirred solution of the aminoketone (1.62 g, 7.0 mmol) in dry pyridine (30 mL) was added drop wise a solution of the sulfonyl chloride in 1.0 mL of dichloromethane and the slightly turbid reaction was stirred at ambient temperature. After 5 h, the reaction was diluted with ethyl acetate (25 mL) and washed with cold 3M HCl, followed by washing with aqueous NaHCO₃, then washed with water. The organic layer was dried (MgSO4), filtered and concentrated to give a pale yellow waxy solid. The product was purified by preparative hplc and pure material lyophilized to give the desired product. ¹H NMR (CDCl3) δ 8.84 (br s, 2H), 7.69 (dm, 2H, J=8.4 Hz), 7.65 (d, 1H, J=8.8 Hz), 7.46 (dm, 1H, J=2.2 Hz), 7.43 (dm, 2H, J=8.4 Hz), 7.36 (ddd, 1H, J=8.8 Hz, J=2.6 Hz, J=0.7 Hz), 7.24 (2H, obscured), 7.15 (br s, 1H), 3.19 (s, 3H), 3.13 (s, 3H). MS: m/z 468 (M+1).

Synthesis of 4-tert-Butyl-N-[4-chloro-2-(2-methyl-pyridine-3-carbonyl)-phenyl]-benzenesulfonamide

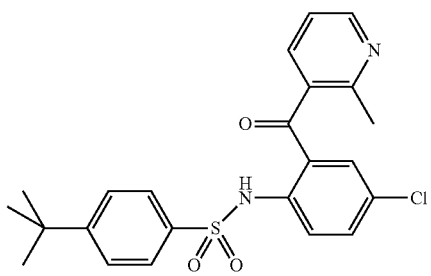 [SMILES: Cc1ncccc1C(=O)c1cc(Cl)ccc1NS(=O)(=O)c1ccc(C(C)(C)C)cc1]

The title compound was prepared according to the general procedure for the synthesis of N-Aryl-benzenesulfonamides previously described using (2-Amino-5-chloro-phenyl)-(2-methyl-pyridin-3-yl)-methanone (243 mg, 1.0 mmol) and 4-tert-Butyl-benzenesulfonyl chloride (232 mg, 1.0 mmol) and purified by HPLC. ¹H NMR (CDCl3) δ 10.71 (br s, 1H, NH), 8.63 (dd, 1H, J=5.1 Hz, J=1.6 Hz), 7.83 (d, 1H, J=8.8 Hz), 7.73 (dm, 2H, J=8.4 Hz), 7.49 (dd, 1H, J=8.8 Hz, J=2.6 Hz), 7.43 (dm, 2H, J=8.5 Hz), 7.27 (dd, 1H, J=9.5 Hz, J=1.8 Hz), 7.18 (dd, 1H, J=7.7 Hz, J=4.8 Hz), 7.13 (d, 1H, J=2.6 Hz), 2.29 (s, 3H), 1.29 (s, 9H). MS: m/z 443 (M+1).

Synthesis of N-[4-Chloro-2-(2-methyl-pyridine-3-carbonyl)-phenyl]-4-isopropoxy-benzenesulfonamide

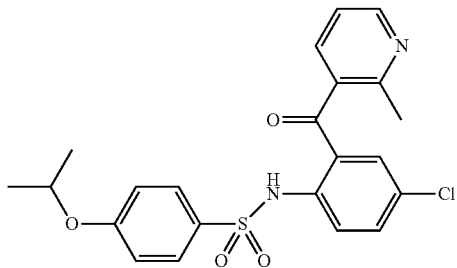 [SMILES: Cc1ncccc1C(=O)c1cc(Cl)ccc1NS(=O)(=O)c1ccc(OC(C)C)cc1]

The title compound was prepared according to the general procedure for the synthesis of N-Aryl-benzenesulfonamides previously described using (2-amino-5-chloro-phenyl)-(2-methyl-pyridin-3-yl)-methanone and 4-isopropoxy-benzenesulfonyl chloride and purified by HPLC. ¹H NMR (CDCl3) δ 10.63 (br s, 1H, NH), 8.63 (dd, 1H, J=4.8 Hz, J=1.8 Hz), 7.79 (d, 1H, J=8.8 Hz), 7.71 (d, 1H, J=8.8 Hz), 7.48 (dd, 1H, J=9.0 Hz, J=2.2 Hz), 7.27 (dd, 1H, J=7.7 Hz, J=1.8 Hz), 7.19 (dd, 1H, J=7.7 Hz, J=4.8 Hz), 7.14 (d, 1H, J=2.2 Hz), 4.55 (septet, 1H, J=6 Hz), 2.35 (s, 3H), 1.35 (d, 3H, J=6 Hz). MS: m/z 445 (M+1).

Synthesis of N-[4-Chloro-2-(2-methyl-pyridine-3-carbonyl)-phenyl]-4-trifluoromethoxy-benzenesulfonamide

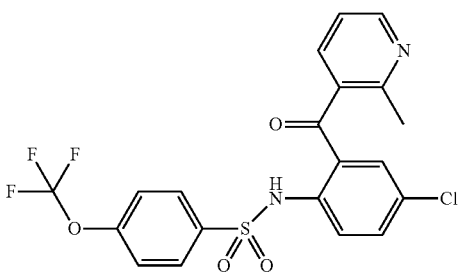 [SMILES: Cc1ncccc1C(=O)c1cc(Cl)ccc1NS(=O)(=O)c1ccc(OC(F)(F)F)cc1]

The title compound was prepared according to the general procedure for the synthesis of N-Aryl-benzenesulfonamides previously described using (2 amino-5-chloro-phenyl)-(2-methyl-pyridin-3-yl)-methanone and 4-trifluoromethoxy-benzenesulfonyl chloride and purified by HPLC.

¹H NMR (CDCl3) δ 10.76 (br s, 1H, NH), 8.65 (dd, 1H, J=4.8 Hz, J=2.0 Hz), 7.88 (dm, 2H, J=8.8 Hz), 7.80 (d, H1, J=9.2 Hz), 7.52 (dd, 1H, J=9.0 Hz, J=2.2 Hz), 7.1-7.3 (m, 4H), 7.18 (d, 1H, J=2.6 Hz), 2.35 (s, 3H). MS: m/z 471 (M+1).

Synthesis of 4-Acetyl-N-[4-chloro-2-(2-methyl-pyridine-3-carbonyl)-phenyl]-benzenesulfonamide

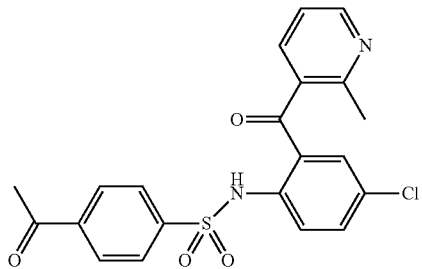 [SMILES: CC(=O)c1ccc(S(=O)(=O)Nc2ccc(Cl)cc2C(=O)c2cccnc2C)cc1]

The title compound was prepared according to the general procedure for the synthesis of N-Aryl-benzenesulfonamides previously described using (2 amino-5-chloro-phenyl)-(2-methyl-pyridin-3-yl)-methanone and 4-acetyl-benzenesulfonyl chloride and purified by HPLC. $^1$H NMR (CDCl3) δ 10.79 (br s, 1H, NH), 8.65 (dd, 1H, J=4.8 Hz, J=1.8 Hz), 7.98 (d, 2H, J=8.8 Hz), 7.92 (d, 2H, J=8.8 Hz), 7.79 (d, 1H, J=9.2 Hz), 7.50 (dd, 1H, J=9.0 Hz, J=2.2 Hz), 7.22 (dd, 1H, J=7.7 Hz, J=1.5 Hz), 7.16 (m, 2H), 2.60 (s, 3H), 2.36 (s, 3H). MS: m/z 429 (M+1).

Synthesis of N-[4-Chloro-2-(2-methyl-pyridine-3-carbonyl)-phenyl]-4-methanesulfonyl-benzenesulfonamide

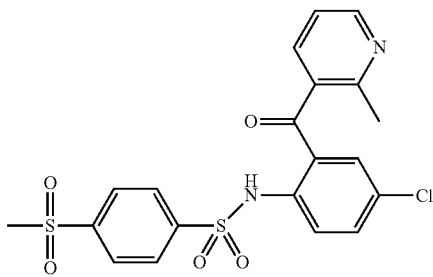 [SMILES: Cc1ncccc1C(=O)c1cc(Cl)ccc1NS(=O)(=O)c1ccc(S(C)(=O)=O)cc1]

The title compound was prepared according to the general procedure for the synthesis of N-Aryl-benzenesulfonamides previously described using (2 amino-5-chloro-phenyl)-(2-methyl-pyridin-3-yl)-methanone and 4-methanesulfonyll-benzenesulfonyl chloride and purified by HPLC. $^1$H NMR (CDCl3) δ 10.86 (br s, 1, NH), 8.65 (dd, 1H, J=4.8 Hz, J=1.8 Hz), 8.02 (m, 4H), 7.78 (d, 1H, J=8.8 Hz), 7.53 (dd, 1H, J=8.8 Hz, J=2.6 Hz), 7.1-7.3 (m, 3H), 3.07 (s, 3H), 2.41 (s, 3H). MS: m/z 465 (M+1).

Synthesis of 3-{4-[4-Chloro-2-(2-methyl-pyridine-3-carbonyl)-phenylsulfamoyl]-phenyl}-propionic acid methyl ester

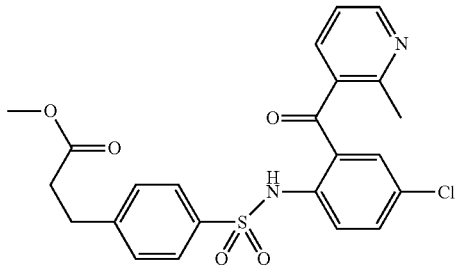 [SMILES: COC(=O)CCc1ccc(S(=O)(=O)Nc2ccc(Cl)cc2C(=O)c2cccnc2C)cc1]

The title compound was prepared according to the general procedure for the synthesis of N-Aryl-benzenesulfonamides previously described using (2 amino-5-chloro-phenyl)-(2-methyl-pyridin-3-yl)-methanone and 3-(4-Chlorosulfonyl-phenyl)-propionic acid methyl ester and purified by HPLC. $^1$H-NMR (CDCl3) δ 10.75 (br s, 1H, NH), 8.64 (dm, 1H, J=4.8 Hz), 7.79 (dd, 1H, J=9.2 Hz, J=1.1 Hz), 7.75 (d, 2H, J=7.3 Hz), 7.49 (dm, 1H, J=9.2 Hz), 7.1-7.3 (m, 5H), 3.65 (s, 3H), 2.97 (t, 2H, J=7.6 Hz), 2.61 (t, 2H, J=7.6 Hz), 2.35 (s, 3H). MS: m/z 473 (M+1).

Synthesis of 4-tert-Butyl-N-[4-chloro-2-(6-methyl-pyridine-3-carbonyl)-phenyl]-benzenesulfonamide

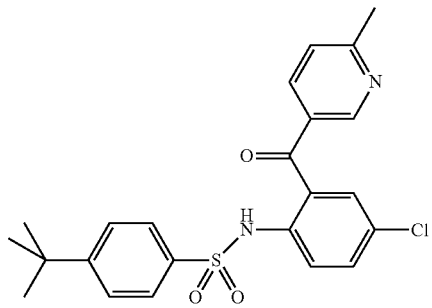 [SMILES: Cc1ccc(C(=O)c2cc(Cl)ccc2NS(=O)(=O)c2ccc(C(C)(C)C)cc2)cn1]

The title compound was prepared according to the general procedure for the synthesis of N-Aryl-benzenesulfonamides previously described using (2-Amino-5-chloro-phenyl)-(6-methyl-pyridin-3-yl)-methanone and 4-tert-butyl-benzenesulfonyl chloride and purified by HPLC. $^1$H NMR (CDCl$_3$) δ 9.77 (br s, 1H, NH), 8.40 (dm, 1H, J=1.8 Hz), 7.77 (dm, 1H, J=8.6 Hz), 7.71 (dd, 1H, J=8.1 Hz, J=2.2 Hz), 7.58 (dm, 2H, J=8.6 Hz), 7.50 (dd, 1H, J=9.0 Hz, J=2.4 Hz), 7.32 (d, 1H, J=2.2 Hz), 7.29 (dm, 2H, J=8.6 Hz), 7.23 (d, 1H, J=8.1 Hz), 2.63 (s, 3H), 1.20 (s, 9H). MS: m/z 443 (M+1).

Synthesis of N-[4-Chloro-2-(6-methyl-pyridine-3-carbonyl)-phenyl]-4-trifluoromethoxy-benzenesulfonamide

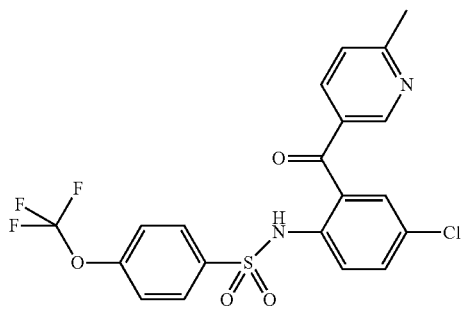 [SMILES: Cc1ccc(C(=O)c2cc(Cl)ccc2NS(=O)(=O)c2ccc(OC(F)(F)F)cc2)cn1]

The title compound was prepared according to the general procedure for the synthesis of N-Aryl-benzenesulfonamides previously described using (2-Amino-5-chloro-phenyl)-(6-methyl-pyridin-3-yl)-methanone and 4-trifluoromethyl-benzenesulfonyl chloride and purified by HPLC. $^1$H-NMR (CDCl3) δ 9.76 (br s, 1, NH), 8.50 (d, 1H, J=2.2 Hz), 7.76 (d, 1H, J=8.8), 7.73 (d, 2H, J=9.2), 7.66 (dd, 1H, J=8.0, J=2.2), 7.54 (ddm, 1H, J=8.8 Hz, J=2.6 Hz), 7.37 (d, 1H, J=2.6), 7.24 (d, 1H, J=6 Hz), 7.10 (d, 2H, J=8.8 Hz), 2.35 (s, 3). MS: m/z 471 (M+1).

Synthesis of N-[4-Chloro-2-(6-methyl-pyridine-3-carbonyl)-phenyl]-4-isopropoxy-benzenesulfonamide

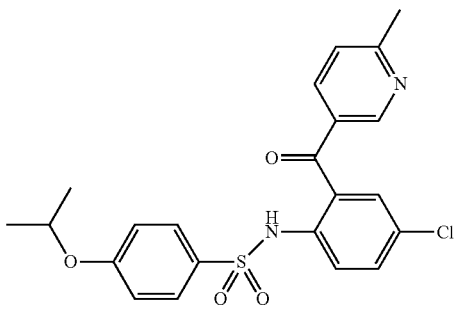 [SMILES: Cc1ccc(C(=O)c2cc(Cl)ccc2NS(=O)(=O)c2ccc(OC(C)C)cc2)cn1]

The title compound was prepared according to the general procedure for the synthesis of N-Aryl-benzenesulfonamides previously described using (2-Amino-5-chloro-phenyl)-(6-methyl-pyridin-3-yl)-methanone and 4-isopropoxy-benzenesulfonyl chloride and purified by HPLC. $^1$H NMR (CDCl$_3$) δ 9.67 (br s, 1H, NH), 8.45 (d, 1H, J=1.8 Hz), 7.75 (d, 1H, J=8.8 Hz), 7.68 (dd, 1H, J=8.0 Hz, J=2.2 Hz), 7.55 (d, 2H, J=9.0 Hz), 7.50 (dd, 1H, J=8.8 Hz, J=2.6 Hz), 7.32 (d, 1H, J=2.6 Hz), 7.24 (d, 1H, J=8.0 Hz), 6.68 (d, 2H, J=9.0 Hz), 4.43 (septet, 1H, J=6 Hz), 2.65 (s, 3H), 1.28 (d, 3H, J=6 Hz). MS: m/z 445 (M+1).

Synthesis of 4-Acetyl-N-[4-chloro-2-(6-methyl-pyridine-3-carbonyl)-phenyl]-benzenesulfonamide

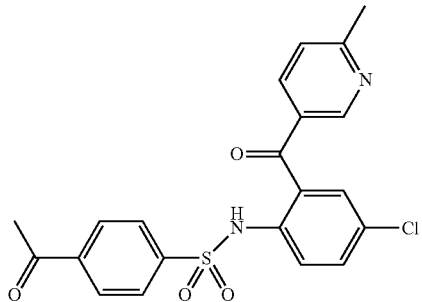 [SMILES: CC(=O)c1ccc(S(=O)(=O)Nc2ccc(Cl)cc2C(=O)c2ccc(C)nc2)cc1]

The title compound was prepared according to the general procedure for the synthesis of N-Aryl-benzenesulfonamides previously described using (2-Amino-5-chloro-phenyl)-(6-methyl-pyridin-3-yl)-methanone and 4-acetyl-benzenesulfonyl chloride and purified by HPLC. $^1$H NMR (CDCl$_3$) δ 9.54 (br s, 1, NH), 8.30 (m, 1), 7.77 (d, 2, J=8.8 Hz), 7.71 (d, 2, J=8.8 Hz), 7.69 (m, 1), 7.54 (dd, 1, J=8.8 Hz, J=2.2 Hz), 7.33 (d, 1, J=2.2 Hz), 7.26 (m, 1), 7.21 (d, 1, J=8.0 Hz), 2.63 (s, 3), 2.52 (s, 3). MS: m/z 429 (M+1).

Synthesis of N-[4-Chloro-2-(6-methyl-pyridine-3-carbonyl)-phenyl]-4-methanesulfonyl-benzenesulfonamide

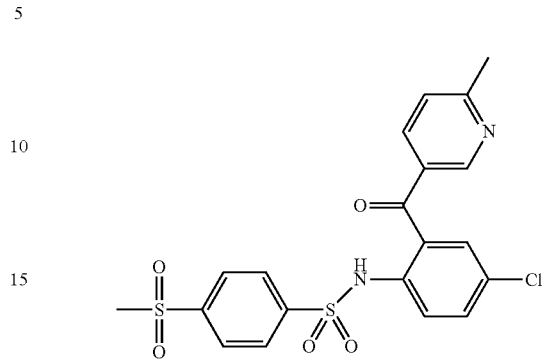

The title compound was prepared according to the general procedure for the synthesis of N-Aryl-benzenesulfonamides previously described using (2-Amino-5-chloro-phenyl)-(6-methyl-pyridin-3-yl)-methanone and 4-Methanesulfonyl-benzenesulfonyl chloride and purified by HPLC. $^1$H NMR (CDCl$_3$) δ 9.77 (br s, 1H, NH), 8.44 (dm, 1H, J=2.2 Hz), 7.87 (d, 2H, J=8.8 Hz), 7.83 (d, 2H, J=8.8 Hz), 7.76 (d, 1H, J=8.8 Hz), 7.60 (dd, 1H, J=8.0 Hz, J=2.2 Hz), 7.55 (dd, 1H, J=8.8 Hz, J=2.2 Hz), 7.36 (d, 1H, J=2.2), 7.26 (d, 1H, J=8.0 Hz), 3.00 (s, 3H), 2.66 (s, 3H). MS: m/z 465 (M+1).

Synthesis of 3-{4-[4-Chloro-2-(6-methyl-pyridine-3-carbonyl)-phenylsulfamoyl]-phenyl}-propionic acid methyl ester

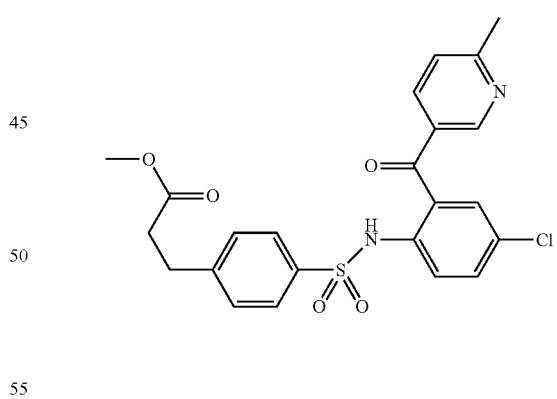

The title compound was prepared according to the general procedure for the synthesis of N-Aryl-benzenesulfonamides previously described using (2-Amino-5-chloro-phenyl)-(6-methyl-pyridin-3-yl)-methanone and 3-(4-Chlorosulfonyl-phenyl)-propionic acid methyl ester and purified by HPLC. $^1$H NMR (CDCl3) δ 9.66 (br s, 1H, NH), 8.34 (d, 1H, J=2.2 Hz), 7.75 (d, 1H, J=8.8 Hz), 7.72 (d, 1H, J=8.0 Hz, J=2.2 Hz), 7.56 (d, 2H, J=8.4 Hz), 7.51 (dd, 1H, J=8.8 Hz, J=2.2 Hz), 7.32 (d 1H, J=2.2 Hz), 7.26 (d, 1H, J=7 Hz), 7.09 (d, 2H, J=8.4 Hz), 3.65 (s, 3H), 2.97 (t, 2H, J=7.6 Hz), 2.66 (s, 3H), 2.51 (t, 2H, J=7.6 Hz). MS: m/z 473 (M+1).

187

Synthesis of 4-tert-Butyl-N-[4-chloro-2-(1-methyl-[1,2,3]triazole-4-carbonyl)-phenyl]-benzenesulfonamide

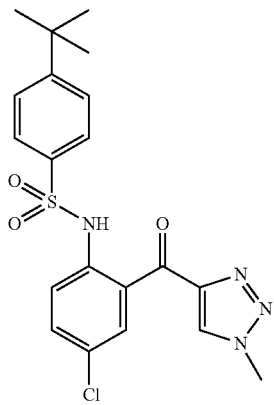 [SMILES: Cn1cc(C(=O)c2cc(Cl)ccc2NS(=O)(=O)c2ccc(C(C)(C)C)cc2)nn1]

Following the general procedure for synthesis of N-aryl-benzenesulfonamides, 28 mg (0.12 mmol) of (2-Amino-5-chloro-phenyl)-(1-methyl-[1,2,3]triazol-4-yl) methanone and 56 mg (0.24 mmol) of 4-tert-butylphenylsulfonyl chloride were combined in 0.5 ml of anhydrous pyridine at 60° C. to give, after purification, the title product as a pale yellow solid: $^1$H NMR CD$_3$OD δ (ppm): 1.21 (s, 9H), 4.25 (s, 3H), 7.38 (d, 2H), 7.53 (d, 2H), 7.54-7.63 (m, 2H), 8.11 (s, 1H), 8.22 (d, 1H); MS: (M+H)/z=433.1.

Synthesis of 4-tert-Butyl-N-[4-chloro-2-(3-methyl-[1,2,3]triazole-4-carbonyl)-phenyl]-benzenesulfonamide

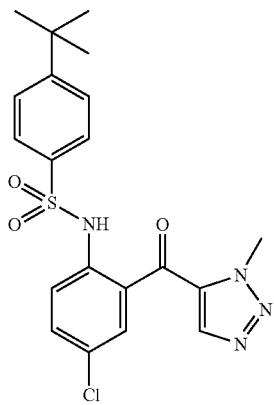 [SMILES: Cn1nncc1C(=O)c1cc(Cl)ccc1NS(=O)(=O)c1ccc(C(C)(C)C)cc1]

Following the general procedure for synthesis of N-aryl-benzenesulfonamides, 28 mg (0.12 mmol) of (2-Amino-5-chloro-phenyl)-(3-methyl-[1,2,3]triazol-4-yl) methanone and 56 mg (0.24 mmol) of 4-tert-butylphenylsulfonyl chloride were combined in 0.5 ml of anhydrous pyridine at 60° C. to give, after purification, the title product as a pale yellow solid: $^1$H NMR CD$_3$OD δ (ppm): 1.20 (s, 9H), 4.15 (s, 3H), 7.37 (d, 2H), 7.52 (d, 2H), 7.59-7.62 (m, 2H), 8.27 (d, 1H), 8.53 (s, 1H); MS: (M+H)/z=433.0.

188

Synthesis of N-[4-Chloro-2-(pyridine-4-carbonyl)-phenyl]-4-(1-methylenyl-[1H]-3-methyl-5-trifluoromethyl-oxazolyl)-benzenesulfonamide

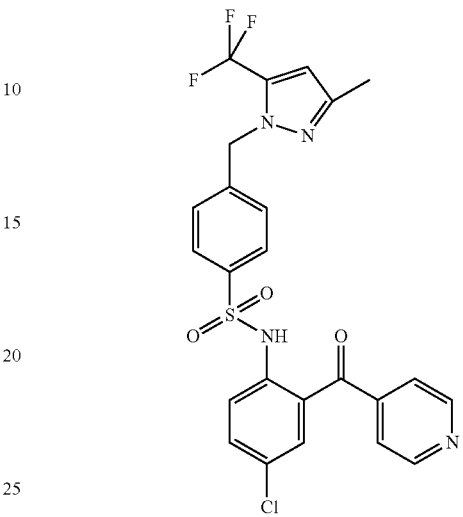

Title compound was prepared according to the standard general procedures. $^1$H NMR (400 MHz, CDCl$_3$); 10.277 (s, 1H), 8.79-8.85 (m, 2H), 7.76-7.79 (m, 3H), 7.53-7.55 (m, 1H), 7.36-7.37 (m, 1H), 7.23-7.33 (m, 2H), 7.08-7.1 (d, 2H), 6.38 (s, 1H), 5.26-5.3 (d, 2H), 2.2 (s, 3H). MS (ES) (M+H) expected 534.95 found 534.8.

Synthesis of N-[4-Chloro-2-(pyridine-4-carbonyl)-phenyl]-4-(1-methylenyl-[1H]-oxazolyl)-benzenesulfonamide

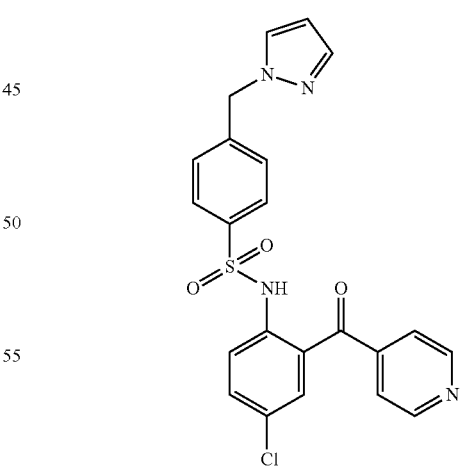

Title compound was prepared according to the standard general procedures. $^1$H NMR (400 MHz, CDCl$_3$); 9.07 (s, 1H), 8.79-8.84 (m, 2H), 7.71-7.78 (m, 3H), 7.53-7.55 (m, 1H), 7.36-7.37 (m, 2H), 7.23-7.33 (m, 2H), 7.08-7.1 (d, 2H), 6.38 (s, 1H), 5.26-5.3 (d, 2H). MS (ES) (M+H) expected 452.92 found 452.

Synthesis of N-[4-Chloro-2-(pyridine-4-carbonyl)-phenyl]-4-(1-methyl-1-oxazol-4-yl-ethyl)-benzenesulfonamide

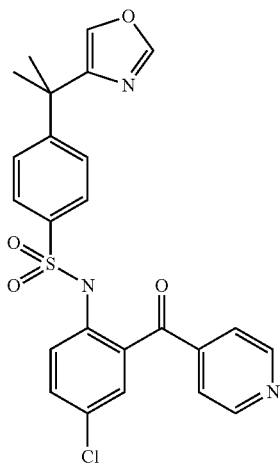 [SMILES: CC(C)(c1ccc(S(=O)(=O)Nc2ccc(Cl)cc2C(=O)c2ccncc2)cc1)c1cocn1]

Following the general procedure for synthesis of N-aryl-benzenesulfonamides, 73 mg (0.32 mmol) of (2-Amino-5-chloro-phenyl)-pyridin-4-yl-methanone and 36 mg (0.13 mmol) of 4-(1-Methyl-1-oxazol-4-yl-ethyl)-benzenesulfonyl chloride were combined in 1 ml of anhydrous pyridine at 60° C. to give, after purification, the title product as a pale yellow solid: $^1$H NMR (CDCl$_3$): δ (ppm): 1.61 (s, 6H), 7.26-7.66 (m, 12H), 8.90 (br, 1H), 10.13 (br, 1H) ppm; MS: (M+H)/z=482.0.

Synthesis of N-[4-Chloro-2-(6-methyl-pyridine-3-carbonyl)-phenyl]-4-(1-methyl-1-oxazol-4-yl-ethyl)-benzenesulfonamide

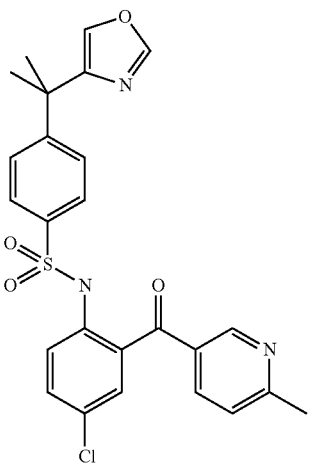 [SMILES: Cc1ccc(C(=O)c2cc(Cl)ccc2NS(=O)(=O)c2ccc(C(C)(C)c3cocn3)cc2)cn1]

Following the general procedure for synthesis of N-aryl-benzenesulfonamides, 63 mg (0.26 mmol) of (2-Amino-5-chloro-phenyl)-(6-methyl-pyridin-3-yl)-methanone and 50 mg (0.17 mmol) of 4-(1-Methyl-1-oxazol-4-yl-ethyl)-benzenesulfonyl chloride were combined in 0.8 ml of anhydrous pyridine at 60° C. to give, after purification, the title product as a pale yellow solid: $^1$H NMR (CDCl$_3$): δ (ppm): 1.54 (s, 6H), 2.63 (s, 3H), 7.22-7.30 (m, 2H), 7.32 (m, 2H), 7.55 (m, 1H), 7.61-7.63 (m, 2H), 7.70-7.80 (m, 3H), 8.49 (d, 1H), 9.95 (s, 1H); MS: (M+H)/z=496.0.

Synthesis of N-[4-Chloro-2-(pyridine-4-carbonyl)phenyl]-4-(2-oxazol-2-ylethyl)benzenesulfonamide

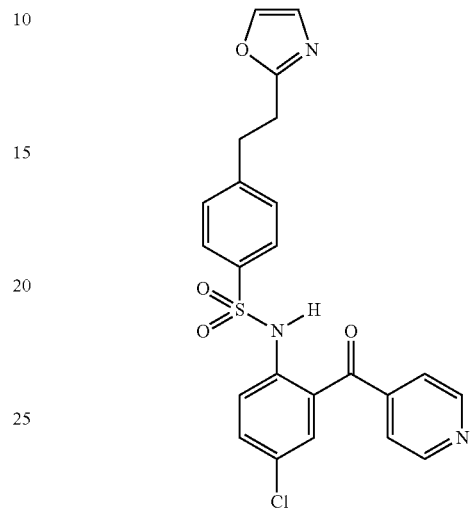

The title compound was prepared according to the general procedure for the synthesis of N-Aryl-benzenesulfonamides previously described and purified by HPLC. $^1$H NMR: δ (400 MHz, CDCl$_3$) 10.07 (s, 1H), 8.75 (m, 2H), 7.73 (d, 2H), 7.63 (d, 2H), 7.50 (s, 1H), 7.28 (d, 1H), 7.22 (m, 2H), 7.15 (d, 2H), 6.96 (s, 1H), 3.02 (m, 4H). MS (M+H$^+$): 468.0

Synthesis of N-[4-Chloro-2-(pyridine-4-carbonyl)phenyl]-4-(1-methyl-1-oxazol-5-ylethyl)-benzenesulfonamide

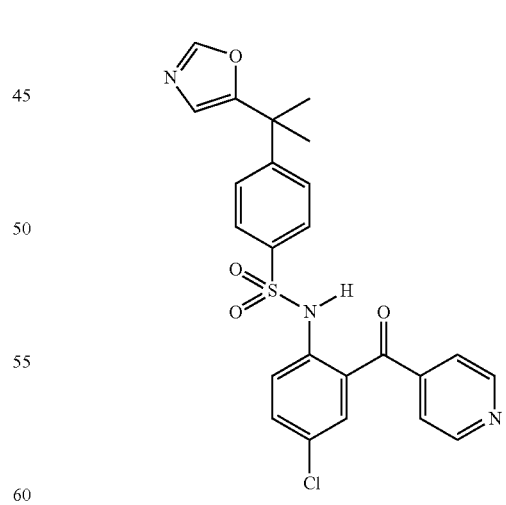

The title compound was prepared according to the general procedure for the synthesis of N-Aryl-benzenesulfonamides previously described and purified by HPLC. $^1$H NMR: δ (400 MHz, CDCl$_3$) 10.16 (s, 1H), 8.77 (d, 2H), 7.73 (d, 2H), 7.67 (d, 2H), 7.51 (dd, 1H), 7.29 (d, 1H), 7.23 (m, 2H), 7.22 (m, 2H), 6.84 (s, 1H), 1.60 (s, 6H). MS (M+H$^+$): 482.0

Synthesis of N-[4-Chloro-2-(6-methylpyridine-3-carbonyl)phenyl]-4-(1-methyl-1-oxazol-5-ylethyl)-benzenesulfonamide

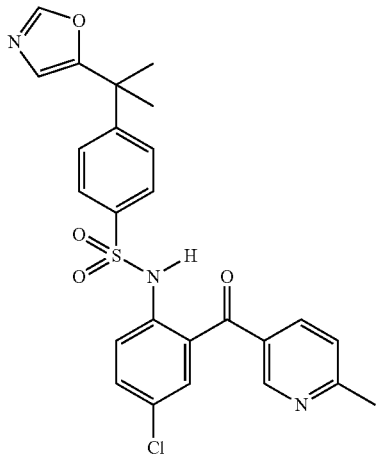 [SMILES: Cc1ccc(C(=O)c2cc(Cl)ccc2NS(=O)(=O)c2ccc(C(C)(C)c3cnco3)cc2)cn1]

The title compound was prepared according to the general procedure for the synthesis of N-Aryl-benzenesulfonamides previously described and purified by HPLC. $^1$H NMR: δ (400 MHz, CDCl$_3$) 9.67 (s, 1H), 8.77 (d, 1H), 8.35 (dd, 1H), 8.03 (s, 1H), 7.67 (m, 3H), 7.51 (s, 2H), 7.45 (s, 1H), 7.29 (d, 2H), 6.94 (s, 1H), 2.87 (s, 3H), 1.66 (s, 6H). MS (M+H$^+$): 496.0

Synthesis of N-[4-Bromo-2-(pyridine-4-carbonyl)-phenyl]-4-oxazol-5-yl-benzenesulfonamide

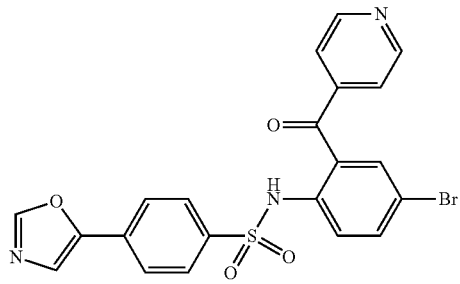 [SMILES: O=C(c1ccncc1)c1cc(Br)ccc1NS(=O)(=O)c1ccc(-c2cnco2)cc1]

The title compound was prepared according the general procedure for the synthesis of N-aryl-benzenesulfonamides using (2-Amino-5-bromo-phenyl)-pyridin-4-yl-methanone and 4-oxazol-5-yl-benzenesulfonyl chloride and purified by HPLC. MS: m/z 485 (M$^+$+1).

Synthesis of N-[4-bromo-2-(pyridine-4-carbonyl)-phenyl]-4-isopropyl-benzenesulfonamide

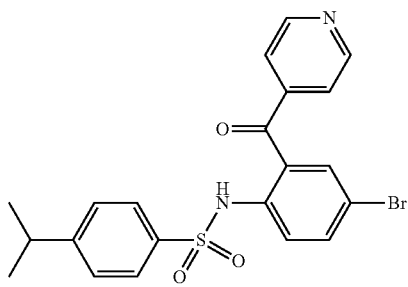 [SMILES: CC(C)c1ccc(S(=O)(=O)Nc2ccc(Br)cc2C(=O)c2ccncc2)cc1]

The title compound was prepared according the general procedure for the synthesis of N-aryl-benzenesulfonamides using 4-isopropyl-benzenesulfonyl chloride and (2-amino-5-bromo-phenyl)-pyridin-4-yl-methanone and purified by HPLC. MS: m/z 460 (M$^+$+1).

Synthesis of N-[4-Chloro-2-(2-methyl-pyridine-3-carbonyl)-phenyl]-4-oxazol-5-yl-benzenesulfonamide

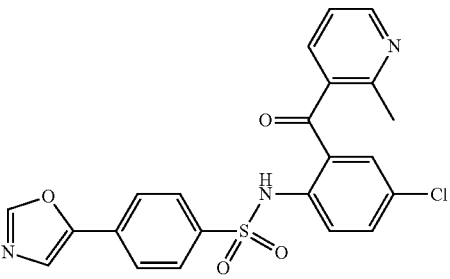 [SMILES: Cc1ncccc1C(=O)c1cc(Cl)ccc1NS(=O)(=O)c1ccc(-c2cnco2)cc1]

The title compound was prepared according to the general procedure using (2-amino-5-chloro-phenyl)-(2-methyl-pyridin-3-yl)-methanone and 4-oxazol-5-yl-benzenesulfonyl chloride and purified by HPLC. MS: m/z 454 (M$^+$+1).

Synthesis of N-[4-cloro-2-(6-methyl-pyridine-3-carbonyl)-phenyl]-4-(2-methyl-oxazol-5-yl)-benzenesulfonamide

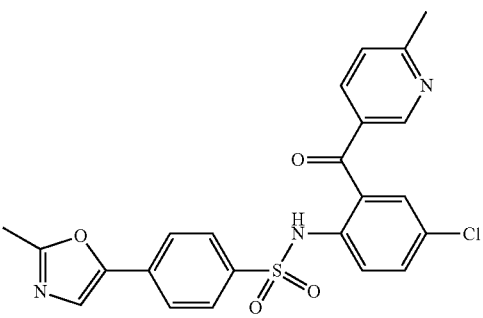 [SMILES: Cc1ccc(C(=O)c2cc(Cl)ccc2NS(=O)(=O)c2ccc(-c3cnc(C)o3)cc2)cn1]

The title compound was prepared according to the general procedure for the preparation of N-aryl-benzenesulfonamides using 4-(2-methyl-oxazol-5-yl)-benzenesulfonyl chloride and (2-amino-5-chloro-phenyl)-(6-methyl-pyridin-3-yl)-methanone and purified by HPLC. MS: m/z 468.0 (M$^+$+1).

Synthesis N-[4-Chloro-2-(6-methyl-pyridine-2-carbonyl)-phenyl]-4-(2-methyl-oxazol-5-yl)-benzenesulfonamide

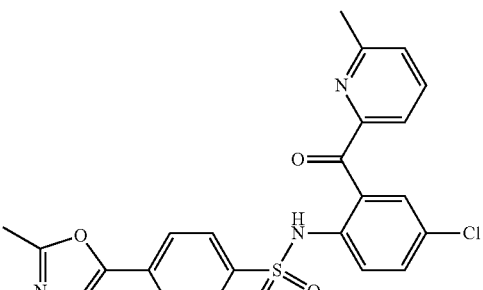

The title compound was prepared according to the general procedure for the preparation of N-aryl-benzenesulfonamides using 4-(2-methyl-oxazol-5-yl)-benzenesulfonyl chloride and (2-Amino-5-chloro-phenyl)-(6-methyl-pyridin-2-yl)-methanone and purified by HPLC. MS: m/z 468.0 (M$^+$+1).

Synthesis of 4-tert-Butyl-N-[4-chloro-2-(1-methyl-1H-indazole-3-carbonyl)-phenyl]-benzenesulfonamide

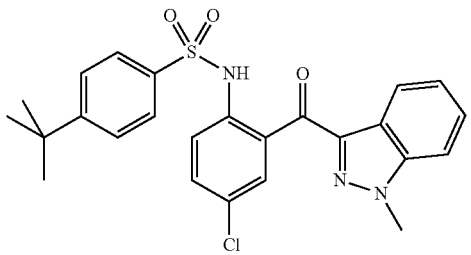 [SMILES: Cn1nc(C(=O)c2cc(Cl)ccc2NS(=O)(=O)c2ccc(C(C)(C)C)cc2)c2ccccc21]

The title compound was prepared according to the general procedure for the preparation of N-aryl-benzenesulfonamides using 4-tert-butyl-benzenesulfonyl chloride and (2-Amino-5-chloro-phenyl)-(1-methyl-1H-indazol-3-yl)-methanone and purified by HPLC: MS: m/z 483 (M$^+$+1).

Synthesis of N-[4-Chloro-2-(6-methyl-pyridine-3-carbonyl)-phenyl]-4-(4-methyl-oxazol-5-yl)-benzenesulfonamide

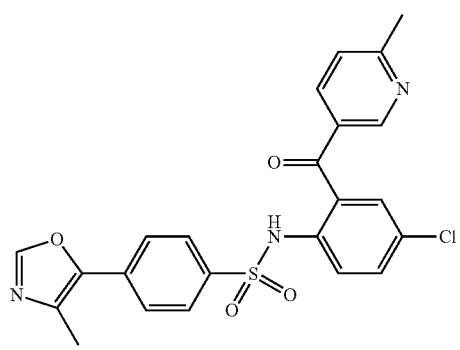 [SMILES: Cc1ccc(C(=O)c2cc(Cl)ccc2NS(=O)(=O)c2ccc(-c3ocnc3C)cc2)cn1]

The title compound was prepared according to the general procedure for the preparation of N-aryl-benzenesulfonamides using by the reaction of 4-(4-methyl-oxazol-5-yl)-benzenesulfonyl chloride with (2-amino-5-chloro-phenyl)-(6-methyl-pyridin-3-yl)-methanone and purified by HPLC: MS: m/z 468.0 (M$^+$+1).

Synthesis of N-[4-Chloro-2-(4-methyl-pyridine-3-carbonyl)-phenyl]-4-oxazol-5-yl-benzenesulfonamide

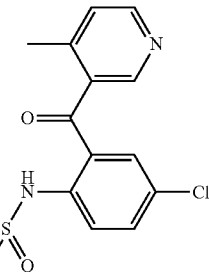

The title compound was prepared using 4-oxazol-5-yl-benzenesulfonyl chloride and (2-amino-5-chloro-phenyl)-(4-methyl-pyridin-3-yl)-methanone according to the general procedure for the preparation of the N-aryl-benzenesulfonamides.
MS: m/z 454.0 (M$^+$+1).

Synthesis of 4-tert-Butyl-N-[4-chloro-2-(1-methyl-1H-imidazole-2-carbonyl)-phenyl]-benzenesulfonamide

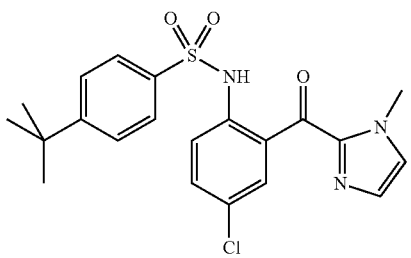 [SMILES: Cn1ccnc1C(=O)c1cc(Cl)ccc1NS(=O)(=O)c1ccc(C(C)(C)C)cc1]

The title compound was prepared using 4-t-butyl-benzenesulfonyl chloride and (2-Amino-5-chloro-phenyl)-(1-methyl-1H-imidazol-2-yl)-methanone following the general procedure described for the preparation of N-aryl-benzenesulfonamides. MS: m/z 452.1 (M$^+$+1).

Synthesis of N-[4-Chloro-2-(pyridine-4-carbonyl)-phenyl]-4-isopropylsulfanyl-benzenesulfonamide

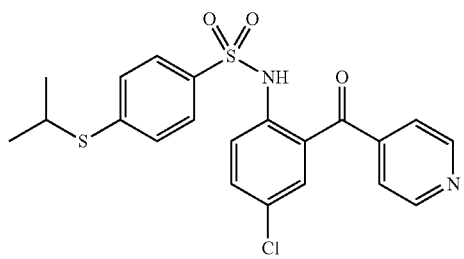 [SMILES: CC(C)Sc1ccc(S(=O)(=O)Nc2ccc(Cl)cc2C(=O)c2ccncc2)cc1]

The intermediate 4-isopropylsulfanyl-benzenesulfonyl chloride, which was prepared from isopropylsulfanyl-benzene following general chlorosulfonylation procedure, was reacted with (2-Amino-5-chloro-phenyl)-pyridin-4-yl-methanone to yield the title compound. MS: m/z 447.0 (M⁺+1).

Synthesis of 4-tert-butyl-N-[4-chloro-2-(thiazole-2-carbonyl)-phenyl]benzenesulfonamide

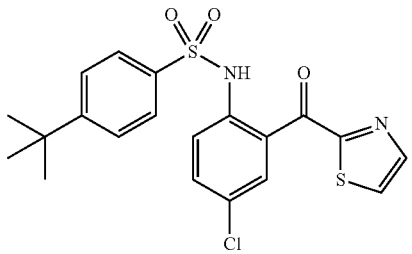 [SMILES: CC(C)(C)c1ccc(S(=O)(=O)Nc2ccc(Cl)cc2C(=O)c2nccs2)cc1]

The title compound was prepared by the reaction of 4-t-butylbenzenesulfonyl chloride with (2-Amino-5-chloro-phenyl)-thiazol-2-yl-methanone following the general procedure. MS: m/z 435.0 (M⁺+1).

Synthesis of 4-tert-Butyl-N-[4-chloro-2-(1H-pyrazole-3-carbonyl)-phenyl]-benzenesulfonamide

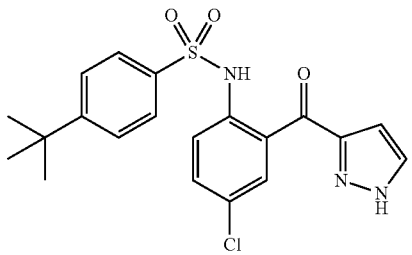 [SMILES: CC(C)(C)c1ccc(S(=O)(=O)Nc2ccc(Cl)cc2C(=O)c2cc[nH]n2)cc1]

The title compound was prepared by the reaction of 4-t-butylbenzenesulfonyl chloride with (2-Amino-5-chloro-phenyl)-(1H-pyrazol-3-yl)-methanone following the general procedure. MS: m/z 418.1 (M⁺+1). Remove this example—same as [0676 below]

Synthesis of N-[4-Chloro-2-(pyridine-2-carbonyl)-phenyl]-4-methoxy-benzenesulfonamide

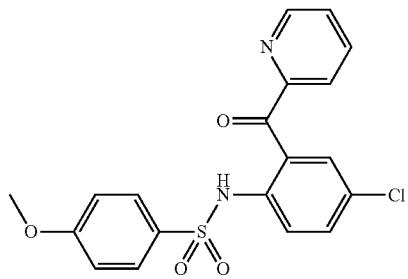 [SMILES: COc1ccc(S(=O)(=O)Nc2ccc(Cl)cc2C(=O)c2ccccn2)cc1]

The title compound was prepared according to the general procedure for the synthesis of N-Aryl-benzenesulfonamides previously described using 116 mg of (2-Amino-5-chloro-phenyl)-pyridin-2-yl-methanone and 101 mg of 4-methoxy-benzenesulfonyl chloride. ¹H-NMR (400 MHz, CDCl₃): δ 3.75 (s, 3H), 6.76 (m, 2H, 7.45 (m, 2H), 7.63 (m, 2H), 7.71 (d, 1H, J=8.8 Hz), 7.78 (m, 1H), 7.88 (m, 2H), 8.64 (m, 1H), 10.24 (s, 1H). MS: m/z 403.9 (M⁺+1).

Synthesis of 4-tert-Butyl-N-[3,4-difluoro-2-(pyridine-3-carbonyl)-phenyl]-benzenesulfonamide

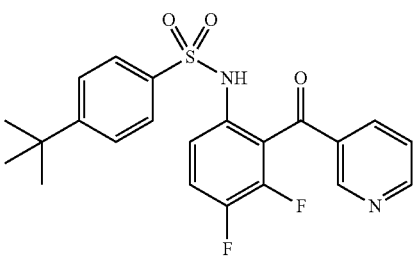 [SMILES: CC(C)(C)c1ccc(S(=O)(=O)Nc2ccc(F)c(F)c2C(=O)c2cccnc2)cc1]

The title compound was prepared by the reaction of 4-t-butylbenzenesulfonyl chloride with (6-Amino-2,3-difluoro-phenyl)-pyridin-3-yl-methanone following the general procedure. MS: m/z 431.1 (M⁺+1).

Synthesis of N-[4-Chloro-2-(pyridine-4-carbonyl)-phenyl]-4-(4-methyl-tetrahydro-pyran-4-yl)-benzenesulfonamide

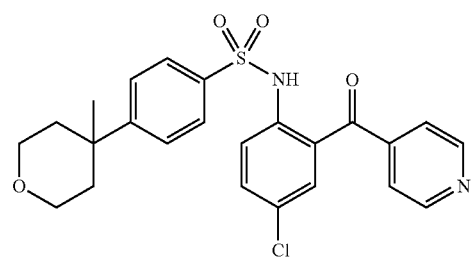 [SMILES: CC1(c2ccc(S(=O)(=O)Nc3ccc(Cl)cc3C(=O)c3ccncc3)cc2)CCOCC1]

The title compound was prepared by the reacting 4-(4-methyl-tetrahydro-pyran-4-yl)-benzenesulfonyl chloride with (2-amino-5-chloro-phenyl)-pyridin-4-yl-methanone according to the general procedure described for the preparation of (N-aryl-benzenesulfonamides. ¹H NMR (CDCl₃) δ 10.21 (s, 1H), 8.77 (d, 2H, J=6.0 Hz), 7.79 (d, 1H, J=8.8 Hz), 7.73 (m, 2H), 7.51-7.54 (m, 1H), 7.31-7.36 (m, 3H), 7.24-7.26 (m, 2H), 3.58-3.80 (m, 4H), 1.95-1.99 (m, 2H), 1.70-1.74 (m, 2H), 1.22 (s, 3H). MS: m/z 471 (M⁺+1).

Synthesis of N-[4-Chloro-2-(pyridine-3-carbonyl)-phenyl]-4-(4-methyl-tetrahydro-pyran-4-yl)-benzenesulfonamide

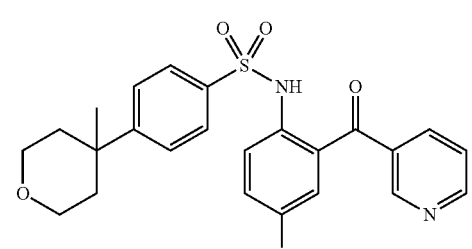

The title compound was prepared by the reacting 4-(4-methyl-tetrahydro-pyran-4-yl)-benzenesulfonyl chloride with (2-amino-5-chloro-phenyl)-pyridin-3-yl-methanone according to the general procedure described for the preparation of (N-aryl-benzenesulfonamides. MS: m/z 471 (M⁺+1).

Synthesis of N-[4-Chloro-2-(pyridine-2-carbonyl)-phenyl]-4-(4-methyl-tetrahydro-pyran-4-yl)-benzenesulfonamide

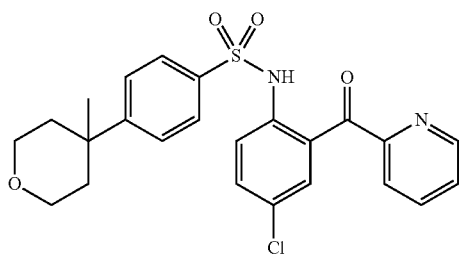 [SMILES: CC1(c2ccc(S(=O)(=O)Nc3ccc(Cl)cc3C(=O)c3ccccn3)cc2)CCOCC1]

The title compound was prepared by the reacting 4-(4-methyl-tetrahydro-pyran-4-yl)-benzenesulfonyl chloride with (2-amino-5-chloro-phenyl)-pyridin-2-yl-methanone according to the general procedure described for the preparation of (N-aryl-benzenesulfonamides. MS: m/z 471 (M⁺+1).

Synthesis of N-[4-Chloro-2-(6-methyl-pyridine-2-carbonyl)-phenyl]-4-(4-methyl-tetrahydro-pyran-4-yl)-benzenesulfonamide

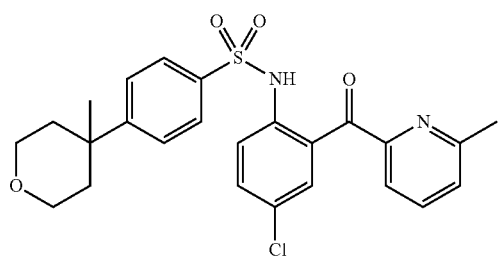 [SMILES: Cc1cccc(C(=O)c2cc(Cl)ccc2NS(=O)(=O)c2ccc(C3(C)CCOCC3)cc2)n1]

The title compound was prepared by the reacting 4-(4-methyl-tetrahydro-pyran-4-yl)-benzenesulfonyl chloride with (2-amino-5-chloro-phenyl)-(6-methyl-pyridin-2-yl)-methanone according to the general procedure described for the preparation of (N-aryl-benzenesulfonamides. MS: m/z 486 (M⁺+1).

Synthesis of N-[4-Chloro-2-(6-methyl-pyridine-3-carbonyl)-phenyl]-4-(4-methyl-tetrahydro-pyran-4-yl)-benzenesulfonamide

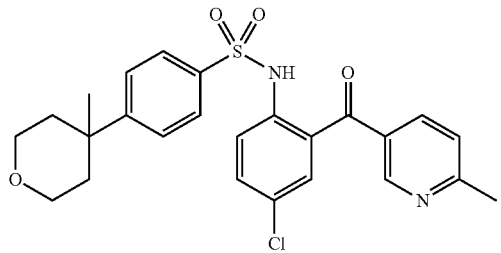 [SMILES: Cc1ccc(C(=O)c2cc(Cl)ccc2NS(=O)(=O)c2ccc(C3(C)CCOCC3)cc2)cn1]

The title compound was prepared by the reacting 4-(4-methyl-tetrahydro-pyran-4-yl)-benzenesulfonyl chloride with (2-Amino-5-chloro-phenyl)-(6-methyl-pyridin-3-yl)-methanone according to the general procedure described for the preparation of (N-aryl-benzenesulfonamides. MS: m/z 486 (M⁺+1).

Synthesis of N-[4-Chloro-2-(2-methyl-pyridine-3-carbonyl)-phenyl]-4-(4-methyl-tetrahydro-pyran-4-yl)-benzenesulfonamide

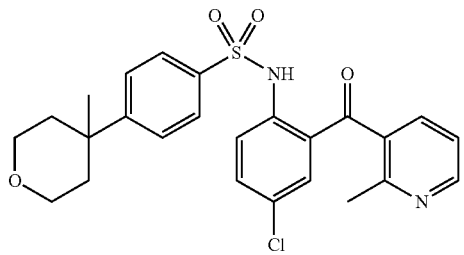 [SMILES: Cc1ncccc1C(=O)c1cc(Cl)ccc1NS(=O)(=O)c1ccc(C2(C)CCOCC2)cc1]

The title compound was prepared by the reacting 4-(4-methyl-tetrahydro-pyran-4-yl)-benzenesulfonyl chloride with (2-Amino-5-chloro-phenyl)-(2-methyl-pyridin-3-yl)-methanone according to the general procedure described for the preparation of (N-aryl-benzenesulfonamides. MS: m/z 486 (M⁺+1).

Synthesis of 4-tert-butyl-N-[4-chloro-2-(1H-pyrazole-3-carbonyl)-phenyl]-benzenesulfonamide

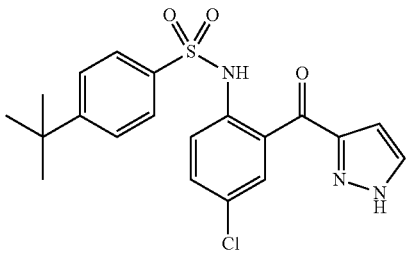 [SMILES: CC(C)(C)c1ccc(S(=O)(=O)Nc2ccc(Cl)cc2C(=O)c2cc[nH]n2)cc1]

The title compound was prepared by the reacting 4-t-butyl-benzenesulfonyl chloride with (2-amino-5-chloro-phenyl)-(1H-pyrazol-3-yl)-methanone according to the general procedure described for the preparation of (N-aryl-benzenesulfonamides. MS: m/z 418 (M+ +1).

Synthesis of N-[4-Chloro-2-(pyridine-4-carbonyl)-phenyl]-4-(1-methyl-1-oxazol-2-yl-ethyl)-benzene-sulfonamide

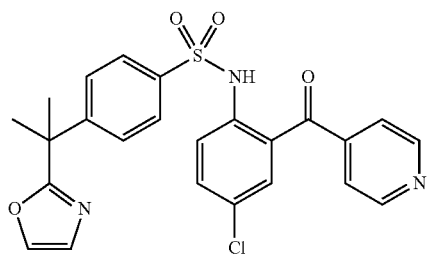 [SMILES: CC(C)(c1ccc(S(=O)(=O)Nc2ccc(Cl)cc2C(=O)c2ccncc2)cc1)c1ncco1]

The title compound was prepared from (2-amino-5-chloro-phenyl)-pyridin-4-yl-methanone and 4-(1-methyl-1-oxazol-2-yl-ethyl)-benzenesulfonyl chloride following the general procedure described for the preparation of N-aryl-benzenesulfonamides. MS: m/z 482 (M+ +1).

Synthesis of N-[4-Chloro-2-(6-methyl-pyridine-3-carbonyl)-phenyl]-4-(1-methyl-1-oxazol-2-yl-ethyl)-benzenesulfonamide

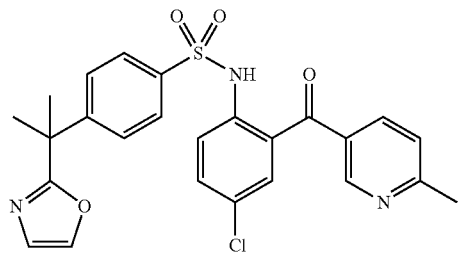 [SMILES: Cc1ccc(C(=O)c2cc(Cl)ccc2NS(=O)(=O)c2ccc(C(C)(C)c3ncco3)cc2)cn1]

The title compound was prepared from (2-amino-5-chloro-phenyl)-(6-methyl-pyridin-3-yl)-methanone and 4-(1-methyl-1-oxazol-2-yl-ethyl)-benzenesulfonyl chloride following the general procedure described for the preparation of N-aryl-benzenesulfonamides. MS: m/z 496 (M+ +1).

Synthesis of N-[4-Chloro-2-(pyridine-3-carbonyl)-phenyl]-4-(1-methyl-1-oxazol-2-yl-ethyl)-benzene-sulfonamide

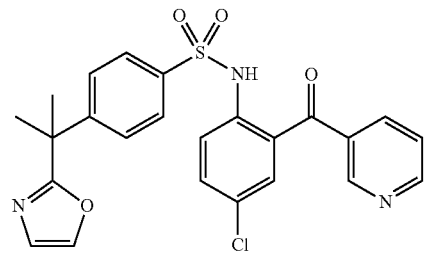 [SMILES: CC(C)(c1ccc(S(=O)(=O)Nc2ccc(Cl)cc2C(=O)c2cccnc2)cc1)c1ncco1]

The title compound was prepared from (2-Amino-5-chloro-phenyl)-pyridin-3-yl-methanone and 4-(1-methyl-1-oxazol-2-yl-ethyl)-benzenesulfonyl chloride following the general procedure described for the preparation of N-aryl-benzenesulfonamides. MS: m/z 482 (M+ +1).

Synthesis of N-[4,5-Difluoro-2-(pyridine-3-carbonyl)-phenyl]-4-(1-methyl-1-oxazol-2-yl-ethyl)-benzenesulfonamide

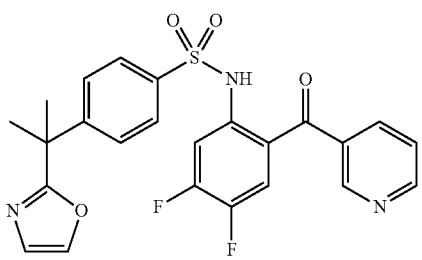 [SMILES: CC(C)(c1ccc(S(=O)(=O)Nc2cc(F)c(F)cc2C(=O)c2cccnc2)cc1)c1ncco1]

The title compound was prepared from (2-Amino-4,5-difluoro-phenyl)-pyridin-3-yl-methanone and 4-(1-methyl-1-oxazol-2-yl-ethyl)-benzenesulfonyl chloride following the general procedure described for the preparation of N-aryl-benzenesulfonamides. MS: m/z 484 (M+ +1).

Synthesis of N-[4-Chloro-2-(pyridine-2-carbonyl)-phenyl]-4-(1-methyl-1-oxazol-2-yl-ethyl)-benzene-sulfonamide

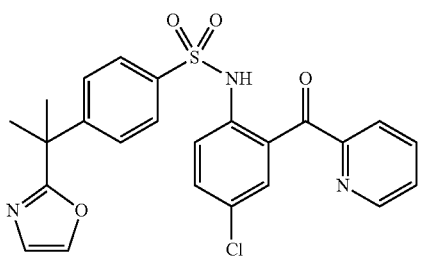 [SMILES: CC(C)(c1ccc(S(=O)(=O)Nc2ccc(Cl)cc2C(=O)c2ccccn2)cc1)c1ncco1]

The title compound was prepared from (2-amino-5-chloro-phenyl)-pyridin-2-yl-methanone and 4-(1-methyl-1-oxazol-2-yl-ethyl)-benzenesulfonyl chloride following the general procedure described for the preparation of N-aryl-benzenesulfonamides. MS: m/z 482 (M+ +1).

Synthesis of N-[4-Chloro-2-(6-methyl-pyridine-2-carbonyl)-phenyl]-4-(1-methyl-1-oxazol-2-yl-ethyl)-benzenesulfonamide

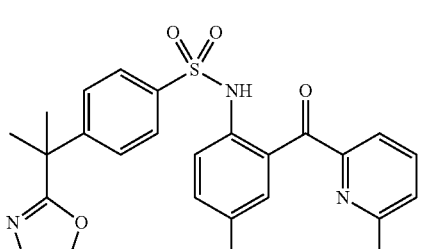

The title compound was prepared from (2-Amino-5-chloro-phenyl)-(6-methyl-pyridin-2-yl)-methanone and 4-(1-methyl-1-oxazol-2-yl-ethyl)-benzenesulfonyl chloride following the general procedure described for the preparation of N-aryl-benzenesulfonamides. MS: m/z 496 (M$^+$+1).

Synthesis of N-[4-Chloro-2-(pyridine-4-carbonyl)-phenyl]-4-(1-methyl-1-oxazol-4-yl-ethyl)-benzenesulfonamide

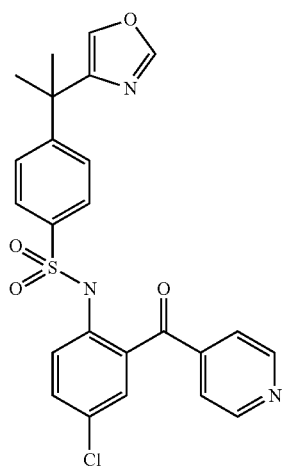 [SMILES: CC(C)(c1ccc(S(=O)(=O)Nc2ccc(Cl)cc2C(=O)c2ccncc2)cc1)c1cocn1]

Following the general procedure for synthesis of N-aryl-benzenesulfonamides, 73 mg (0.32 mmol) of (2-Amino-5-chloro-phenyl)-pyridin-4-yl-methanone and 36 mg (0.13 mmol) of 4-(1-Methyl-1-oxazol-4-yl-ethyl)-benzenesulfonyl chloride were combined in 1 ml of anhydrous pyridine at 60° C. to give, after purification, the title product as a pale yellow solid: $^1$H NMR (CDCl$_3$): δ (ppm): 1.61 (s, 6H), 7.26-7.66 (m, 12H), 8.90 (br, 1H), 10.13 (br, 1H) ppm; MS: (M+H)/z=482.0.

Synthesis of N-[4-Chloro-2-(6-methyl-pyridine-3-carbonyl)-phenyl]-4-(1-methyl-1-oxazol-4-yl-ethyl)-benzenesulfonamide

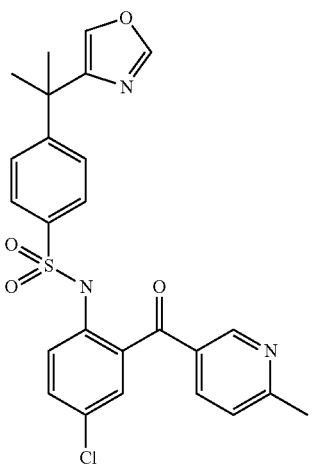 [SMILES: Cc1ccc(C(=O)c2cc(Cl)ccc2NS(=O)(=O)c2ccc(C(C)(C)c3cocn3)cc2)cn1]

Following the general procedure for synthesis of N-aryl-benzenesulfonamides, 63 mg (0.26 mmol) of (2-Amino-5-chloro-phenyl)-(6-methyl-pyridin-3-yl)-methanone and 50 mg (0.17 mmol) of 4-(1-Methyl-1-oxazol-4-yl-ethyl)-benzenesulfonyl chloride were combined in 0.8 ml of anhydrous pyridine at 60° C. to give, after purification, the title product as a pale yellow solid: $^1$H NMR (CDCl$_3$): δ (ppm): 1.54 (s, 6H), 2.63 (s, 3H), 7.22-7.30 (m, 2H), 7.32 (m, 2H), 7.55 (m, 1H), 7.61-7.63 (m, 2H), 7.70-7.80 (m, 3H), 8.49 (d, 1H), 9.95 (s, 1H); MS: (M+H)/z=496.0.

Synthesis of N-[4-Chloro-2-(pyridine-4-carbonyl)phenyl]-4-(2-oxazol-2-ylethyl)benzenesulfonamide

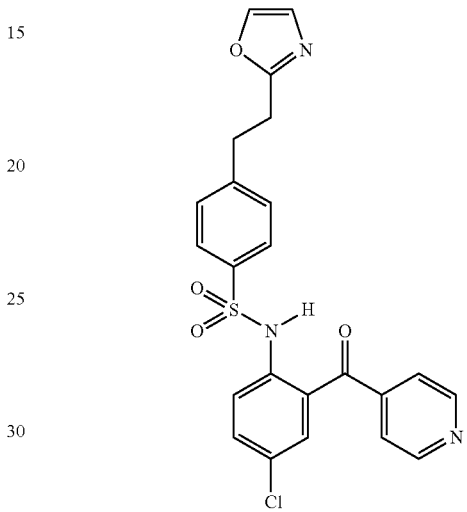

The title compound was prepared according to the general procedure for the preparation of N-aryl-benzenesulfonamides: $^1$H NMR: δ (400 MHz, CDCl$_3$) 10.07 (s, 1H), 8.75 (m, 2H), 7.73 (d, 2H), 7.63 (d, 2H), 7.50 (s, 1H), 7.28 (d, 1H), 7.22 (m, 2H), 7.15 (d, 2H), 6.96 (s, 1H), 3.02 (m, 4H). MS (M+H$^+$): 468.0

Synthesis of 4-Acetyl-N-[4-chloro-2-(hydroxy-pyridin-4-yl-methyl)-phenyl]-benzenesulfonamide

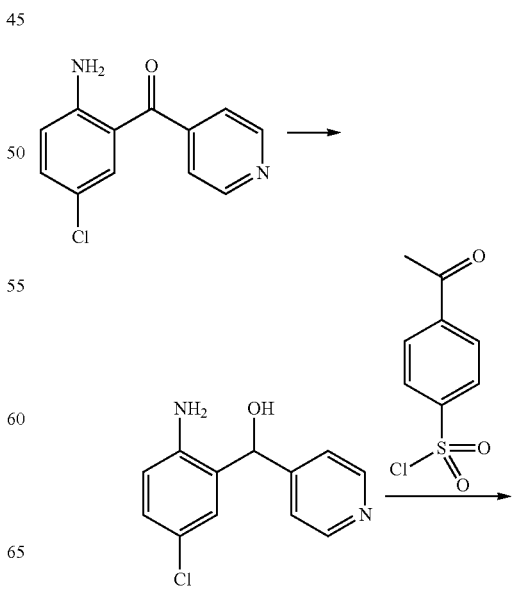

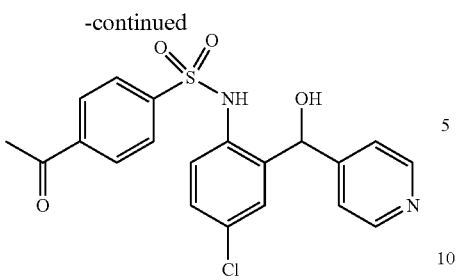

(2-Amino-5-chloro-phenyl)-pyridin-4-yl-methanone (2.2 g, 9.4 mmol) suspended in 20 mL of anhydrous EtOH was treated with NaBH$_4$ (3.4 g, 89.4 mmol) in small portions. The reaction mixture was stirred vigorously and within minutes changed from deep yellow to an off-white color. After 30 minutes the crude reaction mixture was concentrated by rotary evaporation and the resulting residue was partitioned between 75 mL EtOAc and 75 mL 50% aqueous NaHCO$_3$. The EtOAc layer was collected and the aqueous layer was washed with 75 mL EtOAc. The two organic fractions were combined, dried on MgSO$_4$ and concentrated by rotary evaporation. The resulting solid was dried under vacuum to yield 1.7 g of a white powder. The white powder was dissolved in 10 mL anhydrous pyridine and treated with 1.6 g (7.4 mmol) of 4-acetylbenzenesulfonyl chloride. The sulfonylation reaction monitored by LC-MS was complete after 1 h. The pyridine was evaporated under vacuum and the resulting crude residue was partitioned between 50 mL EtOAc and 50 mL 50% aqueous NaHCO$_3$. The bicarbonate layer was extracted with EtOAc (1×50 mL). The two organic fractions were combined, dried on MgSO$_4$ and concentrated by rotary evaporation to yield the title compound as a pale-amber solid. MS: m/z 417 (M$^+$+1).

Syntheses of Sulfonamide Pyridine-N-Oxides

Synthesis of N-[4-Chloro-2-(6-methyl-1-oxy-pyridine-3-carbonyl)-phenyl]-4-trifluoromethoxy-benzenesulfonamide

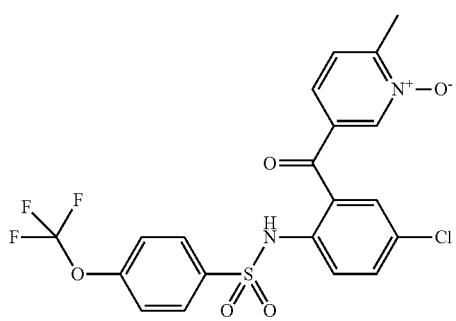 [SMILES: Cc1ccc(C(=O)c2cc(Cl)ccc2NS(=O)(=O)c2ccc(OC(F)(F)F)cc2)c[n+]1[O-]]

The title compound was prepared by the mCPBA oxidation of N-[4-Chloro-2-(6-methyl-pyridine-3-carbonyl)-phenyl]-4-trifluoromethoxy-benzenesulfonamide according to the general procedure. $^1$H NMR (CDCl3) δ 9.60 (br s, 1, NH), 8.42 (m, 1H), 7.78 (dm, 2H, J=8.4 Hz), 7.70 (dm, 1H, J=8.8 Hz), 7.56 (dd, 1H, J=8.0 Hz, J=2.2 Hz), 7.44 (d, 1H, J=8.0 Hz), 7.41 (d, 1H, J=2.2 Hz), 7.38 (dm, 1H, J=8.0 Hz), 7.20 (dm, 2H, J=8.4 Hz), 2.65 (s, 3H). MS: m/z 487 (M+1).

Synthesis of N-[4-Chloro-2-(6-methyl-1-oxy-pyridine-3-carbonyl)-phenyl]-4-isopropoxy-benzenesulfonamide

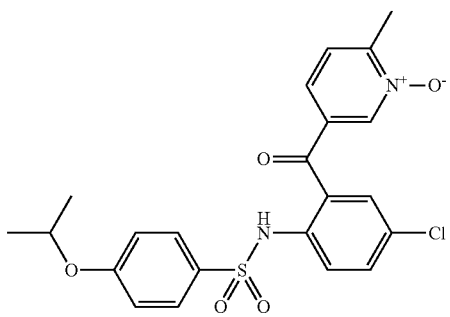 [SMILES: Cc1ccc(C(=O)c2cc(Cl)ccc2NS(=O)(=O)c2ccc(OC(C)C)cc2)c[n+]1[O-]]

The title compound was prepared by the mCPBA oxidation of N-[4-Chloro-2-(6-methyl-pyridine-3-carbonyl)-phenyl]-4-isopropoxy-benzenesulfonamide according to the general procedure. $^1$H-NMR (CDCl$_3$) δ 9.53 (br s, 1H, NH), 8.25 (dm, 1H, J=1.5 Hz), 7.74 (d, 1H, J=8.8 Hz), 7.59 (dm, 2H, J=8.8 Hz), 7.52 (dd, 1H, J=8.8 Hz, J=2.6 Hz), 7.24 (d, 1H, J=8.0 Hz), 7.33 (d, 1H, J=2.6 Hz), 7.20 (dd, 1H, J=8.0 Hz, J=1.6 Hz), 6.75 (dm, 2H, J=8.8 Hz), 4.51 (septet, 1H, J=6 Hz), 2.59 (s, 3H), 1.30 (d, 3H, J=6 Hz). MS: m/z 461 (M+1).

Synthesis of N-[4-Chloro-2-(1-oxy-pyridine-3-carbonyl)-phenyl]-4-methanesulfonyl-benzenesulfonamide

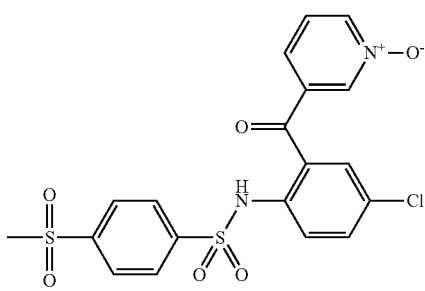 [SMILES: CS(=O)(=O)c1ccc(S(=O)(=O)Nc2ccc(Cl)cc2C(=O)c2ccc[n+]([O-])c2)cc1]

The title compound was prepared by the mCPBA oxidation of 4-methanesufonyl-N-[4-chloro-2-(pyridine-3-carbonyl)-phenyl]-benzenesulfonamide according to the general procedure. $^1$H NMR (DMSO-d6): δ 3.27 (s, 3H), 6.90 (d, J=8.8 Hz, 1H), 7.47 & 7.49 (dd, J=8.0 Hz, 1.2 Hz, 1H), 7.51-7.55 (m, 1H), 7.56 & 7.58 (dd, J=8.0 Hz, 2.4 Hz, 1H), 7.62 (d, J=2.0 Hz, 1H), 7.79 (d, J=7.6 Hz, 2H), 8.05 (d, J=8.8 Hz, 2H), 8.19 (d, J=2.0 Hz, 1H), 8.41 & 8.42 (dd, J=6.8 Hz, 1.2 Hz, 1H), 10.46 (s, 1H). MS: M/z 467.0 (M$^+$+1).

Synthesis of 4-Acetyl-N-[4-chloro-2-(6-methyl-1-oxy-pyridine-3-carbonyl)-phenyl]-benzenesulfonamide

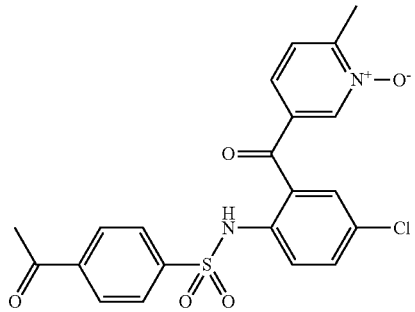 [SMILES: CC(=O)c1ccc(S(=O)(=O)Nc2ccc(Cl)cc2C(=O)c2ccc(C)[n+]([O-])c2)cc1]

The title compound was prepared by the mCPBA oxidation of 4-Acetyl-N-[4-chloro-2-(6-methyl-pyridine-3-carbonyl)-phenyl]-benzenesulfonamide according to the general procedure. $^1$H-NMR (CDCl3) δ 9.16 (br s, 1H, NH), 8.15 (dm, 1H, J=2.0 Hz), 7.83 (d, 2H, J=8.1 Hz), 7.71 (d, 2H, J=8.1 Hz), 7.71-7.67 (m, 2H), 7.58 (dd, 1H, J=8.8 Hz, J=2.2 Hz), 7.52 (d, 1H, J=8.4 Hz), 7.37 (d, 1H, J=2.2 Hz), 2.66 (s, 3H), 2.60 (s, 3H). MS: m/z 445 (M+1).

Synthesis of N-[4-Chloro-2-(6-methyl-1-oxy-pyridine-3-carbonyl)-phenyl]-4-methanesulfonyl-benzenesulfonamide

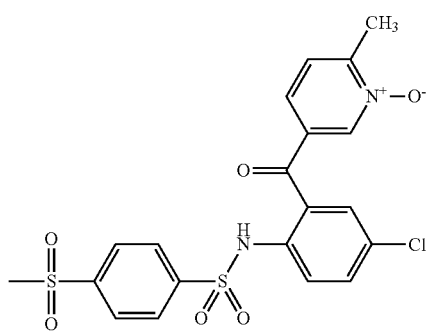 [SMILES: Cc1ccc(C(=O)c2cc(Cl)ccc2NS(=O)(=O)c2ccc(S(C)(=O)=O)cc2)c[n+]1[O-]]

The title compound was prepared by the mCPBA oxidation of N-[4-Chloro-2-(6-methyl-pyridine-3-carbonyl)-phenyl]-4-methanesulfonyl-benzenesulfonamide according to the general procedure. $^1$H-NMR (CDCl3) δ 9.39 (br s, 1H, NH), 8.61 (m, 1H), 7.88 (m, 4H), 7.68 (d, 1H, J=8.8 Hz), 7.60 (m, 2H), 7.40 (m, 2H), 3.03 (s, 3H), 2.69 (s, 3H). m/z 481 (M+1)

Synthesis of 4-tert-Butyl-N-[4-chloro-2-(1-oxy-pyridine-4-carbonyl)-phenyl]-benzenesulfonamide

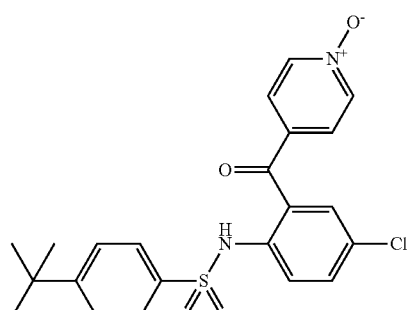

4-tert-Butyl-N-[4-chloro-2-(pyridine-4-carbonyl)-phenyl]-benzenesulfonamide (107 mg, 0.25 mmol) was dissolved in 4 mL DCM and m-chloroperoxybenzoic (0.26 mmol) was added. The mixture was stirred at room temperature for 16 h. The solvent was evaporated on a rotary evaporator and the product was purified by reversed phase HPLC to yield title compound. $^1$H-NMR (400 MHz, CDCl$_3$): δ 1.24 (s, 9H), 7.32-7.4 (m, 5H), 7.52 (dd, 1H, J=8.8, Hz, 2.4 Hz), 7.63 (d, 2H, J=8.8 Hz), 7.74 (d, 1H, J=8.8 Hz), 8.18 (d, 2H, J=7.6 Hz), 9.60 (s, 1H). MS: m/z 445.9 (M$^+$+1).

Synthesis of 3-{4-[4-Chloro-2-(6-methyl-1-oxy-pyridine-3-carbonyl)-phenylsulfamoyl]-phenyl}-propionic acid methyl ester

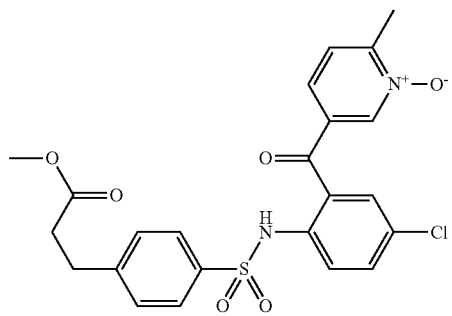 [SMILES: COC(=O)CCc1ccc(S(=O)(=O)Nc2ccc(Cl)cc2C(=O)c2ccc(C)[n+]([O-])c2)cc1]

The title compound was prepared by the mCPBA oxidation of 3-{4-[4-Chloro-2-(6-methyl-pyridine-3-carbonyl)-phenylsulfamoyl]-phenyl}-propionic acid methyl ester according to the general procedure. $^1$H-NMR (CDCl3) δ 9.47 (br s, 1H, NH), 8.26 (m, 1H), 7.69 (d, 1H, J=8.8 Hz), 7.59 (dm, 2H, J=8.4 Hz), 7.53 (dd, 1H, J=8.8 Hz, J=2.6 Hz), 7.48 (m, 2H), 7.35 (d, 1H, J=2.6 Hz), 7.18 (dm, 2H, J=8.4 Hz), 3.64 (s, 3H), 2.88 (t, 2H, J=7.6 Hz), 2.67 (s, 3H), 2.51 (t, 2H, J=7.6 Hz). MS: m/z 489 (M+1).

Synthesis of 4-Acetyl-N-[4-chloro-2-(1-oxy-pyridine-3-carbonyl)-phenyl]-benzenesulfonamide

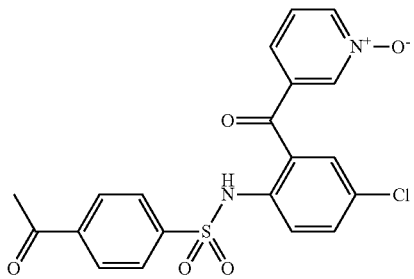 [SMILES: CC(=O)c1ccc(S(=O)(=O)Nc2ccc(Cl)cc2C(=O)c2ccc[n+]([O-])c2)cc1]

The title compound was prepared by the mCPBA oxidation of 4-Acetyl-N-[4-chloro-2-(pyridine-3-carbonyl)-phenyl]-benzenesulfonamide according to the general procedure.

Synthesis of N-[4-Chloro-2-(1-oxypyridine-4-carbonyl)phenyl]-4-(1-methyl-1-oxazol-5-ylethyl)-benzenesulfonamide

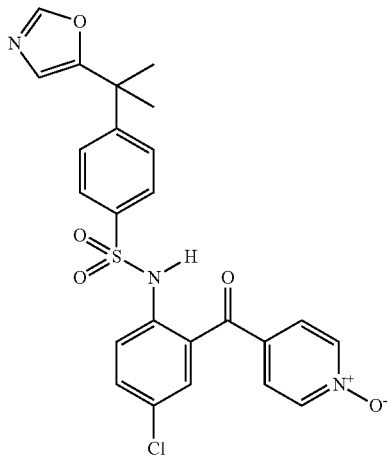 [SMILES: CC(C)(c1ccc(S(=O)(=O)Nc2ccc(Cl)cc2C(=O)c2cc[n+]([O-])cc2)cc1)c1cnco1]

The title compound was prepared by the general oxidation procedure using mCPBA described for the synthesis of pyridine N-oxides: ¹H NMR: δ (400 MHz, CDCl₃) 9.80 (s, 1H), 8.41 (d, 2H), 8.79 (s, 1H), 7.74 (s, 1H), 7.72 (d, 2H), 7.70 (s, 1H), 7.56 (d, 1H), 7.53 (m, 2H), 7.51 (s, 1H), 6.95 (s, 1H), 1.65 (s, 6H). MS (M+H⁺): 498.0

Synthesis of 4-tert-Butyl-N-[4-chloro-2-(2-methyl-1-oxy-pyridine-3-carbonyl)-phenyl]-benzenesulfonamide

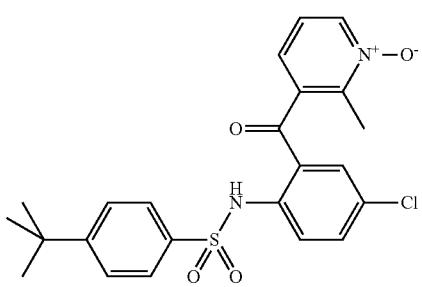 [SMILES: Cc1c(C(=O)c2cc(Cl)ccc2NS(=O)(=O)c2ccc(C(C)(C)C)cc2)ccc[n+]1[O-]]

The title compound was prepared by the mCPBA oxidation of 4-tert-Butyl-N-[4-chloro-2-(2-methyl-pyridine-3-carbonyl)-phenyl]-benzenesulfonamide according to the general procedure. ¹H NMR (CDCl₃) δ 10.71 (br s, 1H, NH), 8.62 (dm, 1H, J=5.9 Hz), 7.81 (d, 1H, J=9.1 Hz), 7.78 (dm, 2H, J=8.4 Hz), 7.54 (dd, 1H, J=8.8 Hz, J=2.6 Hz), 7.48 (dm, 2H, J=8.4 Hz), 7.44 (m, 2H), 7.18 (d, 1H, J=2.6 Hz), 2.32 (s, 3H), 1.32 (s, 9H). MS: m/z 459 (M+1).

Synthesis of N-[4-Chloro-2-(1-oxy-pyridine-4-carbonyl)-phenyl]-4-(4-methyl-tetrahydro-pyran-4-yl)-benzenesulfonamide

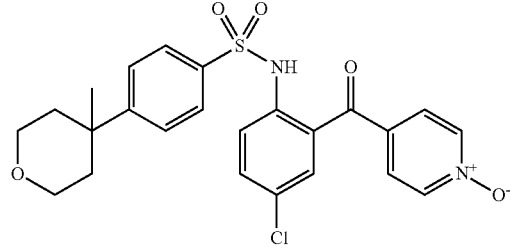 [SMILES: CC1(c2ccc(S(=O)(=O)Nc3ccc(Cl)cc3C(=O)c3cc[n+]([O-])cc3)cc2)CCOCC1]

The title compound was prepared by the mCPBA oxidation of N-[4-chloro-2-(pyridine-4-carbonyl)-phenyl]-4-(4-methyl-tetrahydro-pyran-4-yl)-benzenesulfonamide according to the general procedure described for the synthesis of pyridine N-oxides. MS: m/z 487 (M⁺+1).

Synthesis 4-tert-Butyl-N-[4-chloro-2-(2-methyl-1-oxy-pyridine-4-carbonyl)-phenyl]-benzenesulfonamide

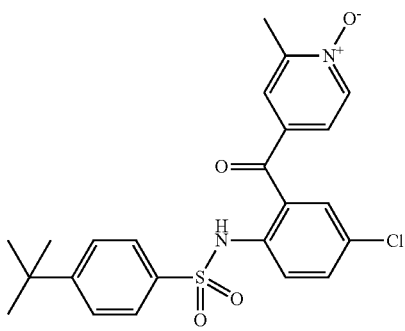 [SMILES: Cc1cc(C(=O)c2cc(Cl)ccc2NS(=O)(=O)c2ccc(C(C)(C)C)cc2)cc[n+]1[O-]]

The title compound was prepared according to the general procedure by mCPBA oxidation of 4-tert-butyl-N-[4-chloro-2-(2-methyl-pyridine-4-carbonyl)-phenyl]-benzenesulfonamide. ¹H-NMR (400 MHz, CDCl₃): δ 1.26 (s, 9H), 2.63 (s, 3H) 7.29 (d, 1H, J=2.8 Hz), 7.50-7.57 (m, 3H), 7.67 (m, 2H), 7.87 (m, 2H), 8.24 (s, 1H), 8.89 (d, 1H, J=5.6 Hz), 10.31 (s, 1H). MS: m/z 459.0 (M⁺+1)

Synthesis of 4-tert-Butyl-N-[4-chloro-2-(1-oxy-pyridine-3-carbonyl)-phenyl]-benzenesulfonamide

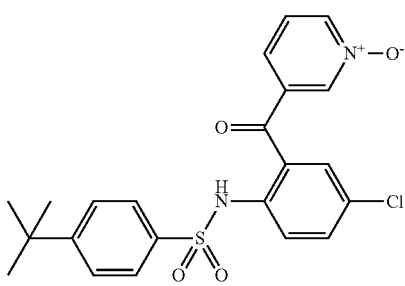 [SMILES: CC(C)(C)c1ccc(S(=O)(=O)Nc2ccc(Cl)cc2C(=O)c2ccc[n+]([O-])c2)cc1]

The title compound was prepared by the mCPBA oxidation of 4-tert-Butyl-N-[4-chloro-2-(pyridine-3-carbonyl)-phenyl]-benzenesulfonamide according to the general procedure and purified by HPLC. 1H NMR (CDCl3) δ 9.71 (s, 1H) 8.56 (d, J=7.6 Hz, 1H) 8.43 (s, 1H) 7.71-7.66 (m, 4H) 7.61-7.53 (m, 2H) 7.44-7.38 (m, 3H) 1.28 (s, 9H). MS (ES) m/z=445.0 (M$^+$+1).

Synthesis of N-[4-Chloro-2-(2-methyl-1-oxy-pyridine-4-carbonyl)-phenyl]-4-trifluoromethoxy-benzenesulfonamide

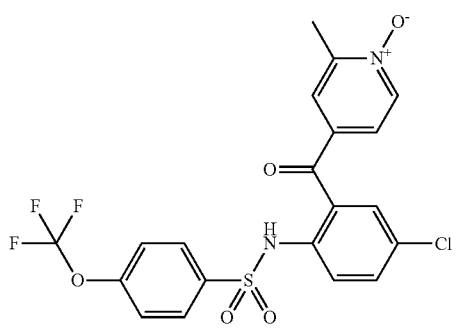 [SMILES: Cc1cc(C(=O)c2cc(Cl)ccc2NS(=O)(=O)c2ccc(OC(F)(F)F)cc2)cc[n+]1[O-]]

The title compound was prepared by the mCPBA oxidation of N-[4-Chloro-2-(2-methyl-pyridine-4-carbonyl)-phenyl]-4-trifluoromethoxy-benzenesulfonamide according to the general procedure and purified by HPLC. 1H NMR (CDCl3) δ 9.66 (s, 1H) 8.26 (d, J=6.8 Hz, 1H) 7.89 (d, 2H, J=8.4 Hz) 7.85 (s, 1H) 7.81 (d, 2H, J=8.4 Hz) 7.73 (d, 1H, J=8.8 Hz) 7.54 (dd, 1H, J=12 Hz, 2 Hz) 7.36 (t, 1H, J=5.6 Hz, 3.2 Hz) 7.24-7.19 (m, 1H) 2.55 (s, 3H). MS (ES) m/z=486.9 (M$^+$+1).

Synthesis of N-[4-Chloro-2-(2-methyl-1-oxy-pyridine-4-carbonyl)-phenyl]-4-isopropoxy-benzenesulfonamide

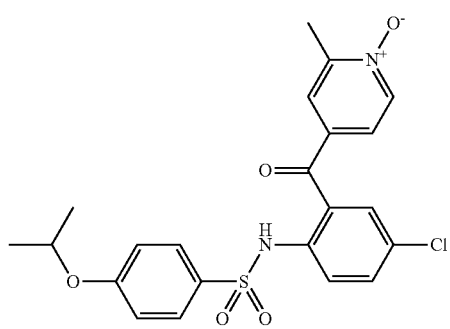 [SMILES: Cc1cc(C(=O)c2cc(Cl)ccc2NS(=O)(=O)c2ccc(OC(C)C)cc2)cc[n+]1[O-]]

The title compound was prepared by the mCPBA oxidation of N-[4-Chloro-2-(2-methyl-pyridine-4-carbonyl)-phenyl]-4-isopropoxy-benzenesulfonamide according to the general procedure and purified by HPLC. 1H NMR (CDCl3) δ 9.39 (s, 1H) 8.32 (d, J=6.8 Hz, 1H) 7.75 (d, J=11.2, 1 H) 7.57-7.52 (m, 3H) 7.36 (d, J=2.4 Hz, 1H) 7.30 (d, J=2.4 Hz, 1H) 7.21 (dd, J=7.2 Hz, 2.8 Hz, 1H) 6.71 (d, J=7.2 Hz, 2H) 4.46 (p, J=6.0 Hz, 1H) 2.57 (s, 3H) 1.29 (d, J=5.6 Hz, 6H). MS (ES) m/z=461.0 (M++1).

Synthesis of N-[4-Chloro-2-(1-oxy-pyridine-3-carbonyl)-phenyl]-4-(4-methyl-tetrahydro-pyran-4-yl)-benzenesulfonamide

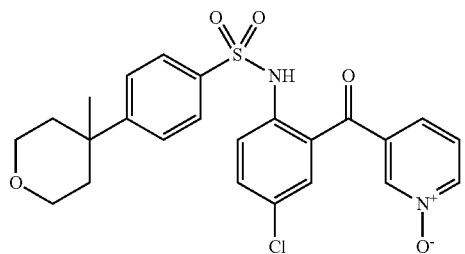 [SMILES: CC1(c2ccc(S(=O)(=O)Nc3ccc(Cl)cc3C(=O)c3ccc[n+]([O-])c3)cc2)CCOCC1]

The title compound was prepared by the mCPBA oxidation of N-[4-chloro-2-(pyridine-4-carbonyl)-phenyl]-4-(4-methyl-tetrahydro-pyran-4-yl)-benzenesulfonamide according to the general procedure described for the synthesis of pyridine N-oxides. MS: m/z 487 (M$^+$+1).

Synthesis of N-[4-Chloro-2-(6-methyl-1-oxy-pyridine-3-carbonyl)-phenyl]-4-(4-methyl-tetrahydro-pyran-4-yl)-benzenesulfonamide

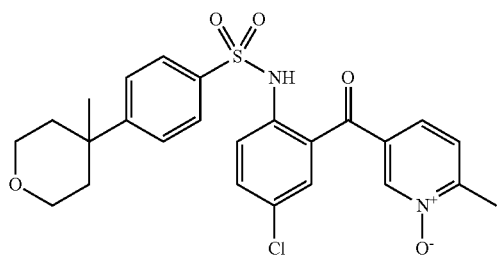 [SMILES: Cc1ccc(C(=O)c2cc(Cl)ccc2NS(=O)(=O)c2ccc(C3(C)CCOCC3)cc2)c[n+]1[O-]]

The title compound was prepared by the mCPBA oxidation of N-[4-Chloro-2-(6-methyl-pyridine-3-carbonyl)-phenyl]-4-(4-methyl-tetrahydro-pyran-4-yl)-benzenesulfonamide according to the general procedure described for the synthesis of pyridine N-oxides. MS: m/z 502 (M$^+$+1).

Synthesis of N-[4-Chloro-2-(1-oxy-pyridine-4-carbonyl)-phenyl]-4-(1-methyl-1-oxazol-2-yl-ethyl)-benzenesulfonamide

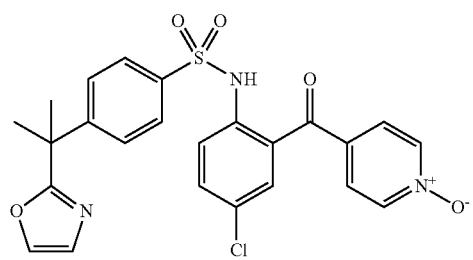 [SMILES: CC(C)(c1ccc(S(=O)(=O)Nc2ccc(Cl)cc2C(=O)c2cc[n+]([O-])cc2)cc1)c1ncco1]

This compound was prepared by the mCPBA oxidation of N-[4-chloro-2-(pyridine-4-carbonyl)-phenyl]-4-(1-methyl-1-oxazol-2-yl-ethyl)-benzenesulfonamide following the general procedure described for the synthesis of pyridine N-oxides.

Synthesis of N-[4-Chloro-2-(6-methyl-1-oxy-pyridine-3-carbonyl)-phenyl]-4-(1-methyl-1-oxazol-2-yl-ethyl)-benzenesulfonamide The title compound was prepared by mCPBA oxidation of N-[4-Chloro-2-(6-methyl-pyridine-3-carbonyl)-phenyl]-4-(1-methyl-1-oxazol-2-yl-ethyl)-benzenesulfonamide according to the general procedure described for the synthesis of pyridine N-oxides. MS: m/z 512 (M$^+$+1).

Synthesis of N-[4-Chloro-2-(1-oxy-pyridine-3-carbonyl)-phenyl]-4-(1-methyl-1-oxazol-2-yl-ethyl)-benzenesulfonamide

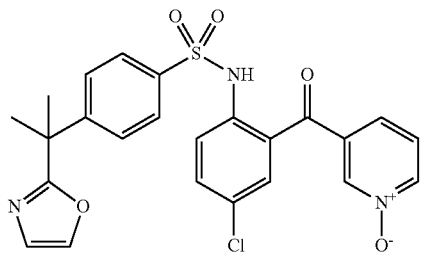 [SMILES: CC(C)(c1ccc(S(=O)(=O)Nc2ccc(Cl)cc2C(=O)c2ccc[n+]([O-])c2)cc1)c1ncco1]

The title compound was prepared by the mCPBA oxidation of N-[4-Chloro-2-(pyridine-3-carbonyl)-phenyl]-4-(1-methyl-1-oxazol-2-yl-ethyl)-benzenesulfonamide following the general procedure described for the synthesis of pyridine N-oxides. MS: m/z 498 (M$^+$+1).

Synthesis of Pivaloyl protected (2-Amino-5-chloro-phenyl)-(1-oxy-pyridin-4-yl)-methanon

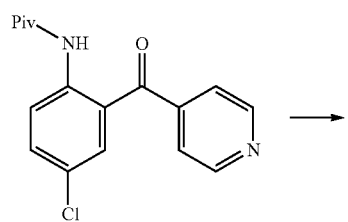

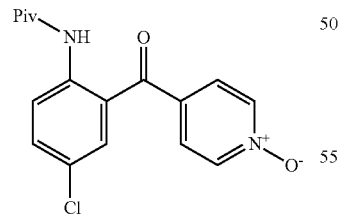

To a solution of pivaloyl protected (2-Amino-5-chloro-phenyl)-1-oxy-pyridin-4-yl-methanone (1.4 g, 0.0044 mol) in glacial acetic acid (15 ml) was added H$_2$O$_2$ (0.376 g, 0.011 mols) and the reaction mixture was heated at 90° C. for 3 h under N$_2$ atmosphere. After 3 h H$_2$O$_2$ (0.1496 g, 0.0044 mols) was added again with further reflux at 90° C. overnight, and the reaction mixture concentrated to get the title compound.

Synthesis of (2-nitro-5-chloro-phenyl)-(1-oxy-pyridin-4-yl)-methanone

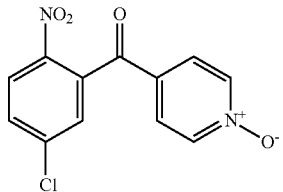 [SMILES: O=C(c1cc[n+]([O-])cc1)c1cc(Cl)ccc1[N+](=O)[O-]]

The title compound was synthesized using standard procedures. $^1$H NMR (300 MHz, CDCl$_3$); 8.25-8.28 (m, 3H), 7.83-8.86 (m, 1H), 7.61-7.73 (m, 2H), 7.46-5.48 (m, 1H). MS (ES) M+H) expected=278.65. found 278.8.

Synthesis of 4-Bromo-N-[4-chloro-2-(1-oxy-pyridine-4-carbonyl)-phenyl]-benzenesulfonamide

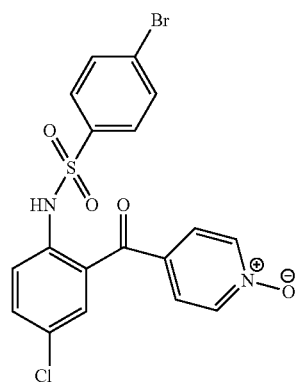 [SMILES: O=C(c1cc[n+]([O-])cc1)c1cc(Cl)ccc1NS(=O)(=O)c1ccc(Br)cc1]

4-Bromo-N-[4-chloro-2-(pyridine-4-carbonyl)-phenyl]-benzenesulfonamide 1 g (2.19 mmol) was dissolved in 10 ml anhydrous dichloromethane. To this solution was added meta-chloroperbenzoic acid (77%) 0.49 g (2.19 mmol), and the mixture was stirred at room temperature overnight. The resulting white solid was filtered and washed with dichloromethane.

LC-MSD, m/z for C$_{18}$H$_{12}$ClN$_2$O$_4$S [M+H]+: 468.9

R. time Reverse phase HPLC gradient 20%-95% in 7 minutes: 3.774

Synthesis of 4-Bromo-N-[4-chloro-2-(6-methyl-1-oxy-pyridine-3-carbonyl)-phenyl]-3-fluoro-benzenesulfonamide

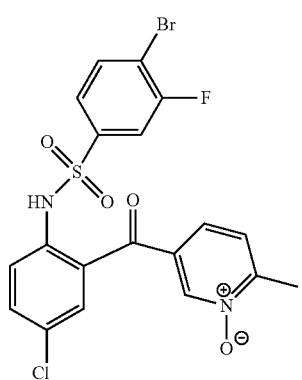 [SMILES: Cc1ccc(C(=O)c2cc(Cl)ccc2NS(=O)(=O)c2ccc(Br)c(F)c2)c[n+]1[O-]]

4-Bromo-N-[4-chloro-2-(6-methyl-pyridine-3-carbonyl)-phenyl]-3-fluoro-benzenesulfonamide 1.7 g (3.5 mmol) was dissolved in 10 ml anhydrous dichloromethane, and to this solution was added meta-chloroperbenzoic acid (77%) 0.787 g (3.5 mmol), and the mixture was stirred at room temperature overnight. Purification using flash column chromatography on silica (elution with, 2.9 Dichloromethane-0.1 methanol), gave an off-white solid.

LC-MSD, m/z for $C_{19}H_{13}ClN_2O_4SBrF$ [M+H]+: 500.9

R. time Reverse phase HPLC gradient 20%-95% in 7 minutes: 4.206

Synthesis of N-[4-Chloro-2-(1-oxy-pyridine-4-carbonyl)-phenyl]-4-furan-3-yl-benzenesulfonamide

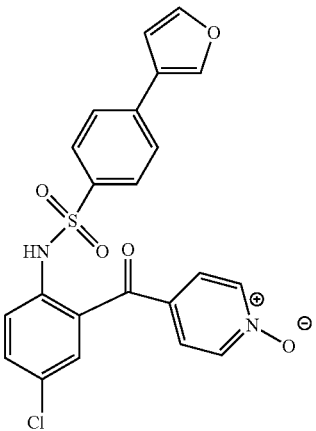 [SMILES: O=C(c1cc[n+]([O-])cc1)c1cc(Cl)ccc1NS(=O)(=O)c1ccc(-c2ccoc2)cc1]

N-[4-Chloro-2-(pyridine-4-carbonyl)-phenyl]-4-furan-3-yl-benzenesulfonamide 0.1 g (0.22 mmol) was dissolved in 10 ml anhydrous dichloromethane, and to this solution was added meta-chloroperbenzoic acid (77%) 76 mg (0.3 mmol), and the mixture was stirred at room temperature overnight. Purification using preparative HPLC (20-70% acetonitrile in 50 min), gave a white solid.

LC-MSD, m/z for $C_{22}H_{15}ClN_2O_5S$ [M+H]+: 455.0

R. time Reverse phase HPLC gradient 20%-95% in 7 minutes: 3.988

Synthesis of 4-Bromo-N-[4-chloro-2-(1-oxy-pyridine-4-carbonyl)-phenyl]-3-fluoro-benzenesulfonamide

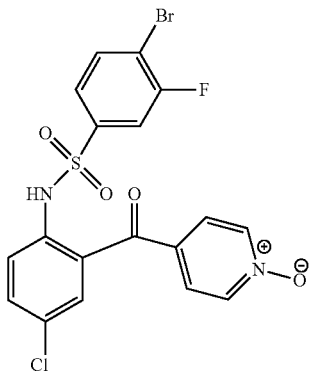 [SMILES: O=C(c1cc[n+]([O-])cc1)c1cc(Cl)ccc1NS(=O)(=O)c1ccc(Br)c(F)c1]

4-Bromo-N-[4-chloro-2-(2-pyridine-4-carbonyl)-phenyl]-3-fluoro-benzenesulfonamide 2 g (4.06 mmol) was dissolved in 10 ml anhydrous dichloromethane, and to this solution was added meta-chloroperbenzoic acid (77%) 1.62 g (7 mmol). Purification using flash column chromatography on silica (elution with, 2.9 Dichloromethane-0.1 methanol), gave an off-white solid.

LC-MSD, m/z for $C_{18}H_{11}ClN_2O_4SBrF$ [M+H]+: 486.9

R. time Reverse phase HPLC gradient 20%-95% in 7 minutes: 4.180

Synthesis of N-[4-Chloro-2-(1-oxy-pyridine-4-carbonyl)-phenyl]-4-(2-methyl-[1,3]dioxolan-2-yl)-benzenesulfonamide

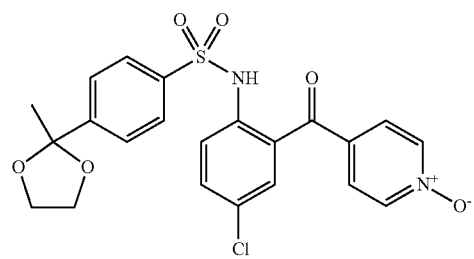 [SMILES: CC1(c2ccc(S(=O)(=O)Nc3ccc(Cl)cc3C(=O)c3cc[n+]([O-])cc3)cc2)OCCO1]

The title compound was prepared by mCPBA oxidation of N-[4-chloro-2-(pyridine-4-carbonyl)-phenyl]-4-(2-methyl-[1,3]dioxolan-2-yl)-benzenesulfonamide prepared in the preceding example as described in the general procedure for the preparation of pyridine N-oxides. MS: m/z 475 (M$^+$+1).

Synthesis of N-[4-Chloro-2-(2-methyl-1-oxy-pyridine-3-carbonyl)-phenyl]-4-trifluoromethoxy-benzenesulfonamide

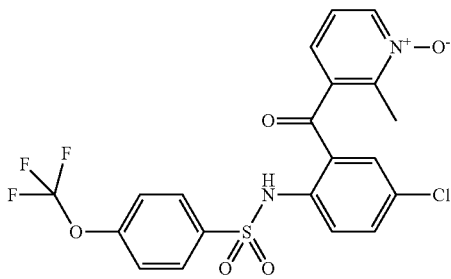 [SMILES: Cc1c(C(=O)c2cc(Cl)ccc2NS(=O)(=O)c2ccc(OC(F)(F)F)cc2)ccc[n+]1[O-]]

The title compound was prepared by the mCPBA oxidation of N-[4-Chloro-2-(2-methyl-pyridine-3-carbonyl)-phenyl]-4-trifluoromethoxy-benzenesulfonamide according to the general procedure. $^1$H NMR (CDCl3) δ 10.68 (br s, 1H, NH), 8.54 (dm, 1H, J=6.6 Hz), 7.92 (dm, 2H, J=8.8 Hz), 7.78 (d, 1, J=8.8 Hz), 7.56 (dd, 1, J=8.8 Hz, J=2.2 Hz), 7.45-7.15 (m, 4), 7.18 (d, 1, J=2.6 Hz), 2.33 (s, 3H). MS: m/z 487 (M+1).

Synthesis of N-[4-Chloro-2-(2-methyl-1-oxy-pyridine-3-carbonyl)-phenyl]-4-isopropoxy-benzenesulfonamide

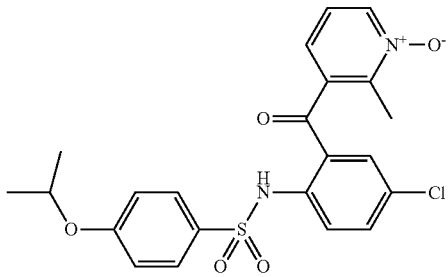 [SMILES: Cc1c(C(=O)c2cc(Cl)ccc2NS(=O)(=O)c2ccc(OC(C)C)cc2)ccc[n+]1[O-]]

The title compound was prepared by the mCPBA oxidation of N-[4-chloro-2-(2-methyl-pyridine-3-carbonyl)-phenyl]-4-isopropoxy-benzenesulfonamide according to the general procedure. $^1$H NMR (CDCl3) δ 10.56 (br s, 1H, NH), 8.56 (dm, 1H, J=6.6 Hz), 7.79 (d, 1H, J=8.8 Hz), 7.75 (d, 2H, J=8.8 Hz), 7.53 (dd, 1H, J=8.8 Hz, J=2.6 Hz), 7.39 (t, 1H, J=7.2 Hz), 7.21 (d, 1H, J=8.0 Hz), 7.17 (d, 1H, J=2.6 Hz), 6.87 (d, 2H, J=8.8 Hz), 4.58 (septet, 1H, J=6 Hz), 2.32 (s, 3H), 1.35 (d, 3H, J=6 Hz). MS: m/z 461 (M+1).

Synthesis of 4-Acetyl-N-[4-chloro-2-(2-methyl-1-oxy-pyridine-3-carbonyl)-phenyl]-benzenesulfonamide

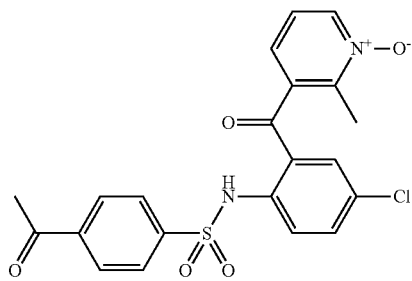 [SMILES: CC(=O)c1ccc(S(=O)(=O)Nc2ccc(Cl)cc2C(=O)c2ccc[n+]([O-])c2C)cc1]

The title compound was prepared by the mCPBA oxidation of 4-Acetyl-N-[4-chloro-2-(2-methyl-pyridine-3-carbonyl)-phenyl]-benzenesulfonamide according to the general procedure. $^1$H NMR (CDCl3) δ 10.7 (br s, 1H, NH), 8.54 (d, 1H, J=6.6 Hz), 8.02 (d, 2H, J=8.4 Hz), 7.95 (d, 2H, J=8.4 Hz), 7.76 (d, 1H, J=8.8 Hz), 7.54 (dd, 1H, J=8.8 Hz, J=2.2 Hz), 7.38 (m, 1H), 7.22 (d, 1H, J=2.6 Hz), 7.16 (dm, 1H, J=7.7 Hz), 2.62 (s, 3H), 2.33 (s, 3H). MS: m/z 445 (M+1).

Synthesis of N-[4-Chloro-2-(2-methyl-1-oxy-pyridine-3-carbonyl)-phenyl]-4-methanesulfonyl-benzenesulfonamide

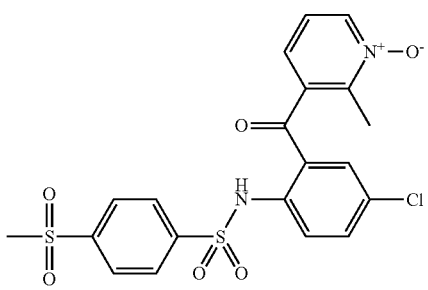 [SMILES: Cc1c(C(=O)c2cc(Cl)ccc2NS(=O)(=O)c2ccc(S(C)(=O)=O)cc2)ccc[n+]1[O-]]

The title compound was prepared by the mCPBA oxidation of N-[4-Chloro-2-(2-methyl-pyridine-3-carbonyl)-phenyl]-4-methanesulfonyl-benzenesulfonamide according to the general procedure. $^1$H NMR (CDCl3) δ 10.78 (br s, 1H, NH), 8.38 (dm, 1H, J=6.6 Hz), 8.05 (s, 4H), 7.76 (d, 1H, J=8.8 Hz), 7.55 (dd, 1H, J=8.8 Hz, J=2.2 Hz), 7.25 (m, 1H), 7.22 (d, 1H, J=2.2 Hz), 6.76 (dm, 1H, J=7.7 Hz), 3.09 (s, 3H), 2.32 (s, 3H). MS: m/z 481 (M+1).

Synthesis of 3-{4-[4-Chloro-2-(2-methyl-1-oxy-pyridine-3-carbonyl)-phenylsulfamoyl]-phenyl}-propionic acid methyl ester

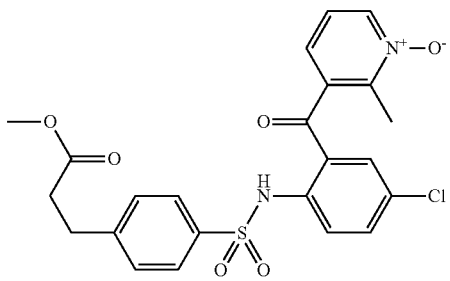 [SMILES: COC(=O)CCc1ccc(S(=O)(=O)Nc2ccc(Cl)cc2C(=O)c2ccc[n+]([O-])c2C)cc1]

The title compound was prepared by the mCPBA oxidation of 3-{4-[4-Chloro-2-(2-methyl-pyridine-3-carbonyl)-phenylsulfamoyl]-phenyl}-propionic acid methyl ester according to the general procedure. $^1$H NMR (CDCl3) δ 10.66 (br s, 1H, NH), 8.54 (dm, 1H, J=6.2 Hz), 7.78 (m, 3H), 7.52 (dd, 1H, J=8.8 Hz, J=2.2 Hz), 7.39 (t, 1H, J=7.2 Hz), 7.31 (d, 2H, J=8.0 Hz), 7.18 (m, 2H), 3.65 (s, 3H), 2.99 (t, 2H, J=7.6 Hz), 2.64 (t, 2H, J=7.6 Hz), 2.31 (s, 3H). MS: m/z 489 (M+1).

Synthesis of 4-tert-Butyl-N-[4-chloro-2-(6-methyl-1-oxy-pyridine-3-carbonyl)-phenyl]-benzenesulfonamide

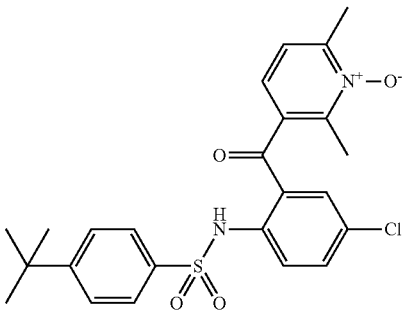 [SMILES: Cc1ccc(C(=O)c2cc(Cl)ccc2NS(=O)(=O)c2ccc(C(C)(C)C)cc2)c(C)[n+]1[O-]]

The title compound was prepared by the mCPBA oxidation of 4-tert-butyl-N-[4-chloro-2-(6-methyl-pyridine-3-carbonyl)-phenyl]-benzenesulfonamide according to the general procedure. $^1$H NMR (CDCl$_3$) δ 9.64 (br s, 1H, NH), 8.47 (m, 1H), 7.68 (d, 1H, J=8.8 Hz), 7.66 (d, 2H, J=8.8 Hz), 7.64 (m, 1H), 7.53 (m, 2H), 7.41 (d, 1H, J=2.2 Hz), 7.40 (d, 2H, J=8.8 Hz), 2.69 (s, 3H), 1.26 (s, 9H). MS: m/z 459 (M+1).

Approaches Towards the Synthesis of 2-sulphonamido-5-chloro-benzamide derivatives

Example A

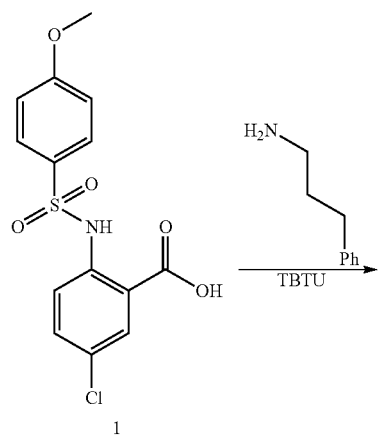

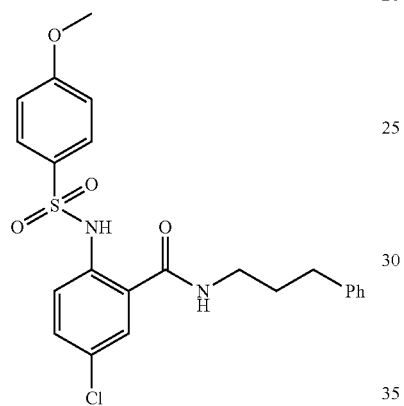

3-phenylpropyl amine (0.217 g, 1.61 mmol) and the acid (0.5 g, 1.5 mmol) were taken into dry DCM (30 ml). Triethyl amine (0.2 ml) was added to the mixture and this stirred at rt for 20 min. TBTU (0.987 g, 3.07 mmol) was then added to the mixture in portions and the mixture left overnight at rt with stirring. Then 10 ml of water was added to the mixture with stirring for a further 5 min. The layers were separated. The aqueous layer was extracted with DCM and combined with the organic layer obtained before. The combined organic layer was then dried concentrated and subjected to column chromatography (3:7:Ethyl acetate:Pet-ether as eluent) on silica.

Example B

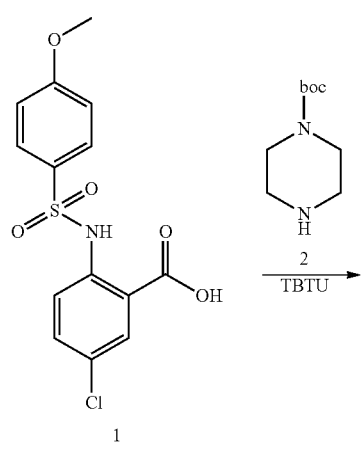

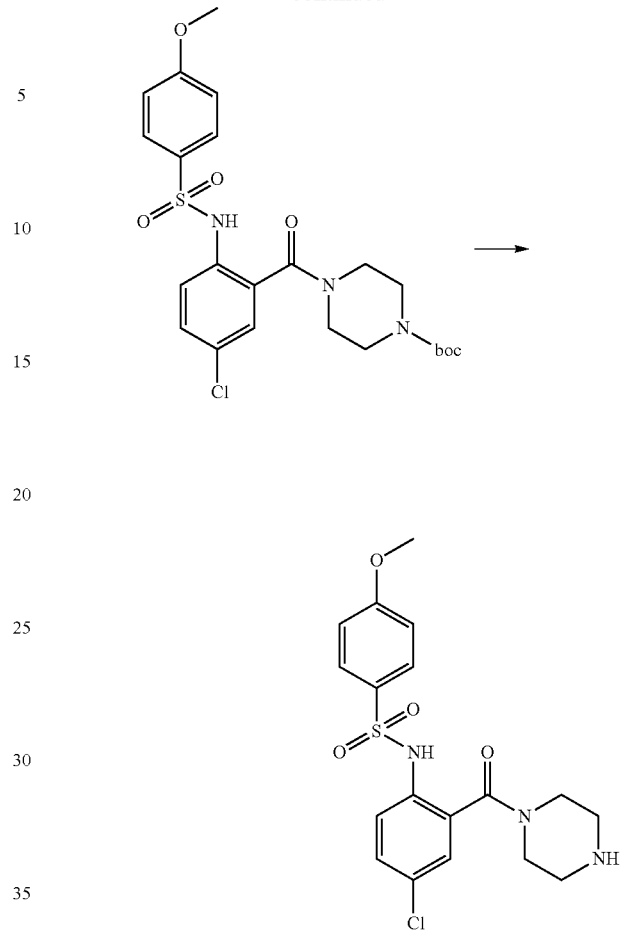

N-boc-piperazine (0.226 g, 1.21 mmol) and the acid (0.5 g, 1.4 mmol) were taken into dry DCM (30 ml). Triethyl amine (0.2 ml) was added to the mixture, which was then stirred at rt for 20 min. TBTU (1.974 g) was then added to the mixture in portions and the mixture left overnight at rt with stirring. 10 ml of water was then added to the mixture, with stirring for a further 5 min. The layers were separated. The aqueous layer was extracted with DCM and combined with the organic layer obtained before. The combined organic layer then dried. concentrated and subjected to column chromatography (3:7:Ethyl acetate:Pet-ether as eluent) on silica gel to obtain BOC-protected intermediate.

The BOC-protected compound from the previous step (300 mg) was taken in dry ether (10 ml), cooled to 0° C. and a saturated solution of ether in dry HCl (10 ml) was added slowly and the reaction kept overnight at room temperature with stirring. Next day the reaction mixture was washed with water and brine and dried with $Na_2SO_4$. Concentration, followed by purification of the crude product through column chromatography on silica gel (60-120 mesh, pet-ether/ethyl acetate) afforded product as pale yellow solid.

Approaches Towards the Synthesis of [4-chloro-2-(pyridin-4-ylsulfanyl)-phenyl]-benzenesulfonamide derivatives and [4-chloro-2-(heteroaryl-sulfanyl)-phenyl]-benzenesulfonamide derivatives Synthesis of 4-tert-Butyl-N-[4-chloro-2-(pyridin-4-ylsulfanyl)-phenyl]-benzenesulfonamide

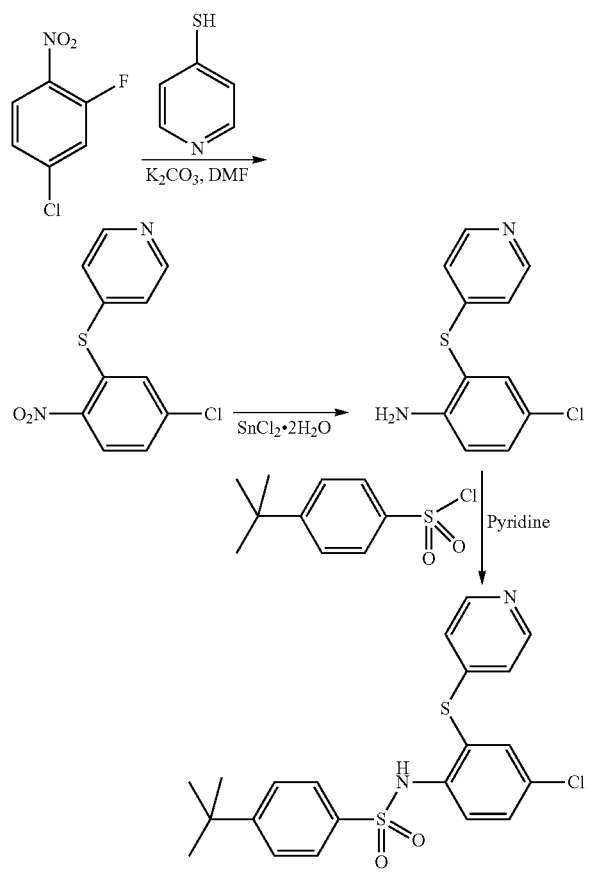

4-Mercaptopyridine (1.11 g, 10 mmol) and K$_2$CO$_3$ (1.38 g, 10 mmol) were suspended in DMF (10 mL) and stirred at room temperature for 15 min. The mixture was treated with 4-chloro-2-fluoro-1-nitro-benzene (1.75 g, 10 mmol) and heated at 50° C. for 16 h. After cooling to room temperature, water (50 mL) was added and the mixture extracted 3 times with ethyl acetate. The organic layer was combined the ethyl acetate and then reduced in vacuo. The residue was dissolved in DMF (30 mL) and treated with SnCl$_2$.2H$_2$O. The mixture was heated at 50° C. for 16 hr. The DMF was distilled off under vacuum and the reduction product was purified by flash chromatography on silica gel column (50-100% EtOAc/hexane) to afford 4-chloro-2-(pyridin-4-ylsulfanyl)-phenylamine as light yellow solid. The title sulfonamide compound was prepared according to the general procedure using 118 mg of 4-chloro-2-(pyridin-4-ylsulfanyl)-phenylamine prepared above and 116 mg of 4-tert-Butyl-benzenesulfonyl chloride. $^1$H-NMR (400 MHz, CDCl$_3$): δ 1.33 (s, 9H), 7.06 (d, 2H, J=6.8 Hz), 7.45 (d, 2H, J=8.4 Hz), 7.51 (m, 2H), 7.66 (d, 2H, 8.4 Hz), 7.71 (d, 1H, J=9.2 Hz), 8.43 (d, 2H, J=6.4 Hz). MS: m/z 433.9 (M$^+$+1).

Approaches Towards the Synthesis of [4-chloro-2-(1-oxy-pyridine-4-sulfonyl)-phenyl]-benzenesulfonamide derivatives and [4-chloro-2-(heteroaryl-sulfonyl)-phenyl]-benzenesulfonamide derivatives Synthesis of 4-tert-Butyl-N-[4-chloro-2-(1-oxy-pyridine-4-sulfonyl)-phenyl]-benzenesulfonamide

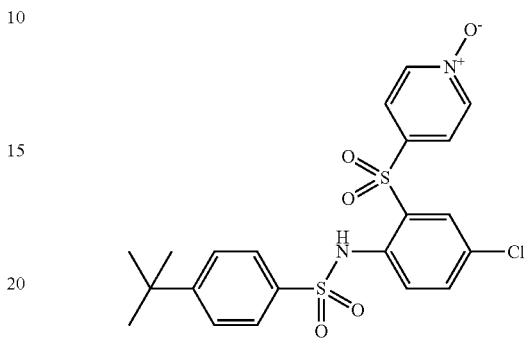

4-tert-Butyl-N-[4-chloro-2-(pyridin-4-ylsulfanyl)-phenyl]-benzenesulfonamide (59 mg, 0.25 mmol) and mCPBA (129 mg, 0.75 mmol) were dissolved in DCM (4 mL) and the mixture stirred at room temperature for 16 h. The solvent was evaporated and product was purified by HPLC. $^1$H-NMR (400 MHz, CDCl$_3$): δ 1.32 (s, 9H), 7.00 (d, 1H, J=8.4 Hz), 7.409 (b, 2H), 7.53 (dd, 1H, J=8.8 Hz, 2.0 Hz), 7.57 (d, 2H, J=8.4 Hz), 7.90 (d, 2H, J=8.4 Hz), 8.37 (b, 3H). MS: m/z 481.0 (M$^+$+1).

Measuring Efficacy of CCR9 Modulators

In Vitro Assays

A variety of assays can be used to evaluate the compounds provided herein, including signaling assays, migration assays, and other assays of cellular response. CCR9 receptor signaling assays can be used to measure the ability of a compound, such as a potential CCR9 antagonist, to block CCR9 ligand—(e.g. TECK)-induced signaling. A migration assay can be used to measure the ability of a compound of interest, such as a possible CCR9 antagonist, to block CCR9-mediated cell migration in vitro. The latter is believed to resemble chemokine-induced cell migration in vivo.

In a suitable assay, a CCR9 protein (whether isolated or recombinant) is used which has at least one property, activity, or functional characteristic of a mammalian CCR9 protein. The property can be a binding property (to, for example, a ligand or inhibitor), a signaling activity (e.g., activation of a mammalian G protein, induction of rapid and transient increase in the concentration of cytosolic free calcium [Ca$^{++}$]), cellular response function (e.g., stimulation of chemotaxis or inflammatory mediator release by leukocytes), and the like.

The assay can be a cell based assay that utilizes cells stably or transiently transfected with a vector or expression cassette having a nucleic acid sequence which encodes the CCR9 receptor. The cells are maintained under conditions appropriate for expression of the receptor and are contacted with a putative agent under conditions appropriate for binding to occur. Binding can be detected using standard techniques. For example, the extent of binding can be determined relative to a suitable control (for example, relative to background in the absence of a putative agent, or relative to a known ligand). Optionally, a cellular fraction, such as a membrane fraction, containing the receptor can be used in lieu of whole cells.

Detection of binding or complex formation can be detected directly or indirectly. For example, the putative agent can be labeled with a suitable label (e.g., fluorescent label, chemiluminescent label, isotope label, enzyme label, and the like) and binding can be determined by detection of the label. Specific and/or competitive binding can be assessed by competition or displacement studies, using unlabeled agent or a ligand (e.g., TECK) as a competitor.

Binding inhibition assays can be used to evaluate the present compounds. In these assays, the compounds are evaluated as inhibitors of ligand binding using, for example, TECK. In this embodiment, the CCR9 receptor is contacted with a ligand such as TECK and a measure of ligand binding is made. The receptor is then contacted with a test agent in the presence of a ligand (e.g., TECK) and a second measurement of binding is made. A reduction in the extent of ligand binding is indicative of inhibition of binding by the test agent. The binding inhibition assays can be carried out using whole cells which express CCR9, or a membrane fraction from cells which express CCR9.

The binding of a G protein coupled receptor by, for example, an agonist, can result in a signaling event by the receptor. Accordingly, signaling assays can also be used to evaluate the compounds of the present invention and induction of signaling function by an agent can be monitored using any suitable method. For example, G protein activity, such as hydrolysis of GTP to GDP, or later signaling events triggered by receptor binding can be assayed by known methods (see, for example, PCT/US97/15915; Neote, et al., *Cell*, 72:415425 (1993); Van Riper, et al., *J. Exp. Med.*, 177:851-856 (1993) and Dahinden, et al., *J. Exp. Med.*, 179:751-756 (1994)).

Chemotaxis assays can also be used to assess receptor function and evaluate the compounds provided herein. These assays are based on the functional migration of cells in vitro or in vivo induced by an agent, and can be used to assess the binding and/or effect on chemotaxis of ligands, inhibitors, or agonists. A variety of chemotaxis assays are known in the art, and any suitable assay can be used to evaluate the compounds of the present invention. Examples of suitable assays include those described in PCT/US97/15915; Springer, et al., WO 94/20142; Berman et al., *Immunol. Invest.*, 17:625-677 (1988); and Kavanaugh et al., *J. Immunol.*, 146:4149-4156 (1991)).

Calcium signaling assays measure calcium concentration over time, preferably before and after receptor binding. These assays can be used to quantify the generation of a receptor signaling mediator, $Ca^{++}$, following receptor binding (or absence thereof). These assays are useful in determining the ability of a compound, such as those of the present invention, to generate the receptor signaling mediator by binding to a receptor of interest. Also, these assays are useful in determining the ability of a compound, such as those of the present invention, to inhibit generation of the receptor signaling mediator by interfering with binding between a receptor of interest and a ligand.

In calcium signaling assays used to determine the ability of a compound to interfere with binding between CCR9 and a known CCR9 ligand, CCR9-expressing cells (such as a T cell line MOLT-4 cells) are first incubated with a compound of interest, such as a potential CCR9 antagonist, at increasing concentrations. The cell number can be from $10^5$ to $5 \times 10^5$ cells per well in a 96-well microtiter plate. The concentration of the compound being tested may range from 0 to 100 uM. After a period of incubation (which can range from 5 to 60 minutes), the treated cells are placed in a Fluorometric Imaging Plate Reader (FLIPR®) (available from Molecular Devices Corp., Sunnyvale, Calif.) according to the manufacturer's instruction. The FLIPR system is well known to those skilled in the art as a standard method of performing assays. The cells are then stimulated with an appropriate amount of the CCR9 ligand TECK (e.g. 5-100 nM final concentration) and the signal of intracellular calcium increase (also called calcium flux) is recorded. The efficacy of a compound as an inhibitor of binding between CCR9 and the ligand can be calculated as an 1050 (the concentration needed to cause 50% inhibition in signaling) or 1090 (at 90% inhibition).

In vitro cell migration assays can be performed (but are not limited to this format) using the 96-well microchamber (called ChemoTX™). The ChemoTX system is well known to those skilled in the art as a type of chemotactic/cell migration instrument. In this assay, CCR9-expressing cells (such as MOLT-4) are first incubated with a compound of interest, such as a possible CCR9 antagonist, at increasing concentrations. Typically, fifty thousand cells per well are used, but the amount can range from $10^3$-$10^6$ cells per well. CCR9 ligand TECK, typically at 50 nM (but can range from 5-100 nM), is placed at the lower chamber and the migration apparatus is assembled. Twenty microliters of test compound-treated cells are then placed onto the membrane. Migration is allowed to take place at 37 C. for a period of time, typically 2.5 hours. At the end of the incubation, the number of cells that migrated across the membrane into the lower chamber is then quantified. The efficacy of a compound as an inhibitor of CCR9-mediated cell migration is calculated as an 1050 (the concentration needed to reduce cell migration by 50%) or 1090 (for 90% inhibition).

In Vivo Efficacy Models for Human IBD

T cell infiltration into the small intestine and colon have been linked to the pathogenesis of human inflammatory bowel diseases which include Coeliac disease, Crohn's disease and ulcerative colitis. Blocking trafficking of relevant T cell populations to the intestine is believed to be an effective approach to treat human IBD. CCR9 is expressed on gut-homing T cells in peripheral blood, elevated in patients with small bowel inflammation such as Crohn's disease and Coeliac disease. CCR9 ligand TECK is expressed in the small intestine. It is thus believed that this ligand-receptor pair plays a role in IBD development by mediating migration of T cells to the intestine. Several animal models exist and can be used for evaluating compounds of interest, such as potential CCR9 antagonists, for an ability to affect such T cell migration and/or condition or disease, which might allow efficacy predictions of antagonists in humans.

Animal Models with Pathology Similar to Human Ulcerative Colitis

A murine model described by Panwala and coworkers (Panwala, et al., *J Immunol.*, 161(10):5733-44 (1998)) involves genetic deletion of the murine multi-drug resistant gene (MDR). MDR knockout mice (MDR−/−) are susceptible to developing a severe, spontaneous intestinal inflammation when maintained under specific pathogen-free facility conditions. The intestinal inflammation seen in MDR−/− mice has a pathology similar to that of human inflammatory bowel disease (IBD) and is defined by Th1 type T cells infiltration into the lamina propria of the large intestine.

Another murine model was described by Davidson et al., *J Exp Med.*, 184(1):241-51 (1986). In this model, the murine IL-10 gene was deleted and mice rendered deficient in the production of interleukin 10 (IL-10−/−). These mice develop a chronic inflammatory bowel disease (IBD) that predominates in the colon and shares histopathological features with human IBD.

Another murine model for IBD has been described by Powrie et al., *Int Immunol.*, 5(11):1461-71 (1993), in which a subset of CD4+ T cells (called CD45RB(high)) from immunocompetent mice are purified and adoptively transferred into immunodeficient mice (such as C.B-17 scid mice). The animal restored with the CD45RBhighCD4+ T cell population developed a lethal wasting disease with severe mononuclear cell infiltrates in the colon, pathologically similar with human IBD.

Murine Models with Pathology Similar to Human Crohn's Disease

The TNF ARE(−/−) Model.

The role of TNF in Crohn's disease in human has been demonstrated more recently by success of treatment using anti-TNF alpha antibody by Targan et al., *N Engl J Med.*, 337(15):1029-35 (1997). Mice with aberrant production of TNF-alpha due to genetic alteration in the TNF gene (ARE−/−) develop Crohn's-like inflammatory bowel diseases (see Kontoyiannis et al., *Immunity*, 10(3):387-98 (1999)).

The SAMP/Yit Model.

This is model described by Kosiewicz et al., *J Clin Invest.*, 107(6):695-702 (2001). The mouse strain, SAMP/Yit, spontaneously develops a chronic inflammation localized to the terminal ileum. The resulting ileitis is characterized by massive infiltration of activated T lymphocytes into the lamina propria, and bears a remarkable resemblance to human Crohn's disease.

Biological Activity

The compound in [00755] illustrates the activity associated with representative compounds of the invention.

Materials and Methods (In Vitro Assays)

Reagents and Cells

MOLT-4 cells were obtained from the American Type Culture Collection (Manassas, Va.) and cultured in RPMI tissue culture medium supplemented with 10% fetal calf serum (FCS) in a humidified 5% $CO_2$ incubator at 37° C. Recombinant human chemokine protein TECK was obtained from R&D Systems (Minneapolis, Minn.). ChemoTX® chemotaxis microchambers were purchased from Neuro Probe (Gaithersburg, Md.). CyQUANT® cell proliferation kits were purchased from Molecular Probes (Eugene, Oreg.). Calcium indicator dye Fluo-4 AM was purchased from Molecular Devices (Mountain View, Calif.).

Conventional Migration Assay

Conventional migration assay was used to determine the efficacy of potential receptor antagonists in blocking migration mediated through CCR9. This assay was routinely performed using the ChemoTX® microchamber system with a 5-µm pore-sized polycarbonate membrane. To begin such an assay, MOLT-4 cells were harvested by centrifugation of cell suspension at 1000 PRM on a GS-6R Beckman centrifuge. The cell pellet was resuspended in chemotaxis buffer (HBSS with 0.1% BSA) at $5\times10^6$ cells/mL. Test compounds at desired concentrations were prepared from 10 mM stock solutions by serial dilutions in chemotaxis buffer. An equal volume of cells and compounds were mixed and incubated at room temperature for 15 minutes. Afterwards, 20 µL of the mixture was transferred onto the porus membrane of a migration microchamber, with 29 µL of 50 nM chemokine TECK protein placed at the lower chamber. Following a 150-minute incubation at 37° C., during which cells migrated against the chemokine gradient, the assay was terminated by removing the cell drops from atop the filter. To quantify cells migrated across the membrane, 5 µL of 7X CyQUANT® solution was added to each well in the lower chamber, and the fluorescence signal measured on a Spectrafluor Plus fluorescence plate reader (TECAN, Durham, N.C.). The degree of inhibition was determined by comparing migration signals between compound-treated and untreated cells. 1050 calculation was further performed by non-linear squares regression analysis using Graphpad Prism (Graphpad Software, San Diego, Calif.).

RAM Assay

The primary screen to identify CCR9 antagonists was carried out using RAM assay (WO 02101350), which detects potential hits by their ability to activate cell migration under inhibitory TECK concentration. To begin such an assay, MOLT-4 cells were harvested by centrifugation of cell suspension at 1000 RPM on a GS-6R Beckman centrifuge. The cell pellet was resuspended in chemotaxis buffer (HBSS/0.1% BSA) at $5\times10^6$ cells/mL. Twenty-five microliters of cells was mixed with an equal volume of a test compound diluted to 20 µM in the same buffer. Twenty microliters of the mixture was transferred onto the filter in the upper chemotaxis chamber, with 29 µL of 500 nM chemokine protein TECK placed in the lower chamber. Following a 150-minute incubation at 37° C., the assay was terminated by removing the cell drops from atop the filter. To quantify cells migrated across the membrane, 5 µL of 7X CyQUANT® solution was added to each well in the lower chamber, and the fluorescence signal measured on a Spectrafluor Plus fluorescence plate reader (TECAN, Durham, N.C.).

For selection of potential hits, the level of migration activation was calculated as a RAM index—the ratio between the signal of a particular well and the median signal of the whole plate. Compounds with a RAM index of greater than 1.8 were regarded as RAM positive, and were selected for $IC_{50}$ determinations in conventional functional assays.

Calcium Flux Assay

Calcium flux assay measures an increase in intracellular calcium following ligand-induced receptor activation. In the screen of CCR9 antagonists, it was used as a secondary assay carried out on a FLIPR® machine (Molecular Devices, Mountain View, Calif.). To begin an assay, MOLT-4 cells were harvested by centrifugation of cell suspension, and resuspended to $1.5\times10^6$ cells/mL in HBSS (with 1% fetal calf serum). Cells were then labeled with a calcium indicator dye Fluo-4 AM for 45 minutes at 37° C. with gentle shaking. Following incubation, cells were pelletted, washed once with HBSS and resuspended in the same buffer at a density of $1.6\times10^6$ cells/mL. One hundred microliters of labeled cells were mixed with 10 µL of test compound at the appropriate concentrations on an assay plate. Chemokine protein TECK was added at a final concentration of 25 nM to activate the receptor. The degree of inhibition was determined by comparing calcium signals between compound-treated and untreated cells. IC50 calculations were further performed by non-linear squares regression analysis using Graphpad Prism (Graphpad Software, San Diego, Calif.).

Discovery of CCR9 Antagonists

The discovery of CCR9 antagonists was carried out in two steps: First, RAM assay was used to screen a compound library in a high-throughput manner. The assay detected compounds by their ability to cause a positive migration signal under RAM condition. Secondly, RAM positive compounds were tested to determine their $IC_{50}$s using the conventional migration and calcium flux assays.

For instance, in a screen of approximately 100,000 compounds, 2000 individual wells representing approximately 2% of total compounds showed a RAM index greater than 1.8. These compounds were cheery-picked and retested in duplicate wells by RAM assay. A total of 270 compounds, or 0.27% of the library, were confirmed RAM positives.

Since a RAM positive signal indicates only the presence of a receptor antagonist and not how strongly it blocks receptor functions, the RAM positive compounds were further tested for potency in calcium flux assay using MOLT-4 cells. $IC_{50}$ determinations on this subset discovered several compounds with $IC_{50}$'s less than 1 μM and that did not inhibit other chemokine receptors examined at significant levels.

In Vivo Efficacy Studies

The MDR1a-knockout mice, which lack the P-glycoprotein gene, spontaneously develop colitis under specific pathogen-free condition. The pathology in these animals has been characterized as Th1-type T cell-mediated inflammation similar to ulcerative colitis in humans. Disease normally begins to develop at around 8-10 weeks after birth. However the ages at which disease emerges and the ultimate penetrance level often vary considerably among different animal facilities.

In a study using the MDR1a-knockout mice, the CCR9 antagonist shown below:

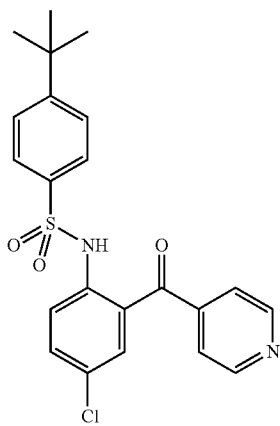 [SMILES: CC(C)(C)c1ccc(S(=O)(=O)Nc2ccc(Cl)cc2C(=O)c2ccncc2)cc1]

was evaluated by prophylactic administration for its ability to delay disease onset. Female mice (n=34) were dosed with 50 mg/kg twice a day by subcutaneous injections for 14 consecutive weeks starting at age 10 weeks. The study showed that the compound prevented IBD-associated growth retardation. Moreover, the number of mice developing diarrhea was also lower among compound-treated mice (17%), compared to mice receiving vehicle alone (24%) (FIG. 1).

In the tables below, structures and activity are provided for representative compounds described herein. Activity is provided as follows for either or both of the chemotaxis assay and/or calcium mobilization assays, described above: +, $IC_{50}$>1000 nM; and ++, $IC_{50}$<1000 nM.

TABLE 1

Compounds with activity in either or both of the chemotaxis assay and calcium mobilization assays, with $IC_{50}$ < 1000 nM (++)

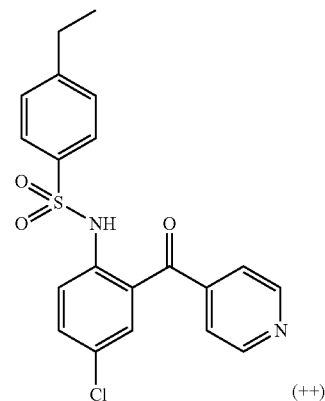 [SMILES: CCc1ccc(S(=O)(=O)Nc2ccc(Cl)cc2C(=O)c2ccncc2)cc1]

(++)

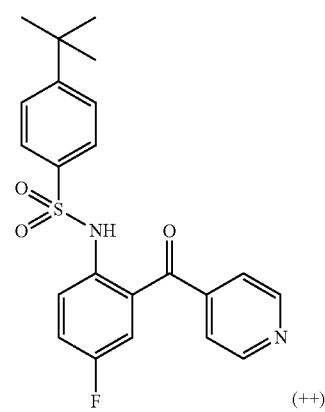 [SMILES: CC(C)(C)c1ccc(S(=O)(=O)Nc2ccc(F)cc2C(=O)c2ccncc2)cc1]

(++)

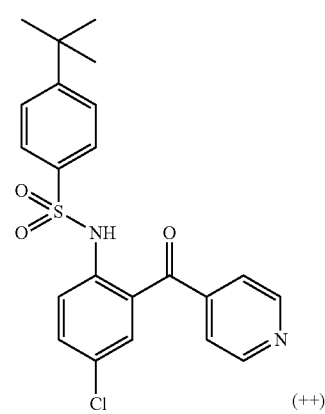 [SMILES: CC(C)(C)c1ccc(S(=O)(=O)Nc2ccc(Cl)cc2C(=O)c2ccncc2)cc1]

(++)

TABLE 1-continued
Compounds with activity in either or both of the chemotaxis assay and calcium mobilization assays, with IC$_{50}$ < 1000 nM (++)
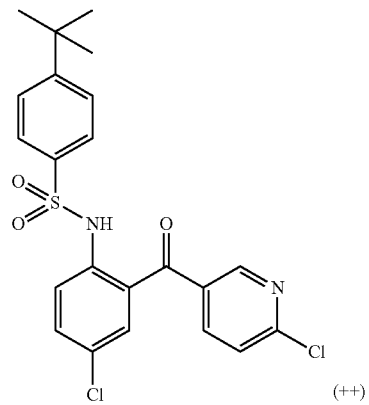 [SMILES: CC(C)(C)c1ccc(S(=O)(=O)Nc2ccc(Cl)cc2C(=O)c2ccc(Cl)nc2)cc1]
(++)
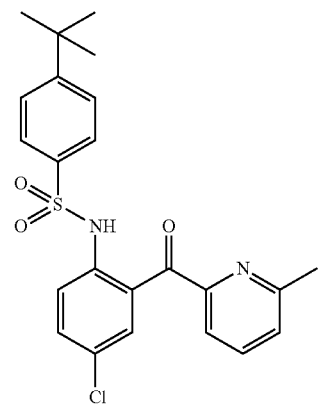
(++)
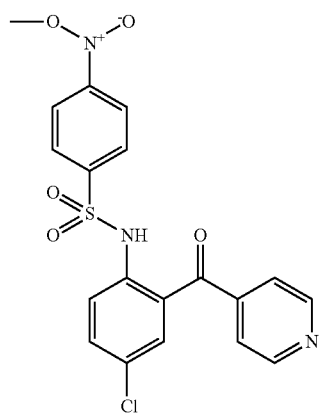
(++)
TABLE 1-continued
Compounds with activity in either or both of the chemotaxis assay and calcium mobilization assays, with IC$_{50}$ < 1000 nM (++)
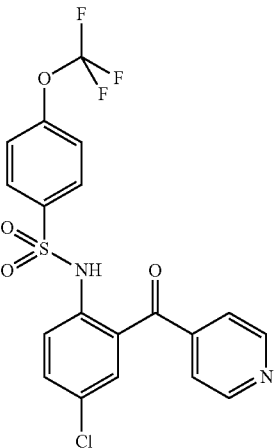
(++)
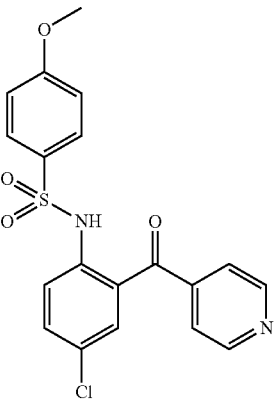
(++)
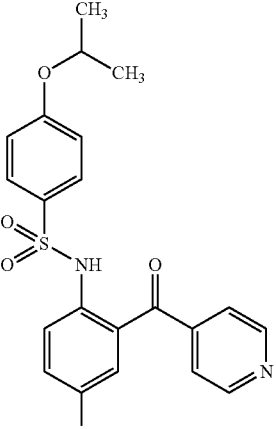
(++)

TABLE 1-continued
Compounds with activity in either or both of the chemotaxis assay and calcium mobilization assays, with IC$_{50}$ < 1000 nM (++)
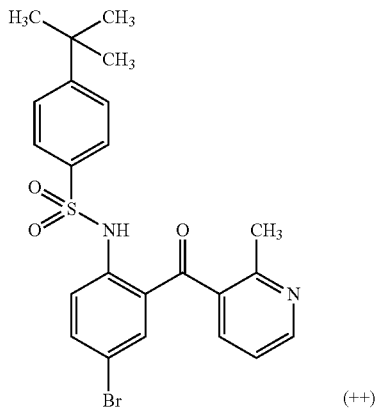 [SMILES: Cc1ncccc1C(=O)c1cc(Br)ccc1NS(=O)(=O)c1ccc(C(C)(C)C)cc1]
(++)
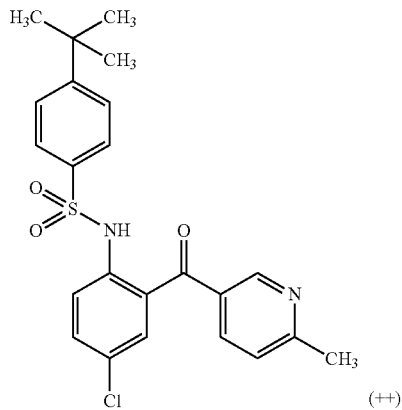
(++)
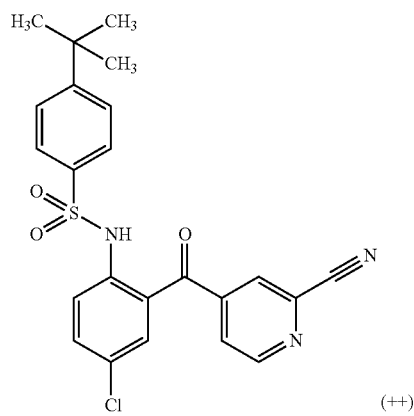 [SMILES: CC(C)(C)c1ccc(S(=O)(=O)Nc2ccc(Cl)cc2C(=O)c2ccnc(C#N)c2)cc1]
(++)
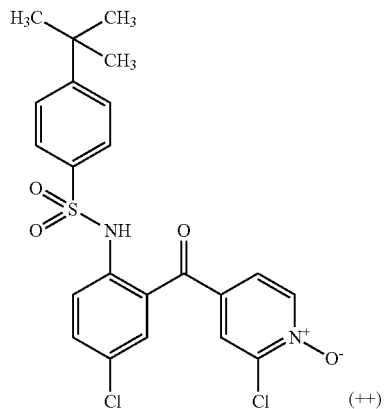
(++)
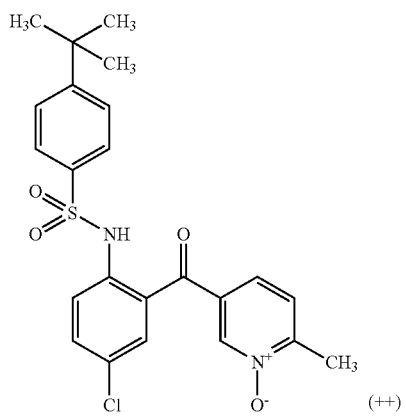 [SMILES: Cc1ccc(C(=O)c2cc(Cl)ccc2NS(=O)(=O)c2ccc(C(C)(C)C)cc2)c[n+]1[O-]]
(++)
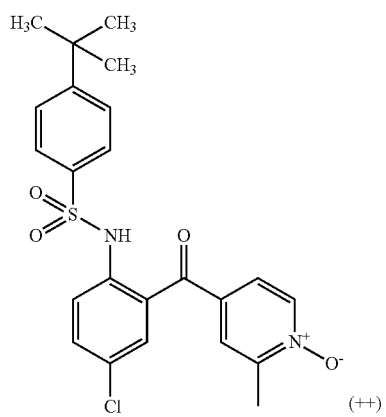 [SMILES: Cc1cc(C(=O)c2cc(Cl)ccc2NS(=O)(=O)c2ccc(C(C)(C)C)cc2)cc[n+]1[O-]]
(++)

TABLE 1-continued
Compounds with activity in either or both of the chemotaxis assay and calcium mobilization assays, with IC$_{50}$ < 1000 nM (++)
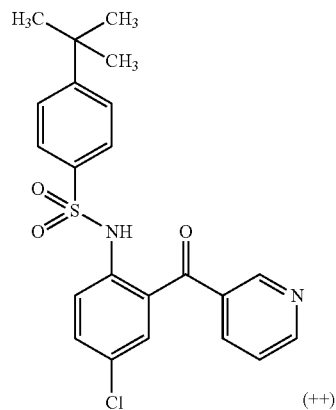 [SMILES: CC(C)(C)c1ccc(S(=O)(=O)Nc2ccc(Cl)cc2C(=O)c2cccnc2)cc1]
(++)
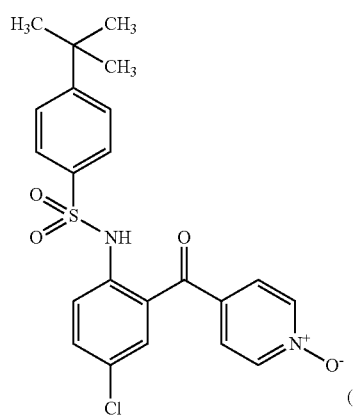
(++)
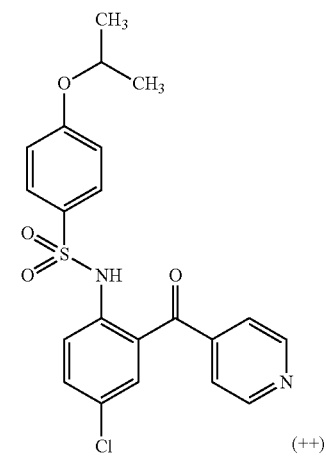 [SMILES: CC(C)Oc1ccc(S(=O)(=O)Nc2ccc(Cl)cc2C(=O)c2ccncc2)cc1]
(++)
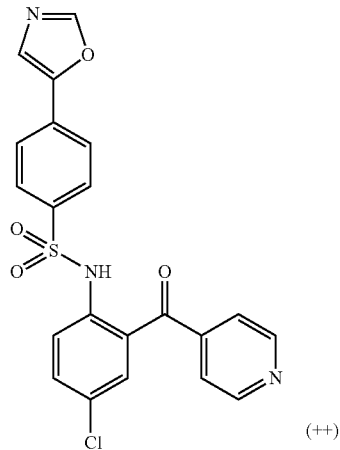
(++)
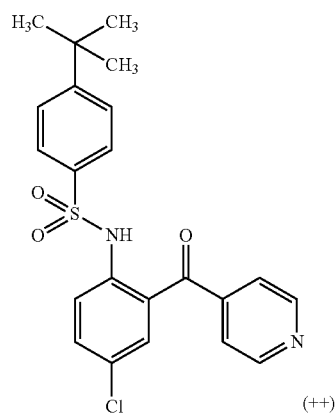 [SMILES: CC(C)(C)c1ccc(S(=O)(=O)Nc2ccc(Cl)cc2C(=O)c2ccncc2)cc1]
(++)
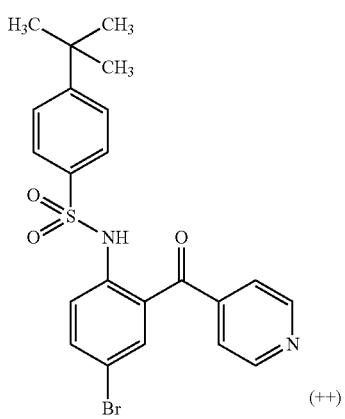
(++)

TABLE 1-continued
Compounds with activity in either or both of the chemotaxis assay and calcium mobilization assays, with IC$_{50}$ < 1000 nM (++)
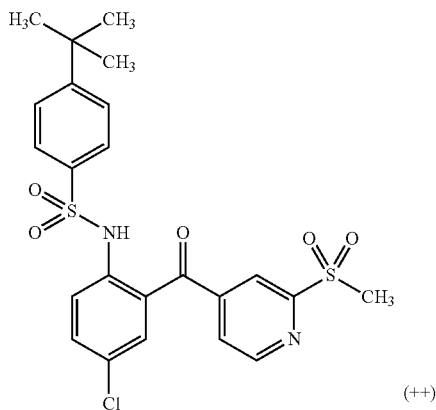 [SMILES: CC(C)(C)c1ccc(S(=O)(=O)Nc2ccc(Cl)cc2C(=O)c2ccnc(S(C)(=O)=O)c2)cc1]
(++)
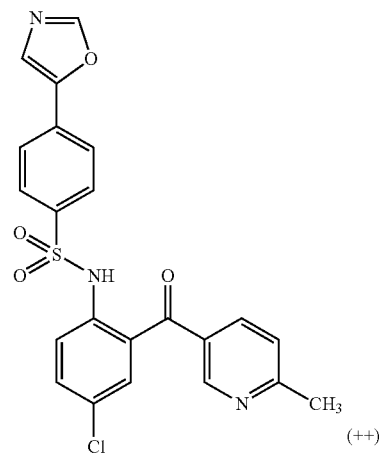 [SMILES: Cc1ccc(C(=O)c2cc(Cl)ccc2NS(=O)(=O)c2ccc(-c3cnco3)cc2)cn1]
(++)
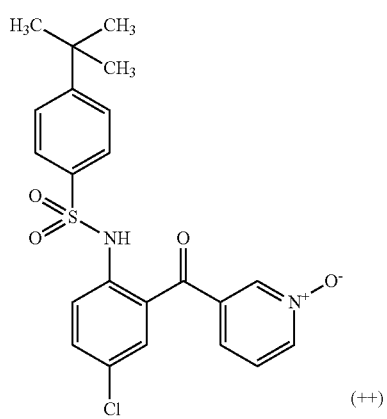 [SMILES: CC(C)(C)c1ccc(S(=O)(=O)Nc2ccc(Cl)cc2C(=O)c2ccc[n+]([O-])c2)cc1]
(++)
TABLE 1-continued
Compounds with activity in either or both of the chemotaxis assay and calcium mobilization assays, with IC$_{50}$ < 1000 nM (++)
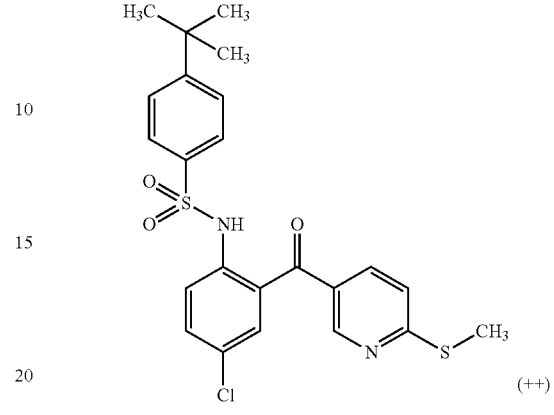
(++)
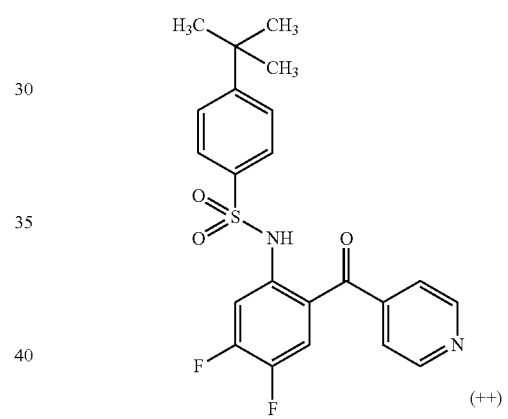
(++)
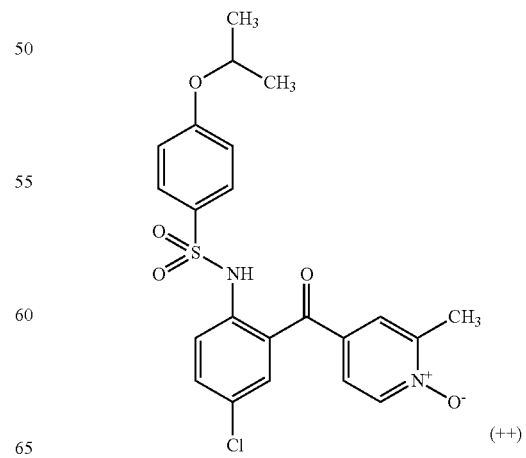
(++)

TABLE 1-continued
Compounds with activity in either or both of the chemotaxis assay and calcium mobilization assays, with IC$_{50}$ < 1000 nM (++)
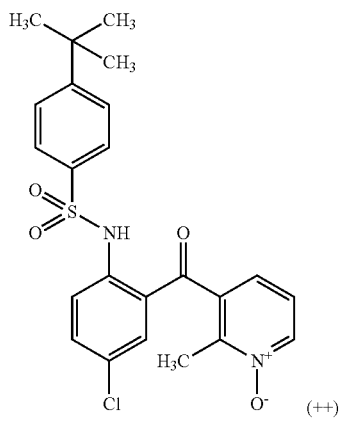 [SMILES: Cc1c(C(=O)c2cc(Cl)ccc2NS(=O)(=O)c2ccc(C(C)(C)C)cc2)ccc[n+]1[O-]]
(++)
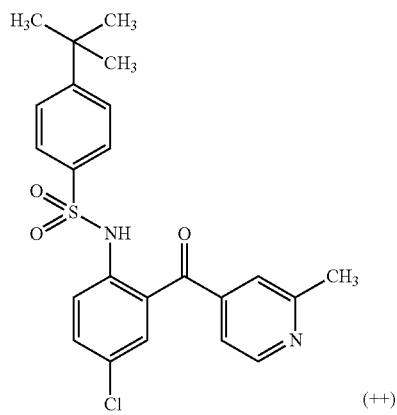
(++)
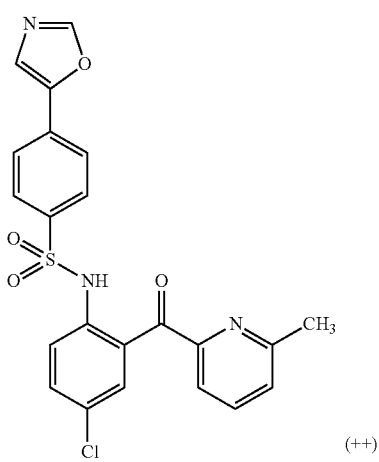 [SMILES: Cc1cccc(C(=O)c2cc(Cl)ccc2NS(=O)(=O)c2ccc(-c3cnco3)cc2)n1]
(++)
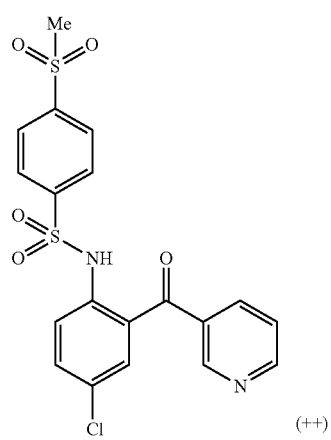
(++)
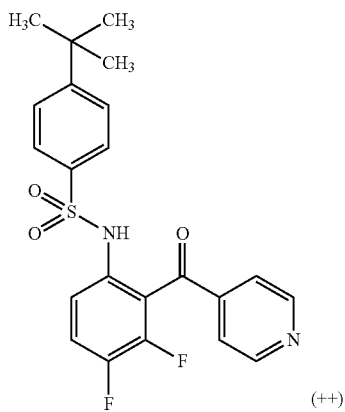 [SMILES: CC(C)(C)c1ccc(S(=O)(=O)Nc2ccc(F)c(F)c2C(=O)c2ccncc2)cc1]
(++)
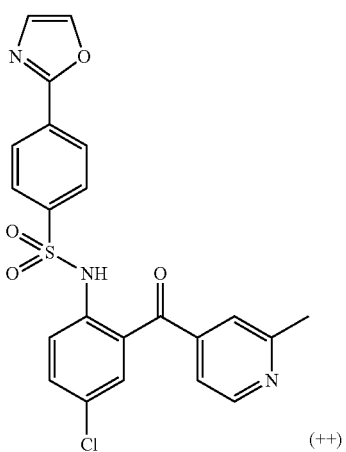 [SMILES: Cc1cc(C(=O)c2cc(Cl)ccc2NS(=O)(=O)c2ccc(-c3ncco3)cc2)ccn1]
(++)

TABLE 1-continued
Compounds with activity in either or both of the chemotaxis assay and calcium mobilization assays, with IC$_{50}$ < 1000 nM (++)
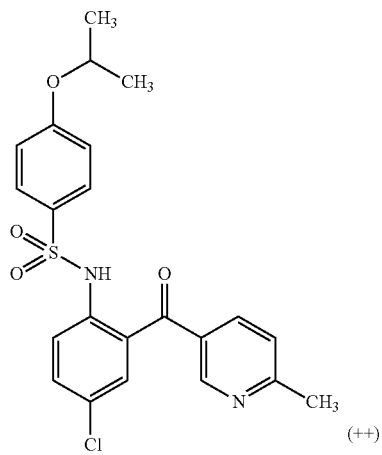 [SMILES: Cc1ccc(C(=O)c2cc(Cl)ccc2NS(=O)(=O)c2ccc(OC(C)C)cc2)cn1]
(++)
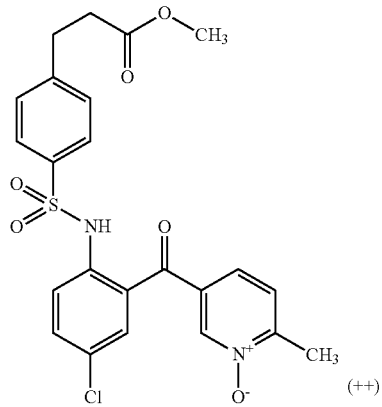 [SMILES: COC(=O)CCc1ccc(S(=O)(=O)Nc2ccc(Cl)cc2C(=O)c2ccc(C)[n+]([O-])c2)cc1]
(++)
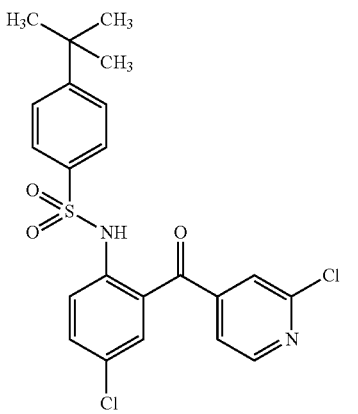
(++)
TABLE 1-continued
Compounds with activity in either or both of the chemotaxis assay and calcium mobilization assays, with IC$_{50}$ < 1000 nM (++)
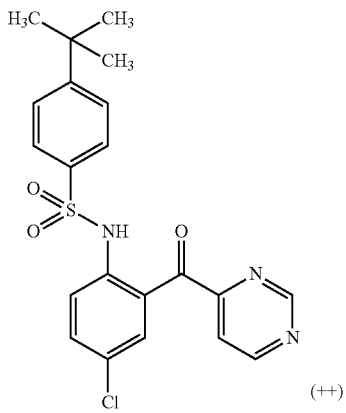
(++)
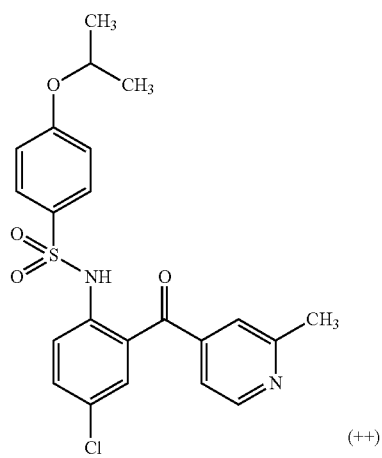 [SMILES: Cc1cc(C(=O)c2cc(Cl)ccc2NS(=O)(=O)c2ccc(OC(C)C)cc2)ccn1]
(++)
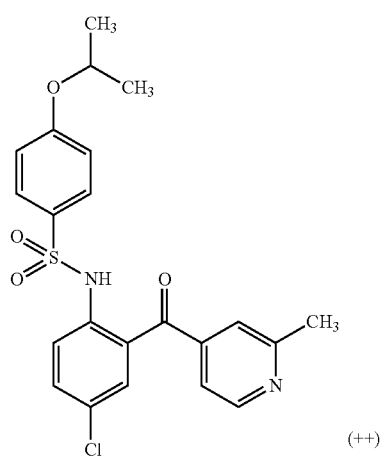 [SMILES: Cc1cc(C(=O)c2cc(Cl)ccc2NS(=O)(=O)c2ccc(OC(C)C)cc2)ccn1]
(++)

TABLE 1-continued
Compounds with activity in either or both of the chemotaxis assay and calcium mobilization assays, with IC$_{50}$ < 1000 nM (++)
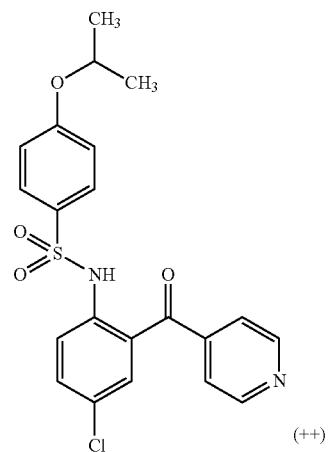 [SMILES: CC(C)Oc1ccc(S(=O)(=O)Nc2ccc(Cl)cc2C(=O)c2ccncc2)cc1]
(++)
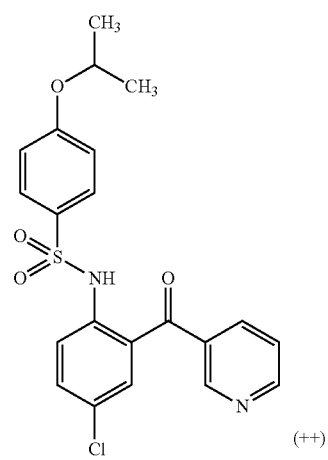 [SMILES: CC(C)Oc1ccc(S(=O)(=O)Nc2ccc(Cl)cc2C(=O)c2cccnc2)cc1]
(++)
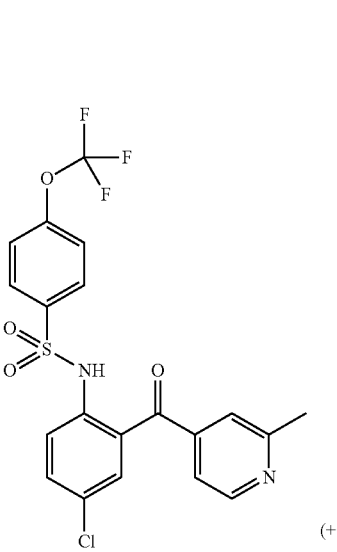
(++)
TABLE 1-continued
Compounds with activity in either or both of the chemotaxis assay and calcium mobilization assays, with IC$_{50}$ < 1000 nM (++)
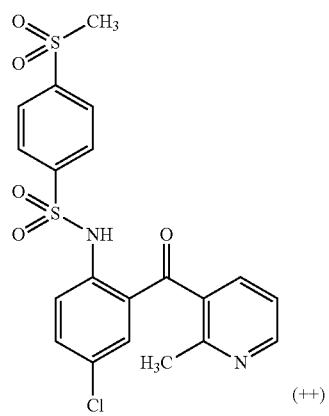 [SMILES: Cc1ncccc1C(=O)c1cc(Cl)ccc1NS(=O)(=O)c1ccc(S(C)(=O)=O)cc1]
(++)
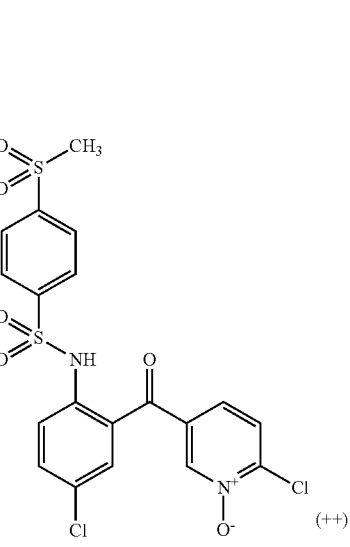
(++)
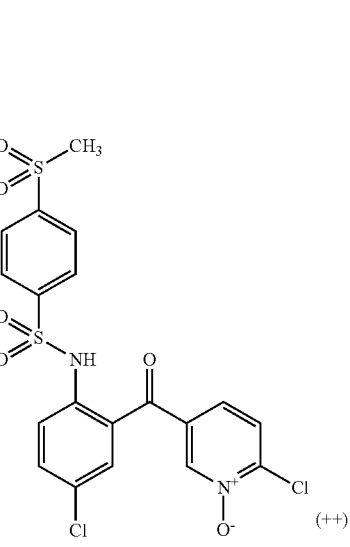
(++)

TABLE 1-continued
Compounds with activity in either or both of the chemotaxis assay and calcium mobilization assays, with IC$_{50}$ < 1000 nM (++)
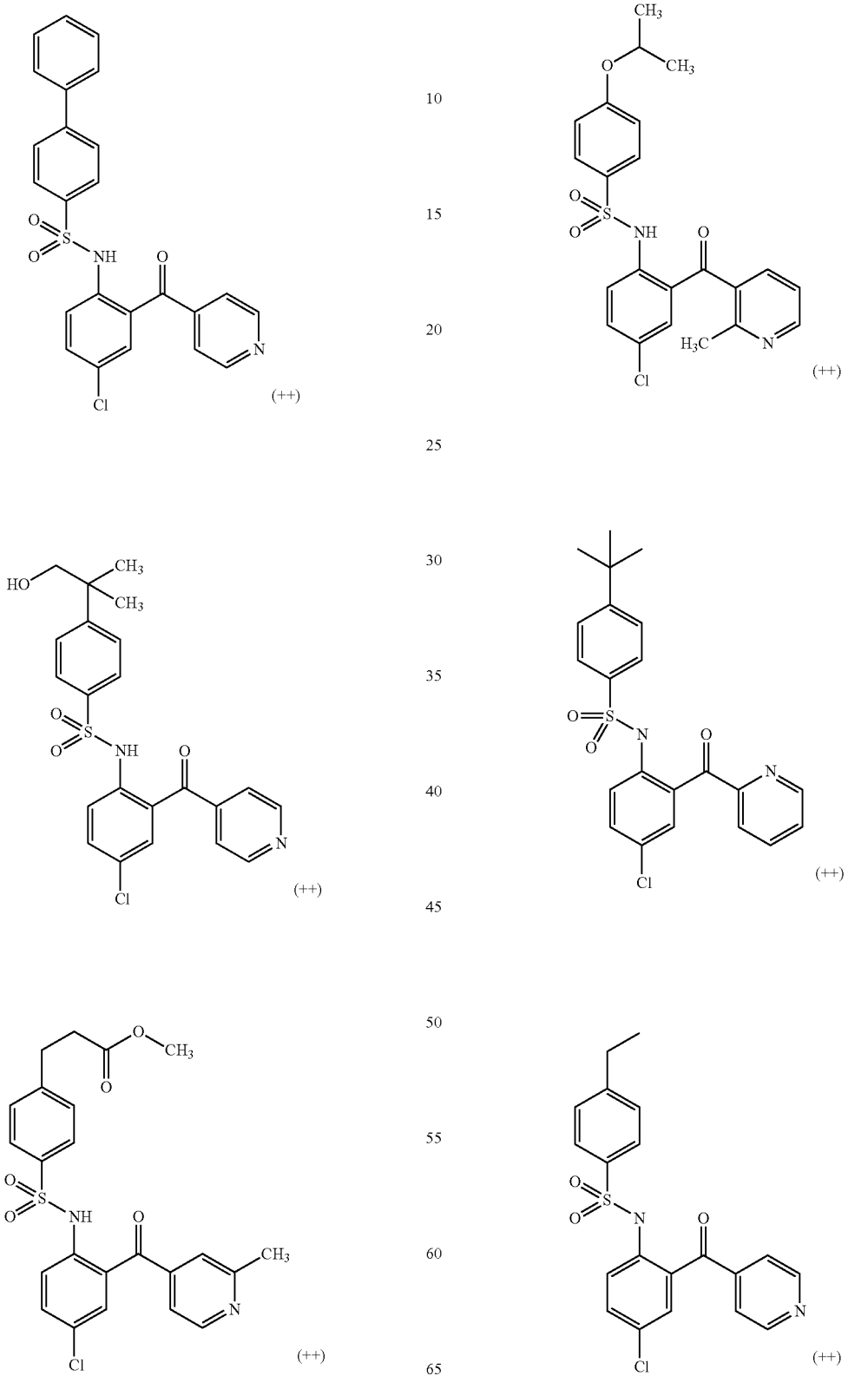

TABLE 1-continued
Compounds with activity in either or both of the chemotaxis assay and calcium mobilization assays, with $IC_{50} < 1000$ nM (++)
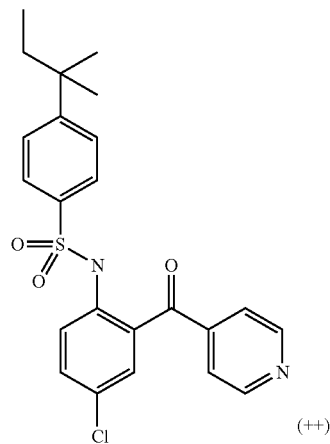 [SMILES: CCC(C)(C)c1ccc(S(=O)(=O)Nc2ccc(Cl)cc2C(=O)c2ccncc2)cc1]
(++)
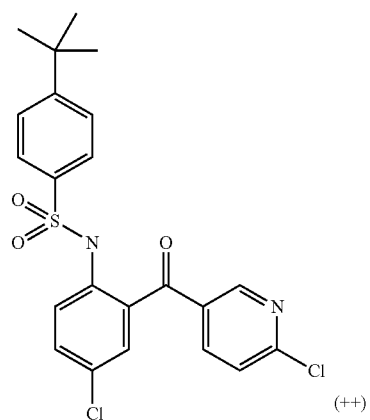 [SMILES: CC(C)(C)c1ccc(S(=O)(=O)Nc2ccc(Cl)cc2C(=O)c2ccc(Cl)nc2)cc1]
(++)
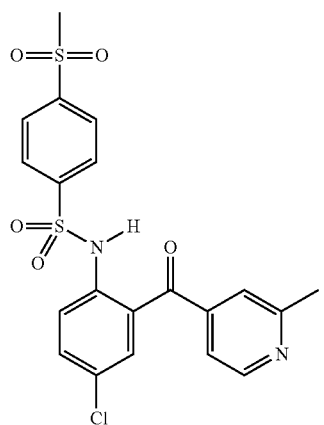
(++)
TABLE 1-continued
Compounds with activity in either or both of the chemotaxis assay and calcium mobilization assays, with $IC_{50} < 1000$ nM (++)
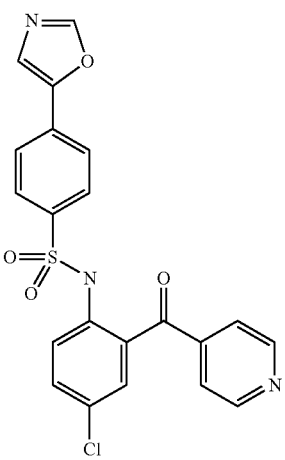
(++)
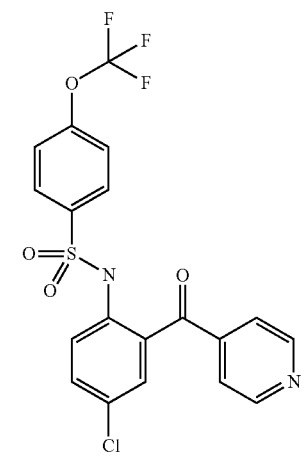
(++)
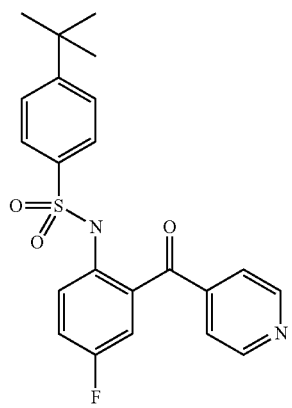
(++)

TABLE 1-continued
Compounds with activity in either or both of the chemotaxis assay and calcium mobilization assays, with IC$_{50}$ < 1000 nM (++)
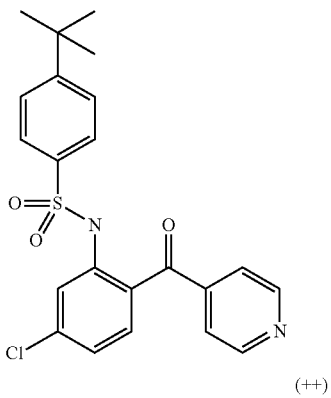 [SMILES: CC(C)(C)c1ccc(S(=O)(=O)Nc2cc(Cl)ccc2C(=O)c2ccncc2)cc1]
(++)
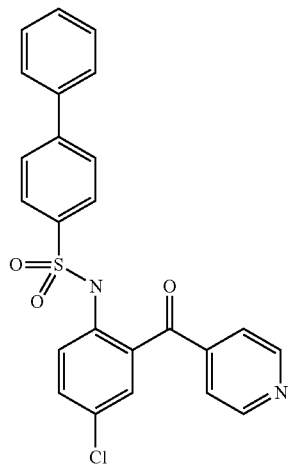
(++)
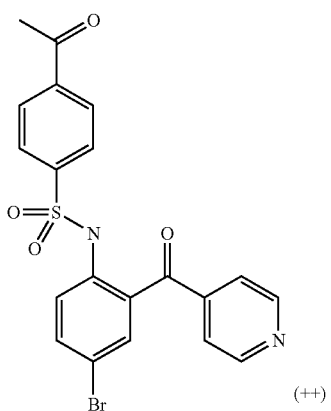 [SMILES: CC(=O)c1ccc(S(=O)(=O)Nc2ccc(Br)cc2C(=O)c2ccncc2)cc1]
(++)
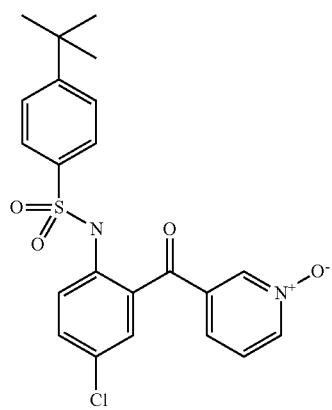
(++)
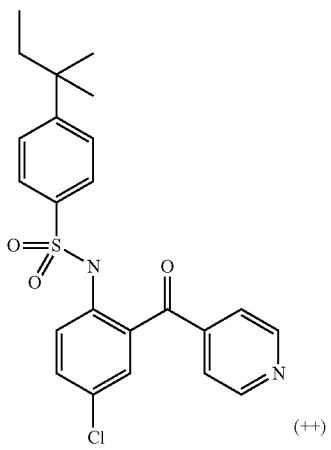 [SMILES: CCC(C)(C)c1ccc(S(=O)(=O)Nc2ccc(Cl)cc2C(=O)c2ccncc2)cc1]
(++)
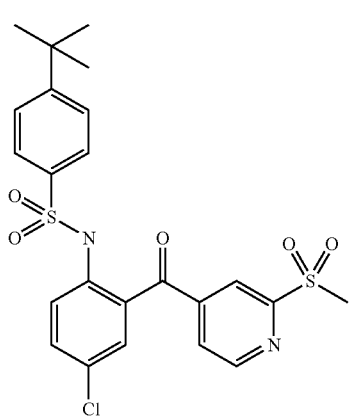
(++)

TABLE 1-continued
Compounds with activity in either or both of the chemotaxis assay and calcium mobilization assays, with $IC_{50} < 1000$ nM (++)
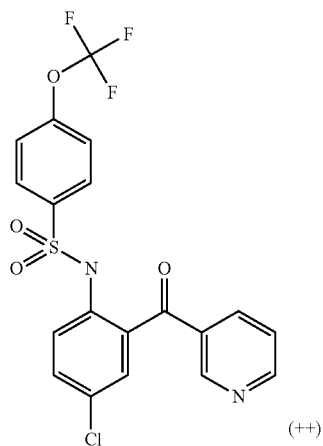 [SMILES: O=C(c1cccnc1)c1cc(Cl)ccc1NS(=O)(=O)c1ccc(OC(F)(F)F)cc1]
(++)
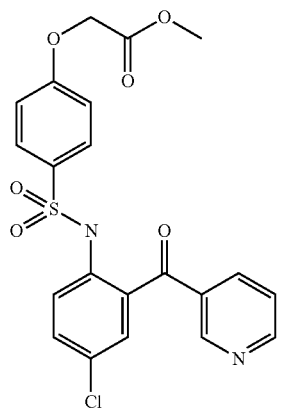
(++)
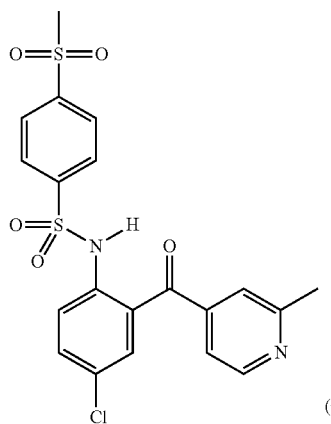
(++)
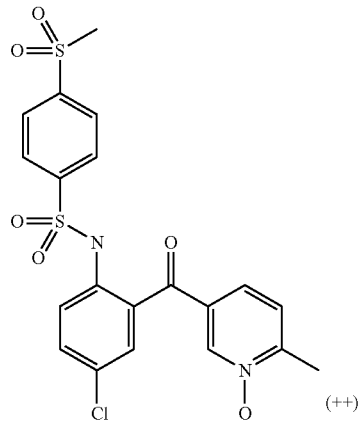
(++)
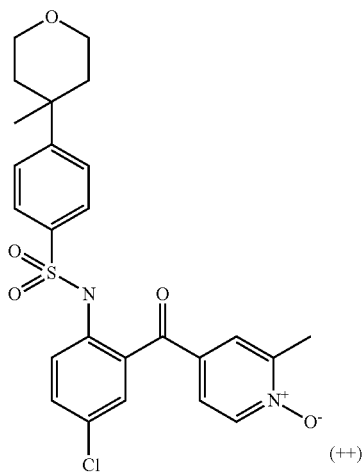 [SMILES: Cc1cc(C(=O)c2cc(Cl)ccc2NS(=O)(=O)c2ccc(C3(C)CCOCC3)cc2)cc[n+]1[O-]]
(++)
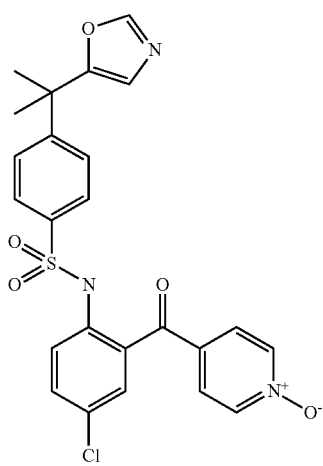
(++)

TABLE 1-continued
Compounds with activity in either or both of the chemotaxis assay and calcium mobilization assays, with $IC_{50} < 1000$ nM (++)
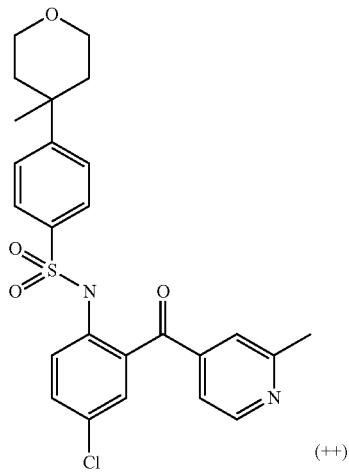 [SMILES: Cc1cc(C(=O)c2cc(Cl)ccc2NS(=O)(=O)c2ccc(C3(C)CCOCC3)cc2)ccn1]
(++)
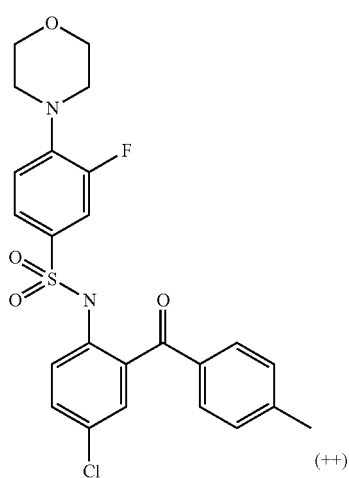 [SMILES: Cc1ccc(C(=O)c2cc(Cl)ccc2NS(=O)(=O)c2ccc(N3CCOCC3)c(F)c2)cc1]
(++)
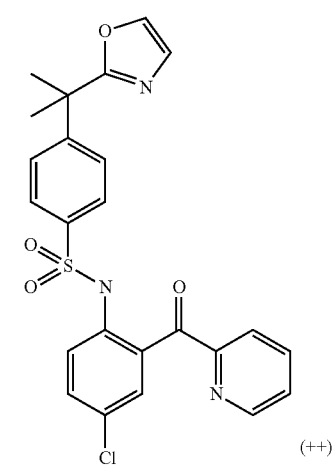 [SMILES: CC(C)(c1ccc(S(=O)(=O)Nc2ccc(Cl)cc2C(=O)c2ccccn2)cc1)c1ncco1]
(++)
TABLE 1-continued
Compounds with activity in either or both of the chemotaxis assay and calcium mobilization assays, with $IC_{50} < 1000$ nM (++)
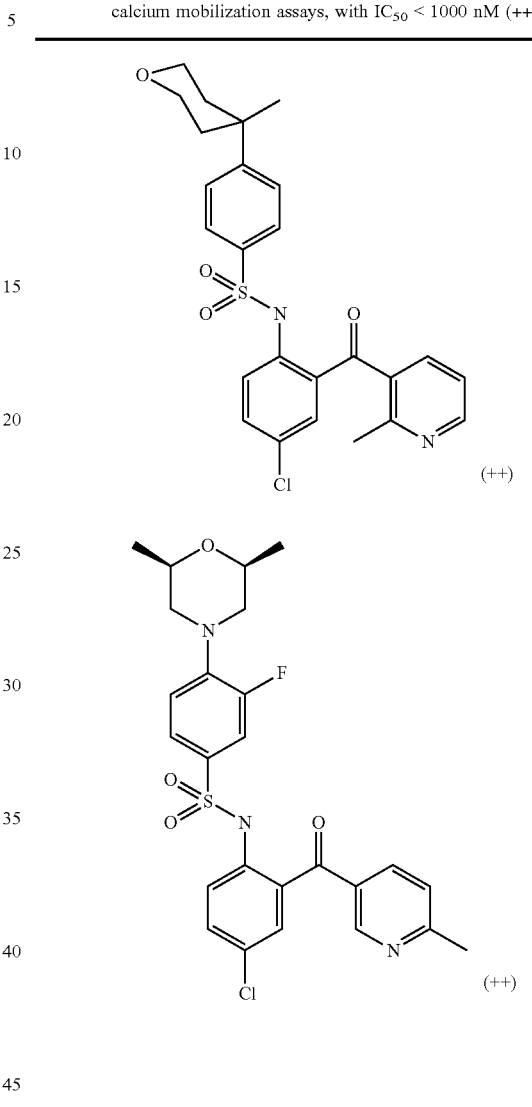
(++)
(++)
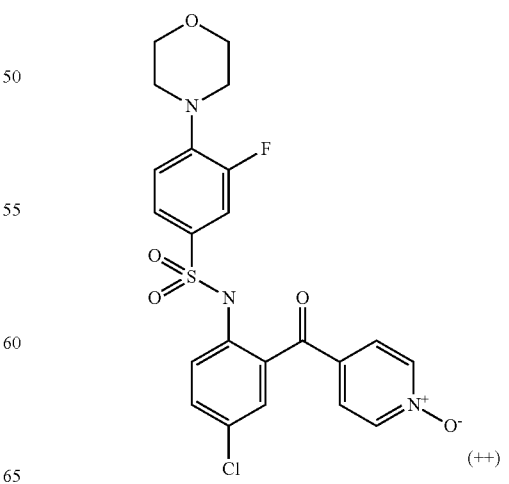
(++)

TABLE 1-continued
Compounds with activity in either or both of the chemotaxis assay and calcium mobilization assays, with IC$_{50}$ < 1000 nM (++)
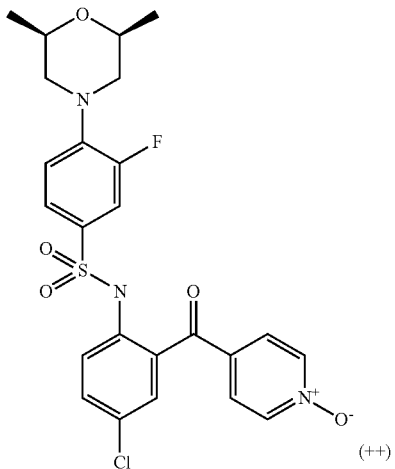 [SMILES: C[C@@H]1CN(c2ccc(S(=O)(=O)Nc3ccc(Cl)cc3C(=O)c3cc[n+]([O-])cc3)cc2F)C[C@H](C)O1]
(++)
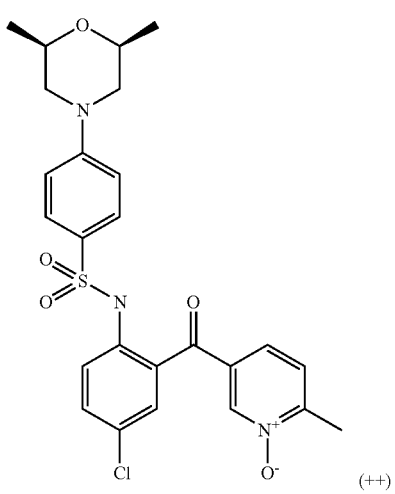
(++)
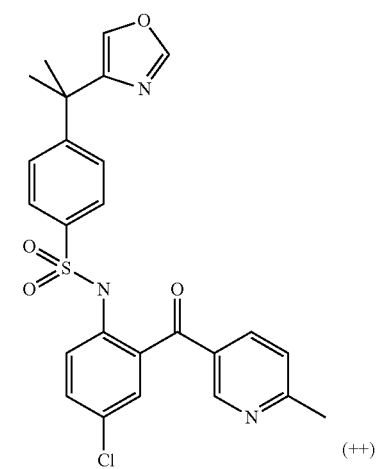 [SMILES: Cc1ccc(C(=O)c2cc(Cl)ccc2NS(=O)(=O)c2ccc(C(C)(C)c3cocn3)cc2)cn1]
(++)
TABLE 1-continued
Compounds with activity in either or both of the chemotaxis assay and calcium mobilization assays, with IC$_{50}$ < 1000 nM (++)
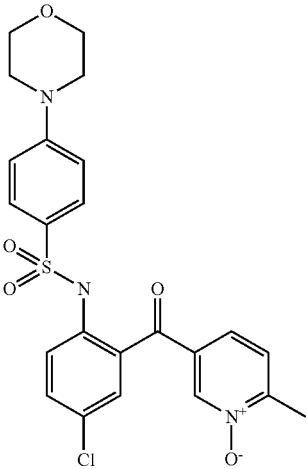
(++)
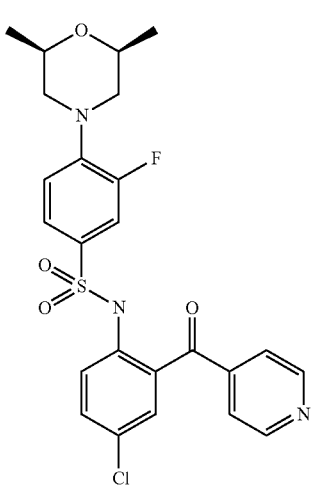
(++)
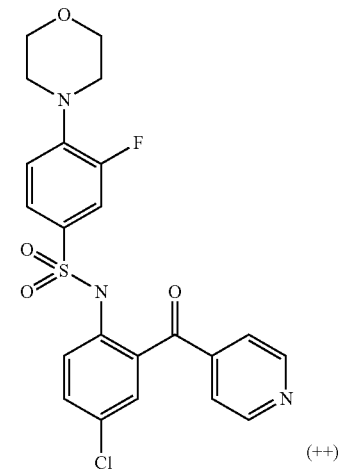 [SMILES: O=C(c1ccncc1)c1cc(Cl)ccc1NS(=O)(=O)c1ccc(N2CCOCC2)c(F)c1]
(++)

TABLE 1-continued
Compounds with activity in either or both of the chemotaxis assay and calcium mobilization assays, with IC$_{50}$ < 1000 nM (++)
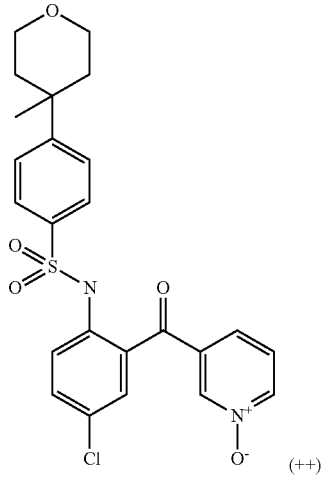 [SMILES: CC1(c2ccc(S(=O)(=O)Nc3ccc(Cl)cc3C(=O)c3ccc[n+]([O-])c3)cc2)CCOCC1]
(++)
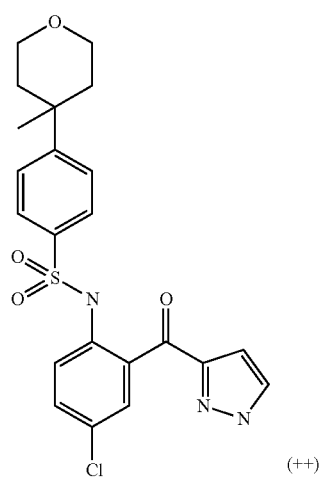 [SMILES: CC1(c2ccc(S(=O)(=O)Nc3ccc(Cl)cc3C(=O)c3cc[nH]n3)cc2)CCOCC1]
(++)
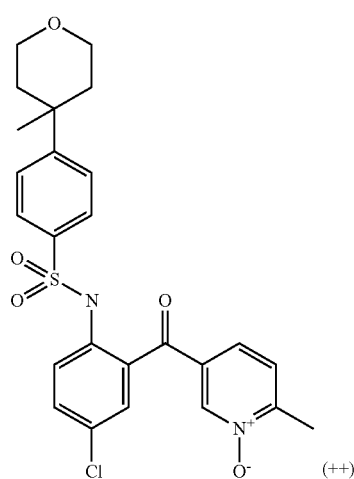 [SMILES: Cc1ccc(C(=O)c2cc(Cl)ccc2NS(=O)(=O)c2ccc(C3(C)CCOCC3)cc2)c[n+]1[O-]]
(++)
TABLE 1-continued
Compounds with activity in either or both of the chemotaxis assay and calcium mobilization assays, with IC$_{50}$ < 1000 nM (++)
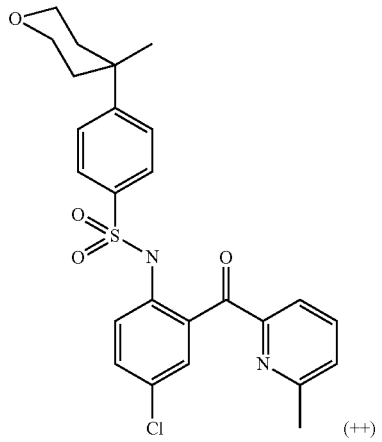 [SMILES: Cc1cccc(C(=O)c2cc(Cl)ccc2NS(=O)(=O)c2ccc(C3(C)CCOCC3)cc2)n1]
(++)
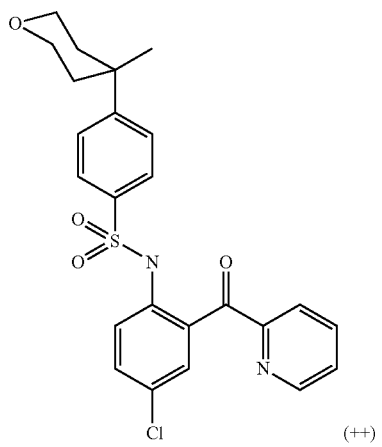 [SMILES: CC1(c2ccc(S(=O)(=O)Nc3ccc(Cl)cc3C(=O)c3ccccn3)cc2)CCOCC1]
(++)
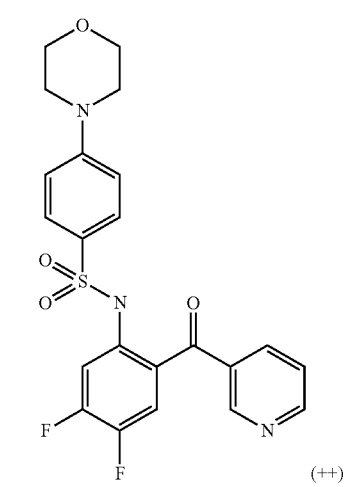 [SMILES: O=C(c1cccnc1)c1cc(F)c(F)cc1NS(=O)(=O)c1ccc(N2CCOCC2)cc1]
(++)

TABLE 1-continued
Compounds with activity in either or both of the chemotaxis assay and calcium mobilization assays, with $IC_{50} < 1000$ nM (++)
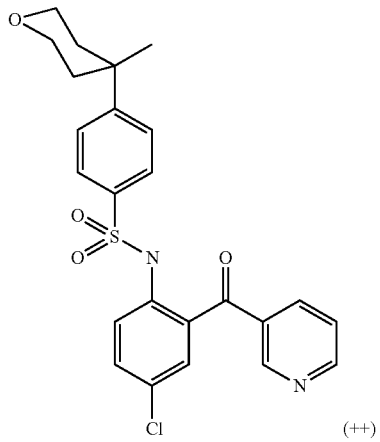 [SMILES: CC1(c2ccc(S(=O)(=O)Nc3ccc(Cl)cc3C(=O)c3cccnc3)cc2)CCOCC1]
(++)
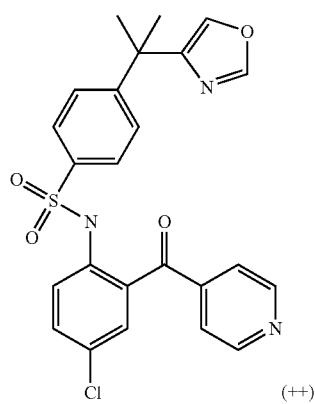 [SMILES: CC(C)(c1ccc(S(=O)(=O)Nc2ccc(Cl)cc2C(=O)c2ccncc2)cc1)c1cocn1]
(++)
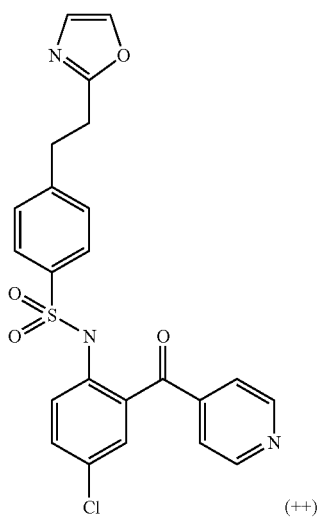 [SMILES: O=C(c1ccncc1)c1cc(Cl)ccc1NS(=O)(=O)c1ccc(CCc2ncco2)cc1]
(++)
TABLE 1-continued
Compounds with activity in either or both of the chemotaxis assay and calcium mobilization assays, with $IC_{50} < 1000$ nM (++)
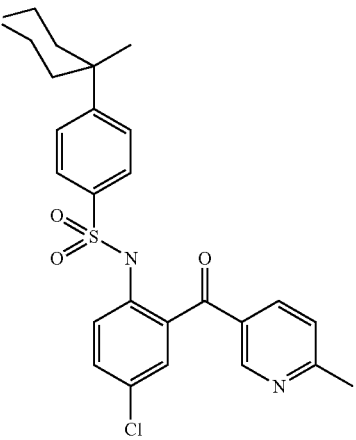
(++)
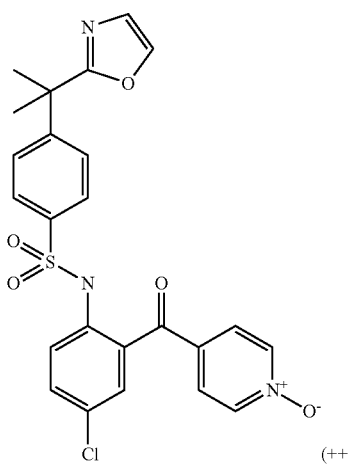
(++)
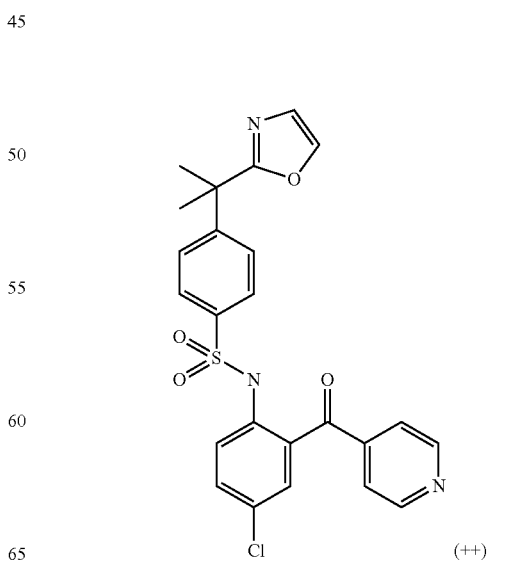
(++)

TABLE 1-continued
Compounds with activity in either or both of the chemotaxis assay and calcium mobilization assays, with IC$_{50}$ < 1000 nM (++)
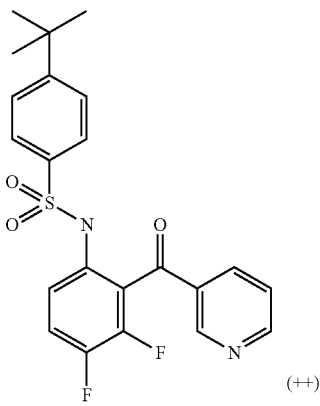 [SMILES: CC(C)(C)c1ccc(S(=O)(=O)Nc2ccc(F)c(F)c2C(=O)c2cccnc2)cc1]
(++)
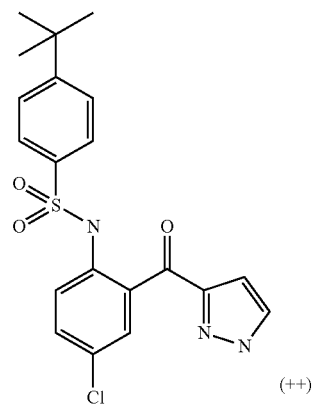 [SMILES: CC(C)(C)c1ccc(S(=O)(=O)Nc2ccc(Cl)cc2C(=O)c2cc[nH]n2)cc1]
(++)
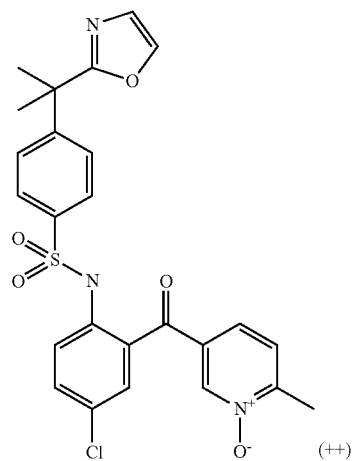 [SMILES: Cc1ccc(C(=O)c2cc(Cl)ccc2NS(=O)(=O)c2ccc(C(C)(C)c3ncco3)cc2)c[n+]1[O-]]
(++)
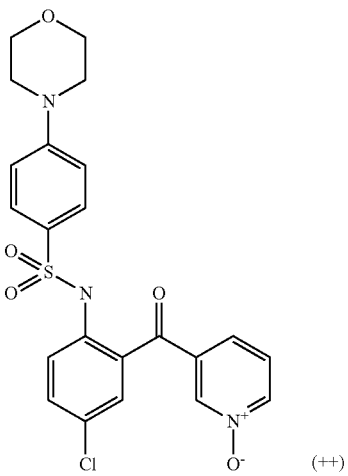 [SMILES: O=C(c1ccc[n+]([O-])c1)c1cc(Cl)ccc1NS(=O)(=O)c1ccc(N2CCOCC2)cc1]
(++)
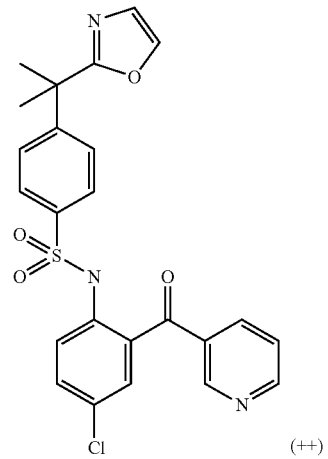 [SMILES: CC(C)(c1ccc(S(=O)(=O)Nc2ccc(Cl)cc2C(=O)c2cccnc2)cc1)c1ncco1]
(++)
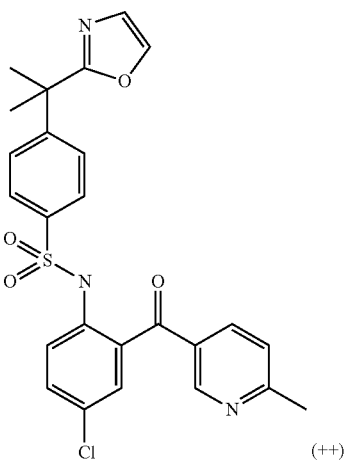 [SMILES: Cc1ccc(C(=O)c2cc(Cl)ccc2NS(=O)(=O)c2ccc(C(C)(C)c3ncco3)cc2)cn1]
(++)

TABLE 1-continued
Compounds with activity in either or both of the chemotaxis assay and calcium mobilization assays, with IC$_{50}$ < 1000 nM (++)
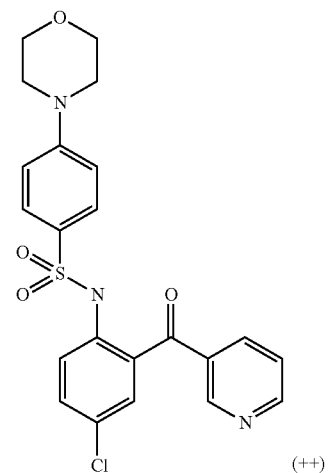 [SMILES: O=C(c1cccnc1)c1cc(Cl)ccc1NS(=O)(=O)c1ccc(N2CCOCC2)cc1]
(++)
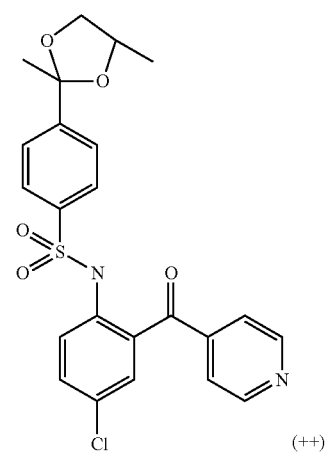 [SMILES: CC1COC(C)(c2ccc(S(=O)(=O)Nc3ccc(Cl)cc3C(=O)c3ccncc3)cc2)O1]
(++)
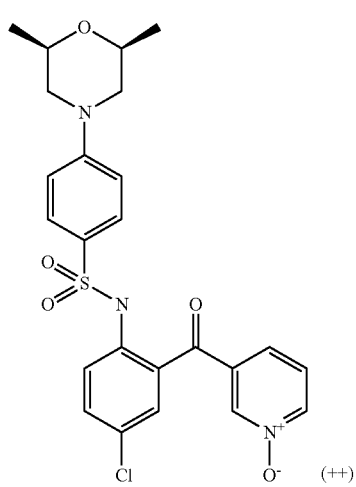 [SMILES: C[C@@H]1CN(c2ccc(S(=O)(=O)Nc3ccc(Cl)cc3C(=O)c3ccc[n+]([O-])c3)cc2)C[C@H](C)O1]
(++)
TABLE 1-continued
Compounds with activity in either or both of the chemotaxis assay and calcium mobilization assays, with IC$_{50}$ < 1000 nM (++)
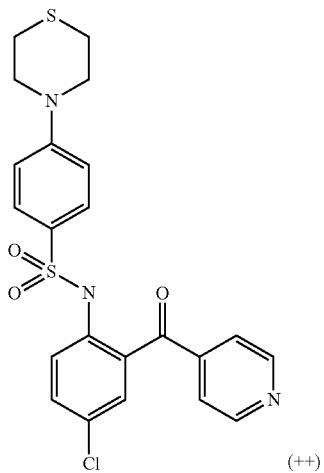 [SMILES: O=C(c1ccncc1)c1cc(Cl)ccc1NS(=O)(=O)c1ccc(N2CCSCC2)cc1]
(++)
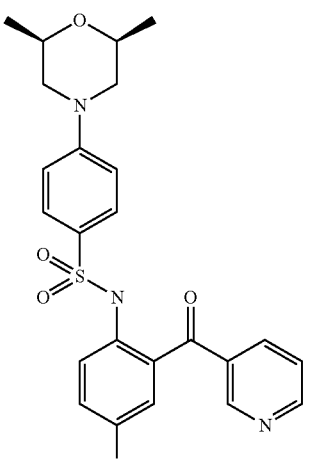
(++)
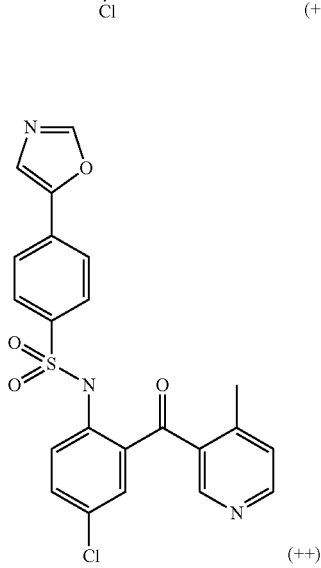
(++)

TABLE 1-continued
Compounds with activity in either or both of the chemotaxis assay and calcium mobilization assays, with IC$_{50}$ < 1000 nM (++)
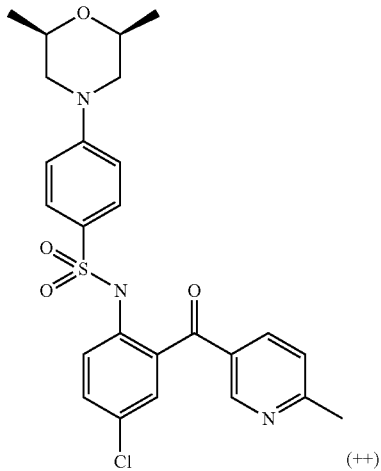
(++)
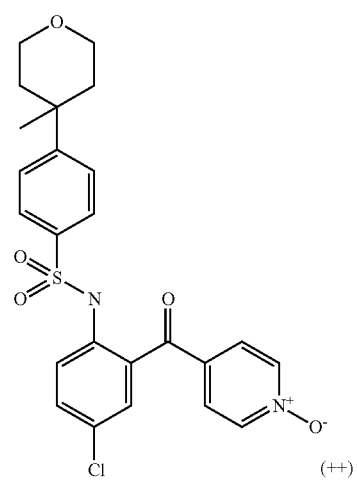 [SMILES: CC1(c2ccc(S(=O)(=O)Nc3ccc(Cl)cc3C(=O)c3cc[n+]([O-])cc3)cc2)CCOCC1]
(++)
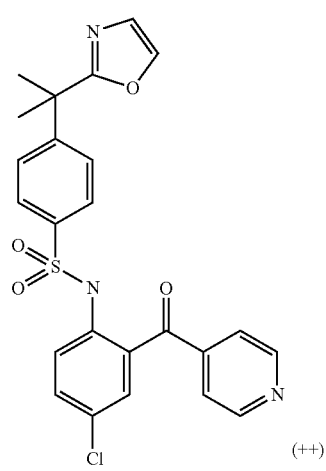 [SMILES: CC(C)(c1ccc(S(=O)(=O)Nc2ccc(Cl)cc2C(=O)c2ccncc2)cc1)c1ncco1]
(++)
TABLE 1-continued
Compounds with activity in either or both of the chemotaxis assay and calcium mobilization assays, with IC$_{50}$ < 1000 nM (++)
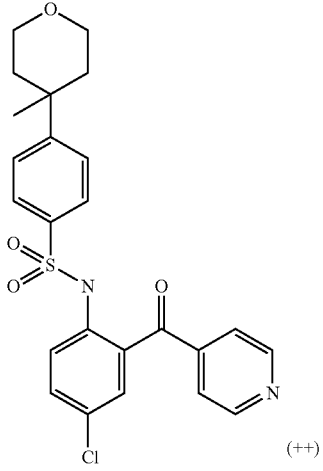 [SMILES: CC1(c2ccc(S(=O)(=O)Nc3ccc(Cl)cc3C(=O)c3ccncc3)cc2)CCOCC1]
(++)
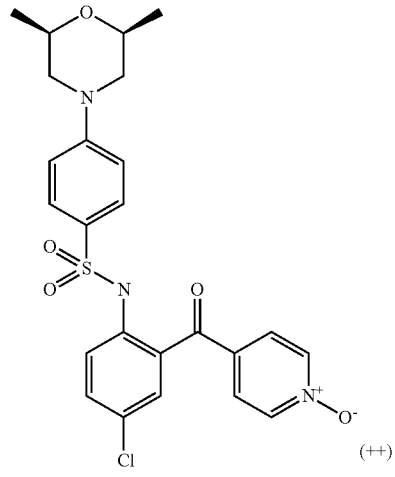 [SMILES: C[C@@H]1CN(c2ccc(S(=O)(=O)Nc3ccc(Cl)cc3C(=O)c3cc[n+]([O-])cc3)cc2)C[C@H](C)O1]
(++)
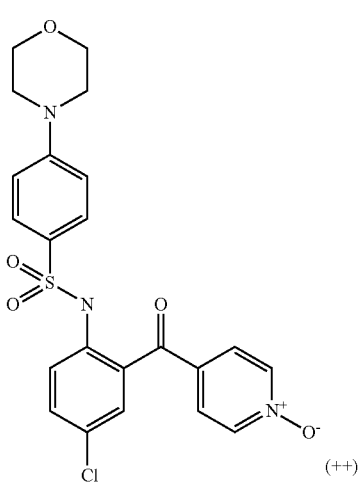 [SMILES: O=C(c1cc[n+]([O-])cc1)c1cc(Cl)ccc1NS(=O)(=O)c1ccc(N2CCOCC2)cc1]
(++)

TABLE 1-continued
Compounds with activity in either or both of the chemotaxis assay and calcium mobilization assays, with IC$_{50}$ < 1000 nM (++)
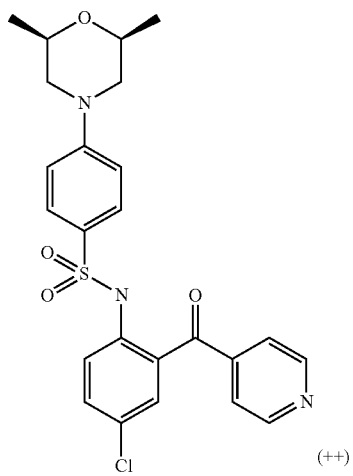 [SMILES: C[C@@H]1CN(c2ccc(S(=O)(=O)Nc3ccc(Cl)cc3C(=O)c3ccncc3)cc2)C[C@H](C)O1]
(++)
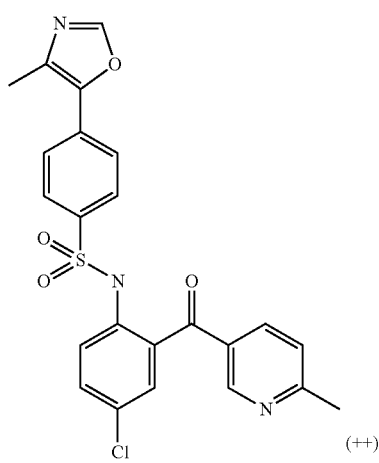
(++)
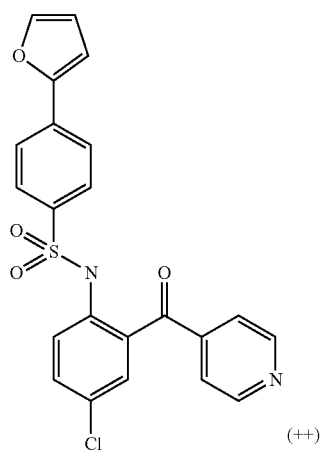 [SMILES: O=C(c1ccncc1)c1cc(Cl)ccc1NS(=O)(=O)c1ccc(-c2ccco2)cc1]
(++)
TABLE 1-continued
Compounds with activity in either or both of the chemotaxis assay and calcium mobilization assays, with IC$_{50}$ < 1000 nM (++)
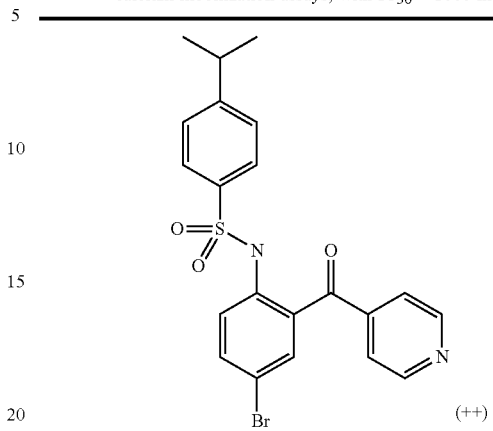
(++)
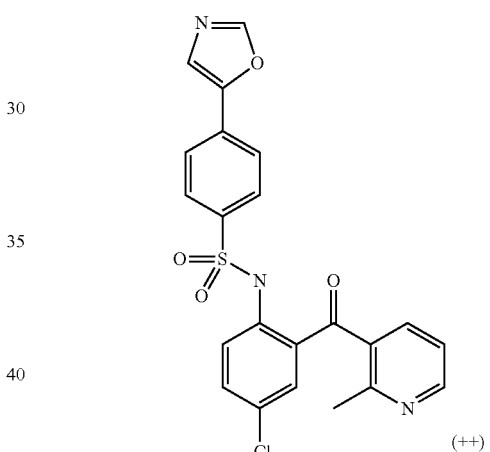
(++)
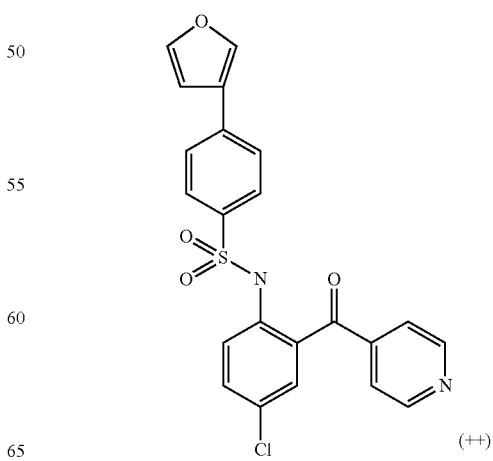
(++)

TABLE 1-continued
Compounds with activity in either or both of the chemotaxis assay and calcium mobilization assays, with IC$_{50}$ < 1000 nM (++)
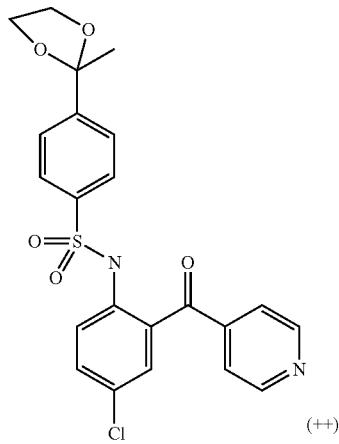 [SMILES: CC1(c2ccc(S(=O)(=O)Nc3ccc(Cl)cc3C(=O)c3ccncc3)cc2)OCCO1]
(++)
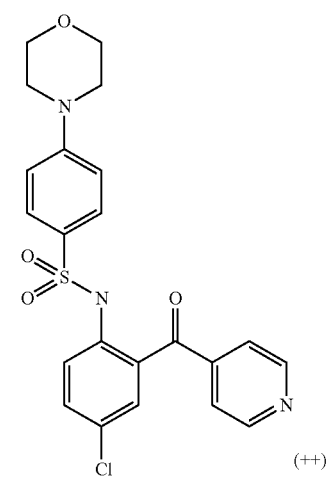 [SMILES: O=C(c1ccncc1)c1cc(Cl)ccc1NS(=O)(=O)c1ccc(N2CCOCC2)cc1]
(++)
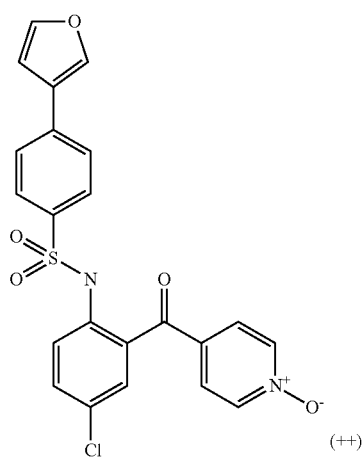 [SMILES: O=C(c1cc[n+]([O-])cc1)c1cc(Cl)ccc1NS(=O)(=O)c1ccc(-c2ccoc2)cc1]
(++)
TABLE 1-continued
Compounds with activity in either or both of the chemotaxis assay and calcium mobilization assays, with IC$_{50}$ < 1000 nM (++)
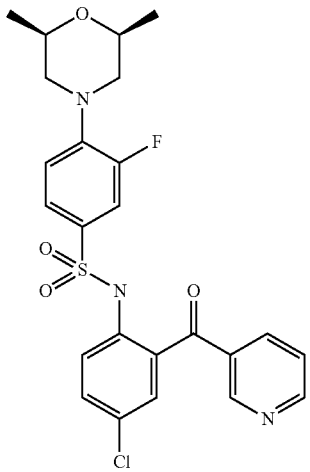
(++)
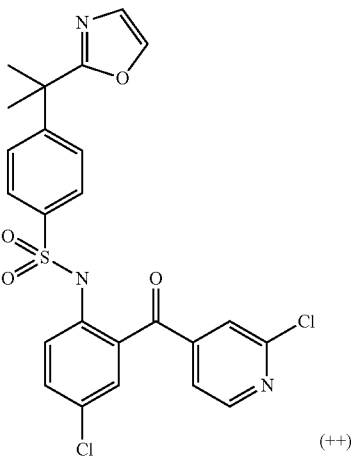 [SMILES: CC(C)(c1ccc(S(=O)(=O)Nc2ccc(Cl)cc2C(=O)c2ccnc(Cl)c2)cc1)c1ncco1]
(++)
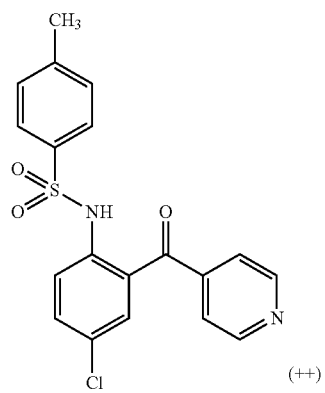 [SMILES: Cc1ccc(S(=O)(=O)Nc2ccc(Cl)cc2C(=O)c2ccncc2)cc1]
(++)

TABLE 1-continued
Compounds with activity in either or both of the chemotaxis assay and calcium mobilization assays, with IC$_{50}$ < 1000 nM (++)
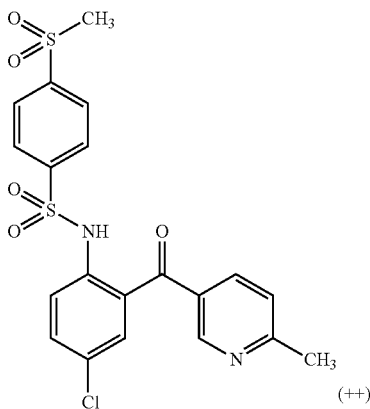 [SMILES: Cc1ccc(C(=O)c2cc(Cl)ccc2NS(=O)(=O)c2ccc(S(C)(=O)=O)cc2)cn1]
(++)
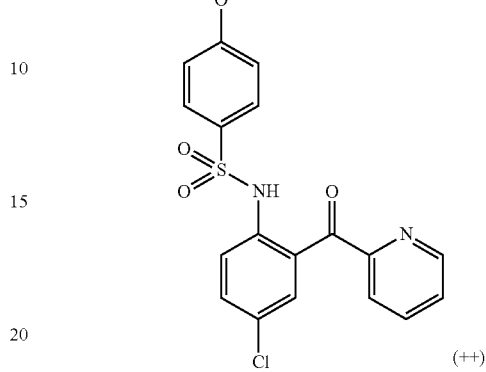
(++)
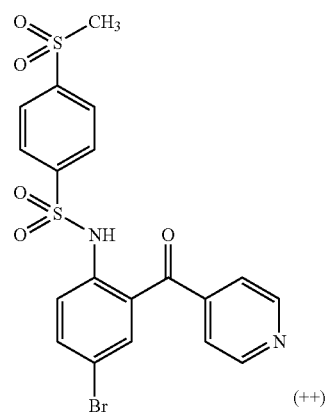 [SMILES: CS(=O)(=O)c1ccc(S(=O)(=O)Nc2ccc(Br)cc2C(=O)c2ccncc2)cc1]
(++)
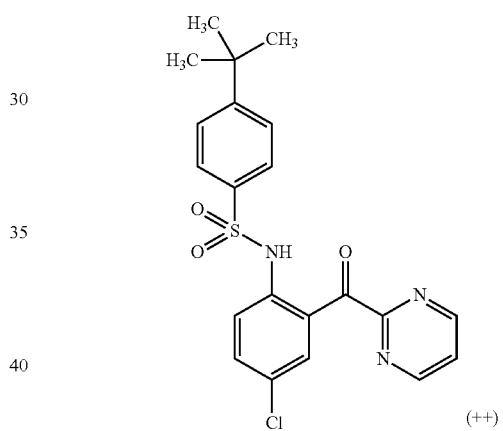
(++)
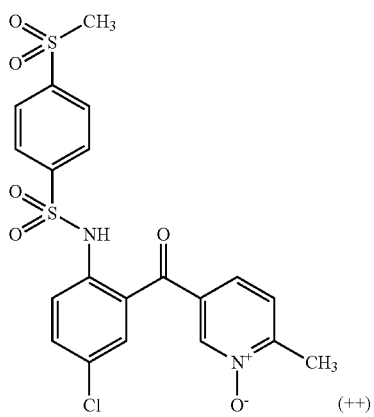 [SMILES: Cc1ccc(C(=O)c2cc(Cl)ccc2NS(=O)(=O)c2ccc(S(C)(=O)=O)cc2)c[n+]1[O-]]
(++)
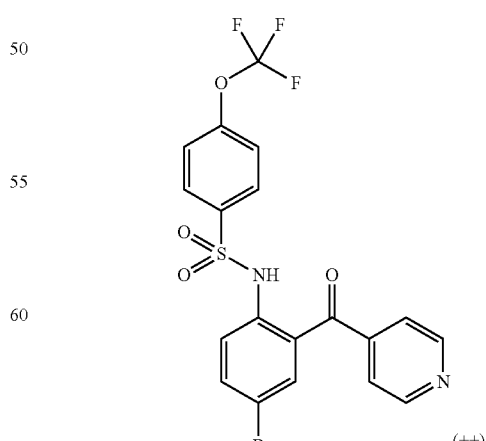
(++)

TABLE 1-continued
Compounds with activity in either or both of the chemotaxis assay and calcium mobilization assays, with IC$_{50}$ < 1000 nM (++)
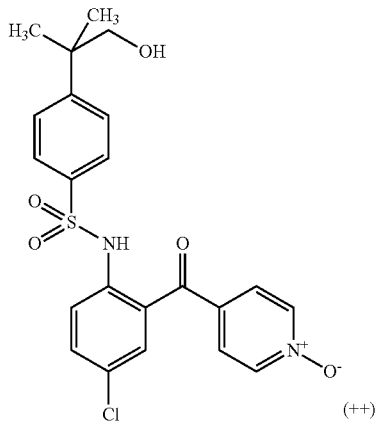 [SMILES: CC(C)(CO)c1ccc(S(=O)(=O)Nc2ccc(Cl)cc2C(=O)c2cc[n+]([O-])cc2)cc1]
(++)
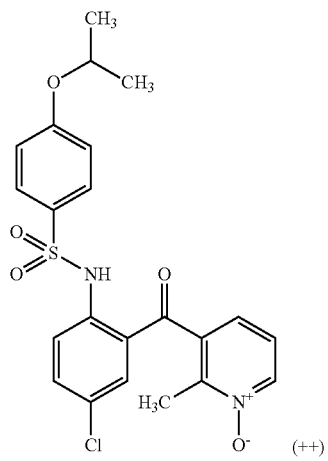
(++)
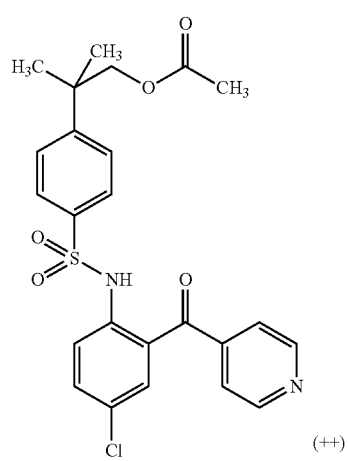 [SMILES: CC(=O)OCC(C)(C)c1ccc(S(=O)(=O)Nc2ccc(Cl)cc2C(=O)c2ccncc2)cc1]
(++)
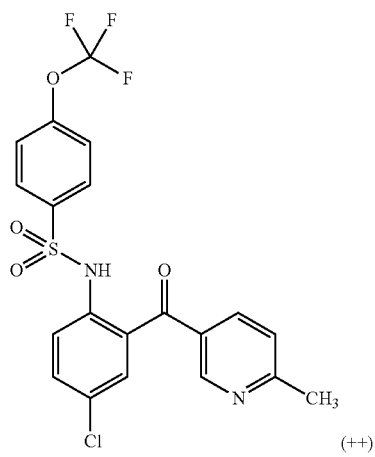
(++)
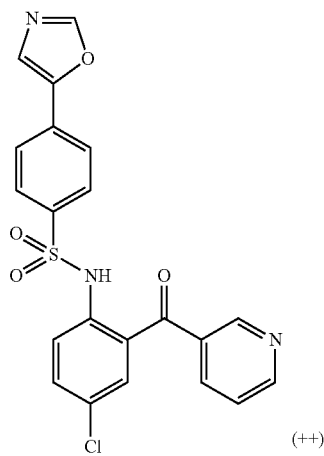 [SMILES: O=C(c1cccnc1)c1cc(Cl)ccc1NS(=O)(=O)c1ccc(-c2cnco2)cc1]
(++)
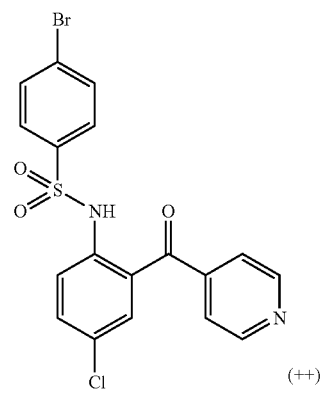 [SMILES: O=C(c1ccncc1)c1cc(Cl)ccc1NS(=O)(=O)c1ccc(Br)cc1]
(++)

TABLE 1-continued
Compounds with activity in either or both of the chemotaxis assay and calcium mobilization assays, with IC$_{50}$ < 1000 nM (++)
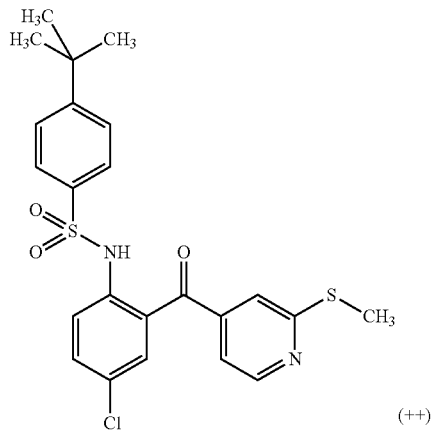 [SMILES: CSc1cc(C(=O)c2cc(Cl)ccc2NS(=O)(=O)c2ccc(C(C)(C)C)cc2)ccn1]
(++)
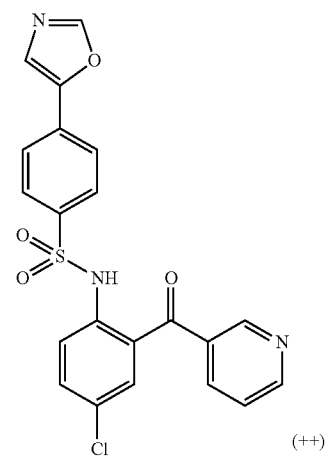 [SMILES: O=C(c1cccnc1)c1cc(Cl)ccc1NS(=O)(=O)c1ccc(-c2cnco2)cc1]
(++)
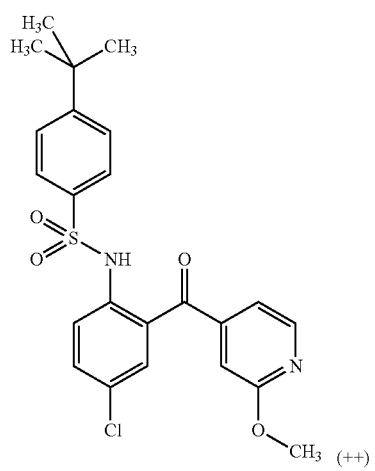 [SMILES: COc1cc(C(=O)c2cc(Cl)ccc2NS(=O)(=O)c2ccc(C(C)(C)C)cc2)ccn1]
(++)
TABLE 1-continued
Compounds with activity in either or both of the chemotaxis assay and calcium mobilization assays, with IC$_{50}$ < 1000 nM (++)
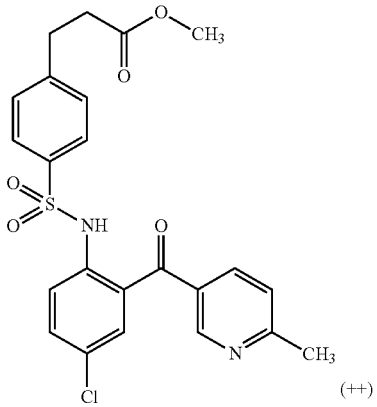 [SMILES: COC(=O)CCc1ccc(S(=O)(=O)Nc2ccc(Cl)cc2C(=O)c2ccc(C)nc2)cc1]
(++)
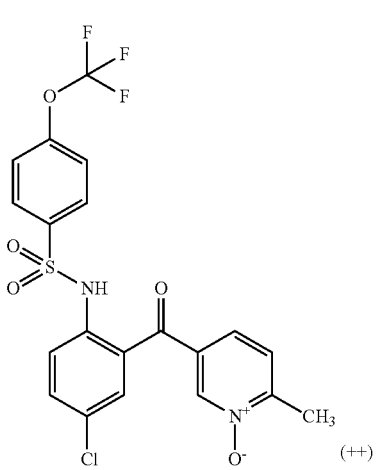 [SMILES: Cc1ccc(C(=O)c2cc(Cl)ccc2NS(=O)(=O)c2ccc(OC(F)(F)F)cc2)c[n+]1[O-]]
(++)
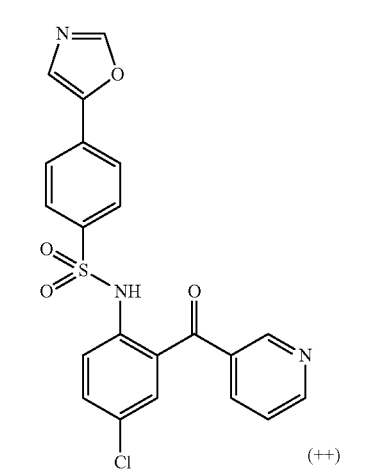 [SMILES: O=C(c1cccnc1)c1cc(Cl)ccc1NS(=O)(=O)c1ccc(-c2cnco2)cc1]
(++)

TABLE 1-continued
Compounds with activity in either or both of the chemotaxis assay and calcium mobilization assays, with IC$_{50}$ < 1000 nM (++)
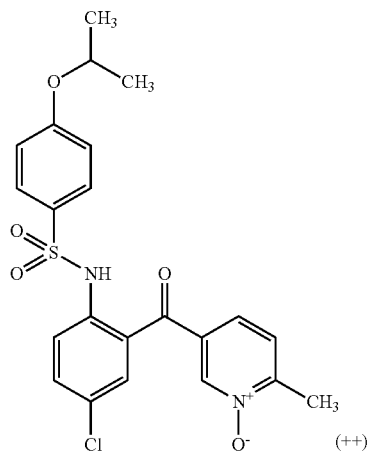 [SMILES: Cc1ccc(C(=O)c2cc(Cl)ccc2NS(=O)(=O)c2ccc(OC(C)C)cc2)c[n+]1[O-]]
(++)
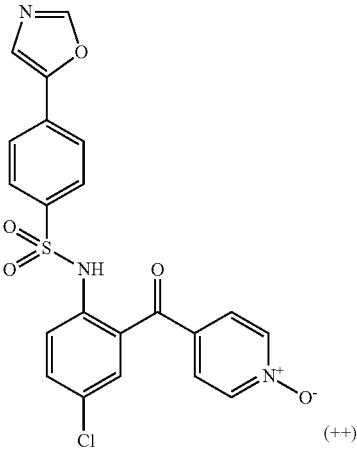
(++)
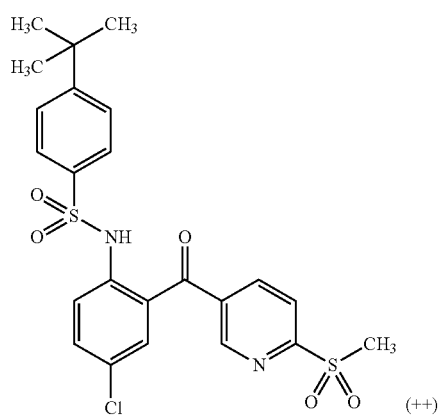 [SMILES: CC(C)(C)c1ccc(S(=O)(=O)Nc2ccc(Cl)cc2C(=O)c2ccc(S(C)(=O)=O)nc2)cc1]
(++)
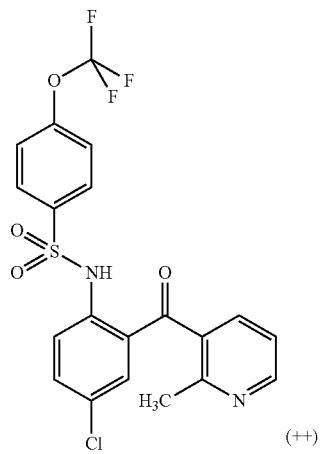
(++)
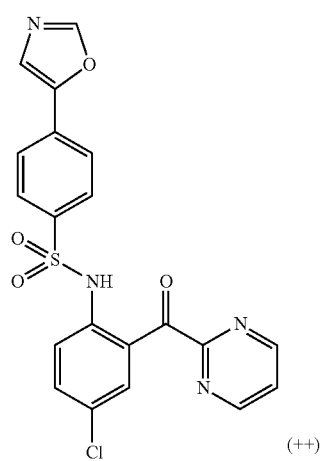 [SMILES: O=C(c1ncccn1)c1cc(Cl)ccc1NS(=O)(=O)c1ccc(-c2cnco2)cc1]
(++)
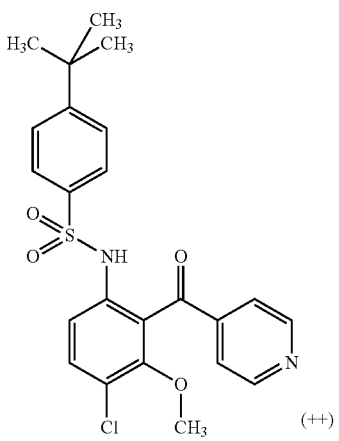 [SMILES: COc1c(Cl)ccc(NS(=O)(=O)c2ccc(C(C)(C)C)cc2)c1C(=O)c1ccncc1]
(++)

TABLE 1-continued
Compounds with activity in either or both of the chemotaxis assay and calcium mobilization assays, with IC$_{50}$ < 1000 nM (++)
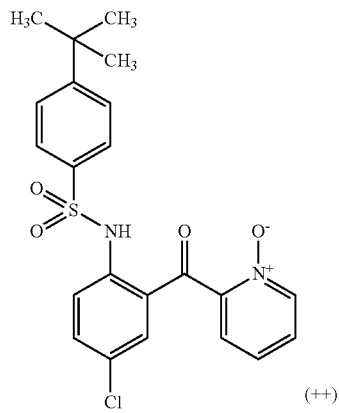 [SMILES: CC(C)(C)c1ccc(S(=O)(=O)Nc2ccc(Cl)cc2C(=O)c2cccc[n+]2[O-])cc1]
(++)
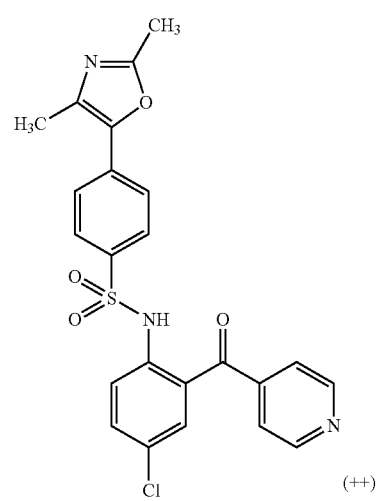 [SMILES: Cc1nc(C)c(-c2ccc(S(=O)(=O)Nc3ccc(Cl)cc3C(=O)c3ccncc3)cc2)o1]
(++)
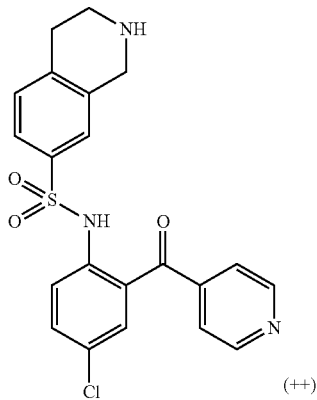 [SMILES: O=C(c1ccncc1)c1cc(Cl)ccc1NS(=O)(=O)c1ccc2c(c1)CNCC2]
(++)
TABLE 1-continued
Compounds with activity in either or both of the chemotaxis assay and calcium mobilization assays, with IC$_{50}$ < 1000 nM (++)
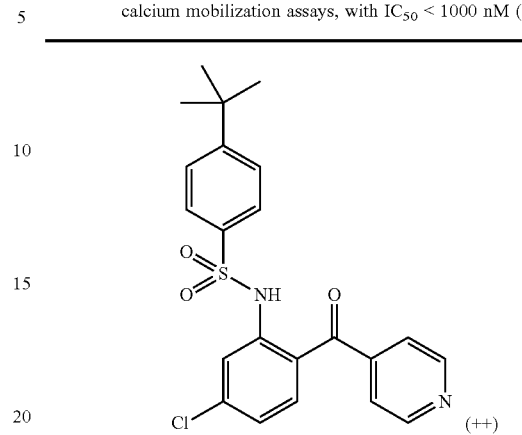
(++)
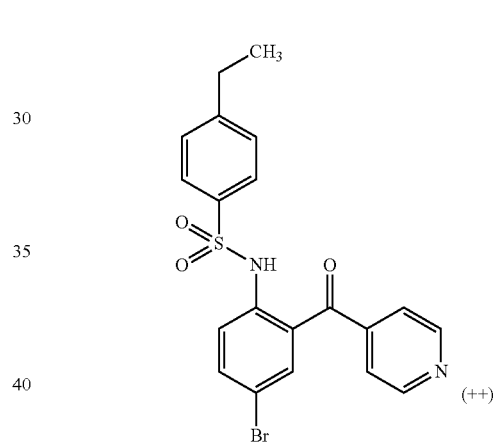
(++)
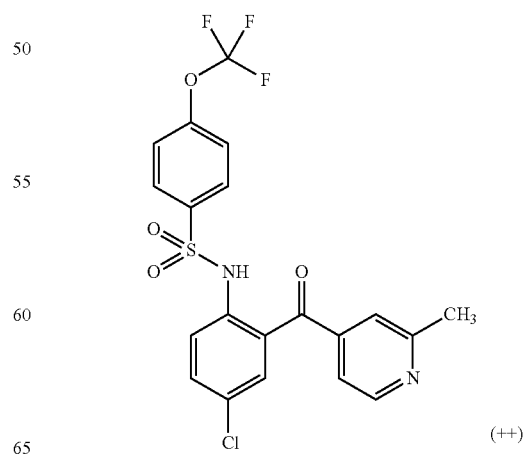
(++)

TABLE 1-continued
Compounds with activity in either or both of the chemotaxis assay and calcium mobilization assays, with IC$_{50}$ < 1000 nM (++)
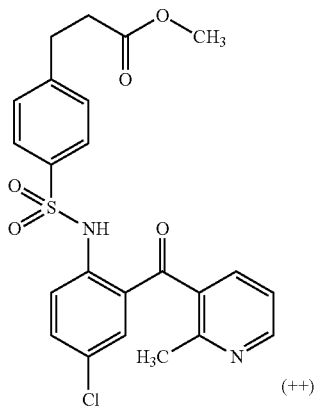 [SMILES: COC(=O)CCc1ccc(S(=O)(=O)Nc2ccc(Cl)cc2C(=O)c2cccnc2C)cc1]
(++)
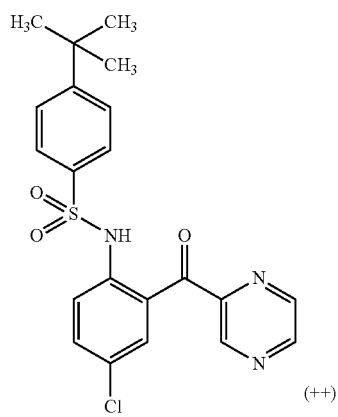 [SMILES: CC(C)(C)c1ccc(S(=O)(=O)Nc2ccc(Cl)cc2C(=O)c2cnccn2)cc1]
(++)
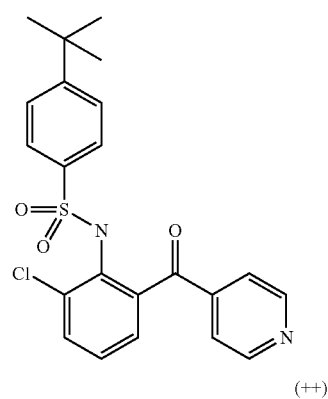 [SMILES: CC(C)(C)c1ccc(S(=O)(=O)Nc2c(Cl)cccc2C(=O)c2ccncc2)cc1]
(++)
TABLE 1-continued
Compounds with activity in either or both of the chemotaxis assay and calcium mobilization assays, with IC$_{50}$ < 1000 nM (++)
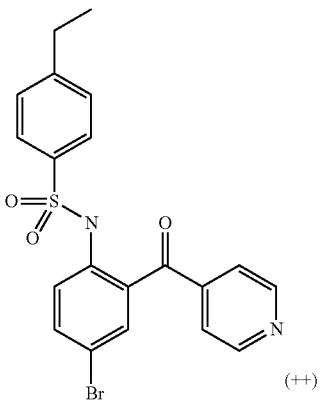 [SMILES: CCc1ccc(S(=O)(=O)Nc2ccc(Br)cc2C(=O)c2ccncc2)cc1]
(++)
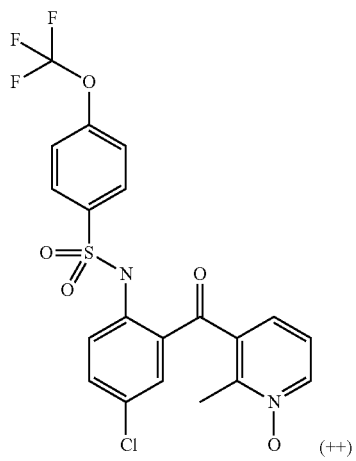
(++)
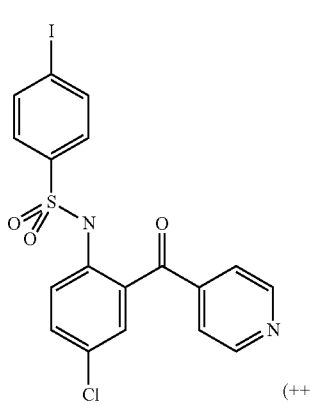
(++)

TABLE 1-continued
Compounds with activity in either or both of the chemotaxis assay and calcium mobilization assays, with IC$_{50}$ < 1000 nM (++)
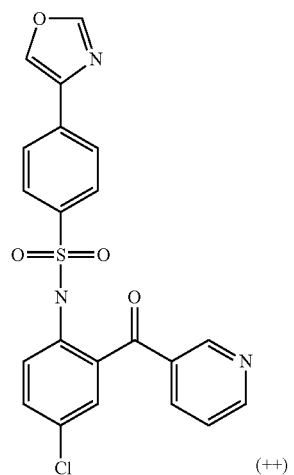 [SMILES: O=C(c1cccnc1)c1cc(Cl)ccc1NS(=O)(=O)c1ccc(-c2cocn2)cc1]
(++)
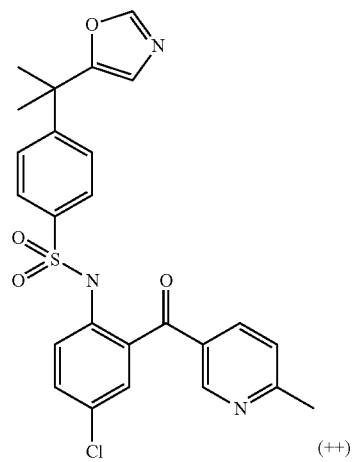 [SMILES: Cc1ccc(C(=O)c2cc(Cl)ccc2NS(=O)(=O)c2ccc(C(C)(C)c3cnco3)cc2)cn1]
(++)
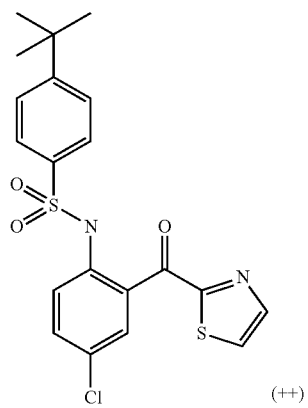 [SMILES: CC(C)(C)c1ccc(S(=O)(=O)Nc2ccc(Cl)cc2C(=O)c2nccs2)cc1]
(++)
TABLE 1-continued
Compounds with activity in either or both of the chemotaxis assay and calcium mobilization assays, with IC$_{50}$ < 1000 nM (++)
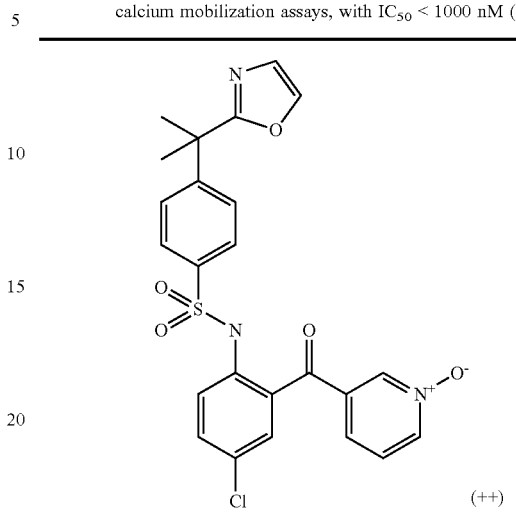
(++)
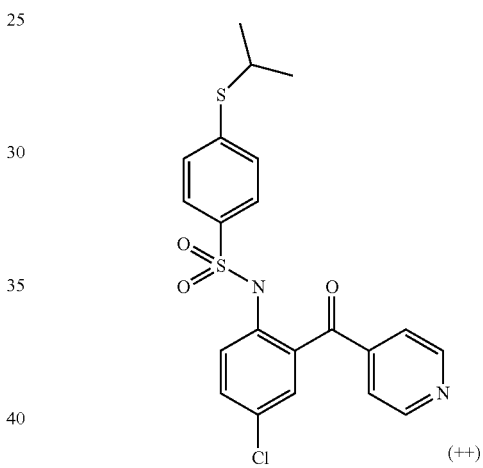
(++)
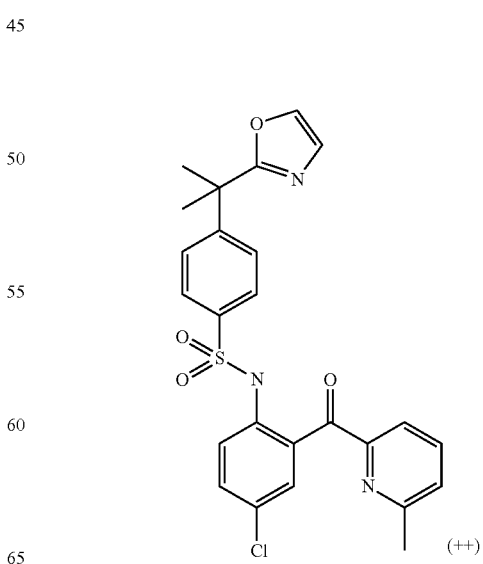
(++)

TABLE 1-continued
Compounds with activity in either or both of the chemotaxis assay and calcium mobilization assays, with IC$_{50}$ < 1000 nM (++)
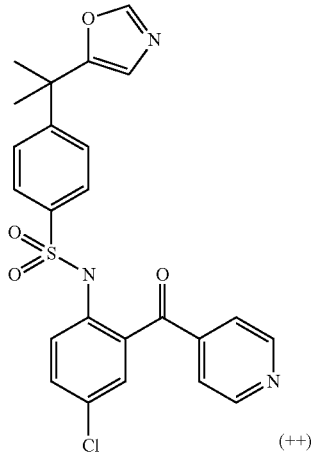 [SMILES: CC(C)(c1ccc(S(=O)(=O)Nc2ccc(Cl)cc2C(=O)c2ccncc2)cc1)c1cnco1]
(++)
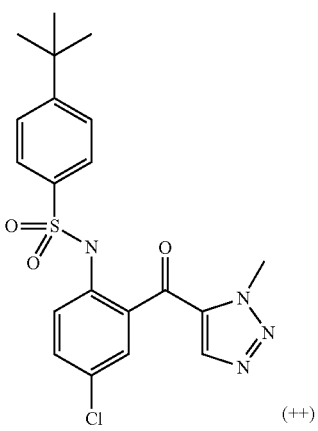 [SMILES: Cn1nncc1C(=O)c1cc(Cl)ccc1NS(=O)(=O)c1ccc(C(C)(C)C)cc1]
(++)
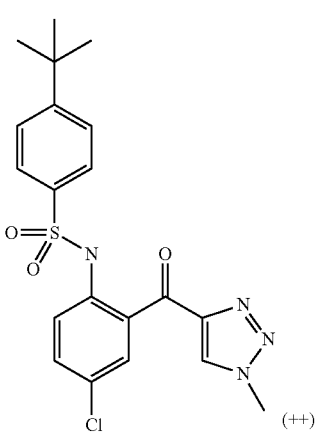 [SMILES: Cn1cc(C(=O)c2cc(Cl)ccc2NS(=O)(=O)c2ccc(C(C)(C)C)cc2)nn1]
(++)
TABLE 1-continued
Compounds with activity in either or both of the chemotaxis assay and calcium mobilization assays, with IC$_{50}$ < 1000 nM (++)
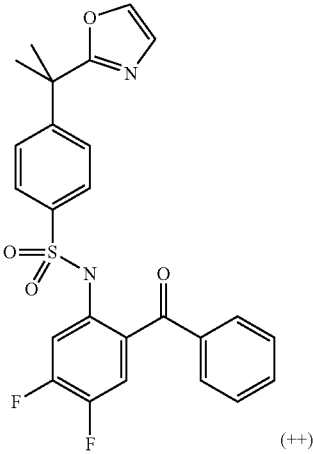 [SMILES: CC(C)(c1ccc(S(=O)(=O)Nc2cc(F)c(F)cc2C(=O)c2ccccc2)cc1)c1ncco1]
(++)
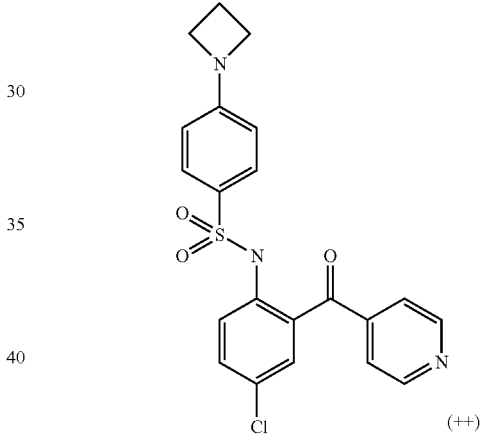
(++)
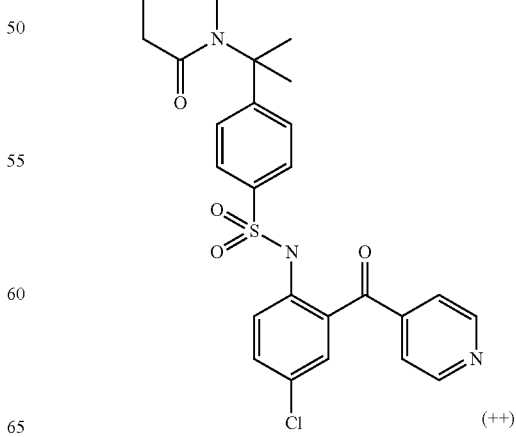
(++)

TABLE 1-continued
Compounds with activity in either or both of the chemotaxis assay and calcium mobilization assays, with IC$_{50}$ < 1000 nM (++)
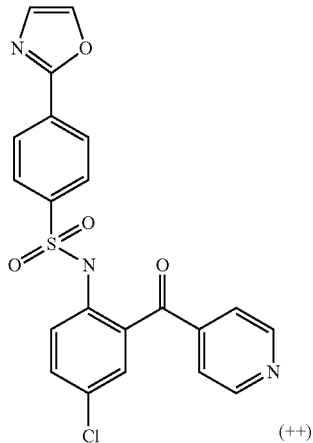 [SMILES: O=C(c1ccncc1)c1cc(Cl)ccc1NS(=O)(=O)c1ccc(-c2ncco2)cc1]
(++)
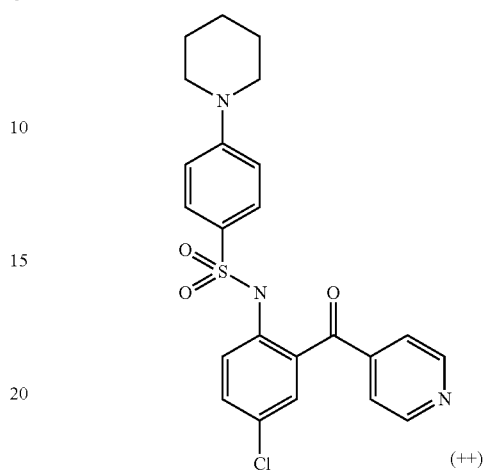
(++)
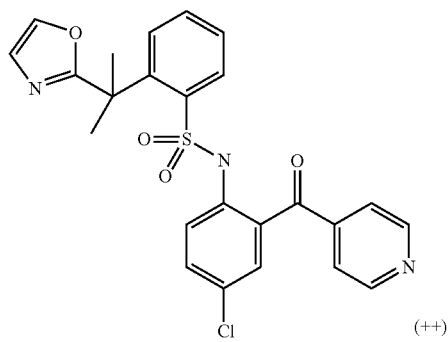 [SMILES: CC(C)(c1ncco1)c1ccccc1S(=O)(=O)Nc1ccc(Cl)cc1C(=O)c1ccncc1]
(++)
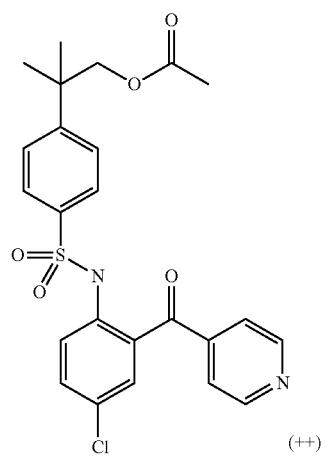
(++)
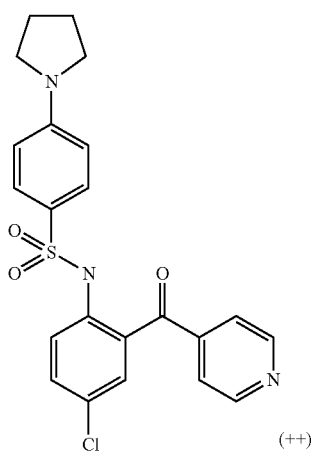 [SMILES: O=C(c1ccncc1)c1cc(Cl)ccc1NS(=O)(=O)c1ccc(N2CCCC2)cc1]
(++)
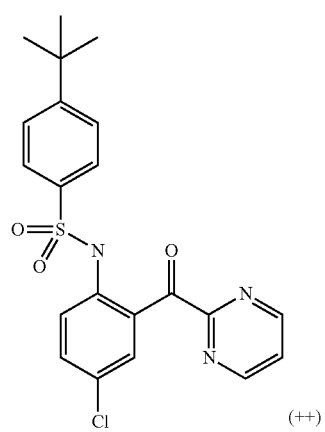 [SMILES: CC(C)(C)c1ccc(S(=O)(=O)Nc2ccc(Cl)cc2C(=O)c2ncccn2)cc1]
(++)

TABLE 1-continued
Compounds with activity in either or both of the chemotaxis assay and calcium mobilization assays, with IC$_{50}$ < 1000 nM (++)
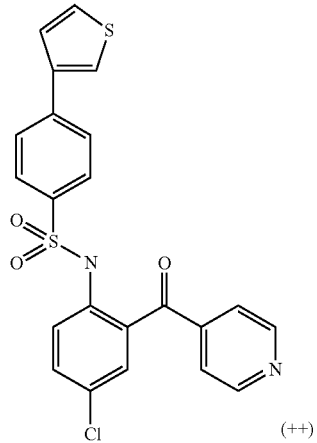 [SMILES: O=C(c1ccncc1)c1cc(Cl)ccc1NS(=O)(=O)c1ccc(-c2ccsc2)cc1]
(++)
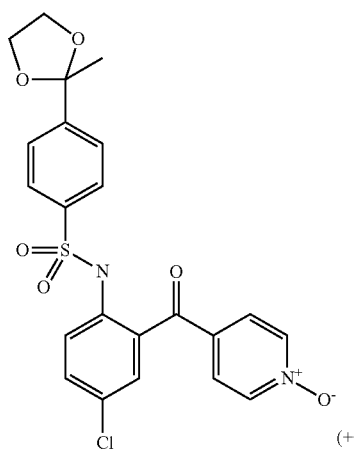
(++)
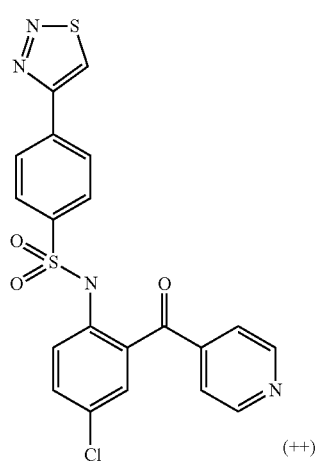 [SMILES: O=C(c1ccncc1)c1cc(Cl)ccc1NS(=O)(=O)c1ccc(-c2csnn2)cc1]
(++)
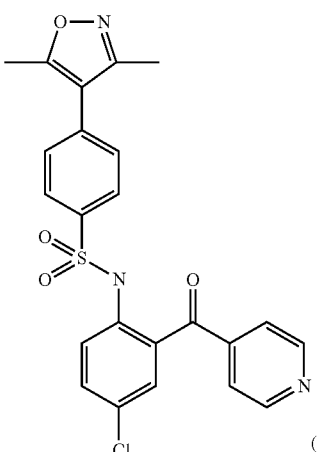
(++)
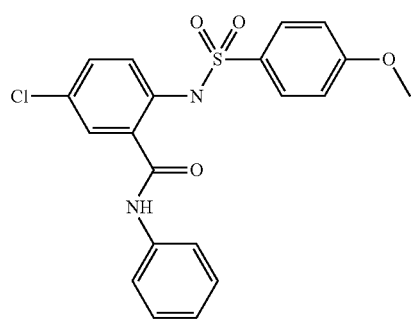
(++)
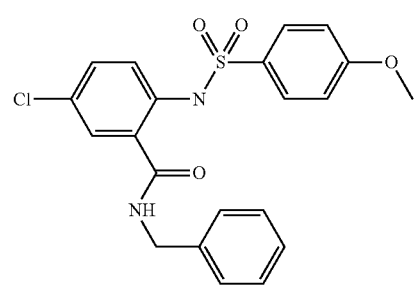
(++)
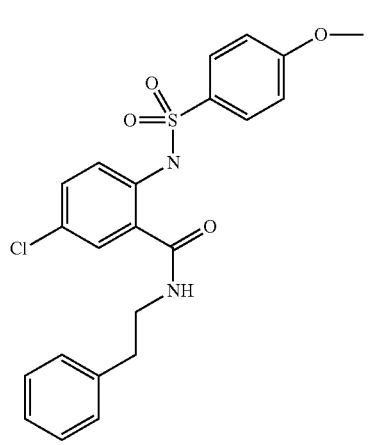 [SMILES: COc1ccc(S(=O)(=O)Nc2ccc(Cl)cc2C(=O)NCCc2ccccc2)cc1]
(++)

TABLE 2
Compounds with activity in either or both of the chemotaxis assay and calcium mobilization assays, with $IC_{50} > 1000$ nM (+):
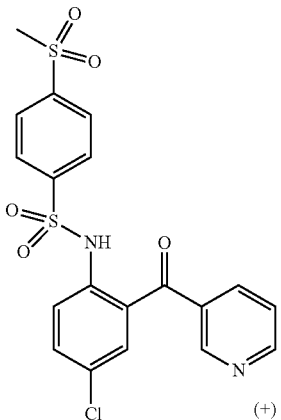 [SMILES: CS(=O)(=O)c1ccc(S(=O)(=O)Nc2ccc(Cl)cc2C(=O)c2cccnc2)cc1]
(+)
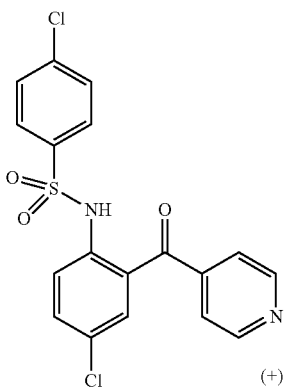 [SMILES: O=C(c1ccncc1)c1cc(Cl)ccc1NS(=O)(=O)c1ccc(Cl)cc1]
(+)
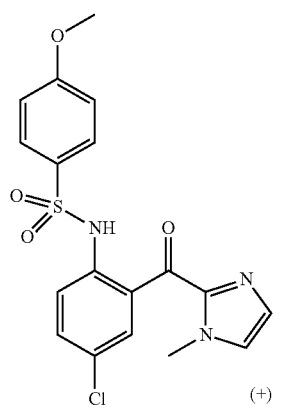 [SMILES: COc1ccc(S(=O)(=O)Nc2ccc(Cl)cc2C(=O)c2nccn2C)cc1]
(+)
TABLE 2-continued
Compounds with activity in either or both of the chemotaxis assay and calcium mobilization assays, with $IC_{50} > 1000$ nM (+):
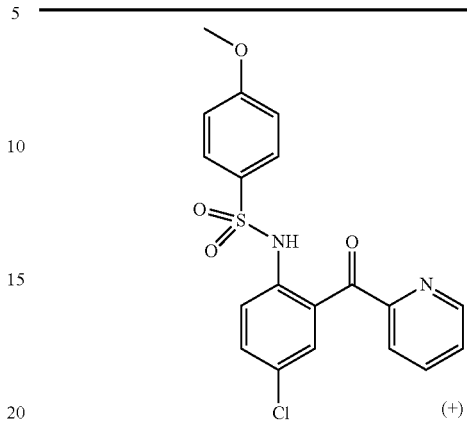
(+)
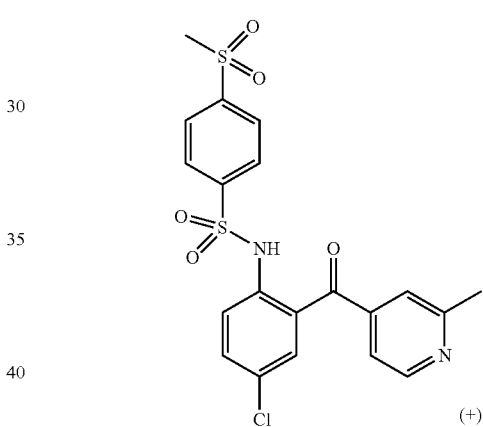
(+)
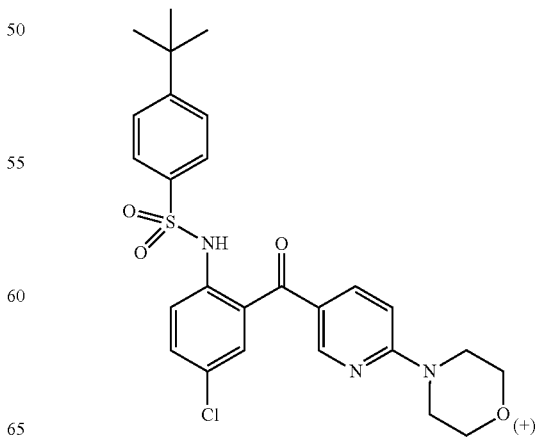
(+)

TABLE 2-continued
Compounds with activity in either or both of the chemotaxis assay and calcium mobilization assays, with $IC_{50} > 1000$ nM (+):
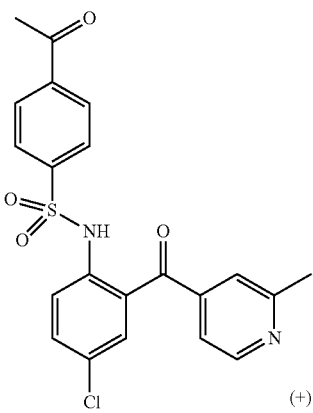 [SMILES: CC(=O)c1ccc(S(=O)(=O)Nc2ccc(Cl)cc2C(=O)c2ccnc(C)c2)cc1]
(+)
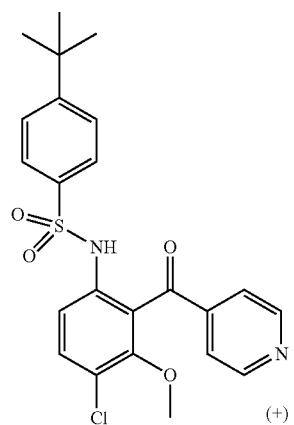 [SMILES: COc1c(Cl)ccc(NS(=O)(=O)c2ccc(C(C)(C)C)cc2)c1C(=O)c1ccncc1]
(+)
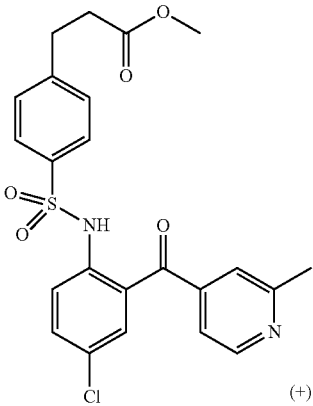 [SMILES: COC(=O)CCc1ccc(S(=O)(=O)Nc2ccc(Cl)cc2C(=O)c2ccnc(C)c2)cc1]
(+)
TABLE 2-continued
Compounds with activity in either or both of the chemotaxis assay and calcium mobilization assays, with $IC_{50} > 1000$ nM (+):
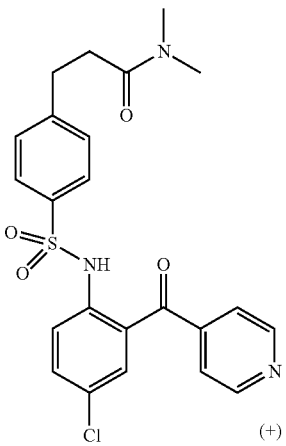 [SMILES: CN(C)C(=O)CCc1ccc(S(=O)(=O)Nc2ccc(Cl)cc2C(=O)c2ccncc2)cc1]
(+)
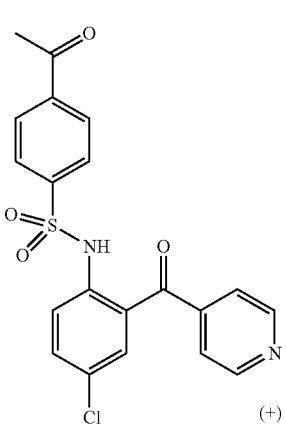 [SMILES: CC(=O)c1ccc(S(=O)(=O)Nc2ccc(Cl)cc2C(=O)c2ccncc2)cc1]
(+)
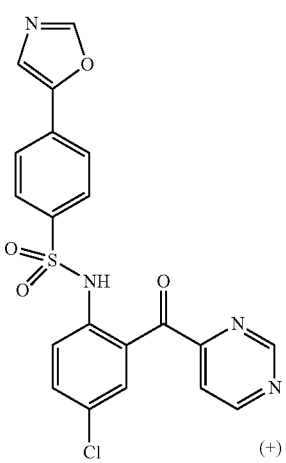 [SMILES: O=C(c1ccncn1)c1cc(Cl)ccc1NS(=O)(=O)c1ccc(-c2cnco2)cc1]
(+)

TABLE 2-continued
Compounds with activity in either or both of the chemotaxis assay and calcium mobilization assays, with $IC_{50} > 1000$ nM (+):
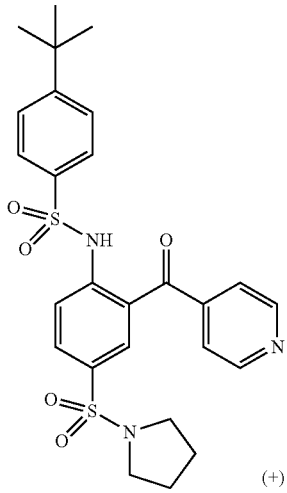 [SMILES: CC(C)(C)c1ccc(S(=O)(=O)Nc2ccc(S(=O)(=O)N3CCCC3)cc2C(=O)c2ccncc2)cc1]
(+)
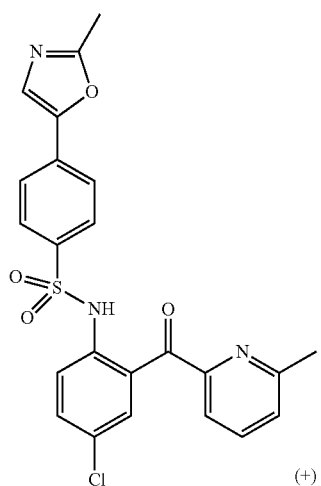 [SMILES: Cc1cccc(C(=O)c2cc(Cl)ccc2NS(=O)(=O)c2ccc(-c3cnc(C)o3)cc2)n1]
(+)
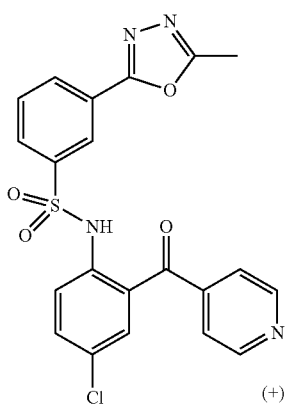 [SMILES: Cc1nnc(-c2cccc(S(=O)(=O)Nc3ccc(Cl)cc3C(=O)c3ccncc3)c2)o1]
(+)
TABLE 2-continued
Compounds with activity in either or both of the chemotaxis assay and calcium mobilization assays, with $IC_{50} > 1000$ nM (+):
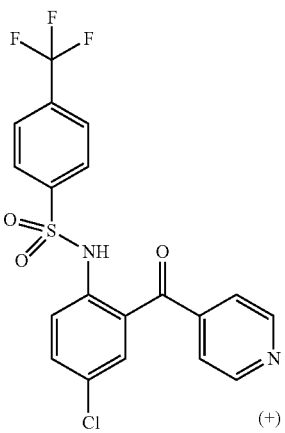 [SMILES: O=C(c1ccncc1)c1cc(Cl)ccc1NS(=O)(=O)c1ccc(C(F)(F)F)cc1]
(+)
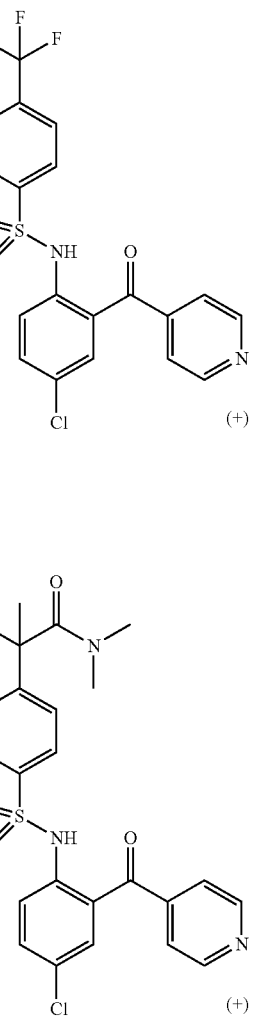
(+)
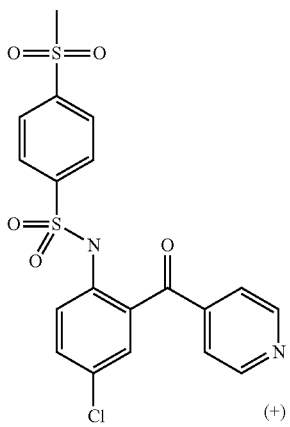 [SMILES: CS(=O)(=O)c1ccc(S(=O)(=O)Nc2ccc(Cl)cc2C(=O)c2ccncc2)cc1]
(+)

TABLE 2-continued
Compounds with activity in either or both of the chemotaxis assay
and calcium mobilization assays, with IC$_{50}$ > 1000 nM (+):
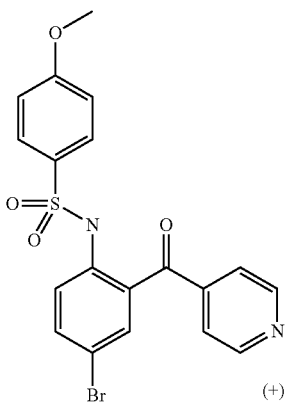 [SMILES: COc1ccc(S(=O)(=O)Nc2ccc(Br)cc2C(=O)c2ccncc2)cc1]
(+)
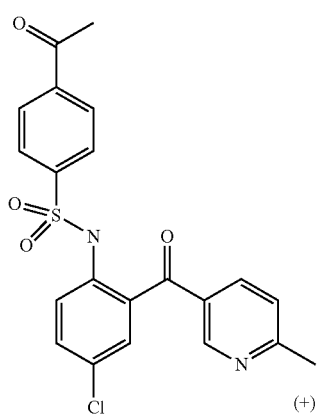 [SMILES: CC(=O)c1ccc(S(=O)(=O)Nc2ccc(Cl)cc2C(=O)c2ccc(C)nc2)cc1]
(+)
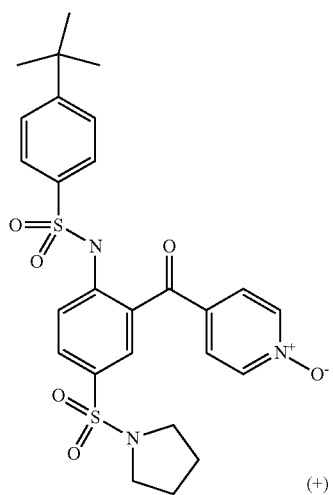 [SMILES: CC(C)(C)c1ccc(S(=O)(=O)Nc2ccc(S(=O)(=O)N3CCCC3)cc2C(=O)c2cc[n+]([O-])cc2)cc1]
(+)
TABLE 2-continued
Compounds with activity in either or both of the chemotaxis assay
and calcium mobilization assays, with IC$_{50}$ > 1000 nM (+):
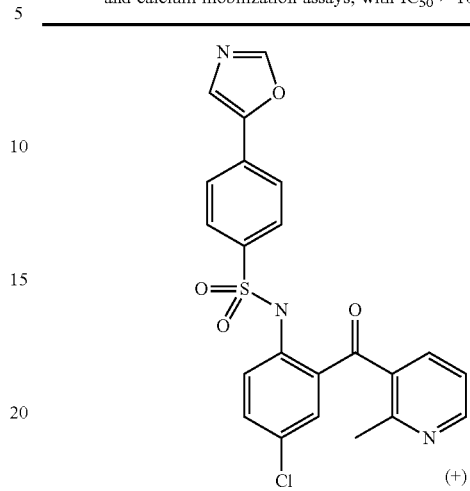
(+)
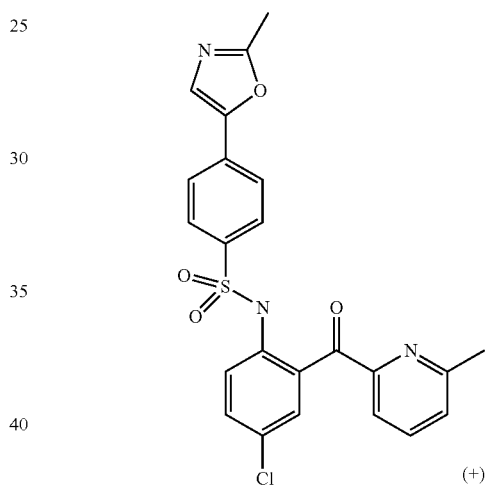
(+)
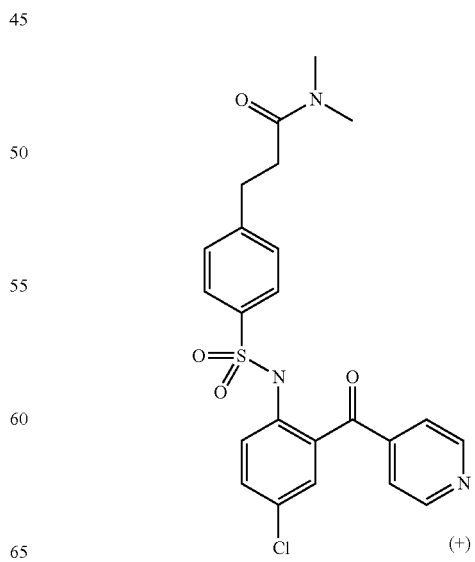
(+)

TABLE 2-continued
Compounds with activity in either or both of the chemotaxis assay and calcium mobilization assays, with IC$_{50}$ > 1000 nM (+):
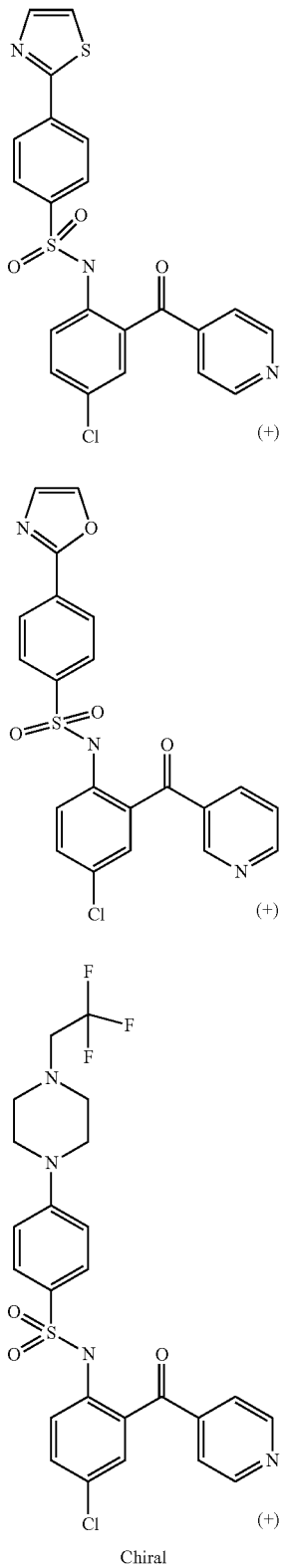
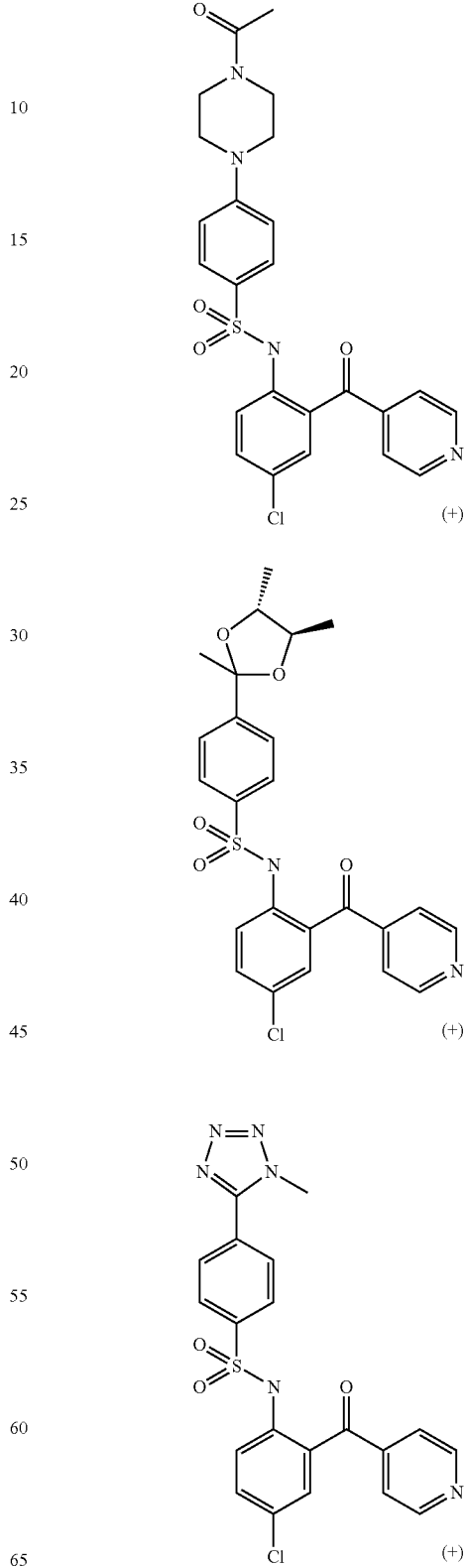

TABLE 2-continued
Compounds with activity in either or both of the chemotaxis assay and calcium mobilization assays, with IC$_{50}$ > 1000 nM (+):
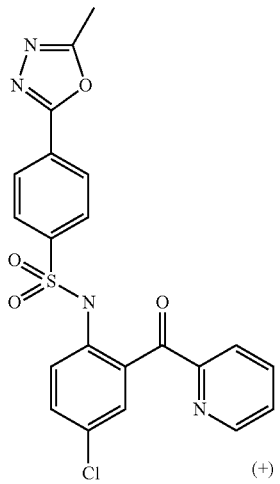 [SMILES: Cc1nnc(-c2ccc(S(=O)(=O)Nc3ccc(Cl)cc3C(=O)c3ccccn3)cc2)o1]
(+)
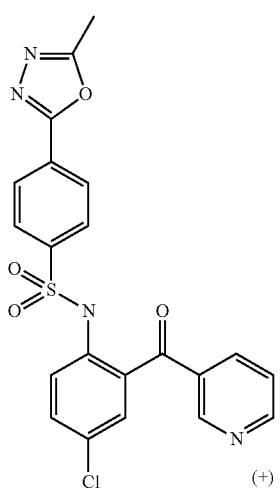 [SMILES: Cc1nnc(-c2ccc(S(=O)(=O)Nc3ccc(Cl)cc3C(=O)c3cccnc3)cc2)o1]
(+)
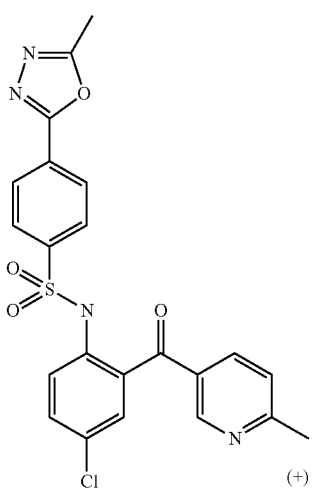 [SMILES: Cc1ccc(C(=O)c2cc(Cl)ccc2NS(=O)(=O)c2ccc(-c3nnc(C)o3)cc2)cn1]
(+)
TABLE 2-continued
Compounds with activity in either or both of the chemotaxis assay and calcium mobilization assays, with IC$_{50}$ > 1000 nM (+):
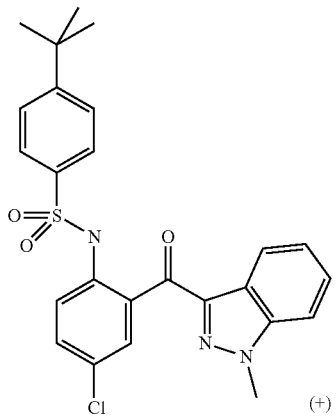 [SMILES: Cn1nc(C(=O)c2cc(Cl)ccc2NS(=O)(=O)c2ccc(C(C)(C)C)cc2)c2ccccc21]
(+)
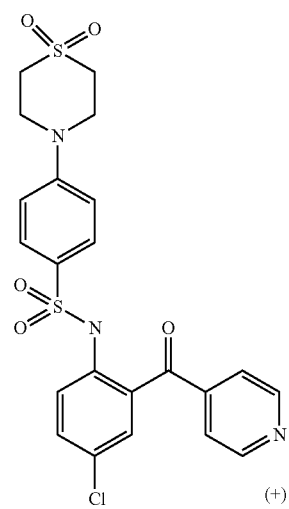 [SMILES: O=C(c1ccncc1)c1cc(Cl)ccc1NS(=O)(=O)c1ccc(N2CCS(=O)(=O)CC2)cc1]
(+)
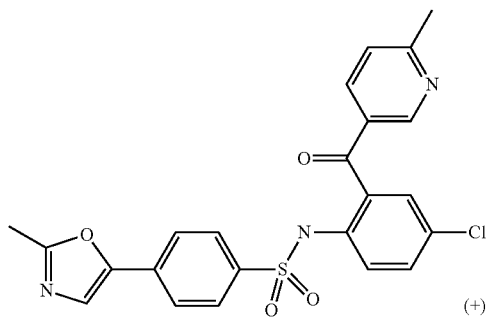 [SMILES: Cc1ccc(C(=O)c2cc(Cl)ccc2NS(=O)(=O)c2ccc(-c3cnc(C)o3)cc2)cn1]
(+)

TABLE 2-continued
Compounds with activity in either or both of the chemotaxis assay and calcium mobilization assays, with $IC_{50} > 1000$ nM (+):
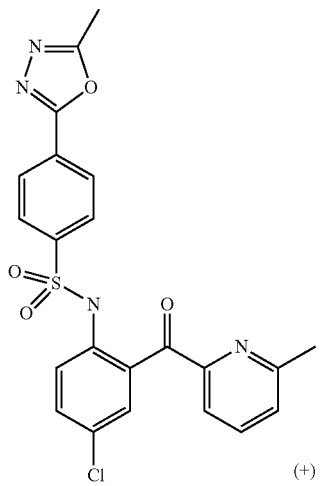 [SMILES: Cc1cccc(C(=O)c2cc(Cl)ccc2NS(=O)(=O)c2ccc(-c3nnc(C)o3)cc2)n1]
(+)
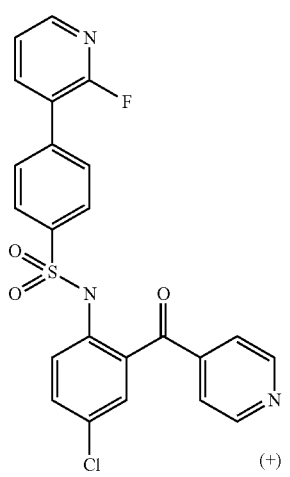 [SMILES: O=C(c1ccncc1)c1cc(Cl)ccc1NS(=O)(=O)c1ccc(-c2cccnc2F)cc1]
(+)
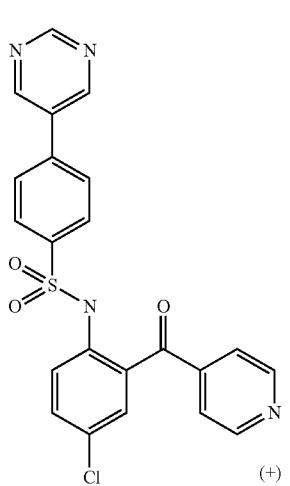 [SMILES: O=C(c1ccncc1)c1cc(Cl)ccc1NS(=O)(=O)c1ccc(-c2cncnc2)cc1]
(+)
TABLE 2-continued
Compounds with activity in either or both of the chemotaxis assay and calcium mobilization assays, with $IC_{50} > 1000$ nM (+):
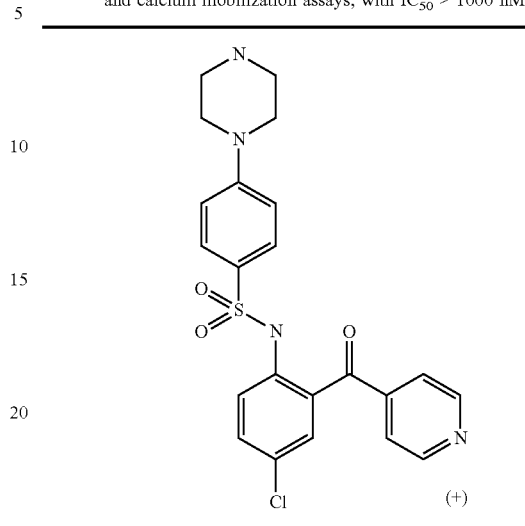
(+)
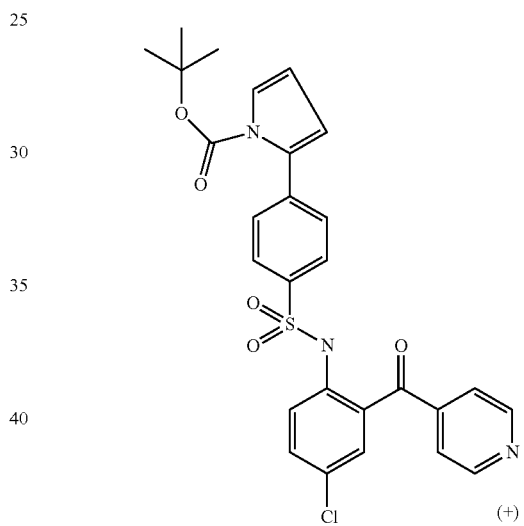
(+)
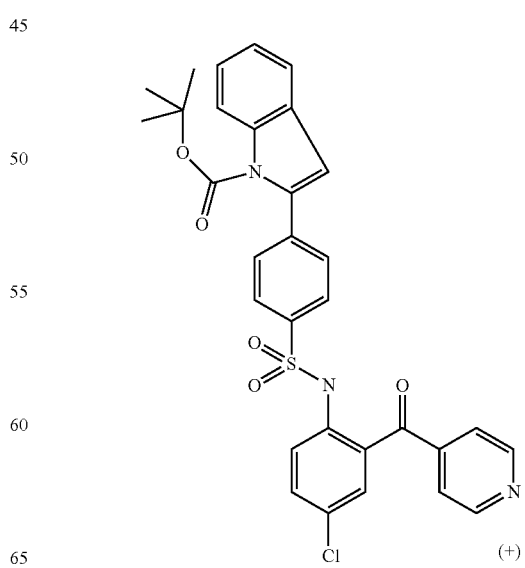
(+)

TABLE 2-continued

Compounds with activity in either or both of the chemotaxis assay and calcium mobilization assays, with $IC_{50} > 1000$ nM (+):

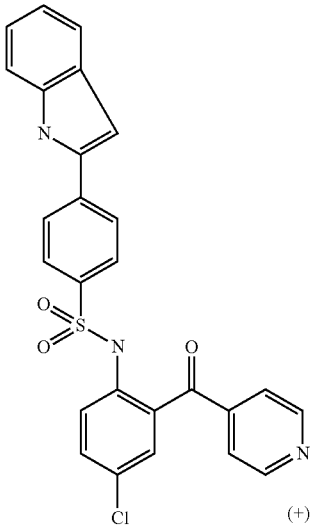 [SMILES: O=C(c1ccncc1)c1cc(Cl)ccc1NS(=O)(=O)c1ccc(-c2cc3ccccc3[nH]2)cc1]
(+)

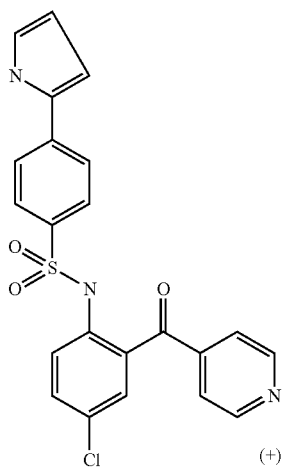 [SMILES: O=C(c1ccncc1)c1cc(Cl)ccc1NS(=O)(=O)c1ccc(-c2ccc[nH]2)cc1]
(+)

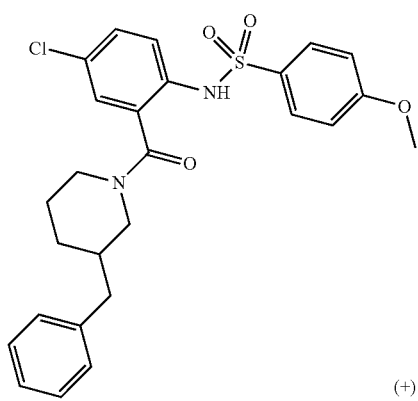 [SMILES: COc1ccc(S(=O)(=O)Nc2ccc(Cl)cc2C(=O)N2CCCC(Cc3ccccc3)C2)cc1]
(+)

TABLE 2-continued

Compounds with activity in either or both of the chemotaxis assay and calcium mobilization assays, with $IC_{50} > 1000$ nM (+):

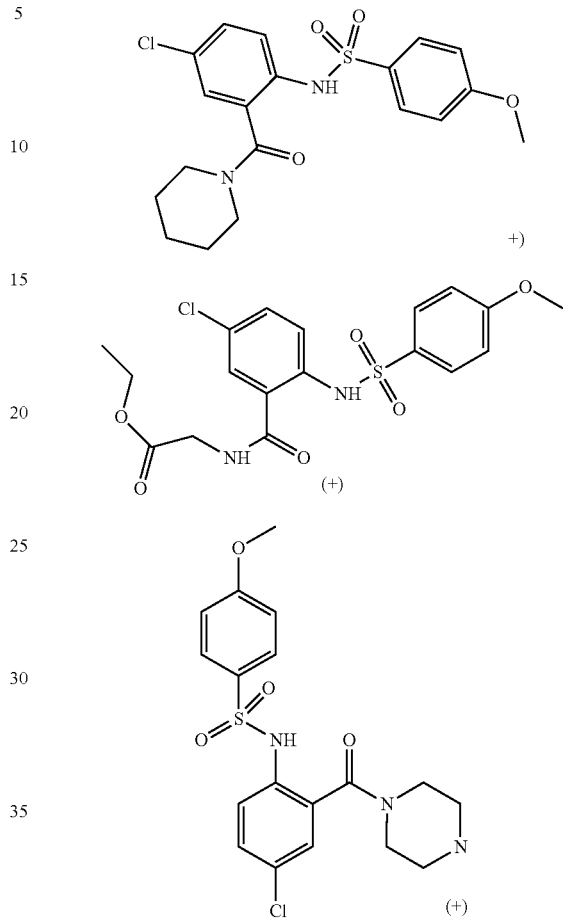
(+)

(+)

(+)

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A compound of the formula (I), or a salt thereof:

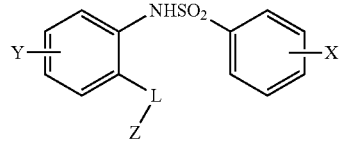

where X represents from 1 to 4 substituents independently selected from the group consisting of halogen, —CN, —NO$_2$, —OH, —OR$^1$, —C(O)R$^1$, —CO$_2$R$^1$, —O(CO)R$^1$, —C(O)NR$^1$R$^2$, —OC(O)NR$^1$R$^2$, —SR$^1$, —SOR$^1$, —SO$_2$R$^1$, —SO$_2$NR$^1$R$^2$, —NR$^1$R$^2$, —NR$^1$C(O)R$^2$, —NR$^1$C(O)$_2$R$^2$, —NR$^1$SO$_2$R$^2$, —NR$^1$(CO)NR$^2$R$^3$, unsubstituted C$_{1-8}$ alkyl, unsubstituted C$_{2-8}$ alkenyl, and unsubstituted C$_{2-8}$ alkynyl, R¹, R² and R³ are each independently selected from the group consisting of hydrogen, unsubstituted $C_{1-6}$ haloalkyl, unsubstituted $C_{1-6}$alkyl, unsubstituted $C_{2-6}$ alkenyl, and unsubstituted $C_{2-6}$ alkynyl, or two of R¹, R² and R³ together with the atom(s) to which they are attached, may form an unsubstituted 5-, 6- or 7-membered ring;

Y represents from 1 to 3 substituents, each independently selected from the group consisting of halogen, —CN, —NO₂, —OH, —OR⁴, —C(O)R⁴, —CO₂R⁴, —SR⁴, —SOR⁴, —SO₂R⁴, and unsubstituted $C_{1-4}$ alkyl;

R⁴ is selected from the group consisting of hydrogen, unsubstituted $C_{1-6}$ haloalkyl, unsubstituted $C_{1-6}$ alkyl, unsubstituted $C_{2-6}$alkenyl, and unsubstituted $C_{2-6}$ alkynyl; L is —C(O)—, —S—, —SO— or —S(O)₂; and Z is an unsubstituted or substituted heteroaryl selected from indazolyl, pyrimidinyl, pyridazinyl, and pyrazinyl.

2. The compound of claim 1, where L is —CO—.

3. A composition comprising a pharmaceutically acceptable carrier and a compound of claim 1.

4. The compound of claim 1, where the compound is selected from one of formulas XXI-XXVI

(XXI)

(XXII)

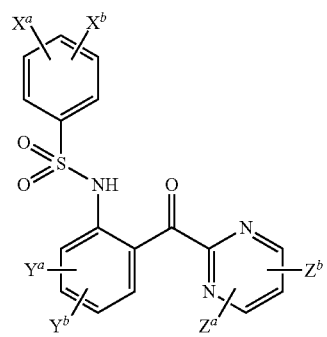

(XXIII)

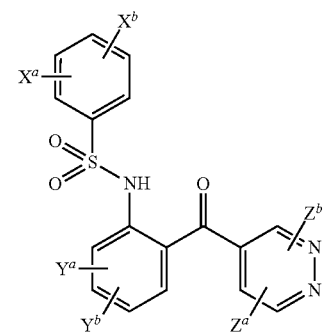

(XXIV)

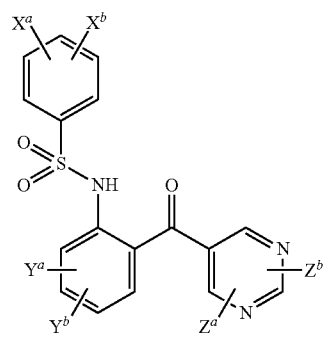

(XXV)

(XXVI)

where $X^a$ and $X^b$ are independently selected from the group consisting of: hydrogen, halogen, —CN, —NO₂, —OH, —OR¹, —C(O)R¹, —CO₂R, —O(CO)R¹, —C(O)NR¹R², —OC(O)NR¹R², —SR¹, —SOR¹, —SO₂R¹, —SO2NR¹R², —NR¹R², —NR¹C(O)R², —NR¹C(O)₂R², —NR¹SO₂R², —NR¹(CO)NR²R³, unsubstituted $C_{1-8}$ alkyl, unsubstituted $C_{2-8}$ alkenyl, unsubstituted $C_{2-8}$ alkynyl, and unsubstituted $C_{3-8}$ cycloalkyl;

R¹, R² and R³ are each independently selected from the group consisting of hydrogen, unsubstituted $C_{1-6}$ haloalkyl, unsubstituted $C_{1-6}$alkyl, unsubstituted $C_{2-5}$ alkenyl, and unsubstituted $C_{2-6}$ alkynyl; or two of R¹, R² and R³ together with the atom(s) to which they are attached, may form an unsubstituted 5-, 6- or 7-membered ring; where $Y^a$ and $Y^b$ are independently selected from the group consisting of: hydrogen, halogen, —CN, —NO₂, —OH, —OR⁴, —C(O)R⁴, —CO2R⁴, —SR⁴, —SOR⁴, —SO2R⁴, and unsubstituted $C_{1-4}$ alkyl;

R⁴ is selected from the group consisting of hydrogen, unsubstituted $C_{1-6}$ haloalkyl, unsubstituted $C_{1-6}$ alkyl, unsubstituted $C_{3-6}$ cycloalkyl, unsubstituted $C_{2-6}$ alkenyl, and unsubstituted $C_{2-6}$ alkynyl;

where $Z^a$ and $Z^b$ are independently selected from the group consisting of: hydrogen, halogen, unsubstituted $C_{1-8}$ alkyl, unsubstituted $C_{2-8}$ alkenyl, unsubstituted $C_{2-8}$ alkynyl, —CN, =O, —NO$_2$, —OR$^{10}$, —OC(O)R$^{10}$, —CO$_2$R$^{10}$, —C(O)R$^{10}$, —C(O)NR$^{11}$R$^{12}$, —OC(O)NR$^{11}$R$^{12}$, —NR$^{10}$C(O)R$^{11}$, —NR$^{10}$C(O)NR$^{11}$R$^{12}$, —NR$^{11}$R$^{12}$, —NR$^{10}$CO$_2$R$^{11}$, —SR$^{10}$, —S(O)R$^{10}$, —S(O)$_2$R$^{10}$, —S(O)$_2$NR$^{11}$R$^{12}$, and —NR$^{10}$S(O)$_2$R$^{11}$;

$R^{10}$, $R^{11}$ and $R^{12}$ are each selected from hydrogen, $C_{1-8}$alkyl, $C_{2-8}$ alkenyl, and $C_{2-8}$ alkynyl.

5. The compound of claim 4, where the compound is of formula XXI.

6. The compound of claim 4, where the compound is of formula XXII.

7. The compound of claim 4, where the compound is of formula XXIII.

8. The compound of claim 4, where the compound is of formula XXIV.

9. The compound of claim 4, where the compound is of formula XXV.

10. The compound of claim 4, where the compound is of formula XXVI.

11. A compound which is

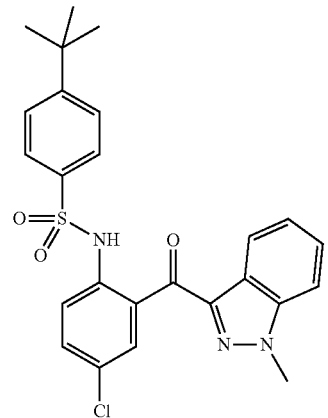

* * * * *